(12) United States Patent
Osterkamp et al.

(10) Patent No.: US 10,799,605 B2
(45) Date of Patent: Oct. 13, 2020

(54) CONJUGATE COMPRISING A NEUROTENSIN RECEPTOR LIGAND AND USE THEREOF

(71) Applicant: 3B PHARMACEUTICALS GMBH, Berlin (DE)

(72) Inventors: Frank Osterkamp, Berlin (DE); Christian Haase, Berlin (DE); Ulrich Reineke, Berlin (DE); Christiane Smerling, Berlin (DE); Matthias Paschke, Berlin (DE); Jan Ungewiß, Berlin (DE)

(73) Assignee: 3B Pharmaceuticals GMBH, Berlin (DE)

( * ) Notice: Subject to any disclaimer, the term of this patent is extended or adjusted under 35 U.S.C. 154(b) by 722 days.

(21) Appl. No.: 15/317,598

(22) PCT Filed: Jun. 10, 2015

(86) PCT No.: PCT/EP2015/001166
§ 371 (c)(1),
(2) Date: Dec. 9, 2016

(87) PCT Pub. No.: WO2015/188934
PCT Pub. Date: Dec. 17, 2015

(65) Prior Publication Data
US 2017/0119913 A1   May 4, 2017

(30) Foreign Application Priority Data

Jun. 10, 2014 (EP) .................... 14001992
Jun. 11, 2014 (EP) .................... 14002002

(51) Int. Cl.
*A61K 9/00* (2006.01)
*A61K 51/04* (2006.01)
(Continued)

(52) U.S. Cl.
CPC ........ *A61K 51/0482* (2013.01); *A61K 31/337* (2013.01); *A61K 47/545* (2017.08);
(Continued)

(58) Field of Classification Search
CPC .................................... A61K 51/0482
See application file for complete search history.

(56) References Cited

U.S. PATENT DOCUMENTS

| 5,723,483 A | 3/1998 | Labeeuw et al. |
| 2006/0062729 A1 | 3/2006 | Carraway |
| 2010/0256055 A1 | 10/2010 | Castaigne et al. |

FOREIGN PATENT DOCUMENTS

EP  2740726  6/2014

OTHER PUBLICATIONS

Lang, Christopher et al.; "Synthesis and Evaluation of a 18F-Labeled Diarylpyrazole Glycoconjugate for the Imaging of NTS1-Positive Tumors"; Journal of Medical Chemistry; 2013; pp. 9361-9365.

(Continued)

*Primary Examiner* — Paul W Dickinson
(74) *Attorney, Agent, or Firm* — DLA Piper LLP

(57) ABSTRACT

The present invention is related to a conjugate comprising a structure of general formula (1) [TM1]-[AD1]-[LM]-[AD2]-[TM2] (1), wherein TM1 is a first targeting moiety, wherein the first targeting moiety is capable of binding to a first target, AD1 is a first adapter moiety or is absent, LM is a linker moiety or is absent, AD2 is a second adapter moiety or is absent, and TM2 is a second targeting moiety, wherein the second targeting moiety is capable of binding to a second target; wherein the first targeting moiety and/or the second targeting moiety is a compound of formula (2): wherein $R^1$ is selected from the group consisting of hydrogen, methyl (Continued)

and cyclopropylmethyl; AA-COOH is an amino acid selected from the group consisting of 2-amino-2 adamantane carboxylic acid, cyclohexylglycine and 9-amino-bicyclo [3.3.1]nonane-9 carboxylic acid; $R^2$ is selected from the group consisting of $(C_1-C_6)$alkyl, $(C_3-C_8)$cycloalkyl, $(C_3C_8)$ cycloalkylmethyl, halogen, nitro and trifluoromethyl; ALK' is $(C_2-C_5)$alkylidene; $R^3$, $R^4$ and $R^5$ are each and independently selected from the group consisting of hydrogen and $(C_1-C_4)$alkyl under the proviso that one of $R^3$, $R^4$ and $R^5$ is of the following formula (3) wherein ALK' is $(C_2-C_5)$ alkylidene; $R^6$ is selected from the group consisting of hydrogen and $(C_1-C_4)$alkyl; and $R^7$ is a bond; or a pharmacologically acceptable salt, solvate or hydrate thereof.

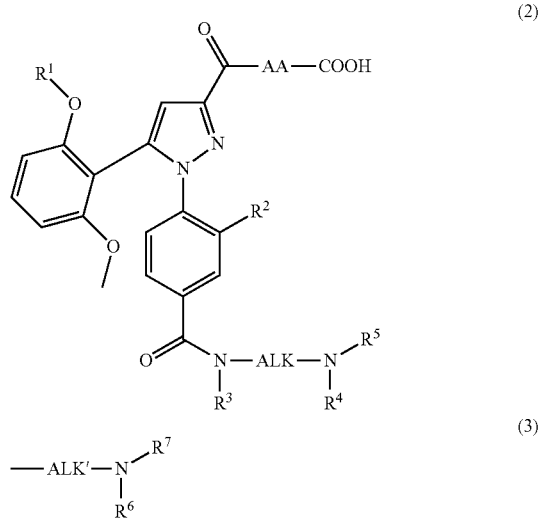

36 Claims, 15 Drawing Sheets

Specification includes a Sequence Listing.

(51) Int. Cl.

| | | |
|---|---|---|
| *A61K 51/08* | (2006.01) |
| *A61K 47/54* | (2017.01) |
| *A61K 47/68* | (2017.01) |
| *A61K 47/58* | (2017.01) |
| *A61K 31/337* | (2006.01) |
| *A61K 49/00* | (2006.01) |

(52) U.S. Cl.
CPC .......... *A61K 47/555* (2017.08); *A61K 47/557* (2017.08); *A61K 47/585* (2017.08); *A61K 47/68* (2017.08); *A61K 49/0043* (2013.01); *A61K 51/04* (2013.01); *A61K 51/0497* (2013.01); *A61K 51/088* (2013.01)

(56) References Cited

OTHER PUBLICATIONS

Singh, Nidhi et al.; "Synthetic FXR Agonist GW4064 Is a Modulator of Multiple G Protein-Coupled Receptors"; Mol Endocrinol; May 2014;28(5); pp. 659-673.

Thomas, James B. et al.; "Identification of N-[5-{[4-Methylphenyl)sulfonyl]amino}-3-(trifluoroacetyl)-1H-indol-1-yl)acetyl]-L-leucine (NTRC-824), a Neurotensin-like Nonpeptide Compound Selective for the Neurotensin Receptor Type 2"; Journal of Medical Chemistry; 2014; 57; pp. 7472-7477.

Thomas, James B. et al.; "Identification of N-(6-chloro-4-(2,6-dimethoxyphenyl)quinazolin-2-yl}carbonyl}-L-leucine (NTRC-808), a novel nonpeptide chemotype selective for the neurotensin receptor type 2"; Bioorganice & Medicinal Chemistry Letters; 2015; 25; pp. 292-296.

PCT International Search Report for PCT Patent Application No. PCT/EP2015/001166; dated Aug. 25, 2015; 4 pages.

PCT Written Opinion for for PCT Patent Application No. PCT/EP2015/001166; dated Aug. 25, 2015; 6 pages.

```
                        SEQUENCE LISTING

<160> NUMBER OF SEQ ID NOS: 24

<210> SEQ ID NO 1
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: Neurotensin

<400> SEQUENCE: 1

Glu Leu Tyr Glu Asn Lys Pro Arg Arg Pro Tyr Ile Leu
1               5                   10

<210> SEQ ID NO 2
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: Eight C-terminal amino acids of neurotensin

<400> SEQUENCE: 2

Lys Pro Arg Arg Pro Tyr Ile Leu
1               5

<210> SEQ ID NO 3
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Six C-terminal amino acids of neurotensin

<400> SEQUENCE: 3

Arg Arg Pro Tyr Ile Leu
1               5

<210> SEQ ID NO 4
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (4)..(4)
<223> OTHER INFORMATION: Xaa is
```

```
            N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (5)..(5)
<223> OTHER INFORMATION: Xaa is gamma-amino butyric acid

<400> SEQUENCE: 4

Xaa Xaa Lys Xaa Xaa
1               5

<210> SEQ ID NO 5
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (3)..(3)
<223> OTHER INFORMATION: Xaa is gamma-amino butyric acid

<400> SEQUENCE: 5

Xaa Lys Xaa
1

<210> SEQ ID NO 6
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is 6-aminohexanoic acid
<220> FEATURE:
<221> NAME/KEY: MISC_FEATURE
<222> LOCATION: (4)..(4)
<223> OTHER INFORMATION: Xaa is lysine amide
<220> FEATURE:
<221> NAME/KEY: MISC_FEATURE
<222> LOCATION: (5)..(5)
<223> OTHER INFORMATION: Xaa is glutaric acid

<400> SEQUENCE: 6

Xaa Xaa Lys Xaa Xaa
1               5

<210> SEQ ID NO 7
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
```

N-(3-
[2-(3-Amino-propoxy)-ethoxy]-ethoxy
-propyl)-succinamic
       acid
<220> FEATURE:
<221> NAME/KEY: MISC_FEATURE
<222> LOCATION: (3)..(3)
<223> OTHER INFORMATION: Xaa is
       N-(3-
[2-(3-Amino-propoxy)-ethoxy]-ethoxy
-propyl)-succinamic
       acid
<220> FEATURE:
<221> NAME/KEY: MISC_FEATURE
<222> LOCATION: (4)..(4)
<223> OTHER INFORMATION: Xaa is
       N-(3-
[2-(3-Amino-propoxy)-ethoxy]-ethoxy
-propyl)-succinamic
       acid
<220> FEATURE:
<221> NAME/KEY: MISC_FEATURE
<222> LOCATION: (6)..(6)
<223> OTHER INFORMATION: Xaa is
       N-(3-
[2-(3-Amino-propoxy)-ethoxy]-ethoxy
-propyl)-succinamic
       acid
<220> FEATURE:
<221> NAME/KEY: MISC_FEATURE
<222> LOCATION: (7)..(7)
<223> OTHER INFORMATION: Xaa is
       N-(3-
[2-(3-Amino-propoxy)-ethoxy]-ethoxy
-propyl)-succinamic
       acid
<220> FEATURE:
<221> NAME/KEY: MISC_FEATURE
<222> LOCATION: (8)..(8)
<223> OTHER INFORMATION: Xaa is
       N-(3-
[2-(3-Amino-propoxy)-ethoxy]-ethoxy
-propyl)-succinamic
       acid
<220> FEATURE:
<221> NAME/KEY: MISC_FEATURE
<222> LOCATION: (9)..(9)
<223> OTHER INFORMATION: Xaa is lysine amide
<220> FEATURE:
<221> NAME/KEY: MISC_FEATURE
<222> LOCATION: (10)..(10)
<223> OTHER INFORMATION: Xaa is glutaric acid

<400> SEQUENCE: 7

Xaa Xaa Xaa Xaa Lys Xaa Xaa Xaa Xaa Xaa
1               5                   10

<210> SEQ ID NO 8
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
       N-(3-
[2-(3-Amino-propoxy)-ethoxy]-ethoxy
-propyl)-succinamic
       acid
<220> FEATURE:
<221> NAME/KEY: MISC_FEATURE
<222> LOCATION: (4)..(4)
<223> OTHER INFORMATION: Xaa is

```
                N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (5)..(5)
<223> OTHER INFORMATION: Xaa is gamma-amino butyric acid
<220> FEATURE:
<221> NAME/KEY: MISC_FEATURE
<222> LOCATION: (10)..(10)
<223> OTHER INFORMATION: Xaa is tert. butyl glycine

<400> SEQUENCE: 8

Xaa Xaa Lys Xaa Xaa Arg Arg Pro Tyr Xaa Leu
1               5                   10

<210> SEQ ID NO 9
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
            N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (4)..(4)
<223> OTHER INFORMATION: Xaa is
            N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (5)..(5)
<223> OTHER INFORMATION: Xaa is gamma-amino butyric acid
<220> FEATURE:
<221> NAME/KEY: MISC_FEATURE
<222> LOCATION: (10)..(10)
<223> OTHER INFORMATION: Xaa is tert. butyl glycine

<400> SEQUENCE: 9

Xaa Xaa Lys Xaa Xaa Arg Arg Pro Tyr Xaa Leu
1               5                   10

<210> SEQ ID NO 10
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
            N-(3-
      [2-(3-Amino-propoxy)-ethoxy]-ethoxy
      -propyl)-succinamic
            acid
<220> FEATURE:
<221> NAME/KEY: MISC_FEATURE
```

```
<222> LOCATION: (3)..(3)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (4)..(4)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (6)..(6)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (7)..(7)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (8)..(8)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (9)..(9)
<223> OTHER INFORMATION: Xaa is gamma-amino butyric acid
<220> FEATURE:
<221> NAME/KEY: MISC_FEATURE
<222> LOCATION: (14)..(14)
<223> OTHER INFORMATION: Xaa is tert. butyl glycine

<400> SEQUENCE: 10

Xaa Xaa Xaa Xaa Lys Xaa Xaa Xaa Xaa Arg Arg Pro Tyr Xaa Leu
1               5                   10                  15

<210> SEQ ID NO 11
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (4)..(4)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
```

```
<222> LOCATION: (5)..(5)
<223> OTHER INFORMATION: Xaa is lysine amide
<220> FEATURE:
<221> NAME/KEY: MISC_FEATURE
<222> LOCATION: (6)..(6)
<223> OTHER INFORMATION: Xaa is glutamic acid

<400> SEQUENCE: 11

Xaa Xaa Lys Xaa Xaa Xaa
1               5

<210> SEQ ID NO 12
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (4)..(4)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (5)..(5)
<223> OTHER INFORMATION: Xaa is lysine amide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Xaa Xaa Lys Xaa Xaa Xaa
1               5

<210> SEQ ID NO 13
<211> LENGTH: 25
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (4)..(4)
<223> OTHER INFORMATION: Xaa is
      N-(3-
[2-(3-Amino-propoxy)-ethoxy]-ethoxy
-propyl)-succinamic
      acid
```

```
<220> FEATURE:
<221> NAME/KEY: MISC_FEATURE
<222> LOCATION: (5)..(5)
<223> OTHER INFORMATION: Xaa is gamma-amino butyric acid

<400> SEQUENCE: 13

Xaa Xaa Lys Xaa Xaa Asn Ala Val Pro Asn Leu Arg Gly Asp Leu Gln
1               5                   10                  15

Val Leu Ala Gln Lys Val Ala Arg Thr
            20                  25

<210> SEQ ID NO 14
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: Xaa is gamma-amino butyric acid
<220> FEATURE:
<221> NAME/KEY: MISC_FEATURE
<222> LOCATION: (22)..(22)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (23)..(23)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (24)..(24)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (26)..(26)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (27)..(27)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (28)..(28)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (29)..(29)
<223> OTHER INFORMATION: Xaa is lysine amide
<220> FEATURE:
<221> NAME/KEY: MISC_FEATURE
<222> LOCATION: (30)..(30)
<223> OTHER INFORMATION: Xaa is glutaric acid
```

-continued

<400> SEQUENCE: 14

Asn Ala Val Pro Asn Leu Arg Gly Asp Leu Gln Val Leu Ala Gln Lys
1               5                   10                  15

Val Ala Arg Thr Xaa Xaa Xaa Xaa Lys Xaa Xaa Xaa Xaa Xaa
            20                  25                  30

<210> SEQ ID NO 15
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: Xaa is gamma-amino butyric acid
<220> FEATURE:
<221> NAME/KEY: MISC_FEATURE
<222> LOCATION: (22)..(22)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (23)..(23)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (24)..(24)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (26)..(26)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (27)..(27)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (28)..(28)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (29)..(29)
<223> OTHER INFORMATION: Xaa is cysteine amide
<220> FEATURE:
<221> NAME/KEY: MISC_FEATURE
<222> LOCATION: (30)..(30)
<223> OTHER INFORMATION: Xaa is 3-(N-maleimido) propionic acid

<400> SEQUENCE: 15

Asn Ala Val Pro Asn Leu Arg Gly Asp Leu Gln Val Leu Ala Gln Lys

```
                1               5                    10                   15

Val Ala Arg Thr Xaa Xaa Xaa Xaa Lys Xaa Xaa Xaa Xaa
            20                  25                   30

<210> SEQ ID NO 16
<211> LENGTH: 27
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (3)..(3)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (4)..(4)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (5)..(5)
<223> OTHER INFORMATION: Xaa is lysine amide
<220> FEATURE:
<221> NAME/KEY: MISC_FEATURE
<222> LOCATION: (26)..(26)
<223> OTHER INFORMATION: Xaa is gamma-amino butyric acid
<220> FEATURE:
<221> NAME/KEY: MISC_FEATURE
<222> LOCATION: (27)..(27)
<223> OTHER INFORMATION: Xaa is
      N-(3-
[2-(3-Amino-propoxy)-ethoxy]-ethoxy
-propyl)-succinamic
      acid

<400> SEQUENCE: 16

Xaa Xaa Xaa Xaa Xaa Asn Ala Val Pro Asn Leu Arg Gly Asp Leu Gln
1               5                   10                  15

Val Leu Ala Gln Lys Val Ala Arg Thr Xaa Xaa
            20                  25

<210> SEQ ID NO 17
<211> LENGTH: 27
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
```

```
                N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (4)..(4)
<223> OTHER INFORMATION: Xaa is lysine amide
<220> FEATURE:
<221> NAME/KEY: MISC_FEATURE
<222> LOCATION: (5)..(5)
<223> OTHER INFORMATION: Xaa is
            N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (26)..(26)
<223> OTHER INFORMATION: Xaa is gamma-amino butyric acid
<220> FEATURE:
<221> NAME/KEY: MISC_FEATURE
<222> LOCATION: (27)..(27)
<223> OTHER INFORMATION: Xaa is
            N-(3-
      [2-(3-Amino-propoxy)-ethoxy]-ethoxy
      -propyl)-succinamic
            acid

<400> SEQUENCE: 17

Xaa Xaa Lys Xaa Xaa Asn Ala Val Pro Asn Leu Arg Gly Asp Leu Gln
1               5                   10                  15

Val Leu Ala Gln Lys Val Ala Arg Thr Xaa Xaa
            20                  25

<210> SEQ ID NO 18
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
            N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (4)..(4)
<223> OTHER INFORMATION: Xaa is
            N-(3-
      [2-(3-Amino-propoxy)-ethoxy]-ethoxy
      -propyl)-succinamic
            acid
<220> FEATURE:
<221> NAME/KEY: MISC_FEATURE
<222> LOCATION: (5)..(5)
<223> OTHER INFORMATION: Xaa is gamma-amino butyric acid
<220> FEATURE:
<221> NAME/KEY: MISC_FEATURE
<222> LOCATION: (9)..(9)
<223> OTHER INFORMATION: Xaa is hydroxy proline
<220> FEATURE:
<221> NAME/KEY: MISC_FEATURE
<222> LOCATION: (11)..(11)
<223> OTHER INFORMATION: Xaa is cyclohexalamine

<400> SEQUENCE: 18

Xaa Xaa Lys Xaa Xaa Lys Arg Pro Xaa Gly Xaa Ser Pro Leu
```

```
<210> SEQ ID NO 19
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
     N-(3-
[2-(3-Amino-propoxy)-ethoxy]-ethoxy
-propyl)-succinamic
     acid
<220> FEATURE:
<221> NAME/KEY: MISC_FEATURE
<222> LOCATION: (4)..(4)
<223> OTHER INFORMATION: Xaa is
     N-(3-
[2-(3-Amino-propoxy)-ethoxy]-ethoxy
-propyl)-succinamic
     acid
<220> FEATURE:
<221> NAME/KEY: MISC_FEATURE
<222> LOCATION: (5)..(5)
<223> OTHER INFORMATION: Xaa is gamma-amino butyric acid
<220> FEATURE:
<221> NAME/KEY: MISC_FEATURE
<222> LOCATION: (6)..(6)
<223> OTHER INFORMATION: Xaa is ornithine
<220> FEATURE:
<221> NAME/KEY: MISC_FEATURE
<222> LOCATION: (8)..(8)
<223> OTHER INFORMATION: Xaa is octahydroindol-2-carbonic acid
<220> FEATURE:
<221> NAME/KEY: MISC_FEATURE
<222> LOCATION: (11)..(11)
<223> OTHER INFORMATION: Xaa is  alpha-methyl-L-phenylalanine
<220> FEATURE:
<221> NAME/KEY: MISC_FEATURE
<222> LOCATION: (13)..(13)
<223> OTHER INFORMATION: Xaa is D-2-Naphtylalanine

<400> SEQUENCE: 19

Xaa Xaa Lys Xaa Xaa Xaa Arg Xaa Pro Gly Xaa Ser Xaa Ile
1               5                   10

<210> SEQ ID NO 20
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
     N-(3-
[2-(3-Amino-propoxy)-ethoxy]-ethoxy
-propyl)-succinamic
     acid
<220> FEATURE:
<221> NAME/KEY: MISC_FEATURE
<222> LOCATION: (3)..(3)
<223> OTHER INFORMATION: Xaa is lysine amide
<220> FEATURE:
<221> NAME/KEY: MISC_FEATURE
```

```
<222> LOCATION: (4)..(4)
<223> OTHER INFORMATION: Xaa is glutaric acid

<400> SEQUENCE: 20

Xaa Xaa Xaa Xaa
1

<210> SEQ ID NO 21
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MISC_FEATURE
<222> LOCATION: (2)..(2)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (3)..(3)
<223> OTHER INFORMATION: Xaa is lysine amide
<220> FEATURE:
<221> NAME/KEY: MISC_FEATURE
<222> LOCATION: (4)..(4)
<223> OTHER INFORMATION: Xaa is glutaric acid

<400> SEQUENCE: 21

Xaa Xaa Xaa Xaa
1

<210> SEQ ID NO 22
<211> LENGTH: 4
<212> TYPE: PRT
<213> ORGANISM: Artificial
<220> FEATURE:
<223> OTHER INFORMATION: Synthetic

<400> SEQUENCE: 22

Gly Phe Leu Gly
1

<210> SEQ ID NO 23
<211> LENGTH: 4
<212> TYPE: PRT
<213> ORGANISM: Artificial
<220> FEATURE:
<223> OTHER INFORMATION: Synthetic

<400> SEQUENCE: 23

Ala Leu Ala Leu
1

<210> SEQ ID NO 24
<211> LENGTH: 24
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is
      N-(1-(4,4-dimethyl-2,6-dioxocyclohexylidene)ethyl)
<220> FEATURE:
```

```
<221> NAME/KEY: MISC_FEATURE
<222> LOCATION: (3)..(3)
<223> OTHER INFORMATION: Xaa is
      N-(3-
[2-(3-Amino-propoxy)-ethoxy]-ethoxy
-propyl)-succinamic
      acid
<220> FEATURE:
<221> NAME/KEY: MISC_FEATURE
<222> LOCATION: (4)..(4)
<223> OTHER INFORMATION: Xaa is gamma-amino butyric acid

<400> SEQUENCE: 24

Xaa Lys Xaa Xaa Asn Ala Val Pro Asn Leu Arg Gly Asp Leu Gln Val
1               5                   10                  15

Leu Ala Gln Lys Val Ala Arg Thr
            20
```

CONJUGATE COMPRISING A NEUROTENSIN RECEPTOR LIGAND AND USE THEREOF

CROSS REFERENCE TO RELATED APPLICATIONS

This application is a U.S. National Stage application based on PCT International Application No. PCT/EP2015/001166 filed Jun. 10, 2015, which claims priority to European Patent Application No. 14001992.8 filed Jun. 10, 2014 and European Patent Application No. 14002002.5 filed Jun. 11, 2014, each of which is hereby incorporated by reference herein in its entirety.

The present invention is related to a conjugate; a composition comprising the conjugate; the conjugate and composition, respectively, for use in a method for the diagnosis of a disease; the conjugate and composition, respectively, for use in a method for the treatment of a disease; the conjugate and composition, respectively, for use in a method of diagnosis and treatment of a disease which is also referred to as "thera(g)nosis" or "thera(g)nostics"; the conjugate and composition, respectively, for use in a method for the identification of a subject, wherein the subject is likely to respond or likely not to respond to a treatment of a disease; the conjugate and composition, respectively, for use in a method for the selection of a subject from a group of subjects, wherein the subject is likely to respond or likely not to respond to a treatment of a disease; the conjugate and composition, respectively, for use in a method for the stratification of a group of subjects into subjects which are likely to respond to a treatment of a disease, and into subjects which are not likely to respond to a treatment of a disease; the conjugate and the composition, respectively, for use in a method for delivering an effector to a neurotensin receptor expressing tissue; a method for the diagnosis of a disease using the conjugate and the composition, respectively; a method for the treatment of a disease using the conjugate and the composition, respectively; a method for the diagnosis and treatment of a disease which is also referred to as "thera(g)nosis" or "thera(g)nostics, using the conjugate and the composition, respectively; a method for the delivery of an effector to a neurotensin receptor expressing tissue using the conjugate and the composition, respectively; and a kit comprising the compound and composition, respectively.

Neurotensin NT is a 13 amino acid neuropeptide (pyro-Glu$^1$-Leu$^2$-Tyr$^3$-Glu$^4$-Asn-Lys$^6$-Pro$^7$-Arg$^8$-Arg$^9$-Pro$^{10}$-Tyr$^{11}$-Ile$^{12}$-Leu$^{13}$-OH) (SEQ ID NO: 1) that is implicated in the regulation of luteinizing hormone and prolactin release and has significant interaction with the dopaminergic system. Neurotensin was first isolated from extracts of bovine hypothalamus based on its ability to cause a visible vasodilation in the exposed cutaneous regions of anesthetized rats (Carraway et al., *J. Biol. Chem.*, 1973, 248, 6854-6861).

Neurotensin is distributed throughout the central nervous system, with highest levels in the hypothalamus, amygdala and nucleus accumbens. It induces a variety of effects, including analgesia, hypothermia and increased locomotor activity. It is also involved in regulation of dopamine pathways. In the periphery, neurotensin is found in endocrine cells of the small intestine, where it leads to secretion and smooth muscle contraction (Friry et al., *Biochem. Biophys. Res. Commun.*, 2002, 290, 1161-1168).

Neurotensin is bound by neurotensin receptors. Three neurotensin receptors are known, namely neurotensin receptor 1, also referred to as NTR1, neurotensin receptor 2, also referred to as NTR2, and neurotensin receptor 3, also referred to as NTR3. These neurotensin receptors are transmembrane receptors that bind the neurotransmitter neurotensin (Vincent et al., *Trends Pharmacol. Sci.,* 1999, 20, 302-309; Pelaprat, *Peptides,* 2006, 27, 2476-2487). NTR1 and NTR2 which are encoded by the NTSR1 and NTSR2 genes, contain seven transmembrane helices and are G protein coupled. NTR3 has a single transmembrane domain and is encoded by the SORT1 gene.

The neurotensin receptor 1 (NTR1) was cloned in 1990 from rat brain and found to act as a high affinity, levocabastine insensitive receptor for neurotensin (Tanaka et al., *Neuron,* 1990, 4, 847-854). The affinity of neurotensin for the receptor could be decreased by both sodium ions and guanosine triphosphate (GTP) (Vincent et al., *Trends Pharmacol. Sci.,* 1999, 20, 302-309). NTR1 is expressed predominantly in the central nervous system and intestine (smooth muscle, mucosa and nerve cells). In the central nervous system, expression has been found in the diagonal band of Broca, medial septal nucleus, nucleus basalis magnocellularis, suprachiasmatic nucleus, supramammillary area, substantia nigra and ventral tegmental area. The receptor is also expressed in the dorsal root ganglion neurones of the spinal cord. The predominant response upon activation of the receptor by neurotensin is activation of phospholipase C, causing an increase in intracellular calcium levels. The receptor can also stimulate cAMP formation, MAP kinase activation and the induction of growth related genes, such as krox-24 (Vincent et al., *Trends Pharmacol. Sci.,* 1999, 20, 302-309).

Neurotensin receptor 2 (NTR2) is a protein that in humans is encoded by the NTSR2 gene (Vincent et al., *Trends Pharmacol. Sci.,* 1999, 20, 302-309; Mazella et al., *J. Neurosci.,* 1996, 16, 5613-5620; Ramez et al., *J. Invest. Dermatol.,* 2001, 117, 687-693). The protein encoded by this gene belongs to the G protein-coupled receptor family that activates a phosphatidylinositol-calcium second messenger system. Binding and pharmacological studies demonstrate that this receptor binds neurotensin as well as several other ligands already described for NTR1. However, unlike NTR1, NTR2 recognizes, with high affinity, levocabastine, a histamine H1 receptor antagonist previously shown to compete with neurotensin for low-affinity binding sites in the central nervous system. These activities suggest that this receptor may be of physiological importance and that a natural agonist for the receptor may exist.

Neurotensin receptor 3 (NTR3) is a non-G-protein coupled receptor. The cDNA encodes an 833-amino acid protein 100% identical to the recently cloned gp95/sortilin and was then designated NTR3/gp95/sortilin (Mazella, *Cell Signal.,* 2001, 13, 1-6; Vincent et al., *Trends Pharmacol. Sci.,* 1999, 20, 302-309). NTR3 is a sorting protein involved in cellular trafficking and neuropeptide signalling. The physiological and cellular roles of sortilin/NTR3 are putative in many aspects and still under discussion.

Apart from the central nervous system, NTR1 is highly expressed in a mammalian body and a human body in particular on several neoplastic cells in several tumor indications, whereas the expression of NTR1 in most other tissues of the mammalian and the human body is either not existent or low. Only for colon weak or moderate expression under physiological conditions is described.

The following table summarizes the expression of NTR1 as described in the prior art indicating the tissue, degree of expression, detection method and the respective references.

| Tissue | Expression | Detection method Reference |
| --- | --- | --- |
| Central Nervous System (e.g. substantia nigra, suprachiasmatic nucleus) | +++ | Autoradiography, immunohistochemistry, in situ hybridization<br>e.g. Boudin et al., *J Comp. Neurol.*, 1996, 373, 76-89 (and references herein) |
| Colon (mucosa, normal) | +/− | In situ hybridization<br>Gui et al., *Peptides*, 2008, 29, 1609-15 |
| Colon (smooth muscle, normal) | +/++ | Autoradiography<br>Rettenbacher et al., *Naunyn Schmiedebergs Arch. Pharmacol.*, 2001, 364, 291-304 |
| Ductal pancreatic adenocarcinoma | +++ | Autoradiography, RT-PCR, Immunohistochemistry, cell line studies<br>Reubi et al., *Gut*, 1998, 42, 546-50; Ehlers et al., *Ann. Surg.*, 2000, 231, 838-48; Iwase et al., *Cancer*, 1997, 79, 1787-1793; Wang et al., *Neuropeptides*, 2011, 45, 151-156; Wang et al., *Clin. Cancer Res.*, 2000, 6, 566-571 |
| Small cell lung cancer | ++ | Autoradiography, cell line studies<br>Reubi et al., *Int. J. Cancer*, 1999, 82, 213-218; Moody et al., *Peptides*, 2001, 22, 109-115 |
| Prostate cancer | ++ | RT-PCR (xenografts), functional studies, Taylor et al., *Prostate*, 2012, 72, 523-32; Amorino et al., *Oncogene*, 2007, 26, 745-756; Valerie et al., *Cancer Res.*, 2011, 71, 6817-6826; Swift et al., *Cancer Res.*, 2010, 70, 347-356; Almeida et al., *Peptides*, 2010, 31, 242-247 |
| Colorectal carcinoma | ++/+++ | RT-PCR, in situ hybridization, immunohistochemistry, mouse model, cell line studies<br>Chao et al., *J. Surg. Res.*, 2005, 129, 313-321; Gui et al., *Peptides*, 2008, 29, 1609-1615; Bossard et al., *Peptides*, 2007, 28, 2030-2035; Bugni et al., *Int. J. Cancer*, 2012, 130, 1798-1805; Haase et al., *Anitcancer Res.*, 2006, 26, 3527-3533; Martin et al., *Gastroenterology*, 2002, 123, 1135-1143 |
| Breast cancer | + | Immunohistochemistry<br>Souaze et al., *Cancer Res.*, 2006, 66, 6243-6249; Dupouy et al., *PLoS One*, 2009, 4, e4223 |
| Meningioma | +++ | Autoradiography<br>Reubi et al., *Int. J. Cancer*, 1999, 82, 213-218 |
| Ewing's Sarcoma | +++ | Autoradiography<br>Reubi et al., *Int. J. Cancer*, 1999, 82, 213-218 |
| Pleural Mesothelioma | ++ | Immunohistochemistry<br>Alifano et al., *Biochimie*, 2010, 92, 164-170 |
| Head and Neck Cancer | + | Functional study<br>Shimizu et al., *Int. J. Cancer*, 2008, 123, 1816-1823 |
| Lung Cancer | ++ | Immunohistochemistry, cell line studies, RT-PCR<br>Alifano et al., *Clin. Cancer Res.*, 2010, 16, 4401-4410; Moody et al., *Panminerva Med.*, 2006, 48, 19-26; Ocejo-Garcia et al., *Lung Cancer*, 2001, 33, 1-9 |
| Gastrointestinal Stromal Tumors | ++ | Gromova et al., *PLoS One*, 2011, 6, e14710 |
| Uterine Leiomyoma | ++ | Immunohistochemistry, RT-PCR<br>Rodriguez et al., *Biol. Reprod.*, 2010, 83, 641-647; Rodriguez et al., *Int. J. Gynecol Pathol*, 2011, 30, 354-363 |
| Cutaneous T-Cell Lymphoma | ++ | Flow cytometry<br>Ramez et al., *J. Invest. Dermatol*, 2001, 117, 687-693 |

These NTR1 expressing tumor indications include but are not limited to ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma. A preferred group of NTR1 expressing tumor indications are ductal pancreatic adenocarcinoma, small cell lung cancer, prostate cancer, colorectal cancer, breast cancer, meningioma and Ewing's sarcoma.

Because of this selective expression of NTR1, NTR1 is regarded as a suitable target for drugs and diagnostic agents. Agonists and antagonists binding to NTR1 have been described in the prior art. One class of such NTR1 agonists are peptides binding to NTR1.

Most of these agonist peptides are derivatives of neurotensin, its C-terminal eight amino acids $Lys^6$-$Pro^7$-$Arg^8$-$Arg^9$-$Pro^{10}$-$Tyr^{11}$-$Ile^{12}$-$Leu^{13}$ (NT6-13) (SEQ ID NO: 2) or its C-terminal six amino acids $Arg^8$-$Arg^9$-$Pro^{10}$-$Tyr^{11}$-$Ile^{12}$-$Leu^{13}$ (NT8-13) (SEQ ID NO: 3). Modifications include for example N-methylations, reduced amide bonds, β-Ala or D-Lys at position 7, Gly(PipAm) at position 8, Dab or Phe(4-Gu) at position 9, Dmt at position 11, Tle or tBuGly at position 12, D-Leu or Cha at position 13 as well as combinations thereof. U.S. Pat. No. 4,439,359 discloses cyclic octapeptide analogs of neurotensin. U.S. Pat. No. 4,425,269 discloses metabolically protected analogs of neurotensin. WO 1999/052539 discloses neurotensin analogs with the novel non-natural amino acid Neo-tryptophan. WO 2000/078796 discloses labeled neurotensin derivatives, some of them with improved resistance to enzymatic degradation. WO 1995/022341 discloses labeled peptide compounds. US 2010/0256055 discloses conjugates of neurotensin or neurotensin analogs and uses thereof. U.S. Pat. No. 4,110,321 discloses a synthetic tridecapeptide [$Gln^4$]-neurotensin having hormonal activity. WO 2011006985 discloses neurotensin analogues for radioisotope targeting to neurotensin receptor-positive tumors. EP 0606804, WO 1996/031531, WO 1997/004311 and WO 1998/001472 disclose marker for the neurotensin receptor including fluorescently labeled markers. U.S. Pat. No. 5,407,916 discloses neurotensin mimetics as central nervous system agents.

These peptides as well as the further ligands of NTR1, namely neuromedin N and xenin, can be used for imaging purposes and therapeutic purposes. Typically, the agonist carries a therapeutically or diagnostically active effector such as a chelated metal label and more specifically a chelated radiolabel suitable for therapy and diagnosis, respectively. The effector bearing agonist binds to the receptor and, upon binding to the receptor, the effector bearing agonist is internalized by the receptor and the effector bearing agonist thus trapped in the target cell. It will be understood by a person skilled in the art that such trapping of the effector bearing agonist may go along with the release of the effector from the agonist. Additionally, upon such trapping, the effector and/or the agonist may be subject to metabolic conversion. Such metabolic conversion may occur through the metabolism and enzymatic activities in particular of the organism to which the effector bearing agonist has been administered and more specifically the metabolism of the cell and tissue, respectively, into which the effector bearing agonist has been internalized.

The potential utility of metal labeled neurotensin receptor specific peptidic agonists for scintigraphic or SPECT or PET imaging and radiotherapy is exemplified by the $^{99m}$Tc-labelled neurotensin (NT) analog NT-XI (Buchegger et al., *J. Nucl. Med.*, 2003, 44, 1649-1654) or $^{99m}$Tc-labelled neurotensin (NT) analog $^{99m}$Tc-Demotensin VI (Gabriel et al., *Cancer Biother. Radiopharm.*, 2011, 26, 557-563).

Metal labeled neurotensin receptor specific ligands have also been used for preclinical tumor imaging for example of NTR1-expressing HT29 xenograft tumors using $^{99m}$Tc-NTXIX (Garcia-Garayoa et al., *Eur. J. Nucl. Med. Mol. Imaging*, 2009, 36, 37-47). Such neurotensin receptor specific ligands are NT(8-13) analogs (Garcia-Garayoa et al., *Nucl. Med. Biol.*, 2001, 28, 75-84; Garcia-Garayoa et al., *J. Nucl. Med.*, 2002, 43, 374-383; Garcia-Garayoa et al., *Nucl. Med. Biol.*, 2006, 33, 495-503; Garcia-Garayoa et al., *Eur. J. Nucl. Med. Mol. Imaging*, 2009, 36, 37-47; Bergmann et al., *Nucl. Med. Biol.*, 2002, 29, 61-72; Bruehlmeier et al., *Nucl. Med. Biol.*, 2002, 29, 321-327; Blauenstein et al., *Cancer Biother. Radiopharm.*, 2004, 19, 181-188; Maes et al., *J. Med. Chem.*, 2006, 49, 1833-1836), demotensins (Nock et al., *J. Med. Chem.*, 2006, 49, 4767-4776; Maina et al., *Eur. J. Nucl. Med. Mol. Imaging*, 2007, 34, 1804-1814), NT(6-13) analogs (Alshoukr et al., *Bioconjug. Chem.*, 2009, 20, 1602-1610; Alshoukr et al., *Bioconjug. Chem.*, 2011, 22, 1374-1385) and neurotensin analogs developed by Biosynthema (Achilefu et al., *J. Med. Chem.*, 2003, 46, 3403-3411; de Visser et al., *Eur. J. Nucl. Med. Mol. Imaging*, 2003, 30, 1134-1139; and Janssen et al., *Cancer Biother. Radiopharm.*, 2007, 22, 374-381).

It was found that (most) neurotensin-derived metal labeled peptides have a very short circulation half-life due to rapid renal clearance as often observed for peptidic molecules. Consequently, tumor accumulation is rather limited for such molecules.

International patent application WO 98/33531 discloses methods for the detection and localization of malignant human tumors using neurotensin, peptide NTR agonists and peptide NTR antagonists, respectively. The example part of WO 98/33531 shows the use of $^{125}$I labeled and unlabeled neurotensin and fragments thereof acting as agonists in receptor autoradiography of cryostat sections of tumor samples.

U.S. Pat. No. 5,723,483 discloses small molecule compounds which are active as NTR1 antagonists such as SR142948. These small molecule compounds and SR142948 in particular, however, cross the blood-brain barrier and are thus suitable neither for the radionuclide therapy of tumors nor for the radioactive diagnosis of tumors and imaging in particular, whereby the tumors are preferably those expressing NTR1, since irradiation of the central nervous system or any other non-radioactive cell-killing effect may have detrimental effects on the patient. Additionally, the radiolabeling of these compounds is difficult. Even more difficult is designing and synthesizing a radiolabeled derivative of these compounds without diminishing or destroying the original and desired high NTR1 affinity.

The above overview of the prior art attempting to provide a compound which can be used in the diagnosis and/or therapy of NTR1-expressing tumors, whereby such diagnosis and therapy typically makes use of a radiolabeled version of such compound, illustrates the difficulties in designing this kind of compounds being effective and thus suitable for such diagnostic and therapeutic purpose. It is imperative that the compound has appropriate in vivo targeting and pharmacokinetic properties. It is, however, well known that the radionuclide chemistry and associated linkages are crucial particularly with respect to the attachment to the compound of an effector which provides the signal needed for diagnosis or which provides the therapeutically effective activity. Such effector can be attached to the compound either directly or through a connecting moiety. In case the effector is a radiolabel and the radiolabel is attached to the compound by a connecting moiety such as, for example, a chelator, the labeling of such a connecting moiety and chelator, respectively, is a further crucial step in the identification of a suitable compound (Fritzberg et al., *J. Nucl. Med.*, 1992, 33, 394-397). Hence the type of radionuclide, the type of compound which mediates target binding, and the method used for linking them to one another may have unpredictable effects on the properties of the radiolabeled version of the compound. Theoretically, a high affinity of the compound as such, i.e. without the radiolabel, a connecting moiety and/or chelator, respectively, if any, for the target receptor facilitates retention of the compound and the radiolabeled version thereof in particular in target receptor expressing tissues. However, it is well known that the affinity and receptor specificity of the compound as such, i.e. without the radiolabel and the linker and chelator, respectively, if any, may be completely altered during chemical modification and radionuclide labeling (Fani et al., *J. Nucl. Med.*, 2012, 53, 1481-1489). Therefore, an optimal compound and even more so a radiolabeled version thereof suitable for diagnosis and therapy, respectively, of a disease is a matter of luck rather than of a rational and predictable development process. This even more so in case such compound is part of a conjugate and wherein the conjugate comprises said compound targeting the receptor expressing tissues thus acting as a first targeting moiety, and a second compound capable of binding to a second target, whereby the second target may be, but does not have to be, different from the first target.

The problem underlying the present invention is the provision of a compound which is suitable as a diagnostic agent and/or a pharmaceutical agent, particularly if said compound comprises a diagnostically and/or therapeutically active effector. A further problem underlying the present invention is the provision of a compound which is suitable as a diagnostic agent and/or a pharmaceutical agent, particularly if conjugated to a diagnostically and/or therapeutically active effector, and which does not penetrate the blood-brain barrier. A further problem underlying the present invention is the provision of a compound which is suitable as a diagnostic agent and/or a pharmaceutical agent, particularly if conjugated to a diagnostically and/or therapeutically active effector, in the diagnosis and/or therapy of a disease where the diseased cells and/or diseased tissues express NTR1. A still further problem underlying the instant invention is the provision of a compound which is suitable for delivering a diagnostically and/or therapeutically effective agent to a diseased cell and/or diseased tissue, respectively, and more particularly an NTR1-expressing diseased cell and/or diseased tissue. Also, a problem underlying the present invention is the provision of a method for the diagnosis of a disease, of a method for the treatment and/or prevention of a disease, and a method for the combined diagnosis and treatment of a disease; preferably such disease is a disease involving NTR1-expressing cells and/or tissues. A still further problem underlying the present invention is the provision of a method for the identification of a subject, wherein the subject is likely to respond or likely not to respond to a treatment of a disease, a method for the selection of a subject from a group of subjects, wherein the subject is likely to respond or likely not to respond to a treatment of a disease. Also, a problem underlying the present invention is the provision of a pharmaceutical composition containing a compound having the characteristics as outlined above. Furthermore, a problem underlying the present invention is the provision of a kit which is suitable for use in any of the above methods.

These and other problems are solved by the subject matter of the attached independent claims. Preferred embodiments may be taken from the attached dependent claims.

Furthermore, these and other problems are solved by the following embodiments.

EMBODIMENT 1

A conjugate comprising a structure of general formula (1)

[TM1]-[AD1]-[LM]-[AD2]-[TM2]     (1), wherein
TM1 is a first targeting moiety, wherein the first targeting moiety is capable of binding to a first target,
AD1 is a first adapter moiety or is absent,
LM is a linker moiety or is absent,
AD2 is a second adapter moiety or is absent, and
TM2 is a second targeting moiety, wherein the second targeting moiety is capable of binding to a second target;
wherein the first targeting moiety and/or the second targeting moiety is a compound of formula (2):

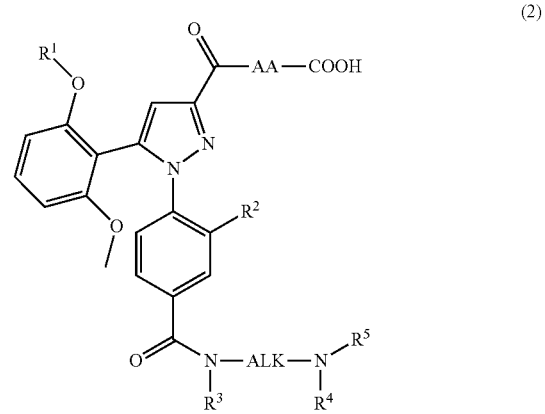

(2)

wherein
$R^1$ is selected from the group consisting of hydrogen, methyl and cyclopropylmethyl;
AA-COOH is an amino acid selected from the group consisting of 2-amino-2-adamantane carboxylic acid, cyclohexylglycine and 9-amino-bicyclo[3.3.1]nonane-9-carboxylic acid;
$R^2$ is selected from the group consisting of $(C_1-C_6)$alkyl, $(C_3-C_8)$cycloalkyl, $(C_3-C_8)$cycloalkylmethyl, halogen, nitro and trifluoromethyl; ALK is $(C_2-C_5)$alkylidene;
$R^3$, $R^4$ and $R^5$ are each and independently selected from the group consisting of hydrogen and $(C_1-C_4)$alkyl under the proviso that one of $R^3$, $R^4$ and $R^5$ is of the following formula (3)

(3)

wherein
ALK' is $(C_2-C_5)$alkylidene;
$R^6$ is selected from the group consisting of hydrogen and $(C_1-C_4)$alkyl; and
$R^7$ is a bond;

or a pharmacologically acceptable salt, solvate or hydrate thereof.

EMBODIMENT 2

The conjugate of embodiment 1, wherein the conjugate comprises an Effector moiety, wherein the Effector moiety comprises or is capable of comprising an Effector, wherein the Effector is selected from the group comprising a diagnostically active agent, a therapeutically active agent and a combination thereof.

EMBODIMENT 3

The conjugate of any one of embodiments 1 and 2, wherein the $R^1$ is methyl.

EMBODIMENT 4

The conjugate of any one of embodiments 1, 2 and 3, wherein AA-COOH is an amino acid selected from the group consisting of 2-amino-2-adamantane carboxylic acid and cyclohexylglycine.

EMBODIMENT 5

The conjugate of embodiment 4, wherein AA-COOH is 2-amino-2-adamantane carboxylic acid.

EMBODIMENT 6

The conjugate of embodiment 4, wherein AA-COOH is cyclohexylglycine.

EMBODIMENT 7

The conjugate of any one of embodiments 1, 2, 3, 4, 5 and 6, preferably any one of embodiments 1 and 2, wherein $R^2$ is isopropyl.

EMBODIMENT 8

The conjugate of any one of embodiments 1, 2, 3, 4, 5, 6 and 7, preferably any one of embodiments 1 and 2, wherein R3, R4 and R5 are each and independently selected from the group consisting of hydrogen and methyl under the proviso that one of R3, R4 and R5 is of the following formula (3)

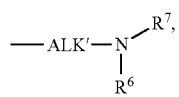

wherein
ALK' is $(C_2-C_5)$alkylidene;
$R^6$ is selected from the group consisting of hydrogen and $(C_1-C_4)$alkyl.

EMBODIMENT 9

The conjugate of embodiment 8, wherein $R^6$ is selected from the group consisting of hydrogen and methyl.

EMBODIMENT 10

The conjugate of any one of embodiments 1, 2, 3, 4, 5, 6, 7, 8 and 9, wherein $R^3$, $R^4$ and $R^5$ are each and independently methyl under the proviso that one of $R^3$, $R^4$ and $R^5$ is of the following formula (3):

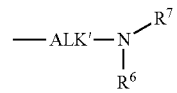

wherein
ALK' is $(C_2-C_5)$alkylidene;
$R^6$ is selected from the group consisting of hydrogen and methyl.

EMBODIMENT 11

The conjugate of any one of embodiments 1, 2, 3, 4, 5, 6, 7, 8, 9 and 10, preferably any one of embodiments 1, 2 and 10, wherein ALK and ALK' are both propylene, or wherein either ALK is propylene and ALK' is $(C_2-C_5)$alkylidene or ALK is $(C_2-C_5)$alkylidene and ALK' is propylene.

EMBODIMENT 12

The conjugate of any one of embodiments 1 and 2, wherein
$R^1$ is methyl;
AA-COOH is an amino acid selected from the group consisting of 2-amino-2-adamantane carboxylic acid and cyclohexylglycine; and
$R^2$ is isopropyl.

EMBODIMENT 13

The conjugate of any one of embodiments 1, 2 and 12, wherein
$R^3$, $R^4$ and $R^5$ are each and independently selected from the group consisting of hydrogen and methyl under the proviso that one of $R^3$, $R^4$ and $R^5$ is of the following formula (3):

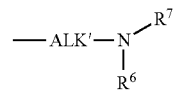

wherein
ALK' is $(C_2-C_5)$alkylidene;
$R^6$ is selected from the group consisting of hydrogen and methyl.

EMBODIMENT 14

The conjugate of any one of embodiments 1 and 2, wherein
$R^1$ is methyl;
AA-COOH is an amino acid selected from the group consisting of 2-amino-2-adamantane carboxylic acid and cyclohexylglycine;
$R^2$ is isopropyl;
$R^3$, $R^4$ and $R^5$ are each and independently selected from the group consisting of hydrogen and methyl under the proviso that one of $R^3$, $R^4$ and $R^5$ is of the following formula (3):

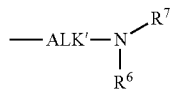
(3)

wherein
ALK' is (C$_2$-C$_5$)alkylidene; and
R$^6$ is selected from the group consisting of hydrogen and methyl.

EMBODIMENT 15

The conjugate of any one of embodiments 1, 2, 3, 4, 5, 6, 7, 8, 9, 10, 11, 13 and 14, preferably any one of embodiments 12, 13 and 14, wherein
R$^3$, R$^4$ and R$^5$ are each and independently methyl under the proviso that one of R$^3$, R$^4$ and R$^5$ is of the following formula (3):

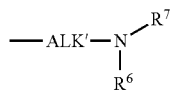
(3)

wherein
ALK' is (C$_2$-C$_5$)alkylidene; and
R$^6$ is selected from the group consisting of hydrogen and methyl.

EMBODIMENT 16

The conjugate of any one of embodiments 1, 2, 3, 4, 5, 6, 7, 8, 9, 10, 11, 12, 13, 14 and 15, preferably of any one of embodiments 12, 13, 14 and 15, wherein
ALK and ALK' are both propylene, or wherein either ALK is propylene and ALK' is (C$_2$-C$_5$)alkylidene or ALK is (C$_2$-C$_5$)alkylidene and ALK' is propylene.

EMBODIMENT 17

The conjugate according to any one of embodiments 1 and 2, wherein
R$^1$ is methyl;
AA-COOH is an amino acid selected from the group consisting of 2-amino-2-adamantane carboxylic acid and cyclohexylglycine;
R$^2$ is isopropyl; and
ALK and ALK' are both propylene, or wherein either ALK is propylene and ALK' is (C$_2$-C$_5$)alkylidene or ALK is (C$_2$-C$_5$)alkylidene and ALK' is propylene.

EMBODIMENT 18

The conjugate according to any one of embodiments 1 and 2, wherein
R$^1$ is methyl;
AA-COOH is an amino acid selected from the group consisting of 2-amino-2-adamantane carboxylic acid and cyclohexylglycine;
R$^2$ is isopropyl;
R$^3$, R$^4$ and R$^5$ are each and independently selected from the group consisting of hydrogen and methyl under the proviso that one of R$^3$, R$^4$ and R$^5$ is of the following formula (3)

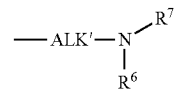
(3)

wherein
R$^6$ is selected from the group consisting of hydrogen and methyl; and
ALK and ALK' are both propylene, or wherein either ALK is propylene and ALK' is (C$_2$-C$_5$)alkylidene or ALK is (C$_2$-C$_5$)alkylidene and ALK' is propylene.

EMBODIMENT 19

The conjugate of any one of embodiments 1 to 18, wherein the first targeting moiety is selected from the group consisting of a compound of formula (4), a compound of formula (5) and a compound of formula (6), wherein the compound of formula (4) is

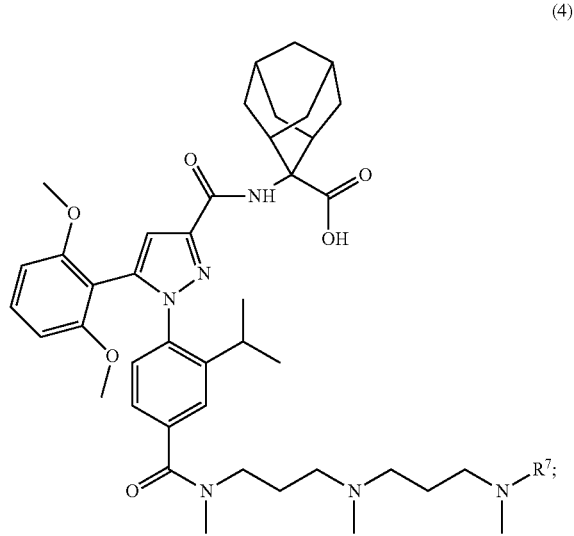
(4)

the compound of formula (5) is

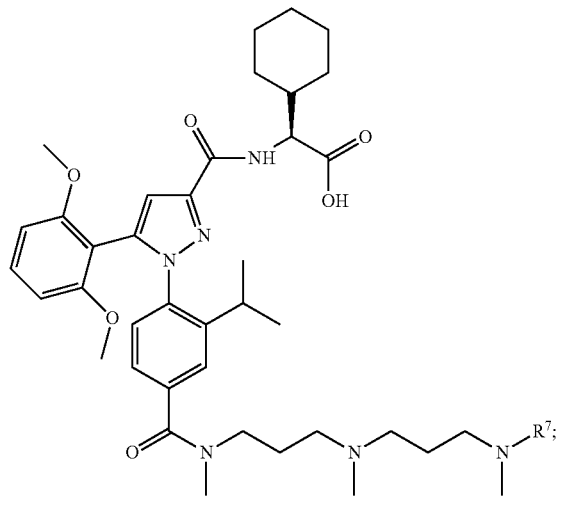
(5)

the compound of formula (6) is

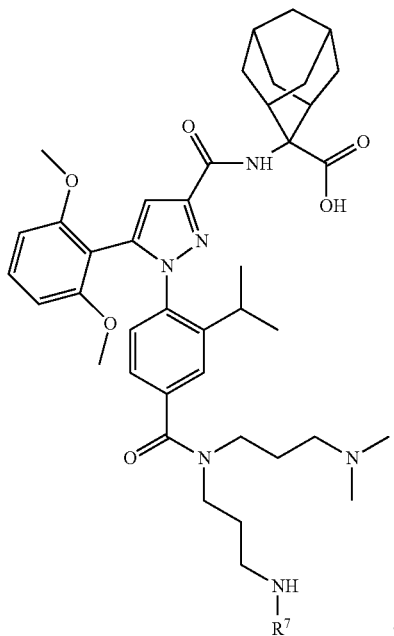

(6)

EMBODIMENT 20

The conjugate of any one of embodiments 1 to 19, wherein the second targeting moiety and the first targeting moiety is a targeting moiety as defined in any one of embodiments 1 to 19.

EMBODIMENT 21

The conjugate of embodiment 20, wherein the first targeting moiety is selected from the group comprising a compound of formula (4)

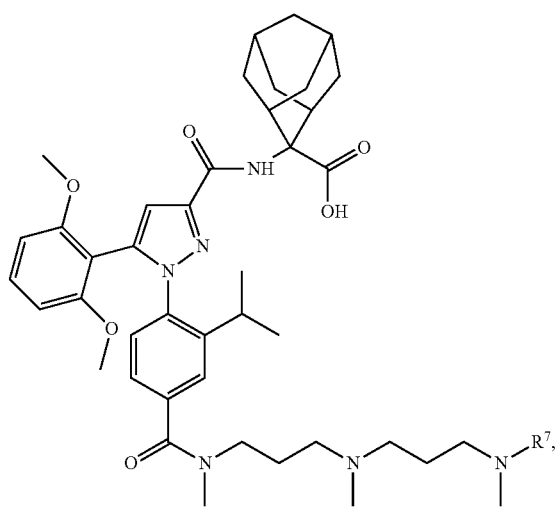

(4)

a compound of formula (5) is

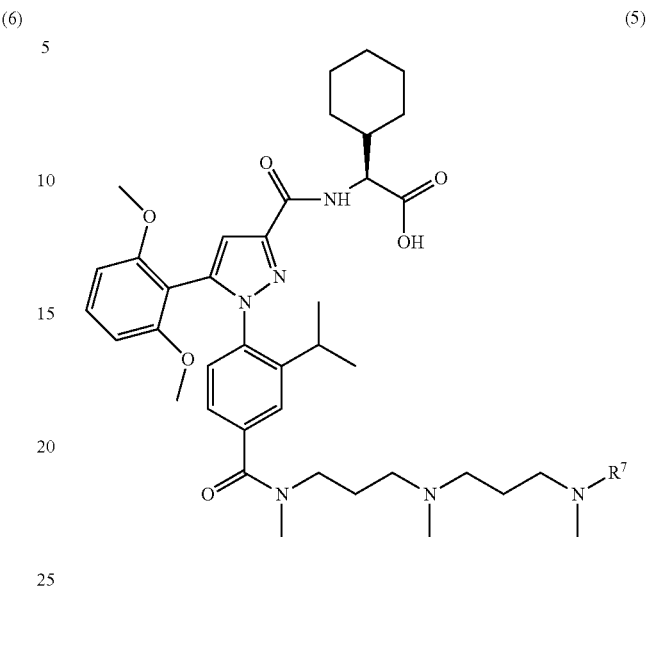

(5)

and
a compound of formula (6) is

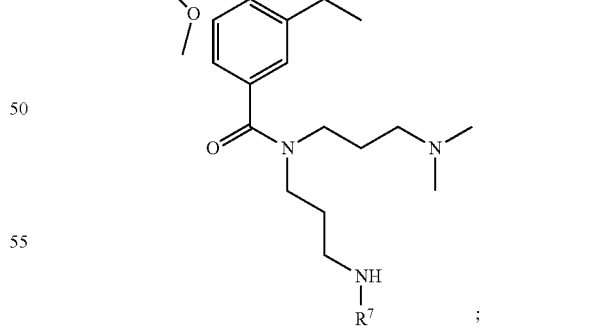

(6)

;

and
wherein the second targeting moiety is selected from the group comprising a compound of formula (4)
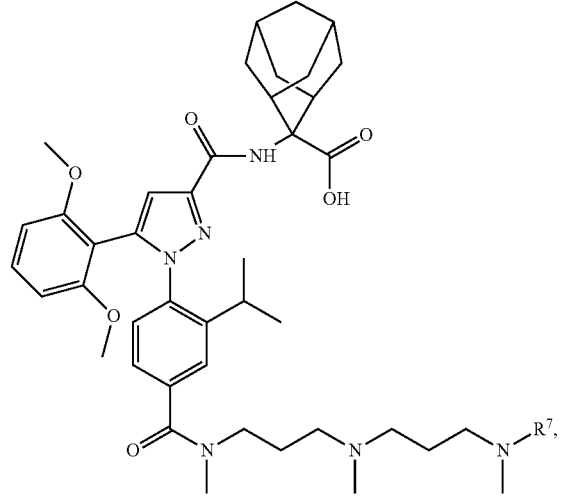
a compound of formula (5) is
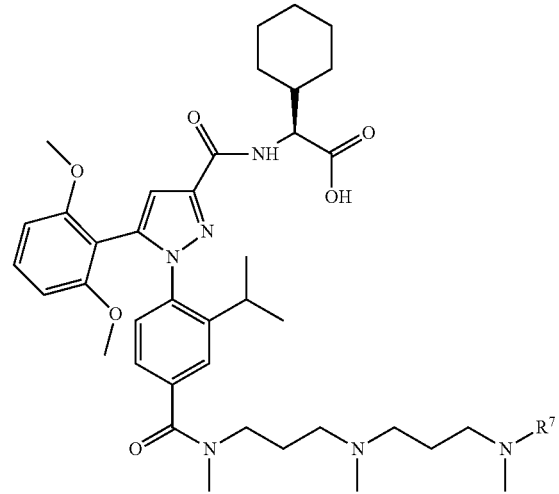
and
a compound of formula (6) is
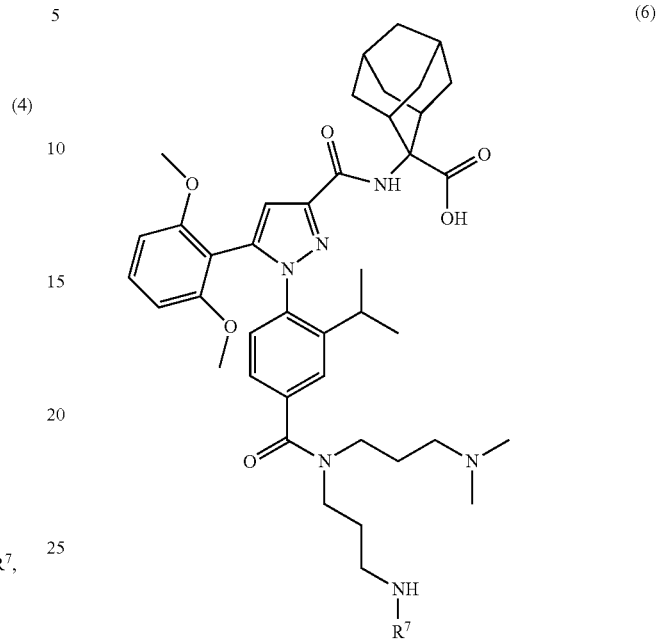
EMBODIMENT 22
The conjugate of any one of embodiments 20 and 21, wherein the first targeting moiety is a compound of formula (4)
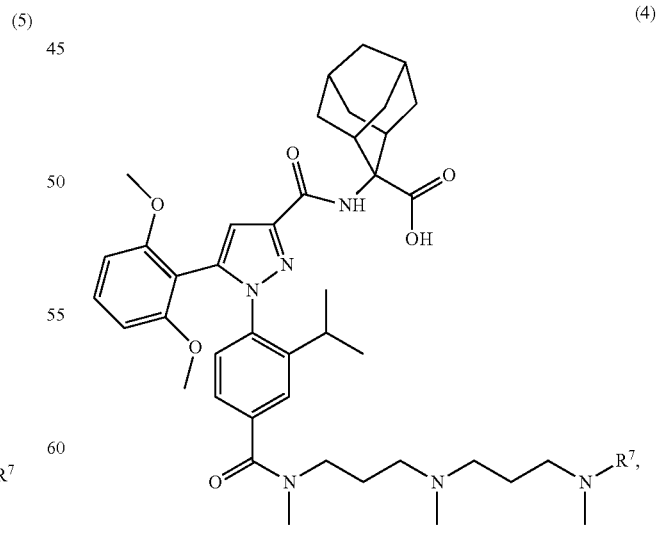
and
wherein the second targeting moiety is a compound of formula (4)

(4)

[structure of formula (4)]

EMBODIMENT 23

The conjugate of any one of embodiments 20 and 21, wherein the first targeting moiety is a compound of formula (4)

(4)

[structure of formula (4)]

and
wherein the second targeting moiety is a compound of formula (5)

(5)

[structure of formula (5)]

EMBODIMENT 24

The conjugate of any one of embodiments 20 and 21, wherein the first targeting moiety is a compound of formula (4)

(4)

[structure of formula (4)]

and
wherein the second targeting moiety is a compound of formula (6)

19

(6)

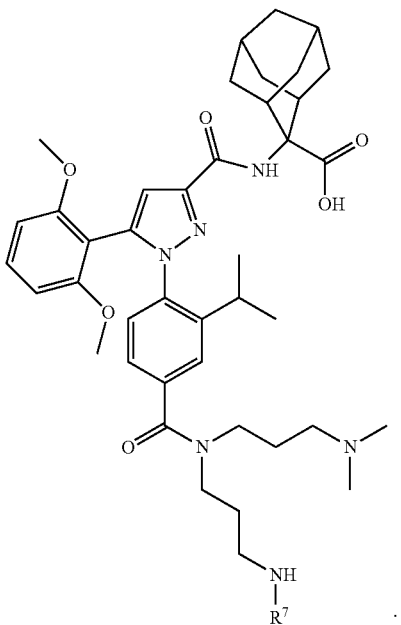

EMBODIMENT 25

The conjugate of any one of embodiments 1 to 24, wherein the first targeting moiety and/or the second targeting moiety is different from a compound of formula (7)

(7)

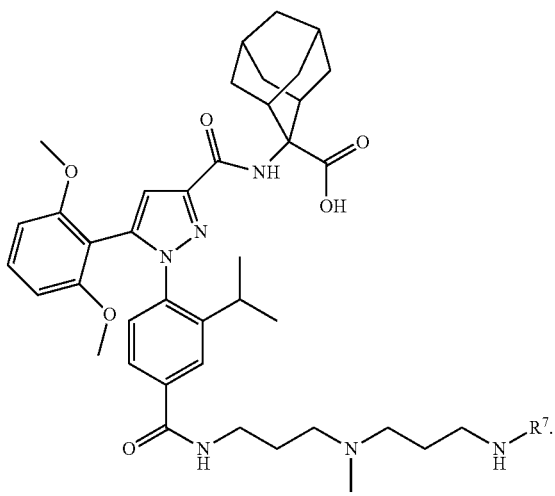

EMBODIMENT 26

The conjugate of any one of embodiments 1 to 25, preferably any one of embodiments 20 to 25, wherein the first targeting moiety and the second targeting moiety are separated by 4 to 1000 covalent bonds, preferably 5 to 150 covalent bonds, more preferably 10 to 40 covalent bonds.

20

EMBODIMENT 27

The conjugate of any one of embodiments 1 to 26, preferably any one of embodiments 20 to 26, wherein the linker moiety LM is of general formula:

$$—[X]_a—[Y]—[Z]_b—  \quad (VIII)$$

wherein
[X]$_a$ is a building block moiety formed of "a" building blocks X, or is absent
[Y] is a branching moiety or is absent,
[Z]$_b$ is a building block moiety formed of "b" building blocks Z, or is absent
and wherein "a" and "b" are individually and independently any integer from 0, 1, 2, 3, 4, 5, 6, 7, 8, 9, 10, 11, 12, 13, 14, 15, 16, 17, 18, 19 and 20 under the proviso that a+b is 20, 19, 18, 17, 16, 15, 14, 13, 12, 11, 10, 9, 8, 7, 6, 5, 4, 3, 2, 1 or 0; preferably "a" and "b" are individually and independently any integer from 0, 1, 2, 3, 4, 5, 6, 7, 8, 9 and 10, more preferably any integer from 0, 1, 2, 3, 4 and 5.

EMBODIMENT 28

The conjugate of embodiment 27, wherein building block moiety [X]$_a$ is linked to an adjacent moiety through a linkage, wherein the linkage is individually and independently selected from the group comprising an amide linkage, a urea linkage, a carbamate linkage, an ester linkage, an ether linkage, a thioether linkage and a disulfide linkage, and wherein the adjacent moiety is selected from the group comprising branching moiety [Y], building block moiety [Z]$_b$, second adapter moiety AD2, second targeting moiety TM2, first adapter moiety AD1 and first targeting moiety TM1.

EMBODIMENT 29

The conjugate of any one of embodiment 27 and 28, wherein the building block X is of general formula $$\text{—}[\text{Lin}^2\text{-R}^9\text{-Lin}^3]\text{—} \quad (8)$$

wherein,
Lin$^2$, if present, and Lin$^3$, if present, are each individually and independently selected from the group comprising —CO—, —NR$^{10}$—, —S—, —CO—NR$^{10}$—, —CS—NR$^{10}$—, —O—, -succinimide- and —CH$_2$—CO—NR$^{10}$—;
wherein
"-succinimide-" means (9)

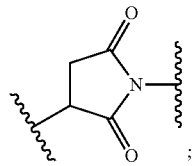

;

R$^{10}$ is selected from the group consisting of hydrogen and (C$_1$-C$_4$)alkyl.
and the nitrogen of all nitrogen containing fragments is linked to R$^9$,
and wherein R$^9$ is selected from selected from —(C$_1$-C$_{10}$) alkylidene-, —(C$_3$-C$_8$)carbocyclo-, -arylene-, —(C$_1$-C$_{10}$) alkylidene-arylene-, -arylene-(C$_1$-C$_{10}$)alkylidene-, —(C$_1$-C$_{10}$)alkylidene-arylene-(C$_1$-C$_{10}$)alkylidene-, —(C$_1$-C$_{10}$)

alkylidene-$(C_3-C_8)$carbocyclo-, —$(C_3-C_8)$carbocyclo-$(C_1-C_{10})$alkylidene-, —$(C_1-C_{10})$alkylidene-$(C_3-C_8)$carbocyclo-$(C_1-C_{10})$alkylidene-, —$(C_3-C_8)$heterocyclo-, $(C_1-C_{10})$alkylidene-$(C_3-C_8)$heterocyclo-, —$(C_3-C_8)$heterocyclo-$(C_1-C_{10})$alkylidene-, —$(C_1-C_{10})$alkylidene-$(C_3-C_8)$heterocyclo-$(C_1-C_1)$alkylidene-, —$(CH_2CH_2O)_r$—, and —$(CH_2)_s$—$(CH_2CH_2O)_r$—$(CH_2)_t$—;
and wherein
r is any integer from 1, 2, 3, 4, 5, 6, 7, 8, 9 and 10;
s is any integer from 0, 1, 2, 3 and 4; and
t is any integer from 0, 1, 2, 3 and 4.

EMBODIMENT 30

The conjugate of any one of embodiments 27 to 29, wherein the building block moiety $[X]_a$ is a peptide.

EMBODIMENT 31

The conjugate of any one of embodiments 27 to 30, wherein building block moiety $[Z]_b$ is linked to an adjacent moiety through a linkage, wherein the linkage is individually and independently selected from the group comprising an amide linkage, a urea linkage, a carbamate linkage, an ester linkage, an ether linkage, a thioether linkage and a disulfide linkage, and wherein the adjacent moiety is selected from the group comprising branching moiety [Y], building block moiety $[X]_a$, first adapter moiety AD1, first targeting moiety TM1, second adapter moiety AD2 and second targeting moiety TM2.

EMBODIMENT 32

The conjugate of embodiment 31, wherein the building block Z is of general formula

 (8)

wherein,
Lin², if present, and Lin³, if present, are each individually and independently selected from the group comprising —CO—, —NR¹⁰—, —S—, —CO—NR¹⁰—, —CS—NR¹⁰—, —O—, -succinimide- and —CH₂—CO—NR¹⁰—;
wherein
"-succinimide-" means

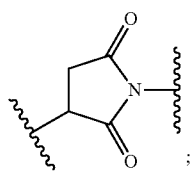 (9)

$R^{10}$ is selected from the group consisting of hydrogen and $(C_1-C_4)$alkyl;
and the nitrogen of all nitrogen containing fragments is linked to $R^9$;
and wherein $R^9$ is selected from selected from —$(C_1-C_{10})$alkylidene-, —$(C_3-C_8)$carbocyclo-, -arylene-, —$(C_1-C_{10})$alkylidene-arylene-, -arylene-$(C_1-C_{10})$alkylidene-, —$(C_1-C_{10})$alkylidene-arylene-$(C_1-C_{10})$alkylidene-, —$(C_1-C_{10})$alkylidene-$(C_3-C_8)$carbocyclo-, —$(C_3-C_8)$carbocyclo-$(C_1-C_{10})$alkylidene-, —$(C_1-C_{10})$alkylidene-$(C_3-C_8)$carbocyclo-$(C_1-C_{10})$alkylidene-, —$(C_3-C_8)$heterocyclo-, $(C_1-C_{10})$alkylidene-$(C_3-C_8)$heterocyclo-, —$(C_3-C_8)$heterocyclo-$(C_1-C_{10})$alkylidene-, —$(C_1-C_{10})$alkylidene-$(C_3-C_8)$heterocyclo-$(C_1-C_{10})$alkylidene-, —$(CH_2CH_2O)_r$—, and —$(CH_2)_s$—$(CH_2CH_2O)_r$—$(CH_2)_t$—;
and wherein
r is any integer from 1, 2, 3, 4, 5, 6, 7, 8, 9 and 10;
s is any integer from 0, 1, 2, 3 and 4; and
t is any integer from 0, 1, 2, 3 and 4.

EMBODIMENT 33

The conjugate of any one of embodiments 27 to 32, wherein the building block moiety $[Z]_b$ is a peptide.

EMBODIMENT 34

The conjugate of any one of embodiments 27 to 33, wherein the branching moiety [Y] is linked to an adjacent moiety through a linkage, wherein the linkage is individually and independently selected from the group comprising an amide linkage, a urea linkage, a carbamate linkage, an ester linkage, an ether linkage, a thioether linkage and a disulfide linkage, and wherein the adjacent moiety is selected from the group comprising building block moiety $[X]_a$, first adapter moiety AD1, first targeting moiety TM1, building block moiety $[Z]_b$, second adapter moiety AD2 and second targeting moiety TM2.

EMBODIMENT 35

The conjugate of embodiment 34, wherein the branching moiety [Y] is of a structure as described in any one of embodiment 28 to 33 for building block moiety $[X]_a$ and building block moiety $[Z]_b$.

EMBODIMENT 36

The conjugate of any one of embodiments 34 and 35, wherein the branching moiety [Y] comprises a reactive group which allows, together with a corresponding complementary reactive group, forming of a linkage individually and independently selected from the group comprising an amide linkage, a urea linkage, a thiourea linkage and an amine linkage.

EMBODIMENT 37

The conjugate of any one of embodiments 1 to 36, wherein the first adapter moiety AD1 mediates linkage to the first targeting moiety TM1 and to an adjacent moiety, wherein the adjacent moiety is selected from the group comprising linker moiety LM, building block moiety $[X]_a$, branching moiety Y, building block moiety $[Z]_b$, second adapter moiety AD2 and second targeting moiety TM2.

EMBODIMENT 38

The conjugate of embodiment 37, wherein the linkage is individually and independently selected from the group comprising an amide linkage, a sulfonamide linkage, a urea linkage, a thioether linkage, an ether linkage, a carbamate linkage, an amine linkage, a triazole linkage, an oxime linkage, a hydrazone linkage, a disulfide linkage, a pyrazine linkage and a dihydropyrazine linkage.

EMBODIMENT 39

The conjugate of any one of embodiments 37 to 38, wherein the first adapter moiety AD1, preferably prior to forming any linkage, is of the following structure:

RG3-R8-RG4 (10)

wherein RG3 is a reactive group as described herein, preferably a reactive group as indicated in Table 2 or selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine;

wherein RG4 is a reactive group as described herein, preferably a reactive group as indicated in Table 2 or selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine; and wherein R8 is selected from $-(C_1-C_{10})$alkylidene-, $-(C_3-C_8)$carbocyclo-, $-O-(C_1-C_8)$alkyl-, -arylene-, $-(C_1-C_{10})$alkylidene-arylene-, -arylene-$(C_1-C_{10})$alkylidene-, $-(C_1-C_{10})$alkylidene-$(C_3-C_8)$carbocyclo, $-(C_3-C_8)$carbocyclo-$(C_1-C_{10})$alkylidene-, $-(C_3-C_8)$heterocyclo-, $(C_1-C_{10})$alkylidene-$(C_3-C_8)$heterocyclo-, $-(C_3-C_8)$heterocyclo-$(C_1-C_{10})$alkylidene-, $-(CH_2CH_2O)_r-$, and $-(CH_2CH_2O)_r-CH_2-$; and wherein r is any integer of 1, 2, 3, 4, 5, 6, 7, 8, 9 and 10;

preferably R8 is a) $-(CH_2-CH_2-O)_r-CH_2-$ with r being an integer from 1, 2, 3, 4, 5, 6, 7, 8, 9 and 10, preferably r is 2; or b) $-(C_1-C_{10})$alkylidene-, more preferably $-(CH_2)_n-$; wherein n is an integer from 1, 2, 3, 4, 5, 6, 7, 8, 9 and 10, preferably n is 1, 2, 3, 4, and 5.

EMBODIMENT 40

The conjugate of any one of embodiments 1 to 39, wherein the second adapter moiety AD2 mediates linkage to the second targeting moiety TM2 and to an adjacent moiety, wherein the adjacent moiety is selected from the group comprising linker moiety LM, building block moiety $[Z]_b$, branching moiety Y, building block moiety $[X]_a$, first adapter moiety AD1 and first targeting moiety TM1.

EMBODIMENT 41

The conjugate of embodiment 40, wherein the linkage is individually and independently selected from the group comprising an amide linkage, a sulfonamide linkage, a urea linkage, a thioether linkage, an ether linkage, a carbamate linkage, an amine linkage, a triazole linkage, an oxime linkage, a hydrazone linkage, a disulfide linkage, a pyrazine linkage and a dihydropyrazine linkage.

EMBODIMENT 42

The conjugate of any one of embodiments 40 to 31, wherein the second adapter moiety AD2, preferably prior to forming any linkage, is of the following structure:

RG3-R8-RG4 (10)

wherein RG3 is a reactive group as described herein, preferably a reactive group as indicated in Table 2 or selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine;

wherein RG4 is a reactive group as described herein, preferably a reactive group as indicated in Table 2 or selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine; and wherein R8 is selected from $-(C_1-C_{10})$alkylidene-, $-(C_3-C_8)$carbocyclo-, $-O-(C_1-C_8)$alkyl-, -arylene-, $-(C_1-C_{10})$alkylidene-arylene-, -arylene-$(C_1-C_{10})$alkylidene-, $-(C_1-C_{10})$alkylidene-$(C_3-C_8)$carbocyclo, $-(C_3-C_8)$carbocyclo-$(C_1-C_{10})$alkylidene-, $-(C_3-C_8)$heterocyclo-, $(C_1-C_{10})$alkylidene-$(C_3-C_8)$heterocyclo-, $-(C_3-C_8)$heterocyclo-$(C_1-C_{10})$alkylidene-, $-(CH_2CH_2O)_r-$, and $-(CH_2CH_2O)_r-CH_2-$; and wherein r is any integer of 1, 2, 3, 4, 5, 6, 7, 8, 9 and 10;

preferably R8 is a) $-(CH_2-CH_2-O)_r-CH_2-$ with r being an integer from 1, 2, 3, 4, 5, 6, 7, 8, 9 and 10, preferably r is 2; or b) $-(C_1-C_{10})$alkylidene-, more preferably $-(CH_2)_n-$; wherein n is an integer from 1, 2, 3, 4, 5, 6, 7, 8, 9 and 10, preferably n is 1, 2, 3, 4, and 5.

EMBODIMENT 43

The conjugate of any one of embodiments 2 to 42, wherein the Effector moiety EM is linked, preferably covalently linked to the branching moiety Y.

EMBODIMENT 44

The conjugate of any one of embodiments 2 to 42, wherein the Effector moiety EM is linked, preferably covalently linked to the second targeting moiety TM2.

EMBODIMENT 45

The conjugate of embodiment 44, wherein the second targeting moiety TM2 is different from a compound of formula (2) and/or different from a compound of formula (7)

(7)

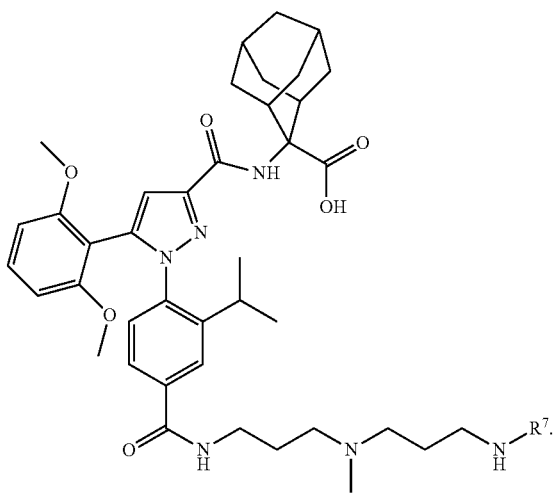

EMBODIMENT 46

The conjugate of any one of embodiments 1 to 45, wherein the conjugate comprises a third adapter moiety AD3.

EMBODIMENT 47

The conjugate of embodiment 46, wherein the adapter moiety AD3 mediates the linkage between branching moiety [Y] and the effector moiety EM.

EMBODIMENT 48

The conjugate of embodiment 47, wherein the adapter moiety AD3 mediated the linkage between the second targeting moiety TM2 and the effector moiety EM.

EMBODIMENT 49

The conjugate of embodiment 48, wherein the second targeting moiety TM2 is different from a compound of formula (2) and/or different from a compound of formula (7)

(7)

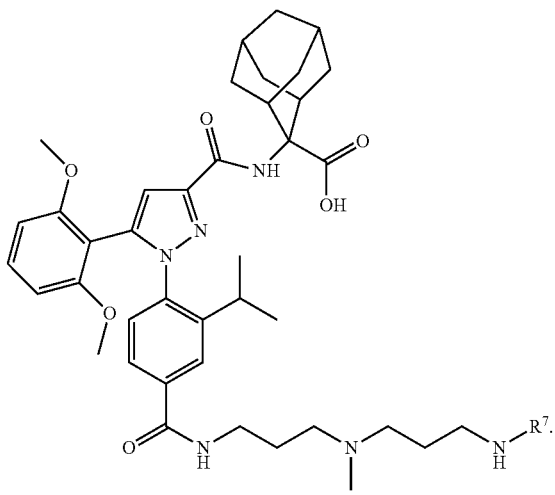

EMBODIMENT 50

The conjugate of any one of embodiments 47 to 49, wherein the linkage is selected from the group comprising an amide linkage, a sulfonamide linkage, a urea linkage, a thiourea linkage, a thioether linkage, an ether linkage, a carbamate linkage, an amine linkage, a triazole linkage, an oxime linkage, a hydrazone, a disulfide linkage, a pyrazine linkage and a dihydro-pyrazine linkage.

EMBODIMENT 51

The conjugate of any one of embodiments 46 to 50, wherein the third adapter moiety AD3 is a structure of formula $$-Lin^4-R^9-Lin^5- \quad (11);$$

wherein
$R^9$ is selected from selected from —$(C_1-C_{10})$alkylidene-, —$(C_3-C_8)$carbocyclo-, -arylene-, —$(C_1-C_{10})$alkylidene-arylene-, -arylene-$(C_1-C_{10})$alkylidene-, —$(C_1-C_{10})$alkylidene-arylene-$(C_1-C_{10})$alkylidene-, —$(C_1-C_{10})$alkylidene-$(C_3-C_8)$carbocyclo-, —$(C_3-C_8)$carbocyclo-$(C_1-C_{10})$alkylidene-, —$(C_1-C_{10})$alkylidene-$(C_3-C_8)$carbocyclo-$(C_1-C_{10})$alkylidene-, —$(C_3-C_8)$heterocyclo-, $(C_1-C_{10})$alkylidene-$(C_3-C_8)$heterocyclo-, —$(C_3-C_8)$heterocyclo-$(C_1-C_{10})$alkylidene-, —$(C_1-C_{10})$alkylidene-$(C_3-C_8)$heterocyclo-$(C_1-C_{10})$alkylidene-, —$(CH_2CH_2O)_r$—, and —$(CH_2)_s$—$(CH_2CH_2O)_r$—$(CH_2)_t$—;
and wherein
r is any integer from 1, 2, 3, 4, 5, 6, 7, 8, 9 and 10;
s is any integer from 0, 1, 2, 3 and 4; and
t is any integer from 0, 1, 2, 3 and 4;
$Lin^4$ is selected from the group comprising —CO—, —$NR^{10}$—, —CO—$NR^{10}$—, —CS—$NR^{10}$—, —$CH_2$— and a bond, preferably a covalent bond, more preferably a single bond;
wherein $R^{10}$ is selected from the group consisting of hydrogen and $(C_1-C_4)$alkyl, and;
$Lin^5$ is selected from the group comprising —CO—, —S—, —$NR^{10}$—, —CO—$NR^{10}$—, —CS—$NR^{10}$—, —O—, —$CH_2$—, —$SO_2$—, -succinimide-, —$CH_2$—CO—$NR^{10}$—, —C=C— (in case of, for example triazole), =N—O—, =N—N—, =N—N—CO—, —N=N—N— (in case of, for example triazole), —HC= and —$R^3$C= (of oxime and hydrazone);
wherein $R^{10}$ is selected from the group consisting of hydrogen and $(C_1-C_4)$alkyl.

EMBODIMENT 52

The conjugate of any one of embodiments 1 to 51, wherein both the first adaptor moiety AD1 and the second adaptor moiety AD2 are present.

EMBODIMENT 53

The conjugate of any one of embodiments 1 to 52, wherein the linker moiety LM is present.

EMBODIMENT 54

The conjugate of any one of embodiments 1 to 53, wherein the linker moiety LM is present, wherein the linker moiety LM is a peptide and wherein the peptide is inserted into formula (1) either in N→C direction or in C→N direction.

EMBODIMENT 55

The conjugate of any one of embodiments 1 to 54, wherein the conjugate further comprises a third adaptor moiety [AD3], wherein the third adaptor moiety is mediating the linkage of the Effector moiety to the conjugate.

EMBODIMENT 56

The conjugate of any one of embodiments 2 to 55, wherein the Effector moiety is selected from the group comprising an Effector, Acceptor and -[Acceptor-Effector], wherein
Acceptor is a moiety which mediates linking of an Effector to the third adapter moiety AD3, if present, or Acceptor is a moiety which mediates linking of an Effector to the branching moiety [Y], and
Effector is selected from the group comprising a diagnostically active agent and a therapeutically active agent.

EMBODIMENT 57

The conjugate of embodiment 56, wherein the Acceptor is a chelator, preferably the chelator is selected from the group comprising DOTA, NOTA, DTPA, TETA, EDTA, NODAGA, NODASA, TRITA, CDTA, BAT, DFO, or HYNIC, more preferably the chelator is DOTA.

EMBODIMENT 58

The conjugate of any one of embodiments 56 to 57, wherein the Acceptor comprises an aromatic moiety, wherein the aromatic moiety is selected from the group comprising indole and benzene, preferably benzene is substituted with at least one heteroatom, wherein the heteroatom is selected from the group comprising an O, an N and S.

EMBODIMENT 59

The conjugate of any one of embodiments 2 to 58, preferably embodiment 57, wherein the Effector is a diagnostically active nuclide, preferably a diagnostically active radionuclide, or a therapeutically active nuclide, preferably a therapeutically active radionuclide.

EMBODIMENT 60

The conjugate of any one of embodiments 1 to 59, wherein one of the first targeting moiety TM1 and the second targeting moiety TM2 is selected from the group comprising an antibody, an antigen-binding antibody fragment, a camelid heavy chain IgG (hcIgG), a cartilaginous fish IgNAR antibody, a protein scaffold, a target-binding peptide, a peptide nucleic acid (PNA), a target-binding polypeptide or protein, a target binding nucleic acid molecule, a carbohydrate, a lipid and a target-binding small molecule.

EMBODIMENT 61

The conjugate of any one of embodiments 1 to 60, wherein the conjugate is selected from the group comprising a conjugate of formulae (12), (12a), (13), (13a), (14), (14a), (15), (15a), (16), (16a), (17), (17a), (18), (18a), (19), (19a), (20), (20a), (21), (21a), (22), (22a), (23), (23a), (24), (24a), (25), (25a), (26), (26a), (27), (27a), (28), (29) and (30):

(12)

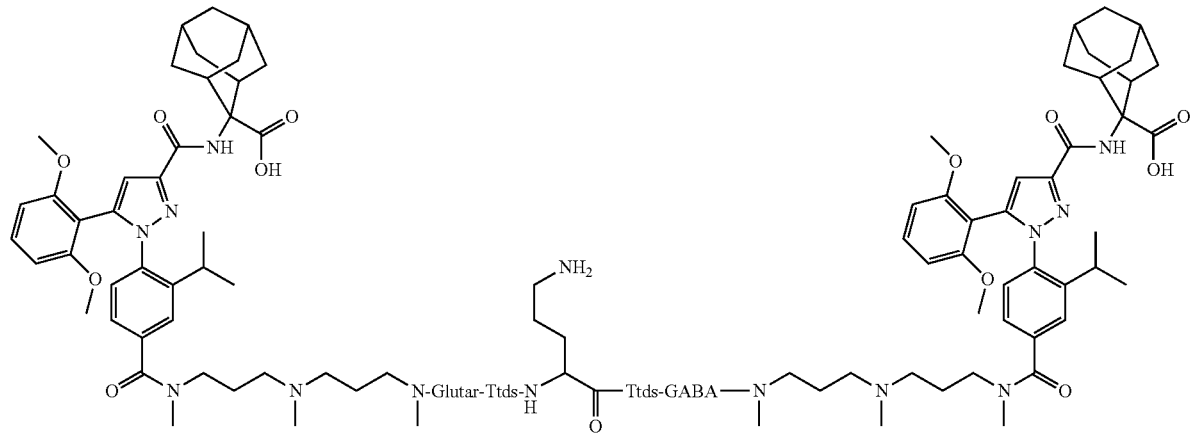
(12a)
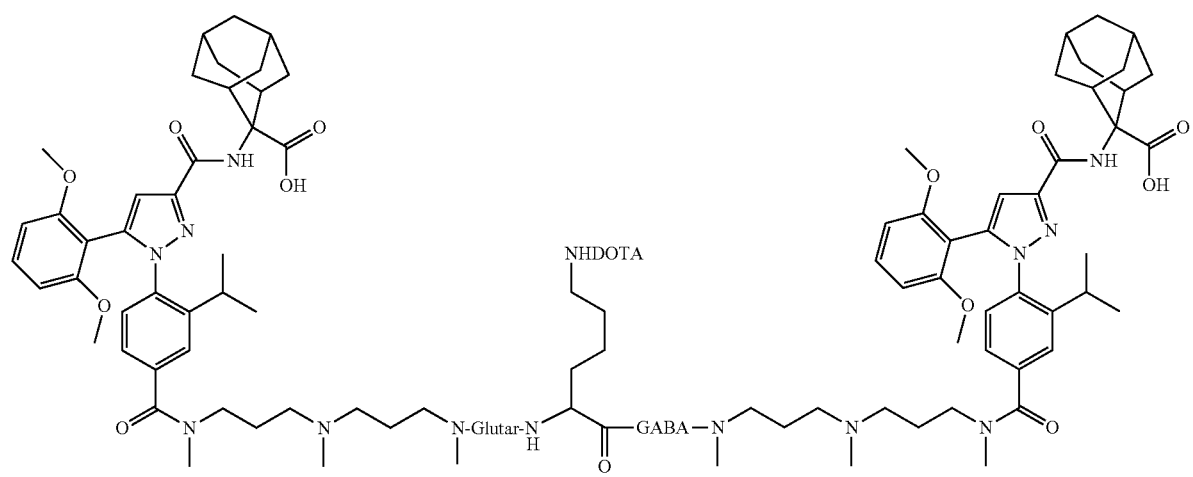
(13)
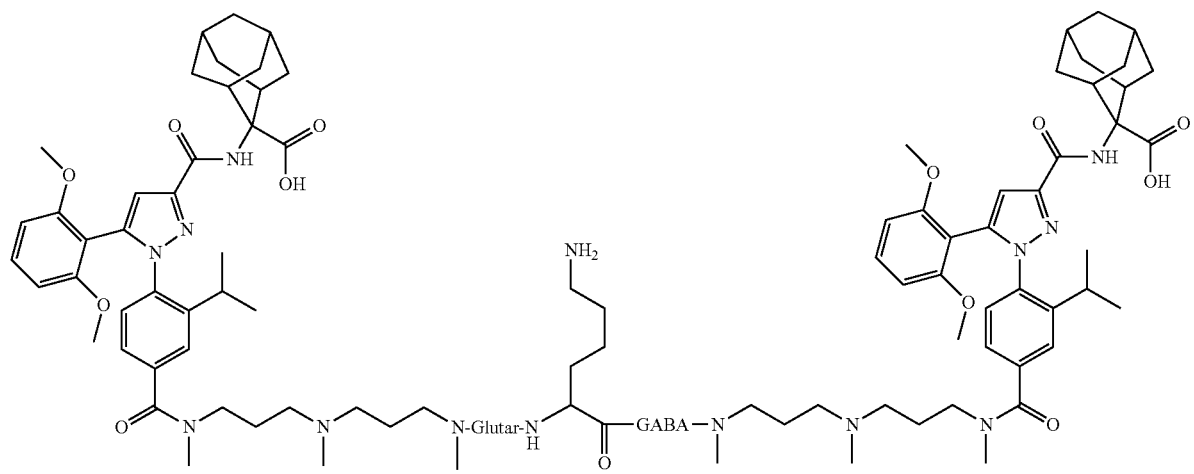
(13a)

-continued
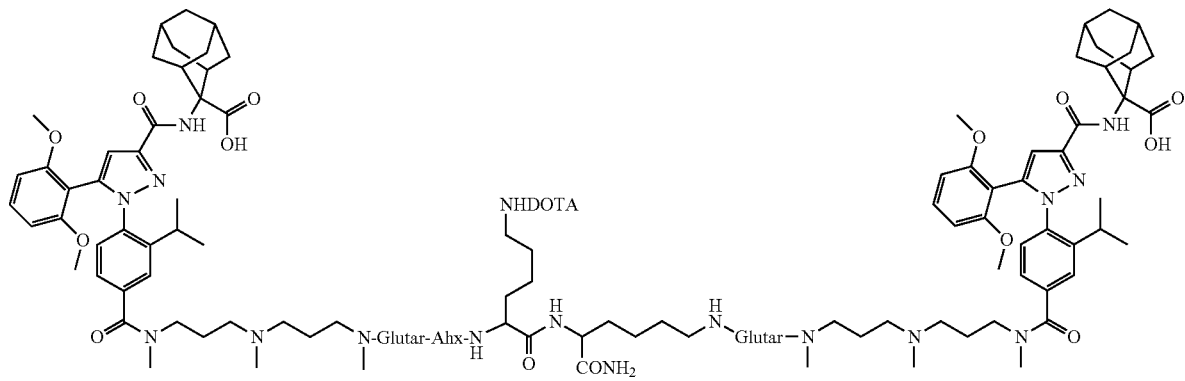
(14)
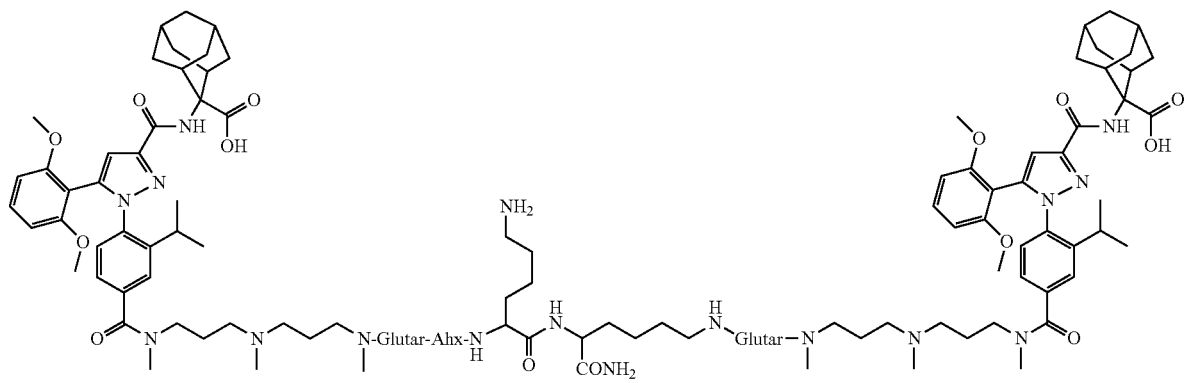
(14a)
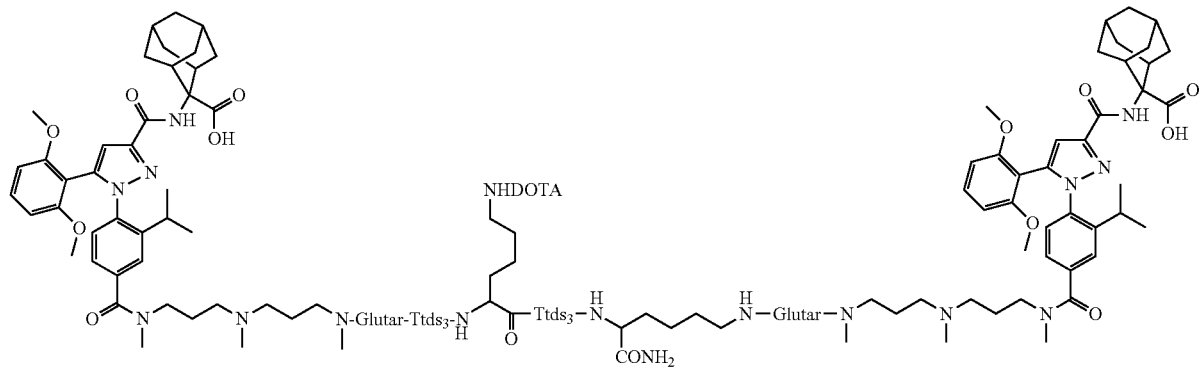
(15)
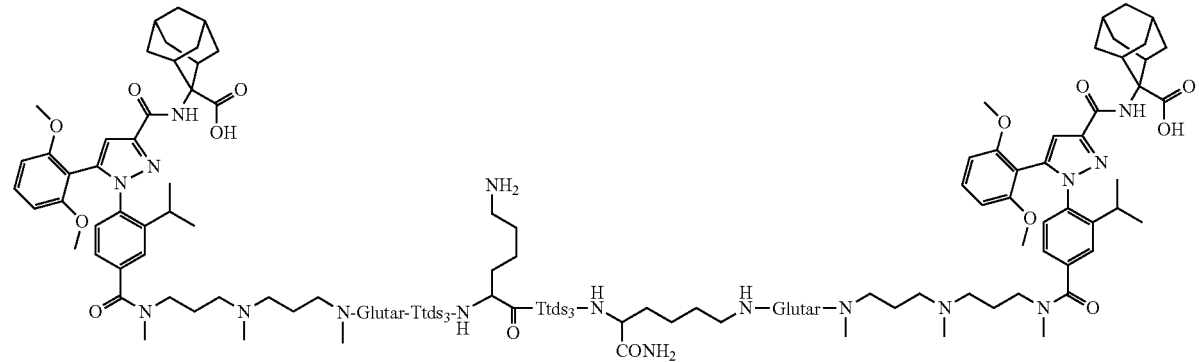
(15a)

-continued
(16)
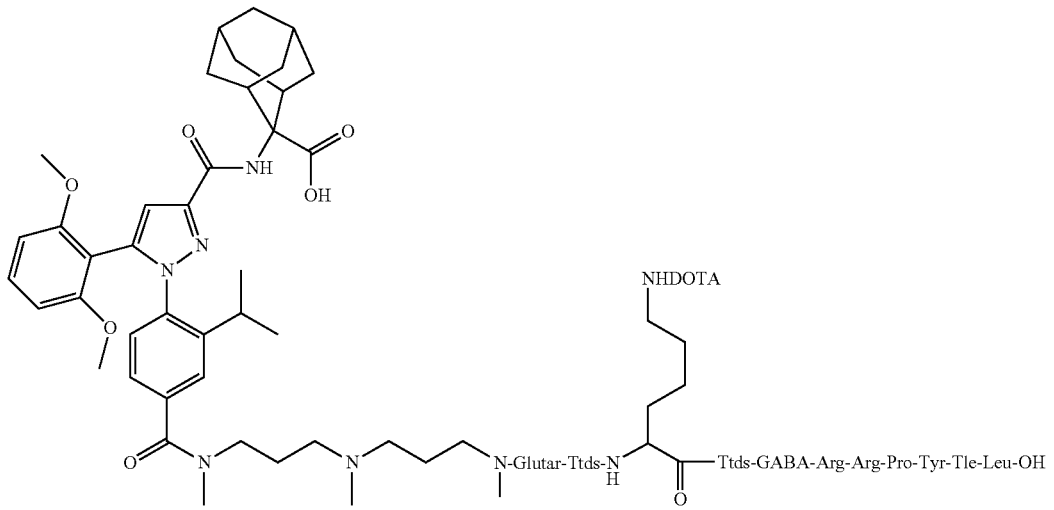
(16a)
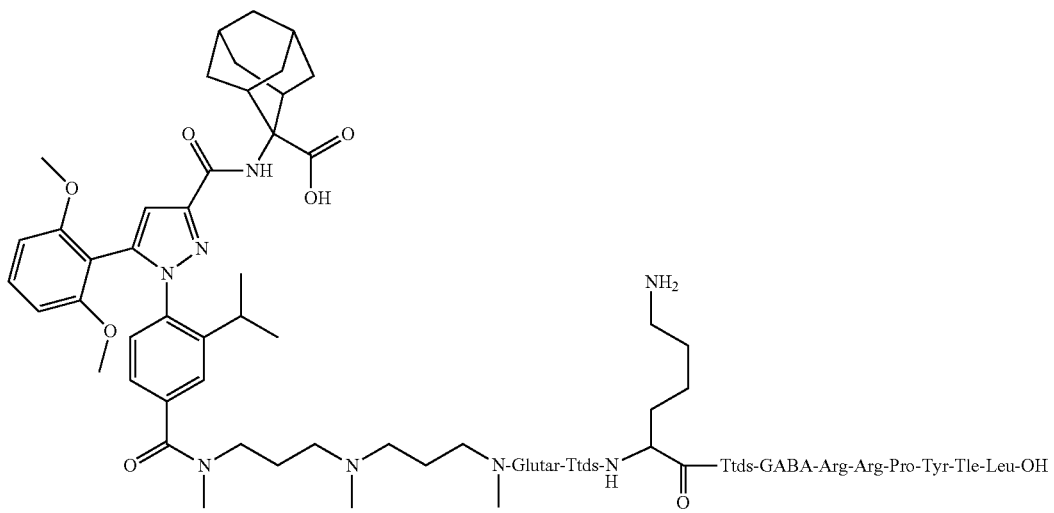
(17)
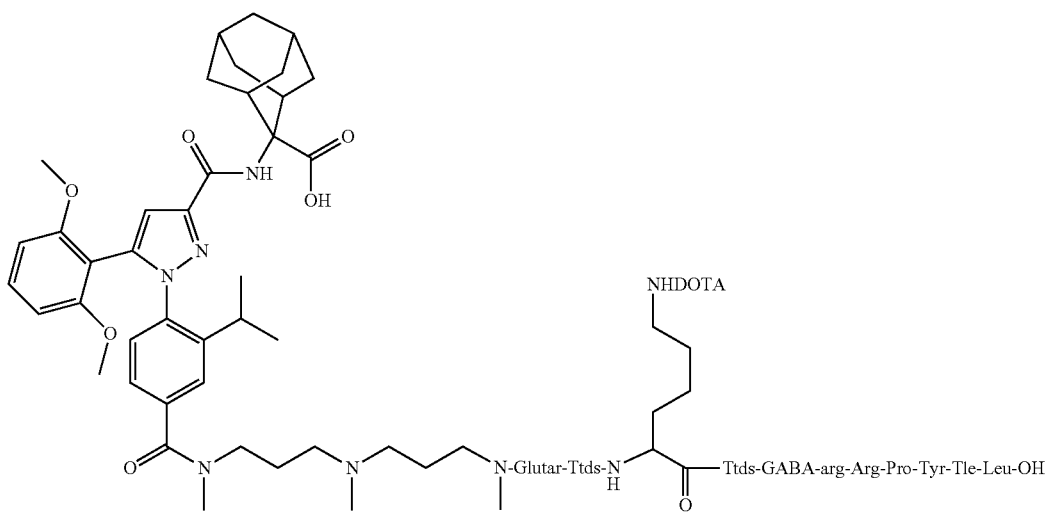

(17a)
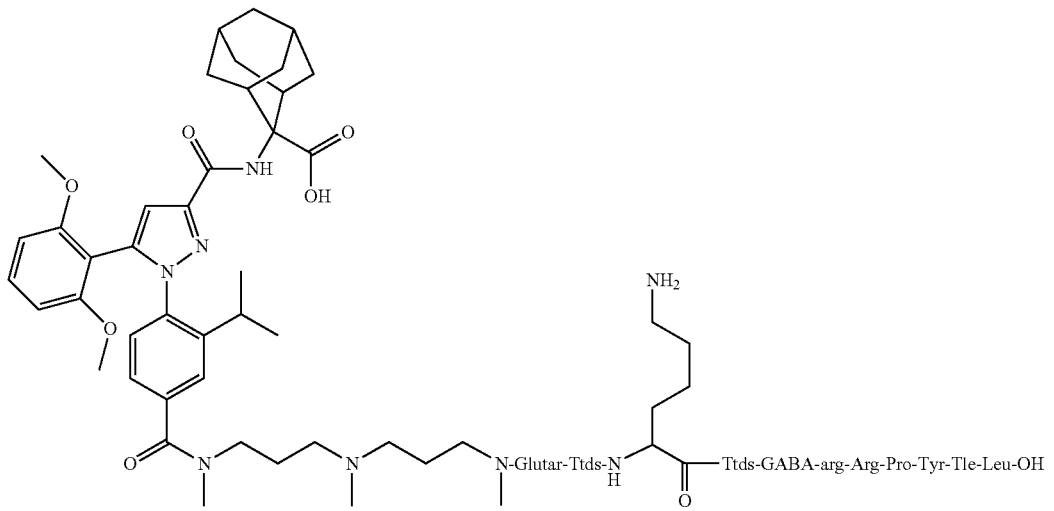
(18)
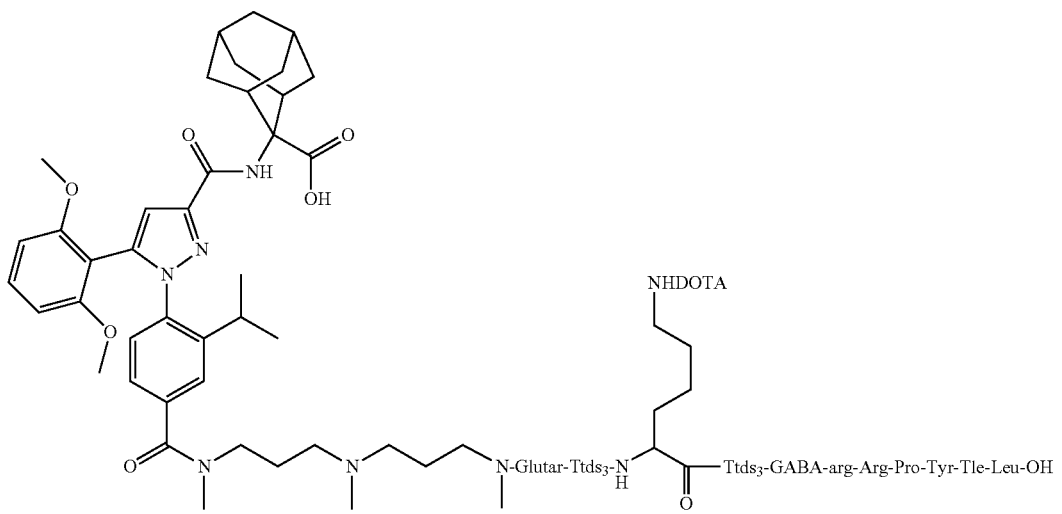
(18a)
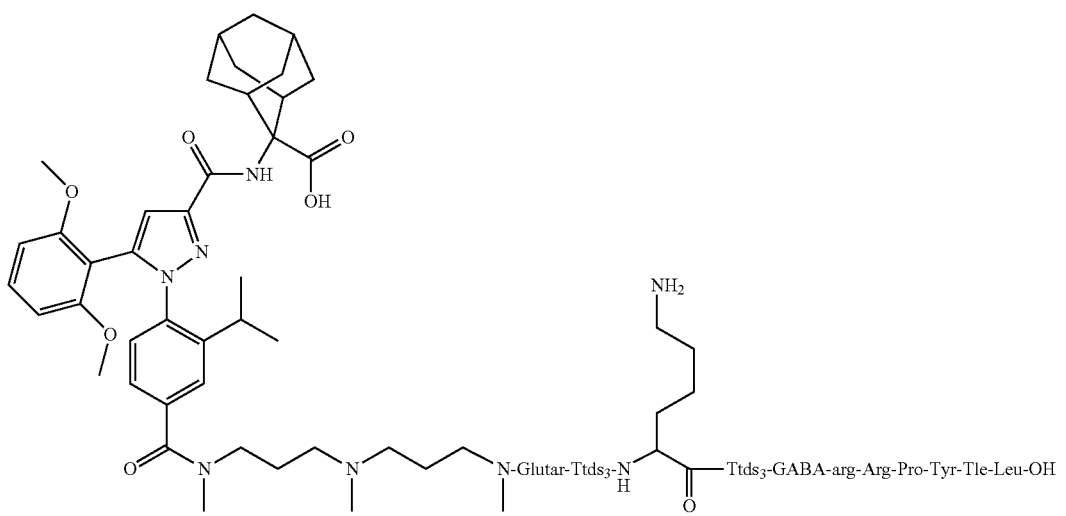

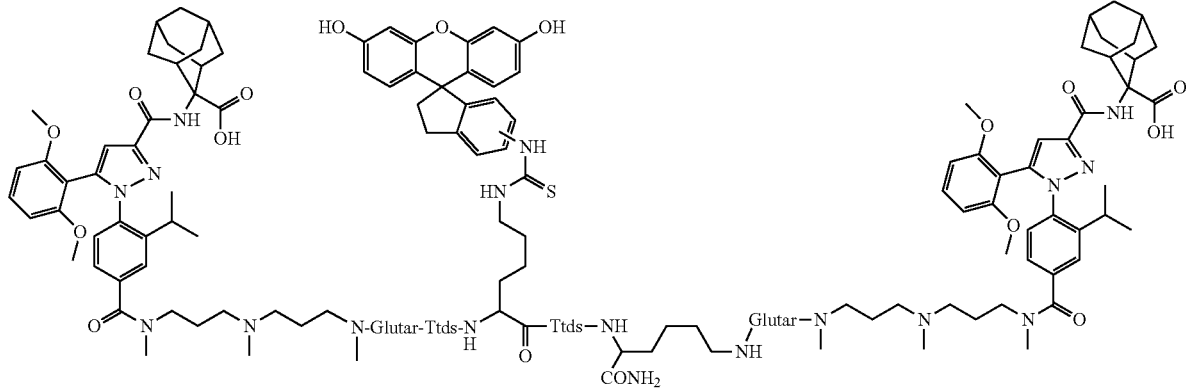
(19)
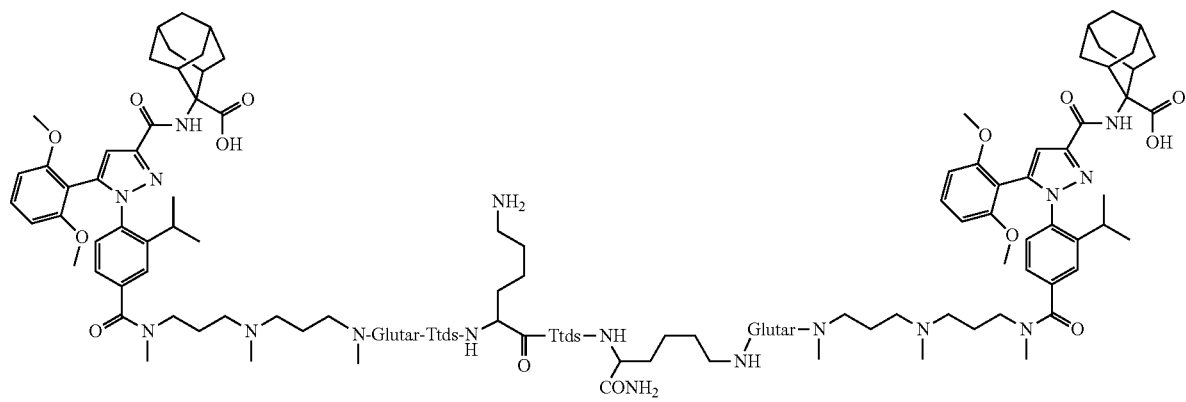
(19a)
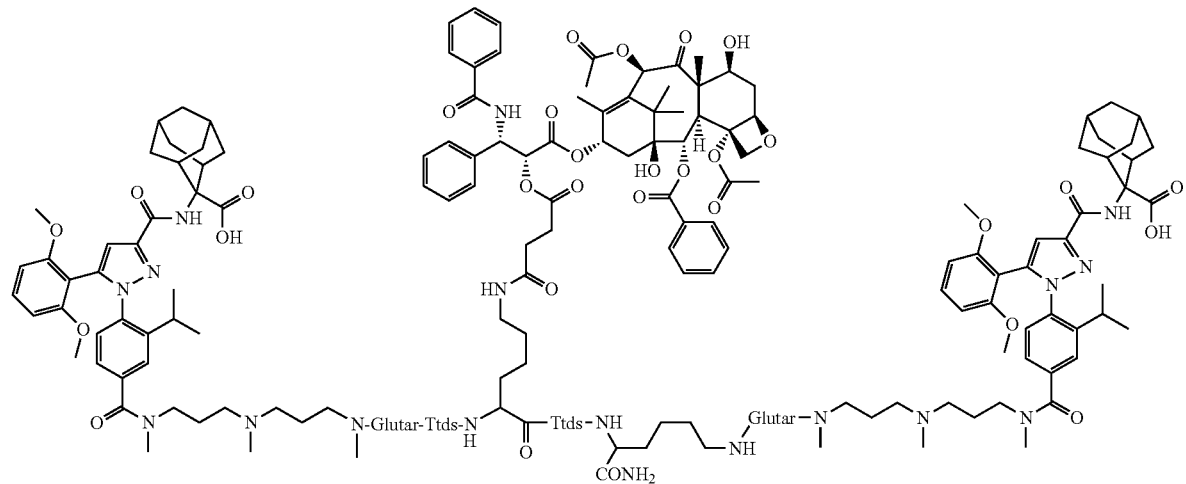
(20)

(20a)
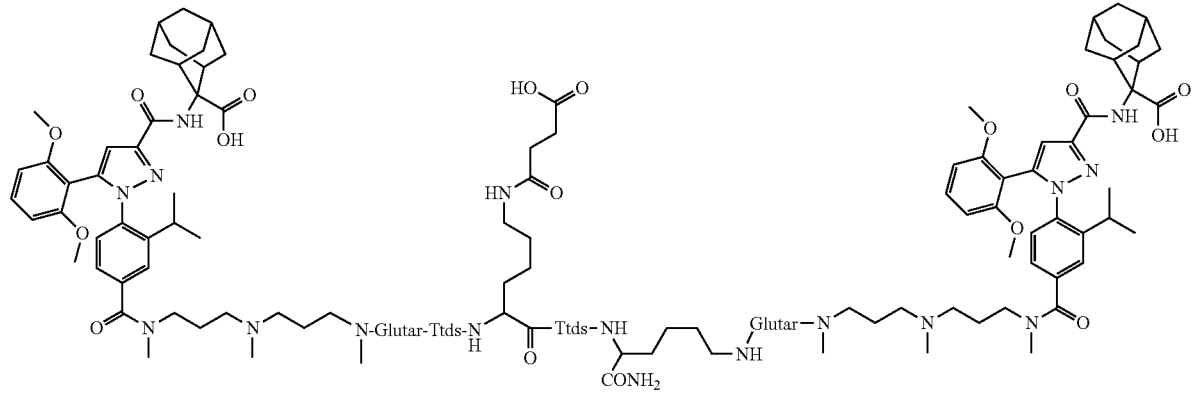
(21)
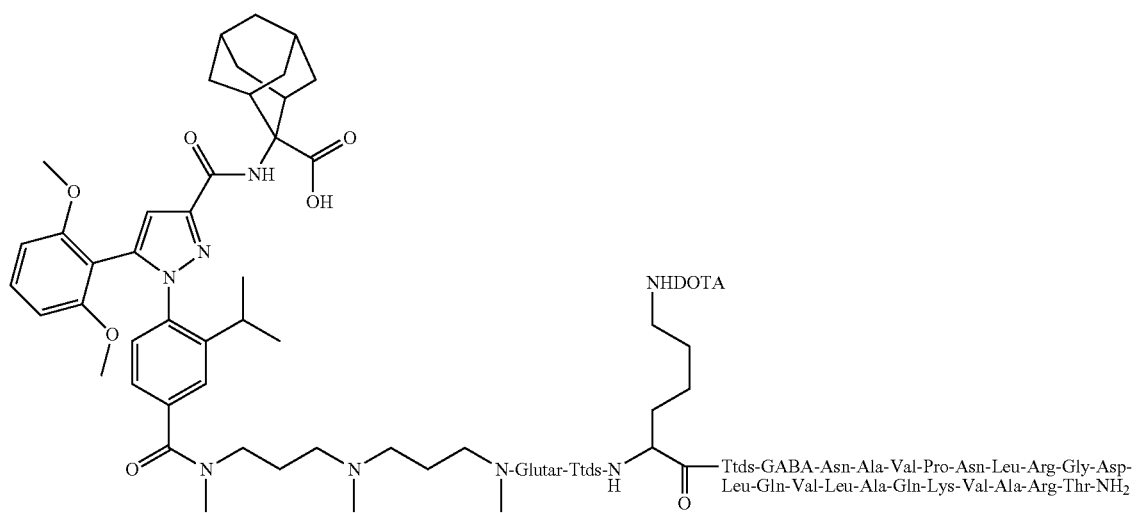
(21a)
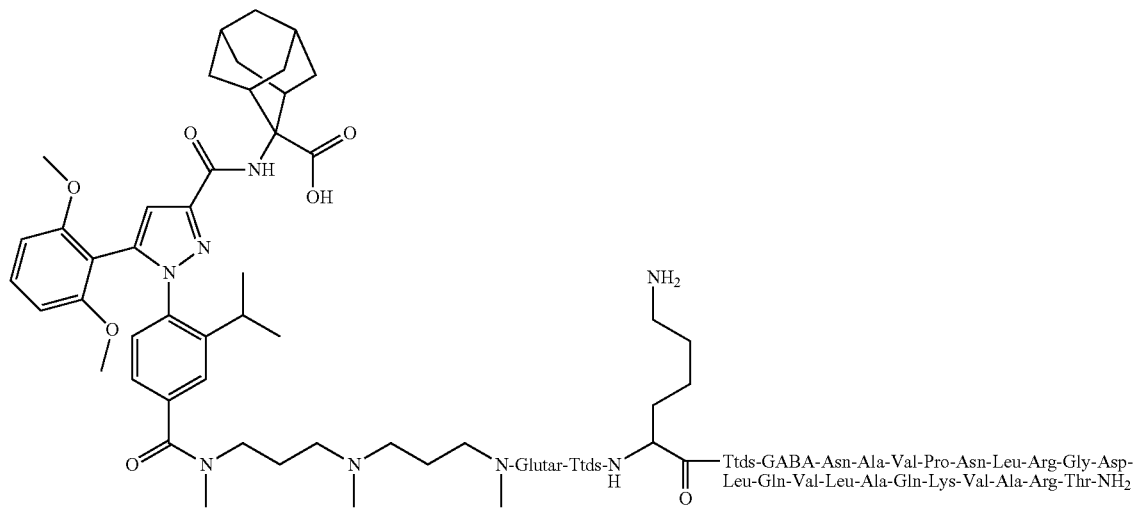

(22)
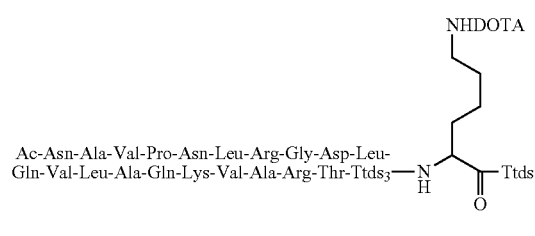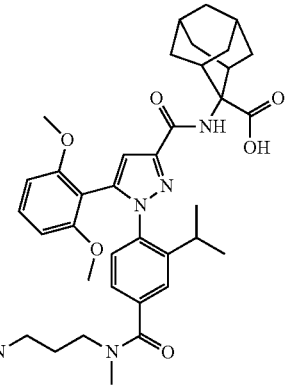
(22a)
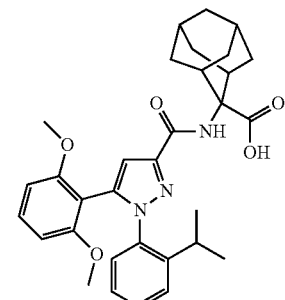
(23)
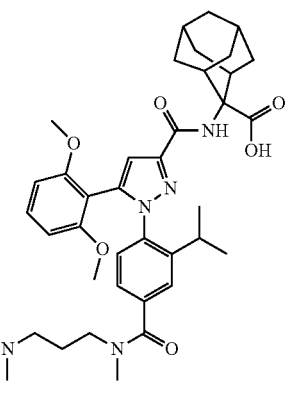

(23a)
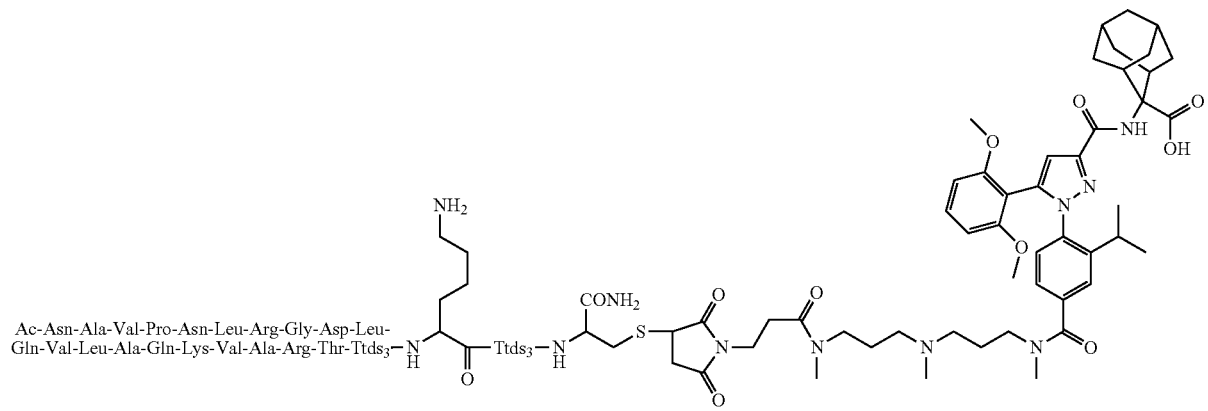
(24)
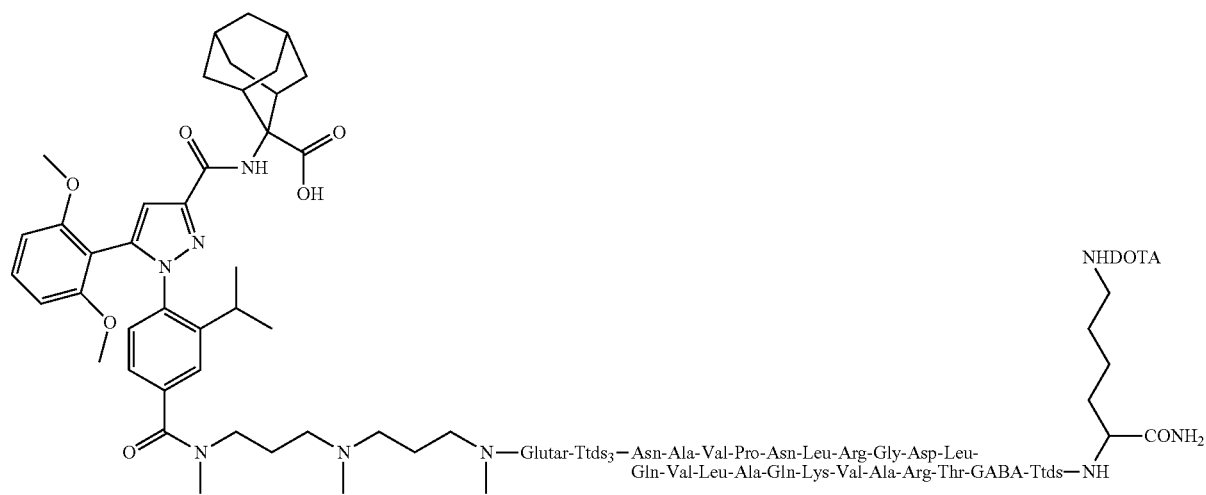
(24a)
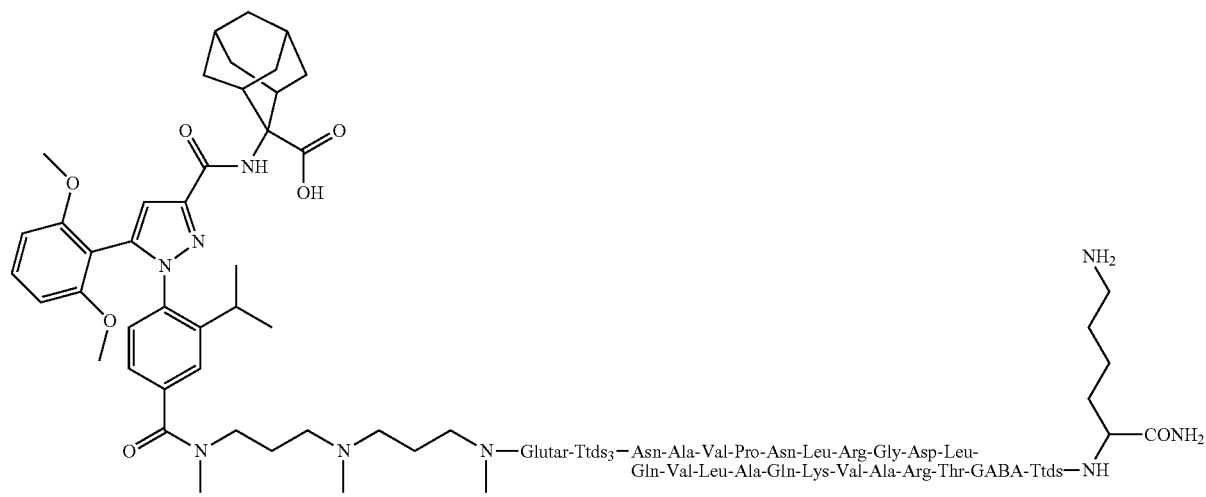

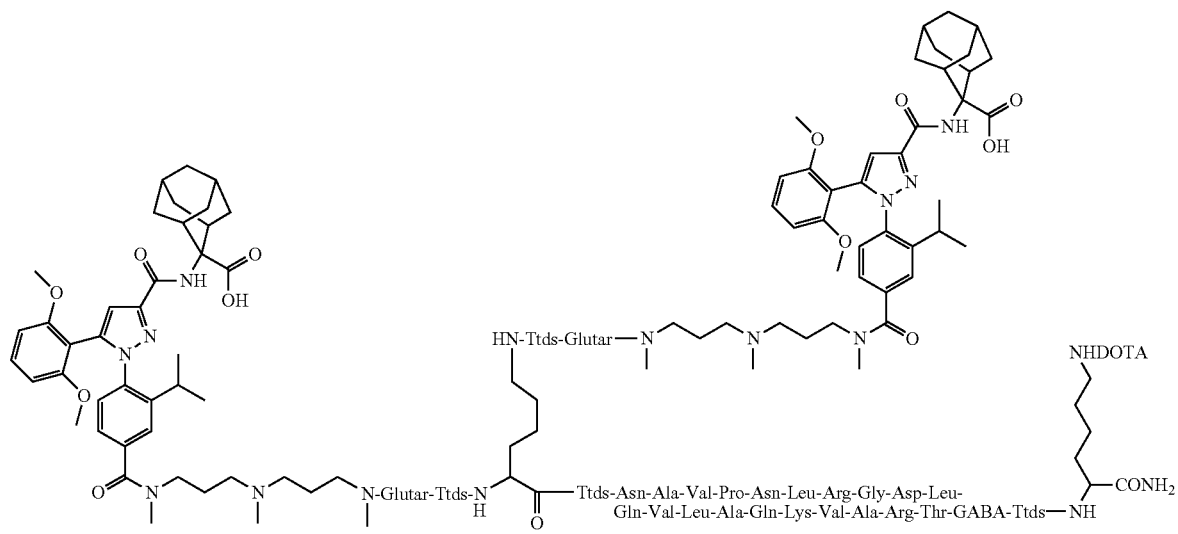
(25)
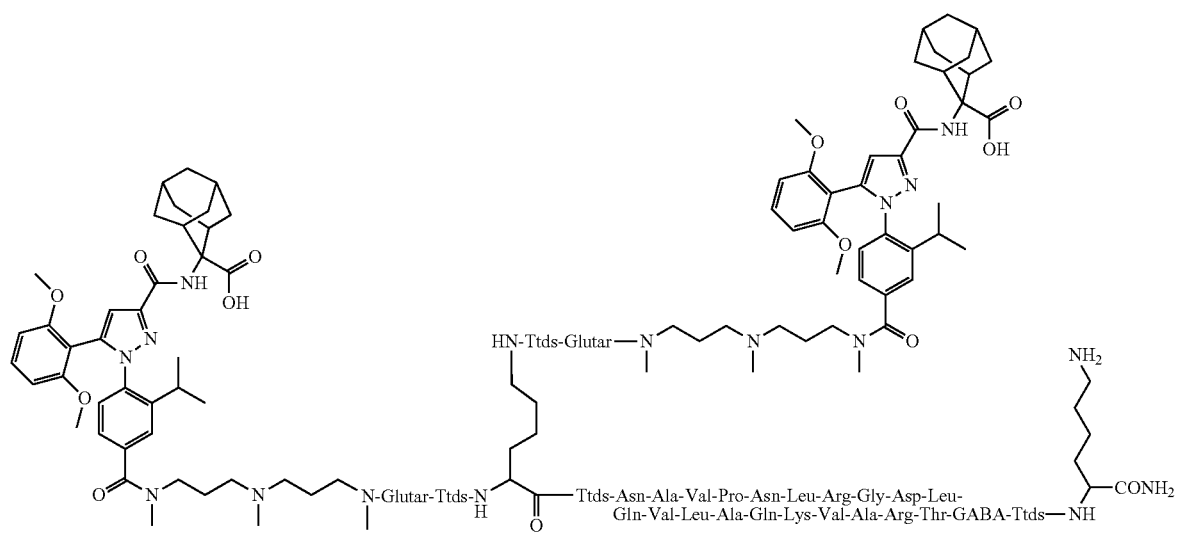
(25a)
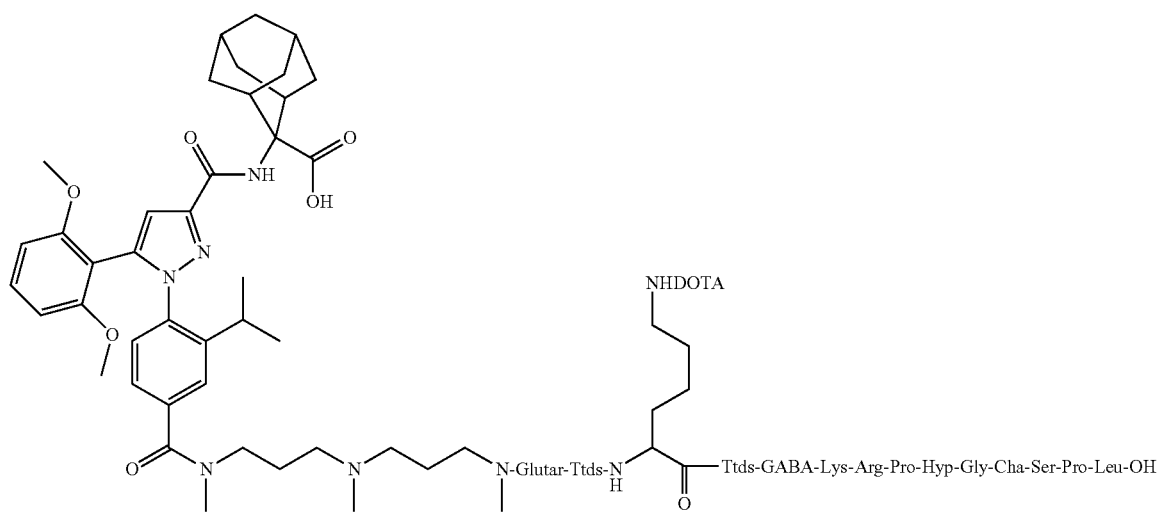
(26)

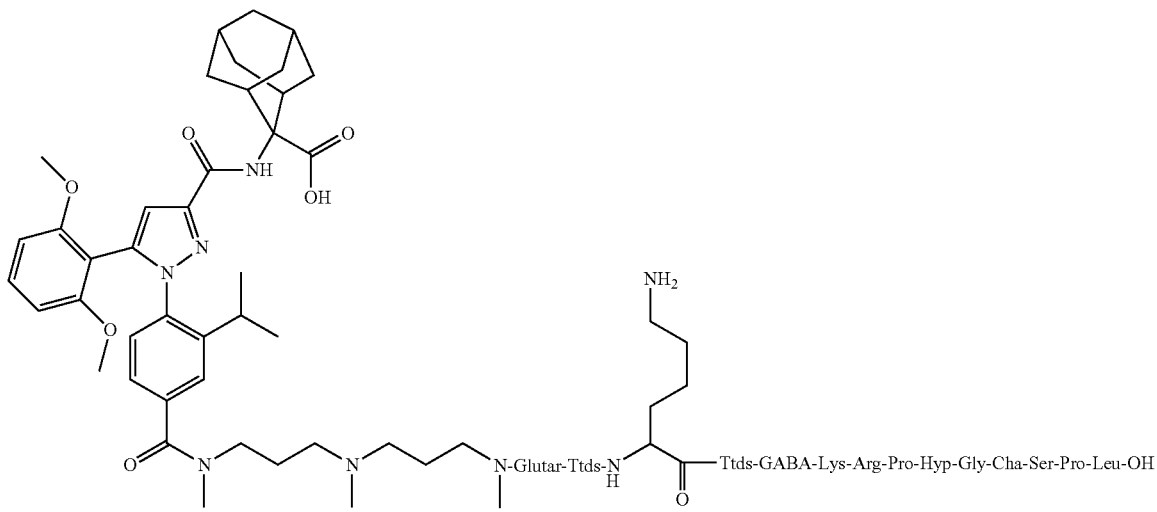
(26a)
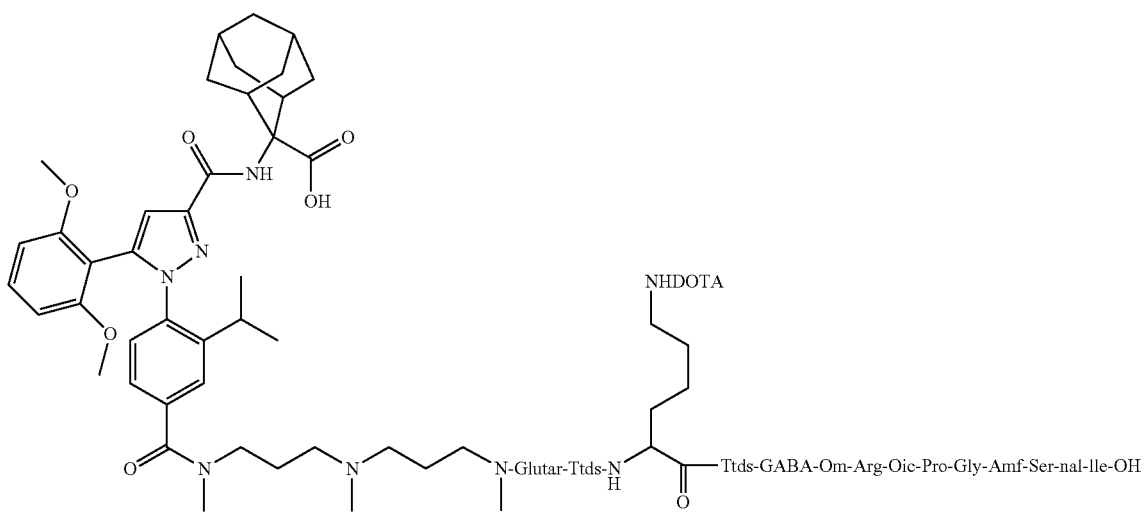
(27)
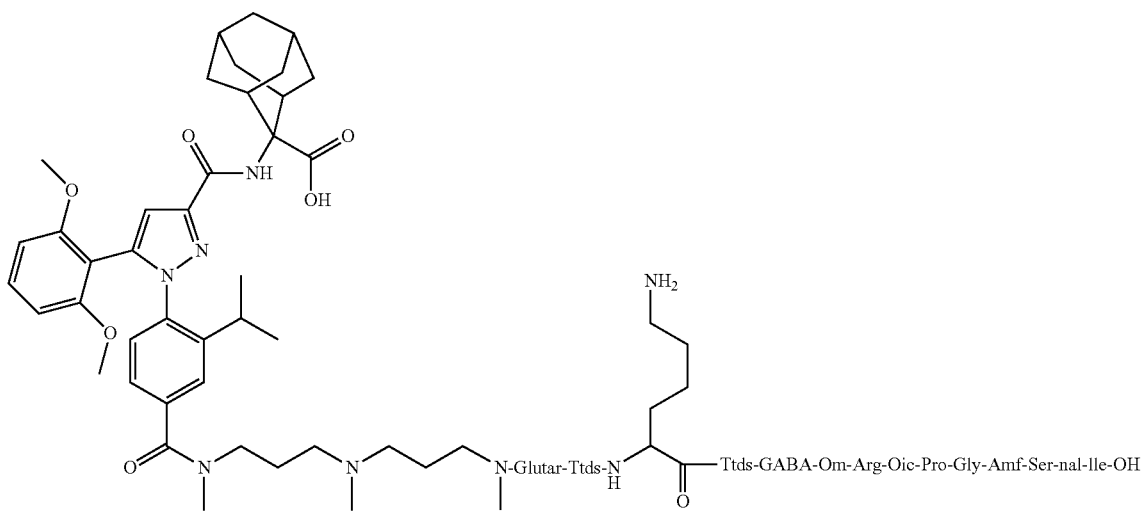
(27a)

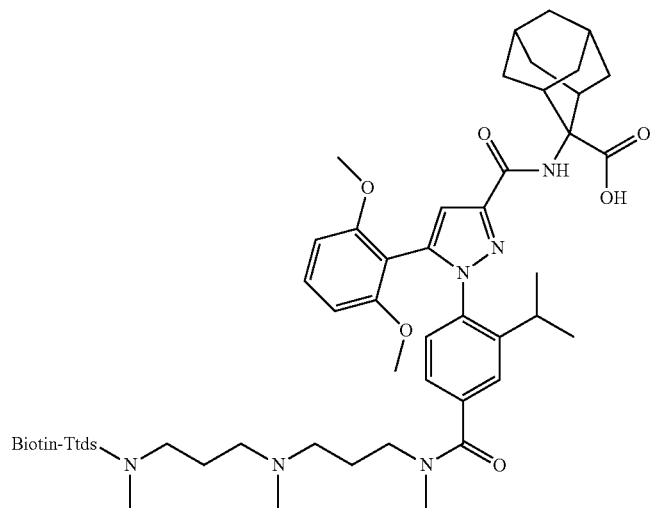
(28)
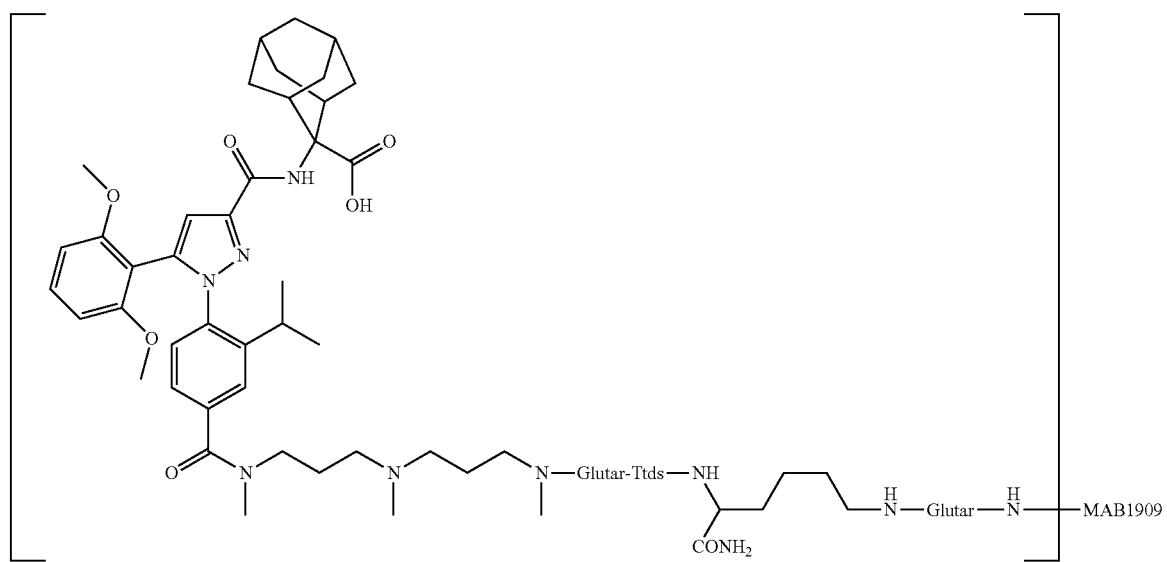
(29)

-continued

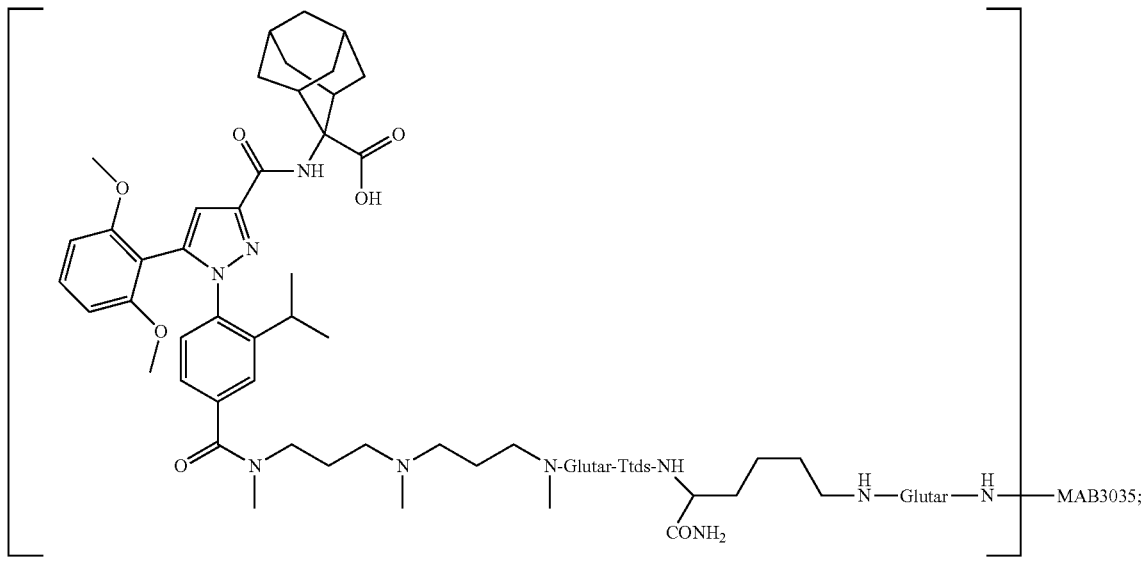

(30)

preferably the conjugate is a conjugate of formulae (12), (13), (14), (15), (16), (17), (18), (21), (22), (23), (24), (25), (26), and (27) and the diagnostically active radionuclide and the therapeutically active radionuclide is chelated by the chelator of formulae (12), (13), (14), (15), (16), (17), (18), (21), (22), (23), (24), (25), (26), and (27); more preferably the diagnostically active radionuclide and the therapeutically active radionuclide is selected from the group comprising $^{111}$In, $^{177}$Lu, $^{67}$Ga, $^{68}$Ga, $^{64}$Cu and $^{90}$Y.

EMBODIMENT 62

The conjugate of any one of embodiments 2 to 61, wherein the Effector is selected from the group comprising a small molecule, an antibody, an antigen-binding fragment of an antibody, an anticalin, an aptamer, a spiegelmer, an anti-proliferative agent, an antimigration agent, an antiangiogenic agent, a cytostatic agent, a cytotoxic agent, an antithrombotic agent, an anti-inflammatory agent, an antiphlogistic agent, an anticoagulative agent, an antibacterial agent, an antiviral agent, an antimycotic agent, an endogenous fluorophore, a polycyclic aromatic, a coumarin, a quinoline, an indole, an imidazole, an UV-excited fluorophore, a fluorescein, a rhodamine, a naphthoxanthene dye, a phenanthridine, a BODIPY dye, a cyanine, a phthalocyanine, a xanthene, an acridine, an oxazine, a polyene, an oxonol, a benzimidazole, an azamethine, a styryl, a thiazole, an anthraquinone, a naphthalimide, an aza[18]annulene, a porphin, a metal-ligand-complexe, a squaraine, an 8-hydroxyquinoline-derivative, a polymethin, a nanocrystal, a fluorescent protein, a protein, a perylene, a phthalocyanine, an upconversion dye, a diketopyrrolopyrrole, a molecule of the porphyrin family, including but not limited to a hematoporphyrin derivative and a molecule based on a hematoporphyrin derivative, a benzoporphyrin derivative, a 5-aminolevulinic acid, and texaphyrin; a molecule of the chlorophyll family, including but not limited to a chlorin, a purpurin, and a bacteriochlorin; a dye, including but not limited to phtalocyanine and naphthalocyanine, a small mononuclear or polynuclear paramagnetic chelate, a metalloporphyrin, a polymeric or macromolecular carrier, preferably covalently or noncovalently labeled with a paramagnetic chelate), a particulate CA including a fluorinated or a nonfluorinated paramagnetic micelle or liposome and a paramagnetic or a superparamagnetic particle e.g. an iron oxide, a Gd3+-labeled zeolite, a diamagnetic CEST polymer; a diamagnetic hyperpolarization probe including but not limited to gases and aerosols, a $^{13}$C-labeled compound or ion, an ultrasound contrast enhancing agent comprising a shell an a core, whereby the shell preferably consista of a material selected from the group comprising a phospholipid, a poly-[D,L-lactide-co-glycolide] acid (PLGA), serum albumin, a polymer, a perflutren, a carbon-based phase shift colloid, a perflexane, a lipid/galactose, a sulphur hexafluoride, a perfluorocyl bromide, a surfactant, anoligopeptide, and galactose and the core preferably consists of a material selected from the group comprising air, a perfluorocarbon, a decafluorobutane, an octafluoropropane, a dodecafluoropentane and a perfluorobutane, a carbon nanotube, preferably a single-walled carbon nanotube or a multi-walled carbon nanotube, a fullerene, a dendrimer, a quantum dot, a liposome, a silica nanoparticle, a magnetic nanoparticle, a lipid nanoparticle including but not limited to a nanoemulsion, a polymeric nanoparticle, a albumin-based nanoparticle and a nanocrystal and a nucleic acid, a small molecule, an amino acid, a peptide, a protein, a carbohydrate, a lipid, glycoprotein, a glycan or lipoproteins preferably having antiproliferative, antimigration, antiangiogenic, cytostatic and/or cytotoxic properties.

EMBODIMENT 63

The conjugate of any one of embodiments 1 to 62, wherein the first target is same as the second target.

EMBODIMENT 64

The conjugate of any one of embodiments 1 to 63, wherein the first targeting moiety and the second targeting moiety are targeting the same target.

EMBODIMENT 65

The conjugate of any one of embodiments 1 to 64, wherein the first targeting moiety and the second targeting moiety are targeting the same target molecule.

EMBODIMENT 66

The conjugate of any one of embodiments 1 to 62, wherein the second targeting moiety TM2 is targeting a target different from the target targeted by the first targeting moiety.

EMBODIMENT 67

The conjugate of embodiment 66, wherein the second targeting moiety is targeting a target different from neurotensin receptor 1, preferably the first targeting moiety TM1 is targeting NTR, preferably NTR1, and wherein.

EMBODIMENT 68

The conjugate of any one of embodiments 1 to 67, wherein the target targeted by the second targeting moiety is a target expressed by tumor cells.

EMBODIMENT 69

The conjugate of embodiment 68, wherein the tumor is selected from group A, wherein group A comprises Neoplasms; Neoplasm, benign; Neoplasm, uncertain whether benign or malignant; Neoplasm, malignant; Neoplasm, metastatic; Neoplasm, malignant, uncertain whether primary or metastatic; Tumor cells, benign; Tumor cells, uncertain whether benign or malignant; Tumor cells, malignant; Malignant tumor, small cell type; Malignant tumor, giant cell type; Malignant tumor, fusiform cell type; Epithelial neoplasms; Epithelial tumor, benign; Carcinoma in situ; Carcinoma; Carcinoma, metastatic; Carcinomatosis; Epithelioma, benign; Epithelioma, malignant; Large cell carcinoma; Carcinoma, undifferentiated type; Carcinoma, anaplastic type; Pleomorphic carcinoma; Giant cell and spindle cell carcinoma; Giant cell carcinoma; Spindle cell carcinoma; Pseudosarcomatous carcinoma; Polygonal cell carcinoma; Spheroidal cell carcinoma; Tumorlet; Small cell carcinoma; Oat cell carcinoma; Small cell carcinoma, fusiform cell type; Papillary and squamous cell neoplasms; Papilloma (except Papilloma of urinary bladder M81201); Papillary carcinoma in situ; Papillary carcinoma; Verrucous papilloma; Verrucous carcinoma; Squamous cell papilloma; Papillary squamous cell carcinoma; Inverted papilloma; Papillomatosis; Squamous cell carcinoma in situ; Squamous cell carcinoma; Squamous cell carcinoma, metastatic; Squamous cell carcinoma, keratinizing type; Squamous cell carcinoma, large cell, nonkeratinizing type; Squamous cell carcinoma, small cell, nonkeratinizing type; Squamous cell carcinoma, spindle cell type; Adenoid squamous cell carcinoma; Squamous cell carcinoma in situ with questionable stromal invasion; Squamous cell carcinoma, microinvasive; Queyrat's erythroplasia; Bowen's disease; Lymphoepithelial carcinoma; Basal cell neoplasms; Basal cell tumor; Basal cell carcinoma; Multicentric basal cell carcinoma; Basal cell carcinoma, morphea type; Basal cell carcinoma, fibroepithelial type; Basosquamous carcinoma; Metatypical carcinoma; Intraepidermal epithelioma of Jadassohn; Trichoepithelioma; Trichofolliculoma; Tricholemmoma; Pilomatrixoma; Transitional cell papillomas and carcinomas; Transitional cell papilloma; Urothelial papilloma; Transitional cell carcinoma in situ; Transitional cell carcinoma; Schneiderian papilloma; Transitional cell papilloma, inverted type; Schneiderian carcinoma; Transitional cell carcinoma, spindle cell type; Basaloid carcinoma; Cloacogenic carcinoma; Papillary transitional cell carcinoma; Adenomas and adenocarcinomas; Adenoma; Bronchial adenoma; Adenocarcinoma in situ; Adenocarcinoma; Adenocarcinoma, metastatic; Scirrhous adenocarcinoma; Linitis plastic; Superficial spreading adenocarcinoma; Adenocarcinoma, intestinal type; Carcinoma, diffuse type; Monomorphic adenoma; Basal cell adenoma; Islet cell adenoma; Islet cell carcinoma; Insulinoma; Insulinoma, malignant; Glucagonoma; Glucagonoma, malignant; Gastrinoma; Gastrinoma, malignant; Mixed islet cell and exocrine adenocarcinoma; Bile duct adenoma; Cholangiocarcinoma; Bile duct cystadenoma; Bile duct cystadenocarcinoma; Liver cell adenoma; Hepatocellular carcinoma; Hepatocholangioma, benign; Combined hepatocellular carcinoma and cholangiocarcinoma; Trabecular adenoma; Trabecular adenocarcinoma; Embryonal adenoma; Eccrine dermal cylindroma; Adenoid cystic carcinoma; Cribriform carcinoma; Adenomatous polyp; Adenocarcinoma in adenomatous polyp; Tubular adenoma; Tubular adenocarcinoma; Adenomatous polyposis coli; Adenocarcinoma in adenomatous polyposis coli; Multiple adenomatous polyps; Solid carcinoma; Carcinoma simplex; Carcinoid tumor; Carcinoid tumor, malignant; Carcinoid tumor, argentaffin; Carcinoid tumor, argentaffin, malignant; Carcinoid tumor, nonargentaffin; Carcinoid tumor, nonargentaffin, malignant; Mucocarcinoid tumor, malignant; Composite carcinoid; Pulmonary adenomatosis; Bronchiolo-alveolar adenocarcinoma; Alveolar adenoma; Alveolar adenocarcinoma; Papillary adenoma; Papillary adenocarcinoma; Villous adenoma; Adenocarcinoma in villous adenoma; Villous adenocarcinoma; Tubulovillous adenoma; Chromophobe adenoma; Chromophobe carcinoma; Acidophil adenoma; Acidophil carcinoma; Mixed acidophil-basophil adenoma; Mixed acidophil-basophil carcinoma; Oxyphilic adenoma; Oxyphilic adenocarcinoma; Basophil adenoma; Basophil carcinoma; Clear cell adenoma; Clear cell adenocarcinoma; Hypernephroid tumor; Renal cell carcinoma; Clear cell adenofibroma; Granular cell carcinoma; Chief cell adenoma; Water-clear cell adenoma, Water-clear cell adenocarcinoma; Mixed cell adenoma; Mixed cell adenocarcinoma; Lipoadenoma; Follicular adenoma; Follicular adenocarcinoma; Follicular adenocarcinoma, well differentiated type; Follicular adenocarcinoma, trabecular type; Microfollicular adenoma; Macrofollicular adenoma; Papillary and follicular adenocarcinoma; Nonencapsulated sclerosing carcinoma; Multiple endocrine adenomas; Juxtaglomerular tumor; Adrenal cortical adenoma; Adrenal cortical carcinoma; Adrenal cortical adenoma, compact cell type; Adrenal cortical adenoma, heavily pigmented variant; Adrenal cortical adenoma, clear cell type; Adrenal cortical adenoma, glomerulosa cell type; Adrenal cortical adenoma, mixed cell type; Endometrioid adenoma; Endometrioid adenoma, borderline malignancy; Endometrioid carcinoma; Endometrioid adenofibroma; Endometrioid adenofibroma, borderline malignancy; Endometrioid adenofibroma, malignant; Adnexal and skin appendage neoplasms; Skin appendage adenoma; Sweat gland adenoma; Sweat gland tumor; Sweat gland adenocarcinoma; Apocrine adenoma; Apocrine adenocarcinoma; Eccrine acrospiroma; Eccrine spiradenoma; Hidrocystoma; Papillary hydradenoma; Papillary syringadenoma; Syringoma; Sebaceous adenoma; Sebaceous adenocarcinoma; Ceruminous adenoma; Ceruminous adenocarcinoma;

Mucoepidermoid neoplasms; Mucoepidermoid tumor; Mucoepidermoid carcinoma; Cystic, mucinous, and serous neoplasms; Cystadenoma; Cystadenocarcinoma; Serous cystadenoma; Serous cystadenoma, borderline malignancy; Serous cystadenocarcinoma; Papillary cystadenoma; Papillary cystadenoma, borderline malignancy; Papillary cystadenocarcinoma; Papillary serous cystadenoma; Papillary serous cystadenoma, borderline malignancy; Papillary serous cystadenocarcinoma; Serous surface papilloma; Serous surface papilloma, borderline malignancy; Serous surface papillary carcinoma; Mucinous cystadenoma; Mucinous cystadenoma, borderline malignancy; Mucinous cystadenocarcinoma; Papillary mucinous cystadenoma; Papillary mucinous cystadenoma, borderline malignancy; Papillary mucinous cystadenocarcinoma; Mucinous adenoma; Mucinous adenocarcinoma; Pseudomyxoma peritonei; Mucin-producing adenocarcinoma; Signet ring cell carcinoma; Metastatic signet ring cell carcinoma; Ductal, lobular, and medullary neoplasms; Intraductal carcinoma, noninfiltrating; Infiltrating duct carcinoma; Comedocarcinoma, noninfiltrating; Comedocarcinoma; Juvenile carcinoma of the breast; Intraductal papilloma; Noninfiltrating intraductal papillary adenocarcinoma; Intracystic papillary adenoma; Noninfiltrating intracystic carcinoma; Intraductal papillomatosis; Subareolar duct papillomatosis; Medullary carcinoma; Medullary carcinoma with amyloid stroma; Medullary carcinoma with lymphoid stroma; Lobular carcinoma in situ; Lobular carcinoma; Infiltrating ductular carcinoma; Inflammatory carcinoma; Paget's disease, mammary; Paget's disease and infiltrating duct carcinoma of breast; Paget's disease, extramammary (except Paget's disease of bone); Acinar cell neoplasms; Acinar cell adenoma; Acinar cell tumor; Acinar cell carcinoma; Complex epithelial neoplasms; Adenosquamous carcinoma; Adenolymphoma; Adenocarcinoma with squamous metaplasia; Adenocarcinoma with cartilaginous and osseous metaplasia; Adenocarcinoma with spindle cell metaplasia; Adenocarcinoma with apocrine metaplasia; Thymoma, benign; Thymoma, malignant; Specialized gonadal neoplasms; Sex cord-stromal tumor; Thecoma; Theca cell carcinoma; Luteoma; Granulosa cell tumor; Granulosa cell tumor, malignant; Granulosa cell-theca cell tumor; Androblastoma, benign; Androblastoma, Androblastoma, malignant; Sertoli-Leydig cell tumor; Gynandroblastoma; Tubular androblastoma; Sertoli cell carcinoma; Tubular androblastoma with lipid storage; Leydig cell tumor, benign; Leydig cell tumor; Leydig cell tumor, malignant; Hilar cell tumor; Lipid cell tumor of ovary; Adrenal rest tumor; Paragangliomas and glomus tumors; Paraganglioma, Paraganglioma, malignant; Sympathetic paraganglioma; Parasympathetic paraganglioma; Glomus jugulare tumor; Aortic body tumor; Carotid body tumor; Extra-adrenal paraganglioma; Extra-adrenal paraganglioma, malignant; Pheochromocytoma, Pheochromocytoma, malignant; Glomangiosarcoma; Glomus tumor; Glomangioma; Nevi and melanomas; Pigmented nevus; Malignant melanoma; Nodular melanoma; Balloon cell nevus; Balloon cell melanoma; Halo nevus; Fibrous papule of the nose; Neuronevus; Magnocellular nevus; Nonpigmented nevus; Amelanotic melanoma; Junctional nevus; Malignant melanoma in junctional nevus; Precancerous melanosis; Malignant melanoma in precancerous melanosis; Hutchinson's melanotic freckle; Malignant melanoma in Hutchinson's melanotic freckle; Superficial spreading melanoma; Intradermal nevus; Compound nevus; Giant pigmented nevus; Malignant melanoma in giant pigmented nevus; Epithelioid and spindle cell nevus; Epithelioid cell melanoma; Spindle cell melanoma; Spindle cell melanoma, type A; Spindle cell melanoma, type B; Mixed epithelioid and spindle cell melanoma; Blue nevus; Blue nevus, malignant; Cellular blue nevus; Soft tissue tumors and sarcomas; Soft tissue tumor, benign; Sarcoma; Sarcomatosis; Spindle cell sarcoma; Giant cell sarcoma (except of bone M92503); Small cell sarcoma; Epithelioid cell sarcoma; Fibromatous neoplasms; Fibroma; Fibrosarcoma; Fibromyxoma; Fibromyxosarcoma; Periosteal fibroma; Periosteal fibrosarcoma; Fascial fibroma; Fascial fibrosarcoma; Infantile fibrosarcoma; Elastofibroma; Aggressive fibromatosis; Abdominal fibromatosis; Desmoplastic fibroma; Fibrous histiocytoma; Atypical fibrous histiocytoma; Fibrous histiocytoma, malignant; Fibroxanthoma; Atypical fibroxanthoma; Fibroxanthoma, malignant; Dermatofibroma; Dermatofibroma protuberans; Dermatofibrosarcoma; Myxomatous neoplasms; Myxoma; Myxosarcoma; Lipomatous neoplasms; Lipoma; Liposarcoma; Fibrolipoma; Liposarcoma, well differentiated type; Fibromyxolipoma; Myxoid liposarcoma; Round cell liposarcoma; Pleomorphic liposarcoma; Mixed type liposarcoma; Intramuscular lipoma; Spindle cell lipoma; Angiomyolipoma; Angiomyoliposarcoma; Angiolipoma; Angiolipoma, infiltrating; Myelolipoma; Hibernoma; Lipoblastomatosis; Myomatous neoplasms; Leiomyoma; Intravascular leiomyomatosis; Leiomyosarcoma; Epithelioid leiomyoma; Epithelioid leiomyosarcoma; Cellular leiomyoma; Bizarre leiomyoma; Angiomyoma; Angiomyosarcoma; Myoma; Myosarcoma; Rhabdomyoma; Rhabdomyosarcoma; Pleomorphic rhabdomyosarcoma; Mixed type rhabdomyosarcoma; Fetal rhabdomyoma; Adult rhabdomyoma; Embryonal rhabdomyosarcoma; Alveolar rhabdomyosarcoma; Complex mixed and stromal neoplasms; Endometrial stromal sarcoma; Endolymphatic stromal myosis; Adenomyoma; Pleomorphic adenoma; Mixed tumor, malignant; Mullerian mixed tumor; Mesodermal mixed tumor; Mesoblastic nephroma; Nephroblastoma; Epithelial nephroblastoma; Mesenchymal nephroblastoma; Hepatoblastoma; Carcinosarcoma; Carcinosarcoma, embryonal type; Myoepithelioma; Mesenchymoma, benign; Mesenchymoma; Mesenchymoma, malignant; Embryonal sarcoma; Fibroepithelial neoplasms; Brenner tumor; Brenner tumor, borderline malignancy; Brenner tumor, malignant; Fibroadenoma; Intracanalicular fibroadenoma; Pericanalicular fibroadenoma; Adenofibroma; Serous adenofibroma; Mucinous adenofibroma; Cellular intracanalicular fibroadenoma; Cystosarcoma phyllodes; Cystosarcoma phyllodes, malignant; Juvenile fibroadenoma; Synovial neoplasms; Synovioma, benign; Synovial sarcoma; Synovial sarcoma, spindle cell type; Synovial sarcoma, epithelioid cell type; Synovial sarcoma, biphasic type; Clear cell sarcoma of tendons and aponeuroses; Mesothelial neoplasms; Mesothelioma, benign; Mesothelioma, malignant; Fibrous mesothelioma, benign; Fibrous mesothelioma, malignant; Epithelioid mesothelioma, benign; Epithelioid mesothelioma, malignant; Mesothelioma, biphasic type, benign; Mesothelioma, biphasic type, malignant; Adenomatoid tumor; Germ cell neoplasms; Dysgerminoma; Seminoma; Seminoma, anaplastic type; Spermatocytic seminoma; Germinoma; Embryonal carcinoma; Endodermal sinus tumor; Polyembryoma; Gonadoblastoma; Teratoma, benign; Teratoma; Teratoma, malignant; Teratocarcinoma; Malignant teratoma, undifferentiated type; Malignant teratoma, intermediate type; Dermoid cyst; Dermoid cyst with malignant transformation; Struma ovarii; Struma ovarii, malignant; Strumal carcinoid; Trophoblastic neoplasms; Hydatidiform mole; Invasive hydatidiform mole; Choriocarcinoma; Choriocarcinoma combined with teratoma; Malignant teratoma; trophoblastic; Mesonephromas; Mesonephroma, benign;

Mesonephric tumor; Mesonephroma, malignant; Endosalpingioma; Blood vessel tumors; Hemangioma; Hemangiosarcoma; Cavernous hemangioma; Venous hemangioma; Racemose hemangioma; Kupffer cell sarcoma; Hemangioendothelioma, benign; Hemangioendothelioma; Hemangioendothelioma, malignant; Capillary hemangioma; Intramuscular hemangioma; Kaposi's sarcoma; Angiokeratoma; Verrucous keratotic hemangioma; Hemangiopericytoma, benign; Hemangiopericytoma; Hemangiopericytoma, malignant; Angiofibroma; Hemangioblastoma; Lymphatic vessel tumors; Lymphangioma; Lymphangiosarcoma; Capillary lymphangioma; Cavernous lymphangioma; Cystic lymphangioma; Lymphangiomyoma; Lymphangiomyomatosis; Hemolymphangioma; Osteomas and osteosarcomas; Osteoma; Osteosarcoma; Chondroblastic osteosarcoma; Fibroblastic osteosarcoma; Telangiectatic osteosarcoma; Osteosarcoma in Paget's disease of bone; Juxtacortical osteosarcoma; Osteoid osteoma; Osteoblastoma; Chondromatous neoplasms; Osteochondroma; Osteochondromatosis; Chondroma; Chondromatosis; Chondrosarcoma; Juxtacortical chondroma; Juxtacortical chondrosarcoma; Chondroblastoma; Chondroblastoma, malignant; Mesenchymal chondrosarcoma; Chondromyxoid fibroma; Giant cell tumors; Giant cell tumor of bone; Giant cell tumor of bone, malignant; Giant cell tumor of soft parts; Malignant giant cell tumor of soft parts; Miscellaneous bone tumors; Ewing's sarcoma; Adamantinoma of long bones; Ossifying fibroma; Odontogenic tumors; Odontogenic tumor, benign; Odontogenic tumor; Odontogenic tumor, malignant; Dentinoma; Cementoma; Cementoblastoma, benign; Cementifying fibroma; Gigantiform cementoma; Odontoma; Compound odontoma; Complex odontoma; Ameloblastic fibroodontoma; Ameloblastic odontosarcoma; Adenomatoid odontogenic tumor; Calcifying odontogenic cyst; Ameloblastoma; Ameloblastoma, malignant, Odontoameloblastoma; Squamous odontogenic tumor; Odontogenic myxoma; Odontogenic fibroma; Ameloblastic fibroma; Ameloblastic fibrosarcoma; Calcifying epithelial odontogenic tumor; Miscellaneous tumors; Craniopharyngioma; Pinealoma; Pineocytoma; Pineoblastoma; Melanotic neuroectodermal tumor; Chordoma; Gliomas; Glioma, malignant; Gliomatosis cerebri; Mixed glioma; Subependymal glioma; Subependymal giant cell astrocytoma; Choroid plexus papilloma; Choroid plexus papilloma, malignant; Ependymoma; Ependymoma, anaplastic type; Papillary ependymoma; Myxopapillary ependymoma; Astrocytoma; Astrocytoma, anaplastic type; Protoplasmic astrocytoma; Gemistocytic astrocytoma; Fibrillary astrocytoma; Pilocytic astrocytoma; Spongioblastoma; Spongioblastoma polare; Astroblastoma; Glioblastoma; Giant cell glioblastoma; Glioblastoma with sarcomatous component; Primitive polar spongioblastoma; Oligodendroglioma; Oligodendroglioma, anaplastic type; Oligodendroblastoma; Medulloblastoma; Desmoplastic medulloblastoma; Medullomyoblastoma; Cerebellar sarcoma; Monstrocellular sarcoma; Neuroepitheliomatous neoplasms; Ganglioneuroma; Ganglioneuroblastoma; Ganglioneuromatosis; Neuroblastoma; Medulloepithelioma; Teratoid medulloepithelioma; Neuroepithelioma; Spongioneuroblastoma; Ganglioglioma; Neurocytoma; Pacinian tumor; Retinoblastoma; Retinoblastoma, differentiated type; Retinoblastoma, undifferentiated type; Olfactory neurogenic tumor; Esthesioneurocytoma; Esthesioneuroblastoma; Esthesioneuroepithelioma; Meningiomas; Meningioma; Meningiomatosis; Meningioma, malignant; Meningotheliomatous meningioma; Fibrous meningioma; Psammomatous meningioma; Angiomatous meningioma; Hemangioblastic meningioma; Hemangiopericytic meningioma; Transitional meningioma; Papillary meningioma; Meningeal sarcomatosis; Nerve sheath tumor; Neurofibroma; Neurofibromatosis; Neurofibrosarcoma; Melanotic neurofibroma; Plexiform neurofibroma; Neurilemmoma; Neurinomatosis; Neurilemmoma, malignant; Neuroma; Granular cell tumors and alveolar soft part sarcoma; Granular cell tumor; Granular cell tumor, malignant; Alveolar soft part sarcoma; Lymphomas; NOS or diffuse, Lymphomatous tumor; benign, Malignant lymphoma; Malignant lymphoma, non Hodgkin's type; Malignant lymphoma, undifferentiated cell type; Malignant lymphoma, stem cell type; Malignant lymphoma, convoluted cell type; Lymphosarcoma; Malignant lymphoma, lymphoplasmacytoid type; Malignant lymphoma, immunoblastic type; Malignant lymphoma, mixed lymphocytic-histiocytic; Malignant lymphoma, centroblastic-centrocytic, diffuse; Malignant lymphoma, follicular center cell; Malignant lymphoma, lymphocytic, well differentiated; Malignant lymphoma, lymphocytic, intermediate differentiation; Malignant lymphoma, centrocytic; Malignant lymphoma, follicular center cell, cleaved; Malignant lymphoma, lymphocytic, poorly differentiated; Prolymphocytic lymphosarcoma; Malignant lymphoma, centroblastic type; Malignant lymphoma, follicular center cell, noncleaved; Reticulosarcomas; Reticulosarcoma; Reticulosarcoma, pleomorphic cell type; Reticulosarcoma, nodular; Hodgkin's disease; Hodgkin's disease; Hodgkin's disease, lymphocytic predominance; Hodgkin's disease, mixed cellularity; Hodgkin's disease, lymphocytic depletion; Hodgkin's disease, lymphocytic depletion, diffuse fibrosis; Hodgkin's disease, lymphocytic depletion, reticular type; Hodgkin's disease, nodular sclerosis; Hodgkin's disease, nodular sclerosis, cellular phase; Hodgkin's paragranuloma; Hodgkin's granuloma; Hodgkin's sarcoma; Lymphomas, nodular or follicular; Malignant lymphoma, nodular; Malignant lymphoma, mixed lymphocytic-histiocytic; nodular; Malignant lymphoma, centroblastic-centrocytic, follicular; Malignant lymphoma, lymphocytic, well differentiated, nodular; Malignant lymphoma, lymphocytic, intermediate differentiation, nodular; Malignant lymphoma, follicular center cell, cleaved, follicular; Malignant lymphoma, lymphocytic, poorly differentiated, nodular; Malignant lymphoma, centroblastic type, follicular; Malignant lymphoma, follicular center cell, noncleaved, follicular; Mycosis fungoides; Mycosis fungoides; Sezary's disease; Miscellaneous reticuloendothelial neoplasms; Microglioma; Malignant histiocytosis; Histiocytic medullary reticulosis; Letterer-Siwe's disease; Plasma cell tumors; Plasma cell myeloma; Plasma cell tumor, benign; Plasmacytoma; Plasma cell tumor, malignant; Mast cell tumors; Mastocytoma; Mast cell sarcoma; Malignant mastocytosis; Burkitt's tumor; Burkitt's tumor; Leukemias; Leukemias; Leukemia; Acute leukemia; Subacute leukemia; Chronic leukemia; Aleukemic leukemia; Compound leukemias; Compound leukemia; Lymphoid leukemias; Lymphoid leukemia; Acute lymphoid leukemia; Subacute lymphoid leukemia; Chronic lymphoid leukemia; Aleukemic lymphoid leukemia; Prolymphocytic leukemia; Plasma cell leukemias; Plasma cell leukemia; Erythroleukemias; Erythroleukemia; Acute erythremia; Chronic erythremia; Lymphosarcoma cell leukemias; Lymphosarcoma cell leukemia; Myeloid leukemias; Myeloid leukemia; Acute myeloid leukemia; Subacute myeloid leukemia; Chronic myeloid leukemia; Aleukemic myeloid leukemia; Neutrophilic leukemia; Acute promyelocytic leukemia; Basophilic leukemias; Basophilic leukemia; Eosinophilic leukemias; Eosinophilic leukemia; Monocytic leukemias; Monocytic leukemia; Acute monocytic leukemia; Subacute monocytic leukemia; Chronic monocytic leukemia; Aleukemic monocytic leukemia; Miscellaneous leukemias; Mast cell leukemia; Megakaryocytic leukemia; Megakaryocytic myelosis; Myeloid sarcoma; Hairy cell leukemia; Miscellaneous myeloproliferative and lymphoproliferative disorders; Polycythemia vera; Acute panmyelosis; Chronic myeloproliferative disease; Myelosclerosis with myeloid metaplasia; Idiopathic thrombocythemia; Chronic lymphoproliferative disease; and Acute Lymphoblastic Leukemia (ALL), Acute Myeloid Leukemia (AML), Adrenocortical Carcinoma, AIDS-Related Cancers, Kaposi Sarcoma, Lymphoma, Anal Cancer, Appendix Cancer, Astrocytomas, Childhood, Atypical Teratoid/Rhabdoid Tumor, Basal Cell Carcinoma, Bile Duct Cancer, Extrahepatic, Bladder Cancer, Bone Cancer, Ewing Sarcoma Family of Tumors, Osteosarcoma and Malignant Fibrous Histiocytoma, Brain Stem Glioma, Brain Tumor, Astrocytomas, Brain and Spinal Cord Tumors, Central Nervous System Atypical Teratoid/Rhabdoid Tumor, Central Nervous System Embryonal Tumors, Central Nervous System Germ Cell Tumors, Craniopharyngioma, Ependymoma, Breast Cancer, Male Breast Cancer, Bronchial Tumors, Burkitt Lymphoma, Carcinoid Tumor, Gastrointestinal Cancer, Carcinoma of Unknown Primary, Cardiac Tumors, Childhood, Central Nervous System, Atypical Teratoid/Rhabdoid Tumor, Embryonal Tumors, Germ Cell Tumor, Childhood, Lymphoma, Primary, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Cutaneous T-Cell Lymphoma, Extrahepatic Bile Duct Cancer, Ductal Carcinoma In Situ (DCIS), Embryonal Tumors of the Central Nervous System, Endometrial Cancer, Ependymoma, Childhood, Esophageal Cancer, Esthesioneuroblastoma, Ewing Sarcoma, Extracranial Germ Cell Tumor, Extragonadal Germ Cell Tumor, Eye Cancer, Intraocular Melanoma, Retinoblastoma, Malignant Fibrous Histiocytoma of Bone, Osteosarcoma, Gallbladder Cancer, Gastric Cancer, Gastrointestinal Carcinoid Tumor, Gastrointestinal Stromal Tumors (GIST), Germ Cell Tumor, Central Nervous System Germ Cell Tumor, Ovarian Germ Cell Tumor, Testicular Germ Cell Tumor, Gestational Trophoblastic Disease, Glioma, Hairy Cell Leukemia, Head and Neck Cancer, Heart Cancer, Childhood, Hepatocellular Cancer, Histiocytosis, Langerhans Cell, Hodgkin Lymphoma, Hypopharyngeal Cancer, Islet Cell Tumors, Pancreatic Neuroendocrine Tumors, Kidney, Renal Cell Cancer, Wilms Tumor, Langerhans Cell Histiocytosis, Laryngeal Cancer, Leukemia, Lip and Oral Cavity Cancer, Liver Cancer (Primary), Lobular Carcinoma In Situ (LCIS), Lung Cancer, Non-Small Cell Lung Cancer, Small Cell Lung cancer, AIDS-Related Lymphoma, Non-Hodgkin Lymphoma, Primary Central Nervous System (CNS) Lymphoma, Macroglobulinemia, Waldenström, Melanoma, Intraocular (Eye), Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Childhood, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma, Multiple, Myeloproliferative Disorders, Chronic, Nasal Cavity and Paranasal Sinus Cancer, Nasopharyngeal Cancer, Neuroblastoma, Oral Cancer, Oral Cavity Cancer, Lip and, Oropharyngeal Cancer, Osteosarcoma and Malignant Fibrous Histiocytoma of Bone, Ovarian Cancer, Epithelial, Low Malignant Potential Tumor, Pancreatic Cancer, Pancreatic Neuroendocrine Tumors (Islet Cell Tumors), Papillomatosis, Childhood, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Childhood, Pregnancy and Breast Cancer, Prostate Cancer, Rectal Cancer, Renal Cell (Kidney) Cancer, Renal Pelvis and Ureter, Transitional Cell Cancer, Rhabdomyosarcoma, Childhood, Salivary Gland Cancer, Sarcoma, Ewing, Kaposi, Osteosarcoma (Bone Cancer), Rhabdomyosarcoma, Soft Tissue, Uterine, Sézary Syndrome, Skin Cancer, Nonmelanoma, Small Intestine Cancer, Soft Tissue Sarcoma, Squamous Cell Carcinoma—see Skin Cancer (Nonmelanoma), Squamous Neck Cancer with Occult Primary, Metastatic, Stomach (Gastric) Cancer, T-Cell Lymphoma, Cutaneous—see Mycosis Fungoides and Sézary Syndrome, Testicular Cancer, Throat Cancer, Thymoma and Thymic Carcinoma, Thyroid Cancer, Transitional Cell Cancer of the Renal Pelvis and Ureter, Unknown Primary, Carcinoma of, Unusual Cancers of Childhood, Ureter and Renal Pelvis, Transitional Cell Cancer, Urethral Cancer, Uterine Cancer, Endometrial, Uterine Sarcoma, Vaginal Cancer, Vulvar Cancer, Waldenström Macroglobulinemia and Women's Cancers.

EMBODIMENT 70

The conjugate of any one of embodiments 1 to 69, wherein the target is selected from the group comprising targets expressed in any tumor, cancer, tumor disease, cancer disease, tumor indication or cancer indication, preferably the target is selected from group B, wherein group B comprises 14C5 antigen, 18-22 kDa cell surface antigen for human squamous-cell carcinoma, 3H11 antigen, A33 antigen, Abl kinase, Activated leukocyte cell adhesion molecule (AL-CAM), Activin receptor-like kinase-1, AKT1, AKT2, AKT3, Aldehyde oxidase, Aldosterone synthase, ALK, Alkaline phosphatase, Alpha folate receptor, Alpha(3)beta(1) integrin, Alpha(4)beta(1) integrin, Alpha(5)beta(1), Alpha(v)beta (3) integrin, Alpha(v)beta(6) integrin, Alpha-1A adrenergic receptor, Alpha-3 integrin receptor, Amino acid transporter ASC, Amino acid transporter ASCT2, Amino acid transporter L, Aminopeptidase N (ANP, CD13), Androgen receptor (AR), Angiopoietin-/-2, Angiopoietin-1, Angiopoietin-1 receptor, Antiapoptotic protein BCL-XL, Anti-dansyl (DNS) receptor, Antigen OC183B2, Aromatic L?amino acid decarboxylase (AAAD), Atrial natriuretic peptide receptor 1, Atrial natriuretic peptide receptor 2, A-type amino acid transporter, Aurora C, Aurora-A, Aurora-B, Avidin, B7-H3, BAFF, Bcl-2, Bcr-Abl tyrosine kinase, Beta-2-microglobulin (B2M), Beta-galactosidase, Beta-glucuronidase, Beta-human chorionic gonadotropin (Beta-hCG), Biotin, Bombesin receptor, Bombesin receptor subtype-3, BRAF, Btk, CA 125 antigen, CA19.9, CA27.29, CAAG-1/KAAG-1, Cadherin 2, Calcitonin, Calcitonin receptor, Calcium-activated chloride channel, Calpain, Cancer cell surface-bound nucleosomes, Carbonic Anhydrase II, Carbonic anhydrase IX, Carcinoembryonic antigen (CEA), Cartilage proteoglycans, Caspase-3, Caspase-7, catenin, Cathepsin, Cathepsin B, Cathepsin D, Cathepsin E, Cathepsin K, Cathepsins H, CBP, CC49, CCK-1 receptor (CCK-A), CCND1 (cyclin D1), CD105 (Endoglin, EDG), CD117 (c-kit), CD111b, CD123, CD13, CD137 antigen, CD14 antigens, CD15, CD16a, CD16b, CD19, CD20, CD21, CD22, CD25, CD27, CD3, CD30, CD33, CD37, CD4, CD40, CD44 (splice variants, e.g. v6), CD44 receptor, CD52, CD70, CD77 (glycosphingolipid Gb3), CD95, CD96, CDK1, CDK2, CDK2, CDK4, CDK4, CDK6, CDK7, CDK9, CEACAM cell adhesion molecule, CEACAM5 (carcinoembryonic antigen-related cell adhesion molecule 5), Cell surface nucleolin, Cellular tumor antigen p53, Centromeric protein E, Chemokine receptor 4 (CXCR4), Cholecystokinin receptor subtype 2 (CCK-2), Cholecystokinin type A (CCK-A) receptor, Choline kinase, Choline transporter, Choline transporter-like protein 4, Chondroitin sulphate proteoglycan TENB2, Chromogranin A (CgA), CIF, CK2, Claudin 4 receptor, Claudin-18, Claudin-6, Clusterin, c-MET, c-MYC, Collagen, collagen XXIII, Colon cancer surface glycoprotein, Colony stimulating factor-1 receptor (CSF-1R), Copper transporter 1, Corticotropin-releasing factor receptor 1 (CRFR1), Corticotropin-releasing factor receptor 2 (CRFR2), COX-2, Coxsackie-adenovirus receptor (CAR), CTLA4, Cyclin-dependent kinase, Cystine/glutamate exchanger, Cytochrome p450 (Hypoxic tissue), Cytochrome P450 family 11B enzymes, de2-7 epidermal growth factor receptor, Delta-like 4, Disialoganglioside 2 (GD2), Disialogangliosides, DKK2 protein, DNA topoisomerase I, DNA topoisomerase II, Dopamine D2 receptor, DPPIV, DR5, E2F1, E-Cadherin, ED-A fibronectin, ED-B fibronectin, EGF HER2 receptor, EGFR (HER1), EGFR Tyrosine kinase, EGFR2, EGFRivIII, EGFRvIII, EGP-1 (epithelial glycoprotein-1), eIF4E, Elongation factor 1A, EMMPRIN (CD147), endosialin, Endostatin receptor, Endothelin A (ETA) receptor, Endothelin B receptor, ENG protein, EpCAM (epithelial cell adhesion molecule), EphA2 receptor, EphrinB4 receptor, Epidermal growth factor domain-like-7 (EGFL7), Epidermal growth factor receptor 3, Epidermal growth factor receptor deletion variant, de2-8, ErbB2, ErbB-2 extracellular domain, Erythropoitin receptor, E-selectin, Estrogen receptor (ER), FAK, Farnesyl protein transferase, Ferritin, FGF receptor, FGF-3 receptor, Fibrin, alpha-chain, Fibrin?fibronectin complexes, Fibrinogen, Fibroblast activation protein-alpha (FAPa), Fibronectin, Flt3, Foetal antigen-2, folate hydrolase, Folate receptor, G protein-coupled estrogen receptor, Galactose receptor, Galectin-3, Gamma-secretase, Gamma-seminoprotein, Gastric Mucin, gastrin receptors, Gastrin releasing peptide (GRP) receptor, Gastrin/cholecystokinin-2 (CCK-2, CCK-B) receptor, GD3 antigen, Gelatinase B (matrix metalloproteinase 9, MMP-9), Gelatinases (MMP-2), GIP (gastric inhibitory polypeptide), Glucagon like peptide 1 receptor, Glucocorticoid receptor (GR), Glucose transporter, Glucose transporter (GLUT1), Glucose transporter (GLUT5), Glucosidase, GLUT transporter system, glutamate carboxypeptidase II (GCP II), Glutamate transporters, Glutamine transporter, Glycogen synthase kinase-3 beta, Glycoprotein IIb/IIIa receptor (GPIIb/IIIa receptor), Glypican 3, GnRH, Gonadotropin releasing hormone receptor, gpA33, GPNMB, GPR54 receptor, Guanylate cyclase C (GC-C) receptor, Haptoglobin-β chain derived from prostate cancer cells, HB-EGF, HDM2, HE4, Heat shock protein HSP 90, Heparan sulfate proteoglycans(HSPG), Heparanase, Heparin cofactor II (neovascular endothelium), Hepatocyte growth factor (HGF), Hepatocyte growth factor receptor, Hepsin, HER3, Hexokinase, High-density lipoprotein receptor (HDLR), Histone deacetylase (HDAC), Histone deacetylase 4, Histone deacetylase 6, HLA-DR antigen, HLA-DR10, HMW-MAA (high molecular weight melanoma-associated antigen), hsp70, Human glioma cell-surface antigen, Human sperm protein 17, Hyaluronidase (HAdase), Hypoxia-inducible factor 1 (HIF-1), IGF1R, IgG1, IL-13 receptor, IL-1β, IL-4R, IL-6, IL-6R, IL-8RB, Inducible nitric oxide synthase (iNOS), insulin like-growth-factor binding protein 7 (IGFBP7), Insulin receptor, Insulin-like growth factor, Insulin-like growth factor 1 receptor (IGF-1R), Integrin α2β1, Integrin αvβ4, Integrins αvβ5, Intercellular adhesion molecule 1 (ICAM-1), Interleukin 11 receptor (IL-11R), Interleukin 11 receptor, alpha-chain, Interleukin 13 receptor alpha 2, Interleukin 18 receptor (IL-18R), Interleukin 2 receptor (IL-2R), Interleukin 6 receptor (IL-6R), Interleukin-18, Interleukin-7 receptor, Intestinal alkaline phosphatase, JAK1, JAK2, JAK3, JNK1/MAPK8, kinase insert domain receptor (KDR), Kinesin Spindle Protein, KIR, L1 cell adhesion protein, L1-CAM antigen, La antigen, Lactate dehydrogenase, Lactoferrin receptor, LAG3, Laminin, Laminin receptor, L-Amino acid transporter (LAT), LAT1, LAT2, Lectin, Lectin, Legumain/Asparaginyl endopeptidase, Leukotriene A4 Hydrolase, Leukotriene B4 receptor 1, Lewis Y antigen, Low-density lipoprotein receptor (LDLR), Low-density lipoprotein receptor-related protein-1, LRRC15, Luteinizing hormone releasing hormone receptor, Luteinizing hormone/chorionic gonadotropin (LH/CG) receptor, Lymphatic vessel endothelial hyaluronan receptor-1 (LYVE-1), Macrophage colony-stimulating factor 1, Mammaglobin-A, MAP kinase p38, MARK3, Matrix metalloproteinase 2 (MMP-2), Matrix metalloproteinase 7 (MMP-7), Matrix metalloproteinase-12, Matrix metalloproteinase-13, Matrix metalloproteinase-9, Matrix metalloproteinases (membrane type-1), Mcl-1, MCT1, MCT4, Mdrl, MEK1, MEK2, Melancortin-1 receptor (MC1R), Melanin, Melanin, phenomelanin, Melanocyte stimulating hormone receptor, Melanocyte-stimulating hormone receptor, Mesenchymal-epithelial transition factor (c-Met), Mesothelin, Mesothelin-ADC, Microsomal epoxide hydrolase, Microtubules, MIF, Mindin/RG-1 extracellular matrix protein, Mitotic kinesin Eg5, MMP14, MMP-3, Monoamine oxidase B (MAO-B), Monosialoganglioside (sialosylated Lea antigen), MTF-1, mTOR, MTORC1, MTORC2, MUC1, Mucin MUC2, Multidrug resistance-associated protein 1, Na+-dependent myo-inositol cotransporter-1/2 (SMIT-1/2), N-acetyl α-linked acidic dipeptidase (NAALADase), N-acetylated alpha-linked L-amino dipeptidase, NAD-dependent deacetylase sirtuin-1, NADH oxidase, NCAM, Nectin-4, Neprilysin, Neural cadherin, Neural cell adhesion molecule (NCAM), Neuroblastoma-specific cell surface antigen, Neurokinin 1 (NK1) receptor, Neuromedin-B receptor (NMBR), Neuromedin-K receptor (NK-3R), neuropeptide Y receptor 1 (NPY1-R), neuropeptide Y receptor 2 (NPY2-R), Neuropeptide Y receptor type 4 (NPY4-R), Neuropeptide Y receptor type 4 (NPY4-R), Neuropilin-1, neuropilin-1 receptors, Neurotensin, Neurotensin receptor, Neurotensin receptor 1 (NTSR1), Neurotensin receptor 2 (NTSR2), Nicotinic acetylcholine receptor, alpha4beta2, Non-camptothecin topoI, Notch, NPY, NRH dehydrogenase [quinone] 2, NRP1, NTRK1, Nuclear factor NF-kappa-B, Nuclear matrix protein 22, Nucleolin, NY-ESO-1, OX40, Oxytocin receptor, P70-S6 Kinase 1, PARP-1, PD-1, PDGFR, PDGFRA, PDGFRB, Peripheral benzodiazepine receptor (PBR), Peroxiredoxin I, Peroxisome proliferator-activated receptor-gamma (PPARgamma), P-glycoprotein (Pgp), phosphatidylethanolamine, Phosphatidylserine, PI3K, PIGF, PIK-1, PIM kinase, Pituitary adenylate cyclase-activating polypeptide type I receptor, Placental alkaline phosphatase (PLAP), plasminogen activator inhibitor (PAI-1), Plectin-1, P1GF, PLK-1, PNK3 (protein kinase N3), Polo-like kinase 1 (PLK1), Poly [ADP-ribose] polymerase 1, Polyamine receptor, Progesterone receptor (PR), Progestin receptor, Programmed cell death-1 ligand 1 (PD-L1), Prolactin receptor, Propressophysin-like protein cell surface antigen, Prostate specific antigen, Prostate stem cell antigen (PSCA), Prostate-specific membrane antigen (PSMA), Protein kinase B, Protein kinase C, Protein kinase D, Protein-tyrosine phosphatase SHP-1, Proto-oncogene c-Kit; tyrosine-protein kinase kit; mast/stem cell growth factor receptor; CD117, PSCA, PTPN1, Puromycin-sensitive aminopeptidase (PSA), Raf-1, RANKL, Ras, Receptor for advanced glycation endproducts (RAGE), Renin, Retinoic acid receptor alpha, Ribosyldihydronicotinamide dehydrogenase, Robo1, Robo4, RON, Secretin, Serine protease matriptase, Serine Racemase, Serine/threonine kinase (Akt), Serine/threonine-protein kinase Chk1, Serine/threonine-protein kinase Chk2, Serine/threonine-protein kinase PLK, Siglec-15, Sigma 2 receptor, Sigma receptor, SIRT1, Smoothened, somatostatin receptor, Somatostatin receptor 1 (SSTR1), Somatostatin receptor 2 (SSTR2), Somatostatin receptor 3 (SSTR3), Somatostatin receptor sub-type 4, Somatostatin receptor type 5, Sortilin (NTR3), Sphingosine kinase, Src, STAT3, Stathim, STEAP1, Sterylsulfatase, Substance P receptor (NK-1R), Substance-K receptor (NK-2R), Survivin, Syk, TAG 72, Telomerase, TEM5, TEM8, Tenascin, Tenascin-C, TENB2, TFPI, TGF-beta 1, TGF-beta 2, TGF-beta 3, Thioredoxin, Thioredoxin reductases, Thomsen-Friedenreich antigen, Thymidine kinase, Thymidine phosphorylase, Thyroglobulin, Tissue factor, Toll-like receptor 9, topoisomerase, TORC1, Transferrin receptor (TfR), Translocator protein, TRPM8 protein, Tubulin (microtubules), Tumor associated glycoprotein 72 (TAG-72), Tumor endothelial marker 1 (TEM1), Tumor necrosis factor receptor, Tumor necrosis factor-related apoptosis-inducing ligand receptor 1 (TRAIL-R1), Tumor necrosis factor-related apoptosis-inducing ligand receptor 2 (TRAILR2), Tumor necrosis factor-α, Tumor specific glycoprotein antigen IOR C2, TWEAK, TYK2, Tyrosine hydroxylase, Underglycosylated mucin-1 antigen (uMUC-1), Uridine-cytidine kinase 2 (UCK2), Urokinase, Urokinase plasminogen activator receptor, Urokinase-type plasminogen activator receptor (uPAR), Vascular cell adhesion molecule 1 (VCAM-1), Vascular endothelial growth factor (VEGF), Vascular endothelial growth factor receptor (VEGFR), Vascular endothelial growth factor receptor 2 (VEGFR2), Vascular endothelial growth factor receptor 3, Vasoactive intestinal peptide receptor (VPAC1), Vasoactive intestinal polypeptide receptor 2 (VPAC2), VEGF A isoform, VEGFB, VEGF-C, Voltage-dependent anion-selective channel protein 2 (VDAC2), Voltage-dependent anion-selective channel protein 3 (VDAC3), Wee1A kinase, XIAP, α-Fetoprotein (AFP), β-D-galactose receptor and β-Glucuronidase.

EMBODIMENT 71

The conjugate of any one of embodiments 1 to 70, wherein the second targeting moiety is selected from the group comprising an antibody, an antigen-binding antibody fragment, a camelid heavy chain IgG (hcIgG), a cartilaginous fish IgNAR antibody, a protein scaffold, a target-binding peptide, a peptide nucleic acid (PNA), a target-binding polypeptide or protein, a target binding nucleic acid molecule, a carbohydrate, a lipid and a target-binding small molecule.

EMBODIMENT 72

The conjugate of any one of embodiments 2 to 71, wherein the Effector is a diagnostically active nuclide or a therapeutically active nuclide, wherein the diagnostically active nuclide and the therapeutically active radionuclide is individually and independently selected from the group comprising $^{113m}$In, $^{99m}$Tc, $^{67}$Ga, $^{52}$Fe, $^{68}$Ga, $^{72}$As, $^{111}$In, $^{97}$Ru, $^{203}$Pb, $^{62}$Cu, $^{64}$Cu, $^{51}$Cr, $^{52m}$Mn, $^{157}$Gd, $^{64}$Cu, $^{89}$Zr, and $^{177}$Lu, $^{186}$Re, $^{90}$Y, $^{67}$Cu, $^{68}$Ga, $^{69}$Er, $^{121}$Sn, $^{127}$Te, $^{142}$Pr, $^{143}$Pr, $^{198}$Au, $^{199}$Au, $^{161}$Tb, $^{109}$Pd, $^{188}$Rd, $^{188}$Re, $^{77}$As, $^{166}$Dy, $^{166}$Ho, $^{149}$Pm, $^{151}$Pm, $^{153}$Sm, $^{159}$Gd, $^{172}$Tm, $^{90}$Y, $^{169}$Yb, $^{175}$Yb, $^{105}$Rh, $^{111}$Ag, $^{213}$Bi, $^{225}$Ac, $^{177m}$Sn and $^{227}$Th.

EMBODIMENT 73

The conjugate of any one of embodiments 1 to 72, wherein the conjugate interacts with a neurotensin receptor, wherein the neurotensin receptor is preferably selected from the group comprising neurotensin receptor 1 (NTR1) and neurotensin receptor 2 (NTR2).

EMBODIMENT 74

The conjugate of embodiment 73, wherein the conjugate is an antagonist for NTR, preferably NTR1.

EMBODIMENT 75

The conjugate of any one of embodiments 1 to 74, wherein the conjugate has an $IC_{50}$ of 100 nM or less, preferably 50 nM or less, for a target targeted by either the first targeting moiety TM1 or the target targeted by the second targeting target TM2, preferably the conjugate has an $IC_{50}$ of 100 nM or less, preferably 50 nM or less for NTR, more preferably for NTR1.

EMBODIMENT 76

The conjugate of any one of embodiments 1 to 75, wherein the targeting moiety is different from a glycoside.

EMBODIMENT 77

The conjugate of embodiment 76, wherein the glycoside is a N-glycoside, C-glycoside, O-gylcoside or an S-glycoside, preferably the glycoside is N-glycoside.

EMBODIMENT 78

The conjugate of any one of embodiments 1 to 77, wherein the conjugate is different from compound (89), including the $^{18}$F analog of this compound:

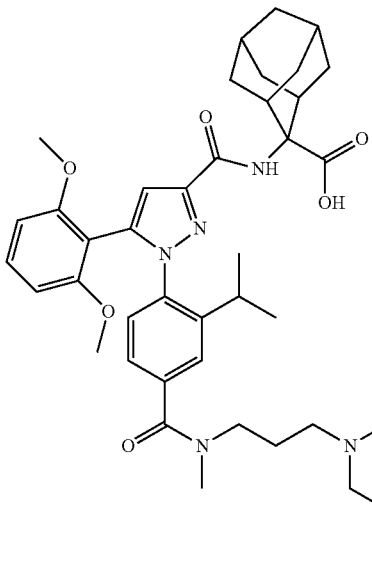

(89)

EMBODIMENT 79

The conjugate of any one of embodiments 1 to 78, for use in a method for the diagnosis of a disease.

EMBODIMENT 80

The conjugate of embodiment 79, wherein the disease is a disease involving a target targeted by the first targeting moiety TM1 or by the second targeting moiety TM2, preferably the disease is one involving neurotensin receptor, more preferably the disease is a disease involving neurotensin receptor 1.

EMBODIMENT 81

The conjugate of embodiment 80, wherein the disease is a disease not involving tissue of the central nervous system and/or cells of the central nervous system.

EMBODIMENT 82

The conjugate of any one of embodiments 79 to 81, wherein the disease is selected from the group comprising tumors and hematological malignancies.

EMBODIMENT 83

The conjugate of embodiment 82, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma, Ewing's sarcoma, and indications subject to group A as defined herein.

EMBODIMENT 84

The conjugate of any one of embodiments 79 to 83, wherein Effector is a radioactive metal, wherein preferably the radioactive metal is chelated by Acceptor, wherein Acceptor is a chelator.

EMBODIMENT 85

The conjugate of embodiment 84, wherein the radioactive metal is a diagnostically effective radioactive metal.

EMBODIMENT 86

The conjugate of embodiment 85, wherein the radioactive metal is selected from the group comprising $^{113m}$In, $^{99m}$Tc, $^{67}$Ga, $^{52}$Fe, $^{68}$Ga, $^{72}$As, $^{111}$In, $^{97}$Ru, $^{203}$Pb, $^{62}$Cu, $^{64}$Cu, $^{51}$Cr, $^{52m}$Mn, $^{157}$Gd, $^{64}$Cu, $^{89}$Zr, and $^{177}$Lu; more preferably the radioactive metal is selected from the group comprising $^{99m}$Tc, $^{67}$Ga, $^{68}$Ga, $^{111}$In, $^{89}$Zr and $^{177}$Lu; and more preferably the radioactive metal is $^{111}$In, $^{177}$Lu or $^{89}$Zr.

EMBODIMENT 87

The conjugate of any one of embodiments 79 to 83, wherein Effector is a radionuclide, wherein preferably the radionuclide is covalently bound by Acceptor, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

EMBODIMENT 88

The conjugate of embodiment 87, wherein the radionuclide is a diagnostically effective radioactive halogen.

EMBODIMENT 89

The conjugate of embodiment 88, wherein the radioactive halogen is selected from the group comprising $^{18}$F, $^{123}$I, $^{124}$I, $^{125}$I, $^{131}$I, $^{75}$Br $^{76}$Br, $^{77}$Br, $^{82}$Br, and $^{211}$At; more preferably the radionuclide is selected from the group comprising $^{123}$I, $^{124}$I.

EMBODIMENT 90

The conjugate of any one of embodiments 79 to 89, wherein the method for the diagnosis is an imaging method.

EMBODIMENT 91

The conjugate of embodiment 90, wherein the imaging method is selected from the group consisting of scintigraphy, Single Photon Emission Computed Tomography (SPECT) and Positron Emission Tomography (PET).

EMBODIMENT 92

The conjugate of any one of embodiments 79 to 91, wherein the method comprises the administration of a diagnostically effective amount of the compound to a subject, preferably to a mammal, wherein the mammal is selected from the group comprising man, companion animals, pets and livestock, more preferably the subject is selected from the group comprising man, dog, cat, horse and cow, and most preferably the subject is a human being.

EMBODIMENT 93

The conjugate of any one of embodiments 1 to 78, for use in a method for the treatment of a disease.

EMBODIMENT 94

The conjugate of embodiment 93, wherein the disease is a disease involving a target targeted by the first targeting moiety TM1 or by the second targeting moiety TM2, preferably the disease is one involving neurotensin receptor, preferably the disease is a disease involving neurotensin receptor 1.

EMBODIMENT 95

The conjugate of embodiment 94, wherein the disease is a disease not involving tissue of the central nervous system and/or cells of the central nervous system.

EMBODIMENT 96

The conjugate of any one of embodiments 93 to 94, wherein the disease is selected from the group comprising tumors and hematological malignancies.

EMBODIMENT 97

The conjugate of embodiment 96, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma, Ewing's sarcoma, and indications subject to group A defined herein.

EMBODIMENT 98

The conjugate of any one of embodiments 95 to 97, wherein Effector is a therapeutically active agent.

EMBODIMENT 99

The conjugate of any one of embodiments 93 to 98, wherein the method comprises the administration of a therapeutically effective amount of the conjugate to a subject, preferably to a mammal, wherein the mammal is selected from the group comprising man, companion animals, pets and livestock, more preferably the subject is selected from the group comprising man, dog, cat, horse and cow, and most preferably the subject is a human being.

EMBODIMENT 100

The conjugate of any one of embodiments 93 to 97, wherein Effector is a radioactive metal, wherein preferably the radioactive metal is chelated by Acceptor, wherein Acceptor is a chelator.

EMBODIMENT 101

The conjugate of embodiment 100, wherein the radioactive metal is selected from the group comprising $^{186}$Re, $^{90}$Y, $^{67}$Cu, $^{68}$Ga, $^{69}$Er, $^{121}$Sn, $^{127}$Te, $^{142}$Pr, $^{143}$Pr, $^{198}$Au, $^{199}$Au, $^{161}$Tb, $^{109}$Pd, $^{188}$Rd, $^{188}$Re, $^{77}$As, $^{166}$Dy, $^{166}$Ho, $^{149}$Pm, $^{151}$Pm, $^{153}$Sm, $^{159}$Gd, $^{172}$Tm, $^{90}$Y, $^{111}$In, $^{169}$b, $^{175}$Yb, $^{177}$Lu, $^{105}$Rh, $^{111}$Ag, $^{213}$Bi, $^{225}$Ac, $^{64}$Cu, $^{177m}$Sn and $^{227}$Th, preferably the radioactive metal is selected from the group comprising $^{186}$Re, $^{188}$Re, $^{90}$Y, $^{153}$Sm, $^{68}$Ga, and $^{177}$Lu; and more preferably the radioactive metal is selected from the group comprising $^{90}$Y and $^{177}$Lu.

EMBODIMENT 102

The conjugate of any one of embodiments 93 to 99, wherein Effector is a radionuclide, wherein preferably the radionuclide is covalently bound by Acceptor, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

EMBODIMENT 103

The conjugate of embodiment 102, wherein the radionuclide is a radioactive halogen.

EMBODIMENT 104

The conjugate of embodiment 103, wherein the radioactive halogen is selected from the group comprising $^{123}$I, $^{125}$I and $^{129}$I.

EMBODIMENT 105

The conjugate of any one of embodiments 1 to 78, for use in a method for the identification of a subject, wherein the subject is likely to respond or likely not to respond to a treatment of a disease, wherein the method for the identification of a subject comprises carrying out a method of diagnosis using the compound of any one of embodiments 1

EMBODIMENT 106

The conjugate of any one of embodiments 1 to 78, for use in a method for the selection of a subject from a group of subjects, wherein the subject is likely to respond or likely not to respond to a treatment of a disease, wherein the method for the selection of a subject from a group of subjects comprises carrying out a method of diagnosis using the compound of any one of embodiments 1 to 78, preferably a method for the diagnosis of a disease as described in any one of embodiments 79 to 92.

EMBODIMENT 107

The conjugate of any one of embodiments 1 to 78, for use in a method for the stratification of a group of subjects into subjects which are likely to respond to a treatment of a disease, and into subjects which are not likely to respond to a treatment of a disease, wherein the method for the stratification of a group of subjects comprises carrying out a method of diagnosis using the compound of any one of embodiments 1 to 78, preferably a method for the diagnosis of a disease as described in any one of embodiments 79 to 92.

EMBODIMENT 108

The conjugate of any one of embodiments 105 to 107, wherein the disease is a disease involving neurotensin receptor, preferably the disease is a disease involving neurotensin receptor 1.

EMBODIMENT 109

The conjugate of embodiment 108, wherein the disease is a disease not involving tissue of the central nervous system and/or cells of the central nervous system.

EMBODIMENT 110

The conjugate of any one of embodiments 105 to 109, wherein the disease is selected from the group comprising tumors and hematological malignancies.

EMBODIMENT 111

The conjugate of embodiment 110, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma, Ewing's sarcoma, and indications subject to group A as defined herein.

EMBODIMENT 112

The conjugate of any one of embodiments 105 to 111, wherein the method of diagnosis is an imaging method.

EMBODIMENT 113

The conjugate of embodiment 112, wherein the imaging method is selected from the group comprising scintigraphy, Single Photon Emission Computed Tomography (SPECT) and Positron Emission Tomography (PET).

EMBODIMENT 114

The conjugate of any one of embodiments 105 to 113, preferably any one of embodiments 112 and 113, wherein Effector is a radioactive metal, wherein preferably the radioactive metal is chelated by Acceptor, wherein Acceptor is a chelator.

EMBODIMENT 115

The conjugate of any one of embodiments 105 to 113, preferably any one of embodiments 112 and 113, wherein Effector is a radioactive halogen, wherein preferably the radioactive halogen is covalently bound by Acceptor, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

EMBODIMENT 116

The conjugate of any one of embodiments 1 to 78, for use in a method for delivering an effector to neurotensin receptor, preferably neurotensin receptor 1, or for use in a method for delivering an effector to a target targeted by either the first tarteing moiety TM1 or the second targeting moiety TM2, wherein the effector is selected from the group comprising a diagnostically active agent and a therapeutically active agent.

EMBODIMENT 117

The conjugate of embodiment 116, wherein the neurotensin receptor is expressed by a cell and/or a tissue, wherein preferably the neurotensin expressing cell and/or neurotensin expressing tissue is different from a cell of the central nervous system and/or tissue of the central nervous system.

EMBODIMENT 118

The conjugate of any one of embodiments 116 to 117, wherein the NTR1 expressing tissue is NTR1 expressing tissue of a tumor or NTR1 expressing tissue of a hematological malignancy, and wherein the NTR1 expressing cell is a NTR1 expressing tumor cell or an NTR1 expressing hematological malignancy cell.

EMBODIMENT 119

The conjugate of embodiment 118, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma, Ewing's sarcoma, and indications subject to group A as defined herein.

EMBODIMENT 120

The conjugate of any one of embodiments 105 to 119, wherein the effector is a radionuclide, preferably a metal radioactive or a halogen radioactive, more preferably the effector is Effector of the compound of any one of embodiments 1 to 78.

EMBODIMENT 121

The conjugate of any one of embodiments 116 to 120, wherein the method comprises the administration of an effective amount of the compound and/or of the effector to a subject, preferably to a mammal, wherein the mammal is selected from the group comprising man, companion animals, pets and livestock, more preferably the subject is selected from the group comprising man, dog, cat, horse and cow, and most preferably the subject is a human being.

EMBODIMENT 122

The conjugate of any one of embodiments 116 to 121, wherein the delivery is for diagnosis, treatment and/or a combination of diagnosis and treatment.

EMBODIMENT 123

The conjugate of any one of embodiments 121 to 122, wherein the effective amount is a diagnostically effective amount and/or a therapeutically effective amount.

EMBODIMENT 124

A composition, preferably a pharmaceutical composition, wherein the composition comprises a compound according to any one of embodiments 1 to 78 and a pharmaceutically acceptable excipient.

EMBODIMENT 125

The composition of embodiment 124 for use in any method as defined in any of the preceding embodiments.

EMBODIMENT 126

A method for the diagnosis of a disease in a subject, wherein the method comprises administering to the subject a diagnostically effective amount of a compound according to any one of embodiments 1 to 78.

EMBODIMENT 127

The method of embodiment 126, wherein the conjugate comprises a diagnostically active agent, whereby the agent is preferably a radionuclide.

EMBODIMENT 128

A method for the treatment of a disease in a subject, wherein the method comprises administering to the subject a therapeutically effective amount of a conjugate according to any one of embodiments 1 to 79.

EMBODIMENT 129

The method of embodiment 128, wherein the conjugate comprises a therapeutically active agent, whereby the agent is preferably a radionuclide.

EMBODIMENT 130

The method according to any one of embodiments 126 to 129, wherein the disease is a disease involving neurotensin receptor, preferably the disease is a disease involving neurotensin receptor 1, or from a disease involving a target targeted by the first targeting moiety TM1 or by the second targeting moiety TM2.

EMBODIMENT 131

The method according to any one of embodiments 126 to 129, wherein the disease is selected from the group comprising tumors and hematological malignancies.

EMBODIMENT 132

A kit comprising a conjugate according to any one of embodiments 1 to 78, one or more optional excipient(s) and optionally one or more device(s), whereby the device(s) is/are selected from the group comprising a labeling device, a purification device, a handling device, a radioprotection device, an analytical device or an administration device.

EMBODIMENT 133

The kit of embodiment 132 for use in any method as defined in any of the preceding embodiments.

The present invention is based on the surprising finding of the present inventors that the conjugate of the invention is not only binding to NTR1 with a high affinity, but is also not crossing the blood-brain barrier. This characteristic allows the use of the conjugate of the invention in the diagnosis as well as in the treatment of diseases such as, but not limited to, tumors, particularly tumors different from tumors of the central nervous system in its various forms, more particularly those forms thereof which require passage of the diagnostically and/or therapeutically effective agent across the blood-brain barrier. Along with these characteristics go a high and persistent uptake by tumors and NTR1 expressing tumors in particular as well as NTR1 expressing hematological malignancies, combined with a low uptake and rapid clearance in non-target organs thus providing an excellent tumor-to-background ratio. Using the compound of the invention, the tumor-to-background ratio is at least 1.5, preferably greater than 2, and more preferably greater than 5. The tumor-to-background ratio is preferably defined as the signal intensity of the tumor divided by the background signal intensity. Signal intensities are typically measured with a region-of-interest (ROI) analysis of the tumor and ROI analysis of surrounding healthy tissue as background (see Palmedo et al., *Nucl Med Biol,* 2002, 29, 809-815). The above finding is insofar even more surprising as the conjugate of the invention comprises a second targeting moiety, whereby such second targeting moiety does not interfere with the binding characteristics of the first targeting moiety. Without wishing to be bound by any theory, the present inventors assume that the binding of the conjugate to NTR1 is mediated by a targeting moiety wherein such targeting moiety is a compound of formula (2):

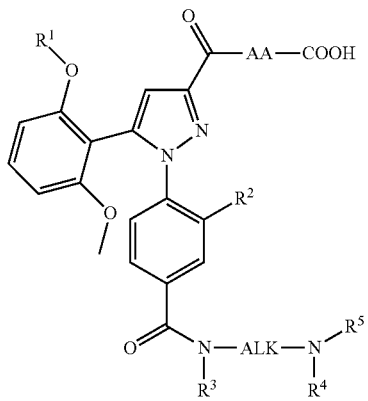
(2)

wherein
$R^3$, $R^4$ and $R^5$ are each and independently selected from the group consisting of hydrogen and $(C_1-C_4)$alkyl under the proviso that one of $R^3$, $R^4$ and $R^5$ is of the following formula (3)

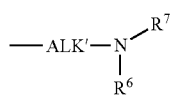
(3)

wherein
ALK' is $(C_2-C_5)$alkylidene;
$R^6$ is selected from the group consisting of hydrogen and $(C_1-C_4)$alkyl; and
$R^7$ is a bond.

A further surprising finding underlying the present invention is that by linking the compound of formula (2) to any one of the other moieties of the conjugate of the invention through a bond represented by $R^7$, such other moiety and other moieties, respectively, do not have an impact on the overall binding characteristics of the compounds of the invention to NTR1, at least not to such extent which would render the binding of the conjugate of the invention unspecific such as, preferably, resulting in an IC50 value of the conjugate of the invention to NTR1 greater than 10 µM or which would not allow the use of the conjugate of the invention in the various methods disclosed herein and in particular methods for the treatment and/or prevention of a disease as defined herein and methods for the diagnosis of a disease as defined herein. Insofar, surprisingly the position of $R^7$, i.e. the forming of a bond represented by $R^7$, does not seem to interfere with the binding of the conjugate of the invention to NTR1. Because of this, the other moieties attached to the compound of formula (2) in the conjugate of the invention can vary in a broad manner as is further supported by the example part.

In light of these surprising characteristics it is possible that, without wishing to be bound by any theory, because of the two targeting moieties more patients can be positively diagnosed and treated, respectively, within an indication. Also, it is possible that more lesions can be diagnosed and treated, respectively, per patient. Also it is possible that a lesion can be treated more homogenously and thereby more efficiently if the two targeting moieties of the conjugate of the invention target different targets and if the targets are heterogeneously expressed within the lesion but each of the targets of the conjugate of the invention is differently expressed as to its expression level and/or spatial expression pattern. Additionally, it is thus possible to diagnose and treat, respectively, tumors expressing a target with low density, such as, for example 5000 copies of the target or less per tumor cell while said tumors express a second target with high density, such as, for example, more than 5000 copies of the second target per tumor cell. Additionally, it is thus possible to diagnose and treat, respectively, tumors expressing a first target with low density, such as, for example 5000 copies of the target or less per tumor cell while said tumors express any number of copies of a second target targeted by a conjugate of the invention. Consequently, also due to avidity and re-binding effects a longer retention time is achieved which goes along with a higher effective dose and thus improvement in diagnosis and therapy of the respective disease. Due to the binding characterisitics of the conjugate of the invention it is also possible to target a first target targeted by the first targeting moiety and thus a cell, tissue and organ, respectively, expressing such first target, independently from the targeting of a second target targeted by the second targeting moiety and thus a cell, tissue and organ, respectively, expressing such second target; and vice versa. Finally, the target of the invention if conjugated to an effector provides such effector in an active form despite of the effector being linked to the conjugate.

Depending on the characteristics of the first targeting moiety of the conjugate of the invention in terms of whether such first targeting moiety is an agonist or an antagonist of the target targeted by the first targeting moiety and the characteristics of the second targeting moiety of the conjugate of the invention in terms of whether such second targeting moiety is an agonist or an antagonist of the target targeted by the second targeting moiety, the overall characteristics of the conjugate of the invention be more of an agonist or more of an antagonist. For example, in case the first targeting moiety is targeting NTR1 the first targeting moiety is typically an antagonist; if under such conditions the second targeting moiety is targeting a second target which, in an embodiment, is different from NTR1 or which, in an alternative embodiment is NTR1, and such second targeting moiety also acts as an antagonist of such second target, the conjugate of the invention is typically regarded as an antagonist; if, however, the second targeting moiety is targeting a second target which, in an embodiment, is different from NTR1 or which, in an alternative embodiment, is NTR1 and such second targeting moiety acts as an agonist of such second target, the conjugate of the invention inherently bears both the characteristic of an antagonist and of an agonist. In an embodiment of the conjugate of the invention such conjugate is internalized by a cell, whereby preferably such internalization renders the effector, i.e. the diagnostically active effector and/or the therapeutically active effector, diagnostically effective and, respectively, therapeutically effective. In a preferred embodiment of the conjugate of the invention the conjugate comprises a targeting moiety which acts as an agonist of the target targeted by such targeting moiety and wherein such agonist activity leads to internalization into a cell of the conjugate of the invention In an embodiment the conjugate of the invention is an antagonist to NTR1. The suitability of an antagonist to NTR1 for use in the diagnosis and/or therapy of diseases and diseases involving NTR1 expressing cells and NTR1 expressing tissue in particular, is a surprising finding. The prevailing understanding in the art is that in order to provide a suitable means for diagnosis and/or therapy of such diseases an agonist to NTR1 is to be used, particularly if the diagnostically active agent or the therapeutically active agent, generally referred to as effector, is a radiolabel such as a radionuclide. The rationale behind this understanding in the art is that an effective in vivo diagnosis and therapy, particular in case such diagnosis and therapy makes use of a radiolabel such as a radionuclide attached to a compound having an affinity to a target molecule such as a receptor, requires that such compound shows good internalization properties leading to a high in vivo accumulation and retention of the compound and thus of the effector in the tissue and cells, respectively, expressing the target molecule. As well-known from molecular-pharmacologic investigations efficient internalization is usually provided predominantly by agonists (Bodei et al., *J. Nucl. Med.*, 2006, 47, 375-377; Koenig et al., *Trends Pharmacol. Sci.*, 1997, 18, 276-287; Cescato et al., *J. Nucl. Med.*, 2006, 47, 502-511; Ginj et al., *Proc. Natl. Acad. Sci. USA*, 2006, 103, 16436-16441) thus suggesting the use of target molecule agonists rather than target molecule antagonists. In accordance therewith and as evident from the prior art recited above, the compound suitable for use in the diagnosis and/or therapy of a disease whereby the disease involves NTR1 expressing cells and NTR1 expressing tissue, respectively, is to produce or elicit a diagnostic or therapeutic effect by NTR1 upon interaction with NTR1, whereby the compound is subsequently internalized into NTR1 expressing cells. Because of this, this kind of compound of the prior art acts as an agonist to NTR1. Such internalization preferably occurs by means of endocytosis. In contrast thereto, an antagonist to NTR1 as the conjugate of the invention counteracts the effect of an agonist to NTR1 and is preferably not internalized into NTR1 expressing cells. In connection therewith it is noteworthy that the present inventors found that the conjugate of the invention surprisingly binds to a higher number of binding sites compared to an agonist of comparable binding affinity.

The expression alkyl as preferably used herein refers each and individually to a saturated, straight-chain or branched hydrocarbon group and is usually accompanied by a qualifier which specifies the number of carbon atoms it may contain. For example the expression $(C_1-C_6)$alkyl means each and individually any of methyl, ethyl, n-propyl, isopropyl, n-butyl, isobutyl, sec-butyl, tert-butyl, n-pentyl, 1-methyl-butyl, 1-ethyl-propyl, 3-methyl-butyl, 1,2-dimethyl-propyl, 2-methyl-butyl, 1,1-dimethyl-propyl, 2,2-dimethylpropyl, n-hexyl, 1,1-dimethyl-butyl and any other isoform of alkyl groups containing six saturated carbon atoms.

In an embodiment and as preferably used herein, $(C_1-C_4)$ alkyl means each and individually any of methyl, ethyl, n-propyl, isopropyl, n-butyl, isobutyl, sec-butyl and tert-butyl.

In an embodiment and as preferably used herein, $(C_2-C_5)$ alkyl means each and individually any of ethyl, n-propyl, isopropyl, n-butyl, isobutyl, sec-butyl, tert-butyl, n-pentyl, 2-pentyl, 2-methyl-butyl, 3-methyl-butyl, 3-pentyl, 3-methyl-but-2-yl, 2-methyl-but-2-yl and 2,2-dimethylpropyl.

In an embodiment and as preferably used herein, $(C_1-C_5)$ alkyl means each and individually any of methyl, ethyl, n-propyl, isopropyl, n-butyl, isobutyl, sec-butyl, tert-butyl, n-pentyl, 2-pentyl, 2-methyl-butyl, 3-methyl-butyl, 3-pentyl, 3-methyl-but-2-yl, 2-methyl-but-2-yl and 2,2-dimethylpropyl.

In an embodiment and as preferably used herein, $(C_1-C_6)$ alkyl means each and individually any of methyl, ethyl, n-propyl, n-butyl, isobutyl, sec-butyl, tert-butyl, n-pentyl, 2-pentyl, 2-methyl-butyl, 3-methyl-butyl, 3-pentyl, 3-methyl-but-2-yl, 2-methyl-but-2-yl, 2,2-dimethylpropyl, n-hexyl, 2-hexyl, 2-methyl-pentyl, 3-methyl-pentyl, 4-methyl-pentyl, 3-hexyl, 2-ethyl-butyl, 2-methyl-pent-2-yl, 2,2-dimethyl-butyl, 3,3-dimethyl-butyl, 3-methyl-pent-2-yl, 4-methyl-pent-2-yl, 2,3-dimethyl-butyl, 3-methyl-pent-3-yl, 2-methyl-pent-3-yl, 2,3-dimethyl-but-2-yl and 3,3-dimethyl-but-2-yl.

In an embodiment and as preferably used herein, $(C_1-C_5)$ alkyl refers to a saturated or unsaturated, straight-chain or branched hydrocarbon group having from 1 to 8 carbon atoms. Representative $(C_1-C_8)$alkyl groups include, but are not limited to, any of methyl, ethyl, n-propyl, isopropyl, n-butyl, isobutyl, sec-butyl, tert-butyl, n-pentyl, 2-pentyl, 2-methyl-butyl, 3-methyl-butyl, 3-pentyl, 3-methyl-but-2-yl, 2-methyl-but-2-yl, 2,2-dimethylpropyl, n-hexyl, 2-hexyl, 2-methyl-pentyl, 3-methyl-pentyl, 4-methyl-pentyl, 3-hexyl, 2-ethyl-butyl, 2-methyl-pent-2-yl, 2,2-dimethyl-butyl, 3,3-dimethyl-butyl, 3-methyl-pent-2-yl, 4-methyl-pent-2-yl, 2,3-dimethyl-butyl, 3-methyl-pent-3-yl, 2-methyl-pent-3-yl, 2,3-dimethyl-but-2-yl, 3,3-dimethyl-but-2-yl, n-heptyl, 2-heptyl, 2-methyl-hexyl, 3-methyl-hexyl, 4-methyl-hexyl, 5-methyl-hexyl, 3-heptyl, 2-ethyl-pentyl, 3-ethyl-pentyl, 4-heptyl, 2-methyl-hex-2-yl, 2,2-dimetyhl-pentyl, 3,3-dimetyhl-pentyl, 4,4-dimetyhl-pentyl, 3-methyl-hex-2-yl, 4-methyl-hex-2-yl, 5-methyl-hex-2-yl, 2,3-dimethyl-pentyl, 2,4-dimethyl-pentyl, 3,4-dimethyl-pentyl, 3-methyl-hex-3-yl, 2-ethyl-2-methyl-butyl, 4-methyl-hex-3-yl, 5-methyl-hex-3-yl, 2-ethyl-3-methyl-butyl, 2,3-dimethyl-pent-2-yl, 2,4-dimethyl-pent-2-yl, 3,3-dimethyl-pent-2-yl, 4,4-dimethyl-pent-2-yl, 2,2,3-trimethyl-butyl, 2,3,3-trimethyl-butyl, 2,3,3-trimethyl-but-2-yl, n-octyl, 2-octyl, 2-methyl-heptyl, 3-methyl-heptyl, 4-methyl-heptyl, 5-methyl-heptyl, 6-methyl-heptyl, 3-octyl, 2-ethyl-hexyl, 3-ethyl-hexyl, 4-ethyl-hexyl, 4-octyl, 2-propyl-pentyl, 2-methyl-hept-2-yl, 2,2-dimethyl-hexyl, 3,3-dimethyl-hexyl, 4,4-dimethyl-hexyl, 5,5-dimethyl-hexyl, 3-methyl-hept-2-yl, 4-methyl-hept-2-yl, 5-methyl-hept-2-yl, 6-methyl-hept-2-yl, 2,3-dimethyl-hex-1-yl, 2,4-dimethyl-hex-1-yl, 2,5-dimethyl-hex-1-yl, 3,4-dimethyl-hex-1-yl, 3,5-dimethyl-hex-1-yl, 3,5-dimethyl-hex-1-yl, 3-methyl-hept-3-yl, 2-ethyl-2-methyl-1-yl, 3-ethyl-3-methyl-1-yl, 4-methyl-hept-3-yl, 5-methyl-hept-3-yl, 6-methyl-hept-3-yl, 2-ethyl-3-methyl-pentyl, 2-ethyl-4-methyl-pentyl, 3-ethyl-4-methyl-pentyl, 2,3-dimethyl-hex-2-yl, 2,4-dimethyl-hex-2-yl, 2,5-dimethyl-hex-2-yl, 3,3-dimethyl-hex-2-yl, 3,4-dimethyl-hex-2-yl, 3,5-dimethyl-hex-2-yl, 4,4-dimethyl-hex-2-yl, 4,5-dimethyl-hex-2-yl, 5,5-dimethyl-hex-2-yl, 2,2,3-trimethyl-pentyl, 2,2,4-trimethyl-pentyl, 2,3,3-trimethyl-pentyl, 2,3,4-trimethyl-pentyl, 2,4,4-trimethyl-pentyl, 3,3,4-trimethyl-pentyl, 3,4,4-trimethyl-pentyl, 2,3,3-trimethyl-pent-2-yl, 2,3,4-trimethyl-pent-2-yl, 2,4,4-trimethyl-pent-2-yl, 3,4,4-trimethyl-pent-2-yl, 2,2,3,3-tetramethyl-butyl, 3,4-dimethyl-hex-3-yl, 3,5-dimethyl-hex-3-yl, 4,4-dimethyl-hex-3-yl, 4,5-dimethyl-hex-3-yl, 5,5-dimethyl-hex-3-yl, 3-ethyl-3-methyl-pent-2-yl, 3-ethyl-4-methyl-pent-2-yl, 3-ethyl-hex-3-yl, 2,2-diethyl-butyl, 3-ethyl-3-methyl-pentyl, 4-ethyl-hex-3-yl, 5-methyl-hept-3-yl, 2-ethyl-3-methyl-pentyl, 4-methyl-hept-4-yl, 3-methyl-hept-4-yl, 2-methyl-hept-4-yl, 3-ethyl-hex-2-yl, 2-ethyl-2-methyl-pentyl, 2-isopropyl-pentyl, 2,2-dimethyl-hex-3-yl, 2,2,4-trimethyl-pent-3-yl and 2-ethyl-3-methyl-pentyl. A $(C_1-C_8)$alkyl group can be unsubstituted or substituted with one or more groups, including, but not limited to, $(C_1-C_8)$alkyl, —O—[$(C_1-C_8)$alkyl], -aryl, —CO—R', —O—CO—R', —CO—OR', —CO—NH$_2$, —CO—NHR', —CO—NR', —CO—NR'$_2$, —NH—CO—R', —SO$_2$—R', —SO—R', —OH, -halogen, —N$_3$, —NH$_2$, —NHR', —NR'$_2$ and —CN; where each R' is independently selected from —(C$_1$-C$_5$)alkyl and aryl.

In an embodiment and as preferably used herein, (C$_3$-C$_6$) alkyl means each and individually any of n-propyl, isopropyl, n-butyl, isobutyl, sec-butyl, tert-butyl, n-pentyl, 2-pentyl, 2-methyl-butyl, 3-methyl-butyl, 3-pentyl, 3-methyl-but-2-yl, 2-methyl-but-2-yl, 2,2-dimethylpropyl, n-hexyl, 2-hexyl, 2-methyl-pentyl, 3-methyl-pentyl, 4-methyl-pentyl, 3-hexyl, 2-ethyl-butyl, 2-methyl-pent-2-yl, 2,2-dimethyl-butyl, 3,3-dimethyl-butyl, 3-methyl-pent-2-yl, 4-methyl-pent-2-yl, 2,3-dimethyl-butyl, 3-methyl-pent-3-yl, 2-methyl-pent-3-yl, 2,3-dimethyl-but-2-yl and 3,3-dimethyl-but-2-yl.

The expression alkylidene as preferably used herein refers to a saturated straight chain or branched hydrocarbon group wherein two points of substitution are specified. Simple alkyl chains wherein the two points of substitutions are in a maximal distance to each other like methane-1,1-diyl, ethane-1,2-diyl, propane-1,3-diyl, butane-1,4-diyl and pentane-1,5-diyl are also referred to as methylene (which is also referred to as methane-1,1-diyl), ethylene (which is also referred to as ethane-1,2-diyl), propylene (which is also referred to as propane-1,3-diyl), butylene (which is also referred to as butane-1,4-diyl) and pentylene (which is also referred to as pentane-1,5-diyl).

In an embodiment and as preferably used herein, (C$_1$-C$_4$) alkylidene means each and individually any of methylene, ethane-1,2-diyl, propane-1,3-diyl, propane-1,2-diyl, butane-1,4-diyl, butane-1,3-diyl, butane-1,2-diyl, 2-methyl-propane-1,2-diyl and 2-methyl-propane-1,3-diyl.

In an embodiment and as preferably used herein, (C$_2$-C$_5$) alkylidene means each and individually any of ethane-1,2-diyl, propane-1,3-diyl, propane-1,2-diyl, butane-1,4-diyl, butane-1,3-diyl, butane-1,2-diyl, 2-methyl-propane-1,2-diyl, 2-methyl-propane-1,3-diyl, pentane-1,5-diyl, pentane-1,4-diyl, pentane-1,3-diyl, pentane-1,2-diyl, pentane-2,3-diyl, pentane-2,4-diyl and any other branched isomer with 5 carbon atoms, preferably (C$_2$-C$_5$)alkylidene means each and individually any of ethane-1,2-diyl, propane-1,3-diyl, butane-1,4-diyl and pentane-1,5-diyl.

In an embodiment and as preferably used herein, (C$_2$-C$_{10}$)alkylidene means each and individually any of ethane-1,2-diyl, propane-1,3-diyl, propane-1,2-diyl, butane-1,4-diyl, butane-1,3-diyl, butane-1,2-diyl, 2-methyl-propane-1,2-diyl, 2-methyl-propane-1,3-diyl, pentane-1,5-diyl, pentane-1,4-diyl, pentane-1,3-diyl, pentane-1,2-diyl, pentane-2,3-diyl, pentane-2,4-diyl, any other isomer with 5 carbon atoms, hexane-1,6-diyl, any other isomer with 6 carbon atoms, heptane-1,7-diyl, any other isomer with 7 carbon atoms, octane-1,8-diyl, any other isomer with 8 carbon atoms, nonane-1,9-diyl, any other isomer with 9 carbon atoms, decane-1,10-diyl and any other isomer with 10 carbon atoms, preferably (C$_2$-C$_{10}$) alkylidene means each and individually any of ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl and decane-1,10-diyl.

In an embodiment and as preferably used herein, (C$_1$-C$_{10}$)alkylidene means each and individually any of methylene, ethane-1,2-diyl, propane-1,3-diyl, propane-1,2-diyl, butane-1,4-diyl, butane-1,3-diyl, butane-1,2-diyl, 2-methyl-propane-1,2-diyl, 2-methyl-propane-1,3-diyl, pentane-1,5-diyl, pentane-1,4-diyl, pentane-1,3-diyl, pentane-1,2-diyl, pentane-2,3-diyl, pentane-2,4-diyl, any other isomer with 5 carbon atoms, hexane-1,6-diyl, any other isomer with 6 carbon atoms, heptane-1,7-diyl, any other isomer with 7 carbon atoms, octane-1,8-diyl, any other isomer with 8 carbon atoms, nonane-1,9-diyl, any other isomer with 9 carbon atoms, decane-1,10-diyl and any other isomer with 10 carbon atoms, preferably (C$_1$-C$_{10}$) alkylidene means each and individually any of methylene, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl and decane-1,10-diyl. A (C$_1$-C$_{10}$)alkylidene group can be unsubstituted or substituted with one or more groups, including, but not limited to, (C$_1$-C$_8$)alkyl, —O—[(C$_1$-C$_5$)alkyl], -aryl, —CO—R', —O—CO—R', —CO—OR', —CO—NH$_2$, —CO—NHR', —CO—NR'$_2$, —NH—CO—R', —SO$_2$—R', —SO—R', —OH, -halogen, —N$_3$, —NH$_2$, —NHR', —NR'$_2$ and —CN; where each R' is independently selected from —(C1-C5)alkyl and aryl.

In an embodiment and as preferably used herein, "Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —(C$_1$-C$_8$) alkyl, —O—[(C$_1$-C$_8$)alkyl], -aryl, —CO—R', —O—CO—R', —CO—OR', —CO—NH$_2$, —CO—NHR', —CO—NR', —CO—NR'$_2$, —NH—CO—R', —SO$_2$—R', —SO—R', —OH, -halogen, —N$_3$, —NH$_2$, —NHR', —NR'$_2$ and —CN; where each R' is independently selected from —(C$_1$-C$_5$) alkyl and aryl.

In an embodiment and as preferably used herein, (C$_3$-C$_8$) cycloalkyl means each and individually any of cyclopropyl, cyclobutyl, cyclopentyl, cyclohexyl, cycloheptyl and cyclooctyl.

In an embodiment and as preferably used herein, (C$_3$-C$_8$) carbocycle refers to a 3-, 4-, 5-, 6-, 7- or 8-membered saturated or unsaturated non-aromatic carbocyclic ring. Representative (C$_3$-C$_8$)carbocycles include, but are not limited to, any of -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cylooctadienyl. A (C$_3$-C$_8$)carbocycle group can be unsubstituted or substituted with one or more groups, including, but not limited to, (C$_1$-C$_5$)alkyl, —O—[(C$_1$-C$_5$)alkyl], -aryl, —CO—R', —O—CO—R', —CO—OR', —CO—NH$_2$, —CO—NHR', —CO—NR'$_2$, —NH—CO—R', —SO$_2$—R', —SO—R', —OH, -halogen, —N$_3$, —NH$_2$, —NHR', —NR'$_2$ and —CN; where each R' is independently selected from —(C$_1$-C$_5$)alkyl and aryl.

In an embodiment and as preferably used herein, (C$_3$-C$_8$) carbocyclo refers to a (C$_3$-C$_8$)carbocycle group defined above wherein one of the carbocycles group hydrogen atoms is replaced with a bond.

In an embodiment and as preferably used herein, (C$_3$-C$_8$) cycloalkylmethyl means each and individually any of cyclopropylmethyl, cyclobutylmethyl, cyclopentylmethyl, cyclohexylmethyl, cycloheptylmethyl and cyclooctylmethyl.

In an embodiment and as preferably used herein, arylene refers to an aryl group which has two covalent bonds and can be in the ortho, meta, or para configurations as shown in the following structures:

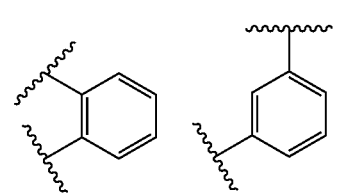

(31)

-continued

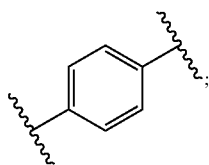

in which the phenyl group can be unsubstituted or substituted with four groups, including, but not limited to, $(C_1-C_5)$alkyl, —O—[$(C_1-C_8)$alkyl], -aryl, —CO—R', —O—CO—R', —CO—OR', —CO—NH$_2$, —CO—NHR', —CO—NR'$_2$, —NH—CO—R', —SO$_2$—R', —SO—R', —OH, -halogen, —N$_3$, —NH$_2$, —NHR', —NR'$_2$ and —CN; where each R' is independently selected from —$(C_1-C_5)$ alkyl and aryl.

In an embodiment and as preferably used herein, $(C_3-C_8)$ heterocycle refers to an aromatic or non-aromatic $(C_3-C_8)$ carbocycle in which one to four of the ring carbon atoms are independently replaced with a heteroatom from the group consisting of O, S and N. Representative examples of a $(C_3-C_8)$heterocycle include, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $(C_3-C_8)$heterocycle can be unsubstituted or substituted with up to seven groups including, $(C_1-C_8)$alkyl, —O—[$(C_1-C_5)$alkyl], -aryl, —CO—R', —O—CO—R', —CO—OR', —CO—NH$_2$, —CO—NHR', —CO—NR'$_2$, —NH—CO—R', —SO$_2$—R', —SO—R', —OH, -halogen, —N$_3$, —NH$_2$, —NHR', —NR'$_2$ and —CN; where each R' is independently selected from —$(C_1-C_5)$alkyl and aryl.

In an embodiment and as preferably used herein, $(C_3-C_8)$ heterocyclo refers to a $(C_3-C_8)$heterocycle group defined above wherein one of the carbocycles group hydrogen atoms is replaced with a bond. A $(C_3-C_8)$heterocyclo can be unsubstituted or substituted with up to six groups including, $(C_1-C_8)$alkyl, —O—[$(C_1-C_8)$alkyl], -aryl, —CO—R', —O—CO—R', —CO—OR', —CO—NH$_2$, —CO—NHR', —CO—NR'$_2$, —NH—CO—R', —SO$_2$—R', —SO—R', —OH, -halogen, —N$_3$, —NH$_2$, —NHR', —NR'$_2$ and —CN; where each R' is independently selected from —$(C_1-C_8)$ alkyl and aryl.

In an embodiment and as preferably used herein, the term "halogen" or "halogenide" means each and individually any of F, Cl, Br, I and At.

In an embodiment and as preferably used herein, the term "-succinimide-" refer to a bivalent structure according to formula (9)

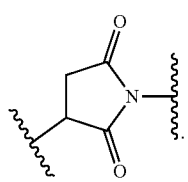

(9)

In an embodiment and as preferably used herein atoms with unspecified atomic mass numbers in any structural formula or in any passage of the instant specification including the claims are either of unspecified isotopic composition, naturally occurring mixtures of isotopes or individual isotopes. This applies in particular to halogen atoms, including, but not limited to F Cl, Br, I and At and to metal atoms, including but not limited to Sc, Cr, Mn, Co, Fe, Cu, Ga, Sr, Zr, Y, Mo, Tc, Ru, Rh, Pd, Pt, Ag, In, Sb, Sn, Te, I, Pr, Pm, Dy, Sm, Gd, Tb, Ho, Dy, Er, Yb, Tm, Lu, Sn, Re, Rd, Os, Ir, Au, Pb, Bi, Po, Fr, Ra, Ac, Th and Fm.

In an embodiment and as preferably used herein, a chelator is a compound which is capable of forming a chelate, whereby a chelate is a compound, preferably a cyclic compound where a metal or a moiety having an electron gap or a lone pair of electrons participates in the formation of the ring. More preferably, a chelator is this kind of compound where a single ligand occupies more than one coordination site at a central atom.

In some embodiments certain parts of the compounds of the invention contain amino acid sequences as provided herein. Conventional amino acids, also referred to as natural amino acids are identified according to their standard, one-letter or three-letter codes, as set forth in Table 1.

TABLE 1

Conventional amino acids and their abbreviations

| 3-letter codes | 1-letter code | Amino acids |
| --- | --- | --- |
| Ala | A | Alanine |
| Cys | C | Cysteine |
| Asp | D | Aspartic acid |
| Glu | E | Glutamic acid |
| Phe | F | Phenylalanine |
| Gly | G | Glycine |
| His | H | Histidine |
| Ile | I | Isoleucine |
| Lys | K | Lysine |
| Leu | L | Leucine |
| Met | M | Methionine |
| Asn | N | Asparagine |
| Pro | P | Proline |
| Gln | Q | Glutamine |
| Arg | R | Arginine |
| Ser | S | Serine |
| Thr | T | Threonine |
| Val | V | Valine |
| Trp | W | Tryptophan |
| Tyr | Y | Tyrosine |

Non-conventional amino acids, also referred to as non-natural amino acids, are any kind of non-oligomeric compound which comprises an amino group and a carboxylic group and is not a conventional amino acid.

Examples of non-natural amino acids, preferably used for the construction of the conjugates of the invention are identified according to their abbreviation or name found in Table 2.

TABLE 2

| Name | Structure | Abbreviation |
| --- | --- | --- |
| pyro glutamic acid | 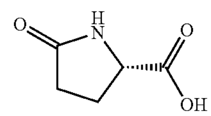 | pyroGlu |
| Amino(piperidinyl)acetic acid | 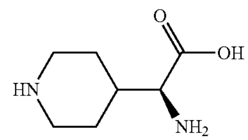 | Gly(PipAm) |
| 1,4-diaminobutyric acid | 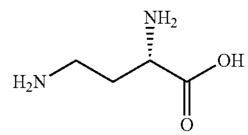 | Dab |
| 4-guanidylphenylalanine | 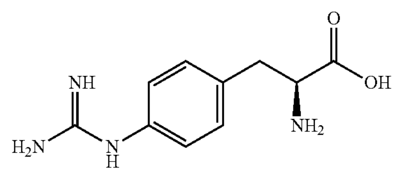 [SMILES: N=C(N)Nc1ccc(C[C@H](N)C(=O)O)cc1] | Phe(4-Gu) |
| 2,5-Dimethyltyrosine | 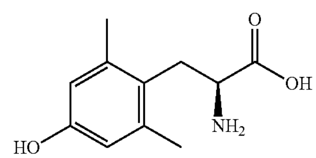 | Dmt |
| tertbutylglycine | 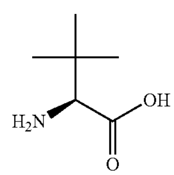 | Tle |
| neo-tryptophane | 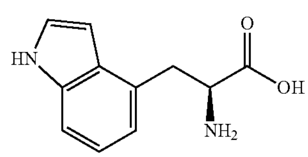 [SMILES: N[C@@H](Cc1cccc2[nH]ccc12)C(=O)O] | neo-Trp |
| cyclohexylglycine | 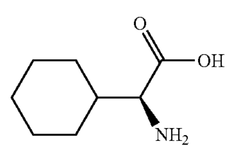 [SMILES: N[C@H](C(=O)O)C1CCCCC1] | Chg |
| 2-amino-2-adamantane carboxylic acid | 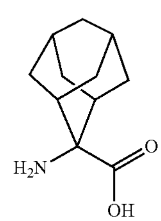 [SMILES: NC1(C(=O)O)C2CC3CC(C2)CC1C3] | |

TABLE 2-continued

| Name | Structure | Abbreviation |
| --- | --- | --- |
| 9-amino-bicyclo[3.3.1]nonane-9-carboxylic acid | 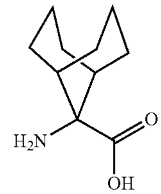 [SMILES: NC1(C(=O)O)C2CCCC1CCC2] | |
| N-(3-{2-[2-(3-Amino-propoxy)-ethoxy]-ethoxy}-propyl)-succinamic acid | 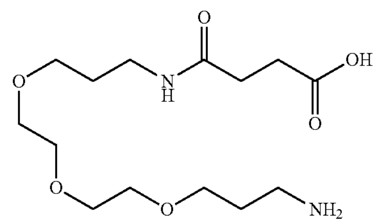 [SMILES: NCCCOCCOCCOCCCNC(=O)CCC(=O)O] | Ttds |
| β-alanine | 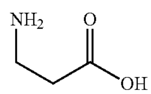 | Bal |
| γ-aminobutyric acid | 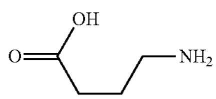 | GABA or Gab |
| aminopentanoic acid | 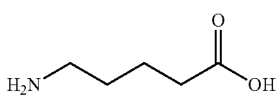 | |
| aminohexanoic acid | 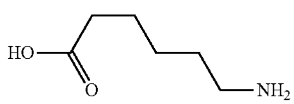 | Ahx |
| 3-aminomethyl-benzoic acid | 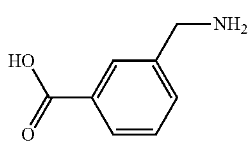 [SMILES: NCc1cccc(C(=O)O)c1] | |
| 4-aminomethyl-benzoic acid | 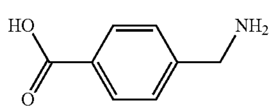 | |
| anthranilic acid | 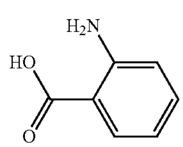 | |
| 3-amino benzoic acid | 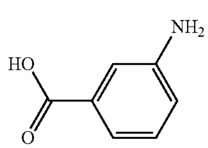 | |
| 4-amino benzoic acid | 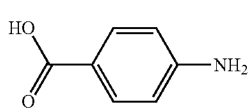 | |

TABLE 2-continued

| Name | Structure | Abbreviation |
| --- | --- | --- |
| 1,3-diamino propionic acid | 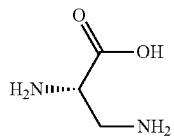 | Dap or Dpr |
| Homolysine | 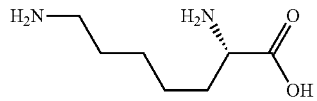 | |
| 2-aminoadipic acid | 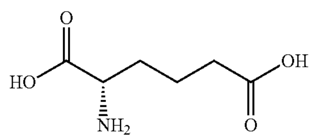 | |
| α-aminosuberic acid | 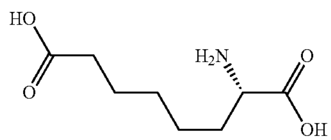 [SMILES: N[C@@H](CCCCCC(=O)O)C(=O)O] | |
| N-carboxymethyl-β-alanine | 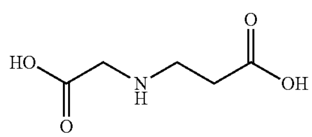 | |
| 3(2-carboxyethylamino) propanoic acid | 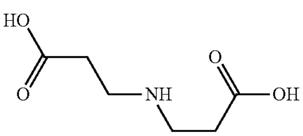 [SMILES: O=C(O)CCNCCC(=O)O] | |
| 4,4-bis(N,N-dibutyric acid) | 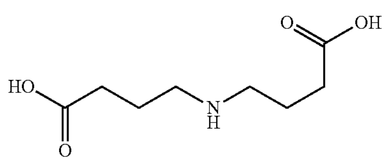 [SMILES: O=C(O)CCCNCCCC(=O)O] | |
| N-(2-Aminoethyl)glycine | 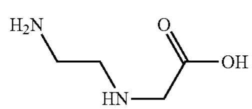 | |
| N-(5-aminopentyl)-glycine | 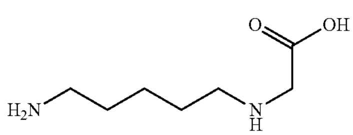 [SMILES: NCCCCCNCC(=O)O] | |
| 4-amino-3-pyrrolidinecarboxylic acid | 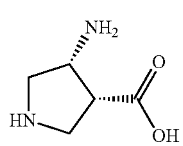 | |
| 3-amino-proline | 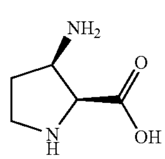 | |

TABLE 2-continued

| Name | Structure | Abbreviation |
| --- | --- | --- |
| 4-amino-proline | 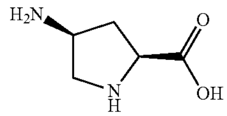 | |
| 2,3-dicarboxypyrrolidine | 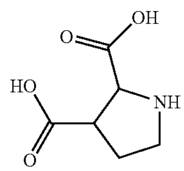 [SMILES: O=C(O)C1CCNC1C(=O)O] | |
| pyrrolidine-2,4-dicarboxylate | 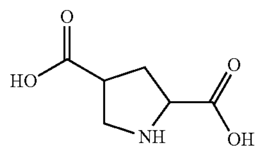 [SMILES: O=C(O)C1CNC(C(=O)O)C1] | |
| 3,5-diaminobenzoic acid | 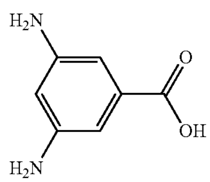 [SMILES: Nc1cc(N)cc(C(=O)O)c1] | |
| 3,5-bis-aminomethyl-benzoic acid | 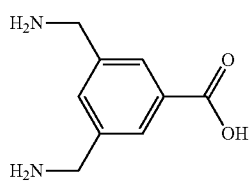 | |
| 5-aminoisophthalic acid | 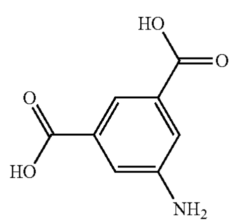 [SMILES: Nc1cc(C(=O)O)cc(C(=O)O)c1] | |
| Citrulline | 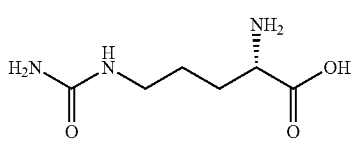 [SMILES: NC(=O)NCCC[C@H](N)C(=O)O] | Cit |
| Hydroxyproline | 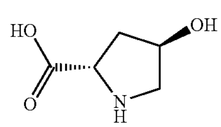 | Hyp |
| Cyclohexylalanine | 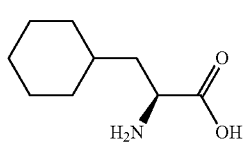 [SMILES: N[C@@H](CC1CCCCC1)C(=O)O] | Cha |

TABLE 2-continued

| Name | Structure | Abbreviation |
|---|---|---|
| Ornithine | 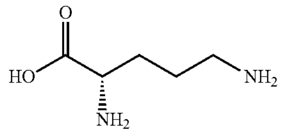 | Orn |
| octahydroindol-2-carbonic acid | 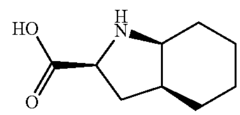 [SMILES: O=C(O)[C@@H]1C[C@@H]2CCCC[C@@H]2N1] | Oic |
| α-methyl-L-phenylalanine | 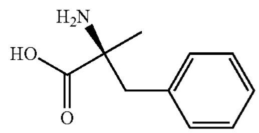 | Amf |
| D-2-Naphtylalanine | 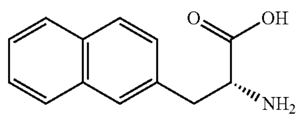 [SMILES: N[C@H](Cc1ccc2ccccc2c1)C(=O)O] | nal |
| N-(4-aminobutyl)-glycine | 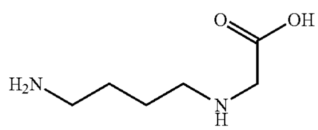 | |
| 2-Aminoindane-2-carboxylic acid | 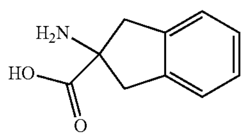 [SMILES: NC1(C(=O)O)Cc2ccccc2C1] | |
| Aminooxyacetic acid | 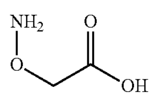 | |
| 1-Amino-(4-N-piperidinyl)carboxylic acid | 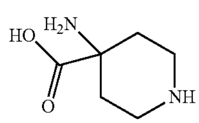 | |
| N-(3-aminopropyl)-glycine | 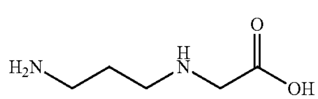 | |
| D-Azetidine-2-carboxylic acid | 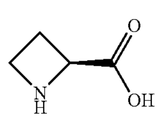 | |
| β-Homoglutamatic acid | 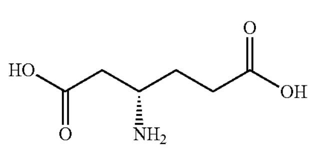 [SMILES: N[C@@H](CCC(=O)O)CC(=O)O] | |
| β-Homolysine | 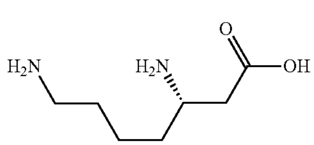 | |

TABLE 2-continued

| Name | Structure | Abbreviation |
|---|---|---|
| β-Homoleucine | 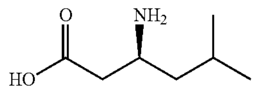 | |
| β-Homoasparagine | 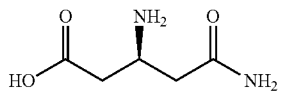 | |
| β-Homoglutamine | 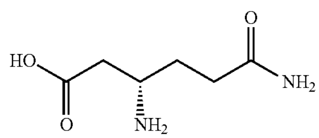 [SMILES: NC(=O)CC[C@H](N)CC(=O)O] | |
| β-Homoarginine | 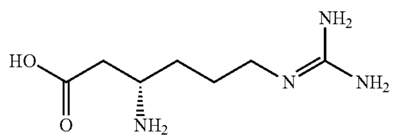 [SMILES: NC(N)=NCCC[C@H](N)CC(=O)O] | |
| β-Homoserine | 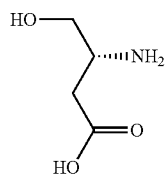 | |
| β-Homotyrosine | 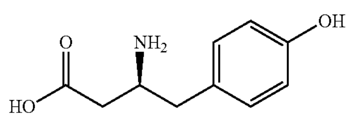 [SMILES: N[C@H](CC(=O)O)Cc1ccc(O)cc1] | |
| L-3-Benzothienylalanine | 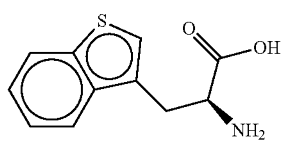 | |
| Carboxymethylen cysteine | 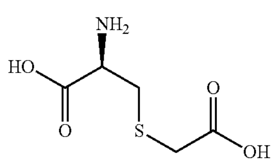 [SMILES: N[C@@H](CSCC(=O)O)C(=O)O] | |
| L-Cyclopentylglycine | 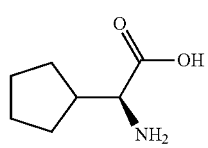 | |
| 5,5-Dimethyl-D-thiazolidine-4-carboxylic acid | 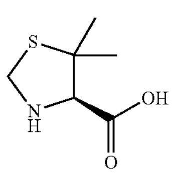 | |
| 3,4-Dihydroxyphenylalanine | 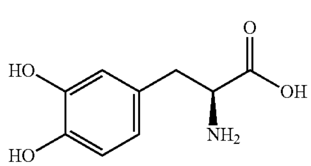 [SMILES: N[C@@H](Cc1ccc(O)c(O)c1)C(=O)O] | |

TABLE 2-continued

| Name | Structure | Abbreviation |
| --- | --- | --- |
| 1-Amino-cyclopentane-1-carboxylic acid | 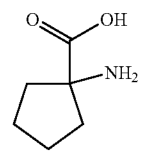 | |
| 1-amino-cyclohexane-1-carboxylic acid | 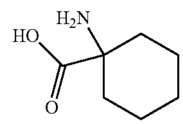 | |
| L-methionine-sulphone | 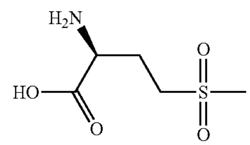 | Moo |
| N-(cyclohexyl)-glycine | 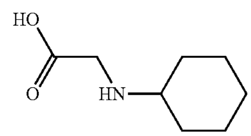 [SMILES: O=C(O)CNC1CCCCC1] | |
| 4-Nitrophenyl alanine | 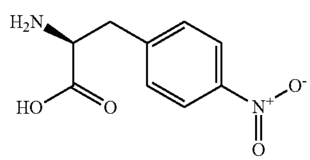 [SMILES: N[C@@H](Cc1ccc([N+](=O)[O-])cc1)C(=O)O] | |
| N-Methyl-asparagine | 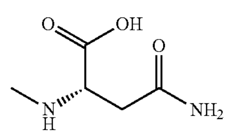 | Nmn |
| Ornithine-(pyrazin-carboxylate) | 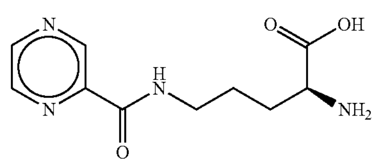 | |
| Pipecolic acid | 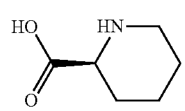 | |
| L-Tyrosinmethylether | 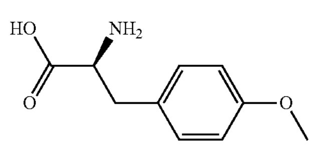 | |
| L-Phosphotyrosine | 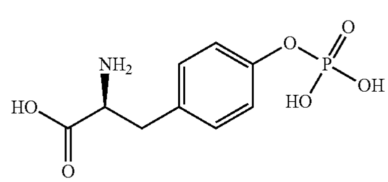 [SMILES: N[C@@H](Cc1ccc(OP(=O)(O)O)cc1)C(=O)O] | |
| N-Methylglycine | 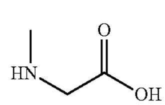 | Nmg or Sar |

TABLE 2-continued

| Name | Structure | Abbreviation |
|---|---|---|
| L-2-Thienylalanine | 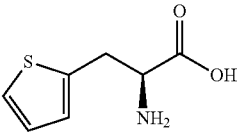 [SMILES: N[C@@H](Cc1cccs1)C(=O)O] | |
| D-thiazolidine-4-carboxylic acid | 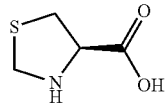 | |
| 3-Nitro-L-tyrosine | 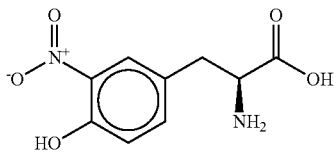 | |
| [2-(2-Amino-ethoxy)-ethoxy]-acetic acid | 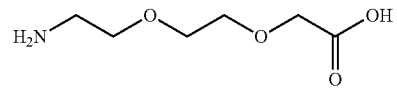 [SMILES: NCCOCCOCC(=O)O] | |
| 3-{2-[2-(2-Amino-ethoxy)-ethoxy]-ethoxy}-propionic acid | 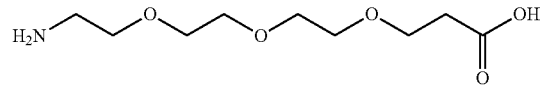 [SMILES: NCCOCCOCCOCCC(=O)O] | |
| 3-(2-{2-[2-(2-Amino-ethoxy)-ethoxy]-ethoxy}-ethoxy)-propionic acid | 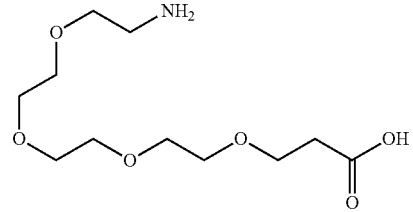 [SMILES: NCCOCCOCCOCCOCCC(=O)O] | |
| 3-[2-(2-{2-[2-(2-Amino-ethoxy)-ethoxy]-ethoxyl}-ethoxy)-ethoxy]-propionic acid | 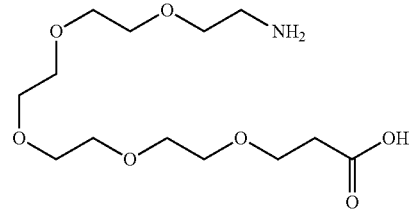 [SMILES: NCCOCCOCCOCCOCCOCCC(=O)O] | |
| homoserine | 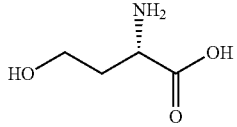 | Hse |
| 2-amino butyric acid | 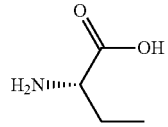 | Abu |
| 2-amino isobutyric acid | 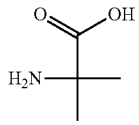 | Aib |

TABLE 2-continued

| Name | Structure | Abbreviation |
| --- | --- | --- |
| norleucine | 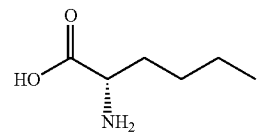 | Nle |
| t-butylalanine | 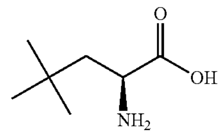 | Npg |
| phenylglycine | 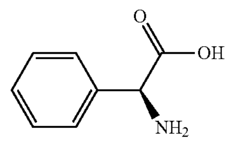 | Phg |
| β-homophenylalanine | 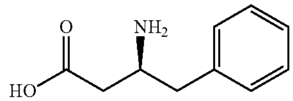 [SMILES: N[C@H](CC(=O)O)Cc1ccccc1] | |
| β-homovaline | 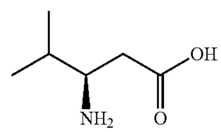 | |
| 2-propargylglycine | 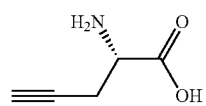 | |
| L-homophenylalanine | 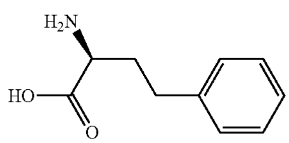 [SMILES: N[C@@H](CCc1ccccc1)C(=O)O] | |

The amino acid sequences of the peptides provided herein are depicted in typical peptide sequence format, as would be understood by the ordinary skilled artisan. For example, the three-letter code or one-letter code of a conventional amino acid, or the code including the abbreviations for additional building blocks, indicates the presence of the amino acid or building block in a specified position within the peptide sequence. The code for each non-conventional amino acid or building block is connected to the code for the next and/or previous amino acid or building block in the sequence by a hyphen. Adjacent building blocks are connected by a chemical bond (typically an amide linkage or thioether linkage). The formation of the chemical bond removes a hydroxyl group from the 1-carboxyl group of the amino acid when it is located to the left of the adjacent amino acid (e.g., Phe-adjacent amino acid), and removes a hydrogen from the amino group of the amino acid when it is located on the right of the adjacent amino acid (e.g., adjacent amino acid-Phe). It is understood that both modifications can apply to the same amino acid and apply to adjacent conventional amino acids present in amino acid sequences without hyphens explicitly illustrated. Where an amino acid contains more than one amino and/or carboxy group in the amino acid side chain, all orientations of this amino acids are in principle possible, otherwise preferred orientations are explicitly specified.

For non-conventional amino acids, a 3-letter code was used where the first letter indicates the stereochemistry of the C-α-atom. For example, a capital first letter indicates that the L-form of the amino acid is present in the peptide sequence, while a lower case first letter indicating that the D-form of the correspondent amino acid is present in the peptide sequence. When one-letter code is used, a lower case letter represents a D-amino acid, while an upper case letter represents an L-amino acid. Unless indicated to the contrary, the amino acid sequences are presented herein in N- to C-terminus direction.

The C-termini of several conjugates of the invention described herein are explicitly illustrated by inclusion of an OH, NH$_2$, or an abbreviation for a specific terminating amine linked to the C-terminal amino acid code via a hyphen. The N-termini of several peptides described herein are explicitly illustrated by inclusion of a hydrogen (for a free N-terminus), or an abbreviation for a specific terminating carboxylic acid like Ac for acetic acid or other chemical group or structural formula of chemical groups linked to the N-terminal amino acid code via a hyphen.

In an embodiment and as preferably used herein an antagonist to NTR1 is a compound which inhibits the activity of a ligand on NTR1 such as neurotensin, and more specifically inhibits the receptor mediated effects which arise from the binding of the ligand to NTR1. More preferably, the antagonist to NTR1 is binding to NTR1.

In an embodiment and as preferably used herein, an effector is a compound which is diagnostically and/or therapeutically active in the diagnosis and therapy, respectively, of a disease.

In an embodiment and as preferably used herein, a diagnostically active compound is a compound which is suitable for or useful in the diagnosis of a disease.

In an embodiment and as preferably used herein, a diagnostic agent or a diagnostically active agent is a compound which is suitable for or useful in the diagnosis of a disease.

In an embodiment and as preferably used herein, a therapeutically active compound is a compound which is suitable for or useful in the treatment of a disease.

In an embodiment and as preferably used herein, a therapeutic agent or a therapeutically active agent is a compound which is suitable for or useful in the treatment of a disease.

In an embodiment and as preferably used herein, a theragnostically active compound is a compound which is suitable for or useful in both the diagnosis and therapy of a disease.

In an embodiment and as preferably used herein, a theragnostical agent or a theragnostically active agent is a compound which is suitable for or useful in both the diagnosis and therapy of a disease.

In an embodiment and as preferably used herein, theragonstics is a method for the combined diagnosis and therapy of a disease; preferably, the combined diagnostically and therapeutically active compounds used in theragnostics are radiolabeled.

In an embodiment and as preferably used herein, treatment of a disease is treatment and/or prevention of a disease.

In an embodiment and as preferably used herein, a disease involving neurotensin receptor is a disease where cells expressing neurotensin receptor and tissue expressing neurotensin receptor, respectively, are either a or the cause for the disease and/or the symptoms of the disease, or are part of the pathology underlying the disease. In an embodiment of the disease, preferably when used in connection with the treatment, treating and/or therapy of the disease, affecting the cells, the tissue and pathology, respectively, results in cure, treatment or amelioration of the disease and/or the symptoms of the disease. In an embodiment of the disease, preferably when used in connection with the diagnosis and/or diagnosing of the disease, labeling of the neurotensin receptor expressing cells and/or of the neurotensin receptor expressing tissue allows discriminating or distinguishing said cells and/or said tissue from healthy or neurotensin receptor non-expressing cells and/or healthy or neurotensin receptor non-expressing tissue. More preferably such discrimination or distinction forms the basis for said diagnosis and diagnosing, respectively. In an embodiment thereof, labeling means the interaction of a detectable label either directly or indirectly with the neurotensin receptor expressing cells and/or with the neurotensin receptor expressing tissue; more preferably such interaction involves or is based on the interaction of the label or a compound bearing such label with the neurotensin receptor.

In an embodiment and as preferably used herein, a disease involving neurotensin receptor 1 (NTR1) is a disease where cells expressing NTR1 and tissue expressing NTR1, respectively, are either a or the cause for the disease and/or the symptoms of the disease, or are part of the pathology underlying the disease. In an embodiment of the disease, preferably when used in connection with the treatment, treating and/or therapy of the disease, affecting the cells, the tissue and pathology, respectively, results in cure, treatment or amelioration of the disease and/or the symptoms of the disease. In an embodiment of the disease, preferably when used in connection with the diagnosis and/or diagnosing of the disease, labeling of the NTR1 expressing cells and/or of the NTR1 expressing tissue allows discriminating or distinguishing said cells and/or said tissue from healthy or NTR1 non-expressing cells and/or healthy or NTR1 non-expressing tissue. More preferably such discrimination or distinction forms the basis for said diagnosis and diagnosing, respectively, of the disease. In an embodiment thereof, labeling means the interaction of a detectable label either directly or indirectly with the NTR1 expressing cells and/or with the NTR1 expressing tissue; more preferably such interaction involves or is based on the interaction of the label or a compound bearing such label with the NTR1 receptor.

In an embodiment and as preferably used herein, a target cell is a cell which is expressing NTR1 and is a or the cause for a disease and/or the symptoms of a disease, or are part of the pathology underlying a disease.

In an embodiment and as preferably used herein, a non-target cell is a cell which is either not expressing NTR1 and/or is not a or the cause for a disease and/or the symptoms of a disease, or is part of the pathology underlying a disease.

In an embodiment and as preferably used herein, an indication is a medical indication.

In an embodiment and as preferably used herein, a target is a target molecule or targeted structure.

In an embodiment and preferably used herein a cell is involved in a disease or indication if such cell is or forms part of the tissue and/or the organ afflicted by such disease or indication, or if such cell is causing the disease or indication, or if the cell is a diseased cell, wherein preferably such diseased cell is causing the disease or indication or wherein the diseased cell is or forms part of the tissue and/or the organ afflicted by such disease or indication.

In an embodiment and as preferably used herein the term "mediating a linkage" means that a linkage or a type of linkage is established, preferably a linkage between two moieties. In a preferred embodiment the linkage and the type of linkage is as defined herein.

To the extent it is referred in the instant application to a range indicated by a lower integer and a higher integer such as, for example, 1-4, such range is a representation of the lower integer, the higher integer and any integer between the lower integer and the higher integer. Insofar, the range is actually an individualized disclosure of said integer. In said example, the range of 1-4 thus means 1, 2, 3 and 4.

Preferably the terms conjugate of the invention and compound of the invention are used interchangeably.

The conjugate of the invention comprises general formula (1)

[TM1]-[AD1]-[LM]-[AD2]-[TM2] (1), wherein
TM1 is a first targeting moiety, wherein the first targeting moiety is capable of binding to a first target,
AD1 is a first adapter moiety or is absent,
LM is a linker moiety or is absent,
AD2 is a second adapter moiety or is absent, and
TM2 is a second targeting moiety, wherein the second targeting moiety is capable of binding to a second target;

wherein the first targeting moiety and/or the second targeting moiety is a compound of formula (2):

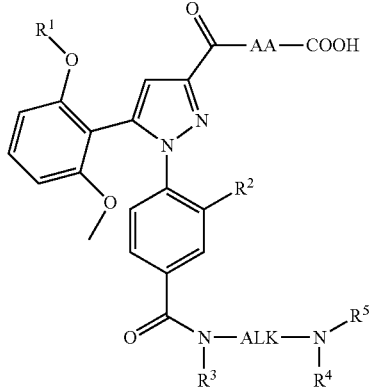

(2)

wherein
R$^1$ is selected from the group consisting of hydrogen, methyl and cyclopropylmethyl;
AA-COOH is an amino acid selected from the group consisting of 2-amino-2-adamantane carboxylic acid, cyclohexylglycine and 9-amino-bicyclo[3.3.1]nonane-9-carboxylic acid;
R$^2$ is selected from the group consisting of (C$_1$-C$_6$)alkyl, (C$_3$-C$_8$)cycloalkyl, (C$_3$-C$_8$)cycloalkylmethyl, halogen, nitro and trifluoromethyl;
ALK is (C$_2$-C$_5$)alkylidene;
R$^3$, R$^4$ and R$^5$ are each and independently selected from the group consisting of hydrogen and (C$_1$-C$_4$)alkyl under the proviso that one of R$^3$, R$^4$ and R$^5$ is of the following formula (3)

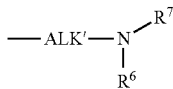

(3)

wherein
ALK' is (C$_2$-C$_5$)alkylidene;
R$^6$ is selected from the group consisting of hydrogen and (C$_1$-C$_4$)alkyl; and
R$^7$ is a bond.

Based on such general formula, the conjugate of the invention may be realized in various embodiments such as embodiments (I) to (VII) outlined in the following

[TM1]-[AD1]-[LM]-[AD2]-[TM2]     (I);

[TM1]-[LM]-[AD2]-[TM2]     (II);

[TM1]-[AD2]-[TM2]     (III);

[TM1]-[TM2]     (IV);

[TM1]-[AD1]-[LM]-[TM2]     (V);

[TM1]-[AD1]-[TM2]     (VI); and

[TM1]-[LM]-[TM2]     (VII);

wherein in each and any case
TM1 is a first targeting moiety, wherein the first targeting moiety is capable of binding to a first target,
AD1 is a first adapter moiety,
LM is a linker moiety,
AD2 is a second adapter moiety, and
TM2 is a second targeting moiety, wherein the second targeting moiety is capable of binding to a second target;
wherein the first targeting moiety and/or the second targeting moiety is a compound of formula (2):

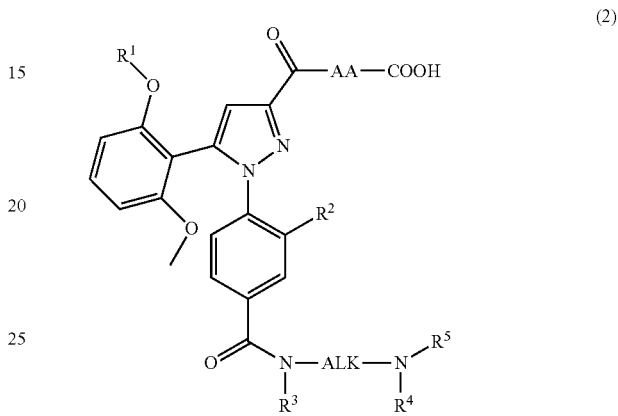

(2)

wherein
R$^1$ is selected from the group consisting of hydrogen, methyl and cyclopropylmethyl;
AA-COOH is an amino acid selected from the group consisting of 2-amino-2-adamantane carboxylic acid, cyclohexylglycine and 9-amino-bicyclo[3.3.1]nonane-9-carboxylic acid;
R$^2$ is selected from the group consisting of (C$_1$-C$_6$)alkyl, (C$_3$-C$_8$)cycloalkyl, (C$_3$C$_8$)cycloalkylmethyl, halogen, nitro and trifluoromethyl;
ALK is (C$_2$-C$_5$)alkylidene;
R$^3$, R$^4$ and R$^5$ are each and independently selected from the group consisting of hydrogen and (C$_1$-C$_4$)alkyl under the proviso that one of R$^3$, R$^4$ and R$^5$ is of the following formula (3)

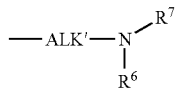

(3)

wherein
ALK' is (C$_2$-C$_5$)alkylidene;
R$^6$ is selected from the group consisting of hydrogen and (C$_1$-C$_4$)alkyl; and
R$^7$ is a bond.

As also disclosed herein, the linker moiety LM, in an embodiment, is of the following general formula:

[X]$_a$—[Y]—[Z]$_b$—     (VIII)

wherein
[X]$_a$ is a building block moiety formed of a building blocks,
[Y] is a branching moiety or is absent,
[Z]$_b$ is a building block moiety formed of b building blocks, and
wherein a and b are individually and independently any integer from 0, 1, 2, 3, 4, 5, 6, 7, 8, 9, 10, 11, 12, 13, 14, 15, 16, 17, 18, 19 and 20 under the proviso that a+b is 20, 19, 18, 17, 16, 15, 14, 13, 12, 11, 10, 9, 8, 7, 6, 5, 4, 3, 2, 1 or 0.

In light thereof, embodiments (VIII) to (XV) of the linker moiety LM are as follows:

—[X]$_a$—[Y]—[Z]$_b$— (VIII),

—[X]$_a$—[Y] (IX),

—[X]$_a$ (X),

—[X]$_a$—[Z]$_b$— (XI),

—[Y]—[Z]$_b$— (XII),

—[X]$_a$—[Z]$_b$— (XIII),

—[Y]— (XIV), and

—[Z]$_b$— (XV),

[X]$_a$ is a building block moiety formed of "a" building blocks X, or is absent
[Y] is a branching moiety or is absent,
[Z]$_b$ is a building block moiety formed of "b" building blocks Z, or is absent
and wherein "a" and "b" are individually and independently any integer from 0, 1, 2, 3, 4, 5, 6, 7, 8, 9, 10, 11, 12, 13, 14, 15, 16, 17, 18, 19 and 20 under the proviso that a+b is 20, 19, 18, 17, 16, 15, 14, 13, 12, 11, 10, 9, 8, 7, 6, 5, 4, 3, 2, 1 or 0; preferably "a" and "b" are individually and independently any integer from 0, 1, 2, 3, 4, 5, 6, 7, 8, 9 and 10, more preferably any integer from 0, 1, 2, 3, 4 and 5.

It is within the present invention that any embodiment of the linker moiety as disclosed herein and in particular embodiments of the linker moiety (VIII) to (XV) as disclosed herein, can be realized in any of the embodiment of the conjugate of the invention and in particular in embodiments (I) to (VII) of the conjugate of the invention as disclosed herein.

It will be appreciated by a person skilled in the art that the various moieties of the conjugate of the invention are linked to or connected with each other by a linkage. Such linkage is typically indicated in the formulae of the conjugate of the invention such as formulae (1) or in embodiments (I) to (VII) of the conjugate of the invention or in embodiments (VIII) to (XV) of the linker moiety by "—".

In an embodiment and as preferably used herein a linkage is an attachment of at least two atoms of two independent moieties and building blocks, respectively to each other. Such moieties are the first target moiety TM1, the first adapter moiety AD1, the linker moiety LM, the second adaptor moiety AD2, the second targeting moiety TM2, the third adapter moiety AD3 and the effector moiety EM, as well as building block moiety X, a building block moiety Z and building block moiety Y. A preferred linkage is a chemical bond or a plurality of chemical bonds. More preferably, a chemical bond is a covalent bond or a plurality of chemical bonds. Most preferably, the linkage is a covalent bond or a coordinate bond. As preferably used herein, an embodiment of a coordinate bond is a bond or group of bonds as realized when a metal is bound by a chelator. Depending on the type of atoms linked and their atomic environment different types of linkages are created. These types of linkage are defined by the type of atom arrangements created by the linkage. For instance, the linking of a moiety comprising a primary or secondary amino with a moiety comprising a carboxylic acid leads to a linkage named amide (which is also referred to as amide linkage, —CO—N—, —N—CO—). It will be appreciated by a person skilled in the art that the linking of a moiety comprising an isothiocyanate with a moiety comprising a primary or secondary amino leads to a linkage named thiourea (which is also referred to as a thiourea linkage, —N—CS—N—), and linking of a moiety comprising a halogen atom with a moiety comprising a sulfhydryl (—SH) leads to thioether (which is also referred to as a thioether linkage, —S—).

In an embodiment and as preferably used herein, an amine linkage is a linkage, wherein an N atom is bound to a C atom (—N—C—). A specific type of amine linkage is one, wherein an N atom is bound to an aliphatic C atom, whereby such linkage is also referred to as alkylamine linkage (—N—C$_{alk}$—). In one embodiment the alkylamine linkage is formed by reacting a moiety comprising a primary or secondary amino group with a moiety comprising an aldehyde group or a ketone group either under reductive conditions or followed by subsequent reduction.

In an embodiment a linkage with a plurality of chemical bonds is triazole, which is also referred to as triazole linkage, wherein a triazole, preferably a 1,2,3-triazoles links two moieties. In one embodiment the triazole linkage is formed by reacting a moiety comprising an azide with a moiety comprising an alkyne with or without catalysis by preferably copper salts.

It is understood by a person skilled in the art that several different technical and mechanistical alternatives exist to realize a specific type of linkage, for instance an amide bond. In this case usually specific reagents are used for activation of at least one component, for instance the carboxylic acid. These activated species like active esters or carboxylic acid halides are in some cases isolated and/or purified prior to use; alternatively, such activated species is/are formed in situ and reacted immediately, i.e. without having been isolated and/or purified.

In an embodiment and as preferably used herein the term "mediating a linkage" means that a linkage or a type of linkage is established, preferably a linkage between two moieties. In a preferred embodiment the linkage and the type of linkage is as defined herein.

A non-limiting list of linkages as preferably used in connection with the conjugate of the invention and the characteristic type of atom arrangement is presented Table 3.

TABLE 3

| Linkage | Characteristic atom arrangement |
|---|---|
| Amide | structure |
| Sulfonamide | structure |
| Urea | structure |
| Thioether | structure |

TABLE 3-continued

| Linkage | Characteristic atom arrangement |
|---|---|
| Ether | |
| Ester | |
| Carbamate | |
| Amine | |
| Thiourea | |
| Triazole | |
| Oxime | |
| Hydrazone | |
| Disulfide | |
| Pyrazine | |
| Dihydro-pyrazine | and isomers |

The following are reactive groups and functionalities which are utilized or amenable of forming linkages between moieties as used in embodiments of the conjugate of the invention: Primary or secondary amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine.

As preferably used herein, the term "activated carboxylic acid" refers to a carboxylic acid group with the general formula —CO—X, wherein X is a leaving group. For example, activated forms of a carboxylic acid group may include, but are not limited to, acyl chlorides, symmetrical or unsymmetrical anhydrides, and esters. In some embodiments, the activated carboxylic acid group is an ester with pentafluorophenol, nitrophenol, benzotriazole, azabenzotriazole, thiophenol or N-hydroxysuccinimide (NHS) as leaving group.

As preferably used herein, the term "activated sulfonic acid" refers to a sulfonic acid group with the general formula —SO$_2$—X, wherein X is a leaving group. For example, activated forms of a sulfonic acid may include, but are not limited to, sulfonyl chlorides or sulfonic acid anhydrides. In some embodiments, the activated sulfonic acid group is sulfonylchloride with chloride as leaving group.

As preferably used herein, the term "Michael acceptor" refers to an olefin that is substituted with an electron deficient group which comprises the minimal characteristic structure (32)

(32)

wherein EWG is an electron withdrawing group, such as —CN, —NO$_2$, —CO—R', —CO—OR', —SO$_2$—R'.

A "Michael acceptor" is capable of reacting with nucleophiles especially sulfhydryl groups in an addition reaction as exemplified as follows:

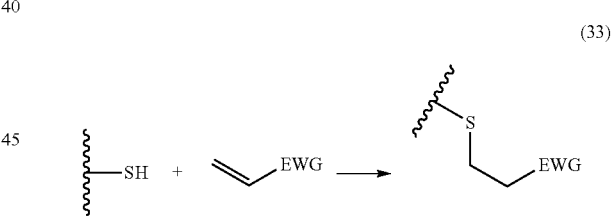
(33)

For example, Michael acceptors include, but are not limited to, α,β-unsaturated nitriles, α,β-unsaturated nitro compounds, α,β-unsaturated aldehydes, α,β-unsaturated ketones and α,β-unsaturated carboxylic acid derivatives. In a preferred embodiment, the Michael acceptor is a maleimide group.

Linking Concept:

The basic concept underlying the present invention in the forming of a linkage between two moieties, whereby, preferably, the two moieties, i.e. a first moiety and a second moiety, are equipped with complementary reactive groups, whereby preferably the first moiety provides a first reactive group and the second moiety provides a second reactive group. Upon the reactive groups having reacted, the reactive groups or the reaction product thereof and thus, ultimately, the two moieties are linked together by at least one covalent bond to form a linkage of a certain type. The nature of the formed linkage depends on the reactive groups involved in the forming of the linkage, as will be appreciated by a person skilled in the art. It will also be appreciated by a person skilled in the art that, in principle, any reactive group can be provided by any of the two moieties. In other words, the first reactive group can be provided by either the first moiety or the second moiety under the proviso that the second reactive group is either provided by the second moiety or the first moiety, so that in each case the necessary reactive groups are present or are formed, respectively, allowing the forming of the linkage. It will also be appreciated by a person skilled in the art that depending on the chemical nature of the first and the second moiety on the one hand and the reactive groups involved in the forming of the linkage between the first and the second moiety on the other hand, some types of reactive group are preferably provided by the first moiety or the second moiety.

Examples of reactive groups which, in some embodiments of the invention, are used in the forming of linkages which may be realized in embodiments the conjugate of the invention are summarized in Table 4. It will, however, be understood by a person skilled in the art that neither the linkages which may be realized in embodiments the conjugate of the invention are limited to the ones of Table 4 nor the reactive groups forming such linkages.

TABLE 4

| first reactive group | second reactive group | (type of) linkage |
|---|---|---|
| amino | carboxylic acid | amide |
| amino | activated carboxylic acid | amide |
| carboxylic acid | amino | amide |
| sulfhydryl | Michael acceptor (e.g. Maleimide) | thioether |
| bromo | sulfhydryl | thioether |
| aminooxy | aldehyde | oxime |
| isothiocyanate | amino | thiourea |
| hydroxyl | carboxylic acid | ester |
| azide | alkyne | triazole |
| sulfhydryl | sulfhydryl | disulfide |
| sulfhydryl | 2-Pyridine-disulfide | disulfide |
| amino | aldehyde | alkylamine |

TM1

The conjugate of the invention comprises at least one compound of formula (2)

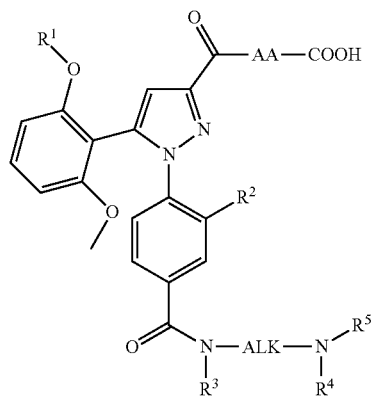

(2)

wherein
$R^1$ is selected from the group consisting of hydrogen, methyl and cyclopropylmethyl;
AA-COOH is an amino acid selected from the group consisting of 2-amino-2-adamantane carboxylic acid, cyclohexylglycine and 9-amino-bicyclo[3.3.1]nonane-9-carboxylic acid;
$R^2$ is selected from the group consisting of $(C_1-C_6)$alkyl, $(C_3-C_8)$cycloalkyl, $(C_3C8)$cycloalkylmethyl, halogen, nitro and trifluoromethyl;
ALK is $(C_2-C_5)$alkylidene;
$R^3$, $R^4$ and $R^5$ are each and independently selected from the group consisting of hydrogen and $(C_1-C_4)$alkyl under the proviso that one of $R^3$, $R^4$ and $R^5$ is of the following formula (3)

$$-\text{ALK}'-\underset{R^6}{\overset{R^7}{N}}$$

(3)

wherein
ALK' is $(C_2-C_5)$alkylidene;
$R^6$ is selected from the group consisting of hydrogen and $(C_1-C_4)$alkyl; and
$R^7$ is a bond, in its various embodiments disclosed herein.

In one embodiment of the conjugate of the invention a compound (2), in any of its embodiments, is present in the conjugate of the invention as targeting moiety TM1. In a further embodiment of the conjugate of the invention a compound of formula (2), in any of its embodiments, is present in the conjugate of the invention as targeting moiety TM2. In a still further embodiment of the conjugate of the invention a compound of formula (2), in any of its embodiments, is present in the conjugate of the invention as targeting moiety TM1 and as targeting moiety TM2. In connection with the latter embodiment of the conjugate of the invention the embodiment of the compound of formula (2) present in the conjugate of the invention as TM1 is different from the embodiment of the compound of formula (2) present in the conjugate of the invention as TM2; alternatively, the embodiment of the compound of formula (2) present in the conjugate of the invention as TM1 is identical to the embodiment of the compound of formula (2) present in the conjugate of the invention as TM2.

It is within the present invention that the conjugate of the invention comprises, under the proviso that either the first targeting moiety TM1 or the second targeting moiety TM2 is a compound of formula (2), in any of its embodiments, a further targeting moiety. Such further targeting moiety is a second targeting moiety TM2 in those embodiments of the conjugate of the invention where the compound of formula (2), in any of its embodiments, is present in the conjugate of the invention as targeting moiety TM1, and such further targeting moiety is a first targeting moiety TM1 in those embodiments of the conjugate of the invention where the compound of formula (2), in any of its embodiments, is present in the conjugate of the invention as targeting moiety TM2.

In an embodiment of the conjugate of the invention the further targeting moiety is preferably selected from the group comprising an antibody (Book: Immunochemistry, edited by Carel J. van Oss and Marc H. V. van Regenmortel, Marcel Dekker, New York 1994), an antigen-binding antibody fragment (Moran, Nat Biotechnol, 2011, 29, 5-6), (Peer et al., Nat Nanotechnol, 2007, 2, 751-760), (Hong et al., Biomark Insights, 2008, 3, 435-451), (Holliger et al., Nat Biotechnol, 2005, 23, 1126-1136), a camelid heavy chain IgG (hcIgG) (Unciti-Broceta et al., *Ther Deliv,* 2013, 4, 1321-1336), (De Vos et al., *Expert Opin Biol Ther,* 2013, 13, 1149-1160), (Vincke et al., *Methods Mol Biol,* 2012, 907, 145-176), (Vincke et al., *Methods Mol Biol,* 2012, 911, 15-26), a cartilaginous fish (e.g. shark) IgNAR antibody (Dooley et al., *Dev Comp Immunol,* 2006, 30, 43-56), a protein scaffold (Skerra, *J Mol Recognit,* 2000, 13, 167-187), (Zoller et al., *Molecules,* 2011, 16, 2467-2485), (Gebauer et al., *Curr Opin Chem Biol,* 2009, 13, 245-255), (Hosse et al., *Protein Sci,* 2006, 15, 14-27), a target-binding peptide (Zhou et al., *Curr Med Chem,* 2013, 20, 1985-1996), (Boohaker et al., *Curr Med Chem,* 2012, 19, 3794-3804), (Aoki et al., *Adv Drug Deliv Rev,* 2012, 64, 1220-1238), (Pirogova et al., *Curr Pharm Biotechnol,* 2011, 12, 1117-1127), (Kliger, *Biopolymers,* 2010, 94, 701-710), a peptidomimetic (Avan et al., *Chem Soc Rev,* 2014, 43, 3575-3594), (Akram et al., *Mol Cancer Res,* 2014), (Hruby et al., *Annu Rev Pharmacol Toxicol,* 2013, 53, 557-580), (Tomasini et al., *Chem Soc Rev,* 2013, 42, 156-172), (Oishi et al., *Org Biomol Chem,* 2012, 10, 5720-5731), (Dietrich et al., *Curr Pharm Biotechnol,* 2013, 14, 501-512), (Wetzler et al., *Biopolymers,* 2011, 96, 556-560), (Chongsiriwatana et al., *Antimicrob Agents Chemother,* 2011, 55, 5399-5402), (Liskamp et al., *Chembiochem,* 2011, 12, 1626-1653), a peptide nucleic acid (PNA) (Gambari, *Expert Opin Ther Pat,* 2014, 24, 267-294), (Sforza et al., *Methods Mol Biol,* 2014, 1050, 143-157), (Corradini et al., *Curr Top Med Chem,* 2011, 11, 1535-1554), (Nielsen, *ArtifDNA PNA XNA,* 2010, 1, 1), (Nielsen, *Chem Biodivers,* 2010, 7, 786-804), (Pensato et al., *Expert Opin Biol Ther,* 2007, 7, 1219-1232), (Lundin et al., *Adv Genet,* 2006, 56, 1-51), a target-binding polypeptide or protein, a target binding nucleic acid molecule, a carbohydrate (Balan et al., *Cancers* (*Basel*), 2010, 2, 592-610), a lipid (Helms et al., *Traffic,* 2004, 5, 247-254), (Resh, *Subcell Biochem,* 2004, 37, 217-232), (Kohli et al., *J Control Release,* 2014) and a target-binding small molecule (Book: Drug Discovery and Development Volumes 1 and 2, edited by Mukund S. Chorghade, John Wiley & Sons, Inc., Hoboken, N.J., 2006), (Book: Optimization in Drug Discovery—In vitro Methods, edited by Zhengyin Yan and Gary W. Caldwell, Humana Press, Totowa, N.J., 2004), (Book: The Organic Chemistry of Drug Design and Drug Action, Richard B. Silverman, Academic Press Ltd., London, 1992). It will be appreciated by a person skilled in the art that any of the above, and further, compounds forming the or being contained in the conjugate of the invention are known in the art as are methods for the preparation and identification, respectively, of such compounds.

In an embodiment of the conjugate of the invention the antibody is a polyclonal or monoclonal antibody. In a further embodiment of the conjugate of the invention the antibody is a human antibody, a humanized antibody, a chimeric antibody, a sub-primate antibody a murine antibody or an antibody from other species, i.e. species different from man and mouse.

In a further embodiment of the conjugate of the invention the antigen-binding antibody fragment is selected from the group comprising Fab, Fab$_2$, scFv, bispecific scFv, scFv-Fc, a minibody, a diabody, a triabody and a tetrabody.

In a further embodiment of the conjugate of the invention the antigen-binding antibody is selected from the group comprising IgG, IgG1, IgG2, IgG3, IgG4, IgM, IgD, IgE, IgA, IgA1, IgA2.

In a further embodiment of the conjugate of the invention the camelid heavy chain IgG (hcIgG) may be present as a full-length heavy chain IgG or as a fragment thereof; such fragment may be a nanobody which is also known in the art as VHH.

In a further embodiment of the conjugate of the invention the cartilaginous fish IgNAR antibody may be present as a full-length IgNAR or as a fragment thereof; such fragment may be vNAR. In an embodiment the cartilaginous fish is shark.

In a further embodiment of the conjugate of the invention the protein scaffold is selected from the group comprising a protein scaffold for molecular recognition; a protein scaffold derived from naturally occurring protein domains; a protein scaffold derived from a venomous animal, preferably such venomous animal is one selected from the group comprising a spider, a scorpion, a see anemonea, an insect, a frog, a snail, a snake and fish; a genetically engineered protein scaffold; an affibody, wherein the affibody is preferably based on the Z-domain of staphylococcal protein A (Nord et al., Protein Eng, 1995, 8, 601-608), (Nord et al., Nat Biotechnol, 1997, 15, 772-777), (Gunneriusson et al., Protein Eng, 1999, 12, 873-878), (Wikman et al., Protein Eng Des Sel, 2004, 17, 455-462); a scaffold based on immunity protein ImmE7 (Chak et al., Proc Natl Acad Sci USA, 1996, 93, 6437-6442); a scaffold based on cytochrome b562 (Ku et al., Proc Natl Acad Sci USA, 1995, 92, 6552-6556); a scaffold based on peptide α2p8 (Barthe et al., Protein Sci, 2000, 9, 942-955); a scaffold based on the ankyrin repeat (Mosavi et al., Proc Natl Acad Sci USA, 2002, 99, 16029-16034), (Binz et al., Nat Biotechnol, 2004, 22, 575-582), (Amstutz et al., J Biol Chem, 2005, 280, 24715-24722); a scaffold based on insect defensins such as insect defensin A (1ICA29) (Zhao et al., Peptides, 2004, 25, 629-635); a scaffold based on Kunitz domains, preferably BPTI/APPI (Roberts et al., Proc Natl Acad Sci USA, 1992, 89, 2429-2433), (Roberts et al., Gene, 1992, 121, 9-15), (Dennis et al., J Biol Chem, 1994, 269, 22129-22136), (Dennis et al., J Biol Chem, 1994, 269, 22137-22144), (Stoop et al., Nat Biotechnol, 2003, 21, 1063-1068); a scaffold based on PDZ domains, preferably the Ras binding protein AF-6 (Schneider et al., Nat Biotechnol, 1999, 17, 170-175); a scaffold based on scorpion toxins such as charybdotoxin (Vita et al., Biopolymers, 1998, 47, 93-100); a scaffold based on the fibronectin type III domain (Koide et al., J Mol Biol, 1998, 284, 1141-1151), (Xu et al., Chem Biol, 2002, 9, 933-942); a scaffold based on the extracellular domain of CTLA-4 (Nuttall et al., Proteins, 1999, 36, 217-227), (Irving et al., J Immunol Methods, 2001, 248, 31-45); a scaffold based on knottins such as Min-23 (Souriau et al., Biochemistry, 2005, 44, 7143-7155); a scaffold based on the cellulose binding domain (Lehtio et al., Proteins, 2000, 41, 316-322); a scaffold based on neocarzinostatin (Heyd et al., Biochemistry, 2003, 42, 5674-5683); a scaffold based on CBM4-2 (Cicortas et al., Protein Eng Des Sel, 2004, 17, 213-221); a scaffold based on tendamistat (McConnell et al., J Mol Biol, 1995, 250, 460-470), (Li et al., Protein Eng, 2003, 16, 65-72); an anticalin, preferably based on apolipoprotein D (Gebauer et al., Methods Enzymol, 2012, 503, 157-188), (Gebauer et al., J Mol Biol, 2013, 425, 780-802), (Vogt et al., Chembiochem, 2004, 5, 191-199); a scaffold based on the bilin-binding protein (Beste et al., Proc Natl Acad Sci USA, 1999, 96, 1898-1903); a scaffold based on FABP (Lamla et al., Protein Expr Purif, 2004, 33, 39-47), (Lamla et al., J Mol Biol, 2003, 329, 381-388); a DARPin (Weidle et al., *Cancer Genomics Proteomics,* 2013, 10, 155-168), (Stumpp et al., *Drug Discov Today,* 2008, 13, 695-701), (Boersma et al., *Curr Opin Biotechnol,* 2011, 22, 849-857); and an adnectin (Lipovsek, *Protein Eng Des Sel,* 2011, 24, 3-9).

In a further embodiment of the conjugate of the invention the target-binding peptide is one selected from the group comprising a peptide with 2 up 50 amino acids in length, a peptide with 3 up 40 amino acids in length (Manfredi et al., *Curr Med Chem*, 2006, 13, 2369-2384), a peptide with 5 up 30 amino acids in length (Harmar et al., *Br J Pharmacol*, 2012, 166, 4-17), a peptide with 5 up 20 amino acids in length (Dockal et al., *J Biol Chem*, 2014, 289, 1732-1741), (Heckmann et al., *Methods Enzymol*, 2007, 426, 463-503), (Schmid, *Mol Cell Endocrinol*, 2008, 286, 69-74); a linear peptide (Dockal et al., *J Biol Chem*, 2014, 289, 1732-1741), (Doehn et al., *IDrugs*, 2006, 9, 565-572), a cyclic peptide (Heckmann et al., *Methods Enzymol*, 2007, 426, 463-503), (Fliri et al., *Ann N Y Acad Sci*, 1993, 696, 47-53), (Schmid, *Mol Cell Endocrinol*, 2008, 286, 69-74); a cyclic peptide (comprising at least one linkage of disulfide, amide, ester, hydrocarbon, thioether and triazole with in the cyclic part) (Roxin et al., *Future Med Chem*, 2012, 4, 1601-1618), (Cemazar et al., *Curr Top Med Chem*, 2012, 12, 1534-1545), (Tam et al., *J Biol Chem*, 2012, 287, 27020-27025), (White et al., *Org Lett*, 2012, 14, 2898-2901), (White et al., *Nat Chem*, 2011, 3, 509-524), (Gentilucci et al., *Curr Pharm Des*, 2010, 16, 3185-3203), (Ovadia et al., *Expert Opin Drug Discov*, 2010, 5, 655-671), (Nestor, *Curr Med Chem*, 2009, 16, 4399-4418), (Kopp et al., *Nat Prod Rep*, 2007, 24, 735-749), a bicyclic peptide, a tricyclic peptide, a tetracyclic peptide, a pentacyclic peptide (MacLachlan et al., *Methods Mol Biol*, 1997, 60, 337-362), (Cemazar et al., *Curr Top Med Chem*, 2012, 12, 1534-1545), (Heinis et al., *Nat Chem Biol*, 2009, 5, 502-507), (Baeriswyl et al., *ChemMedChem*, 2012, 7, 1173-1176), a peptide composed of genetically encoded amino acids (Bernstein et al., *Expert Rev Clin Immunol*, 2010, 6, 29-39), (Dockal et al., *J Biol Chem*, 2014, 289, 1732-1741), a peptide composed of unnatural, preferably non-naturally occurring, amino acids (Wei et al., *Mol Pharm*, 2014); a peptide composed of genetically encoded and unnatural, preferably non-naturally occurring, amino acids (Rhaleb et al., *Eur J Pharmacol*, 1992, 210, 115-120), (Hock et al., *Br J Pharmacol*, 1991, 102, 769-773), (Wirth et al., *Br J Pharmacol*, 1991, 102, 774-777), (Dockal et al., *J Biol Chem*, 2014, 289, 1732-1741), a peptide conjugated with a non-proteinogenic moiety (Guskey et al., *Pharmacotherapy*, 2010, 30, 80-94), a lipopeptide (Grossman, *Pharmacotherapy*, 2009, 29, 25S-32S) and a glycopeptide (Maschauer et al., *Mol Pharm*, 2014, 11, 505-515).

In a further embodiment of the conjugate of the invention the target-binding nucleic acid molecule is selected from the group comprising an aptamer (Kang et al., *Adv Biochem Eng Biotechnol*, 2013, 131, 153-169), (Zhou et al., *Front Genet*, 2012, 3, 234), (Jeong et al., *Biochem Biophys Res Commun*, 2001, 281, 237-243), (Santulli-Marotto et al., *Cancer Res*, 2003, 63, 7483-7489), (Roth et al., *Cancer Res*, 2012, 72, 1373-1383), (Chen et al., *Proc Natl Acad Sci US A*, 2003, 100, 9226-9231), (Bell et al., *In Vitro Cell Dev Biol Anim*, 1999, 35, 533-542), (Esposito et al., *PLoS One*, 2011, 6, e24071), a spiegelmer (Vater et al., *Curr Opin Drug Discov Devel*, 2003, 6, 253-261), (Darisipudi et al., *Am J Pathol*, 2011, 179, 116-124), (Hoellenriegel et al., *Blood*, 2014, 123, 1032-1039), (Schwoebel et al., *Blood*, 2013, 121, 2311-2315), a ribozyme (Mulhbacher et al., *Curr Opin Pharmacol*, 2010, 10, 551-556), (Balke et al., *Appl Microbiol Biotechnol*, 2014, 98, 3389-3399) and a spiegelzym (Wyszko et al., *PLoS One*, 2014, 9, e86673), (Wyszko et al., *PLoS One*, 2013, 8, e54741).

In a further embodiment of the conjugate of the invention the target-binding carbohydrate molecule is selected from the group comprising an natural carbohydrate ligand for carbohydrate binding receptors (Yang et al., *Expert Rev Mol Med*, 2008, 10, e17) and an unnatural carbohydrate ligand (Ramstrom et al., *Chembiochem*, 2000, 1, 41-48), (Liang et al., *Science*, 1996, 274, 1520-1522).

In a further embodiment of the conjugate of the invention the target-binding small molecule is selected from the group comprising a target-binding small molecule fulfilling the rule-of-five (Lipinski, *J Pharmacol Toxicol Methods*, 2000, 44, 235-249), (Lipinski et al., *Adv Drug Deliv Rev*, 2001, 46, 3-26), (Lipinski, *Drug Discov Today*, 2003, 8, 12-16) and a target-binding small molecule violating the rule-of-five.

It will be appreciated by a person skilled in the art that the target recognized by the further targeting moiety, regardless of whether it is within the conjugate of the invention the first targeting moiety TM1 or the second targeting moiety TM2, can, in principle, be any target under the proviso that the further targeting moiety is capable of binding to such target. It will be appreciated by a person skilled in the art that in particular an antibody, an antigen-binding antibody fragment, a camelid heavy chain IgG (hcIgG), a cartilaginous fish (e.g. shark) IgNAR antibody, a protein scaffold, a target-binding peptide, a peptide nucleic acid (PNA), a target-binding polypeptide or protein, and a target binding nucleic acid molecule can, in principle, be identified and generated, respectively, against any target by using routine methods known in the art.

It is within the present invention that a target to which the further targeting moiety of the conjugate of the invention is capable of binding, is a target that is expressed in any oncology indication, preferably in any indication related to oncology, more preferably any tumor and/or cancer disease, and even more preferably any cell, such as a diseased cell, involved in such indication.

It is within the present invention that a target to which the further targeting moiety of the conjugate of the invention is capable of binding, is a target that is expressed in NTR-positive indications, preferably in a disease where cells involved in the disease and/or diseased cells express NTR. In a preferred embodiment the NTR-positive indication is an NTR1-positive indication, preferably in a disease where cells involved in the disease and/or diseased cells express NTR1. In a preferred embodiment the NTR-positive indication is an NTR2-positive indication, preferably in a disease where cells involved in the disease and/or diseased cells express NTR2. In a further preferred embodiment the NTR-positive indication is an NTR1 and an NTR2-positive indication, preferably in a disease where cells involved in the disease and/or diseased cells express both NTR1 and NTR2.

It is within the present invention that a target to which the further targeting moiety of the conjugate of the invention is capable of binding, is a target that is expressed in an indication, preferably a tumor indication, whereby such target can be identified by methods known in the art. Such methods comprise, but are not limited to, receptor autoradiography (Reubi et al., *Int J Cancer*, 1999, 81, 376-386; Waser et al., *Eur J Nucl Med Mol Imaging*, 2014, 41, 1166-1171), immunohistochemistry (Schmidt et al., *Anticancer Res*, 2008, 28, 1719-1724; Patsenker et al., *J Hepatol*, 2010, 52, 362-369; Korner et al., *Am J Surg Pathol*, 2012, 36, 242-252), immunocytochemistry (Chekhun et al., *Exp Oncol*, 2013, 35, 174-179; Ghosh et al., *J Cytol*, 2013, 30, 151-155; Seymour et al., *Am J Clin Pathol*, 1990, 94, S35-40), RT-PCR (Bernard et al., *Clin Chem*, 2002, 48, 1178-1185; Chang et al., *Clin Cancer Res*, 1999, 5, 2674-2681; Kang et al., *Cancer Genet Cytogenet*, 2006, 164, 32-38; Patel et al., *Clin Cancer Res*, 2004, 10, 7511-7519), in situ hybridization (Chang et al., *Clin Cancer Res*, 1999, 5, 2674-2681; Kang et al., Cancer Genet Cytogenet, 2006, 164, 32-38; Heinrich et al., Int J Gynecol Cancer, 2004, 14, 1078-1085), flow cytometry (Chekhun et al., Exp Oncol, 2013, 35, 174-179; Forster et al., Cytometry A, 2007, 71, 945-950; Goodman et al., Biol Open, 2012, 1, 329-340) and Western blot (Schmidt et al., Anticancer Res, 2008, 28, 1719-1724; Goodman et al., Biol Open, 2012, 1, 329-340; Kusagawa et al., Br J Cancer, 1998, 77, 98-102). Samples to be analyzed with the above methods may originate from biopsies, surgically resected specimens, circulating tumor cells, blood, urine or fecal samples, swabs and smears, sputum; preferably such sample is obtained from biopsies, surgically resected specimens, circulating tumor cells. These methods are also suitable for detecting and determining, respectively, homogeneity and/or heterogeneity of expression of a or the target, including expression of receptors such as NTR1 and NTR2, by a cell, a tissue, an organ, a tumor and/or an indication. These methods are also suitable for detecting and determining, respectively, the density of a or the target, including expression of receptors such as NTR1 and NTR2, by a cell, a tissue, an organ, a tumor and/or an indication.

It is within the present invention that a target to which the further targeting moiety of the conjugate of the invention is capable of binding, is a target that is expressed in an indication, preferably a tumor indication, in which more at least 75% or more, at least 50% or more, at least 25% or more, or at least 10% or more of patients, preferably the diseased cell, tissue, organ and/or indication express NTR. In an embodiment thereof NTR is NTR1. In a further embodiment NTR is NTR2. In a still further embodiment NTR is NTR1 and NTR2, i.e. the patients and, preferably the diseased cell, tissue, organ and/or indication express both NTR1 and NTR2.

It is within the present invention that a target to which the further targeting moiety of the conjugate of the invention is capable of binding, is a target that is expressed in an indication, preferably a tumor indication, in which only a small portion of the tumors, preferably a tumor indication where only a small portion of the patients suffering from the tumor indication, express NTR1. Preferably, a small portion of the tumors is about 10% or less of the tumors.

Also preferably, a small portion of the patients is about 10% or less of the patients.

It is within the present invention that a target to which the further targeting moiety of the conjugate of the invention is capable of binding, is a target that is expressed homogeneously in an indication, preferably an oncology indication, more preferably in any indication related to oncology. In an embodiment thereof the indication is any tumor and/or cancer disease. In an embodiment thereof the target is expressed homogenously by a cell in such indication, preferably the cell is involved in such indication and more preferably the cell is a diseased cell.

It is within the present invention that a target to which the further targeting moiety of the conjugate of the invention is capable of binding, is a target that is expressed heterogeneously in an indication, preferably in an oncology indication, more preferably in any indication related to oncology. In an embodiment thereof the indication is any tumor and/or cancer disease. In an embodiment thereof the target is expressed heterogenously by a cell in such indication, preferably the cell is involved in such indication and more preferably the cell is a diseased cell.

It is within the present invention that a target to which the further targeting moiety of the conjugate of the invention is capable of binding, is a target that is expressed in an indication, preferably in an oncology indication, more preferably in any indication related to oncology, where NTR is expressed at a low density. In an embodiment thereof the indication is any tumor and/or cancer disease. In an embodiment thereof the target is expressed heterogenously by a cell in such indication, preferably the cell is involved in such indication and more preferably the cell is a diseased cell. As preferably used herein low density means that less than 5000 copies of NTR per cell are expressed. Suitable methods to identify such indications are listed above. Preferred methods are receptor autoradiography (Reubi et al., supra; Waser et al., supra) and cell binding studies (Kitabgi et al., supra).

It is within the present invention that a target to which the further targeting moiety of the conjugate of the invention is capable of binding, is a target that is expressed in an indication, preferably in an oncology indication, more preferably in any indication related to oncology, where NTR is expressed in the primary tumor, in metastases, preferably metastases of the primary tumor, or in both the primary tumor and metastates, preferably metastases of the primary tumor. In an embodiment thereof NTR is NTR1, NTR2 or both NTR1 and NTR2.

It is within the present invention that a target to which the further targeting moiety of the conjugate of the invention is capable of binding, is a target that is expressed in an indication, preferably in an oncology indication, more preferably in any indication related to oncology, where NTR is not expressed. In an embodiment thereof NTR is NTR1. In another embodiment thereof NTR is NTR2. In still another embodiment thereof NTR is NTR1 and NTR2, i.e. the indication does express neither NTR1 nor NTR2. In an embodiment thereof NTR is not expressed by a cell involved in said indication and more preferably not expressed by a diseased cell involved in said indication.

It is within the present invention that a target to which the further targeting moiety of the conjugate of the invention is capable of binding, is a target that is expressed in an indication, preferably in an oncology indication, more preferably in any indication related to oncology, where at least 20,000 or more copies of NTR or at least 10,000 or more copies of NTR or at least 5,000 or more copies of NTR or at least 1,000 or more copies of NTR are expressed per cell. In an embodiment thereof the cell is involved in such indication and more preferably the cell is a diseased cell. In an embodiment thereof NTR is NTR1, NTR2 or both NTR1 and NTR2. Accordingly, the above copy numbers may refer to the copy number of NTR1 or the copy number of NTR2 or the total copy number of NTR1 and NTR2 taken together.

It is within the present invention that a target to which the further targeting moiety of the conjugate of the invention is capable of binding, is a target that is expressed in an indication, preferably in an oncology indication, more preferably in any indication related to oncology, where the blood brain barrier is intact.

It is within the present invention that a target to which the further targeting moiety of the conjugate of the invention is capable of binding is a target that is expressed in an indication of group A as defined herein Preferably the indication of group A as defined herein is one which occurs in an organ and/or a tissue, wherein the organ and/or the tissue is selected from group C, wherein group C comprises external upper lip, external lower lip, external lip, upper lip mucosa, lower lip mucosa, mucosa lip, commissure lip, overlapping lesion of lip, base of tongue, dorsal surface tongue, border of tongue, ventral surface of tongue, anterior ⅔ of tongue, lingual tonsil, overlapping lesion of tongue, tongue, upper gum, lower gum, gum, anterior floor of mouth, lateral floor of mouth, overlapping lesion of floor of mouth, floor of mouth, hard palate, soft palate, uvula, overlapping lesion of palate, palate, cheek mucosa, vestibule of mouth, retromolar area, overlapping lesion of other and unspecified parts of mouth, mouth, parotid gland, submaxillary gland, sublingual gland, overlapping lesion of major salivary glands, major salivary gland, tonsillar fossa, tonsillar pillar, overlapping lesion of tonsil, tonsil, vallecula, anterior surface of epiglottis, lateral wall oropharynx, posterior wall oropharynx, branchial cleft, overlapping lesion of oropharynx, oropharynx, superior wall of nasopharynx, posterior wall nasopharynx, lateral wall nasopharynx, anterior wall nasopharynx, overlapping lesion of nasopharynx, nasopharynx, pyriform sinus, postcricoid region, hypopharyngeal aspect of aryepiglottic fold, posterior wall hypopharynx, overlapping lesion of hypopharynx, hypopharynx, pharynx, laryngopharynx, waldeyer's ring, overlapping lesion of lip oral cavity and pharynx, cervical esophagus, thoracic esophagus, abdominal esophagus, upper third of esophagus, middle third of esophagus, esophagus lower third, overlapping lesion of esophagus, esophagus, cardia, fundus stomach, body stomach, gastric antrum, pylorus, lesser curvature of stomach, greater curvature of stomach, overlapping lesion of stomach, stomach, duodenum, jejunum, ileum, meckel's diverticulum, overlapping lesion of small intestine, small intestine, cecum, appendix, ascending colon, hepatic flexure of colon, transverse colon, splenic flexure of colon, descending colon, sigmoid colon, overlapping lesion of colon, colon, rectosigmoid junction, rectum, anus, anal canal, cloacogenic zone, overlapping lesion of rectum anus and anal canal, liver, intrahepatic bile duct, gallbladder, extrahepatic bile duct, ampulla of vater, overlapping lesion of biliary tract, biliary tract, head of pancreas, body pancreas, tail pancreas, pancreatic duct, islets of langerhans, neck of pancreas, overlapping lesion of pancreas, pancreas, intestinal tract, overlapping lesion of digestive system, gastrointestinal tract, nasal cavity, middle ear, maxillary sinus, ethmoid sinus, frontal sinus, sphenoid sinus, overlapping lesion of accessory sinuses, accessory sinus, glottis, supraglottis, subglottis, laryngeal cartilage, overlapping lesion of larynx, larynx, trachea, main bronchus, upper lobe lung, middle lobe lung, lower lobe lung, overlapping lesion of lung, lung, thymus, heart, anterior mediastinum, posterior mediastinum, mediastinum, pleura, overlapping lesion of heart mediastinum and pleura, upper respiratory tract, overlapping lesion of respiratory system and intrathoracic organs, respiratory tract, upper limb long bones joints, upper limb short bones joints, lower limb long bones joints, lower limb short bones joints, overlapping lesion of bones joints and articular cartilage of limbs, bone limb, skull and facial bone, mandible, vertebral column, rib sternum clavicle, pelvic bone, overlapping lesion of bones joints and articular cartilage, bone, blood, bone marrow, spleen, reticuloendothelial system, hematopoietic system, skin lip, eyelid, external ear, skin face, skin scalp neck, skin trunk, skin limb upper, skin limb lower, peripheral nerve head neck, peripheral nerve shoulder arm, peripheral nerve leg, peripheral nerve thorax, peripheral nerve abdomen, peripheral nerve pelvis, peripheral nerve trunk, overlapping lesion of peripheral nerves and autonomic nervous system, autonomic nervous system, retroperitoneum, peritoneum, peritoneum, overlapping lesion of retroperitoneum and peritoneum, connective tissue head, connective tissue arm, connective tissue leg, connective tissue thorax, connective tissue abdomen, connective tissue pelvis, connective tissue trunk, overlapping lesion of connective subcutaneous and other soft tissues, connective tissue, nipple, central portion of breast, upper inner quadrant of breast, lower inner quadrant of breast, upper outer quadrant of breast, lower outer quadrant of breast, axillary tail of breast, overlapping lesion of breast, breast, labium majus, labium minus, clitoris, overlapping lesion of vulva, vulva, vagina, endocervix, exocervix, overlapping lesion of cervix uteri, cervix uteri, isthmus uteri, endometrium, myometrium, fundus uteri, overlapping lesion of corpus uteri, corpus uteri, uterus, ovary, fallopian tube, broad ligament, round ligament, parametrium, uterine adnexa, wolffian body, overlapping lesion of female genital organs, female genital tract, prepuce, glans penis, body penis, overlapping lesion of penis, penis, prostate gland, undescended testis, descended testis, testis, epididymis, spermatic cord, scrotum, tunica vaginalis, overlapping lesion of male genital organs, male genital organs, kidney, renal pelvis, ureter, trigone bladder, dome bladder, lateral wall bladder, posterior wall bladder, ureteric orifice, urachus, overlapping lesion of bladder, bladder, urethra, paraurethral gland, overlapping lesion of urinary organs, urinary system, conjunctiva, cornea, retina, choroid, ciliary body, lacrimal gland, orbit, overlapping lesion of eye and adnexa, eye, cerebral meninges, spinal meninges, meninges, cerebrum, frontal lobe, temporal lobe, parietal lobe, occipital lobe, ventricle, cerebellum, brain stem, overlapping lesion of brain, brain, spinal cord, cauda equina, olfactory nerve, optic nerve, acoustic nerve, cranial nerve, overlapping lesion of brain and central nervous system, nervous system, thyroid gland, adrenal gland cortex, adrenal gland medulla, adrenal gland, parathyroid gland, pituitary gland, craniopharyngeal duct, pineal gland, carotid body, aortic body, overlapping lesion of endocrine glands and related structures, endocrine gland, head face or neck, thorax, abdomen, pelvis, upper limb, lower limb, other illdefined sites, overlapping lesion of ill-defined sites, lymph node face head neck, intrathoracic lymph node, intra-abdominal lymph nodes, lymph node axilla arm, lymph node inguinal region leg, lymph node pelvic, lymph nodes of multiple regions, lymph node, unknown primary site.

It is within the present invention that a target to which the further targeting moiety of the conjugate of the invention is capable of binding, is a target that is expressed in an indication subject to the following group D, group E, group F, group G, group H, group I, group J, group K and/or group L:

Group D: Acute Lymphoblastic Leukemia (ALL), Acute Myeloid Leukemia (AML), Adrenocortical Carcinoma, Anal Cancer, Astrocytomas, Basal Cell Carcinoma, Bladder Cancer, Bone Cancer, Brain Stem Glioma, Brain Tumor, Breast Cancer, Burkitt Lymphoma, Carcinoid Tumor, Carcinoma of Unknown Primary, Cervical Cancer, Chronic Lymphocytic Leukemia (CLL), Chronic Myelogenous Leukemia (CML), Colon Cancer, Colorectal Cancer, Ductal Carcinoma In Situ (DCIS), Embryonal Tumors, Endometrial Cancer, Esophageal Cancer, Ewing Sarcoma, Gallbladder Cancer, Gastric Cancer, Glioma, Hairy Cell Leukemia, Head and Neck Cancer, Hepatocellular Cancer, Hodgkin Lymphoma, Hodgkin Lymphoma, Intraocular Melanoma, Laryngeal Cancer, Leukemia, Liver Cancer, Lobular Carcinoma In Situ (LCIS), Lung Cancer, Lymphoma, Melanoma, Mouth Cancer, Multiple Myeloma, Myelodysplastic Syndromes, Nasal Cavity and Paranasal Sinus Cancer, Nasopharyngeal Cancer, Neuroblastoma, Non-Hodgkin Lymphoma, Non-Small Cell Lung Cancer, Oral Cancer, Osteosarcoma, Ovarian Cancer, Pancreatic Cancer, Pancreatic Neuroendocrine Tumors, Paraganglioma, Parathyroid Cancer, Penile Cancer, Pharyngeal Cancer, Pheochromocytoma, Pituitary Tumor, Primary Lymphoma, Prostate Cancer, Rectal Cancer, Renal Cell Cancer, Retinoblastoma, Salivary Gland Cancer, Sarcoma, Sézary Syndrome, Skin Cancer, Small Cell Lung cancer, Small Intestine Cancer, Squamous Cell Carcinoma, Testicular Cancer, Thymoma and Thymic Carcinoma, Thyroid Cancer, Urethral Cancer, Uterine Sarcoma, Vaginal Cancer, Vulvar Cancer, Wilms Tumor.

Group E: Acute Lymphoblastic Leukemia (ALL), Acute Myeloid Leukemia (AML), Anal Cancer, Astrocytomas, Basal Cell Carcinoma, Bladder Cancer, Bone Cancer, Brain Tumor, Breast Cancer, Burkitt Lymphoma, Cervical Cancer, Chronic Lymphocytic Leukemia (CLL), Chronic Myelogenous Leukemia (CML), Colon Cancer, Colorectal Cancer, Endometrial Cancer, Esophageal Cancer, Ewing Sarcoma, Gallbladder Cancer, Gastric Cancer, Glioma, Hairy Cell Leukemia, Head and Neck Cancer, Hepatocellular Cancer, Hodgkin Lymphoma, Leukemia, Liver Cancer, Lung Cancer, Lymphoma, Melanoma, Multiple Myeloma, Nasopharyngeal Cancer, Neuroblastoma, Non-Hodgkin Lymphoma, Non-Small Cell Lung Cancer, Oral Cancer, Osteosarcoma, Ovarian Cancer, Pancreatic Cancer, Pancreatic Neuroendocrine Tumors, Paraganglioma, Parathyroid Cancer, Pharyngeal Cancer, Pheochromocytoma, Primary Lymphoma, Prostate Cancer, Rectal Cancer, Renal Cell Cancer, Sarcoma, Skin Cancer, Small Cell Lung cancer, Squamous Cell Carcinoma, Testicular Cancer, Thyroid Cancer, Uterine Sarcoma, Vaginal Cancer, Vulvar Cancer.

Group F: Acute Lymphoblastic Leukemia (ALL), Acute Myeloid Leukemia (AML), Anal Cancer, Bladder Cancer, Bone Cancer, Brain Tumor, Breast Cancer, Cervical Cancer, Chronic Lymphocytic Leukemia (CLL), Chronic Myelogenous Leukemia (CML), Colon Cancer, Colorectal Cancer, Endometrial Cancer, Esophageal Cancer, Ewing Sarcoma, Gastric Cancer, Glioma, Hairy Cell Leukemia, Head and Neck Cancer, Hepatocellular Cancer, Hodgkin Lymphoma, Leukemia, Lung Cancer, Lymphoma, Melanoma, Non-Hodgkin Lymphoma, Non-Small Cell Lung Cancer, Osteosarcoma, Ovarian Cancer, Pancreatic Cancer, Pancreatic Neuroendocrine Tumors, Primary Lymphoma, Prostate Cancer, Rectal Cancer, Renal Cell Cancer, Sarcoma, Skin Cancer, Small Cell Lung cancer, Squamous Cell Carcinoma, Thyroid Cancer, Vaginal Cancer, Vulvar Cancer.

Group G: Bladder Cancer, Bone Cancer, Breast Cancer, Cervical Cancer, Colon Cancer, Colorectal Cancer, Endometrial Cancer, Ewing Sarcoma, Gastric Cancer, Hepatocellular Cancer, Hodgkin Lymphoma, Leukemia, Lung Cancer, Lymphoma, Melanoma, Non-Hodgkin Lymphoma, Non-Small Cell Lung Cancer, Ovarian Cancer, Pancreatic Cancer, Prostate Cancer, Rectal Cancer, Renal Cell Cancer, Sarcoma, Small Cell Lung cancer, Squamous Cell Carcinoma, Thyroid Cancer.

group H: Pancreatic cancer (Ehlers et al., Ann Surg, 2000, 231, 838-848; Reubi et al., Gut, 1998, 42, 546-550), Small cell lung cancer (Moody, Panminerva Med, 2006, 48, 19-26; Ocejo-Garcia et al., Lung Cancer, 2001, 33, 1-9), Non-small cell lung cancer (Alifano et al., Clin Cancer Res, 2010, 16, 4401-4410; Moody et al., Life Sci, 2014, 100, 25-34), Prostate cancer (Amorino et al., Oncogene, 2007, 26, 745-756; Taylor et al., Prostate, 2012, 72, 523-532; Valerie et al., Cancer Res, 2011, 71, 6817-6826; Swift et al., Cancer Res, 2010, 70, 347-356), Colorectal cancer (Chao et al., J Surg Res, 2005, 129, 313-321; Gui et al., Peptides, 2008, 29, 1609-1615; Bossard et al., Peptides, 2007, 28, 2030-2035), Ewing's sarcoma (Reubi et al., Int J Cancer, 1999, 82, 213-218), Meningioma (Reubi et al., Int J Cancer, 1999, 82, 213-218), Breast cancer (Dupouy et al., PLoS One, 2009, 4, e4223; Souaze et al., Cancer Res, 2006, 66, 6243-6249), Gastric cancer (Schulz et al., J Endocrinol, 2006, 191, 121-128; Thomas et al., Endocr Rev, 2003, 24, 571-599), Mesothelioma (Alifano et al., Biochimie, 2009), Head and neck cancer (Shimizu et al., Int J Cancer, 2008, 123, 1816-1823), Gastrointestinal stromal tumors (GIST) (Gromova et al., PLoS One, 2011, 6, e14710), Neuroblastoma Tavares, Melanoma (Zhang et al., Mol Cell Biochem, 2014, 389, 1-8), Chronic B cell leukemia (Saada et al., J Immunol, 2012, 189, 5293-5303), Leiomyosarcoma (Rodriguez et al., Int J Gynecol Pathol, 2011, 30, 354-363; Rodriguez et al., Biol Reprod, 2010, 83, 641-647), and cutaneous T-cell lymphoma Ramez;

group I: Pancreatic cancer (Ehlers et al., Ann Surg, 2000, 231, 838-848; Reubi et al., Gut, 1998, 42, 546-550), Small cell lung cancer (Moody, Panminerva Med, 2006, 48, 19-26; Ocejo-Garcia et al., Lung Cancer, 2001, 33, 1-9), Non-small cell lung cancer (Alifano et al., Clin Cancer Res, 2010, 16, 4401-4410; Moody et al., Life Sci, 2014, 100, 25-34), Prostate cancer (Amorino et al., Oncogene, 2007, 26, 745-756; Taylor et al., Prostate, 2012, 72, 523-532; Valerie et al., Cancer Res, 2011, 71, 6817-6826; Swift et al., Cancer Res, 2010, 70, 347-356), Colorectal cancer (Chao et al., J Surg Res, 2005, 129, 313-321; Gui et al., Peptides, 2008, 29, 1609-1615; Bossard et al., Peptides, 2007, 28, 2030-2035), Ewing's sarcoma (Reubi et al., Int J Cancer, 1999, 82, 213-218), Meningioma (Reubi et al., Int J Cancer, 1999, 82, 213-218), Breast cancer (Dupouy et al., PLoS One, 2009, 4, e4223; Souaze et al., Cancer Res, 2006, 66, 6243-6249), Gastric cancer (Schulz et al., J Endocrinol, 2006, 191, 121-128; Thomas et al., Endocr Rev, 2003, 24, 571-599), Mesothelioma (Alifano et al., Biochimie, 2009);

group J: Pancreatic cancer (Ehlers et al., Ann Surg, 2000, 231, 838-848; Reubi et al., Gut, 1998, 42, 546-550), Small cell lung cancer (Moody, Panminerva Med, 2006, 48, 19-26; Ocejo-Garcia et al., Lung Cancer, 2001, 33, 1-9), Non-small cell lung cancer (Alifano et al., Clin Cancer Res, 2010, 16, 4401-4410; Moody et al., Life Sci, 2014, 100, 25-34), Prostate cancer (Amorino et al., Oncogene, 2007, 26, 745-756; Taylor et al., Prostate, 2012, 72, 523-532; Valerie et al., Cancer Res, 2011, 71, 6817-6826; Swift et al., Cancer Res, 2010, 70, 347-356), Colorectal cancer (Chao et al., J Surg Res, 2005, 129, 313-321; Gui et al., Peptides, 2008, 29, 1609-1615; Bossard et al., Peptides, 2007, 28, 2030-2035), Breast cancer (Dupouy et al., PLoS One, 2009, 4, e4223; Souaze et al., Cancer Res, 2006, 66, 6243-6249), Ewing's sarcoma (Reubi et al., Int J Cancer, 1999, 82, 213-218);

group K: Pancreatic cancer (Ehlers et al., Ann Surg, 2000, 231, 838-848; Reubi et al., Gut, 1998, 42, 546-550), Prostate cancer (Amorino et al., Oncogene, 2007, 26, 745-756; Taylor et al., Prostate, 2012, 72, 523-532; Valerie et al., Cancer Res, 2011, 71, 6817-6826; Swift et al., Cancer Res, 2010, 70, 347-356), Small cell lung cancer (Moody, Panminerva Med, 2006, 48, 19-26; Ocejo-Garcia et al., Lung Cancer, 2001, 33, 1-9), Breast cancer (Dupouy et al., PLoS One, 2009, 4, e4223; Souaze et al., Cancer Res, 2006, 66, 6243-6249), Colorectal cancer (Chao et al., J Surg Res, 2005, 129, 313-321; Gui et al., Peptides, 2008, 29, 1609-1615; Bossard et al., Peptides, 2007, 28, 2030-2035); and group L: Pancreatic cancer (Ehlers et al., Ann Surg, 2000, 231, 838-848; Reubi et al., Gut, 1998, 42, 546-550), Prostate cancer (Amorino et al., Oncogene, 2007, 26, 745-756; Taylor et al., Prostate, 2012, 72, 523-532; Valerie et al., Cancer Res, 2011, 71, 6817-6826; Swift et al., Cancer Res, 2010, 70, 347-356), Small cell lung cancer (Moody, Panminerva Med, 2006, 48, 19-26; Ocejo-Garcia et al., Lung Cancer, 2001, 33, 1-9).

It is within the present invention that a target to which the further targeting moiety of the conjugate of the invention is capable of binding, is a target selected from the group of target classes comprising a GPCR, an ion channel, an adhesion molecule, an immunoglobulin superfamily receptor, a receptor tyrosine kinase, a receptor tyrosine phosphatase, a member of the tumor necrosis factor receptor family, an extracellular matrix protin, a transport, a matrix metallo proteinase and CD molecules.

In an embodiment of the conjugate of the invention the GPCR to which the further targeting moiety of the conjugate of the invention is capable of binding, is selected from the group comprising a class A GPCR, a class B GPCR, a class C GPCR, an adhesion class GPCR, a frizzled class GPCR and other 7TM proteins.

In an embodiment of the conjugate of the invention the ion channel to which the further targeting moiety of the conjugate of the invention is capable of binding, is selected from the group comprising a voltage-gated ion channel, a ligand-gated ion channel and other ion channels.

In an embodiment of the conjugate of the invention the adhesion molecule to which the further targeting moiety of the conjugate of the invention is capable of binding, is selected from the group comprising an integrin, a cell adhesion molecule (CAMs), a selectin, a cadherin, a lectin and a claudin.

In an embodiment of the conjugate of the invention the immunoglobulin superfamily receptor to which the further targeting moiety of the conjugate of the invention is capable of binding, is selected from the group comprising a cytokine receptor, a growth factor receptor, and an Ig binding receptor.

In an embodiment of the conjugate of the invention the extracellular matrix protein to which the further targeting moiety of the conjugate of the invention is capable of binding, is selected from the group comprising a proteoglycans, a hyaluronic acid, a collagen, an elastin, a fibronectin, a laminin, a fibrillin and a nidogen.

In an embodiment of the conjugate of the invention the transporter to which the further targeting moiety of the conjugate of the invention is capable of binding, is selected from the group comprising an ATP-binding cassette transporter family, an F-type ATPase, a V-type ATPase, a P-type ATPase, a member of the major facilitator superfamily (MFS) of transporters, and a member of the SLC superfamily of solute carriers.

In an embodiment of the conjugate of the invention the target to which the further targeting moiety of the conjugate of the invention is capable of binding, is selected from group B as defined herein.

In an embodiment of the conjugate of the invention the target to which the further targeting moiety of the conjugate of the invention is capable of binding, is selected from group B as defined herein.

In an embodiment of the conjugate of the invention the target to which the further targeting moiety of the conjugate of the invention is capable of binding, is selected from the group comprising CCK receptors (Mailleux et al., *Neurosci Lett*, 1990, 117, 243-247; Reubi et al., *Cancer Res*, 1997, 57, 1377-1386) (Upp et al., *Cancer Res*, 1989, 49, 488-492; Jensen, *Pharmacol Toxicol*, 2002, 91, 333-350), Secretin receptors (Korner et al., *Am J Pathol*, 2005, 167, 959-968), Neurotensin receptors (Ehlers et al., *Ann Surg*, 2000, 231, 838-848; Reubi et al., *Gut*, 1998; Reubi et al., *Int J Cancer*, 1999, 82, 213-218), NPY receptors (Reubi et al., *Cancer Res*, 2001, 61, 4636-4641; Magni et al., *Ann Oncol*, 2001, 12 Suppl 2, S27-29), ED-B fibronectin (Menrad et al., *Expert Opin Ther Targets*, 2005, 9, 491-500), ED-A fibronectin (Xiang et al., *PLoS One*, 2012, 7, e35378), Somatostatin receptors (de Herder et al., *Endocr Relat Cancer*, 2003, 10, 451-458; Reubi et al., *Int J Cancer*, 1999, 81, 376-386; Reubi et al., *J Clin Endocrinol Metab*, 2000, 85, 3882-3891), Bombesin receptors (Reubi et al., *Clin Cancer Res*, 2002, 8, 1139-1146; Fathi et al., *J Cell Biochem* Suppl, 1996, 24, 237-246), Tenascin (Kusagawa et al., *Br J Cancer*, 1998, 77, 98-102; Brack et al., *Clin Cancer Res*, 2006), Integrin avb6 (Bandyopadhyay et al., *Curr Drug Targets*, 2009, Hausner et al., *Cancer Res*, 2007), Integrin a5b1 (Roman et al., *Am J Respir Cell Mol Biol*, 2010, 43, 684-691), Integrin avb3 (Kumar, *Curr Drug Targets*, 2003, 4, 123-131; Danhier et al., *Mol Pharm*, 2012, 9, 2961-2973), Gastric Mucin (Singh et al., *Cancer Biol Ther*, 2007, 6, 481-486), Glypican 3 (Baumhoer et al., *Am J Clin Pathol*, 2008, 129, 899-906), Hepsin (Klezovitch et al., *Cancer Cell*, 2004, 6, 185-195), Robo1 (Wang et al., *Cancer Cell*, 2003, 4, 19-29), Robo4 (Grone et al., *Oncol Rep*, 2006, 15, 1437-1443), CD3, CD19 (Raufi et al., *Cancer Manag Res*, 2013, 5, 225-233), CD20 (Davis et al., *Clin Cancer Res*, 1999, 5, 611-615; Kosmas et al., *Leukemia*, 2002, 16, 2004-2015), CD22 (Tu et al., *J Exp Ther Oncol*, 2011, 9, 241-248), CD25 (Rech et al., *Ann N Y Acad Sci*, 2009, 1174, 99-106), CD30 (Mechtersheimer et al., *Cancer*, 1990, 66, 1732-1737; Engert, *Haematologica*, 2013, 98, 1165-1168), CD33 (Linenberger, *Leukemia*, 2005, 19, 176-182), CD40 (Vonderheide et al., *Clin Cancer Res*, 2013, 19, 1035-1043), CD44 (splice variants, e.g.v6), CD77 (glycosphingolipid Gb3) (Distler et al., *PLoS One*, 2009, 4, e6813), CD96 (Hosen et al., *Proc Natl Acad Sci USA*, 2007, 104, 11008-11013), CD123 (Jin et al., *Cell Stem Cell*, 2009, 5, 31-42), MCT1 (Sonveaux et al., *PLoS One*, 2012, 7, e33418), MCT4 (Gotanda et al., *Anticancer Res*, 2013, 33, 2941-2947), EMMPRIN (CD147) (Nabeshima et al., *Pathol Int*, 2006, 56, 359-367), PKN3 (protein kinase N3) (Unsal-Kacmaz et al., *Mol Oncol*, 2012, 6, 284-298; Aleku et al., *Cancer Res*, 2008, 68, 9788-9798), Mesothelin (Ho et al., *Clin Cancer Res*, 2007, 13, 1571-1575), EpCAM (epithelial cell adhesion molecule) (Munz et al., *Cancer Res*, 2009, 69, 5627-5629) (=HEA, human epithelial antigen a), Vascular cell adhesion molecule-1 (VCAM-1) (Chen et al., *Clin Cancer Res*, 2012, 18, 5520-5525), Endoglin (EDG) (Fonsatti et al., *Cardiovasc Res*, 2010, 86, 12-19), gpA33 (Rageul et al., *Int J Cancer*, 2009, 125, 2802-2809), VEGF-R (Smith et al., *Clin Cancer Res*, 2010, 16, 3548-3561), Transferrin receptor (Daniels et al., *Biochim Biophys Acta*, 2012, 1820, 291-317), Prostate specific membrane antigen (PSMA) (Chang et al., *Cancer Res*, 1999, Ren et al., *Med Oncol*, 2014), prostate stem cell antigen (PSCA) (Reiter et al., *Proc Natl Acad Sci USA*, 1998, 95, 1735-1740), carcinoenbryonic antigen (CEA) (Hong et al., *Biomark Insights*, 2008, 3, 435-451), TEM1 (Nanda et al., *Proc Natl Acad Sci US A*, 2006, 103, 3351-3356), TEM5 (Vallon et al., *J Biol Chem*, 2006, 281, 34179-34188), TEM8 (Frankel et al., *Anticancer Agents Med Chem*, 2011, 11, 983-992), EGF-R (Nicholson et al., *Eur J Cancer*, 2001, 37 Suppl 4, S9-15), ErbB2 (English et al., *Mol Diagn Ther*, 2013, 17, 85-99; Gravalos et al., *Ann Oncol*, 2008, 19, 1523-1529), EphA2 (Biao-Xue et al., *Curr Cancer Drug Targets*, 2011; Cai et al., *Eur J Nucl Med Mol Imaging*, 2007), Claudin-6/-18 (Sahin et al., *Clin Cancer Res*, 2008, 14, 7624-7634; Morin, *Cancer Res*, 2005, 65, 9603-9606; Kominsky, *Expert Rev Mol Med*, 2006, 8, 1-11), CD52 (Rawstron et al., *Haematologica*, 2006, 91, 1577-1578; Piccaluga et al., *Haematologica*, 2007, 92, 566-567), HLA-DR10 (Epstein et al., *Cancer Res*, 1987, 47, 830-840; Balhorn et al., *Clin Cancer Res*, 2007, 13, 5621s-5628s), EGP-1 (epithelial glycoprotein-1) (Muhlmann et al., *J Clin Pathol*, 2009, 62, 152-158; Cubas et al., *Biochim Biophys Acta*, 2009, 1796, 309-314), CEACAM5 (carcinoembryonic antigen-related cell adhesion molecule 5) (Beauchemin et al., *Cancer Metastasis Rev,* 2013, 32, 643-671), E-Cadherin (Kowalski et al., *Breast Cancer Res,* 2003, 5, R217-222; Chan, *World J Gastroenterol,* 2006, 12, 199-203), CXCR4 (Furusato et al., *Pathol Int,* 2010, 60, 497-505), LRRC15 (Schuetz et al., *Cancer Res,* 2006, 66, 5278-5286; O'Prey et al., *J Virol,* 2008, 82, 5933-5939), MMPs (Mitra et al., *JEnviron Pathol Toxicol Oncol,* 2003, 22, 93-100; Davidson et al., *Arkh Patol,* 2002, 64, 47-53), TFPI (Sierko et al., *Thromb Haemost,* 2010, 103, 198-204), secreted form of Clusterin sCLU (Trougakos et al., *Int J Biochem Cell Biol,* 2002, 34, 1430-1448; Rizzi et al., *Endocr Relat Cancer,* 2010, 17, R1-17), Siglec-15 (Takamiya et al., *Glycobiology,* 2013, 23, 178-187), CAAG-1, HMW-MAA (high molecular weight melanoma-associated antigen) (Kageshita et al., *Pigment Cell Res,* 1992, Suppl 2, 132-135; Buraggi, *Nuklearmedizin,* 1986, 25, 220-224), TAG-72 (Qi et al., *J Surg Oncol,* 1995, 59, 3-9; Muxi et al., *Nucl Med Commun,* 1999, 20, 123-130), hsp70 (Murphy, *Carcinogenesis,* 2013, 34, 1181-1188; Guzhova et al., *Int J Hyperthermia,* 2013, 29, 399-408), Foetal antigen-2 (Hakkinen, *Transplant Rev,* 1974, 20, 61-76; Cheung et al., *World J Surg Oncol,* 2010, 8, 38), collagen XXIII (Banyard et al., *J Biol Chem,* 2003, 278, 20989-20994; Banyard et al., *Clin Cancer Res,* 2007, 13, 2634-2642), nucleolin (Joo et al., *Glycobiology,* 2005, 15, 1-9; Destouches et al., *PLoS One,* 2008, 3, e2518), TENB2 (Glynne-Jones et al., *Int J Cancer,* 2001, 94, 178-184), tissue factor receptor (Schaffner et al., *Semin Thromb Hemost,* 2008, 34, 147-153), ASC2 Aminosiuretransporter (Shimizu et al., *Br J Cancer,* 2014, 110, 2030-2039), FAP-alpha (Lee et al., *BMC Cancer,* 2011, 11, 245), Folic Acid Receptor (Serpe et al., *Pharmgenomics Pers Med,* 2014, 7, 31-42; Walters et al., *Gynecol Oncol,* 2013, 131, 493-498), CA19.9 (Haglund et al., *Br J Cancer,* 1991, 63, 386-389), Angiopoietin-/-2 receptor (Holopainen et al., *Cancer Res,* 2009, 69, 4656-4664; Martin et al., *Histol Histopathol,* 2008, 23, 773-780), GIP.

In an embodiment of the conjugate of the invention the target to which the further targeting moiety of the conjugate of the invention is capable of binding, is selected from the group comprising Alpha(v)beta(3) integrin, Alpha(5)beta (1), Alpha(v)beta(6) integrin, Amino acid transporter ASC, Amino acid transporter L, Aminopeptidase N (ANP, CD13), Angiopoietin-1 receptor, Atrial natriuretic peptide receptor 1, Atrial natriuretic peptide receptor 2, A-type amino acid transporter, Avidin, Bcr-Abl tyrosine kinase, Bombesin receptor, Bombesin receptor subtype-3, CA 125 antigen, CA19.9, Cadherin 2, Calcitonin receptor, Carbonic anhydrase IX, Carcinoembryonic antigen, CCK-1 receptor, CD105 (Endoglin, EDG), CD137 antigen, CD19, CD20, CD21, CD22, CD25, CD27, CD3, CD30, CD33, CD37, CD40, CD44 (splice variants, e.g.v6), CD44 receptor, CD52, CEACAM cell adhesion molecule, Cell surface nucleolin, Chemokine receptor 4 (CXCR4), Cholecystokinin receptor subtype 2 (CCK-2), Cholecystokinin type A (CCK-A) receptor, Claudin 4 receptor, Claudin-6, collagen XXIII, Colony stimulating factor-1 receptor (CSF-1R), Corticotropin-releasing factor receptor 1 (CRFR1), Corticotropin-releasing factor receptor 2 (CRFR2), CTLA4, Disialogangliosides, DKK2 protein, DPPIV, E-Cadherin, ED-A fibronectin, ED-B fibronectin, EGF HER2 receptor, EGFR (HER1), EGFR Tyrosine kinase, EGFR2, EGP-1 (epithelial glycoprotein-1), EMMPRIN (CD147), Endothelin A (ETA) receptor, Endothelin B receptor, EpCAM (epithelial cell adhesion molecule), EphA2 receptor, EphrinB4 receptor, Epidermal growth factor receptor 3, E-selectin, FGF receptor, Fibroblast activation protein-alpha (FAPa), Folate receptor, Gastrin releasing peptide (GRP) receptor, Gastrin/cholecystokinin-2 (CCK-2, CCK-B) receptor, Glucagon like peptide 1 receptor, Glucose transporter, GLUT transporter system, Glutamate transporters, Glutamine transporter, Glycoprotein IIb/IIIa receptor (GPIIb/IIIa receptor), Glypican 3, Gonadotropin releasing hormone receptor, gpA33, GPR54 receptor, Hepsin, HLA-DR antigen, Integrins αvβ5, Intercellular adhesion molecule 1 (ICAM-1), L1-CAM antigen, Lactoferrin receptor, L-Amino acid transporter (LAT), Luteinizing hormone releasing hormone receptor, Matrix metalloproteinase-12, Matrix metalloproteinase-9, Matrix metalloproteinases (membrane type-1), Melancortin-1 receptor (MC1R), Mesenchymal-epithelial transition factor (c-Met), MIF, MUC1, Mucin MUC2, Neurokinin 1 (NK1) receptor, neuropeptide Y receptor 1 (NPY1-R), neuropeptide Y receptor 2 (NPY2-R), Neuropeptide Y receptor type 4 (NPY4-R), Neurotensin receptor, Neurotensin receptor 1 (NTSR1), Neurotensin receptor 2 (NTSR2), PDGFR, Prolactin receptor, Prostate specific antigen, Prostate stem cell antigen (PSCA), Prostate-specific membrane antigen (PSMA), RANKL, Robo1, Robo4, somatostatin receptor, Somatostatin receptor 1 (SSTR1), Somatostatin receptor 2 (SSTR2), Somatostatin receptor 3 (SSTR3), Somatostatin receptor sub-type 4, Somatostatin receptor type 5, Substance P receptor (NK-1R), Substance-K receptor (NK-2R), TAG 72, Tenascin-C, Tissue factor, Transferrin receptor (TfR), Tumor endothelial marker 1 (TEM1), Tumor necrosis factor receptor, Tumor necrosis factor-related apoptosis-inducing ligand receptor 1 (TRAIL-R1), Tumor necrosis factor-related apoptosis-inducing ligand receptor 2 (TRAILR2), Urokinase plasminogen activator receptor, Urokinase-type plasminogen activator receptor (uPAR), Vascular cell adhesion molecule 1 (VCAM-1), Vascular endothelial growth factor receptor (VEGFR), Vascular endothelial growth factor receptor 2 (VEGFR2), Vascular endothelial growth factor receptor 3, Vasoactive intestinal peptide receptor, Vasoactive intestinal polypeptide receptor 2 (VPAC2).

In an embodiment of the conjugate of the invention the target to which the further targeting moiety of the conjugate of the invention is capable of binding, is selected from the group comprising Alpha(5)beta(1), Alpha(v)beta(3) integrin, Alpha(v)beta(6) integrin, Angiopoietin-1 receptor, Bombesin receptor, CA 125 antigen, CA19.9, Carbonic anhydrase IX, Carcinoembryonic antigen, CCK-1 receptor, CD137 antigen, CD20, CD30, CD40, CEACAM cell adhesion molecule, Chemokine receptor 4 (CXCR4), Cholecystokinin receptor subtype 2 (CCK-2), Colony stimulating factor-1 receptor (CSF-1R), Corticotropin-releasing factor receptor 1 (CRFR1), Corticotropin-releasing factor receptor 2 (CRFR2), CTLA4, E-Cadherin, ED-A fibronectin, ED-B fibronectin, EGF HER2 receptor, EGFR (HER1), EMMPRIN (CD147), EpCAM (epithelial cell adhesion molecule), EphA2 receptor, EphrinB4 receptor, Epidermal growth factor receptor 3, E-selectin, FGF receptor, Folate receptor, Gastrin releasing peptide (GRP) receptor, Glucagon like peptide 1 receptor, GLUT transporter system, Glycoprotein IIb/IIIa receptor (GPIIb/IIIa receptor), Glypican 3, Gonadotropin releasing hormone receptor, Integrins αvβ5, Intercellular adhesion molecule 1 (ICAM-1), L1-CAM antigen, Luteinizing hormone releasing hormone receptor, Matrix metalloproteinases (membrane type-1), Melancortin-1 receptor (MC1R), Mesenchymal-epithelial transition factor (c-Met), MIF, MUC1, Mucin MUC2, neuropeptide Y receptor 1 (NPY1-R), neuropeptide Y receptor 2 (NPY2-R), Neuropeptide Y receptor type 4 (NPY4-R), Neurotensin receptor, Neurotensin receptor 1 (NTSR1), Neurotensin receptor 2 (NTSR2), PDGFR, Prolactin receptor, Prostate specific antigen, Prostate stem cell antigen (PSCA), Prostate-specific membrane antigen (PSMA), RANKL, Robo1, Robo4, somatostatin receptor, Substance P receptor (NK-1R), Substance-K receptor (NK-2R), Tenascin-C, Transferrin receptor (TfR), Tumor necrosis factor-related apoptosis-inducing ligand receptor 1 (TRAIL-R1), Tumor necrosis factor-related apoptosis-inducing ligand receptor 2 (TRAILR2), Vascular cell adhesion molecule 1 (VCAM-1), Vascular endothelial growth factor receptor (VEGFR), Vascular endothelial growth factor receptor 2 (VEGFR2), Vascular endothelial growth factor receptor 3, Vasoactive intestinal peptide receptor, Vasoactive intestinal polypeptide receptor 2 (VPAC2).

In an embodiment of the conjugate of the invention the target to which the further targeting moiety of the conjugate of the invention is capable of binding, is selected from the group comprising Amino acid transporter L, Angiopoietin-1 receptor, Atrial natriuretic peptide receptor 1, Atrial natriuretic peptide receptor 2, A-type amino acid transporter, Avidin, Bcr-Abl tyrosine kinase, Bombesin receptor, Bombesin receptor subtype-3, Cadherin 2, Calcitonin receptor, CCK-1 receptor, CD20, CD21, CD27, CD30, CD37, Chemokine receptor 4 (CXCR4), Cholecystokinin receptor subtype 2 (CCK-2), Cholecystokinin type A (CCK-A) receptor, Claudin 4 receptor, Colony stimulating factor-1 receptor (CSF-1R), DKK2 protein, E-Cadherin, EGF HER2 receptor, EGFR (HER1), EGFR Tyrosine kinase, EGFR2, Endothelin A (ETA) receptor, Endothelin B receptor, EpCAM (epithelial cell adhesion molecule), EphA2 receptor, EphrinB4 receptor, FGF receptor, Gastrin releasing peptide (GRP) receptor, Gastrin/cholecystokinin-2 (CCK-2, CCK-B) receptor, Gonadotropin releasing hormone receptor, GPR54 receptor, Lactoferrin receptor, Luteinizing hormone releasing hormone receptor, Matrix metalloproteinase-12, Melancortin-1 receptor (MC1R), neuropeptide Y receptor 1 (NPY1-R), neuropeptide Y receptor 2 (NPY2-R), Neurotensin receptor, somatostatin receptor, Substance P receptor (NK-1R), Tumor necrosis factor receptor, Urokinase plasminogen activator receptor, Vascular endothelial growth factor receptor (VEGFR), Vasoactive intestinal peptide receptor.

In an embodiment of the conjugate of the invention the target to which the further targeting moiety of the conjugate of the invention is capable of binding, is selected from the group comprising Alpha(v)beta(3) integrin, Alpha(v)beta(6) integrin, Amino acid transporter ASC, Amino acid transporter L, Aminopeptidase N (ANP, CD13), Angiopoietin-1 receptor, Atrial natriuretic peptide receptor 1, Atrial natriuretic peptide receptor 2, Bombesin receptor, Bombesin receptor subtype-3, CA 125 antigen, CA19.9, Cadherin 2, Calcitonin receptor, Carbonic anhydrase IX, Carcinoembryonic antigen, CCK-1 receptor, CD105 (Endoglin, EDG), CD19, CD20, CD22, CD25, CD3, CD30, CD33, CD40, CD44 (splice variants, e.g.v6), CD44 receptor, CD52, CEACAM cell adhesion molecule, Cell surface nucleolin, Cholecystokinin receptor subtype 2 (CCK-2), Claudin-6, collagen XXIII, Corticotropin-releasing factor receptor 1 (CRFR1), Corticotropin-releasing factor receptor 2 (CRFR2), Disialogangliosides, DPPIV, E-Cadherin, ED-A fibronectin, ED-B fibronectin, EGF HER2 receptor, EGP-1 (epithelial glycoprotein-1), EMMPRIN (CD147), EphA2 receptor, Fibroblast activation protein-alpha (FAP?), Gastrin releasing peptide (GRP) receptor, Glucose transporter, Glutamate transporters, Glutamine transporter, gpA33, GPR54 receptor, Hepsin, HLA-DR antigen, L-Amino acid transporter (LAT), Lactoferrin receptor, Matrix metalloproteinase-9, MUC1, Neurokinin 1 (NK1) receptor, neuropeptide Y receptor 1 (NPY1-R), neuropeptide Y receptor 2 (NPY2-R), Neuropeptide Y receptor type 4 (NPY4-R), Neurotensin receptor, Neurotensin receptor 1 (NTSR1), Neurotensin receptor 2 (NTSR2), Prostate stem cell antigen (PSCA), Prostate-specific membrane antigen (PSMA), Robo1, Somatostatin receptor 1 (SSTR1), Somatostatin receptor 2 (SSTR2), Somatostatin receptor 3 (SSTR3), Somatostatin receptor sub-type 4, Somatostatin receptor type 5, TAG 72, Tenascin-C, Tumor necrosis factor receptor, Urokinase-type plasminogen activator receptor (uPAR), Tumor endothelial marker 1 (TEM1), Tissue factor and Transferrin receptor (TfR).

In an embodiment of the conjugate of the invention the target to which the further targeting moiety of the conjugate of the invention is capable of binding, is selected from the group comprising Atrial natriuretic peptide receptor 1 (Wang et al., *Mol Cancer,* 2011, 10, 56; Kong et al., *Cancer Res,* 2008, 68, 249-256), Atrial natriuretic peptide receptor 2 (Zhao et al., *World J Surg Oncol,* 2014, 12, 154), Bombesin receptor subtype-3 (Reubi et al., *Clin Cancer Res,* 2002, 8, 1139-1146; Moody et al., *Peptides,* 2011, 32, 1677-1684), Calcitonin receptor (Wang et al., *Breast Cancer Res Treat,* 2004, 83, 109-117), Corticotropin-releasing factor receptor 1 (CRFR1) (Wang et al., *Biochem Biophys Res Commun,* 2007, 362, 785-788), Corticotropin-releasing factor receptor 2 (CRFR2) (Wang et al., *Biochem Biophys Res Commun,* 2007, 362, 785-788), Endothelin A (ETA) receptor (Bagnato et al., *J Transl Med,* 2004, 2, 16), Endothelin B receptor (Kandalaft et al., *Clin Cancer Res,* 2009, 15, 4521-4528), Gastrin releasing peptide (GRP) receptor (Sun et al., *Prostate,* 2000, 42, 295-303), Glucagon like peptide 1 receptor (Korner et al., *J Nucl Med,* 2007, 48, 736-743), Gonadotropin releasing hormone receptor (Grundker et al., *Mol Cancer Ther,* 2005, 4, 225-231), Melanocyte-stimulating hormone receptor (Cheng et al., *J Nucl Med,* 2007, 48, 987-994), Neuromedin-B receptor (NMBR) (Park et al., *Cancer Lett,* 2011, 312, 117-127), Neurokinin-3 receptor (NK-3R) (Rameshwar et al., *Blood,* 1995, 86, 482-490), neuropeptide Y receptor 1 (NPY1-R) (Reubi et al., *Cancer Res,* 2001, 61, 4636-4641; Magni et al., *Ann Oncol,* 2001, 12 Suppl 2, S27-29), neuropeptide Y receptor 2 (NPY2-R) (Medeiros et al., *Int J Cancer,* 2012, 131, 276-286; Korner et al., *Peptides,* 2007, 28, 419-425), Neuropeptide Y receptor type 4 (NPY4-R) (Cox et al., *Br J Pharmacol,* 2001, 132, 345-353), Neurotensin receptor 1 (NTSR1) (Ehlers et al., *Ann Surg,* 2000, 231, 838-848; Reubi et al., *Gut,* 1998), Neurotensin receptor 2 (NTSR2) (Reubi et al., *Int J Cancer,* 1999, 82, 213-218), Oxytocin receptor (Bussolati et al., *Am J Pathol,* 1996, 148, 1895-1903), Pituitary adenylate cyclase-activating polypeptide type I receptor (Reubi et al., *Cancer Res,* 2000, 60, 3105-3112), Somatostatin receptor 1 (SSTR1) (Fujita et al., *Life Sci,* 1994, 55, 1797-1806), Somatostatin receptor 2 (SSTR2) (Reubi et al., *J Clin Endocrinol Metab,* 2000, 85, 3882-3891), Somatostatin receptor 3 (SSTR3) (Reubi et al., *Int J Cancer,* 1999, 81, 376-386), Somatostatin receptor sub-type 4 (Plockinger et al., *Eur J Endocrinol,* 2012, 166, 223-234), Somatostatin receptor type 5 (de Herder et al., *Endocr Relat Cancer,* 2003, 10, 451-458), Sortilin (NTSR3) (Hemmati et al., *Avicenna J Med Biotechnol,* 2009, 1, 125-131), Substance P receptor (NK-1R) (Hennig et al., *Int J Cancer,* 1995, 61, 786-792), Substance-K receptor (NK-2R) (Bigioni et al., *Anticancer Drugs,* 2005, 16, 1083-1089), Vasoactive intestinal peptide receptor (VPAC1) (Virgolini et al., *N Engl J Med,* 1994, 331, 1116-1121), Vasoactive intestinal polypeptide receptor 2 (VPAC2) (Reubi et al., *Cancer Res,* 2000, 60, 3105-3112), BB4 (Reubi et al., *Clin Cancer Res,* 2002, 8, 1139-1146).

In an embodiment of the conjugate of the invention the target to which the further targeting moiety of the conjugate of the invention is capable of binding, is selected from the group comprising Alpha(v)beta(3) integrin (Kumar, *Curr Drug Targets*, 2003, 4, 123-131; Danhier et al., *Mol Pharm*, 2012, 9, 2961-2973), Alpha(v)beta(6) integrin (Bandyopadhyay et al., *Curr Drug Targets*, 2009, Hausner et al., *Cancer Res*, 2007), Amino acid transporter L (Haase et al., *J Nucl Med*, 2007, 48, 2063-2071; Imai et al., *Anticancer Res*, 2010, 30, 4819-4828), Atrial natriuretic peptide receptor 1 (Wang et al., *Mol Cancer*, 2011, 10, 56; Kong et al., *Cancer Res*, 2008, 68, 249-256), Atrial natriuretic peptide receptor 2 (Zhao et al., *World J Surg Oncol*, 2014, 12, 154), Bombesin receptor subtype-3 (Reubi et al., *Clin Cancer Res*, 2002, 8, 1139-1146; Moody et al., *Peptides*, 2011, 32, 1677-1684), CA 125 antigen (Devan et al., *Asian Pac J Cancer Prev* 2013, 14, 4545-4548; Seelenmeyer et al., *J Cell Sci*, 2003, 116, 1305-1318), CA19.9 (Haglund et al., *Br J Cancer*, 1991, 63, 386-389), Cadherin 2 (Nakajima et al., *Clin Cancer Res*, 2004, 10, 4125-4133), Calcitonin receptor (Wang et al., *Breast Cancer Res Treat*, 2004, 83, 109-117), Carbonic anhydrase IX (McDonald et al., *Oncotarget*, 2012, 3, 84-97), Carcinoembryonic antigen (Hong et al., *Biomark Insights*, 2008, 3, 435-451), CD40 (Vonderheide et al., *Clin Cancer Res*, 2013, 19, 1035-1043), CEACAM cell adhesion molecule (Beauchemin et al., *Cancer Metastasis Rev*, 2013, 32, 643-671), Chemokine receptor 4 (CXCR4) (Furusato et al., *Pathol Int*, 2010, 60, 497-505), Colony stimulating factor-1 receptor (CSF-1R) (Kacinski, *Ann Med*, 1995, 27, 79-85), Corticotropin-releasing factor receptor 1 (CRFR1) (Wang et al., *Biochem Biophys Res Commun*, 2007, 362, 785-788), Corticotropin-releasing factor receptor 2 (CRFR2) (Wang et al., *Biochem Biophys Res Commun*, 2007, 362, 785-788), ED-A fibronectin (Xiang et al., *PLoS One*, 2012, 7, e35378), ED-B fibronectin (Menrad et al., *Expert Opin Ther Targets*, 2005, 9, 491-500), EGFR (HER1) (Nicholson et al., *Eur J Cancer*, 2001, 37 *Suppl* 4, S9-15), EMMPRIN (CD147) (Nabeshima et al., *Pathol Int*, 2006, 56, 359-367), EpCAM (epithelial cell adhesion molecule) (Munz et al., *Cancer Res*, 2009, 69, 5627-5629), EphrinB4 receptor (Li et al., *Mol Pharm*, 2013, 10, 329-336), FGF receptor (Katoh et al., *Med Res Rev*, 2014, 34, 280-300), Gonadotropin releasing hormone receptor (Grundker et al., *Mol Cancer Ther*, 2005, 4, 225-231), GPR54 receptor (Cho et al., *Cancer Metastasis Rev*, 2012, 31, 585-591), Lactoferrin receptor (Wrba et al., *Verh Dtsch Ges Pathol*, 1986, 70, 247-250), Luteinizing hormone releasing hormone receptor (Buchholz et al., *Int J Oncol*, 2009, 35, 789-796), Melancortin-1 receptor (MC1R) (Cheng et al., *J Nucl Med*, 2007, 48, 987-994), MUC1 (Singh et al., *Cancer Biol Ther*, 2007, 6, 481-486), Neuropeptide Y receptor type 4 (NPY4-R) (Cox et al., *Br J Pharmacol*, 2001, 132, 345-353), Neurotensin receptor 1 (NTSR1) (Ehlers et al., *Ann Surg*, 2000, 231, 838-848; Reubi et al., Gut, 1998), Neurotensin receptor 2 (NTSR2) (Reubi et al., *Int J Cancer*, 1999, 82, 213-218), Prostate stem cell antigen (PSCA) (Reiter et al., *Proc Natl Acad Sci US A*, 1998, 95, 1735-1740), Prostate-specific membrane antigen (PSMA) (Chang et al., *Cancer Res*, 1999, Ren et al., *Med Oncol*, 2014), Robo1 (Wang et al., *Cancer Cell*, 2003, 4, 19-29), somatostatin receptor (Reubi et al., *Int J Cancer*, 1999, 81, 376-386), Substance P receptor (NK-1R) (Hennig et al., *Int J Cancer*, 0.1995, 61, 786-792), Tenascin-C (Kusagawa et al., *Br J Cancer*, 1998, 77, 98-102; Brack et al., *Clin Cancer Res*, 2006), Transferrin receptor (TfR) (Daniels et al., *Biochim Biophys Acta*, 2012, 1820, 291-317), Tumor necrosis factor receptor (Szlosarek et al., *Mol Cancer Ther*, 2006, 5, 382-390), Vascular endothelial growth factor receptor (VEGFR) (Smith et al., *Clin Cancer Res*, 2010, 16, 3548-3561), Vasoactive intestinal peptide receptor (Reubi, *J Nucl Med*, 1995, 36, 1846-1853).

In an embodiment of the conjugate of the invention the target to which the further targeting moiety of the conjugate of the invention is capable of binding, is selected from the group comprising Angiopoietin-1 receptor (Tie-2) (Holopainen et al., *Cancer Res*, 2009, 69, 4656-4664; Martin et al., *Histol Histopathol*, 2008, 23, 773-780), Bombesin receptor (Reubi et al., *Clin Cancer Res*, 2002, 8, 1139-1146; Fathi et al., *J Cell Biochem* Suppl, 1996, 24, 237-246), CCK-1 receptor (Mailleux et al., *Neurosci Lett*, 1990, 117, 243-247; Reubi et al., *Cancer Res*, 1997, 57, 1377-1386), CD20 (Davis et al., *Clin Cancer Res*, 1999, 5, 611-615; Kosmas et al., *Leukemia*, 2002, 16, 2004-2015), CD30 (Mechtersheimer et al., *Cancer*, 1990, 66, 1732-1737; Engert, *Haematologica*, 2013, 98, 1165-1168), Cholecystokinin receptor subtype 2 (CCK-2) (Upp et al., *Cancer Res*, 1989, 49, 488-492; Jensen, *Pharmacol Toxicol*, 2002, 91, 333-350), E-Cadherin (Kowalski et al., *Breast Cancer Res*, 2003, 5, R217-222; Chan, *World J Gastroenterol*, 2006, 12, 199-203), EGF HER2 receptor (English et al., *Mol Diagn Ther*, 2013, 17, 85-99; Gravalos et al., *Ann Oncol*, 2008, 19, 1523-1529), EphA2 receptor (Biao-Xue et al., *Curr Cancer Drug Targets*, 2011; Cai et al., *Eur J Nucl Med Mol Imaging*, 2007), Gastrin releasing peptide (GRP) receptor (Carroll et al., *Peptides*, 1999, 20, 229-237; Saurin et al., *Eur J Cancer*, 1999, 35, 125-132), neuropeptide Y receptor 1 (NPY1-R) (Reubi et al., *Cancer Res*, 2001, 61, 4636-4641; Magni et al., *Ann Oncol*, 2001, 12 *Suppl* 2, S27-29), neuropeptide Y receptor 2 (NPY2-R) (Medeiros et al., *Int J Cancer*, 2012, 131, 276-286; Korner et al., *Peptides*, 2007, 28, 419-425), Neurotensin receptor (Ehlers et al., *Ann Surg*, 2000, 231, 838-848; Reubi et al., Gut, 1998).

In an embodiment of the conjugate of the invention the target to which the further targeting moiety of the conjugate of the invention is capable of binding, is selected from the group comprising Alphavbeta6 integrin (Bandyopadhyay et al., *Curr Drug Targets*, 2009, 10, 645-652; Bates, *Future Oncol*, 2005, 1, 821-828; Eberlein et al., *Oncogene*, 2013, 32, 4406-4416; Hausner et al., *Cancer Res*, 2007, 67, 7833-7840; Hecht et al., *Appl Immunohistochem Mol Morphol*, 2008, 16, 543-547; Kogelberg et al., *PLoS One*, 2013, 8, e73260; Li et al., *Bioorg Med Chem*, 2011, 19, 5480-5489; Liu et al., *J Nucl Med*, 2014; Schittenhelm et al., *Int J Clin Exp Pathol*, 2013, 6, 2719-2732; Vogetseder et al., *Int J Cancer*, 2013, 133, 2362-2371), Bradykinin Bi receptor (Chee et al., *Biol Chem*, 2008, 389, 1225-1233; Esseghir et al., *J Pathol*, 2006, 210, 420-430; Figueroa et al., *Expert Opin Ther Targets*, 2012, 16, 299-312; Molina et al., *Breast Cancer Res Treat*, 2009, 118, 499-510; Moodley et al., *Biol Chem*, 2005, 386, 375-382; Sgnaolin et al., *Invest New Drugs*, 2012; Taub et al., *Cancer Res*, 2003, 63, 2037-2041), EphA2 (Biao-Xue et al., *Curr Cancer Drug Targets*, 2011; Cai et al., *Eur J Nucl Med Mol Imaging*, 2007, 34, 2024-2036; Castano et al., *Histol Histopathol*, 2008, 23, 1011-1023; Herath et al., *Int J Cancer*, 2010, 126, 2003-2011; Jackson et al., *Cancer Res*, 2008, 68, 9367-9374; Kinch et al., *Clin Exp Metastasis*, 2003, 20, 59-68; Pasquale, *Nat Rev Cancer*, 2010, 10, 165-180; Tandon et al., *Expert Opin Ther Targets*, 2011, 15, 31-51; Wang et al., *J Med Chem*, 2012; Wykosky et al., *Mol Cancer Res*, 2008, 6, 1795-1806), Tenascin C (Kusagawa et al., *Br J Cancer*, 1998, 77, 98-102; Brack et al., *Clin Cancer Res*, 2006, 12, 3200-3208; Brunner et al., *J Clin Pathol*, 2004, 57, 927-931; Hancox et al., *Breast Cancer Res*, 2009, 11, R24; Juuti et al., *J Clin Pathol*, 2004, 57, 1151-1155; Leins et al., *Cancer*, 2003, 98, 2430-2439;

Parekh et al., *Lung Cancer,* 2005, 47, 17-29; Silacci et al., *Protein Eng Des Sel,* 2006, 19, 471-478; Tsunoda et al., *Am J Pathol,* 2003, 162, 1857-1867).

In an embodiment of the conjugate of the invention the further targeting moiety is preferably a targeting moiety having an affinity to the target molecule to which the further targeting moiety is capable of binding, of <100 pM, of <1 nM, of <10 nM, of <100 nM, of <1 µM or of <10 µM. It is within the present invention that such affinity of the further targeting moiety is shown by any embodiment of such further targeting moiety. Specifically, such affinity of the further targeting moiety can also be realized in those embodiments of the conjugate of the invention where the further targeting moiety is preferably selected from the group comprising an antibody, an antigen-binding antibody fragments, camelid heavy chain IgG (hcIgG), a cartilaginous fish (e.g. shark) IgNAR antibody, a protein scaffold, a target-binding peptide, a peptide nucleic acid (PNA), a target-binding polypeptide or protein, a target binding nucleic acid molecule, a carbohydrate, a lipid and a target-binding small molecule. Methods for determining the affinity of a compound such as the further targeting moiety to a or the target are known to the one skilled in the art and, for example described in (Schier et al., *Hum Antibodies Hybridomas,* 1996, 7, 97-105)

In an embodiment of the conjugate of the invention the further targeting moiety is preferably a targeting moiety having a stability of 100%, of at least 80%, of at least 50%, of at least 30% or of at least 10% after 24 h, 12 h, 8 h, 4 h, 2 h, 1 h or 30 min in plasma, serum, a homogenate of a tissue of any origin, an enzyme cocktail, a solution of an isolated enzyme, a protease cocktail or a solution of an isolated protease. Preferably, the further targeting moiety has a stability of 100% after 24 hours at 37° C. under the above given reaction conditions, preferably if the stability is tested in plasma, serum or a homogenate of a tissue, more preferably a tissue which contains or expresses the target targeted by the further targeting moiety. It is, however, also within the present invention that the further targeting moiety has a stability of at least 10% after 30 minutes at 37° C. under the above given reaction conditions, preferably if the stability is tested in plasma, serum or a homogenate of a tissue, more preferably a tissue which contains or expresses the target targeted by the further targeting moiety. It is within the present invention that such stability of the further targeting moiety is shown by any embodiment of such further targeting moiety. More specifically, such stability of the further targeting moiety can also be realized in those embodiments of the conjugate of the invention where the further targeting moiety is preferably selected from the group comprising an antibody, an antigen-binding antibody fragments, camelid heavy chain IgG (hcIgG), a cartilaginous fish (e.g. shark) IgNAR antibody, a protein scaffold, a target-binding peptide, a peptide nucleic acid (PNA), a target-binding polypeptide or protein, a target binding nucleic acid molecule, a carbohydrate, a lipid and a target-binding small molecule.

In an embodiment of the conjugate of the invention the further targeting moiety is preferably a targeting moiety having a selectivity factor of equal to ore more than 10,000; of equal to or more than 1000; of equal to or more than 100; of equal to or more than 50; of equal to or more than 10; of equal to or more than 5 or of equal to or more than 2 to an anti-target. The Selectivity factor is the quotient of target dissociation constant and anti-target dissociation constant. The dissociation constant is commonly used to describe the affinity between a ligand (L) (such as a drug) and a protein (P) i.e. how tightly a ligand binds to a particular protein. The formation of a ligand-protein complex (C) can be described by a two-state process

The corresponding dissociation constant is defined as $$K_d = \frac{[P][L]}{[C]}$$

where [P], [L] and [C] represent molar concentrations of the protein, ligand and complex, respectively. The anti-target with regard to the selectivity factor is preferably one which must not or should not be targeted by the further targeting moiety. It is within the present invention that such selectivity of the further targeting moiety is shown by any embodiment of such further targeting moiety. More specifically, such selectivity of the further targeting moiety can also be realized in those embodiments of the conjugate of the invention where the further targeting moiety is preferably selected from the group comprising an antibody, an antigen-binding antibody fragments, camelid heavy chain IgG (hcIgG), a cartilaginous fish (e.g. shark) IgNAR antibody, a protein scaffold, a target-binding peptide, a peptide nucleic acid (PNA), a target-binding polypeptide or protein, a target binding nucleic acid molecule, a carbohydrate, a lipid and a target-binding small molecule. Methods for determining the selectivity factor of a compound such as the further targeting moiety to a or the target are known to the one skilled in the art and, for example described in (Neubauer et al., *J Med Chem,* 2014, 57, 3410-3417).

It is within the present invention that the first targeting moiety TM1 and the second targeting moiety TM2 are linked to or connected with each other by a linkage. Such linkage can be direct such that both TM1 and TM2 are directly linked to each other such as realized in embodiment (4) of the conjugate of the invention disclosed above, i.e. ([TM1]-[TM2], or by one or moieties being introduced between said first targeting moiety TM1 and said second targeting moiety TM2; such or more moieties being the first adaptor moiety AD1, the linker moiety LM and the second adaptor moiety AD2, or any combination thereof, preferably any combination thereof as disclosed herein. Such linkage results in the first targeting moiety TM1 and the second targeting moiety TM2 being separated from each other. Such separation can be expressed by the number of covalent linkages realized between the first targeting moiety TM1 and the second targeting moiety TM2. In preferred embodiment the covalent linkages are provided by the first adaptor moiety AD1, the linker moiety LM and the second adaptor moiety AD2, or any combination thereof. In an embodiment the number of covalent bonds between the first targeting moiety TM1 and the second targeting moiety TM2 is 1. In an alternative embodiment the number of covalent bonds between the first targeting moiety TM1 and the second targeting moiety TM2 is about from 4 to 1000, preferably about from 5 to 150, and more preferably about from 6 to 40.

Adapter Moieties

In an embodiment of the conjugate of the invention the conjugate comprises, in terms of an adapter moiety, a first adapter moiety AD1 only. In another embodiment of the conjugate of the invention the conjugate comprises, in terms of an adapter moiety, a second adapter moiety AD2 only. In another embodiment of the conjugate of the invention the conjugate comprises, in terms of an adapter moiety, a third adapter moiety AD3 only. In another embodiment of the conjugate of the invention the conjugate comprises, in terms of an adapter moiety, only a first adapter moiety AD1 and a second adapter moiety AD2. In another embodiment of the conjugate of the invention the conjugate comprises, in terms of an adapter moiety, only a first adapter moiety AD1 and a third adapter moiety AD3. In another embodiment of the conjugate of the invention the conjugate comprises, in terms of an adapter moiety, only a first adapter moiety AD2 and a third adapter moiety AD3. In another embodiment of the conjugate of the invention the conjugate comprises, in terms of an adapter moiety, a first adapter moiety AD1, a second adapter moiety AD2 and a third adapter moiety AD3.

The following is, in principle, applicable to each and any of the adapter moieties which can be realized in the various embodiments of the conjugate of the invention, i.e. the first adapter moiety, the second adapter moiety and the third adapter moiety.

Adapter moieties mediate the linkage between two different moieties. The main purpose is to selectively generate a linkage between these two moieties which usually have not complementary reactive groups for a selective linkage available. Accordingly, an adapter moiety is present in a conjugate of the invention in cases where two moieties of the conjugate of the invention do not provide reactive groups, more specifically, two addressable groups, i.e. one on each of the two moieties, which are not complementary, preferably which do not allow the formation of a linkage between said two different moieties. Because of this, in a preferred embodiment an adaptor moiety provides for two reactive groups, whereby a first of said two reactive groups is suitable for generating a linkage between a first of the two moieties, and whereby a second of said two reactive groups is suitable for generating a linkage between a second of the two moieties. In a preferred embodiment, the two reactive groups provided by the adapter moiety are different. In an alternative embodiment the two reactive groups provided by the adapter moiety are the same.

In accordance with the function of an adapter moiety in a conjugate of the invention, the backbone of such adaptor moiety can, in principle, be quite diverse as long as such backbone of the adaptor moiety does not interfere with the synthesis and use, respectively, of the conjugate of the invention.

Adapter moieties are in some embodiments bifunctional moieties which are known in the art. See, e.g., *Bioconjugate Techniques*, G. T. Hermanson (Academic Press, San Diego, Calif., 1996), which is incorporated by reference in its entirety.

Also in accordance with the function of an adapter moiety in a conjugate of the invention, the reactive group(s) borne or provided by the adaptor moiety are of importance. It will be appreciated by a person skilled in the art that depending on the structural class and origin of the targeting moiety different types of reactive groups are provided by the targeting molecule. Depending on the type of reactive group provided by the targeting moiety, the adaptor moiety provides a reactive group which is complementary to such reactive group provided by the targeting moiety. If, for example, the targeting moiety is a protein, such as an antibody or antibody fragment, the preferred reactive groups for forming a linkage with another moiety and an adapter moiety in particular, are sulfhydryl groups and amino groups. Sulfhydryl groups can be generated by reduction of an intramolecular disulfide bond of a targeting moiety. Alternatively, sulfhydryl groups can be generated by reaction of an amino group of a lysine moiety of a targeting moiety using 2-iminothiolane (Traut's reagent) or another sulfhydryl generating reagent. In a preferred embodiment thereof, the adapter moiety forms a thioether linkage with a sulfur atom of the targeting moiety.

In the following various design principles and reaction principles of an adapter moiety suitable for use in a conjugate of the invention will be outlined in the following.

Preferred linkages established between two moieties by means of an adapter moiety are the linkages indicated in Table 3 herein.

Preferably, linkages which are established by means of an adaptor moiety are selected from the group comprising an amide linkage, a urea linkage, a thioether linkage, an alkylamine linkage, a triazole linkage, an oxime linkage, a hydrazone linkage, a hydrazide linkage, an ether linkage, a carbamate linkage, an amine linkage, a disulfide linkage, a pyrazine linkage and a dihydropyrazine. Furthermore, any of the linkages summarized in Table 4 herein, can be realized by means of an adapter moiety, preferably the first adapter moiety.

A generic formula of a preferred embodiment of an adapter moiety is as follows:

$$\text{RG3-R8-RG4} \tag{10}$$

wherein RG3 is a reactive group as described herein, preferably a reactive group as indicated in Table 4 or selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine;

wherein RG4 is a reactive group as described herein, preferably a reactive group as indicated in Table 4 or selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine; and wherein R8 is selected
selected from —($C_1$-$C_{10}$)alkylidene-, —($C_3$-$C_8$)carbocyclo-, —O—($C_1$-$C_5$)alkyl-, -arylene-, —($C_1$-$C_{10}$)alkylidene-arylene-, -arylene-($C_1$-$C_{10}$)alkylidene-, —($C_1$-$C_{10}$)alkylidene-($C_3$-$C_8$)carbocyclo, —($C_3$-$C_8$)carbocyclo-($C_1$-$C_{10}$)alkylidene-, —($C_3$-$C_8$)heterocyclo-, ($C_1$-$C_{10}$)alkylidene-($C_3$-$C_8$)heterocyclo-, —($C_3$-$C_8$)heterocyclo-($C_1$-$C_{10}$)alkylidene-, —($CH_2CH_2O$)$_r$—, and —($CH_2CH_2O$)$_r$—$CH_2$—;

and r is any integer of 1, 2, 3, 4, 5, 6, 7, 8, 9 and 10.

In an embodiment R8 is —($C_1$-$C_{10}$)alkylidene-, —($C_1$-$C_{10}$)alkylidene-($C_3$-$C_8$)carbocyclo, —($C_3$-$C_8$)heterocyclo-, —($CH_2CH_2O$)$_r$—, and —($CH_2CH_2O$)$_r$—$CH_2$—].

In a preferred embodiment of the conjugate of the invention R8 of the adapter moiety is —($CH_2$)$_n$— and n is any integer from 1, 2, 3, 4, 5, 6, 7, 8, 9 and 10, preferably n is 5.

In a preferred embodiment of the conjugate of the invention R8 of the adapter moiety is —($CH_2$—$CH_2$—$O$)$_r$—$CH_2$— with r being an integer from 1, 2, 3, 4, 5, 6, 7, 8, 9 and 10, preferably r is 2.

Inserted into a conjugate of the invention an adaptor moiety as preferably used in the conjugate of the invention is one which is indicated in the following formulae, whereby it is understood that to the extent the adapter moiety is represented in the formulae as being inserted between linking moiety LM and targeting moiety TM2 thus being a second adapter moiety, this is made for purpose of illustration only and the adapter moiety as such is the structure contained in square brackets. The very same structure depicted as a second adapter moiety can, in accordance with the instant invention, be equally used as a first targeting moiety:

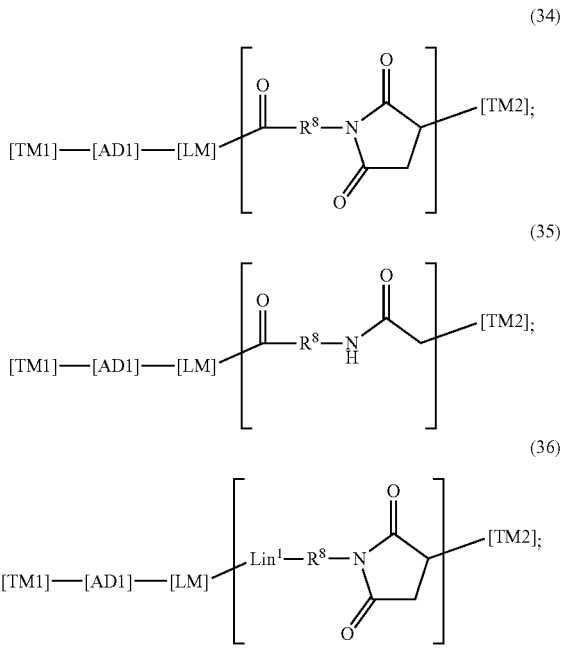

(34)

(35)

(36)

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C═C— (in case of, for example triazole), ═N—O—, ═N—N—, ═N—N—CO—, —N═N—N— (in case of, for example triazole), —HC═ and —R$^3$C═ (of oxime and hydrazone);
wherein
"-succinimide-" means

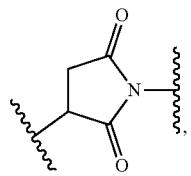

(9)

and R$^{10}$ is selected from the group consisting of hydrogen and (C$_1$-C$_4$)alkyl;

(37)

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C═C— (in case of, for example triazole), ═N—O—, ═N—N—, ═N—N—CO—, —N═N—N— (in case of, for example triazole), —HC═ and —R$^3$C═ (of oxime and hydrazone), and R$^{10}$ is selected from the group consisting of hydrogen and (C$_1$-C$_4$)alkyl; and
wherein the second targeting moiety provides a sulfhydryl group;

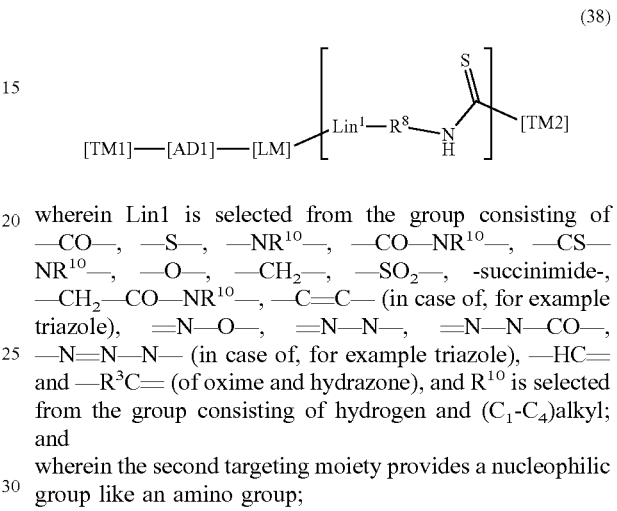

(38)

(39)

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C═C— (in case of, for example triazole), ═N—O—, ═N—N—, ═N—N—CO—, —N═N—N— (in case of, for example triazole), —HC═ and —R$^3$C═ (of oxime and hydrazone), and R$^{10}$ is selected from the group consisting of hydrogen and (C$_1$-C$_4$)alkyl; and
wherein the second targeting moiety provides a nucleophilic group like an amino group;

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C═C— (in case of, for example triazole), ═N—O—, ═N—N—, ═N—N—CO—, —N═N—N— (in case of, for example triazole), —HC═ and —R$^3$C═ (of oxime and hydrazone), and R$^{10}$ is selected from the group consisting of hydrogen and (C$_1$-C$_4$)alkyl; and
wherein the second targeting moiety provides a nucleophilic group like an amino or hydroxyl group;

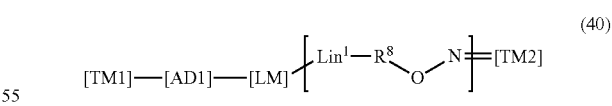

(40)

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C═C— (in case of, for example triazole), ═N—O—, ═N—N—, ═N—N—CO—, —N═N—N— (in case of, for example triazole), —HC═ and —R$^3$C═ (of oxime and hydrazone), and R$^{10}$ is selected from the group consisting of hydrogen and (C$_1$-C$_4$)alkyl; and
wherein the second targeting moiety provides a ketone or aldehyde group;

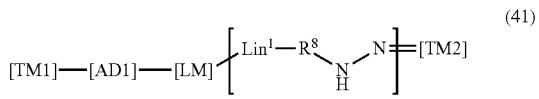

(41)

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C≡C— (in case of, for example triazole), =N—O—, =N—N—, =N—N—CO—, —N=N—N— (in case of, for example triazole), —HC= and —R$^3$C= (of oxime and hydrazone), and R$^{10}$ is selected from the group consisting of hydrogen and (C$_1$-C$_4$)alkyl; and
wherein the second targeting moiety provides a ketone or aldehyde group; and

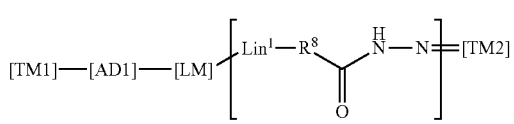

(42)

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C≡C— (in case of, for example triazole), =N—O—, =N—N—, =N—N—CO—, —N=N—N— (in case of, for example triazole), —HC= and —R$^3$C= (of oxime and hydrazone), and R$^{10}$ is selected from the group consisting of hydrogen and (C$_1$-C$_4$)alkyl; and
wherein the second targeting moiety provides a ketone or aldehyde group; and

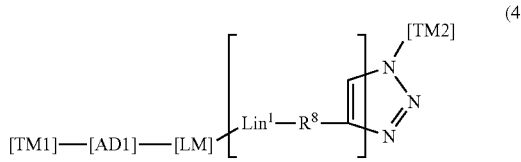

(43)

wherein Lin1 is selected from the group consisting of —CO—, —S—, —NR$^{10}$—, —CO—NR$^{10}$—, —CS—NR$^{10}$—, —O—, —CH$_2$—, —SO$_2$—, -succinimide-, —CH$_2$—CO—NR$^{10}$—, —C≡C— (in case of, for example triazole), =N—O—, =N—N—, =N—N—CO—, —N=N—N— (in case of, for example triazole), —HC= and —R$^3$C= (of oxime and hydrazone), and R$^{10}$ is selected from the group consisting of hydrogen and (C$_1$-C$_4$)alkyl; and
wherein the second targeting moiety provides an azide group.

It will be appreciated by a person skilled in the art that adapter moiety as subject to formulae (38) and (39) and the linkages indicated therein are preferably the result of, on the one hand of a primary or secondary amino group, preferably provided by a targeting moiety, and, on the other hand, of a reactive group selected from the group comprising carboxylic acid, activated carboxylic acid, sulfonic acid, activated sulfonic acid, isocyanates and isothiocyanates, wherein the reactive group is preferably provided by an adapter moiety.

It will be appreciated by a person skilled in the art that adapter moiety as subject to formulae (34) to (37) and the linkages indicated therein are preferably the result of, on the one hand of a sulfhydryl group, preferably provided by a targeting moiety, and, on the other hand, of a reactive group selected from the group comprising Michael acceptor, halogen and sulfhydryl, wherein the reactive group is preferably provided by an adapter moiety.

It will be appreciated by a person skilled in the art that adapter moiety as subject to formulae (40) to (42) and the linkages indicated therein are preferably the result of, on the one hand of a carbohydrate, preferably provided by a targeting moiety, wherein the carbohydrate is preferably mildly oxidized using a reagent such as, for example, sodium periodate and the resulting (—CHO) unit of the oxidized carbohydrate can be condensed with a with reactive group selected from the group comprising hydrazide, aminooxy, primary or secondary amino or hydrazine, such as those described by Kaneko, T. et al. *Bioconjugate Chem* 1991, 2, 133-141, wherein the group is preferably provided by an adapter moiety.

In a further embodiment of the conjugate of the invention an adapter moiety is one of

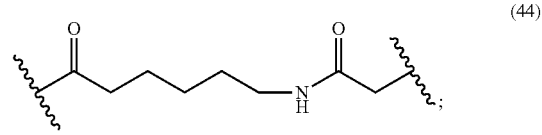

(44)

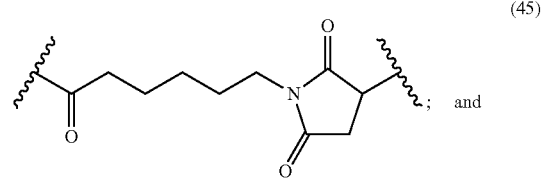

(45); and

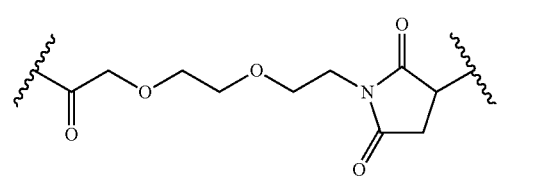

(46)

If, in an embodiment a linkage between a moiety A containing a primary amino group (A-NH$_2$) and a moiety B containing a sulfhydryl group (B-SH) is to be established, in an embodiment an adapter moiety is utilized which is able to form a first linkage with the amino group of moiety A and a second linkage with the sulfhydryl of moiety B. Selected synthetic precursors for the adapter moieties for this application are in either commercially available and also referred to as cross-linkers, or can be prepared by a person skilled in the art by routine measure.

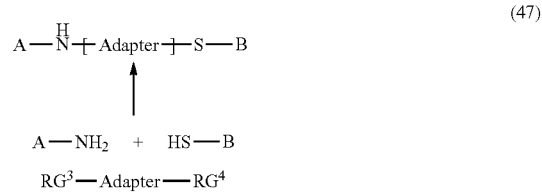

(47)

In this example the first linkage to the amino group of moiety A is preferably selected from the group of amide, urea, thiourea, alkylamine and sulfonamide and the corresponding third reactive group $RG^3$ as provided by the adapter moiety is selected from the group of carboxylic acid, activated carboxylic acid, sulfonic acid, activated sulfonic acid, aldehyde, ketone, isocyanate and isothiocyanate. The second linkage to the sulfhydryl group of moiety B is preferably selected from the group of thioether and disulfide and the corresponding fourth reactive group $RG^4$ as provided by the adapter moiety is selected from the group of halogen, Michael acceptors such as maleimide or vinyl sulfone and activated mixed disulfides like 2-pyridine disulfide.

In an embodiment of the conjugate of the invention an adapter moiety realizing the above principles and which mediates the linkage of an amino containing moiety and a sulfhydryl containing moiety is selected from the group comprising

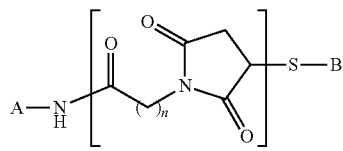
(48)

with n being any integer of 1, 2, 3, 4, 5, 6, 7, 8, and 9, preferably the integer is 2 or 3;

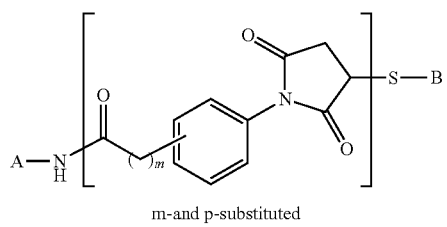
(49)

m-and p-substituted with m being any integer of 0, 1, 2 and 3, preferably the integer is X;

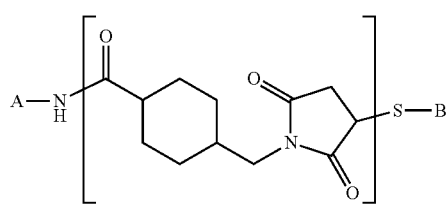
(50)

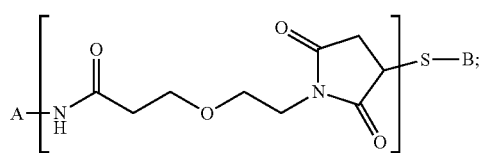
(51)

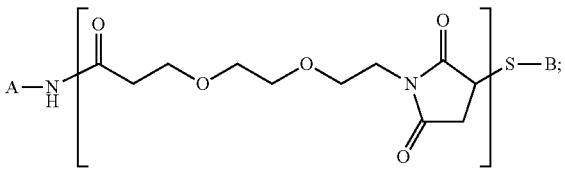
(52)

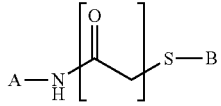
(53)

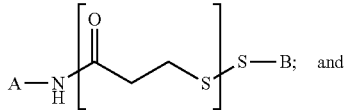
(54)

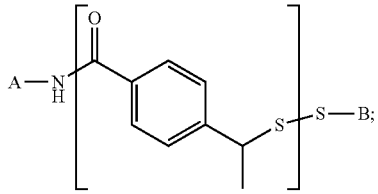
(55)

wherein the adapter moiety is depicted in the square brackets of the above indicated formulae In an embodiment of the conjugate of the invention an adapter moiety realizing the above principles and which mediates the linkage of an amino containing moiety and a amino containing moiety forms linkages to these moieties which are independently selected from the group comprising amide, urea, thiourea, alkylamine and sulfonamide and the corresponding reactive groups as provided by the adapter moiety are independently selected from the group of carboxylic acid, activated carboxylic acid, sulfonic acid, activated sulfonic acid, aldehyde, ketone, isocyanate and isothiocyanate. The preferred type of adapter moieties in one embodiment are dicarboxylic acids, or activated forms thereof.

In an embodiment of the conjugate of the invention an adapter moiety realizing the above principles and which mediates the linkage of an amino containing moiety and a carboxylic acid containing moiety forms linkages to these moieties wherein the first linkage to the amino group is selected from the group comprising amide, urea, thiourea, alkylamine and sulfonamide and the corresponding reactive group as provided by the adapter moiety is independently selected from the group of carboxylic acid, activated carboxylic acid, sulfonic acid, activated sulfonic acid, aldehyde, ketone, isocyanate and isothiocyanate. The second linkage to the carboxylic acid group is an amide linkage and the corresponding reactive group as provided by the adapter moiety is a primary or secondary amino group. The preferred type of adapter moieties in one embodiment are amino acids, or activated forms thereof.

According to the present invention the conjugate of the invention comprises as a first targeting moiety TM1 and/or as a second targeting moiety TM2 a compound of formula (2); in connection with such compound of formula (2) the point of attachment to any other moiety contained in the conjugate of the invention is $R^7$ and thus provide as a reactive group a primary or secondary amino group as point of attachment.

As described in more detail below and in the example part the compounds of the invention are conveniently prepared by either liquid phase or solid phase synthesis methods.

It is well understood that the synthesis of intermediates which contain said compound of formula (2) as a targeting moiety together with some other moieties as contained in the conjugate of the invention in activated form for further conjugation are of specific value by their own right. In an specific embodiment preactivated moieties can be assembled directly before use or even after or during in vivo application.

In the following targeting moieties, either alone or linked to an adapter moiety, are described which are realized in embodiments of the conjugate of the invention.

A representative example of a targeting moiety based on the compound of formula (2) is the one of formula (56):

(56)

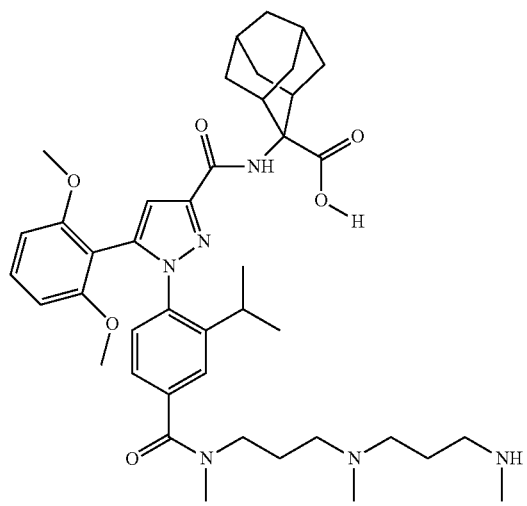

The preparation of (56) is described in Example 5A. This compound is well suited to form amide, urea or thiourea linkages to other moieties especially for the addition of an adapter moiety. One example for this is the attachment of a maleimide containing adapter moiety is described in example 5B:

(57)

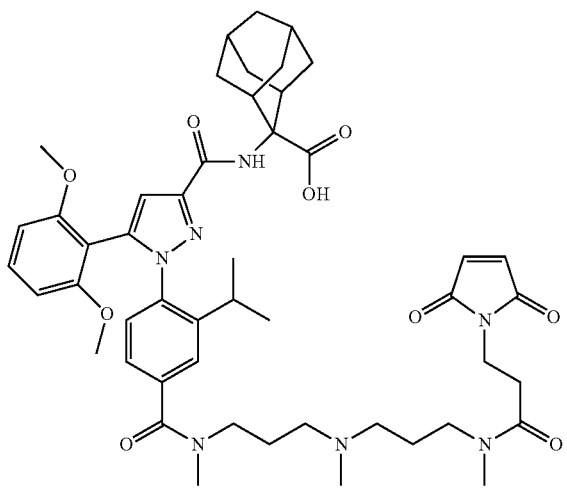

This adapter moiety enables the conjugation of sulfhydryl containing moieties as shown in example 19. Compound (57) is also well suited for the conjugation of proteins or modified oligonucleotides.

More chemical possibilities open up if one synthesizes a tBu protected form of the amino acid (56) which is described in example 3:

(58)

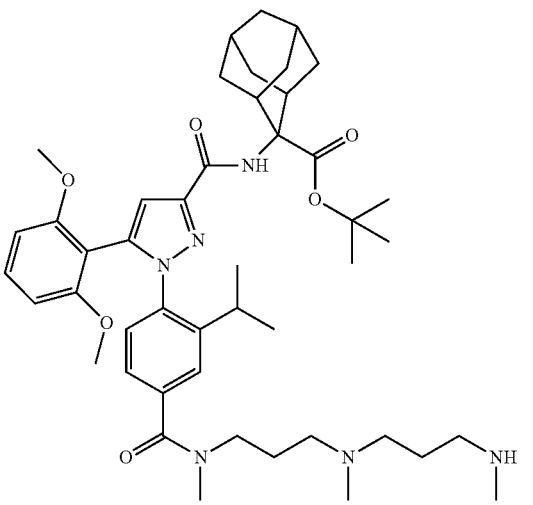

This targeting moiety is utilized for manifold purposes. First of all the amide linkage of this can be formed to a carboxylic acid group of moiety in solution (example 8 and 9) without the need for isolated activated carboxylic groups. Secondly it is simpler modified with adapter an moiety as shown in example 4:

(59)

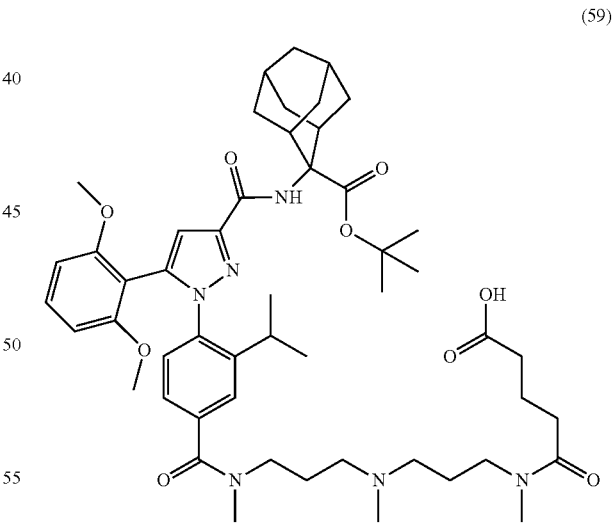

The intermediate (59) was used in many examples. It performs very well for forming linkage to amino containing moieties bound to the solid phase resin.

If, in an embodiment of the conjugate of the invention a larger structure is or is to be conjugated as a targeting moiety to a targeting moiety of formula (2) it is often desirable to have a larger linker moiety separating the two targeting moieties, because this should ensure that their individual function is not impaired. Two respective examples of intermediates are described in more detail in example 6 and 7:

(60)

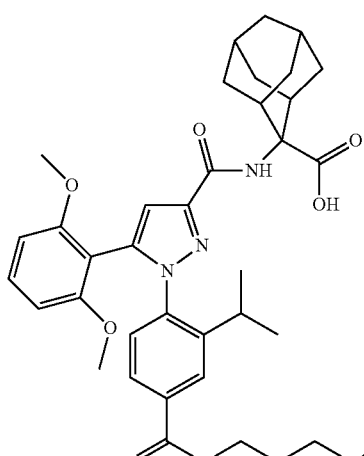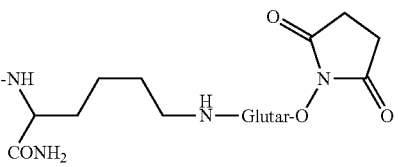

(61)

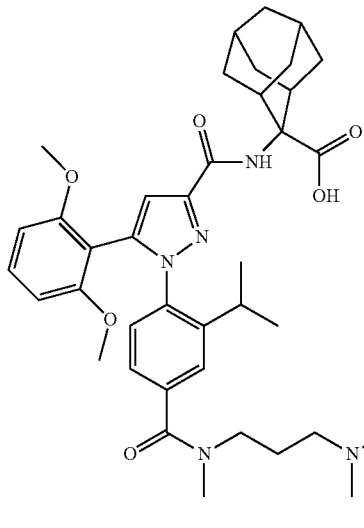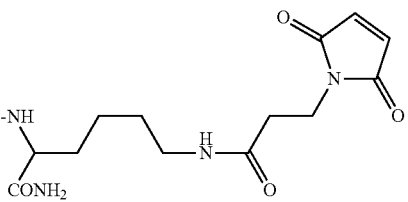

As disclosed herein, the conjugate of the invention may, in an embodiment, consist of a first targeting moiety, a linker moiety and a second targeting moiety. Such embodiment is indicated in formula (28) and is described in more detail in example 24:

(28)

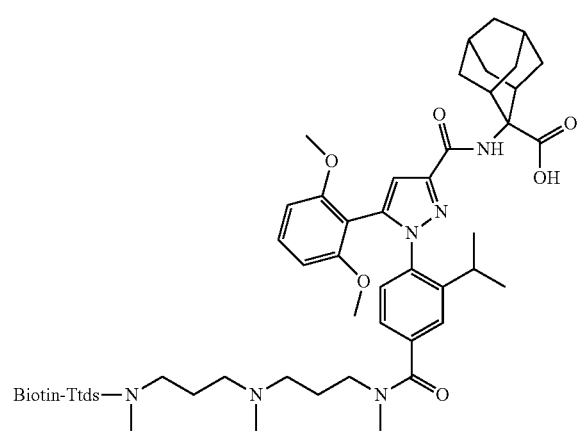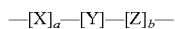

The linkage of the targeting moiety Biotin, targeting avidin or streptavidin, to the targeting moiety (4) is mediated by a single amino acid Ttds as linker moiety without the use of any adapter moieties.

Linker Moiety

It is within the present invention that the conjugate of the invention comprises a linker moiety. It is, however, also within the present invention that the conjugate of the invention does not comprise a linker moiety.

In an embodiment the linker moiety LM of the conjugate of the invention is of the following general formula:

—[X]$_a$—[Y]—[Z]$_b$— wherein

[X]$_a$ is a building block moiety formed of "a" building blocks X,

[Y] is a branching moiety or is absent,

[Z]$_b$ is a building block moiety formed of "b" building blocks Z, and wherein "a" and "b" are individually and independently any integer from 0, 1, 2, 3, 4, 5, 6, 7, 8, 9, 10, 11, 12, 13, 14, 15, 16, 17, 18, 19 and 20 under the proviso that a+b is 20, 19, 18, 17, 16, 15, 14, 13, 12, 11, 10, 9, 8, 7, 6, 5, 4, 3, 2, 1 or 0. In an embodiment "a" and "b" are individually any integer from 1, 2, 3, 4, 5, 6, 7, 8, 9 and 10. In a preferred embodiment "a" and "b" are individually any integer from 1, 2, 3, 4 and 5.

In accordance with the present invention in the conjugate of the invention building block moiety $[X]_a$ may be absent or be present in the form of a single building block X or be present in the form of a polymer, wherein the polymer consists of a number of building blocks X, wherein the number of building blocks X forming such polymer is "a", i.e. any integer from 2, 3, 4, 5, 6, 7, 8, 9, 10, 11, 12, 13, 14, 15, 16, 17, 18, 19 and 20.

In accordance with the present invention in the conjugate of the invention building block moiety $[Z]_b$ may be absent or be present in the form of a single building block Z or be present in the form of a polymer, wherein the polymer consists of a number of building blocks Z, wherein the number of building blocks Z forming such polymer is "b", i.e. any integer from 2, 3, 4, 5, 6, 7, 8, 9, 10, 11, 12, 13, 14, 15, 16, 17, 18, 19 and 20.

In accordance with the present invention in the conjugate of the invention branching moiety [Y] is either present or is absent.

Building block moiety $[X]_a$, if present, is linked to both of its neighbours by a linkage, wherein the linkage is selected from the group comprising an amide linkage, a urea linkage, a carbamate linkage, an ester linkage, an ether linkage, a thioether linkage and a disulfide linkage. One of said two neighbors is either the first adaptor moiety AD1 or, if the conjugate of the invention does not comprise a first adaptor moiety AD1, the first targeting moiety TM1. The other of said two neighbors is branching moiety Y, if such branching moiety Y is present in the conjugate of the invention; is building block moiety $[Z]_b$, if such building block moiety $[Z]_b$ is present and branching moiety Y is absent; is the second adapter moiety AD2, if such second adapter moiety AD2 is present and both the branching moiety Y and the building block moiety $[Z]_b$ are absent; and is the second targeting moiety TM2, if the branching moiety Y, the building block moiety $[Z]_b$ and the second adaptor moiety AD2 is absent.

Building block moiety $[X]_a$ preferably comprises at least two reactive groups. In a preferred embodiment each of the at least two reactive groups is independently and individually selected from the group comprising a primary amino group, a secondary amino group, a carboxylic acid group, an activated carboxylic acid such as acid chloride, an acid bromide, a succinimide ester, a pentafluorophenol ester, a nitrophenol ester, a benzotriazole ester, an azabenotriazoleester, a thioester, a symmetrical anhydride, an unsymmetrical anhydride, chloro, bromo, iodo, a sulfhydryl group and a hydroxyl group.

Building block X preferably also comprises at least two groups. In a preferred embodiment each of the at least two reactive groups is independently and individually selected from the group comprising a primary amino group, a secondary amino group, a carboxylic acid group, an activated carboxylic acid such as acid chloride, an acid bromide, a succinimide ester, a pentafluorophenol ester, a nitrophenol ester, a benzotriazole ester, an azabenotriazoleester, a thioester, a symmetrical anhydride, an unsymmetrical anhydride. If two or more building blocks X are covalently linked to each other the linkage between such two or more building blocks X is selected from the group comprising an amide linkage, a urea linkage, a carbamate linkage, an ester linkage, an ether linkage, a thioether linkage and a disulfide linkage. Preferably, the linkage is an amide linkage.

In an embodiment the building block X is of general formula $$\mathrm{-Lin^2\text{-}R^9\text{-}Lin^3\text{-}} \qquad (8)$$

wherein,
$Lin^2$, if present, and $Lin^3$, if present, are each individually and independently selected from the group comprising —CO—, —NR$^{10}$—, —S—, —CO—NR$^{10}$—, —CS—NR$^{10}$—, —O—, -succinimide- and —CH$_2$—CO—NR$^{10}$—;

wherein $R^{10}$ is selected from the group consisting of hydrogen and (C$_1$-C$_4$)alkyl;

and the nitrogen of all nitrogen containing fragments is linked to $R^9$;

and wherein $R^9$ is selected from selected from —(C$_1$-C$_{10}$)alkylidene-, —(C$_3$-C$_8$)carbocyclo-, -arylene-, —(C$_1$-C$_{10}$)alkylidene-arylene-, -arylene-(C$_1$-C$_{10}$)alkylidene-, —(C$_1$-C$_{10}$)alkylidene-arylene-(C$_1$-C$_{10}$)alkylidene-, —(C$_1$-C$_{10}$)alkylidene-(C$_3$-C$_8$)carbocyclo-, —(C$_3$-C$_8$)carbocyclo-(C$_1$-C$_{10}$)alkylidene-, —(C$_1$-C$_{10}$)alkylidene-(C$_3$-C$_8$)carbocyclo-(C$_1$-C$_{10}$)alkylidene-, —(C$_3$-C$_8$)heterocyclo-, (C$_1$-C$_{10}$)alkylidene-(C$_3$-C$_8$)heterocyclo-, —(C$_3$-C$_8$)heterocyclo-(C$_1$-C$_{10}$)alkylidene-, —(C$_1$-C$_{10}$)alkylidene-(C$_3$-C$_8$)heterocyclo-(C$_1$-C$_{10}$)alkylidene-, —(CH$_2$CH$_2$O)$_r$—, and —(CH$_2$)$_s$—(CH$_2$CH$_2$O)$_r$—(CH$_2$)$_t$—;

and wherein
r is any integer from 1, 2, 3, 4, 5, 6, 7, 8, 9 and 10;
s is any integer from 0, 1, 2, 3 and 4; and
t is any integer from 0, 1, 2, 3 and 4.

In an embodiment the building block X is selected from the group comprising an amino acid, a dicarboxylic acid and a diamine. In an embodiment the amino acid is an amino acid selected from the group comprising natural and non-natural amino acids. In an embodiment an amino acid is one selected from the group comprising β-amino acids, γ-amino acids, δ-amino acids, ε-amino acids and ω-amino acids. In a further embodiment an amino acid is a cyclic amino acid or a linear amino acid. It will be appreciated by a person skilled in the art that in case of an amino acid with stereogenic centers all stereoisomeic forms may be used in the building block X.

In an embodiment the building block X is a amino acid, wherein the amino acid is selected from a group comprising amino acids which differ as to the spacing of the amino group from the carboxylic group. This kind of amino acid can be generically represented as follows:

(62)

It is within the present invention that such amino acid is not further substituted. It is, however, also within the present invention that such amino acid is further substituted; preferably such substitution is CO—NH$_2$ and/or Ac-NH—.

Representative of this kind of amino acid which can be used as a building block X are glycine (Gly), β-alanine, γ-aminobutyric acid (GABA), aminopentanoic acid, aminohexanoic acid and homologs with up to 10 CH$_2$ groups.

In a further embodiment the amino acid is an aromatic amino acid; preferably the amino acid is one the rigidity and orientation of which can be modified. This kind of amino acid can be generically represented as follows:

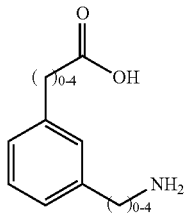

(63)

and the ortho and para-
substituted isomers

It will be acknowledged by a person skilled in the art that the two substitutions indicated in the above generic formula in meta position can also be arranged in either para position or in ortho position. Accordingly, in an embodiment the aromatic amino acid can be one where the two substitutents as indicated in the above generic formula in meta position are arranged either in para position or in ortho position.

Representative of this kind of amino acid which can are preferably used as a building block X are β-aminomethyl-benzoic acid, 4-aminomethyl-benzoic acid, anthranilic acid, β-amino benzoic acid and 4-amino benzoic acid.

In a further embodiment, the amino acid is an amino acid which contains, preferably as a backbone, a polyether. Preferably such polyether is polyethylene glycol and consists of up to 20 monomer units. Preferably, an amino acid comprising such polyether shows an increase in hydrophilicity compared to an amino acid not comprising such polyether. If incorporated into a building block X and, ultimately, into a building block moiety $[X]_a$ and a linker moiety LM, respectively, such building block moiety [X]a and linker moiety LM, respectively, typically shown an increase in hydrophilicity, too. A preferred embodiment of this kind of amino acid is depicted in the following, wherein it will be acknowledged that such amino acid may comprise 0, 1, 2, 3, 4, 5, 6, 7, 8, or 9 ethylene oxide moieties:

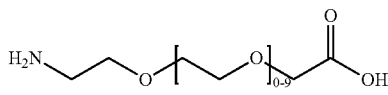

(64)

A preferred amino acid is Ttds (N-(3-{2-[2-(3-Amino-propoxy)-ethoxy]-ethoxy}-propyl)-succinamic acid) the formula of which is as follows:

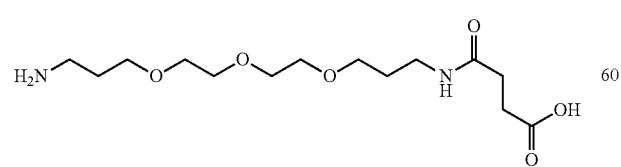

(65)

Ttds

In an embodiment the building block X is a diamine. Such diamine is preferably one selected form the group comprising
a compound of the following formula

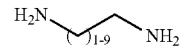

(66)

wherein the diamine may comprise a length of 1, 2, 3, 4, 5, 6, 7, 8, 9 or 10 C atoms;
a compound of the following formula

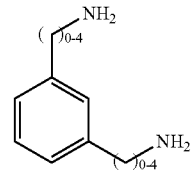

(67)

and the ortho and para-
substituted isomers wherein the length of both chains of C atoms attaching the $NH_2$ group to the phenyl group is individually and independently 1, 2, 3 or 4 C atoms; and wherein it will be acknowledged by a person skilled in the art that the two substitutions indicated in the above generic formula in meta position can also be arranged in either para position or in ortho position; therefore, in an embodiment the diamine can be one where the two substitutents as indicated in the above generic formula in meta position are arranged either in para position or in ortho position;
a compound of the following formula

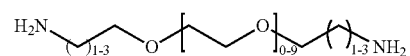

(68)

wherein the length of both chains of C atoms bearing the NH2 group attached to each of the two terminal O atoms of the ethylene oxide backbone contained in the diamin is individually and independently 2, 3 or 4 C atoms; and wherein the ethylene oxide backbone will comprise 1, 2, 3, 4, 5, 6, 7, 8, 9 or 10 of ethylene oxide monomers.

In a preferred embodiment the diamine is a substituted diamine, preferably of the following general formula:

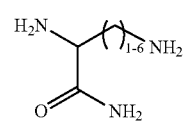

(69)

wherein such substituted diamine comprises 1, 2, 3, 4, 5 or 6 $CH_2$ groups, preferably 4 $CH_2$ groups. As used herein, the abbreviation for this kind of substituted diamine having 4 of said CH2 groups, if present in S-configuration, is ε-Lys-NH$_2$, and the residue in its linked form is abbreviated -(ε-Lys-NH$_2$)—, wherein the hyphen on the left side of the abbreviation symbolizes the attachment to the α-amino group and the hyphen at the right side the attachment to the ε-amino group of this residue.

In an embodiment the building block X is a dicarboxylic acid. Such dicarboxylic acid is preferably one selected from the group comprising:

a compound of the following formula

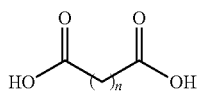
(70)

wherein n is any integer from 1, 2, 3, 4, 5, 6, 7, 8, 9 and 10;

a compound of the following formula

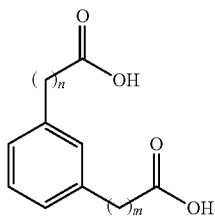
(71)

and the ortho and para- substituted isomers wherein m and n are individually and independently any integer from 1, 2, 3, and 4; and wherein it will be acknowledged by a person skilled in the art that the two substitutions indicated in the above generic formula in meta position can also be arranged in either para position or in ortho position; therefore, in an embodiment the dicarboxylic acid can be one where the two substitutents as indicated in the above generic formula in meta position are arranged either in para position or in ortho position;

a compound of the following formula

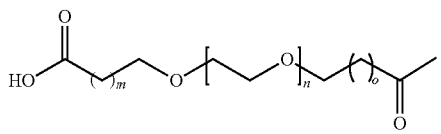
(72)

wherein the integers m and o may individually and independently be any in the range of 0 to 4; and wherein the integer n may be in the range of 1 to 10.

Representative of this kind of dicarboxylic acids which can be used as a building block X are dicarboxylic acids which are preferably related to suitable commercially available cyclic anhydrides. Such dicarboxylic acids comprise glutaric acid, succinic acid, phthalic acid, 1,2-cyclohexanedicarboxylic acid and maleic acid.

In a preferred embodiment the dicarboxylic acid is a substituted dicarboxylic acid, preferably of the following general formula:

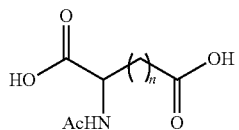
(73)

wherein the integer n of such substituted dicarboxylic acids may be any in a range of 0 to 6, preferably n=1 and n=2.

In an embodiment the building block X is an aminothiol wherein the aminothiol is selected from a group comprising aminothiols which differ as to the spacing of the amino group from the sulfhydryl group:

(74)

wherein the integer may be any in the range of 1, 2, 3, 4, 5, 6, 7, 8 or 9.

Representative of this kind of aminothiols which can be used as a building block X are 2-amino-ethanethiol, β-amino-propane-1-thiol, 4-amino-butane-1-thiol, 5-amino-pentane-1-thiol and 6-amino-hexan-1-thiol.

In a preferred embodiment the aminothiol is a substituted aminothiol, preferably of the following general formula:

(75)

wherein the integer may be any in the range of 1, 2, 3, 4, 5 or 6, preferably n=1 and n=2. As used herein, the abbreviation for this kind of substituted aminothiols with n=1, if present in S-configuration, is β-Cys-NH$_2$, and the residue in its linked form is abbreviated -(β-Cys-NH$_2$)—, wherein the hyphen on the left side of the abbreviation symbolizes the attachment to the α-amino group and the hyphen at the right side the attachment to the β-thiol group of this residue.

In an embodiment the building block X is a thiol group containing carboxylic acid wherein the thiol group containing carboxylic is selected from a group comprising thiol group containing carboxylic acids which differ as to the spacing of the carboxylic group from the sulfhydryl group:

(76)

wherein the integer may be any in the range of 1, 2, 3, 4, 5, 6, 7, 8 or 9.

Representative of this kind of thiol group containing carboxylic acids which can be used as a building block X are mercaptoacetic acid, 3-mercaptopropionic acid, 4-mercaptobutanoic acid, 5-mercaptopentanoic acid and 6-mercaptohexanoic acid.

In a preferred embodiment the thiol group containing carboxylic acid is a substituted aminothiol, preferably of the following general formula:

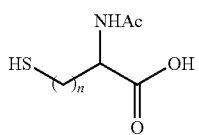

(77)

wherein the integer may be any in the range of 1, 2, 3, 4, 5 or 6, preferably n=1 and n=2.

In an embodiment of the conjugate of the invention the building block moiety $[X]_a$ is a peptide, whereby such peptide is formed by a plurality of building blocks X, preferably building blocks X as defined herein. In this embodiment the linkages linking the building blocks, is an amide linkage. It is within the present invention that the building blocks X forming the building block moiety $[X]_a$ are the same or are different. Accordingly, the peptide forming the building block moiety $[X]_a$ may be a homopolymer or a heteropolymer.

In a further embodiment of the conjugate of the invention the building block moiety $[X]_a$ is a polymer, wherein the monomers forming the polymer are linked to each other by an ether linkage. In this embodiment the building blocks X are compounds having preferably at least two reactive groups, wherein at least one of the at least two reactive groups is selected from the group comprising a hydroxyl group and a halogen group.

In a further embodiment of the conjugate of the invention the building block moiety $[X]_a$ is a polymer, wherein the monomers, i.e. the building blocks X forming the polymer are linked to each other by an ether linkage and an amide linkage under the proviso that the polymer comprises at least three of the building blocks X thus providing at least two linkages.

What has been disclosed herein as to building block moiety $[X]_a$ equally applies to building block moiety $[Z]_b$ and is incorporated insofar herein by reference.

Irrespective of the above it will be appreciated that the building moiety $[Z]_b$, if present is linked to both of its neighbours by a linkage, wherein the linkage is selected from the group comprising an amide linkage, a urea linkage, a carbamate linkage, an ester linkage, an ether linkage, a thioether linkage and a disulfide linkage. One of said two neighbors is either the second adaptor moiety AD2 or, if the conjugate of the invention does not comprise a second adaptor moiety AD2, the second targeting moiety TM1. The other of said two neighbors is branching moiety Y, if such branching moiety Y is present in the conjugate of the invention; is building block moiety $[X]_a$, if such building block moiety $[X]_a$ is present and branching moiety Y is absent; is the first adapter moiety AD1, if such first adapter moiety AD1 is present and both the branching moiety Y and the building block moiety $[X]_a$ are absent; and is the first targeting moiety TM1, if the branching moiety Y, the building block moiety $[X]_a$ and the first adaptor moiety AD1 is absent.

Branching Moiety Y

In an embodiment the conjugate of the invention comprises a branching moiety Y.

Branching moiety Y, if present, is linked to both of its neighbours by a linkage, wherein the linkage is selected from the group comprising an amide linkage, a urea linkage, a carbamate linkage, an ester linkage, an ether linkage, a thioether linkage and a disulfide linkage. A preferred linkage is an amide linkage. One of said neighbors is building block moiety $[X]_a$ if such building block moiety $[X]_a$ is present, is the first adapter moiety AD1, if such adaptor moiety AD1 is present and building block moiety $[X]_a$ is absent; or is the first targeting moiety TM1 of such first targeting moiety TM1 is present and both building block moiety $[X]_a$ and the first adapter moiety AD1 are absent. The other of said two neighbors is building block moiety $[Z]_b$ if such building block moiety $[Z]_b$ is present, is the second adapter moiety AD2, if such adaptor moiety AD2 is present and building block moiety $[Z]_b$ is absent; or is the second targeting moiety TM2 if such second targeting moiety TM2 is present and both building block moiety $[Z]_b$ and the second adapter moiety AD2 are absent.

Preferably, the branching moiety provides a point of attachment to the conjugate of the invention. Such point of attachment allows that a further linkage is established between the conjugate of the invention of formula (1) and a further moiety. In an embodiment the further moiety is a third adapter moiety AD3 or an Effector moiety EM. In an embodiment the further linkage between the conjugate of the invention of formula (1) and a further moiety is selected from the group comprising an amide linkage, a urea linkage, a thiourea linkage and an amine linkage. A preferred further linkage between the conjugate of the invention of formula (1) and a further moiety is an amide linkage.

In an embodiment the structure of branching moiety Y is based on the structure of building block X in its various embodiments as disclosed herein, whereby branching moiety Y comprises at least one further reactive group. In an embodiment the branching moiety comprises at least three reactive groups. Preferably, the at least one further reactive group is one which allows the formation of comprising an amide linkage, a urea linkage, a thiourea linkage and an amine linkage, preferably under the proviso that the further moiety provides a corresponding complementary reactive group. More preferably the at least one further reactive group is selected from the group comprising an amino group and a carboxyl group.

In an embodiment the branching moiety Y comprises a fully acyclic structure in addition to the at least three reactive groups. In another embodiment the branching moiety Y comprises a cyclic structure in addition to the at least three reactive groups. In a still further embodiment the branching moiety Y comprises an aromatic structure in addition to the at least three reactive groups.

In an embodiment the branching moiety Y is an amino acid, wherein the amino acid comprises an additional amino group. Preferably, the amino acid is selected from the group comprising an α-amino acid, a β-amino acid, a γ-amino acid and a cyclic amino acid; more preferably the amino acid is selected from the group comprising an α-amino acid, a β-amino acid and a cyclic amino acid. A particularly preferred branching moiety Y is an amino acid selected from the group comprising 2,3-diaminopropionic acid, 2,4-diaminobutanoic acid, lysine, homolysine and ornithine.

In an embodiment the branching moiety Y is an amino acid, wherein the amino acid comprises an additional carboxyl group. Preferably, the amino acid is selected from the group comprising an α-amino acid, a β-amino acid, a γ-amino acid, a cyclic amino acid; more preferably the amino acid is selected from the group comprising an α-amino acid, a β-amino acid and a cyclic amino acid. A particularly preferred branching moiety Y is an amino acid selected from the group comprising aspartatic acid, glutamic acid, 2-aminoadipic acid, and α-aminosuberic acid.

In a preferred embodiment the branching moiety Y is selected from the group comprising the following compounds In an embodiment the branching moiety Y is an imino acid, wherein the imino acid comprises an additional amino group. This kind of amino acid can be generically represented as follows

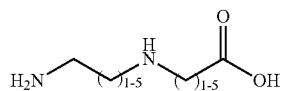
(78)

Preferably, the imino acid is selected from the group comprising an α-imino acid, a β-imino acid, a γ-imino acid and a cyclic imino acid; more preferably the imino acid is selected from the group comprising an α-imino acid, a β-imino acid and a cyclic imino acid. A particularly preferred branching moiety Y is an imino acid selected from the group comprising iminoacetic acid, N-carboxymethyl-β-alanine, 3(2-carboxyethylamino)propanoic acid, 4,4-bis(N, N-dibutyric acid).

In an embodiment the branching moiety Y is an imino acid, wherein the imino acid comprises an additional carboxyl group. This kind of amino acid can be generically represented as follows

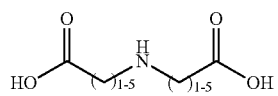
(79)

Preferably, the imino acid is selected from the group comprising an α-imino acid, a β-imino acid, a γ-imino acid and a cyclic imino acid; more preferably the imino acid is selected from the group comprising an α-imino acid, a β-imino acid and a cyclic imino acid. A particularly preferred branching moiety Y is an imino acid selected from the group comprising N-(2-Aminoethyl)glycine, N-(5-aminopentyl)-glycine.

In an embodiment the branching moiety Y is a cyclic imino acid, wherein the imino acid comprises an additional amino group. This kind of amino acid can be generically represented as follows

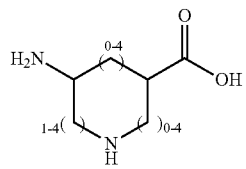
(80)

Preferably, the imino acid is selected from the group comprising an α-imino acid, a β-imino acid, a γ-imino acid and a cyclic imino acid; more preferably the imino acid is selected from the group comprising an α-imino acid, a β-imino acid and a cyclic imino acid. A particularly preferred branching moiety Y is an imino acid selected from the group comprising 4-amino-3-pyrrolidinecarboxylic acid, β-amino-proline and 4-amino-proline.

In an embodiment the branching moiety Y is a cyclic imino acid, wherein the imino acid comprises an additional amino group. This kind of amino acid can be generically represented as follows

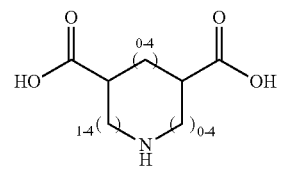
(81)

Preferably, the imino acid is selected from the group comprising an α-imino acid, a β-imino acid, a γ-imino acid and a cyclic imino acid; more preferably the imino acid is selected from the group comprising an α-imino acid, a β-imino acid and a cyclic imino acid. A particularly preferred branching moiety Y is an imino acid selected from the group comprising 2,3-dicarboxypyrrolidine, and pyrrolidine-2,4-dicarboxylate.

In a further embodiment the branching moiety Y is an aromatic amino acid wherein the amino acid comprises an additional amino group; preferably within this amino acid the rigidity and orientation can be modified. This kind of amino acid can be generically represented as follows

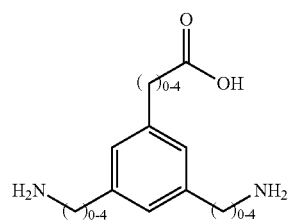
(82)

including all substitution pattern at aryl

It will be acknowledged by a person skilled in the art that the two substitutions indicated in the above generic formula in meta position can also be arranged in either para position or in ortho position. Accordingly, in an embodiment the aromatic amino acid can be one where the two substitutents as indicated in the above generic formula in meta position are arranged either in para position or in ortho position. A particularly preferred branching moiety Y is an aromatic amino acid selected form the group comprising 3,5-diaminobenzoic acid and 3,5-bis-aminomethyl-benzoic acid.

In a further embodiment the branching moiety Y is an aromatic amino acid wherein the amino acid comprises an additional carboxy group; preferably within this amino acid the rigidity and orientation can be modified. This kind of amino acid can be generically represented as follows (83)

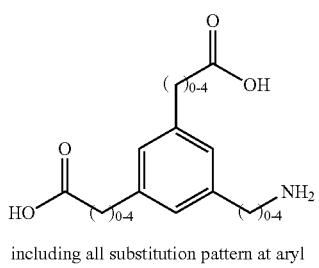

including all substitution pattern at aryl

It will be acknowledged by a person skilled in the art that the two substitutions indicated in the above generic formula in meta position can also be arranged in either para position or in ortho position. Accordingly, in an embodiment the aromatic amino acid can be one where the two substitutents as indicated in the above generic formula in meta position are arranged either in para position or in ortho position. A particularly preferred branching moiety Y is an aromatic amino acid is 5-aminoisophthalic acid.

In an embodiment the branching moiety Y is a triamine. Preferably, the triamine is selected from the group comprising 1,3,5-triazinane, propane-1,2,3-triamine, 1,3,5-triaminobenzene, diethylenetriamine, 3,3'diaminopropylamine and bis(hexamethylene)triamine.

In an embodiment the branching moiety Y is a tricarboxylic acid. Preferably, the tricarboxylic acid is selected from the group comprising 1,3,5-benzenetricarboxylic acid, 1,2,3-benzenetricarboxylic acid and 1,2,4-benzenetricarboxylic acid, 1,3,5-benzenetriacetic acid and citric acid.

Third Adapter Moiety AD3

In an embodiment of the conjugate of the invention the conjugate comprises a third adapter moiety AD3. Preferably, the third adapter moiety AD3 mediates the linkage, or establishes a linkage, between the branching moeity Y and the effector moiety. Alternatively, the third adapter moiety AD3 mediates the linkage, or establishes a linkage, between the second targeting moiety TM2 and the effector moiety EM. The linkage is also referred to herein as the AD3 linkage. In an embodiment the AD3 linkage is one selected from the group comprising an amide linkage, a sulfonamide linkage, a urea linkage, a thiourea linkage, a thioether linkage, an ether linkage, a carbamate linkage, an amine linkage, a triazole linkage, an oxime linkage, a hydrazone linkage, a disulfide linkage, a pyrazine linkage and a dihydro-pyrazine linkage. Preferably, the AD3 linkage is a linkage selected from the group comprising an amide linkage, a urea linkage, a thiourea linkage and an amine linkage.

In order to establish the AD3 linkage the third adapter moiety AD3 comprises a first reactive group and the branching moiety Y comprises a reactive group, wherein the reactive group of the branching moiety Y is complementary to the first reactive group of the third adapter moiety AD3 which allows the formation of an AD3 linkage. Alternatively, in order to establish the AD3 linkage the third adapter moiety AD3 comprises a first reactive group and the second targeting moiety TM2 comprises a reactive group, wherein the reactive group of the second targeting moiety TM2 is complementary to the first reactive group of the third adapter moiety AD3.

In an embodiment the reactive group of the branching moiety Y involved in forming the AD3 linkage is selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine.

In an embodiment the reactive group of the second targeting moiety TM2 involved in forming the AD3 linkage is selected from the group comprising amino, carboxylic acid, activated carboxylic acid, chloro, bromo, iodo, sulfhydryl, hydroxyl, sulfonic acid, activated sulfonic acid, sulfonic acid esters like mesylate or tosylate, Michael acceptors, strained alkenes like trans cyclooctene, isocyanate, isothiocyanate, aldehyde, ketone, aminooxy, hydrazide, hydrazine, azide, alkyne and tetrazine.

In an embodiment the third adapter moiety AD3 is one which is shown in the square brackets of formula (84):

wherein
Y and EM and $R^9$ are as defined herein;
$Lin^4$ is selected from the group comprising —CO—, —$NR^{10}$—, —CO—$NR^{10}$—, —CS—$NR^{10}$—, —$CH_2$— and a direct bond;
wherein $R^{10}$ is selected from the group consisting of hydrogen and $(C_1$-$C_4)$alkyl;
and
$Lin^5$ is selected from the group comprising —CO—, —S—, —$NR^{10}$—, —CO—$NR^{10}$—, —CS—$NR^{10}$—, —O—, —$CH_2$—, —$SO_2$—, -succinimide-, —$CH_2$—CO—$NR^{10}$—, —C=C— (in case of, for example triazole), =N—O—, =N—N—, =N—N—CO—, —N=N—N— (in case of, for example triazole), —HC= and —$R^3$C= (of oxime and hydrazone);
wherein $R^{10}$ is selected from the group consisting of hydrogen and $(C_1$-$C_4)$alkyl.

Depending on the structural class and origin of the effector moiety EM different types of reactive groups are typically preferred. If the effector moiety is a protein, the preferred reactive groups are sulfhydryl and amino.

In a further embodiment the same principles and preferred structures as for the first and second adapter moiety apply to the third adapter moiety AD3.

In a still further embodiment the third adapter moiety AD3 comprises an additional building block moiety $[W]_c$ as disclosed herein. This building block moiety may provide for optimal spacing of the two entities or may further supply a labile linkage that allows the two entities to be separated from each other. Labile linkages include hydrolyzable groups, photocleavable groups, acid-labile moieties, base-labile moieties and enzyme cleavable groups.

In an embodiment this building block moiety $[W]_c$ is an amino acid or a peptide consisting of 2 to 10 amino acids, whereby the amino acids are independently selected from the group of natural and non-natural amino acids. Amino acids as used in the building block moiety $[W]_c$ and thus in the embodiment of the third adapter moiety AD3 include, but are not limited, to α-amino acids and amino acids where the amino and the carboxylic group are spaced further apart such as pβ-amino acids, γ-amino acids, δ-amino acids, ε-amino acids and ω-amino acids. In any case the amino acids may be cyclic or linear. In the case of amino acids with stereogenic centers all stereoisomeric forms may be used. An illustrative example of this adapter moiety is shown within the square brackets of formula (85):

wherein Y, EM, R9 and Lin⁵ are as defined herein, and [W]_c is an amino acid or peptide consisting of up to 10 amino acids, which are independently selected from the group comprising natural amino acids, non-natural amino-acids, α-amino acids and amino acids where the amino and the carboxylic group are spaced further apart such as β-amino acids, γ-amino acids, δ-amino acids, ε-amino acids and ω-amino acids. and c is an integer from 1, 2, 3, 4, 5, 6, 7, 8, 9 and 10, and the linkage to branching moiety Y is amide.

In some embodiments the moiety [W]_c of the conjugates of the invention can be enzymatically cleaved by one or more enzymes, including a tumor-associated protease, to liberate the effector moiety (-EM).

The building block moiety [W]_c comprises illustrative enzymatically cleavable sequences as shown below:

a) Dipeptides: -Phe-Lys-, -Ala-Lys-, -Val-Lys-, -Val-Cit-, -Phe-Cit-, -Ile-Cit-, -Leu-Cit-, -Trp-Cit-, -Phe-Ala-, and -Phe-Arg-; and b) Tripeptides: -Phe-Phe-Lys-, -Val-Phe-Lys-, and -Gly-Phe-Lys-; and c) Tetrapeptides: -Gly-Phe-Leu-Gly (SEQ ID NO: 22), and -Ala-Leu-Ala-Leu- (SEQ ID NO: 23).

The moiety [W]_c in the present invention can be designed and optimized in their selectivity for enzymatic cleavage by particular enzymes, for example, a tumor-associated protease. In one embodiment, [W]_c is that whose cleavage is catalyzed by cathepsin B, C and D, or a plasmin protease.

In one embodiment, [W]_c is a dipeptide, tripeptide or pentapeptide.

In a further embodiment a preferred moiety [W]_c comprises a Gly at the C-terminal end.

In still another embodiment a preferred moiety [W]_c comprises a Gly-Gly Dipeptide at the C-terminal end.

Effector Moiety EM

As disclosed herein in more detail, an Effector moiety is a moiety which comprises or is capable of comprising an Effector, whereby the Effector is preferably selected from the group consisting of a diagnostically active agent, a therapeutically active agent, an agent which is suitable as both a diagnostically active agent and a therapeutically active agent, and a combination of a diagnostically active agent and a therapeutically active agent. In other words, an Effector moiety can be an effector which is already complexed by or covalently bound to the conjugate of the invention, whereby such complexing or binding is realized, in a preferred embodiment by a structure of [Acceptor-Effector]. Alternatively, the conjugate of the invention is capable of reacting readily with an Effector. Accordingly, in embodiments of the invention the Effector moiety is an Effector, an Acceptor or -[Acceptor-Effector].

In a further embodiment, the covalent linkage between the third adapter moiety AD3 and the Acceptor is selected from the group comprising amide (also referred to as amide linkage), alkylamine (also referred to as alkylamine linkage), urea (also referred to as urea linkage), ether (also referred to as ether linkage), thioether (also referred to as thioether linkage), thiourea (also referred to as thiourea linkage) and carbamate (also referred to as carbamate linkage).

Acceptor as preferably used herein is a moiety which is used or present in the conjugate of the invention and which mediates the linking of an Effector to the conjugate of the invention, preferably the conjugate of the invention of formula (1).

In a further embodiment the Acceptor comprises a functional group which is capable of forming a covalent linkage to either the third adapter moiety AD3, if present, or to the branching moiety Y, if present, without destroying the Acceptor's function, i.e. the binding or complexing of the Effector. Such functional group is preferably selected from the group comprising comprising amino, carboxylic acid, activated carboxylic acid, chloro, bromo, iodo, sulfhydryl, hydroxyl, sulfonic acid esters like mesylate or tosylate, Michael acceptors, isocyanate, isothiocyanate, aldehyde and ketone.

It is within the present invention that the Effector is either directly linked to the third adapter moiety AD3 or to the branching moiety Y, or linked to either the third adapter moiety AD3 or to the branching moiety Y by means of the Acceptor if such Acceptor is present. Such Acceptor is, among others, a chelator. In one embodiment thereof, the compound of the invention is bearing a metal, preferably a radioactive transition metal which is chelated by the chelator. In another embodiment, the compound of the invention is bearing the chelator with no metal chelated by the chelator.

The following Table 10 summarizes illustrative examples of a conjugate of the invention. It is within the present invention that each any any of the moieties indicated in said table may be, individually and independently, combined with each any of the other moieties indicated in said table. Insofar, any permutation arising from such combining constitutes an embodiment of the conjugate of the invention which is disclosed herein in an individualized form.

TABLE 10

| Compound/SEQ ID NO: | [TM1] | [AD1] | [X]a | [Y] | [AD3] | [EM] | [Z]b | [AD2] | [TM2] |
|---|---|---|---|---|---|---|---|---|---|
| (12)/4 | 1206 | Glutar | Ttds | Lys | — | DOTA | Ttds | GABA | 1206 |
| (13)/5 | 1206 | Glutar | — | Lys | — | DOTA | - | GABA | 1206 |
| (14)/6 | 1206 | Glutar | Ahx | Lys | — | DOTA | (ε-Lys-NH2) | Glutar | 1206 |
| (15)/7 | 1206 | Glutar | (Ttds)3 | Lys | — | DOTA | (Ttds)3-(ε-Lys-NH2) | Glutar | 1206 |
| (16)/8 | 1206 | Glutar | Ttds | Lys | — | DOTA | Ttds | GABA | RRPY-Tle-L-OH |
| (17)/9 | 1206 | Glutar | Ttds | Lys | — | DOTA | Ttds | GABA | rRPY-Tle-L-OH |
| (18)/10 | 1206 | Glutar | (Ttds)3 | Lys | — | DOTA | (Ttds)3 | GABA | rRPY-Tle-L-OH |

TABLE 10-continued

| Compound/ SEQ ID NO: | [TM1] | [AD1] | [X]a | [Y] | [AD3] | [EM] | [Z]b | [AD2] | [TM2] |
|---|---|---|---|---|---|---|---|---|---|
| (19)/11 | 1206 | Glutar | Ttds | Lys | — | FITC | (Ttds)-(ε-Lys-NH2) | Glutar | 1206 |
| (20)/12 | 1206 | Glutar | Ttds | Lys | Succinyl | Taxol | (Ttds)-(ε-Lys-NH2) | Glutar | 1206 |
| (21)/13 | 1206 | Glutar | Ttds | Lys | — | DOTA | Ttds | GABA | Asn-Ala-Val-Pro-Asn-Leu-Arg-Gly-Asp-Leu-Gln-Val-Leu-Ala-Gln-Lys-Val-Ala-Arg-Thr-NH₂ |
| (22)/14 | Ac-Asn-Ala-Val-Pro-Asn-Leu-Arg-Gly-Asp-Leu-Gln-Val-Leu-Ala-Gln-Lys-Val-Ala-Arg-Thr | GABA | (Ttds)3 | Lys | — | DOTA | (Ttds)3-(ε-Lys-NH2) | Glutar | 1206 |
| (23)/15 | Ac-Asn-Ala-Val-Pro-Asn-Leu-Arg-Gly-Asp-Leu-Gln-Val-Leu-Ala-Gln-Lys-Val-Ala-Arg-Thr | GABA | (Ttds)3 | Lys | — | DOTA | (Ttds)3-(β-Cys-NH2) | Mic | 1206 |
| (24)/16 | 1206 | Glutar | (Ttds)3 | — | (ε-Lys-NH2) | DOTA | — | — | Asn-Ala-Val-Pro-Asn-Leu-Arg-Gly-Asp-Leu-Gln-Val-Leu-Ala-Gln-Lys-Val-Ala-Arg-Thr-GABA-Ttds-* |
| (25)#/17 | 1206 | Glutar | Ttds-Lys(1206-Glutar-Ttds) | — | (ε-Lys-NH2) | DOTA | Ttds | — | Asn-Ala-Val-Pro-Asn-Leu-Arg-Gly-Asp-Leu-Gln-Val-Leu-Ala-Gln-Lys-Val-Ala-Arg-Thr-GABA-Ttds-* |
| (29)/20 | 1206 | Glutar | Ttds | — | — | — | (ε-Lys-NH2) | Glutar | Anti EphA2 (Mab 3035) |
| (30)/21 | 1206 | Glutar | Ttds | — | — | — | (ε-Lys-NH2) | Glutar | Anti TNC (Mab 1909) |
| (26)/18 | 1206 | Glutar | Ttds | Lys | — | DOTA | Ttds | GABA | KRP-Hyp-G-Cha-SPL-OH |
| (27)/19 | 1206 | Glutar | Ttds | Lys | — | DOTA | Ttds | GABA | Orn-R-Oic-PG-Amf-S-nal-Ile-OH |
| (28) | Biotin | — | Ttds | — | — | — | — | — | 1206 |

*AD3-EM [-(ε-Lys-NH2)-DOTA] is linked at the C-terminus of TM2
Compound (25) comprises a conjugate of the invention and is equipped with a second TM1-moiety (1206-Glutar-Ttds)

Possible forms of chelating interaction which allow the practicing of the present invention between a chelator and an Effector, which is preferably a transition metal, are known to the person skilled in the art and respective examples, structures and applications are, for example, described in Wadas et al. (Wadas et al., *Chem. Rev.*, 2010, 110, 2858-2902) and literature cited therein.

In another embodiment Acceptor is or comprises an aromate, preferably an electron rich aromate such as indoles or benzenes optionally substituted by oxygen, nitrogen sulfur atoms.

In one embodiment thereof, the compound of the invention is bearing a halogen, preferably a radioactive halogen which is substituting said aromatic moiety. In another embodiment, the compound of the invention is bearing the aromatic moiety with no halogen bound to this aromatic moiety.

It will be acknowledged by a person skilled in the art that the specific effector which is or which is to be attached to the compound of the invention, is selected taking into consideration the disease to be treated and the disease to be diagnosed, respectively, and the particularities of the patient and patient group, respectively, to be treated and to be diagnosed, respectively.

In an embodiment the Effector is a radioactive nuclide which is also referred to as radionuclide. Radioactive decay is the process by which an atomic nucleus of an unstable atom loses energy by emitting ionizing particles (ionizing radiation). There are different types of radioactive decay. A decay, or loss of energy, results when an atom with one type of nucleus, called the parent radionuclide, transforms to an atom with a nucleus in a different state, or to a different nucleus containing different numbers of protons and neutrons. Either of these products is named the daughter nuclide. In some decays the parent and daughter are different chemical elements, and thus the decay process results in nuclear transmutation (creation of an atom of a new element). For example the radioactive decay can be alpha decay, beta decay, and gamma decay. Alpha decay occurs when the nucleus ejects an alpha particle (helium nucleus). This is the most common process of emitting nucleons, but in rarer types of decays, nuclei can eject protons, or specific nuclei of other elements (in the process called cluster decay). Beta decay occurs when the nucleus emits an electron ($\beta^-$-decay) or positron ($\beta^+$-decay) and a type of neutrino, in a process that changes a proton to a neutron or the other way around. By contrast, there exist radioactive decay processes that do not result in transmutation. The energy of an excited nucleus may be emitted as a gamma ray in gamma decay, or used to eject an orbital electron by interaction with the excited nucleus in a process called internal conversion.

In a preferred embodiment of the present invention, the radionuclide can be used for stable labeling of the compound of the invention.

In a preferred embodiment of the present invention, the radionuclide has a half-life that allows for diagnostic or therapeutic medical use. Specifically, the half-life is between 30 min and 7 days. More specifically, the half-life is between 2 h and 3 days.

In a preferred embodiment of the present invention, the radionuclide has a decay energy and radiation range that allows for diagnostic or therapeutic medical use.

In a preferred embodiment of the present invention, the radionuclide is industrially produced for medical use. Specifically, the radionuclide is available in GMP quality.

In a preferred embodiment of the present invention, the daughter nuclide(s) after radioactive decay of the radionuclide are compatible with the diagnostic or therapeutic medical use.

Specifically, the daughter nuclide(s) remain chemically bound or complexed to the compound of the invention and are not toxic. Furthermore, the daughter nuclides are either stable or further decay in a way that does not interfere with or even support the diagnostic or therapeutic medical use.

In an embodiment of the present invention, the radionuclide which is preferably a metal and more preferably a transition metal, is suitable for being complexed with a metal chelator and leading to radioactive metal chelator for imaging. It will, however, be acknowledged by a person skilled in the art that the radionuclide may also be directly bound to the compound of the invention. Preferably, the radioactive isotope is selected from the group comprising $^{18}$F, $^{110}$In, $^{113m}$In, $^{114m}$In, $^{99m}$Tc, $^{67}$Ga, $^{52}$Fe, $^{59}$Fe, $^{68}$Ga, $^{111}$In, $^{97}$Ru, $^{203}$Pb, $^{62}$Cu, $^{64}$Cu, $^{67}$Cu, $^{51}$Cr $^{51}$Mn, $^{52m}$Mn, $^{55}$Co, $^{57}$Co, $^{58}$Co, $^{72}$As, $^{75}$Se, $^{157}$Gd, $^{120}$I, $^{123}$I, $^{124}$I, $^{125}$I, $^{131}$I, $^{75}$Br, $^{76}$Br, $^{77}$Br, $^{89}$Zr, $^{82m}$Rb, $^{83}$Sr, $^{86}$Y, $^{94m}$Tc, $^{169}$Yb, $^{197}$Hg, $^{201}$Tl, and $^{82}$Br. More preferably, the radioactive metal is selected from the group comprising $^{99m}$Tc, $^{67}$Ga, $^{68}$Ga, $^{111}$In, $^{89}$Zr and $^{123}$I. Even more preferably the radioactive metal is $^{111}$In and $^{89}$Zr. It will however, also be acknowledged by a person skilled in the art that the use of said radioactive metals is not limited to imaging purposes, but encompasses their use in diagnosis, therapy and theragnostics.

In an embodiment of the present invention, the radionuclide which is preferably a metal and more preferably a transition metal is suitable for complexing with a metal chelator and leading to radioactive metal chelator for radiotherapy. It will, however, be acknowledged by a person skilled in the art that the radionuclide may also be directly bound to the compound of the invention. Preferably, the radioactive isotope is selected from the group comprising $^{32}$P, $^{33}$P, $^{47}$Sc, $^{58}$Co, $^{59}$Fe, $^{64}$CU, $^{67}$Cu, $^{67}$Ga, $^{68}$Ga, $^{75}$Se, $^{77}$As, $^{80m}$Br, $^{89}$Sr, $^{89}$Zr, $^{90}$Y, $^{99}$M, $^{103m}$Rh, $^{105}$Rh, $^{109}$Pd, $^{109}$Pt, $^{111}$Ag, $^{111}$In, $^{119}$Sb, $^{121}$Sn, $^{127}$Te, $^{125}$I, $^{123}$I, $^{129}$I, $^{131}$I, $^{142}$Pr, $^{143}$Pr, $^{149}$Pm, $^{151}$Pm, $^{152}$Dy, $^{153}$Sm, $^{159}$Gd, $^{161}$Tb, $^{161}$Ho, $^{166}$Ho, $^{166}$Dy, $^{169}$Er, $^{169}$Yb, $^{175}$Yb, $^{172}$Tm, $^{177}$Lu, $^{177m}$Sn, $^{186}$Re, $^{188}$Re, $^{189}$Re, $^{188}$Rd, $^{189m}$OS, $^{192}$Ir, $^{194}$Ir, $^{198}$Au, $^{199}$Au, $^{211}$At, $^{211}$Pb, $^{212}$Pb, $^{211}$Bi, $^{212}$Bi, $^{213}$Bi, $^{215}$Po, $^{217}$At, $^{219}$Rn, $^{221}$Fr, $^{223}$Ra, $^{225}$Ac, $^{227}$Th, $^{255}$Fm. More preferably, the radioactive isotope is selected from the group comprising $^{111}$In, $^{77}$Lu, $^{89}$Zr, $^{67}$Ga, $^{68}$Ga, $^{67}$Cu, $^{64}$Cu and $^{90}$Y. More preferably, the radioactive metal is selected from the group comprising $^{111}$In, $^{90}$Y and $^{177}$Lu. It will however, also be acknowledged by a person skilled in the art that the use of said radioactive metals is not limited to imaging purposes, but encompasses their use in diagnosis, therapy and theragnostics.

In a further embodiment, the effector is a radioactive halogen such as iodine and bromine isotopes which can be used, when attached to the compound of the invention, for therapy, diagnosis and/or theragnostics. In a preferred embodiment the radioactive halogen is bonded directly to the compound of the invention.

Preferred radionuclides used for diagnosis such as $^{68}$Ga, $^{111}$In and $^{89}$Zr, and preferred radionuclides used for therapy such as $^{90}$Y, $^{153}$Sm and $^{177}$Lu, are trivalent cations from the class of elements known as the lanthanides. Typical radioactive metals in this class include the isotopes $^{90}$Yttrium, $^{111}$Indium, $^{149}$Promethium, $^{153}$Samarium, $^{166}$Dysprosium, $^{166}$Holmium, $^{175}$Ytterbium, and $^{177}$Lutetium. All of these metals and others in the lanthanide series have very similar chemistries, in that they remain in the +3 oxidation state and prefer to chelate to ligands that bear hard donor atoms such as oxygen/nitrogen donor atoms.

As is evident from the above, a radionuclide is, in principle, useful in the treatment and/or diagnosis of a disease when conjugated to the compound of the invention.

In an embodiment of the compound of the invention the compound of the invention comprises a chelator. Preferably, the chelator is part of the Acceptor of the compound of the invention, whereby the chelator is either directly or indirectly such as by a linker attached to the compound of the invention. A preferred chelator is a metal chelator, whereby the metal chelator preferably comprises at least one radioactive metal. The at least one radioactive metal is preferably useful in or suitable for diagnostic and/or therapeutic use and is more preferably useful in or suitable for imaging and/or radiotherapy.

Chelators in principle useful in and/or suitable for the practicing of the instant invention including diagnosis and/or therapy of a disease, are known to the person skilled in the art. A wide variety of respective chelators is available and has been reviewed, e.g. by Banerjee et al. (Banerjee et al., Nucl. Med. Biol., 2005, 32, 1-20, and references therein, Wadas et al., Chem. Rev., 2010, 110, 2858-2902 and references therein) included herein by reference. Such chelators include, but are not limited to linear, macrocyclic, tetrapyridine and $N_3S$, $N_2S_2$ and $N_4$ chelators as disclosed in U.S. Pat. Nos. 5,367,080 A, 5,364,613 A, 5,021,556 A, 5,075,099 A, 5,886,142 A; HYNIC, DTPA, EDTA, DOTA, TETA, bisamino bisthiol (BAT) based chelators as disclosed in U.S. Pat. No. 5,720,934; Desferrioxamin (DFO) as disclosed (Doulias et al., Free Radic. Biol. Med., 2003, 35, 719-728), whereby all of the references are included herein by reference in their entirety.

The diagnostic and/or therapeutic use of some of the above chelators is described in the prior art. For example, 2-hydrazino nicotinamide (HYNIC) has been widely used in the presence of a coligand for incorporation of $^{99m}$Tc and $^{186,188}$Re (Schwartz et al., Bioconj. Chem., 1991, 2, 333-336; Babich et al., J. Nucl. Med., 1993, 34, 1964-1970; Babich et al., Nucl. Med. Biol., 1995, 22, 25-30); DTPA is used in Octreoscan® which is marketed by Covidien, for complexing $^{111}$In and several modifications are described in the literature (Brechbiel et al., Bioconj. Chem., 1991, 2, 187-194; Li et al., Nucl Med. Biol., 2001, 28, 145-154); DOTA type chelators for radiotherapy applications are described by Tweedle et al. (U.S. Pat. No. 4,885,363); other polyaza macrocycles for chelating trivalent isotopes metals are described by Maecke et al., Bioconj. Chem., 2002, 13, 530-541; and $N_4$-chelators such as a $^{99m}$Tc—$N_4$-chelator have been used for peptide labeling in the case of minigastrin for targeting CCK-2 receptors (Nock et al., J. Nucl Med., 2005, 46, 1727-1736).

In a preferred embodiment of the present invention, the metal chelator is a metal chelator for trivalent metals or for pentavalent metals and their close analogs. Many metal chelators of this type are disclosed by WO2009/109332 A1.

In an embodiment the metal chelator for trivalent metals is selected from the group comprising DOTA, NOTA, DTPA, TETA, EDTA, NODAGA, NODASA, TRITA, CDTA, BAT, DFO and HYNIC based chelators and their close analogs, wherein DOTA stands for 1,4,7,10-tetrazacyclododecane-1,4,7,10-tetraacetic acid,
NOTA stands for 1,4,7-triazacyclononanetriacetic acid,
DTPA stands for diethylenetriaminepentaacetic acid,
TETA stands for 1,4,8,11-tetraazacyclododecane-1,4,8,11-tetraacetic acid,
EDTA stands for ethylenediamine-N,N'-tetraacetic acid,
NODAGA stands for 1,4,7-triazacyclononane-N-glutaric acid-N',N''-diacetic acid,
NODASA stands for 1,4,7-triazacyclononane-1-succinic acid-4,7-diacetic acid,
TRITA stands for 1,4,7,10 tetraazacyclotridecane-1,4,7,10-tetraacetic acid,
CDTA stands for trans-1,2-diaminocyclohexane-N,N,N',N'-tetraacetic acid,
DFO stands for the Desferal or Desferrioxamine type group of chelators, the chemical name of the non-limiting example is N-[5-({3-[5-(Acetyl-hydroxy-amino)-pentylcarbamoyl]-propionyl}-hydroxy-amino)-pentyl]-N'-(5-amino-pentyl)-N'-hydroxy-succinamide,
BAT stands for the Bisamino-bisthiol group of chelators, the chemical name of the non limiting example is 1-[2-(2-mercapto-2-methyl-propylamino)-ethylamino]-2-methyl-propane-2-thiol,
HYNIC stands for 6-Hydrazino-nicotinic acid,
and with the chemical structures thereof being as follows:

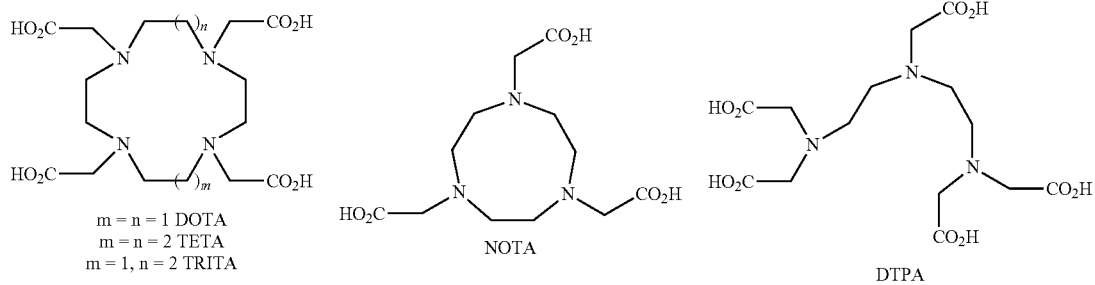

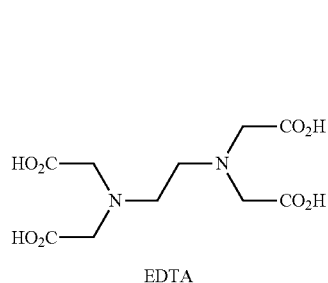
EDTA

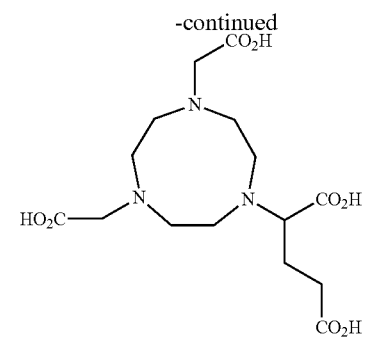
NODAGA

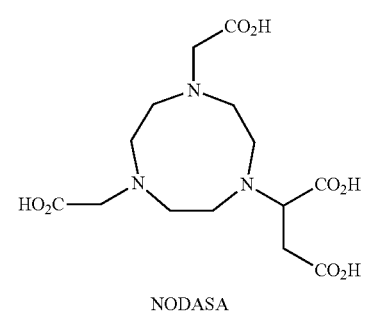
NODASA

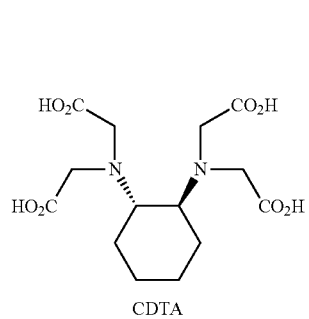
CDTA

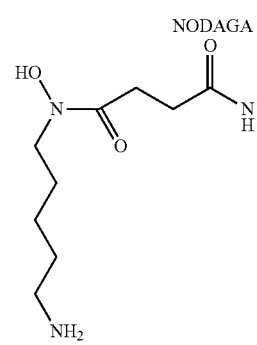
DFO

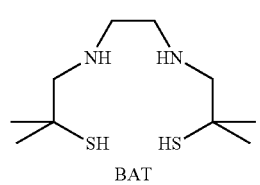
BAT

HYNIC

In a preferred embodiment the metal chelator is selected from the group comprising DOTA-, NOTA-, DTPA-, TETA-DFO and HYNIC based chelators and their close analogs.

Compounds of the invention which are complexes of a metal with a chelator a clearly and precisely termed by the following short notation:

In "$^{xxx}$Metal-(YY)" the optional atomic mass number of specific isotopes (xxx) in superscript is followed directly by the atomic symbol of metal (Metal), separated by an hyphen from number of the formula of the parent uncomplexed compound (YY) in parentheses; Lu-(12), for instance, means Lutethium complexed to a chelator of the compound of formula (12) and $^{111}$In-(12), for instance, means $^{111}$Indium complexed to a chelator of the compound of formula (12).

In a more preferred embodiment the metal chelator for trivalent metals is selected from the group comprising DTPA (diethylenetriaminepentaacetic acid) and polyaza-polycarboxylate macrocycles such as DOTA (1,4,7,10-tetrazacyclododecane-1,4,7,10-tetraacetic acid) and the close analogs thereof.

In one preferred embodiment the metal chelator for $^{89}$Zr is DFO, DTPA, DOTA or EDTA.

It will be acknowledged by the persons skilled in the art that the chelator, in principle, may be used regardless whether the compound of the invention is used in or suitable for diagnosis or therapy. Such principles are, among others, outlined in international patent application WO 2009/109332 A1.

In a further embodiment the conjugate of the invention is conjugated to a therapeutically active or therapeutically effective agent which is also referred to herein as therapeutic effector moiety. Therapeutic effector moieties may be antiproliferative, antimigration, antiangiogenic, cytostatic, cytotoxic, antithrombotic, anti-inflammatory, antiphlogistic, anticoagulative, antibacterial, antiviral and/or antimycotic agents, wherein antiproliferative, antimigration, antiangiogenic, cytostatic and/or cytotoxic substances as well as nucleic acids, small molecules, amino acids, peptides, proteins, carbohydrates, lipids, glycoproteins, glycans or lipoproteins having antiproliferative, antimigration, antiangiogenic, cytostatic and/or cytotoxic properties are preferred.

Furthermore, such substances may also be radiosensitizers or sensitizers or amplifiers of other combined conventional cancer treatment methods or contain such sensitizers.

In an embodiment of the conjugate of the invention the therapeutically active agent is a cytotoxic and/or cytostatic agent.

A cytotoxin or cytotoxic agent includes any agent that is detrimental to (e.g., kills) cells. A cytostatic agent includes any agent that inhibits or suppresses cellular growth and multiplication. As cytotoxic and/or cytostatic compounds, i.e. chemical compounds having cytotoxic and/or cytostatic properties the following may be used: alkaloids (Moudi et al., *Int J Prev Med*, 2013, 4, 1231-1235; Walczak et al., *J Am Acad Orthop Surg*, 2013, 21, 480-491), alkylating agents (Begleiter, *Front Biosci*, 2000, 5, E153-171; Rockwell et al., *Cancer Metastasis Rev*, 1993, 12, 165-176; Spiro et al., *Forum* (Genova), 2000, 10, 274-285; Walczak et al., supra), angiogenesis inhibitors (Cesca et al., *Front Oncol*, 2013, 3, 259; Wang et al., *Mar Drugs*, 2013, 11, 903-933; Zaki et al., *Curr Top Med Chem*, 2012, 12, 32-49), antibiotics having cytostatic properties (Abraham et al., *Drug Saf,* 1996, 15, 406-429; Gewirtz, *Biochem Pharmacol,* 1999, 57, 727-741; Oki, *Biotechnol Bioeng,* 1980, 22 *Suppl* 1, 83-97; Walczak et al., supra), anthracyclins (Shah, *Recent Pat Anticancer Drug Discov,* 2009, 4, 241-245; Gewirtz et al. supra; Walczak et al., supra), antifolates (Purcell et al., *Curr Oncol Rep,* 2003, 5, 114-125; Rollins et al., *Clin Ther,* 2005, 27, 1343-1382; Wright et al., *Expert Opin Ther Pat,* 2011, 21, 1293-1308), anti-mitotic toxins (Antignani et al., *Toxins (Basel),* 2013, 5, 1486-1502; Engedal et al., *Microb Biotechnol,* 2011, 4, 32-46; Potala et al., *Drug Discov Today,* 2008, 13, 807-815), mitotic inhibitors (Casaluce et al., *Expert Opin Emerg Drugs,* 2013, 18, 97-107; Gabrielli et al., *Adv Cancer Res,* 2012, 116, 1-37; Jiang et al., *Mini Rev Med Chem,* 2006, 6, 885-895), antimetabolites (Budde et al., *Curr Treat Options Oncol,* 2005, 6, 83-93; Peters et al., *Pharmacol Ther,* 2000, 87, 227-253; Tiwari, *J Cancer Res Ther,* 2012, 8, 510-519; Walczak et al., supra), anti-proliferative substances (Mader, *Curr Opin Drug Discov Devel,* 2005, 8, 613-618; Rajak et al., *Curr Med Chem,* 2013, 20, 1887-1903; Stadler, *Invest New Drugs,* 2002, 20, 201-208), corticosteroids (Dietrich et al., *Expert Rev Clin Pharmacol,* 2011, 4, 233-242; Wooldridge et al., *Oncology (Williston Park),* 2001, 15, 225-234; discussion 234-226), duocarmycins (Ghosh et al., *Curr Top Med Chem,* 2009, 9, 1494-1524; Tietze et al., *Anticancer Agents Med Chem,* 2009, 9, 304-325), HDAC inhibitors (Khan et al., *Immunol Cell Biol,* 2012, 90, 85-94; Sharma et al., *BJUInt,* 2013, 111, 537-542; West et al., *J Clin Invest,* 2014, 124, 30-39; Gabrielli et al., supra; Rajak et al., supra), hormones (Siegfried et al., *Semin Oncol,* 2014, 41, 5-16; Vesely, *Endocr Relat Cancer,* 2013, 20, R113-125; Vesely, *Anticancer Res,* 2012, 32, 2515-2521), immunotoxins (Choudhary et al., *Drug Discov Today,* 2011, 16, 495-503; Madhumathi et al., *Curr Opin Microbiol,* 2012, 15, 300-309; Pastan et al., *Curr Opin Investig Drugs,* 2002, 3, 1089-1091), kinase inhibitors (Akin et al., *JBUON,* 2014, 19, 42-46; Eigentler et al., *Expert Opin Pharmacother,* 2013, 14, 2195-2201; Sun, *Cancer Lett,* 2013, 340, 1-8), microtubule inhibitors (Higa et al., *Expert Rev Anticancer Ther,* 2008, 8, 671-681; Mareel et al., *Int Rev Cytol,* 1984, 90, 125-168; Rothermel et al., *Semin Oncol,* 2003, 30, 51-55) and topoisomerase inhibitors (Minagawa et al., *Hum Cell,* 2001, 14, 237-243; Munster et al., *Expert Opin Investig Drugs,* 2011, 20, 1565-1574; Takagi et al., *Leuk Lymphoma,* 2001, 42, 577-586; Walczak et al., supra), compounds containing platinum (Bonanno et al., *Anticancer Res,* 2014, 34, 493-501; Poveda et al., *Cancer Treat Rev,* 2014, 40, 366-375; Puisset et al., *Anticancer Res,* 2014, 34, 465-470), retinoids (Garattini et al., *Cancer Treat Rev,* 2014, 40, 739-749; Pasquali et al., *Curr Pharm Des,* 2006, 12, 1923-1929; Tang et al., *Annu Rev Pathol,* 2011, 6, 345-364), taxanes (Binder, Clin *J Oncol* Nurs, 2013, 17 *Suppl,* 9-14; Fauzee, *Asian Pac J Cancer Prev,* 2011, 12, 837-851; Schutz et al., *Crit Rev Oncol Hematol,* 2014), toxins (Ansiaux et al., *Expert Opin Investig Drugs,* 2007, 16, 209-218; Bergan et al., *Toxicon,* 2012, 60, 1085-1107; Li et al., *Toxins (Basel),* 2010, 2, 2645-2662), auristatins (Gerber et al., *Blood,* 2009, 113, 4352-4361; Li et al., *Mol Cancer Ther,* 2013, 12, 1255-1265; Oflazoglu et al., *Clin Cancer Res,* 2008, 14, 6171-6180) and other cytostatics such as, for example, asparaginase (Covini et al., *Recent Pat Anticancer Drug Discov,* 2012, 7, 4-13; Rizzari et al., *Curr Opin Oncol,* 2013, 25 *Suppl* 1, S1-9; Verma et al., *Crit Rev Biotechnol,* 2007, 27, 45-62), tretinoin (Gillis et al., *Drugs,* 1995, 50, 897-923; Makishima et al., *Leuk Lymphoma,* 1997, 26, 43-48; Wong, Cancer Pract, 1996, 4, 220-223), podophyllotoxins (D'Incalci et al., *Cancer Chemother Biol Response Modif* 1992, 13, 75-82; Gordaliza et al., *Curr Pharm Des,* 2000, 6, 1811-1839; Hartmann et al., *Drug Saf,* 2006, 29, 209-230), taxanes and miltefosine® (Clive et al., *Cancer Chemother Pharmacol,* 1999, 44 *Suppl,* S29-30; Clive et al., *Lancet,* 1997, 349, 621-622; Terwogt et al., *Br J Cancer,* 1999, 79, 1158-1161), immunomodulators (Rogalski et al., *J Eur Acad Dermatol Venereol,* 1999, 13, 83-90; Thotathil et al., *Expert Opin Investig Drugs,* 2007, 16, 1391-1403; Villa et al., *J Drugs Dermatol,* 2004, 3, 533-539), monoclonal antibodies (Glassman et al., *Cancer Biol Med,* 2014, 11, 20-33; Vacchelli et al., *Oncoimmunology,* 2014, 3, e27048; Jarboe et al., *Methods Mol Biol,* 2014, 1060, 61-77), signal transducers (molecules for signal transduction) (Koptyra et al., *Int J Biochem Cell Biol,* 2011, 43, 1417-1421; Masciocchi et al., *Future Med Chem,* 2011, 3, 567-597; Catlett-Falcone et al., *Curr Opin Oncol,* 1999, 11, 490-496) and cytokines (Kontermann, *Arch Biochem Biophys,* 2012, 526, 194-205; Matsuo et al., *Curr Pharm Des,* 2012, 18, 2416-2419). Cytotoxic and/or cystatic agents may belong to only one or more of these categories.

In an embodiment of the conjugate of the invention the therapeutically active agent is an alkaloid.

Examples for alkaloids include but are not limited to emetine, lidocaine, procaine, and tetracaine.

In an embodiment of the conjugate of the invention the therapeutically active agent is an alkylating agent.

Examples for alkylating agents include but are not limited to Bendamustine, Ifosfamide, L-Sarcolysin, Phenylalanine Mustard, Carboplatin, Cisplatin, Oxaliplatin, carmustine (or BCNU, bis-chloroethylnitrosourea), Akylsulfonate, Altretamine, analogs or derivatives of CC-1065, Busulfan, Carboquone, Carmustine, CC-1055 (a.k.a. rachelmycin), Chlorambucil, chlorethamine, Cyclophosphamide, Dacarbazine, dibromomannitol, duocarmycin A, duocarmycin SA, Estramustine, Fotemustine, Lomustine, Mannosulfan, Mechlorethamine, Melphalan, Nimustine, Ranimustine, Semustine, Streptozocin, streptozotocin, Temozolomide, Tetraethylenpentamin (ThioTEPA), Treosulfan, Triazene, Triaziquone, and Trofosfamide.

In an embodiment of the conjugate of the invention the therapeutically active agent is an angiogenesis inhibitor.

Examples for angiogenesis inhibitors include but are not limited to Everolimus, Thalidomide, 2-methoxyestradiol, angiostatic steroids+heparin, carboxyamidotriazole, Cartilage-Derived Angiogenesis Inhibitory Factor, CM101, endostatin, IFN-α, itraconazole, linomide, platelet factor-4, prolactin, ranibizumab, SU5416, suramin, tasquinimod, tecogalan, tetrathiomolybdate, TNP-470 (an analog of fumagillin), VEGFR antagonists, αVβ3 inhibitors, 2C3, ABT-510, AEE788, AMG706, Angiostatin, AS1404, AVE8062A, BAY 43-9006, BMS 275291, CDP-791, Combretastatin, EMD12194 (Cilengitide), EP-7055, G013736, GW786034, IMC-1121B, Marimastat, Matrix metalloproteinase inhibitors, Medi-522, Neovastat, P-547,632, Prinomastat, PTK-787, SU1 1248 (sunitinib), VEGF-Trap, ZD6126, and ZD6474.

In an embodiment of the conjugate of the invention the therapeutically active agent is an anthracycline.

Examples for anthracyclins include but are not limited to Doxorubicin and Valrubicin.

In an embodiment of the conjugate of the invention the therapeutically active agent is an antibiotic.

Examples for antibitotics include but are not limited to Bleomycin, actinomycin D, amsacrine, anthramycin (AMC), Calicheamicin yl, dactinomycin (formerly actinomycin), esperamicin, gramicidin D, mithramycin, mitomycin C, plicamycin, puromycin, neocarcinostatin, Daunorubicin, Epirubicin, and Idarubicin.

In an embodiment of the conjugate of the invention the therapeutically active agent is an antifolate.

Examples for antifolates include but are not limited to Pralatrexate.

In an embodiment of the conjugate of the invention the therapeutically active agent is an antimetabolite.

Examples for antimetabolites include but are not limited to Arabinosylcytosine, Azacitidine, Capecitabine, Cladribine, Cytarabine, Decitabine, Gemcitabine, Leucovorin, Mercaptopurine, Methotrexate, Nelarabine, Pemetrexed, Pentostatin, Procarbazine, Raltitrexed, thioguanine, 5-fluorouracil, decarbazine, 6-mercaptopurine, 6-thioguanin, arabinoside, azathioprine, cytosine, fludarabine, Fluorouracil, Tegafur, and Thioguanine.

In an embodiment of the conjugate of the invention the therapeutically active agent is an anti-mitotic toxin.

Examples for anti-mitotic toxins include but are not limited to abrin A chain, *Aleurites fordii* proteins, alorin, alpha-sarcin, C3 toxin, cholera toxin, crotin, curcin, dianthin proteins, diphtheria toxin, enomycin toxin, gelonin, LT toxin, mitogellin, modeccin, modeccin A chain, *Momordica charantia* inhibitor, pertussis toxin, phenomycin, *Phytolacca americana* proteins (PAPI, PAPII, and PAP-S), *Pseudomonas* endotoxin, *Pseudomonas* exotoxin, restrictocin, ribonuclease (RNase), ricin toxin (such as ricin A or a deglycosylated ricin A chain toxin), *Sapaonaria officinalis* inhibitor, saporin, Shiga toxin, Shiga-like toxin (SLT-I, SLT-II, SLT-IIV), soybean Bowman-Birk protease inhibitor, Staphylococcal enterotoxin-A, and tetanus toxin.

In an embodiment of the conjugate of the invention the therapeutically active agent is a mitotic inhibitor.

Examples for mitotic inhibitors include but are not limited to Docetaxel and Ixabepilone.

In an embodiment of the conjugate of the invention the therapeutically active agent is an anti-proliferative substance.

Examples for anti-proliferative substances include but are not limited to Cecropin.

In an embodiment of the conjugate of the invention the therapeutically active agent is an auristatin.

Auristatins are derivatives of the natural product dolastatin 10. Examples for auristatins include but are not limited to Monomethyl auristatin E and Monomethyl auristatin F.

In an embodiment of the conjugate of the invention the therapeutically active agent is a corticosteroid.

Examples for corticosteroids include but are not limited to Hydrocortisone, cortisone, tixocortol pivalate, prednisolone, methylprednisolone, and prednisone.

In an embodiment of the conjugate of the invention the therapeutically active agent is a duocarmycin.

Examples for duocarmycins include but are not limited to adozelesin, bizelesin, carzelesin, CC-1065, Duocarmycin A, Duocarmycin B1, Duocarmycin B2, Duocarmycin C1, Duocarmycin C2, and Duocarmycin D.

In an embodiment of the conjugate of the invention the therapeutically active agent is a HDAC inhibitor.

Examples for HDAC inhibitors include but are not limited to Vorinostat.

In an embodiment of the conjugate of the invention the therapeutically active agent is a hormone.

Examples for hormones include but are not limited to Goserelin, Leuprolide, 1-dehydrotestosterone, aminoglutethimide, anastrozole, buserelin, cyproterone acetate, flutamide, formestane, fosfestrol (estrogen), leuprorelin, triptorelin, Abiraterone, Degarelix, Bicalutamide, Nilutamide, Exemestane, Letrozole, Tamoxifen, Prednisone, Fulvestrant, and Toremifene.

In an embodiment of the conjugate of the invention the therapeutically active agent is an immunomodulator, a cytokine, an antibody or a signal transducer.

Examples for immunomodulators, cytokines antibodies, and signal transducers include but are not limited to ancestim TNFα, CD40L, Flt3 ligand, G-CSF, GM-CSF, IFNa, IFNb, IFNg, IL-10, IL-12, IL-15, IL-18, IL-2, IL-23, IL24, IL-27, IL-28a, IL-28b, IL-29, IL-4, IL-6, IL-7, KGF, levamisole, Stem cell factor, and Aldesleukin.

In an embodiment of the conjugate of the invention the therapeutically active agent is an immunotoxin.

Examples for immunotoxins include but are not limited to pokeweed antiviral protein.

In an embodiment of the conjugate of the invention the therapeutically active agent is a kinase inhibitor.

Examples for kinase inhibitors include but are not limited to Bortezomib, Crizotinib, Dasatinib, Erlotinib, Gefitinib, Imatinib, Lapatinib, Nilotinib, Temsirolimus, GDC-0068, Cobimetinib, GDC-0973, Pictilisib, GDC-0032, Pazopanib, Sorafenib, Axitinib (Inlyta), and Pazopanib (Votrient).

In an embodiment of the conjugate of the invention the therapeutically active agent is a microtubule inhibitor.

Examples for microtubule inhibitors include but are not limited to Halichondrin b, Epothilone A, Epothilone B, Epothilone D, DJ-927, colchicine, cytochalasin B, Vinblastine, Paclitaxel, podophyllotoxin derivatives, Asammitocin, CLIP, derivatives of paclitaxel, Maytansine, Mertansine, Nocodazole, Rhizoxin, Vinblastine sulfate, dolastatin, vinorelbine, Vincristine, and Vindesine.

In an embodiment of the conjugate of the invention the therapeutically active agent is a monoclonal antibody.

Examples for monoclonal antibodies include but are not limited to Cetuximab, alemtuzumab (MabCampath®), Bevacizumab, Brentuximab vedotin, Gemtuzumab ozogamicin, Ibritumomab, Ofatumumab, Panitumumab, Rituximab, Tositumomab, and Trastuzumab.

In an embodiment of the conjugate of the invention the therapeutically active agent is a cytotoxic or cytostatic substance.

Examples for other cytostatic or cytotoxic substances include but are not limited to Arsenic Trioxide, Asparaginase, Denileukin diftitox, Filgrastim, L-asparaginase, Lenalidomide, Pegaspargase, Pegfilgrastim, dihydroxy anthracin dione, DNase I, ethidium bromide, Magainin 2, P18, pyrrolo[2,1-c][1,4]benzodiazepins, GDC-0199/ABT-199, 5'-deoxy-5-fluorouridine, 9-aminocamptothecin, ametantrone, bendamustine, biolimus A9, calicheamicins, hydroxycarbamide (hydroxyurea), maytansinoids, miltefosine®, mitopodozide, oxazaphosphorine, propranolol, rapamycin (sirolimus), rhodomycin D, topotecan (inhibitor of topoisomerase-I), *vinca* alkaloids, and teniposide.

In an embodiment of the conjugate of the invention the therapeutically active agent is a retinoid.

Examples for retinoids include but are not limited to Bexarotene, Isotretinoin, Tretinoninand Alitretinoin.

In an embodiment of the conjugate of the invention the therapeutically active agent is a taxane.

Examples for taxanes include but are not limited to Cabazitaxel, Paclitaxel, docetaxel, and derivatives thereof.

In an embodiment of the conjugate of the invention the therapeutically active agent is a topoisomerase inhibitor.

Examples for topoisomerase inhibitors include but are not limited to Etoposide, Irinotecan, Mitoxantrone, Topotecan, camptothecin, and Teniposide.

In an embodiment of the conjugate of the invention the therapeutically active agent is a toxin Examples for toxins include but are not limited to mellitin.

In a further embodiment the conjugate of the invention is conjugated to a detectable dye moiety. Detectable dyes may be endogenous fluorophores (Thekkek et al., *World J Gastroenterol*, 2011, 17, 53-62; Paoli et al., *Semin Cutan Med Surg*, 2009, 28, 190-195; Monici, *Biotechnol Annu Rev*, 2005, 11, 227-256; Prosst et al., *Int J Colorectal Dis*, 2002, 17, 1-10), polycyclic aromatics (Vineis et al., *Cancer Causes Control*, 1997, 8, 346-355; Zhang et al., *Cancer Res*, 1994, 54, 1976s-1981s), coumarins (Sakuma et al., *Curr Drug Discov Technol*, 2011, 8, 367-378; Musa et al., *Curr Med Chem*, 2008, 15, 2664-2679), quinolines (Lacroix et al., *Electrophoresis*, 2005, 26, 2608-2621; Bates, *Future Oncol*, 2005, 1, 821-828), indoles (Schaafsma et al., *J Surg Oncol*, 2011, 104, 323-332; Oyama, *Dig Endosc*, 2013, 25 *Suppl* 1, 7-12; Gonzalez, *Gastrointest Endosc Clin N Am*, 2013, 23, 581-595), imidazoles (Cox et al., *Cancer Treat Rev*, 1977, 4, 119-134; Ojima, *Acc Chem Res*, 2008, 41, 108-119), UV-excited fluorophores (Monici, *Biotechnol Annu Rev*, 2005, 11, 227-256; Toms et al., *Technol Cancer Res Treat*, 2006, 5, 231-238), fluoresceins (Fukumura et al., *APMIS*, 2008, 116, 695-715; Haimovitz-Friedman et al., *Radiat Res*, 2012, 177, 467-482; Roberts et al., *JInvest Surg*, 2013, 26, 283-293), rhodamines (Gluckman et al., *Cancer Treat Res*, 1990, 52, 95-113; Kessel, *J Photochem Photobiol B*, 1992, 12, 203-204; Villeneuve, *Biotechnol Appl Biochem*, 1999, 30 (Pt 1), 1-17; Makale, *Methods Enzymol*, 2007, 426, 375-401), naphthoxanthene dyes (Eguchi et al., *J Org Chem*, 1999, 64, 5371-5376; Kudo et al., *J Antibiot (Tokyo)*, 2011, 64, 123-132), phenanthridines (Hoberman, *Cancer Res*, 1975, 35, 3332-3335; Damjanovich et al., *Antibiot Chemother* (1971), 1980, 28, 142-146; Ormerod, *Methods Mol Biol*, 1997, 75, 357-365), BODIPY dyes (Banappagari et al., *Eur J Med Chem*, 2013, 65, 60-69; Yang et al., *Chem Commun (Camb)*, 2013, 49, 3940-3942; Yan et al., *Drug Dev Ind Pharm*, 2014), cyanines (Ballou et al., *Biotechnol Prog*, 1997, 13, 649-658; Choy et al., *Mol Imaging*, 2003, 2, 303-312; Leijon et al., *Mol Aspects Med*, 2006, 27, 160-175), phthalocyanines (Carcenac et al., *Bull Cancer*, 2000, 87, 804-812; Wainwright, *Anticancer Agents Med Chem*, 2008, 8, 280-291; Sekkat et al., *Molecules*, 2012, 17, 98-144), xanthenes (Roberts et al., *J Invest Surg*, 2013, 26, 283-293; Kudo et al., *J Antibiot (Tokyo)*, 2011, 64, 123-132; Paiva et al., *Curr Med Chem*, 2013, 20, 2438-2457), acridines (Dethlefsen et al., *Cytometry*, 1980, 1, 89-108; Sebestik et al., *Curr Protein Pept Sci*, 2007, 8, 471-483), oxazines (Motohashi et al., *Med Res Rev*, 1991, 11, 239-294; Thorlacius et al., *Inflamm Bowel Dis*, 2007, 13, 911-917; Hruban, *J Toxicol Environ Health*, 1979, 5, 403-433), polyenes (Sakuma et al., *Curr Drug Discov Technol*, 2011, 8, 367-378; Regelson, *J Med*, 1974, 5, 50-68), oxonols (Kessel et al., *Cancer Res*, 1991, 51, 4665-4670; Whiteaker et al., *Curr Protoc Pharmacol*, 2001, Chapter 9, Unit 9 2; Saar et al., *Anal Biochem*, 2005, 345, 55-65), benzimidazoles (Nawrocka et al., *Farmaco*, 2004, 59, 83-91; Yang et al., *Eur J Med Chem*, 2009, 44, 1808-1812; Woo et al., *Bioorg Med Chem Lett*, 2012, 22, 933-936), azamethines (Kawakami et al., *J Med Chem*, 1998, 41, 130-142; Xin et al., *Bioconjug Chem*, 2013, 24, 1134-1143), styryls (Ding et al., *Adv Healthc Mater*, 2013, 2, 500-507; Kessel et al., supra), thiazoles (Yung, *Neurosurg Rev*, 1989, 12, 197-203; Jorgensen et al., *Biochem Soc Trans*, 2007, 35, 1347-1351; Smith et al., *Br J Biomed Sci*, 2011, 68, 158-166), anthraquinones (Limtrakul, *Adv Exp Med Biol*, 2007, 595, 269-300; Braumann et al., *Mini Rev Med Chem*, 2008, 8, 421-428), naphthalimides (Lee et al., *J Am Chem Soc*, 2012, 134, 12668-12674; Scutaru et al., *Bioconjug Chem*, 2010, 21, 2222-2226; Seliga et al., *Mol Biol Rep*, 2013, 40, 4129-4137), aza[18]annulenes (Tanpure et al., *Bioorg Med Chem*, 2013, 21, 8019-8032; Zhang, *Molecular Imaging and Contrast Agent Database (MICAD)*, 2004), porphins (Berg et al., *Biochim Biophys Acta*, 1993, 1158, 300-306; Malik et al., *Photochem Photobiol*, 1997, 65, 389-396; Takemura et al., *Photochem Photobiol*, 1994, 59, 366-370), metal-ligand-complexes (Brancaleon et al., *Lasers Med Sci*, 2002, 17, 173-186; Gupta et al., *Nat Prod Rep*, 2011, 28, 1937-1955; Munaron et al., *Technol Cancer Res Treat*, 2008, 7, 335-339), squaraines (Avirah et al., *Org Biomol Chem*, 2012, 10, 911-920; Gao et al., *Biomaterials*, 2014, 35, 1004-1014; Gayathri Devi et al., *JPhotochem Photobiol B*, 2008, 92, 153-159), 8-Hydroxyquinoline-Derivatives (Lin et al., *Photochem Photobiol*, 1995, 62, 528-534), polymethins (James et al., *Theranostics*, 2013, 3, 692-702; James et al., *Theranostics*, 2013, 3, 703-718; Toutchkine et al., *Org Lett*, 2007, 9, 2775-2777), nanocrystals (Young et al., *Ann Biomed Eng*, 2012, 40, 438-459; Cheng et al., *Curr Med Chem*, 2012, 19, 4767-4785; Arap et al., *Curr Med Chem*, 2013, 20, 2195-2211), fluorescent proteins (Weiss et al., *Theranostics*, 2013, 3, 76-84; Weigert et al., *J Cell Biol*, 2013, 201, 969-979; Wang et al., *J Mol Med (Berl)*, 2013, 91, 917-927), proteins (Fukase et al., *Curr Opin Chem Biol*, 2012, 16, 614-621; Hoffman, *Prog Mol Biol Transl Sci*, 2013, 113, 389-402; Gandia-Herrero et al., *Trends Plant Sci*, 2013, 18, 334-343), perylenes (Saw et al., *Cancer Lett*, 2006, 241, 23-30; Schmidbauer et al., *Curr Opin Urol*, 2007, 17, 347-351), phthalocyanines (Carcenac et al., *Bull Cancer*, 2000, 87, 804-812; van Lier et al., *Ciba Found Symp*, 1989, 146, 17-26; discussion 26-32; Selbo et al., *Tumour Biol*, 2002, 23, 103-112; Jia et al., *Curr Drug Metab*, 2012, 13, 1119-1122), upconversion dyes (Xu et al., *Biomaterials*, 2011, 32, 9364-9373; Jiang et al., *J R Soc Interface*, 2010, 7, 3-18; Wang et al., *Analyst*, 2010, 135, 1839-1854), and diketopyrolopyroles (Shinohara et al., *Anticancer Drugs*, 2010, 21, 228-242; Dervan et al., *Curr Opin Struct Biol*, 2003, 13, 284-299; Bailly, *Curr Med Chem Anticancer Agents*, 2004, 4, 363-378).

Furthermore, such substances may also be photosensitizers or sensitizers or amplifiers of other combined conventional cancer treatment methods or contain such sensitizers.

Examples for detectable dyes include but are not limited to (CS)2Ir(μ-Cl)2Ir(CS)2, (E)-Stilbene, (Z)-Stilbene, 1,1-Diethyl-4,4-carbocyanine iodide, 1,2-Diphenylacetylene, 1,4-Diphenylbutadiene, 1,6-Diphenylhexatriene, 1-anilinonaphthalene-8-sulfonic acid, 1-Chloro-9,10-bis(phenylethynyl)anthracene, 2,7-Dichlorofluorescein, 2,3-Diaminonaphthalene, 2,5-DIPHENYLOXAZOLE, 2-Chloro-9,10-bis(phenylethynyl)anthracene, 2-Chloro-9,10-diphenylanthracene, 2-Di-1-ASP, 2-dodecylresorufin, 2-Methylbenzoxazole, 3,3-Diethylthiadicarbocyanine iodide, 4-Dimethylamino phenylazophenyl, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluoresceine, 5-(N-hexadecanoyl)aminoeosin, 5,12-Bis(phenylethynyl)naphthacene, 5-chloromethylfluorescein, 5-FAM, 5-ROX, 5-TAMRA, 6,8-difluoro-7-hydroxy-4-methylcoumarin,
6-carboxyrhodamine 6G, 6-HEX, 6-JOE, 6-JOE, 6-TET, 7-AAD, 7-Aminoactinomycin D, 7-Benzylamino-4-Nitrobenz-2-Oxa-1,3-Diazole, 7-Methoxycoumarin-4-Acetic Acid, 8-Anilinonaphthalene-1-sulfonic acid, 8-Benzyloxy-5,7-diphenylquinoline, 9,10-Bis(Phenylethynyl)Anthracene, 9,10-Diphenylanthracene, 9-METHYLCARBA- ZOLE, AAA, Abberior STAR 440SX, Abberior STAR 470SX, Abberior STAR 488, Abberior STAR 512, Abberior STAR 580, Abberior STAR 635, Abberior STAR 635P, AcGFP1, Acridine orange, Acridine Orange, Acridine yellow, Acridone, Adams Apple Red 680, Adirondack Green 520, Alexa Fluor 350, Alexa Fluor 405, Alexa Fluor 430, Alexa Fluor 480, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 610-R-PE, Alexa Fluor 633, Alexa Fluor 635, Alexa Fluor 647, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin (APC), AMCA, AMCA-X, AMCA-X, AmCyan1, Aminocoumarin, Aminomethylcoumarin, Amplex Gold (product), Amplex Red Reagent, Amplex UltraRed, Anilinonaphthalene, Anthracene, APC-Cy7 conjugates, APC-Seta-750, AsRed2, Atto 390, Atto 425, ATTO 430LS, Atto 465, Atto 488, ATTO 490LS, Atto 495, Atto 514, Atto 520, Atto 532, Atto 540Q, Atto 550, Atto 565, Atto 580Q, Atto 590, Atto 594, Atto 610, Atto 612Q, Atto 620, Atto 633, ATTO 635, Atto 647, ATTO 647, ATTO 647N, Atto 647-N, Atto 655, Atto 665, Atto 680, Atto 700, Atto 725, Atto 740, Atto MB2, Atto Oxa12, Atto Rho101, Atto Rho11, Atto Rho12, Atto Rho13, Atto Rho14, Atto Rho3B, Atto Rho6G, Atto Thio12, Auramine O, Auramine-rhodamine stain, Azami Green, Azurite, BBQ 650, BCECF, Benzanthrone, Benzene, Benzophenone, Bexl, BHQ-0, BHQ-1, BHQ-2, BHQ-3, Bimane, Biphenyl, Birch Yellow 580, Bisbenzimide, Blacklight paint, BOBO-1, BOBO-3, BODIPY 493/503, BODIPY 499/508, BODIPY 507/545, BODIPY 530/550, BODIPY 558/568, BODIPY 564/570, BODIPY 576/589, BODIPY 577/618, BODIPY 581/591, BODIPY 630 650-X, BODIPY 630/650, BODIPY 630/650-X †, BODIPY 650/655-X †, BODIPY 650/665-X, BODIPY FL, BODIPY R6G, BODIPY TMR, BODIPY TMR-X, BODIPY TR, BODIPY TR-X, BODIPY TR-X Ph 7.0, BODIPY TR-X phallacidin, BODIPY-DiMe, BODIPY-Phenyl, BODIPY-TMSCC, BO-PRO-1, BO-PRO-3, B-phycoerythrin (BPE), Brainbow, C3-Indocyanine, C3-Oxacyanine, C3-Thiacyanine Dye (EtOH), C3-Thiacyanine Dye (PrOH), C545T, C5-Indocyanine, C5-Oxacyanine, C5-Thiacyanine, C7-Indocyanine, C7-Oxacyanine, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxyfluorescein, Carboxyfluorescein diacetate succinimidyl ester, Carboxyfluorescein succinimidyl ester, Carboxynaphthofluorescein, Carboxyrhodamine 6G, 5-isomer, Carboxy-rhodamine 6G, 6-isomer, Carboxy-X-rhodamine, 5-isomer, Carboxy-X-rhodamine, 6-isomer, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, Cerulean, CF405M, CF405S, CF488A, CF543, CF555, CFP (Campbell Tsien 2003), CFSE, CF™ 350, Chlorophyll A, Chlorophyll B, CHOxAsH-CCXXCC, Chromeo 488, Chromeo 494, Chromeo 505, Chromeo 546, Chromeo 642, Chromomycin A3, Chromomycin A3, Citrine, CM-H2DCFDA, Coumarin, Coumarin 1, Coumarin 30, Coumarin 314, Coumarin 334, Coumarin 343, Coumarin 6, Coumarine 545T, C-Phycocyanin, Cresyl Violet Perchlorate, CryptoLight CF1, CryptoLight CF2, CryptoLight CF3, CryptoLight CF4, CryptoLight CF5, CryptoLight CF6, Crystal Violet, Cumarin 1, Cumarin 102, Cumarin 120, Cumarin 152, Cumarin 153, Cumarin 307, Cumarin 6, Cumarin 153, Cy2, Cy3, Cy3, Cy3.5, Cy3B, Cy3Cy5 ET, Cy5, Cy5.5, Cy5.5® Amidite, Cy5.5® NHS, Cy7, Cy7® NHS, Cyanine5 carboxylic acid, CyPet, CypHer5, CypHer5 pH 9.15, CyQUANT GR, CyTRAK Orange, CyTrak Orange, Dabcyl, Dabcyl SE, DAF-FM, DAMC (Weiss), D-AMCA, Dansyl, dansyl cadaverine, Dansyl Glycine (Dioxane), Dansyl-X, DAPI, Dapoxyl, Dapoxyl (2-aminoethyl) sulfonamide, Dark quencher, DCFH, DCI, DCM, DDAO, Deep Purple, DHR, DHR, di-8-ANEPPS, DiA, Dialkylaminocoumarin, Dibromobimane, Dichlorotris(1,10-phenanthroline)ruthenium(II) chloride, DiD, Diethylaminocoumarin, DiI, DiIC18(3), Dimethoxybenzene, Dimethylaminocoumarin, Dimethylaminonaphthalene, DiO, DiOC6, DiR, *Diversa* Cyan-FP, *Diversa* Green-FP, dKeima-Red, DM-NERF pH 4.0, DNP-biotin, DOCI, Doxorubicin, DPP pH-Probe 590-11.0, DPP pH-Probe 590-7.5, DPP pH-Probe 590-9.0, Dragon Green, DRAQ5, DRAQ7, Dronpa-Green, DsRed monomer, DsRed2 ("RFP"), DsRed-Express, DsRed-Express T1, DsRed-Express2, dTomato, Dy 350, Dy 405, Dy 415, Dy 480 XL, Dy 481 XL, Dy 485 XL, Dy 490, Dy 495, Dy 505, Dy 505-X, Dy 510 XL, Dy 520 XL, Dy 521 XL, Dy 530, Dy 547, Dy 548, Dy 549, Dy 549P1, Dy 550, Dy 554, Dy 555, Dy 556, Dy 560, Dy 590, Dy 591, Dy 594, Dy 605, Dy 610, Dy 615, Dy 630, Dy 631, Dy 632, Dy 633, Dy 634, Dy 635, Dy 636, Dy 647, Dy 648, Dy 649, Dy 649P1, Dy 650, Dy 651, Dy 652, Dy 654, Dy 675, Dy 676, Dy 677, Dy 678, Dy 679, Dy 679P1, Dy 680, Dy 681, Dy 682, Dy 700, Dy 701, Dy 703, Dy 704, Dy 730, Dy 731, Dy 732, Dy 734, Dy 749P1, Dy 750, Dy 751, Dy 752, Dy 754, Dy 776, Dy 777, Dy 778, Dy 780, Dy 781, Dy 782, Dy 831, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-590, DY-590, DY-615, DY-630, DY-631, DY-633, DY-635, DY-636, DY-647, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-1041, Dye-28, Dye-304, Dye-33, Dye-45, DyLight 350, DyLight 405, DyLight 488, DyLight 549, DyLight 594, DyLight 633, DyLight 649, DyLight 680, DyLight 750, DyLight 800, DyLight Fluor, DyQ 1, DyQ 2, DyQ 3, DyQ 4, DyQ 425, DyQ 505, DyQ 660, DyQ 661, DyQ 700, E2-Crimson, E2-Orange, E2-Red/Green, EBFP, EBFP2, ECF, ECFP, ECL Plus, EGFP, eGFP (Tsien), ELF 97, Emerald, Entacmaea quadricolor red fluorescent pr . . . , Envy Green, Eosin, Eosin Y, Epicocconone, EqFP611, ER-Tracke Blue-White DPX, Erythrosin-5-isothiocyanate, Etemeon™ 350/430, Eterneon™ 350/455, Eterneon™ 384/480, Eterneon™ 393/523, Eterneon™ 394/507, Eterneon™ 480/635, Ethidium Bromide, ethidium homodimer-1, Ethyl Eosin, Ethyl Nile Blue A, Ethyl-p-Dimethylaminobenzoate, Eu (Soini), Eu(tta) 3DEADIT, Eu2O3 nanoparticles, EvaGreen, EVOblue-30, EVOblue™ 30, EYFP, EYFP, EYFP, FAD, FAM, 5-isomer, FAM, 6-isomer, FITC, FlAsH (Adams), Flash Red EX, F1AsH-CCPGCC, F1AsH-CCXXCC, F1AsH-EDT2, Fluo-3, Fluo-3, Fluo-4, Fluo-5F, FluoProbes, Fluorescein, Fluorescein isothiocyanate, Fluorescein-5-EX, Fluorescein-Dibase, Fluorescein-EX, Fluorescence image-guided surgery, fluoro-emerald, Fluoro-Jade stain, Fluorol 5G, FluorX, FluoSpheres blue, FluoSpheres crimson, FluoSpheres dark red, FluoSpheres orange, FluoSpheres red, FluoSpheres yellow-green, FM 1-43, FM 4-64, FM4-64 in CTC, FM4-64 in SDS, Fort Orange 600, Fura Red, Fura Red Ca free, Fura-2, Fura-2 Ca free, Fura-2-acetoxymethyl ester, GelGreen, GelRed, GFPuv, Green fluorescent protein, H9-40, HcRed1, HCS CellMask Red, HCS LipidTOX Deep Red, HCS LipidTOX Green neutral lipid stain, HCS Lipid- TOX Green phospholipidosis dete . . . , HCS LipidTOX Red neutral lipid stain, HCS LipidTOX Red phospholipidosis detect . . . , Hemo Red 720, Heptamethine dyes, Heteractis magnifica GFP, HEX, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hops Yellow 560, HPTS, Hydroxycoumarin, HyPer, IBApy 493/503, IBApy 530/550, IBApy FL, IBApy R6G, IBApyTMR-X, Iminocoumarin, Indian yellow, Indo-1, Indo-1 Ca free, Ir(Cn) 2(acac), IR-775 chloride, IR-806, IRDye® 700 phosphoramidite, IRDye® 700DX, IRDye® 800 phosphoramidite, IRDye® 800CW, IRDye® 800RS, Ir-OEP-CO-Cl, JC-1, JOE (520/548), JOE, 6-isomer, JOJO-1, Jonamac Red Evitag T2, J-Red, Kaede Green, Kaede Red, Katusha, Kusabira Orange, Lake Placid 490, Laurdan, LDS 751, Lissamine Rhodamine B, LIVE DEAD Fixable Aqua Dead Cell Stain, LIVE DEAD Fixable Far Red Dead Cell Stain, LIVE DEAD Fixable Green Dead Cell Stain, LIVE DEAD Fixable Near-IR Dead Cell Stain, LIVE DEAD Fixable Red Dead Cell Stain, LIVE DEAD Fixable Violet Dead Cell Stainn, LIVE-DEAD Fixable Blue Dead Cell Stain, LOLO-1, Lucifer yellow, lucifer yellow CH, Lucifer Yellow CH Dilitium salt, Luciferin, Lumio Green, Lumio Red, Lumogen F Orange, Lumogen Red F300, LysoSensor Blue DND-192, LysoSensor Green DND-153, LysoSensor YellowBlue DND-160, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Magnesium Green, Magnesium Octaethylporphyrin, Magnesium Orange, Magnesium Phthalocyanine, Magnesium Tetramesitylporphyrin, Malachite green, malachite green isothiocyanate, Maple Red-Orange 620, Marina Blue, mBanana, mBBr, mCFP, MCherry, mCitrine, Merocyanine, Merocyanine 540, Methoxycoumarin, Methylene Blue, mHoneyDew, Midoriishi Cyan, Mithramycin, MitoTracker Deep Red 633, MitoTracker Green FM, MitoTracker Orange CMTMRos, MitoTracker Red CMXRos, mKate (TagFP635), mKate2, mKeima-Red, mKO, mNeptune, Monobromobimane, mOrange, mOrange2, mOrange2, mPlum, mRaspberry, mRFP, mRFP1, mStrawberry, mTangerine (Shaner), mTFPI, N,N-Bis(2,4,6-trimethylphenyl)-3,4:9,10- . . . , NADH, Naphthalene, Naphthofluorescein, NBD, NBD-X, NeuroTrace 500525, Nilblau perchlorate, Nile blue, Nileblue A, NIR1, NIR2, NIR3, NIR4, NIR820, Octaethylporphyrin, Optical brightener, Orange Fluorescent Protein, Oregon Green 488, Oregon Green 488 DHPE, Oregon Green 514, Oxazin 750, Oxazinl, Oxazine 170, Oyster 488, Oyster 550, Oyster 555, Oyster 647, Oyster 650, Oyster 680, Oyster® 405, Oyster® 568, Oyster® 594, Oyster@ 750, P3, P4-3, Pacific Blue, Pacific Orange, PA-GFP (post-activation), PA-GFP (pre-activation), Palladium(II) meso-tetraphenyl-tetrabenz . . . , PdOEPK, PdTFPP, PE-Cy5 conjugates, PE-Cy7 conjugates, PerCP, PerCP-Cy5.5, Peridinin Chlorophyll (PerCP), Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenanthroline, Phenol, Phenylalanine, PhiYFP, PhiYFP-m, Phloxine, pHrodo Green, pHrodo Red, pHrodo, succinimidyl ester, Phthalocyanine, Phycobilin, Phycoerythrin, Phycoerythrobilin, PicoGreen dsDNA quantitation reagent, Pinacyanol-lodide, Piroxicam, Platinum(II) tetraphenyltetrabenzoporphyrine, Plum Purple, Pontamine fast scarlet 4B, POPO-1, POPO-3, POPOP, PO-PRO-1, PO-PRO-3, Porphin, PPO, P-Quaterphenyl, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, Propidium iodide, propidium iodide, Propidium Iodide (PI), Pro-Q Diamond, Pro-Q Diamond phosphoprotein gel stain, Pro-Q Emerald, Pro-Q Emerald 300 reagent, Protoporphyrin IX, P-Terphenyl, PTIR475/UF, PtOEP, PtOEPK, PtTFPP, PyMPO, Pyranine, Pyrene, QD PbS 950, QD525, QD565, QD585, QD605, QD655, QD705, QD800, QD903, QDot 525, QDot 545, QDot 565, Qdot 585, Qdot 605, Qdot 625, Qdot 655, Qdot 705, Qdot 800, QpyMe2, QSY 21, QSY 35, QSY 7, QSY 9, QSY 9, Quasar 570, Quasar 670, quinine, Quinine sulfate, ReAsH-CCPGCC, ReAsH-CCXXCC, Red 613, Red Beads (Weiss), Redmond Red, Resorufin, rhod-2, Rhodamin 700 perchlorate, rhodamine, rhodamine (TMR), Rhodamine 101, rhodamine 110, Rhodamine 110X, Rhodamine 123, Rhodamine 6G, Rhodamine B, Rhodamine Green (502/527), Rhodamine phalloidin, Rhodamine pH-Probe 585-7.0, Rhodamine pH-Probe 585-7.5, Rhodamine Red, Rhodamine Red-X (580/590), Rhodamine Tag pH-Probe 585-7.0, Rhodol Green, Riboflavin, RiboGreen, RoGFP, Rose Bengal, R-Phycoerythrin (PE), R-phycoerythrin (RPE), Rubrene, S65A, S65C, S65L, S65T, Sapphire, SBFI, SBFI Zero Na, SensiLight PBXL-1, SensiLight PBXL-3, Seta 633-NHS, SeTau-380-NHS, SeTau-647, Snake-Eye Red 900, SNARF, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains A11, Stilben derivate, Stilbene, Styryl8 perchlorate, Sulfonerhodamine, Sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYBR safe, SYBR Safe DNA gel stain, Synapto-pHluorin, SYPRO Ruby, SYTO 11, SYTO 13, SYTO 16, SYTO 17, SYTO 45, SYTO 59, SYTO 60, SYTO 61, SYTO 62, SYTO 82, SYTO 9, SYTO RNASelect, SYTOX Blue, SYTOX Green, SYTOX Orange, SYTOX Red, TagBFP, TagCFP, TagGFP, TagGFP2, TagRFP, TagYFP, TAMRA, 5-isomer, TAMRA, 6-isomer, Tb (Soini), tCO, tdTomato, Terrylen, Terrylendiimid, testdye, TET, Tetracen, Tetrakis(o-Aminophenyl)Porphyrin, Tetramesitylporphyrin, Tetramethylrhodamine, Tetraphenyl butadiene, Tetraphenylporphyrin, Tetrasodium tris(bathophenanthroline disulfonate)ruthenium(II), Tetra-t-Butylazaporphine, Tetra-t-Butylnaphthalocyanine, Texas Red, Texas Red DHPE, Texas Red-X, Thiazole Orange, Thiol-Tracker Violet, Thionin acetate, Titan yellow, TMRE, Toluene, Topaz, Topaz (Tsien1998), TO-PRO: Cyanine Monomer, TO-PRO-1, TO-PRO-3, TOTO-1, TO-PRO-1, TOTO-1, TO-PRO-1, TOTO-3, TO-PRO-3, TOTO-3, TO-PRO-3, Tris(2,2-Bipyridyl)Ruthenium(II) chloride, Tris(4,4-diphenyl-2,2-bipyridine)ruthenium(II) chloride, Tris(4,7-diphenyl-1,10-phenanthroline)ruthenium(II) chloride, TRITC, TruRed, Tryptophan, T-Sapphire, TSQ, TurboFP602, TurboFP635, TurboGFP, TurboRFP, TurboYFP, Tyrosine, Umbelliferone, Venus, Vexl, Violanthrone, Vybrant DyeCycle Green stain, Vybrant DyeCycle Orange stain, Vybrant DyeCycle Violet stain, WEGFP (post-activation), WellRED D2, WellRED D3, WellRED D4, Wild Type GFP, X-rhod-1, X-rhodamine, Y66F, Y66H, Y66W, Yakima Yellow, Yellow fluorescent protein, YFP, YO-PRO-1, YO-PRO-3, YOYO-1, YOYO-3, YPet, Zinc Octaethylporphyrin, Zinc Phthalocyanine, Zinc Tetramesitylporphyrin, ZsGreen1, and ZsYellow1.

In an embodiment of the conjugate of the invention the therapeutically active agent is a xanthene.

Examples for xanthene dyes include but are not limited to 5(6)-Carboxynaphtofluorescein, 5-(N-hexadecanoyl)aminoeosin, 5-(N-hexadecanoyl)aminoeosin, Eosin Y, Fluorescein, Fluorescein, Fluorescein-Dibase, Fluorol 5G, Naphthofluorescein, Naphthofluorescein, Rhodamine 6G, Rhodamine 123, Rhodamine B, Rhodamine pH-Probe 585-7.0, Rhodamine pH-Probe 585-7.5, Rhodamine Tag pH-Probe 585-7.0, Rose Bengal, and Sulforhodamine 101.

In an embodiment of the conjugate of the invention the therapeutically active agent is an acridine.

Examples for acridine dyes include but are not limited to Acridine Orange, Acridine Yellow, DDAO, and Proflavin.

In an embodiment of the conjugate of the invention the therapeutically active agent is an oxazine.

Examples for oxazine dyes include but are not limited to Cresyl Violet Perchlorate, Nile Blue, Nile Blue (EtOH), Nile Red, Oxazinl, Oxazin 750, and Oxazine 1.

In an embodiment of the conjugate of the invention the therapeutically active agent is a cyanine.

Examples for cyanine dyes include but are not limited to 1,1-Diethyl-4,4-carbocyanine iodide, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CBQCA, Cy2, Cy3, Cy3.5, Cy3B, Cy3Cy5 ET, Cy5, Cy5.5, Cy7, Cyanine5 carboxylic acid, CypHer5, Dye-33, Dye-304, Dye-1041, ECF, ECL Plus, IR-775 chloride, IR-806, IRDye® 700 phosphoramidite, IRDye® 800 phosphoramidite, IRDye® 800CW, IRDye® 800RS, Merocyanine 540, NIR1, NIR2, NIR3, NIR4, NIR820, Pinacyanol-Iodide, SNIR1, SNIR2, SNIR4, and Stains A11.

In an embodiment of the conjugate of the invention the therapeutically active agent is a styryl.

Examples for styryl dyes include but are not limited to Dye-28 and Dye-45.

In an embodiment of the conjugate of the invention the therapeutically active agent is a coumarin.

Examples for coumarin dyes include but are not limited to 7-Methoxycoumarin-4-Acetic Acid, Alexa Fluor 350, C545T, Coumarin 1, Coumarin 6, Coumarin 6, Coumarin 30, Coumarin 314, Coumarin 334, Coumarin 343, Coumarine 545T, Cumarin153, Macrolex Fluorescence Red G, and Macrolex Fluorescence Yellow 10GN.

In an embodiment of the conjugate of the invention the therapeutically active agent is a naphthalimide.

Examples for naphthalimide dyes include but are not limited to naphthalene.

In an embodiment of the conjugate of the invention the therapeutically active agent is a porphin.

Examples for porphin dyes include but are not limited to Chlorophyll A and Chlorophyll B.

In an embodiment of the conjugate of the invention the therapeutically active agent is a metal-ligand complex.

Examples for metal-ligand complex dyes include but are not limited to (CS)2Ir(μ-Cl)2Ir(CS)2, Eu(tta)3DEADIT, Ir(Cn)2(acac), Ir(Cs)2(acac), Ir-OEP—CO—Cl, Palladium (II) meso-tetraphenyl-tetrabenzoporphyrin, PdOEPK, Platinum(II) tetraphenyltetrabenzoporphyrin, PtOEP, PtOEPK, and Tris(2,2-Bipyridyl)Ruthenium(II) chloride.

In an embodiment of the conjugate of the invention the therapeutically active agent is a squaraine.

Examples for squaraine dyes include but are not limited to Seta 633-NHS, Seta-633-NHS, and SeTau-647-NHS.

In an embodiment of the conjugate of the invention the therapeutically active agent is a polymethin.

Examples for polymethin dyes include but are not limited to DY-350XL.

In an embodiment of the conjugate of the invention the therapeutically active agent is a nanocrystal.

Examples for nanocrystal dyes include but are not limited to Adams Apple Red 680, Adirondack Green 520, Birch Yellow 580, Catskill Green 540, Fort Orange 600, Hemo Red 720, Lake Placid 490, Maple Red-Orange 620, QD525, QD565, QD585, QD605, QD655, QD705, QD800, and Snake-Eye Red 900.

In an embodiment of the conjugate of the invention the therapeutically active agent is a fluorescent protein.

Examples for fluorescent proteins include but are not limited to Allophycocyanin, AmCyanl, APC, APC-Seta-750, AsRed2, Azami Green, Azami Green monomeric, Bexl, C-Phycocyanin, CFP (Campbell Tsien 2003), Citrine (Campbell Tsien 2003), CryptoLight CF1, CryptoLight CF2, CryptoLight CF3, CryptoLight CF5, CryptoLight CF6, DsRed, DsRed, DsRed-Express T1, EBFP (Patterson 2001), EGFP (Campbell Tsien 2003), EGFP (Patterson 2001), Kaede Green, mBanana, mCherry, mHoneyDew, mOrange, mPlum, mRaspberry, mRFP1.2 (Wang), mStrawberry (Shaner), mTangerine (Shaner), PA-GFP (post-activation), PA-GFP (pre-activation), R-phycoerythrin, SensiLight PBXL-1, SensiLight PBXL-3, SuperGlo BFP, SuperGlo GFP, Vexl, and WEGFP (post-activation).

In an embodiment of the conjugate of the invention the therapeutically active agent is a perylene.

Examples for perylene dyes include but are not limited to Lumogen F Orange, Lumogen Red F300, Lumogen Red F300, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, and Perylne Green pH-Probe 740-5.5.

In an embodiment of the conjugate of the invention the therapeutically active agent is a phthalocyanine.

Examples for phthalocyanine dyes include but are not limited to IRDye® 700DX.

In an embodiment of the conjugate of the invention the therapeutically active agent is a diketopyrolopyrole.

Examples for diketopyrolopyrols dyes include but are not limited to DPP pH-Probe 590-7.5, DPP pH-Probe 590-9.0, and DPP pH-Probe 590-11.0.

In a further embodiment the conjugate of the invention is conjugated to a photosensitizer moiety (Allison et al., *Photodiagnosis and Photodynamic Therapy,* 2004, 1, 27-42). Photosensitizer moieties may be molecules of the porphyrin family, including but not limited to hematoporphyrin derivatives and molecules based on hematoporphyrin derivatives (Mironov et al., *J Photochem Photobiol B,* 1990, 4, 297-306; Bonnett et al., *Adv Exp Med Biol,* 1983, 160, 241-250; Dougherty, *Photochem Photobiol,* 1987, 46, 569-573), benzoporphyrin derivatives (Levy, *Semin Oncol,* 1994, 21, 4-10; Richter et al., *J Natl Cancer Inst,* 1987, 79, 1327-1332), 5-aminolevulinic acid (Loh et al., *Br J Cancer,* 1993, 68, 41-51; Peng et al., *Photochem Photobiol,* 1997, 65, 235-251), and texaphyrins (Sessler et al., *Biochem Pharmacol,* 2000, 59, 733-739; Young et al., *Photochem Photobiol,* 1996, 63, 892-897); molecules of the chlorophyll family, including but not limited to chlorins (Berenbaum et al., *Lasers in Medical Science,* 1993, 8, 235-243; Glanzmann et al., *Photochem Photobiol*, 1998, 67, 596-602), purpurins (Mang et al., *Cancer J Sci Am*, 1998, 4, 378-384; Kaplan et al., *J Surg Oncol*, 1998, 67, 121-125), and bacteriochlorins (Moser, *SPIE Conf Proc*, 1993, 1881, 116-125); and dyes, including but not limited to phtalocyanine and naphthalocyanine (Ben-Hur et al., *Int J Radiat Biol Relat Stud Phys Chem Med*, 1985, 47, 145-147).

Examples of photosensitizers include but are not limited to Allumera, Aminolevulinic acid, Amphinex, Antrin, Azadipyrromethenes, BF-200 ALA, BODIPY, Cevira, Cysview, Foscan, Hexvix, Laserphyrin, Litx, Levulan, LS11, Lumacan, Lutrin, Metvix, Metvixia, mono-L-aspartyl chlorin e6 (NPe6), Optrin, Photochlor, Photofrin, Photosens, Photosens, Photosens, Photrex, Psoralen, Purlytin, Silicon Phthalocyanine Pc 4, Stakel, Temoporfin, Tookad, Visonac, Visudine, and Visudyne.

In a further embodiment the conjugate of the invention is conjugated to an MRI contrast moiety. MRI contrast moieties may be small mononuclear or polynuclear paramagnetic chelates, metalloporphyrins, polymeric or macromolecular carriers (covalently or noncovalently labeled with paramagnetic chelates), particulate CAs (including fluorinated or nonfluorinated paramagnetic micelles or liposomes) and paramagnetic or superparamagnetic particles (e.g. iron oxides, Gd3+-labeled zeolites), diamagnetic CEST polymers; diamagnetic hyperpolarization probes (gases and aerosols), and 13C-labeled compounds or ions (e.g. 6Li$^+$) (Zhang, *Molecular Imaging and Contrast Agent Database (MICAD)*, 2004; Vithanarachchi et al., *Curr Mol Imaging*, 2012, 1, 12-25; Tòth et al., *Contrast Agents I*, 2002, 221, 61-101; Muller et al., *Advances in Inorganic Chemistry*, 2005, Volume 57, 239-292; Laurent et al., *Contrast Media Mol Imaging*, 2006, 1, 128-137; Jacques et al., *Contrast Agents I*, 2002, 221, 123-164; Geraldes et al., *Contrast Media Mol Imaging*, 2009, 4, 1-23; Choy et al., *Mol Imaging*, 2003, 2, 303-312; Chan et al., *Coordination Chemistry Reviews*, 2007, 251, 2428-2451; Caravan et al., *Chem Rev*, 1999, 99, 2293-2352; Aime et al., *Coordination Chemistry Reviews*, 2006, 250, 1562-1579; Aime et al., *Advances in Inorganic Chemistry*, 2005, Volume 57, 173-237).

Examples of MRI contrast moieties include but are not limited to B-19036, B22956, Chromium Labeled Red Blood Cells, Clariscan™, CMC 001, Code 7228, Cr-HIDA, DAB-Am64-(1B4M-Gd)64, Dyamide, Dy-DOTA-4AmCE, Dy-tetraphenyl-porphyrin Sulfonate, ECIII-60, ECIV-7, EP-2104R, Fe O-BPA, Fe-EHPD, Fe-EHPG (Iron(III)), Fe-HBED, Feridex I.V., Ferric Ammonium Citrate, Ferrioxamine, Ferristene, Ferrixan, Ferumoxide, Ferumoxsil, Ferumoxtran, Gadobenate Dimeglumine, Gadobutrol, Gadodiamide, Gadofluorine, Gadolinium Zeolite, Gadomer 17, Gadomer-17, Gadopentetate Dimeglumine, Gadopentetate Gastrointestinal, Gadoterate Meglumine, Gadoteridol, Gadoversetamide, gadoxetate disodium, Gadoxetic Acid, Gd Labeled Albumin, Gd-2,5-BPA-DO3A, Gd-DTPA, Gd-DTPA labeled albumin, Gd-DTPA Labeled Dextran, Gd-DTPA labeled dextran, Gd-DTPA Mesoporphyrin, Gd-DTPA-PEG, Gd-DTPA-Polylysine, Gd-tetraphenyl-porphyrin Sulfonate, GN-1140, Gold nanoparticles, H$_8$OHEC, iopromide, Liposomes, Ln-PK-11195, Magnetic Starch Microspheres, Mangafodipir Trisodium, Manganese Chloride, Manganese Hydroxylapatite, Metallofullerenes, Metalloporphyrins, Mn(III)TPPS4, Mn(III)TPPS4 (manganese (III) tetra-[4-sulfanatophenyl]porphyrin), Monocrystalline Iron Oxide Nanoparticle, MP 2269, MS-325, MS-325, NanoglobularMRI CAs (G3), Nanoparticle, NC100150 Injection, Nitroxides, Oral Magnetic Particles, P717, P760, P792, PAMAM-G4, PEG-feron, Perfluorochemicals, perfluorooctyl bromide, Polycrystalline Iron Oxide Nanoparticles, ProCA1, ProCA1.affi, ProCA1.GRP, Resovist, SHU 555 C, Sinerem, Superparamagnetic iron oxide nanoparticles (SPION), Ventilation Agents, VSOP-C184, and WIN 22181.

In a further embodiment the conjugate of the invention is conjugated to a moiety enhancing ultrasound contrast. Moieties enhancing ultrasound contrast comprise a shell and a core. The shell may consist of a material selected from the group comprising but not limited to phospholipids (Cassano et al., *Cancer Imaging*, 2006, 6, 4-6; Jaquotot-Herranz et al., *Rev Esp Enferm Dig*, 2012, 104, 279-280; Kuenen et al., *Ultrasound Med Biol*, 2013, 39, 1631-1641), poly-[D,L-lactide-co-glycolide] acid (PLGA) (Huang et al., *Biomaterials*, 2010, 31, 1278-1286; Sun et al., *Biomaterials*, 2012, 33, 5854-5864; Xu et al., *J Biomed Opt*, 2009, 14, 034020), serum albumin (Li et al., *BJU Int*, 2009, 104, 1063-1067; Lin et al., *J Clin Gastroenterol*, 1991, 13, 108-110), polymers (Eggen et al., *J Control Release*, 2014; Ninomiya et al., *Ultrason Sonochem*, 2014, 21, 1482-1488; Suzuki et al., *J Control Release*, 2009, 133, 198-205), perflutren (Barua et al., *J Ultrasound Med*, 2011, 30, 333-345; McCarville et al., *Pediatr Radiol*, 2012, 42, 824-833; Schmillevitch et al., *Arq Gastroenterol*, 2011, 48, 119-123), carbon-based phase shift colloid (Kripfgans et al., *Ultrasound Med Biol*, 2000, 26, 1177-1189; Zhang et al., *Ultrasound Med Biol*, 2010, 36, 1856-1866; Kopechek et al., *J Healthc Eng*, 2013, 4, 109-126), perflexane (Mattrey et al., *Acad Radiol*, 2002, 9 Suppl 1, S231-235; Kono et al., *J Vasc Interv Radiol*, 2007, 18, 57-65; Zhou et al., *Adv Mater*, 2013, 25, 4123-4130), lipid/galactose (Catalano et al., *Cardiovasc Intervent Radiol*, 1999, 22, 486-492; Isozaki et al., *Radiology*, 2003, 229, 798-805; Numata et al., *World J Gastroenterol*, 2006, 12, 6290-6298), sulphur hexafluoride (Jaquotot-Herranz et al., *Rev Esp Enferm Dig*, 2012, 104, 279-280; Kuenen et al., *Ultrasound Med Biol*, 2013, 39, 1631-1641; Szabo et al., *Eur Radiol*, 2013, 23, 3228-3236), perfluorocyl bromide, surfactant (Eggen et al., *J Control Release*, 2014; Suzuki et al., *J Control Release*, 2009, 133, 198-205), oligopeptides (Pinault et al., *Urology*, 1992, 39, 254-261; Chang et al., *Ultrason Sonochem*, 2013, 20, 171-179; Borden et al., *Mol Imaging*, 2013, 12, 357-363), and galactose (Maurer et al., *Invest Radiol*, 1997, 32, 441-446; Tsai et al., *Langmuir*, 2014, 30, 5510-5517; Wei et al., *PLoS One*, 2013, 8, e58133). The core may consist of a material selected from the group comprising but not limited to air (Kuo et al., *Chest*, 2007, 132, 922-929; Malich et al., *Clin Radiol*, 2001, 56, 278-283; Wang et al., *Eur J Radiol*, 2014, 83, 117-122), perfluorocarbon (Ke et al., *Small*, 2014, 10, 1220-1227; Williams et al., *Ultrasound Med Biol*, 2013, 39, 475-489), decafluorobutane (Bzyl et al., *Eur Radiol*, 2011, 21, 1988-1995), octafluoropropane (Suzuki et al., *J Control Release*, 2009, 133, 198-205; Hoyt et al., *J Ultrasound Med*, 2010, 29, 577-585), dodecafluoropentane (Williams et al., *Ultrasound Med Biol*, 2013, 39, 475-489), and perfluorobutane (Bzyl et al., *Eur Radiol*, 2011, 21, 1988-1995).

Examples of moieties enhancing ultrasound contrast include but are not limited to Aerosomes, AI-700, Albunex, Bisphere, Definity, EchoGen, Echovist, Filmix, Imagent, Levovist, MP1950, Optison, Quantison, Sonazoid, SonoVue, Myomap, Perflubron, SonoGen, Sonavist, BR14, BY963, MP1550, MP1950, MP2211, MRX-408, SH U616A, and polymeric sulfo-Lewis-x.

In a further embodiment the conjugate of the invention is conjugated to a nanoparticle moiety. Nanoparticles are generally characterized by their size, morphology and surface charge, using microscopic techniques such as scanning electron microscopy (SEM), transmission electron microscopy (TEM) and atomic force microscopy (AFM). These methods are known to the one skilled in the art and for example described in (Liv et al., *Ultramicroscopy*, 2014, 143, 93-99; Baumgardner et al., *ACS Nano*, 2014, 8, 5315-5322; Baalousha et al., *Environ Sci Process Impacts*, 2014, 16, 1338-1347). Nanoparticle moieties may belong to a class selected from the group comprising but not limited to thin films and monolayers (Pal et al., *J Appl Pharmaceut Sci*, 2011, 1, 228-234), carbon nanotubes including but not limited to single-walled carbon nanotubes and multi-walled carbon nanotubes (Pal et al., supra), fullerenes (Li et al., *JNanosci Nanotechnol*, 2014, 14, 4513-4518; Lin et al., *Recent Pat Nanotechnol*, 2012, 6, 105-113; Meng et al., *Integr Biol (Camb)*, 2013, 5, 43-47), dendrimers (Baker, Hematology *Am Soc Hematol Educ Program*, 2009, 708-719; Li et al., *Int J Nanomedicine*, 2013, 8, 2589-2600; Shi et al., *Analyst*, 2009, 134, 1373-1379), quantum dots (Al-Jamal et al., *Small*, 2008, 4, 1406-1415; Zhang et al., *Nanotechnology*, 2014, 25, 255102), liposomes (Northfelt et al., *J Clin Oncol*, 1998, 16, 2445-2451; Sapra et al., *Cancer Res*, 2002, 62, 7190-7194; Torchilin, *Nat Rev Drug Discov*, 2005, 4, 145-160), silica nanoparticles (Capeletti et al., *Langmuir*, 2014; Chen et al., *Sci Rep*, 2014, 4, 5080; Gonzalez et al., *Nanotoxicology*, 2010, 4, 382-395), magnetic nanoparticles (Hua et al., *Biomaterials*, 2011, 32, 516-527; Hua et al., *Biomaterials*, 2010, 31, 7355-7363; Tong et al., *J Nanosci Nanotechnol*, 2011, 11, 3651-3658), lipid nanoparticles including but not limited to nanoemulsions (Aznar et al., *Mol Pharm*, 2014; Han et al., *Int J Mol Med*, 2014, 34, 191-196; Mohammadi Ghalaei et al., *J Drug Deliv*, 2014, 2014, 746325), polymeric nanoparticles (Bilensoy et al., *Int J Pharm*, 2009, 371, 170-176; Park et al., *Nanomedicine*, 2009, 5, 410-418; Rejinold et al., *Int J Biol Macromol*, 2011, 49, 161-172), albumin-based nanoparticles (Fu et al., *Recent Pat Anticancer Drug Discov*, 2009, 4, 262-272; Lluch et al., *Crit Rev Oncol Hematol*, 2014, 89, 62-72; Sasaki et al., *Cancer Sci*, 2014), and nanocrystals (Harrison et al., *Invest New Drugs*, 2011, 29, 1465-1474; Li et al., *Biomaterials*, 2013, 34, 7873-7883; Zhang et al., *Autophagy*, 2009, 5, 1107-1117).

In an embodiment of the conjugate of the invention the nanoparticle is a liposome. Examples of liposomes include but are not limited to Liposomal amphotericin B, Liposomal cytarabine, Liposomal daunorubicin, Liposomal doxorubicin, Liposomal IRIV vaccine, Liposomal IRIV vaccine, Liposomal morphine, Liposomal verteporfin, Liposome-proteins SP-B and SP-C, Liposome-PEG doxorubicin, Micellular estradiol, and Liposomal vincristine.

In an embodiment of the conjugate of the invention the nanoparticle is a silica nanoparticle.

Examples of silica nanoparticles include but are not limited to xerogels and mesoporous silica nanoparticles (MCM-41; SBA-15).

In an embodiment of the conjugate of the invention the nanoparticle is a magnetic nanoparticle. Examples of magnetic nanoparticles include but are not limited to nanoparticles with a shell selected from the group comprising but not limited to cobal+alloys and oxides, nickel+alloys and oxides, manganese+alloys and oxides, and iron+alloys and oxides and a core selected from the group comprising but not limited to gold, polymers, dendrimers, and silane.

In an embodiment of the conjugate of the invention the nanoparticle is a lipid nanoparticle. Examples of lipid nanoparticles include but are not limited to solid lipid nanoparticles, nanostructured lipid carriers, and lipid drug conjugates.

In an embodiment of the conjugate of the invention the nanoparticle is a polymeric nanoparticle. Examples of polymeric nanoparticles include but are not limited to poly-e-caprolactone, polyacrylamide, polyacrylate, albumin, DNA, chitosan, gelatin, poly(L-lactide) (PLA), poly-glycolide (PGA), and polyurethane.

In an embodiment of the conjugate of the invention the nanoparticle is a dendrimer. Examples of dendrimers include but are not limited to glycogen, amylopectin, proteoglycans, and Poly(amido amide) (PAMAM).

In an embodiment the conjugate of the invention is present as a pharmaceutically acceptable salt.

A "pharmaceutically acceptable salt" of the conjugate of the present invention is preferably an acid salt or a base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Conjugates of the invention are capable of forming internal salts which are also pharmaceutically acceptable salts.

Suitable pharmaceutically acceptable salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC-(CH_2)_n-COOH$ where n is any integer from 0 to 4, i.e., 0, 1, 2, 3, or 4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

A "pharmaceutically acceptable solvate" of the conjugate of the invention is preferably a solvate of the conjugate of the invention formed by association of one or more solvent molecules to one or more molecules of a conjugate of the invention. Preferably, the solvent is one which is generally considered in the art to be suitable for use in contact with the tissues of human beings or animals without excessive toxicity or carcinogenicity, and preferably without irritation, allergic response, or other problem or complication. Such solvent includes an organic solvent such as alcohols, ethers, esters and amines.

A "hydrate" of the conjugate of the invention is formed by association of one or more water molecules to one or more molecules of a conjugate of the invention. Such hydrate includes but is not limited to a hemi-hydrate, mono-hydrate, dihydrate, trihydrate and tetrahydrate. Independent of the hydrate composition all hydrates are generally considered as pharmaceutically acceptable.

The conjugate of the invention has a high binding affinity to the first target targeted by the first targeting moiety TM1 of the conjugate of the invention. Also, the conjugate of the invention has a high binding affinity to the second target targeted by the second targeting moiety TM2. In accordance therewith, the conjugate of the invention is suitable for use in treatment and/or prevention and/or diagnosis of any disease which, in the broadest sense, involves, preferably expresses the first target targeted by the first targeting moiety and/or the second target targeted by the second targeting moiety.

In an embodiment of the conjugate of the invention where the first targeting moiety TM1 and/or the second targeting moiety TM2 is a compound of formula (2), medical indications which can be treated and/or prevented and/or diagnosed with or by means of the conjugate of the invention are as follows:

any oncology or tumor indication;

any NTR-positive indication, preferably any disease where cells involved in the disease and/or diseased cells express NTR. In a preferred embodiment the NTR-positive indication as an NTR1-positive indication, preferably in a disease where cells involved in the disease and/or diseased cells express NTR1. In a preferred embodiment the NTR-positive indication as an NTR2-positive indication, preferably in a disease where cells involved in the disease and/or diseased cells express NTR2. In a further preferred embodiment the NTR-positive indication as an NTR1 and an NTR2-positive indication, preferably in a disease where cells involved in the disease and/or diseased cells express both NTR1 and NTR2;

any indication, preferably any tumor indication, whereby the target targeted by compound of formula (2) can be identified by methods known in the art; such methods comprise, but are not limited to, receptor autoradiography (Reubi et al., Int J Cancer, 1999, 81, 376-386; Waser et al., Eur J Nucl Med Mol Imaging, 2014, 41, 1166-1171), immunohistochemistry (Schmidt et al., Anticancer Res, 2008, 28, 1719-1724; Patsenker et al., J Hepatol, 2010, 52, 362-369; Korner et al., Am J Surg Pathol, 2012, 36, 242-252), immunocytochemistry (Chekhun et al., Exp Oncol, 2013, 35, 174-179; Ghosh et al., J Cytol, 2013, 30, 151-155; Seymour et al., Am J Clin Pathol, 1990, 94, S35-40), RT-PCR (Bernard et al., Clin Chem, 2002, 48, 1178-1185; Chang et al., Clin Cancer Res, 1999, 5, 2674-2681; Kang et al., Cancer Genet Cytogenet, 2006, 164, 32-38; Patel et al., Clin Cancer Res, 2004, 10, 7511-7519), in situ hybridization (Chang et al., Clin Cancer Res, 1999, 5, 2674-2681; Kang et al., Cancer Genet Cytogenet, 2006, 164, 32-38; Heinrich et al., Int J Gynecol Cancer, 2004, 14, 1078-1085), flow cytometry (Chekhun et al., Exp Oncol, 2013, 35, 174-179; Forster et al., Cytometry A, 2007, 71, 945-950; Goodman et al., Biol Open, 2012, 1, 329-340) and Western blot (Schmidt et al., Anticancer Res, 2008, 28, 1719-1724; Goodman et al., Biol Open, 2012, 1, 329-340; Kusagawa et al., Br J Cancer, 1998, 77, 98-102); samples to be analyzed with the above methods may originate from biopsies, surgically resected specimens, circulating tumor cells, blood, urine or fecal samples, swabs and smears, sputum; preferably such sample is obtained from biopsies, surgically resected specimens, circulating tumor cells; these methods are also suitable for detecting and determining, respectively, homogeneity and/or heterogeneity of expression of a or the target, including expression of receptors such as NTR1 and NTR2, by a cell, a tissue, an organ, a tumor and/or an indication; these methods are also suitable for detecting and determining, respectively, the density of a or the target, including expression of receptors such as NTR1 and NTR2, by a cell, a tissue, an organ, a tumor and/or an indication;

any indication, preferably any tumor indication, in which more at least 75% or more, at least 50% or more, at least 25% or more, or at least 10% or more of patients, preferably the diseased cell, tissue, organ and/or indication express NTR. In an embodiment thereof NTR is NTR1. In a further embodiment NTR1 is NTR2. In a still further embodiment NTR is NTR1 and NTR2, i.e. the patients and, preferably the diseased cell, tissue, organ and/or indication express both NTR1 and NTR2;

any indication, preferably any tumor indication, in which only a small portion of the tumors, preferably a tumor indication where only a small portion of the patients suffering from the tumor indication, express NTR1. Preferably, a small portion of the tumors is about 10% or less of the tumors. Also preferably, a small portion of the patients is about 10% or less of the patients;

any indication, preferably any tumor indication where NTR, preferably NTR1 and/or NTR2, more preferably NTR1, is homogenously expressed, preferably homogenously expressed by a cell in such indication, preferably the cell is involved in such indication and more preferably the cells is a diseased cell;

any indication, preferably any tumor indication where NTR, preferably NTR1 and/or NTR2, more preferably NTR1, is heterogenously expressed, preferably heterogenously expressed by a cell in such indication, preferably the cell is involved in such indication and more preferably the cells is a diseased cell;

any indication, preferably any oncology indication, more preferably in any indication related to oncology, where NTR is expressed at a low density. In an embodiment thereof the indication is any tumor and/or cancer disease. In an embodiment thereof the target is expressed heterogenously by a cell in such indication, preferably the cell is involved in such indication and more preferably the cell is a diseased cell. As preferably used herein low density means that less than 5000 copies of NTR per cell are expressed. Suitable methods to identify such indications are listed above. Preferred methods are receptor autoradiography (Reubi et al., supra; Waser et al., supra) and cell binding studies (Kitabgi et al., supra); any indication, preferably any oncology indication, more preferably in any indication related to oncology, where NTR is expressed in the primary tumor, in metastases, preferably metastases of the primary tumor, or in both the primary tumor and metastases, preferably metastases of the primary tumor. In an embodiment thereof NTR is NTR1, NTR2 or both NTR1 and NTR2;

any indication, preferably any oncology indication, more preferably in any indication related to oncology, where NTR is not expressed. In an embodiment thereof NTR is NTR1. In another embodiment thereof NTR is NTR2. In still another embodiment thereof NTR is NTR1 and NTR2, i.e. the indication does express neither NTR1 nor NTR2. In an embodiment thereof NTR is not expressed by a cell involved in said indication and more preferably not expressed by a diseased cell involved in said indication;

any indication, preferably any oncology indication, more preferably in any indication related to oncology, where at least 20,000 or more copies of NTR or at least 10,000 or more copies of NTR or at least 5,000 or more copies of NTR or at least 1,000 or more copies of NTR are expressed per cell. In an embodiment thereof the cell is involved in such indication and more preferably the cell is a diseased cell. In an embodiment thereof NTR is NTR1, NTR2 or both NTR1 and NTR2. Accordingly, the above copy numbers may refer to the copy number of NTR1 or the copy number of NTR2 or the total copy number of NTR1 and NTR2 taken together;

any indication, preferably any oncology indication, more preferably in any indication related to oncology, where the blood brain barrier is intact;

any indication of group A as defined herein; preferably the indication of group A as defined herein is one which occurs in an organ and/or a tissue, wherein the organ and/or the tissue is selected from group C as defined herein; and any indication of group H, group I, group J, group K and/or group L, each as defined herein.

The compound of the invention has a high binding affinity to neurotensin receptors and NTR1 in particular. Because of this high binding affinity, the compound of the invention is effective as, useful as and/or suitable as a targeting agent and, if conjugated to another moiety, as a targeting moiety. As preferably used herein a targeting agent is an agent which interacts with the target molecule which are in the instant case said neurotensin receptors. In terms of cells and tissues thus targeted by the compound of the invention any cell and tissue, respectively, expressing said neurotensin receptors and NTR1 in particular is targeted. As is known from the prior art, apart from the central nervous system and intestine, NTR1 is highly expressed in a mammalian body and a human body in particular on several neoplastic cells in several tumor indications whereas the expression of NTR1 in other tissues of the mammalian and the human body is low. These NTR1-expressing tumor indications include but are not limited to ductal pancreatic adenocarcinoma (Reubi et al., Gut, 1998, 42, 546-550; Ehlers et al., *Ann. Surg.*, 2000, 231, 838-848), small cell lung cancer (Reubi et al., *Int. J. Cancer*, 1999, 82, 213-218), prostate cancer (Taylor et al., *Prostate*, 2012, 72, 523-532), colorectal carcinoma (Chao et al., *J. Surg. Res.*, 2005, 129, 313-321; Gui et al., *Peptides*, 2008, 29, 1609-1615), breast cancer (Souaze et al., *Cancer Res.*, 2006, 66, 6243-6249), meningioma (Reubi et al., *Int. J. Cancer*, 1999, 82, 213-218), Ewing's sarcoma (Reubi et al., *Int. J. Cancer*, 1999, 82, 213-218), pleural mesothelioma (Alifano et al., *Biochimie*, 2010, 92, 164-170), head and neck cancer (Shimizu et al., *Int. J. Cancer*, 2008, 123, 1816-1823), non-small lung cancer (Alifano et al., *Clin. Cancer Res.*, 2010, 16, 4401-4410; Moody et al., *Panminerva Med.*, 2006, 48, 19-26; Ocejo-Garcia et al., *Lung Cancer*, 2001, 33, 1-9), gastrointestinal stromal tumors (Gromova et al., *PLoS One*, 2011, 6, e14710), uterine leiomyoma (Rodriguez et al., *Biol. Reprod.*, 2010, 83, 641-647; Rodriguez et al., *Int. J. Gynecol. Pathol.*, 2011, 30, 354-363) and cutaneous T-cell lymphoma (Ramez et al., *J. Invest. Dermatol.*, 2001, 117, 687-693). Accordingly, the compound of the invention is thus particularly suitable for and useful in the diagnosis and treatment, respectively, of these diseases. Insofar, the above indications are indications which can be treated by the compound of the invention. It will be understood by the person skilled in the art that also metastases and metastasis of the above indications in particular can be treated and diagnosed by the compound of the invention and the methods of diagnosis and methods of treatment making use of the compound of the invention.

A further indication in connection with which the compound of the invention may be used, either for therapeutic purposes or for diagnostic purposes, is hematological malignancies which is plausible in view of the expression of NTR1 in blood cells and T-cell lymphoma cells in particular as reported by Ramez et al. In an embodiment the disease is T-cell lymphoma.

In an embodiment of the conjugate of the invention where the first targeting moiety TM1 is a compound of the formula (2) and the second targeting moiety TM2 is targeting a target which is different from the target targeted by the first targeting moiety, medical indications which can be treated and/or prevented and/or diagnosed with or by means of the conjugate are as follows:

any NTR-positive indication, preferably any disease where cells involved in the disease and/or diseased cells express a target as disclosed herein, preferably the target is different from NTR, preferably different from NTR1 and/or NTR1, more preferably different from NTR1, any indication, preferably any tumor indication, whereby the target is one disclosed herein but is different from NTR, preferably different from NTR1 and/or NTR1, more preferably different from NTR1, targeted by the first or the second targeting moiety can be identified by methods known in the art; such methods comprise, but are not limited to, receptor autoradiography (Reubi et al., Int J Cancer, 1999, 81, 376-386; Waser et al., Eur J Nucl Med Mol Imaging, 2014, 41, 1166-1171), immunohistochemistry (Schmidt et al., Anticancer Res, 2008, 28, 1719-1724; Patsenker et al., J Hepatol, 2010, 52, 362-369; Korner et al., Am J Surg Pathol, 2012, 36, 242-252), immunocytochemistry (Chekhun et al., Exp Oncol, 2013, 35, 174-179; Ghosh et al., J Cytol, 2013, 30, 151-155; Seymour et al., Am J Clin Pathol, 1990, 94, S35-40), RT-PCR (Bernard et al., Clin Chem, 2002, 48, 1178-1185; Chang et al., Clin Cancer Res, 1999, 5, 2674-2681; Kang et al., Cancer Genet Cytogenet, 2006, 164, 32-38; Patel et al., Clin Cancer Res, 2004, 10, 7511-7519), in situ hybridization (Chang et al., Clin Cancer Res, 1999, 5, 2674-2681; Kang et al., Cancer Genet Cytogenet, 2006, 164, 32-38; Heinrich et al., Int J Gynecol Cancer, 2004, 14, 1078-1085), flow cytometry (Chekhun et al., Exp Oncol, 2013, 35, 174-179; Forster et al., Cytometry A, 2007, 71, 945-950; Goodman et al., Biol Open, 2012, 1, 329-340) and Western blot (Schmidt et al., Anticancer Res, 2008, 28, 1719-1724; Goodman et al., Biol Open, 2012, 1, 329-340; Kusagawa et al., Br J Cancer, 1998, 77, 98-102); samples to be analyzed with the above methods may originate from biopsies, surgically resected specimens, circulating tumor cells, blood, urine or fecal samples, swabs and smears, sputum; preferably such sample is obtained from biopsies, surgically resected specimens, circulating tumor cells; these methods are also suitable for detecting and determining, respectively, homogeneity and/or heterogeneity of expression of a or the target, including expression of receptors such as NTR1 and NTR2, by a cell, a tissue, an organ, a tumor and/or an indication; these methods are also suitable for detecting and determining, respectively, the density of a or the target, including expression of receptors such as NTR1 and NTR2, by a cell, a tissue, an organ, a tumor and/or an indication;

any indication, preferably any tumor indication, in which more at least 75% or more, at least 50% or more, at least 25% or more, or at least 10% or more of patients, preferably the diseased cell, tissue, organ and/or indication express preferably a target as disclosed herein but which is different from NTR, preferably different from NTR1 and/or NTR1, more preferably different from NTR1. Preferably the diseased cell, tissue, organ and/or indication express both NTR1 and NTR2;

any indication, preferably any tumor indication, in which only a small portion of the tumors, preferably a tumor indication where only a small portion of the patients suffering from the tumor indication, express a target as disclosed herein, wherein the target is different from NTR, preferably different from NTR1 and/or NTR1, more preferably different from NTR1. Preferably, a small portion of the tumors is about 10% or less of the tumors. Also preferably, a small portion of the patients is about 10% or less of the patients;

any indication, preferably any tumor indication where a target disclosed herein but different from NTR, preferably different from NTR1 and/or NTR1, more preferably different from NTR1 is homogenously expressed, preferably homogenously expressed by a cell in such indication, preferably the cell is involved in such indication and more preferably the cells is a diseased cell;

any indication, preferably any tumor indication where a target disclose herein but different from NTR, preferably different from NTR1 and/or NTR1, more preferably different from NTR1 is heterogenously expressed, preferably heterogenously expressed by a cell in such indication, preferably the cell is involved in such indication and more preferably the cells is a diseased cell;

any indication, preferably any oncology indication, more preferably in any indication related to oncology, where a target as disclosed herein but but different from NTR, preferably different from NTR1 and/or NTR1, more preferably different from NTR1 is expressed in the primary tumor, in metastases, preferably metastases of the primary tumor, or in both the primary tumor and metastates, preferably metastases of the primary tumor;

any indication, preferably any oncology indication, more preferably in any indication related to oncology, where NTR is not expressed. In an embodiment thereof NTR is NTR1. In another embodiment thereof NTR is NTR2. In still another embodiment thereof NTR is NTR1 and NTR2, i.e. the indication does not express neither NTR1 nor NTR2. In an embodiment thereof NTR is not expressed by a cell involved in said indication and more preferably not expressed by a diseased cell involved in said indication;

any indication, preferably any oncology indication, more preferably in any indication related to oncology, where at least 20,000 or more copies of a target disclosed herein but different from NTR, preferably different from NTR1 and/or NTR1, more preferably different from NTR1, at least 10,000 or more copies of such target or at least 5,000 or more copies of such target or at least 1,000 or more copies of such target are expressed per cell. In an embodiment thereof the cell is involved in such indication and more preferably the cell is a diseased cell;

any indication, preferably any oncology indication, more preferably in any indication related to oncology, where the blood brain barrier is intact;

any indication of group A, group D, group E, group F, group G, group H, group I, group J, group K and/or group L, each as defined herein; and any indication of group A as defined herein affecting or occurring in the organs and/or tissues of group C as defined herein.

It is within the present invention that the conjugate of the invention is used in a method for the treatment of a disease as disclosed herein. Such method, preferably, comprises the step of administering to a subject in need thereof a therapeutically effective amount of the conjugate of the invention. Such method includes, but is not limited to, curative or adjuvant cancer treatment. It is used as palliative treatment where cure is not possible and the aim is for local disease control or symptomatic relief or as therapeutic treatment where the therapy has survival benefit and it can be curative.

The method for the treatment of a disease as disclosed herein includes the treatment of malignant tumors and cancer, and may be used either as the primary therapy or as second, third, fourth or last line therapy. It is also within the instant invention to combine radiotherapy in accordance with instant invention with other treatments including surgery, chemotherapy, radiation therapy, targeted therapy, anti-angiogenic therapy and hormone therapy which are well known in the art. It is well known to the person skilled in the art that the precise treatment intent including curative, adjuvant, neoadjuvant, therapeutic, or palliative treatment intent will depend on the tumor type, location, and stage, as well as the general health of the patient.

The method for the treatment of a disease as disclosed herein may also target the draining lymph nodes if they are clinically involved with tumor.

Preferably, radionuclide therapy makes use of or is based on different forms of radiation emitted by a radionuclide. Such radiation can, for example, be any one of radiation of photons, radiation of electrons including but not limited to $\beta^-$-particles and Auger-electrons, radiation of protons, radiation of neutrons, radiation of positrons, radiation of $\alpha$-particles or an ion beam. Depending on the kind of particle or radiation emitted by said radionuclide, radionuclide therapy can, for example, be distinguished as photon radionuclide therapy, electron radionuclide therapy, proton radionuclide therapy, neutron radionuclide therapy, positron radionuclide therapy, $\alpha$-particle radionuclide therapy or ion beam radionuclide therapy. All of these forms of radionuclide therapy are encompassed by the present invention, and all of these forms of radionuclide therapy can be realized by the compound of the invention, preferably under the proviso that the radionuclide attached to the compound of the invention, more preferably as an Effector, is providing for this kind of radiation.

Radionuclide therapy preferably works by damaging the DNA of cells. The damage is caused by a photon, electron, proton, neutron, positron, $\alpha$-particle or ion beam directly or indirectly ionizing the atoms which make up the DNA chain. Indirect ionization happens as a result of the ionization of water, forming free radicals, notably hydroxyl radicals, which then damage the DNA.

In the most common forms of radionuclide therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. The DNA damage is inherited through cell division, accumulating damage to the cancer cells, causing them to die or reproduce more slowly.

Oxygen is a potent radiosensitizer, increasing the effectiveness of a given dose of radiation by forming DNA-damaging free radicals. Therefore, use of high pressure oxygen tanks, blood substitutes that carry increased oxygen, hypoxic cell radiosensitizers such as misonidazole and metronidazole, and hypoxic cytotoxins, such as tirapazamine may be applied.

Other factors that are considered when selecting a radioactive dose include whether the patient is receiving chemotherapy, whether radiation therapy is being administered before or after surgery, and the degree of success of surgery.

The total radioactive dose may be fractionated, i.e. spread out over time in one or more treatments for several important reasons. Fractionation allows normal cells time to recover, while tumor cells are generally less efficient in repair between fractions. Fractionation also allows tumor cells that were in a relatively radio-resistant phase of the cell cycle during one treatment to cycle into a sensitive phase of the cycle before the next fraction is given. Similarly, tumor cells that were chronically or acutely hypoxic and, therefore, more radioresistant, may reoxygenate between fractions, improving the tumor cell kill.

It is generally known that different cancers respond differently to radiation therapy. The response of a cancer to radiation is described by its radiosensitivity. Highly radiosensitive cancer cells are rapidly killed by modest doses of radiation. These include leukemias, most lymphomas and germ cell tumors.

It is important to distinguish radiosensitivity of a particular tumor, which to some extent is a laboratory measure, from "curability" of a cancer by an internally delivered radioactive dose in actual clinical practice. For example, leukemias are not generally curable with radiotherapy, because they are disseminated through the body. Lymphoma may be radically curable if it is localized to one area of the body. Similarly, many of the common, moderately radioresponsive tumors can be treated with curative doses of radioactivity if they are at an early stage. This applies, for example, to non-melanoma skin cancer, head and neck cancer, non-small cell lung cancer, cervical cancer, anal cancer, prostate cancer.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radionuclide therapy. A third technique is to enhance the radiosensitivity of the cancer by giving certain drugs during a course of radiotherapy. Examples of radiosensiting drugs include, but are not limited to Cisplatin, Nimorazole, and Cetuximab.

Introperative radiotherapy is a special type of radiotherapy that is delivered immediately after surgical removal of the cancer. This method has been employed in breast cancer (TARGeted Introperative radioTherapy), brain tumors and rectal cancers.

Radionuclide therapy is in itself painless. Many low-dose palliative treatments cause minimal or no side effects. Treatment to higher doses may cause varying side effects during treatment (acute side effects), in the months or years following treatment (long-term side effects), or after re-treatment (cumulative side effects). The nature, severity, and longevity of side effects depends on the organs that receive the radiation, the treatment itself (type of radionuclide, dose, fractionation, concurrent chemotherapy), and the patient.

It is within the present invention that the method for the treatment of a disease of the invention may realize each and any of the above strategies which are as such known in the art, and which insofar constitute further embodiments of the invention.

It is also within the present invention that the conjugate of the invention is used in a method for the diagnosis of a disease as disclosed herein. Such method, preferably, comprises the step of administering to a subject in need thereof a diagnostically effective amount of the compound of the invention.

In accordance with the present invention, an imaging method is selected from the group consisting of scintigraphy, Single Photon Emission Computed Tomography (SPECT) and Positron Emission Tomography (PET).

Scintigraphy is a form of diagnostic test or method used in nuclear medicine, wherein radiopharmaceuticals are internalized by cells, tissues and/or organs, preferably internalized in vivo, and radiation emitted by said internalized radiopharmaceuticals is captured by external detectors (gamma cameras) to form and display two-dimensional images. In contrast thereto, SPECT and PET forms and displays three-dimensional images. Because of this, SPECT and PET are classified as separate techniques to scintigraphy, although they also use gamma cameras to detect internal radiation. Scintigraphy is unlike a diagnostic X-ray where external radiation is passed through the body to form an image.

Single Photon Emission Tomography (SPECT) scans are a type of nuclear imaging technique using gamma rays. They are very similar to conventional nuclear medicine planar imaging using a gamma camera. Before the SPECT scan, the patient is injected with a radiolabeled chemical emitting gamma rays that can be detected by the scanner. A computer collects the information from the gamma camera and translates this into two-dimensional cross-sections. These cross-sections can be added back together to form a three-dimensional image of an organ or a tissue. SPECT involves detection of gamma rays emitted singly, and sequentially, by the radionuclide provided by the radiolabeled chemical. To acquire SPECT images, the gamma camera is rotated around the patient. Projections are acquired at defined points during the rotation, typically every 3-6 degrees. In most cases, a full 360 degree rotation is used to obtain an optimal reconstruction. The time taken to obtain each projection is also variable, but 15-20 seconds is typical. This gives a total scan time of 15-20 minutes. Multi-headed gamma cameras are faster. Since SPECT acquisition is very similar to planar gamma camera imaging, the same radiopharmaceuticals may be used.

Positron Emitting Tomography (PET) is a non-invasive, diagnostic imaging technique for measuring the biochemical status or metabolic activity of cells within the human body. PET is unique since it produces images of the body's basic biochemistry or functions. Traditional diagnostic techniques, such as X-rays, CT scans or MRI, produce images of the body's anatomy or structure. The premise with these techniques is that any changes in structure or anatomy associated with a disease can be seen. Biochemical processes are also altered by a disease, and may occur before any gross changes in anatomy. PET is an imaging technique that can visualize some of these early biochemical changes. PET scanners rely on radiation emitted from the patient to create the images. Each patient is given a minute amount of a radioactive pharmaceutical that either closely resembles a natural substance used by the body or binds specifically to a receptor or molecular structure. As the radioisotope undergoes positron emission decay (also known as positive beta decay), it emits a positron, the antiparticle counterpart of an electron. After traveling up to a few millimeters, the positron encounters an electron and annihilates, producing a pair of annihilation (gamma) photons moving in opposite directions. These are detected when they reach a scintillation material in the scanning device, creating a burst of light, which is detected by photomultiplier tubes or silicon avalanche photodiodes. The technique depends on simultaneous or coincident detection of the pair of photons. Photons that do not arrive in pairs, i.e., within a few nanoseconds, are ignored. All coincidences are forwarded to the image processing unit where the final image data is produced using image reconstruction procedures.

SPECT/CT and PET/CT is the combination of SPECT and PET with computed tomography (CT). The key benefits of combining these modalities are improving the reader's confidence and accuracy. With traditional PET and SPECT, the limited number of photons emitted from the area of abnormality produces a very low-level background that makes it difficult to anatomically localize the area. Adding CT helps determine the location of the abnormal area from an anatomic perspective and categorize the likelihood that this represents a disease.

It is within the present invention that the method for the diagnosis of a disease of the invention may realize each and any of the above strategies which are as such known in the art, and which insofar constitute further embodiments of the invention.

Conjugates of the present invention are useful to stratify patients, i.e. to create subsets within a patient population that provide more detailed information about how the patient will respond to a given drug. Stratification can be a critical component to transforming a clinical trial from a negative or neutral outcome to one with a positive outcome by identifying the subset of the population most likely to respond to a novel therapy.

Stratification includes the identification of a group of patients with shared "biological" characteristics to select the optimal management for the patients and achieve the best possible outcome in terms of risk assessment, risk prevention and achievement of the optimal treatment outcome A conjugate of the present invention may be used to assess or detect, a specific disease as early as possible (which is a diagnostic use), the risk of developing a disease (which is a susceptibility/risk use), the evolution of a disease including indolent vs. aggressive (which is a prognostic use) and it may be used to predict the response and the toxicity to a given treatment (which is a predictive use).

It is also within the present invention that the conjugate of the invention is used in a theranostic method. The concept of theranostics is to combine a therapeutic agent with a corresponding diagnostic test that can increase the clinical use of the therapeutic drug. The concept of theranostics is becoming increasingly attractive and is widely considered the key to improving the efficiency of drug treatment by helping doctors identify patients who might profit from a given therapy and hence avoid unnecessary treatments.

The concept of theranostics is to combine a therapeutic agent with a diagnostic test that allows doctors to identify those patients who will benefit most from a given therapy. In an embodiment and as preferably used herein, a conjugate of the present invention is used for the diagnosis of a patient, i.e. identification and localization of the primary tumor mass as well as potential local and distant metastases. Furthermore, the tumor volume can be determined, especially utilizing three-dimensional diagnostic modalities such as SPECT or PET. Only those patients having neurotensin receptor positive tumor masses and who, therefore, might profit from a given therapy are selected for a particular therapy and hence unnecessary treatments are avoided. Preferably, such therapy is a neurotensin receptor targeted therapy using a compound of the present invention. In one particular embodiment, chemically identical tumor-targeted diagnostics, preferably imaging diagnostics for scintigraphy, PET or SPECT and radiotherapeutics are applied. Such conjugates only differ in the radionuclide and therefore usually have a very similar if not identical pharmacokinetic profile. This can be realized using a chelator and a diagnostic or therapeutic radiometal. Alternatively, this can be realized using a precursor for radiolabeling and radiolabeling with either a diagnostic or a therapeutic radionuclide. In one embodiment diagnostic imaging is used preferably by means of quantification of the radiation of the diagnostic radionuclide and subsequent dosimetry which is known to those skilled in the art and the prediction of drug concentrations in the tumor compared to vulnerable side effect organs. Thus, a truly individualized drug dosing therapy for the patient is achieved.

In an embodiment and as preferably used herein, the theragnostic method is realized with only one theragnostically active conjugate such as a conjugate of the present invention labeled with a radionuclide emitting diagnostically detectable radiation (e.g. positrons or gamma rays) as well as therapeutically effective radiation (e.g. electrons).

The invention also contemplates a method of intraoperatively identifying/disclosing diseased tissues expressing neurotensin receptors in a subject. Such method uses a conjugate of the invention, whereby such conjugate of the invention preferably comprises as Effector a diagnostically active agent.

According to a further embodiment of the invention, the conjugate of the invention, particularly if complexed with a radionuclide, may be employed as adjunct or adjuvant to any other tumor treatment including, surgery as the primary method of treatment of most isolated solid cancers, radiation therapy involving the use of ionizing radiation in an attempt to either cure or improve the symptoms of cancer using either sealed internal sources in the form of brachytherapy or external sources, chemotherapy such as alkylating agents, antimetabolites, anthracyclines, plant alkaloids, topoisomerase inhibitors, and other antitumor agents, hormone treatments that modulate tumor cell behavior without directly attacking those cells, targeted agents which directly target a molecular abnormality in certain types of cancer including monoclonal antibodies and tyrosine kinase inhibitors, angiogenesis inhibitors, immunotherapy, cancer vaccination, palliative care including actions to reduce the physical, emotional, spiritual, and psycho-social distress to improve the patient's quality of life and alternative treatments including a diverse group of health care systems, practices, and products that are not part of conventional medicine.

In an embodiment of the methods of the invention, the subject is a patient. In an embodiment, a patient is a subject which has been diagnosed as suffering from or which is suspected of suffering from or which is at risk of suffering from or developing a disease, whereby the disease is a disease as described herein and preferably a disease involving neurotensin receptor and more preferably neurotensin receptor 1.

Dosages employed in practicing the methods for treatment and diagnosis, respectively, where a radionuclide is used and more specifically attached to or part of the compound of the invention will vary depending e.g. on the particular condition to be treated, for example the known radiosensitivity of the tumor type, the volume of the tumor and the therapy desired. In general, the dose is calculated on the basis of radioactivity distribution to each organ and on observed target uptake. A γ-emitting complex may be administered once or at several times for diagnostic imaging. In animals, an indicated dose range may be from 0.1 µg/kg to 5 mg/kg of the conjugate of the invention complexed e.g. with 1 to 200 MBq of $^{111}$In or $^{89}$Zr. A β-emitting complex of the compound of the invention may be administered at several time points e.g. over a period of 1 to 3 weeks or longer. In animals, an indicated dosage range may be of from 0.1 µg/kg to 5 mg/kg of the conjugate of the invention complexed e.g. with 1 to 200 MBq $^{90}$Y or $^{177}$Lu. In larger mammals, for example humans, an indicated dosage range is from 0.1 to 100 µg/kg of the compound of the invention complexed with e.g. 10 to 400 MBq $^{111}$In or $^{89}$Zr. In larger mammals, for example humans, an indicated dosage range is of from 0.1 to 100 µg/kg of the compound of the invention complexed with e.g. 10 to 5000 MBq $^{90}$Y or $^{177}$Lu.

In a further aspect, the instant invention is related to a composition and a pharmaceutical composition in particular, comprising the conjugate of the invention.

The pharmaceutical composition of the present invention comprises at least one conjugate of the invention and, optionally, one or more carrier substances, excipients and/or adjuvants. The pharmaceutical composition may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included in the pharmaceutical composition of the invention.

The pharmaceutical composition of the invention may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, intrathecal and intraperitoneal injection, as well as any similar injection or infusion technique. A preferred route of administration is intravenous administration.

In an embodiment of the invention the conjugate of the invention comprising a radionuclide is administered by any conventional route, in particular intravenously, e.g. in the form of injectable solutions or suspensions. The conjugate of the invention may also be administered advantageously by infusion, e.g., by an infusion of 30 to 60 min.

Depending on the site of the tumor, the conjugate of the invention may be administered as close as possible to the tumor site, e.g. by means of a catheter. Such administration may be carried out directly into the tumor tissue or into the surrounding tissue or into the afferent blood vessels. The conjugate of the invention may also be administered repeatedly in doses, preferably in divided doses.

According to a preferred embodiment of the invention, a pharmaceutical composition of the invention comprises a stabilizer, e.g. a free radical scavenger, which inhibits autoradiolysis of the conjugate of the invention. Suitable stabilizers include, e.g., serum albumin, ascorbic acid, retinol, gentisic acid or a derivative thereof, or an amino acid infusion solution such, e.g., used for parenteral protein feeding, preferably free from electrolyte and glucose, for example a commercially available amino acid infusion such as Proteinsteril® KE Nephro. Ascorbic acid and gentisic acid are preferred.

A pharmaceutical composition of the invention may comprise further additives, e.g. an agent to adjust the pH between 7.2 and 7.4, e.g. sodium or ammonium acetate or $Na_2HPO_4$. Preferably, the stabilizer is added to the non-radioactive conjugate of the invention and introduction of the radionuclide, for instance the complexation with the radionuclide, is performed in the presence of the stabilizer, either at room temperature or, preferably, at a temperature of from 40 to 120° C. The complexation may conveniently be performed under air free conditions, e.g. under $N_2$ or Ar. Further stabilizer may be added to the composition after complexation.

Excretion of the conjugate of the invention, particularly if the Effector is a radionuclide, essentially takes place through the kidneys. Further protection of the kidneys from radioactivity accumulation may be achieved by administration of lysine or arginine or an amino acid solution having a high content of lysine and/or arginine, e.g. a commercially available amino acid solution such as Synthamin®-14 or -10, prior to the injection of or together with the compound of the invention, particularly if the Effector is a radionuclide. Protection of the kidneys may also be achieved by administration of plasma expanders such as e.g. gelofusine, either instead of or in addition to amino acid infusion. Protection of the kidneys may also be achieved by administration of diuretics providing a means of forced diuresis which elevates the rate of urination. Such diuretics include high ceiling loop diuretics, thiazides, carbonic anhydrase inhibitors, potassium-sparing diuretics, calcium-sparing diuretics, osmotic diuretics and low ceiling diuretics. A pharmaceutical composition of the invention may contain, apart from a conjugate of the invention, at least one of these further compounds intended for or suitable for kidney protection, preferably kidney protection of the subject to which the compound of the invention is administered.

It will be understood by a person skilled in the art that the conjugate of the invention is disclosed herein for use in various methods. It will be further understood by a person skilled in the art that the composition of the invention and the pharmaceutical composition of the invention can be equally used in said various methods. It will also be understood by a person skilled in the art that the composition of the invention and the pharmaceutical composition are disclosed herein for use in various methods. It will be equally understood by a person skilled in the art that the conjugate of the invention can be equally used in said various methods.

It will be acknowledged by a person skilled in the art that the composition of the invention and the pharmaceutical composition of the invention contain one or more further compounds in addition to the conjugate of the invention. To the extent that such one or more further compounds are disclosed herein as being part of the composition of the invention and/or of the pharmaceutical composition of the invention, it will be understood that such one or more further compounds can be administered separately from the compound of the invention to the subject which is exposed to or the subject of a method of the invention. Such administration of the one or more further compounds can be performed prior, concurrently with or after the administration of the conjugate of the invention. It will also be acknowledged by a person skilled in the art that in a method of the invention, apart from a compound of the invention, one or more further compound may be administered to a subject. Such administration of the one or more further compounds can be performed prior, concurrently with or after the administration of the conjugate of the invention. To the extent that such one or more further compounds are disclosed herein as being administered as part of a method of the invention, it will be understood that such one or more further compounds are part of a composition of the invention and/or of a pharmaceutical composition of the invention. It is within the present invention that the conjugate of the invention and the one or more further compounds may be contained in the same or a different formulation. It is also within the present invention that the conjugate of the invention and the one or more further compounds are not contained in the same formulation, but are contained in the same package containing a first formulation comprising a conjugate of the invention, and a second formulation comprising the one or more further compounds, whereby the type of formulation may be the same or may be different.

It is within the present invention that more than one type of a conjugate of the invention is contained in the composition of the invention and/or the pharmaceutical composition of the invention. It is also within the present invention that more than one type of a conjugate of the invention is used, preferably administered, in a method of the invention.

It will be acknowledged that a composition of the invention and a pharmaceutical composition of the invention may be manufactured in conventional manner.

Radiopharmaceuticals have decreasing content of radioactivity with time, as a consequence of the radioactive decay. The physical half-life of the radionuclide is often short for radiopharmaceutical diagnostics. In these cases, the final preparation has to be done shortly before administration to the patient. This is in particular the case for positron emitting radiopharmaceuticals for Tomography (PET radiopharmaceuticals). It often leads to the use of semi-manufactured products such as radionuclide generators, radioactive precursors and kits.

Preferably, a kit of the invention comprises apart from one or more than one conjugates of the invention typically at least one of the followings: instructions for use, final preparation and/or quality control, one or more optional excipient(s), one or more optional reagents for the labeling procedure, optionally one or more radionuclide(s) with or without shielded containers, and optionally one or more device(s), whereby the device(s) is/are selected from the group comprising a labeling device, a purification device, an analytical device, a handling device, a radioprotection device or an administration device.

Shielded containers known as "pigs" for general handling and transport of radiopharmaceutical containers come in various configurations for holding radiopharmaceutical containers such as bottles, vials, syringes, etc. One form often includes a removable cover that allows access to the held radiopharmaceutical container. When the pig cover is in place, the radiation exposure is acceptable.

A labeling device is selected from the group of open reactors, closed reactors, microfluidic systems, nanoreactors, cartridges, pressure vessels, vials, temperature controllable reactors, mixing or shaking reactors and combinations thereof.

A purification device is preferably selected from the group of ion exchange chromatography columns or devices, size-exclusion chromatography columns or devices, affinity chromatography columns or devices, gas or liquid chromatography columns or devices, solid phase extraction columns or devices, filtering devices, centrifugations vials columns or devices.

An analytical device is preferably selected from the group of tests or test devices to determine the identity, radiochemical purity, radionuclidic purity, content of radioactivity and specific radioactivity of the radiolabelled compound.

A handling device is preferably selected from the group consisting of devices for mixing, diluting, dispensing, labeling, injecting and administering radiopharmaceuticals to a subject.

A radioprotection device is used in order to protect doctors and other personnel from radiation when using therapeutic or diagnostic radionuclides. The radioprotection device is preferably selected from the group consisting of devices with protective barriers of radiation-absorbing material selected from the group consisting of aluminum, plastics, wood, lead, iron, lead glass, water, rubber, plastic, cloth, devices ensuring adequate distances from the radiation sources, devices reducing exposure time to the radionuclide, devices restricting inhalation, ingestion, or other modes of entry of radioactive material into the body and devices providing combinations of these measures.

An administration device is preferably selected from the group of syringes, shielded syringes, needles, pumps and infusion devices. Syringe shields are commonly hollow cylindrical structures that accommodate the cylindrical body of the syringe and are constructed of lead or tungsten with a lead glass window that allows the handler to view the syringe plunger and liquid volume within the syringe.

The present invention is now further illustrated by reference to the following figures and examples from which further advantages, features, and embodiments may be taken, wherein FIG. 1 shows the solid phase synthesis of derivatized resin of formula (86);

Figure 14:
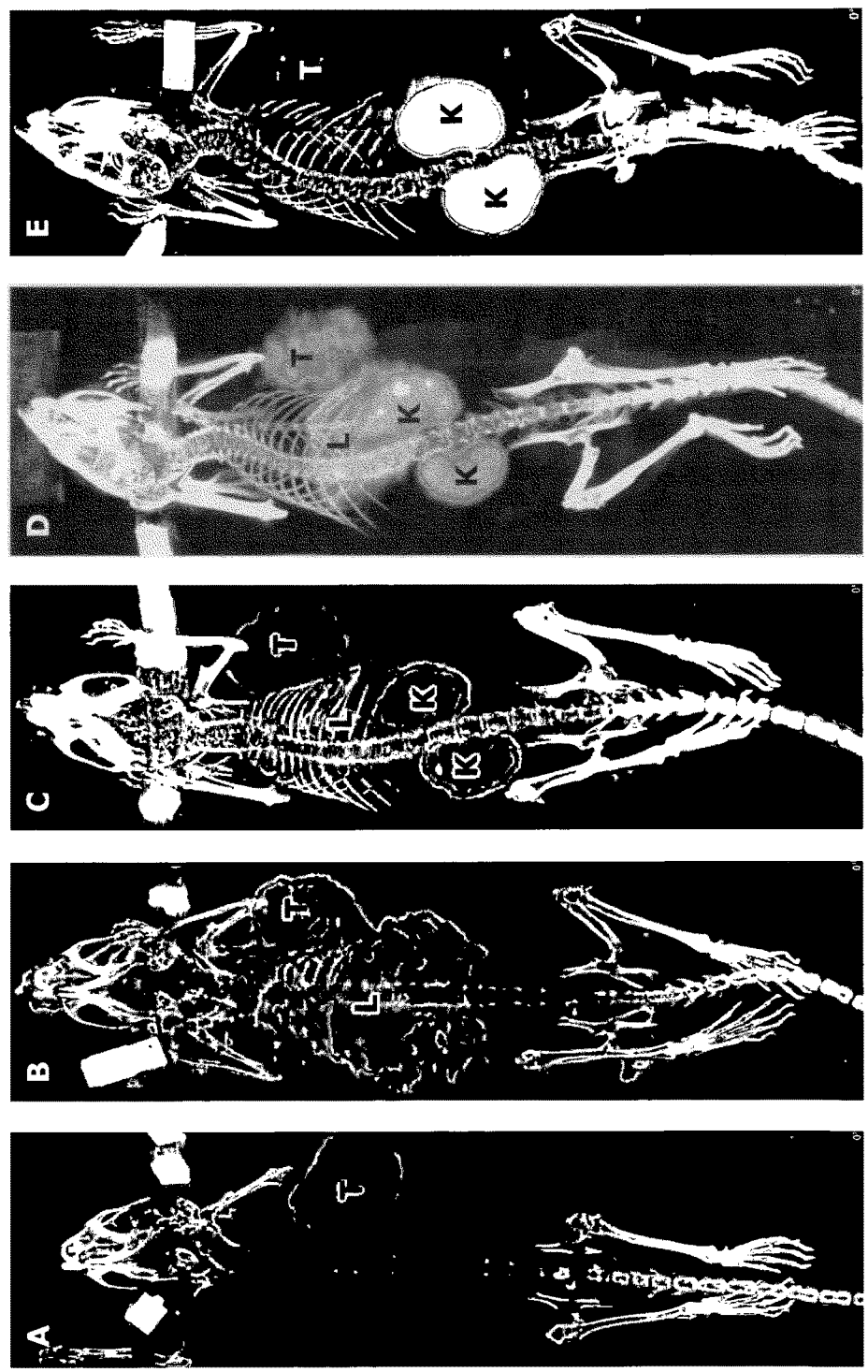
Figure 14:
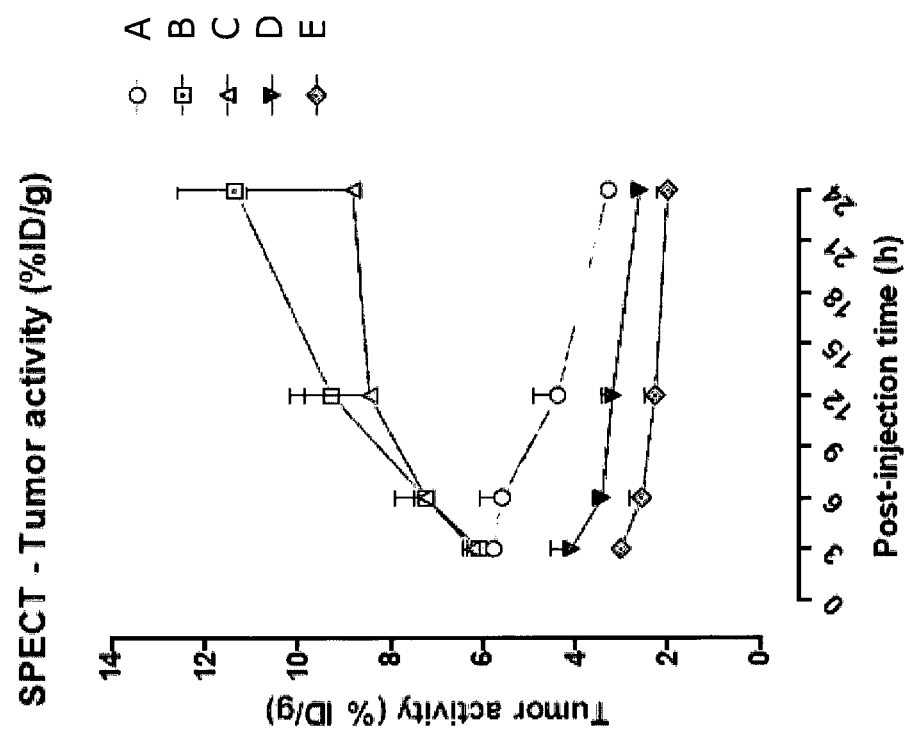

FIG. 14 A shows SPECT-imaging results of 111In-(IIIa) (A), 111In-(13) (B), 111In-(15) (C), 111In-(18) (D) and 111In-(22) (E). 12 h post injection. T denotes HT29 tumor, K denotes kidneys and L denotes liver; and FIG. 14 B shows the accumulated tumor activity over time as percentage of the injected dose normalized to the weight of the tissue.

It will be acknowledged by a person skilled in the art that the examples disclosed herein are grouped in example part I and example part II. Example part I comprise 30 examples which are related to the conjugate of the invention. Example part I refers to FIGS. 1 to 4 of the instant application. Example part II comprises 32 examples which are related to a compound the structure of which corresponds, except $R^7$, to a compound of formula (2) of the conjugate of the invention. The compound the structure of which corresponds, except $R^7$, to a compound of formula (2) of the conjugate of the invention is disclosed in international patent application PCT/EP2013/003700 the disclosure of which is incorporated herein by reference. Example part II refers to FIGS. 5 to 13 of the instant application. Example part II provides evidence that the compound of formula (2) which is contained in the conjugate to the invention as a first targeting moiety TM1 and/or a second targeting moiety TM2 shows, when used in a non-conjugated form surprising and unexpected effects which effects are equally shown by the conjugate of the invention. To the extent identical figure numbers, table number, compound numbers, substituent references, abbreviations or any other potentially or actually conflicting indications are used in both example part I and example part II, it will be understood that example part I and example part II are contained in the instant application independently from each other and that example part I is related to the conjugate of the invention so that any such indication of example part I typically corresponds to the one used in the general part of the instant application and more specifically in the general part of the instant specification.

EXAMPLES

Example Part I

Abbreviations used in the instant application and the following examples in particular are as follows:

1206- or -1206 means

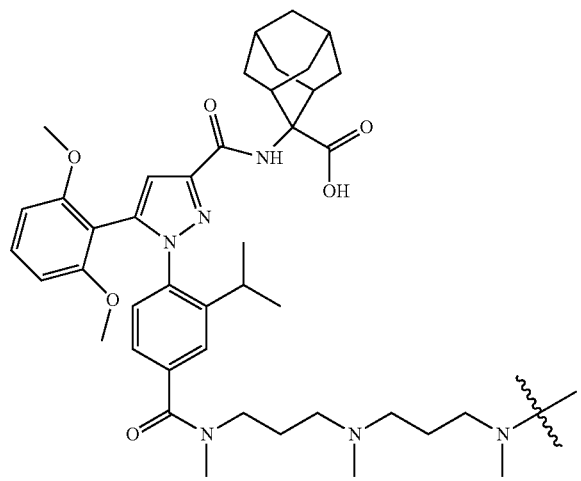 [SMILES: *N(C)CCCN(C)CCCN(C)C(=O)c1ccc(-n2nc(C(=O)NC3(C(=O)O)C4CC5CC(C4)CC3C5)cc2-c2c(OC)cccc2OC)c(C(C)C)c1]

ACN means acetonitrile
Ahx means 6-Aminohexanoic acid
Amf means alpha-methyl-L-phenylalanine
amu means atomic mass unit
aq. means aqueous
Arg means arginine
B1 means bradykinin B1 receptor
β-Cys-$NH_2$ means cysteine amide
-(β-Cys-$NH_2$)— means

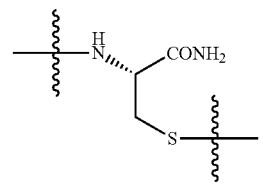 [SMILES: *N[C@@H](CS*)C(N)=O]

CM means ChemMatrix™
DCM means dichloromethane
Dde means N-(1-(4,4-dimethyl-2,6-dioxocyclohexylidene) ethyl)
DEG means di ethylene glycol dimethacrylate
DIC means N,N'-Diisopropylcarbodiimide
DIPEA means diisopropylethylamine
DOTA means 1,4,7,10-tetraazacyclododecane-1,4,7,10-tetraacetic acid
DOTA(tBu)$_3$-OH means Tri-tert-butyl-1,4,7,10-tetraazacyclo-dodecane-1,4,7,10-tetraacetate
DMF means N,N-dimethylformamide
EC50 means half-maximal excitatory concentration
ε-Lys-$NH_2$ means lysine amide
-(ε-Lys-$NH_2$)— means

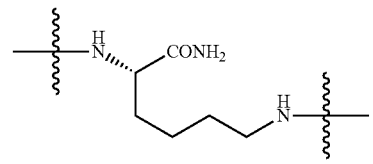 [SMILES: *NCCCC[C@H](N*)C(N)=O]

$Et_2O$ means Diethylether

EtOAc means ethylacetate
FITC means 5(6)-fluorescein isothiocyanate
Fmoc means 9-Fluorenylmethoxycarbonyl
Gab means gamma-amino butyric acid
GABA means gamma-amino butyric acid
Glutar means glutaric acid
-Glutar- means

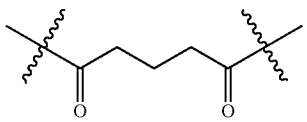 [SMILES: *C(=O)CCCC(*)=O]

h means hour(s)
HATU means O-(7-azabenzotriazol-1-yl)-N,N,N',N'-tetramethyluronium hexafluorophosphate
HFIP means hexafluoro-2-isopanol
HOAc means acetic acid
HOAt means 1-Hydroxy-7-azabenzotriazole
HPLC means high performance liquid chromatography
IC50 means half-maximal inhibitory concentration
kDa means 1000 Dalton
LAP means latency-associated peptide
LC-MS means high performance liquid chromatography coupled with mass spectrometry
LDH means lactate dehydrogenase
LiOH means lithium hydroxide
Leu means leucine
M means molar or mol per Liter
max. means maximum
MeOH means Methanol
Mic means 3-(2,5-Dioxo-2,5-dihydro-pyrrol-1-yl)-propionic acid or 3-(N-maleimido) propionic acid
-Mic- means

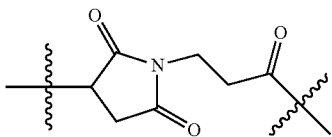 [SMILES: *C(=O)CCN1C(=O)CC(*)C1=O]

min means minute(s)
MTBE means Methyl-tert-butylether
Mtt means Methyltrityl
MWCO means molecular weight cut-off
NaHCO$_3$ means sodium hydrogencarbonate
NaCl means sodium chloride
Na$_2$SO$_4$ means sodium sulfate
n.d. means not determined
NHS means N-Hydroxysuccinimide
NMP means 1-methyl-2-pyrrolidone
NOS means Not otherwise specified
NT means neurotensin
NTR1 means neurotensin receptor 1
Oic means L-octahydroindol-2-carbonsäure
Pbf means 2,2,4,6,7-pentamethyl-2,3-dihydrobenzofuran-5-sulfonyl
PBS means phosphate buffered saline
PET mean positron emission tomography
prep. means preparative
Pro means proline
PS means polystyrene
PyBOP means benzotriazole-1-yl-oxy-tris-pyrrolidino-phosphonium hexafluorophosphate
RLB means radioligand binding assay
RP means reversed phase
RT means room temperature
R$_t$ means retention time
sat. means saturated
SPECT means single photon emission computed tomography
-Succinyl- means

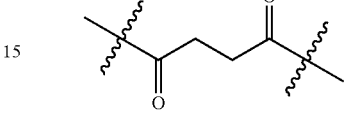

Taxol or Paclitaxel means

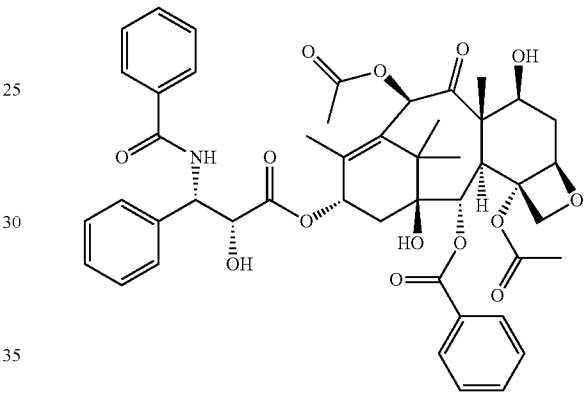

tBu means tert. butyl
TFA means trifluoroacetate or trifluoroacetic acid
TGF means transforming growth factor
TIPS means triisopropylsilane
TLC means thin layer chromatography
Tle means tert. leucine or tert. butyl glycine
Ttds means N-(3-{2-[2-(3-Amino-propoxy)-ethoxy]-ethoxy}-propyl)-succinamic acid
Tyr means tyrosine ⬤ as used in structural formulas or figures represents a functionalized solid material (solid phase synthesis resin)

Example 1: Material and Methods

The materials and methods as well as general methods are further illustrated by the following examples.

Solvents:

Solvents were used in the specified quality without further purification. Acetonitrile (Gradient grade, Sigma-Aldrich); dichloromethane (AnalaR Normapur, VWR); ethylacetate (laboratory reagent grade, Fisher Scientific); N,N-dimethyl-formamide (peptide synthesis grade, Biosolve); 1-methyl-2-pyrolidone (biotech. grade, Sigma-Aldrich) 1,4-dioxane (Emplura, Merck); methanol (p. a., Merck).

Water:

Milli-Q Plus, Millipore, demineralized.

Chemicals:

Chemicals were synthesized according to or in analogy to literature procedures or purchased from Sigma-Aldrich- Fluka (Deisenhofen, Germany), Bachem (Bubendorf, Switzerland), VWR (Darmstadt, Germany), Polypeptide (Strasbourg, France), Novabiochem (Merck Group, Darmstadt, Germany), Acros Organics (distribution company Fisher Scientific GmbH, Schwerte, Germany), Iris Biotech (Marktredwitz, Germany), Amatek Chemical (Jiangsu, China), Roth (Karlsruhe, Deutschland), Molecular Devices (Chicago, USA), Biochrom (Berlin, Germany), Peptech (Cambridge, Mass., USA), Synthetech (Albany, Oreg., USA), Pharmacore (High Point, NC, USA), PCAS Biomatrix Inc (Saint-Jean-sur-Richelieu, Quebec, Canada), Alfa Aesar (Karlsruhe, Germany), Tianjin Nankai Hecheng S&T Co., Ltd (Tianjin, China) and Anaspec (San Jose, Calif., USA) or other companies and used in the assigned quality without further purification.

SR-142948 is (2-[(5-(2,6-Dimethoxy-phenyl)-1-{4-[(3-dimethylamino-propyl)-methyl-carbamoyl]-2-isopropyl-phenyl}-1H-pyrazole-3-carbonyl)-amino]-adamantane-2-carboxylic acid, >97%) and was purchased from Tocris Bioscience (Bristol, UK).

1-(4-Carboxy-2-isopropyl-phenyl)-5-(2,6-dimethoxy-phenyl)-1H-pyrazole-3-carboxylic acid methyl ester (87) was prepared according to literature procedures as disclosed in U.S. Pat. No. 5,723,483.

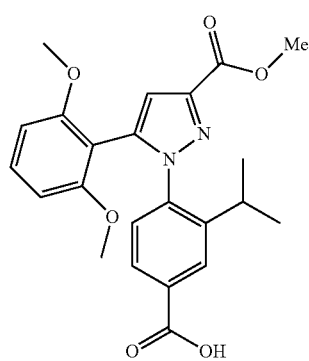

(87)

Paclitaxel hemisuccinyl NHS ester (88) was prepared as described in Ryppa et al., *Int J Pharm*, 2009, 368, 89-97.

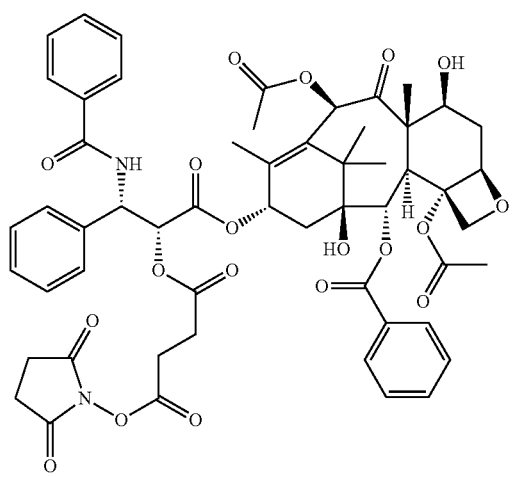

(88)

Biologicals:
MAB1909
Monoclonal anti-Tenascin antibody clone α14-B (Cat-# MAB1909) was purchased from Merck Millipore (Billerica, Mass., USA). This purified murine IgG1κ antibody recognizes an epitope contained within the domain B of human tenascin.
MAB3035
Monoclonal anti-EphA2 antibody clone 371805 (Cat-# MAB3035) was purchased from (R&D Systems, MN, USA). This purified murine IgG2A antibody recognizes human EphA2 (UniProt Accession # P29317).

HPLC/MS analyses were performed by injection of 5 μl of a solution of the sample, using a 2 step gradient for all chromatograms (5-50% B in 5 min, followed by 50-100% B in 2 min, A: 0.05% TFA in water and B: 0.05% TFA in ACN). RP columns were from Phenomenex (Type Luna C-18, 3 μm, 50×2.00 mm, flow 0.5 ml, HPLC at room temperature); Mass spectrometer: Thermo Finnigan Advantage and/or LCQ Classic (both ion trap), ESI ionization, helium served as impact gas in the ion trap. Excalibur version 1.4 was used as software. UV detection was done at λ=230 nm. Retention times ($R_t$) are indicated in the decimal system (e.g. 1.9 min=1 min 54 s) and are referring to detection in the mass spectrometer. The dead time between injection and UV detection (HPLC) was 0.45 min, and for the delay between UV detection and mass detection was corrected in the chromatogram. The accuracy of the mass spectrometer was approx. ±0.5 amu.

Preparative HPLC:
Preparative HPLC separations were done with the columns and gradients described in the individual examples. For the gradient the following solvents were used:
A: 0.05% TFA in $H_2O$
B: 0.05% TFA in ACN A linear binary gradient was used in all separations. For instance: If the gradient is described as: "20 to 60% B in 30 min", this means a linear gradient from 20% B (and 80% A) up to 60% B (and 40% A) within 30 min. The flow-rate depends on the column size: For 25 mm diameter of the column it is 30 ml/min and for 50 mm diameter of the column it is 60 ml/min, respectively.

General procedures for Automated/Semi-automated Solid-Phase Synthesis:
Automated solid-phase of peptides and polyamides was performed on a Tetras Peptide Synthesizer (Advanced Chemtec) in 50 μmol and 100 μmol scales. Manual steps were performed in plastic syringes equipped with frits (material PE, Roland Vetter Laborbedarf OHG, Ammerbuch, Germany). The amount of reagents in the protocols described corresponds to the 100 μmol scale.

Solid-phase synthesis was performed on polystyrene (cross linked with 1,4-divinylbenzene (PS) or di (ethylene glycol) dimethacrylate (DEG)), ChemMatrix (CM) or TentaGel (TG) resin. Resin linkers were trityl, wang and rink amide.

Resin Loading:
In case of the trityl linker the attachment of the first building block (resin loading) was performed as follows. The resin (polystyrene (PS) trityl chloride, initial loading: 1.8 mmol/g) was swollen in DCM (5 ml) for 30 minutes and subsequently washed with DCM (3 ml, 1 minute). Then the resin was treated with a mixture of the corresponding building block (0.5 mmol, 5 eq.) and DIPEA (350 μl, 3.5 mmol, 35 eq.) in DCM (4 ml) for 1 hour. Afterwards the resin was washed with methanol (5 ml, 5 minutes) and DMF (3 ml, 2×1 minute).

In case of the wang linker pre-loaded resins (polystyrene (PS) and TentaGel (TG)) were employed.

In case of the rink amide linker the attachment of the first residue the resin (CM, DEG) was performed with the same procedure as for the chain assembly as described below.

Fmoc-Deprotection:

After swelling in DMF the resin was washed with DMF and then treated with piperidine/DMF (1:4, 3 ml, 2 and 20 minutes) and subsequently washed with DMF (3 ml, 5×1 minute).

Dde-Deprotection:

After swelling in DMF the resin was washed with DMF and then treated with hydrazine-hydrate/DMF (2/98, 3 ml 2×10 minutes) and subsequently washed with DMF (3 ml, 5×1 minute).

Mtt-Deprotection:

After swelling in DCM the resin was washed with DCM and then treated with HFIP/DCM (7/3, 4-6 ml, 4 hours) and subsequently washed with DCM (3 ml, 3×1 minute), DMF (3 ml, 3×1 ml) and DIPEA (0.9 M in DMF, 3 ml, 1 minute) to deprotonate the only just deprotected amine.

Solutions of Reagents:
Building Blocks (0.3 M in DMF or NMP)
DIPEA (0.9 M in DMF)
HATU (0.4 M in DMF)
Acetic anhydride (0.75 M in DMF)
Coupling: Coupling of Building Blocks/Amino Acids (Chain Assembly):

Unless otherwise stated coupling of building blocks was performed as follows: After subsequent addition of solutions of the corresponding building block (1.7 ml, 5 eq.), DIPEA solution (1.15 ml, 10 eq.) and HATU solution (1.25 ml, 5 eq.) the resin was shaken for 45 min. If necessary the resin was washed with DMF (3 ml, 1 minute) and the coupling step was repeated.

Terminal Acetylation:

After addition of DIPEA solution (1.75 ml, 16 eq.) and acetic anhydride solution (1.75 ml, 13 eq.) the resin was shaken for 10 minutes. Afterwards the resin was washed with DMF (3 ml, 6×1 minutes).

Cleavage Method A: Cleavage of Protected Fragments from Hyper-Acid Labile Resin:

After the completion of the assembly of the sequence the resin was finally washed with DCM (3 ml, 4×1 minute). Then the resin was treated HFIP/DCM (7/1, 4 ml, 4 hours) and the collected solution evaporated to dryness. The residue was purified with preparative HPLC or used without further purification.

Cleavage Method B: Cleavage of Unprotected Fragments (Complete Resin Cleavage):

After the completion of the assembly of the sequence the resin was finally washed with DCM (3 ml, 4×1 minute), dried in the vacuum overnight and treated with TFA, TIPS and water (95/2.5/2.5) (unless otherwise stated). Afterwards the cleavage solution was poured into a mixture of MTBE and cyclohexane (1/1, 10-fold excess compared the volume of cleavage solution), centrifuged at 4° C. for 5 minutes and the precipitate collected and dried in the vacuum.

Compounds were named using AutoNom version 2.2 (Beilstein Informationssysteme Copyright© 1988-1998, Beilstein Institut für Literatur der Organischen Chemie licensed to Beilstein Chemiedaten and Software GmbH), where appropiate.

Preparation of Compounds:

The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are incorporated herein by reference.

Specific embodiments for the preparation of compounds of the invention are provided in the following examples. Unless otherwise specified all starting materials and reagents are of standard commercial grade, and are used without further purification, or are readily prepared from such materials by routine methods. Those skilled in the art of organic synthesis will recognize in light of the instant disclosure that starting materials and reaction conditions may be varied including additional steps employed to produce compounds encompassed by the present invention.

Example 2: Synthesis of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester bound to trityl resin (86)

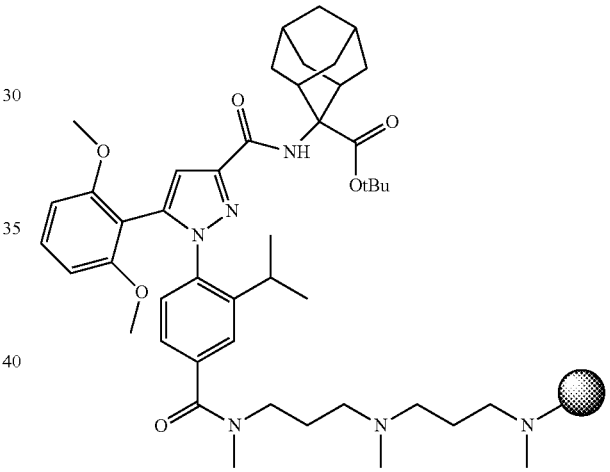

(86)

Figure 1:
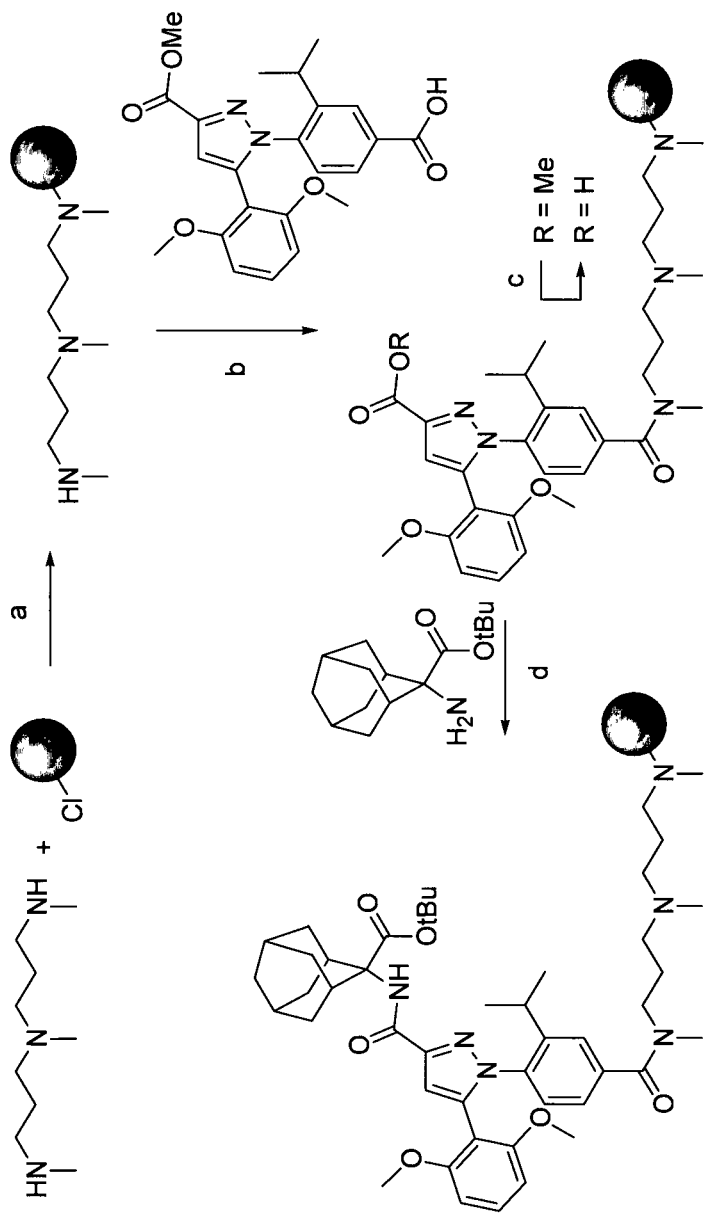

A. Loading of chlorotrityl polystyrene Resin with N,N-Bis[3-(methylamino)-propyl]methylamine (FIG. 1 step a)

Tritylchloride polystyrene resin (initial loading 1.8 mmol/g, 1.11 g, 2 mmol, 1.0 eq.) was swollen in DCM for 30 min. Then N,N-Bis[3-(methylamino)-propyl]methylamine (1.6 ml, 8 mmol, 4 eq.) in DCM (6.5 ml) was added to the resin and the mixture was shaken overnight. Afterwards the resin was washed successively with DMF, DCM and diethyl ether (5×/3×/1×) and dried in the vacuum.

B. Coupling of 1-(4-Carboxy-2-isopropyl-phenyl)-5-(2,6-dimethoxy-phenyl)-1H-pyrazole-3-carboxylic acid methyl ester (FIG. 1 step b)

N,N-Bis[3-(methylamino)-propyl]methylamine charged trityl resin (1 g, 1.8 mmol, 1.0 eq.) was swollen in DMF for 30 min. The resin was washed with DMF/DIPEA (9/1) (to remove residual N,N-Bis[3-(methylamino)-propyl]methyl-amine hydrochloride) and DMF (3×/3×).

1-(4-Carboxy-2-isopropyl-phenyl)-5-(2,6-dimethoxy-phenyl)-1H-pyrazole-3-carboxylic acid methyl ester (87) (1.15 g, 2.7 mmol, 1.5 eq.) [prepared as disclosed in U.S. Pat. No. 5,723,483], HATU (1.03 g, 2.7 mmol, 1.5 eq.) and DIPEA (937 µl, 5.4 mmol, 3 eq.) were dissolved in DMF (18 ml) and mixed thoroughly for 1 min. After addition of the activated building block the resin was shaken overnight. The resin was washed (DMF five times, DCM three times and diethyl ether) and dried in the vacuum. The completeness of the reaction was assured as follows: A resin sample was treated with a solution of benzoic acid, HATU and DIPEA (1/1/2) in DMF for 30 min. After washing with DMF and DCM, TFA was added to the resin. Absence of the benzoic acid N,N-Bis[3-(methylamino)-propyl]methyl amide in LC-MS indicated absence of free amino functions on the resin thus providing evidence of the completed coupling of 1-(4-Carboxy-2-isopropyl-phenyl)-5-(2,6-dimethoxy-phenyl)-1H-pyrazole-3-carboxylic acid methyl ester.

C. Hydrolysis of the methylester (FIG. 1 step c)

The resin (1.64 g, 1.75 mmol, 1.0 eq.) (prepared in section B) was treated overnight with dioxane (35 ml) and LiOH hydrate (689 mg, 16 mmol, 10 eq.) in water (12 ml). The procedure was repeated once, the resin was subsequently washed with water, DMF and DCM (3×/3×/3×) and dried in the vacuum.

D. Coupling of 2-Amino-adamantane-2-carboxylic acid tert-butyl ester (FIG. 1 step d)

The resin (0.7 g, 0.75 mmol, 1.0 eq.) (prepared in section C) was swollen in DMF for 30 min. Then HOAt (153 mg, 1.13 mmol, 1.5 eq.), DIC (232 µl, 1.5 mmol, 2.0 eq.) and 2-amino-adamantane-2-carboxylic acid tert-butyl ester (942 mg, 3.75 mmol, 5.0 eq.) were dissolved in a mixture of DMF and DCM (2:1) (6 ml) and subsequently added to the resin. After 2.5 hours additional DIC (232 µl, 1.5 mmol, 2.0 eq.) was added. The resin was left to shake for 60 hours after which the reaction was complete. Afterwards the resin was washed with DMF (3×) and DCM (3×) and dried in the vacuum.

Example 3: Synthesis of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (58)

(58)

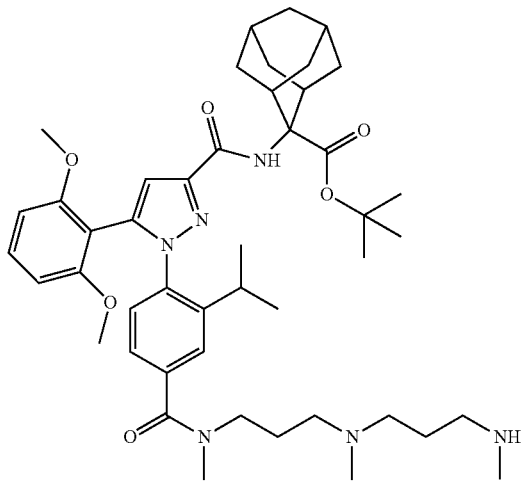

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester resin (86) (0.7 g, 0.75 mmol, 1.0 eq.) was treated four times with a mixture of TFA, TIPS and DCM (2/5/93). To prevent premature loss of the tBu protecting groups the resulting solution was immediately poured into aqueous buffer solution (10 ml, pH=8, 100 mM $NH_4(CO_3)_2$). All DCM-buffer mixtures were combined and the organic layer reduced to a minimum by evaporation. To the remaining aqueous solution ACN (5 ml) was added and the mixture was freeze-dried to yield 800 mg of crude product.

The residue was subjected to HPLC purification (15 to 45% B in 30 min, Agilent PLRP-S 25×150 mm) to give the title compound (210 mg, 26.3 µmol, 35.0%). HPLC: $R_t$=5.5 min. MS: m/z=799.4 ([M+H]$^+$, calculated 799.5). $C_{46}H_{66}N_6O_6$ (MW=799.05).

Example 4: Synthesis of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59)

(59)

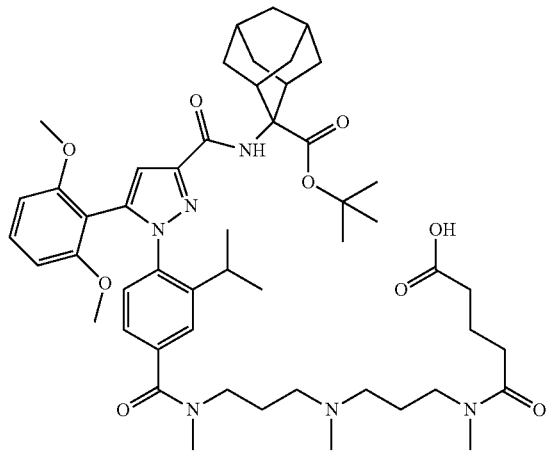

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester resin (86) (1.5 mmol, 1.0 eq.) was treated four times with a mixture of TFA, TIPS and DCM (2/5/93). To prevent premature loss of the tBu protecting group the resulting solution was immediately poured into aqueous buffer solution (10 ml, pH=8, 100 mM $NH_4(CO_3)_2$). All DCM-buffer mixtures were combined and the organic layer reduced to a minimum by evaporation. To the remaining aqueous solution ACN (5 ml) was added and the mixture was freeze-dried to yield 900 mg of crude (58).

The latter was dissolved in DMF (18 ml) and the pH value of solution adjusted to pH=7.5 by addition of DIPEA (0.2 ml). Then glutaric anhydride (193 mg, 1.7 mmol, 1.5 eq.) was added to the solution. The resulting drop of the pH value to pH=4.5 was compensated by addition of DIPEA (0.5 ml) and the solution readjusted to pH=7.5. After 6 hours and after stirring overnight more glutaric anhydride (64 mg, 0.85 mmol, 0.5 eq.) was added. Eventually the solvent was removed in the vacuum. The residue was subjected to HPLC purification (30 to 60% B in 30 min, Agilent PLRP-S 50×150 mm) to give the title compound (425 mg, 46.5 μmol, 31.0%). HPLC: $R_t$=6.2 min. MS: m/z=913.32 ([M+H]$^+$, calculated 913.54). $C_{51}H_{72}N_6O_9$ (MW=913.15).

Example 5: 2-({5-(2,6-Dimethoxy-phenyl)-1-[4-({3-[(3-{[3-(2,5-dioxo-2,5-dihydro-pyrrol-1-yl)-propionyl]-methyl-amino}-propyl)-methyl-amino]-propyl}-methyl-carbamoyl)-2-isopropyl-phenyl]-1H-pyrazole-3-carbonyl}-amino)-adamantane-2-carboxylic acid/1206-Mic (57)

(57)

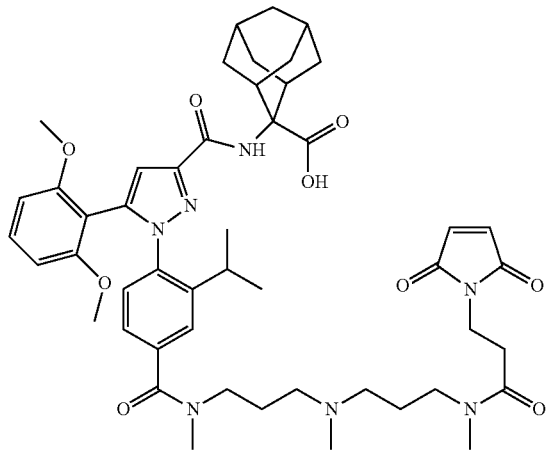

A. 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester resin (86) (0.15 g, 0.16 mmol, 1.0 eq.) was treated with a mixture of TFA and DCM (1/4) for 2 hours. Then all volatiles were evaporated and the residue subjected to HPLC purification (20 to 50% B in 30 min, Agilent PLRP-S 25×150 mm) to yield 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (17.6 mg, 23.7 μmol, 15%). HPLC: $R_t$=4.6 min. MS: m/z=743.44 ([M+H]$^+$, calculated 743.45). $C_{42}H_{58}N_6O_6$ (MW=742.95).

B. 2-({5-(2,6-Dimethoxy-phenyl)-1-[4-({3-[(3-{[3-(2,5-dioxo-2,5-dihydro-pyrrol-1-yl)-propionyl]-methyl-amino}-propyl)-methyl-amino]-propyl}-methyl-carbamoyl}-2-isopropyl-phenyl]-1H-pyrazole-3-carbonyl}-amino)-adamantane-2-carboxylic acid (57)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (15 mg, 20 μmol, 1 eq.) was dissolved in DMF (300 μl). 3-(Maleimido)propionic acid N-succinimidyl ester (5.4 mg, 20 μmol, 1 eq.) dissolved in DMF (150 μl) and DIPEA (2 μl) were added to the solution. After stirring for 6 hours all volatiles were removed in the vacuum. The residue was subjected to HPLC purification (25 to 45% B in 30 min, Agilent PLRP-S 25×150 mm) to give the title compound (6.16 mg, 6.9 μmol, 34.0%). HPLC: $R_t$=5.5 min. MS: m/z=894.35 ([M+H]$^+$, calculated 894.47). $C_{49}H_{63}N_7O_9$ (MW=894.07).

Example 6: 1206-Glutar-Ttds-(ε-Lys-NH$_2$)-Glutar-NHS (60)

(60)

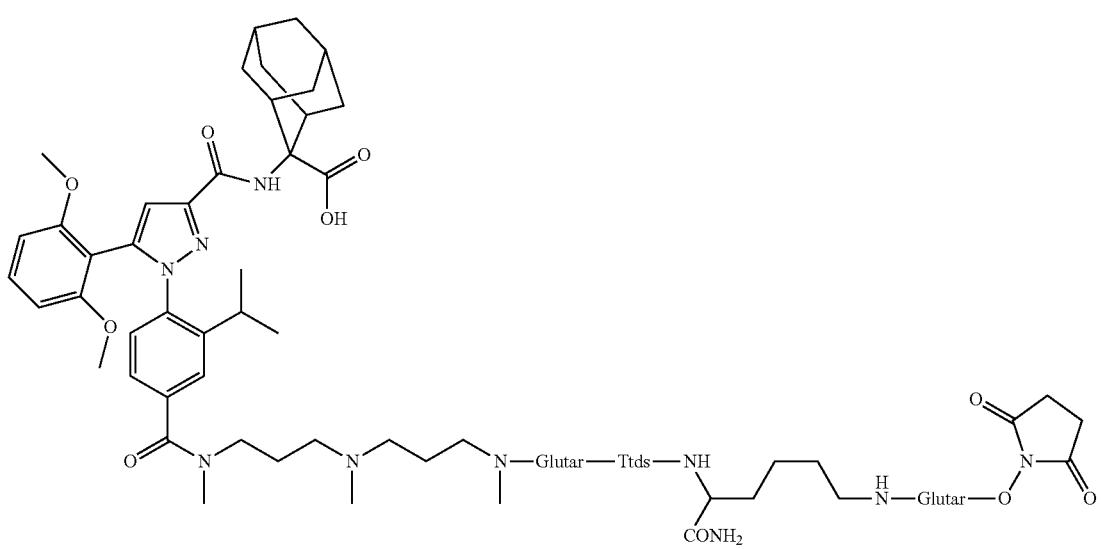

The initial steps of the synthesis of the compound were performed according to the general procedures for Automated/Semi-automated Solid-Phase Synthesis. Rink amide resin (DEG, initial loading 0.45 mmol/g/100 µmol) was charged with Fmoc-Lys(Mtt)-OH (Resin loading) and the Fmoc group of the latter was removed and afterwards Fmoc-Ttds-OH was coupled and Fmoc deprotected. To the resin a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (109.6 mg, 110 µmol, 1.2 eq), HOAt (16.4 mg, 110 µmol, 1.2 eq.), DIPEA (34.4 µl, 240 µmol, 2.4 eq.) and DIC (18.4 µl, 110 µmol, 1.2 eq.) in NMF/DCM (1/1, 4 ml) was added after a pre-activation time of 5 minutes. After 24 hours the resin was washed with DMF (3 ml, 5×1 min). The resin was divided and the following steps were performed with 25 µmol resin, which was subjected to complete resin cleavage (Cleavage method A) for 75 minutes. The cleavage solution was evaporated to dryness and the remaining residue dissolved in DMF (1 ml). DIPEA (15 µl) was added to adjust the pH-value to pH=7.5. To that solution a solution of Disuccinimidyl glutarate (12.23 mg, 37.5 µmol, 1.5 eq.) in DMF (1 ml) was slowly added. After 30 minutes all volatiles were removed in the vacuum. The residue was subjected to HPLC purification (20 to 45% B in 30 min, Agilent PLRP-S 25×150 mm) to give the title compound (6.32 mg, 4.2 µmol, 16.8%). HPLC: $R_t$=5.1 min. MS: m/z=749.93 ([M+2H]$^{2+}$, calculated 749.89). $C_{76}H_{112}N_{12}O_{19}$ (MW=1497.77).

Example 7: 1206-Glutar-Ttds-(ε-Lys-NH$_2$)-Mic (61)

The initial steps of the synthesis of the compound were performed according to the general procedures for Automated/Semi-automated Solid-Phase Synthesis. Rink amide resin (DEG, initial loading 0.45 mmol/g) (100 µmol) was charged with Fmoc-Lys(Mtt)-OH (Resin loading) and the Fmoc group of the latter was removed and afterwards Fmoc-Ttds-OH was coupled and Fmoc deprotected. To the resin a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (109.6 mg, 110 µmol, 1.2 eq), HOAt (16.4 mg, 110 µmol, 1.2 eq.), DIPEA (34.4 µl, 240 µmol, 2.4 eq.) and DIC (18.4 µl, 110 µmol, 1.2 eq.) in NMP/DCM (1/1, 4 ml) was added after a pre-activation time of 5 minutes. After 24 hours the resin was washed with DMF (3 ml, 5×1 min). The resin was divided and the following steps were performed with 25 µmol resin, which was subjected to Mtt cleavage (Mtt-deprotection/removal). To the resin a mixture of 3-maleinimidopropionic acid (22 mg, 125 µmol, 5 eq.) in DMF (425 µl), HATU solution (290 µl, 5 eq.) and DIPEA solution (313 µl, 10 eq.) were added after a pre-activation time of 5 minutes. After 2 hours the resin was washed with DMF (3 ml, 5×1 min) and subjected to complete resin cleavage (Cleavage method A) for 2 hours. The cleavage solution was evaporated to dryness and the residue was lyophilized. Finally the obtained solid was subjected to HPLC purification (25 to 50% B in 30 min, Agilent PLRP-S 25×150 mm) to give the title compound (8.09 mg, 4.2 µmol, 16.8%). HPLC: $R_t$=5.0 min. MS: m/z=719.97 ([M+2H]$^{2+}$, calculated 719.86). $C_{74}H_{108}N_{12}O_{17}$ (MW=1437.72).

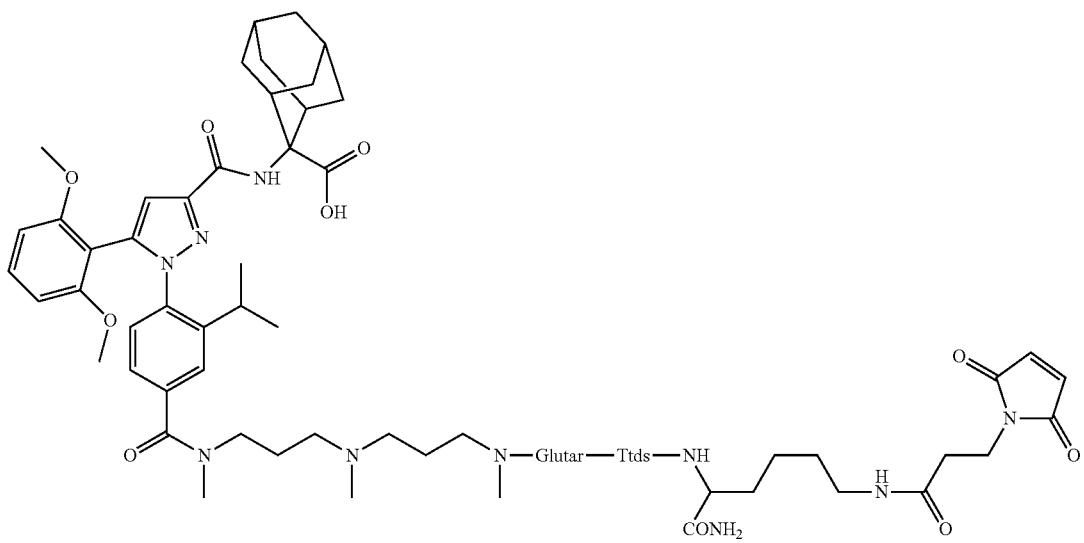

(61)

Example 8:
1206-Glutar-Ttds-Lys(DOTA)-Ttds-GABA-1206
(12)

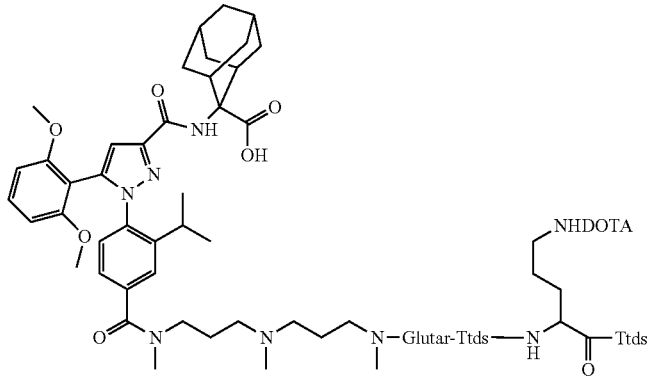
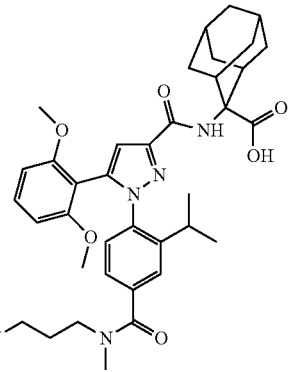

(12)

The initial steps of the synthesis of the compound were performed according to the general procedures for Automated/Semi-automated Solid-Phase Synthesis. Trityl resin (PS, 100 µmol) was charged with Fmoc-GABA-OH and the Fmoc group of the latter was removed. Two iterative repetitions of Coupling (Coupling) and Fmoc removal (Fmoc-deprotection) (Fmoc-Ttds-OH, Dde-Lys(Fmoc)-OH) furnished the resin bound Dde-Lys-Ttds-GABA. Then DOTA (tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection), a further unit of Fmoc-Ttds-OH coupled and the Fmoc group of the latter removed. Afterwards glutaric anhydride (22.8 mg, 0.2 mmol, 2 eq.) in DMF (3 ml) was added to the resin. After 4 hours the resin was washed with DCM (3 ml, 1 minute) and HO-Glutar-Ttds-Lys(DOTA(tBu)$_3$)-Ttds-GABA-OH cleaved from the resin (Cleavage Method B). HPLC purification (15 to 40% B in 30 min, Agilent PLRP-S 25×150 mm) yielded the purified intermediate (41.42 mg, 27.5 µmol, 27.5%). HPLC: R$_t$=4.1 min. MS: m/z=753.24 ([M+2H]$^{2+}$, calculated 753.42). C$_{71}$H$_{129}$N$_{11}$O$_{23}$ (MW=1504.84). The purified HO-Glutar-Ttds-Lys(DOTA(tBu)$_3$)-Ttds-GABA-OH (20 mg, 14.29 µmol, 1 eq.) was dissolved in DMF (2 ml). To the solution 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (58) (22.84 mg, 28.6 µmol, 2 eq.), HOAt (3.9 mg, 28.6 µmol, 2 eq.), DIPEA (7.45 µl, 42.9 µmol, 3 eq.) and DIC (3.3 µl, 21.4 µmol, 1.5 eq.) were added. The addition of DIC (3.3 µl, 21.4 µmol, 1.5 eq.) was repeated after overnight stirring. Furthermore the reaction temperature was increased to 40° C. for 4 hours. Then all volatiles were removed in the vacuum and the residue was treated with TFA/TIPS/water (95/2.5/2.5, 4 hours). The crude product was obtained from the cleavage solution by precipitation with MTBE/cyclohexane and centrifugation. After drying in the vacuum, the residue was subjected to HPLC purification (25 to 50% B in 30 min, Agilent PLRP-S 25×150 mm) to give the title compound (12.96 mg, 4.6 µmol, 16.9%). HPLC: R$_t$=5.6 min. MS: m/z=929.75 ([M+3H]$^{3+}$, calculated 929.80). C$_{143}$H$_{217}$N$_{23}$O$_{33}$ (MW=2786.39).

Example 9: 1206-Glutar-Lys(DOTA)-GABA-1206
(13)

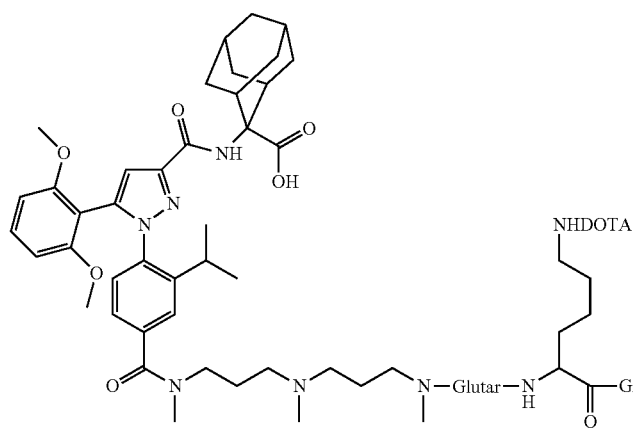
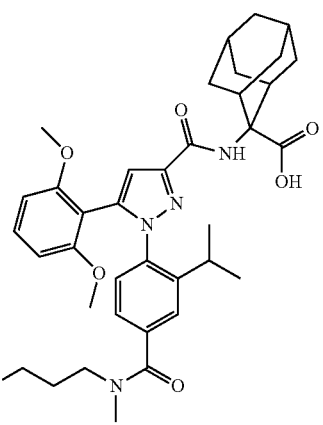

(13)

The initial steps of the synthesis of the compound were performed according to the general procedures for Automated/Semi-automated Solid-Phase Synthesis. Trityl resin (PS, 100 µmol) was charged with Fmoc-GABA-OH (Resin loading) and the Fmoc group of the latter was removed (Fmoc-deprotection). Dde-Lys(Fmoc)-OH was coupled and Fmoc group removed from the lysine side chain. Then DOTA(tBu)$_3$-OH ((172 mg, 0.3 mmol, 3 eq.) directly dissolved in HATU solution (0.75 ml, 3 eq.) and DIPEA solution (0.7 ml, 6 eq.) for pre-activation and improved solubility) was coupled to the latter. The Dde protecting group was removed (Dde-deprotection) and glutaric anhydride (22.8 mg, 0.2 mmol, 2 eq.) in DMF (3 ml) added to the resin. After 4 hours the resin was washed with DCM (3 ml, 1 minute) and HO-Glutar-Lys(DOTA(tBu)$_3$)-GABA-OH cleaved from the resin (Cleavage Methode B). The crude partially protected intermediate (22 mg, 30 µmol, 30%) was dissolved in DMF (1.5 ml). To the solution 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (58) (36 mg, 45 µmol, 1.5 eq.), HOAt (16.3 mg, 120 µmol, 4 eq.), DIPEA (31.3 µl, 180 µmol, 6 eq.) and DIC (14 µl, 90 µmol, 3 eq.) were added. After 4 hours additional (58) (24 mg, 30 µmol, 1 eq.) was added and the solution stirred overnight. Then all volatiles were removed in the vacuum and the residue was treated with TFA/TIPS/water (95/2.5/2.5, 4 hours). The crude product was obtained from the cleavage solution by precipitation with MTBE/cyclohexane and centrifugation. After drying in the vacuum, the residue was subjected to HPLC purification (25 to 55% B in 30 min, Agilent PLRP-S 25×150 mm) to give the title compound (7.2 mg, 3.3 µmol, 11.0%). HPLC: R$_t$=5.8 min. MS: m/z=728.29 ([M+3H]$^{3+}$, calculated 728.22). C$_{115}$H$_{165}$N$_{19}$O$_{23}$ (MW=2181.65).

Example 10: 1206-Glutar-Ahx-Lys(DOTA)-(ε-Lys-NH$_2$)-Glutar-1206 (14)

The initial steps of the synthesis of the compound were performed in accordance with the general procedures for Automated/Semi-automated Solid-Phase Synthesis. Rink amide resin (DEG, initial loading 0.45 mmol/g/100 µmol) was charged with Fmoc-Lys(Mtt)-OH (Resin loading) and the Fmoc group of the latter was removed (Fmoc-deprotection). Dde-Lys(Fmoc)-OH was coupled and Fmoc group removed from the lysine side chain. Then DOTA(tBu)$_3$-OH ((172 mg, 0.3 mmol, 3 eq.) directly dissolved in HATU solution (0.75 ml, 3 eq.) and DIPEA solution (0.7 ml, 6 eq.) for pre-activation and improved solubility) was coupled to the latter. The Dde protecting group was removed (Dde-deprotection) and Fmoc-Ahx-OH was coupled. From the resin bound Fmoc-Ahx-Lys(DOTA(tBu)$_3$)-Lys(Mtt) peptide the Fmoc and the Mtt group were removed. The resin was divided and the following steps were performed with 25 µmol resin (100 mg). To the resin a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (52.2 mg, 55 µmol, 2.2 eq), HOAt (7.5 mg, 55 µmol, 2.2 eq.), DIPEA (17.4 µl, 100 µmol, 4 eq.) and DIC (17.4 µl, 55 µmol, 2.2 eq.) in DMF/DCM (1/1, 1 ml) was added after a pre-activation time of 5 minutes. After 3 hours more DIC (17.4 µl, 55 µmol, 2.2 eq.) was added and the resin agitated over 48 hours. In the following DIC (8.8 µl, 23 µmol, 1.1 eq. after 24 hours), (59) (23.7 mg, 25 µmol, 1.0 eq, after 48 hours) and again DIC (8.8 µl, 23 µmol, 1.1 eq. after 48 hours) were added and the resin agitated for additional 24 hours. The resin was washed with DMF (3 ml, 5×1 min) and subjected to complete resin cleavage (Cleavage Methode B) for 4 hours. The residue obtained was subjected to HPLC purification (25 to 55% B in 30 min, Phenomenex Luna RP-C18 30×150 mm) to give the title compound (19.46 mg, 7.9 µmol, 31.8%). HPLC: R$_t$=5.7 min. MS: m/z=817.89 ([M+3H]$^{3+}$, calculated 818.00). C$_{128}$H$_{188}$N$_{22}$O$_{26}$ (MW=2450.99).

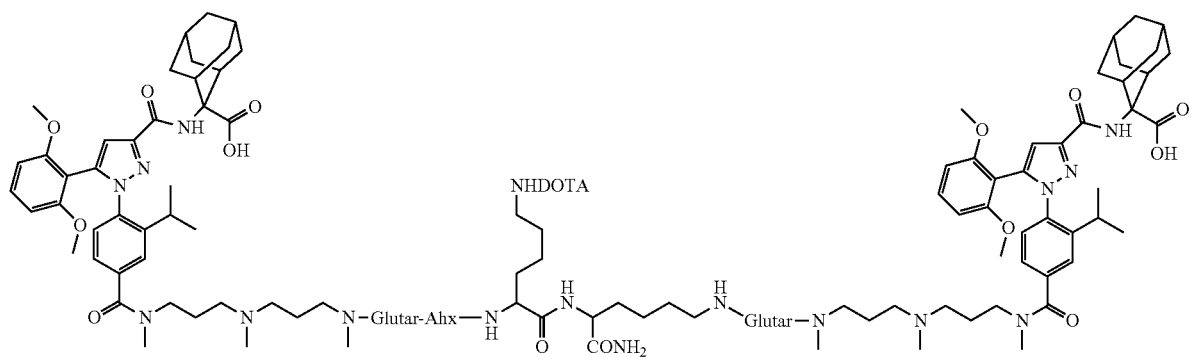

(14)

Example 11: 1206-Glutar-Ttds$_3$-Lys(DOTA)-Ttds$_3$-(ε-Lys-NH$_2$)-Glutar-1206 (15)

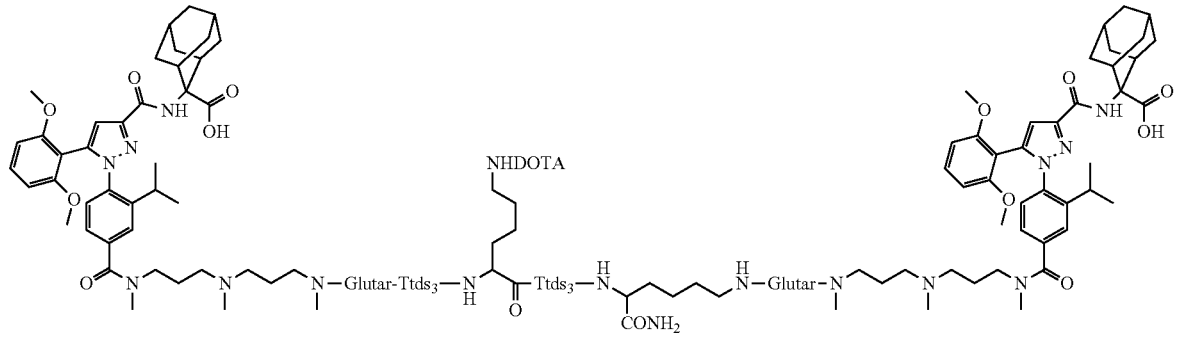

(15)

The initial steps of the synthesis of the compound were performed according to the general procedures for Automated/Semi-automated Solid-Phase Synthesis. Rink amide resin (DEG, initial loading 0.45 mmol/g/100 μmol) was charged with Fmoc-Lys(Mtt)-OH (Resin loading) and the Fmoc group of the latter was removed. Four iterative repetitions of Coupling (Coupling) and Fmoc removal (Fmoc-deprotection) (3× Fmoc-Ttds-OH, Dde-Lys(Fmoc)-OH) furnished the resin bound Dde-Lys-Ttds$_3$-Lys(Mtt) peptide. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection). Another three iterative repetitions of Coupling (Coupling) and Fmoc removal (Fmoc-deprotection) (3× Fmoc-Ttds-OH) furnished the resin bound H-Ttds$_3$-Lys(DOTA(tBu)$_3$)-Ttds$_3$-Lys(Mtt). The Mtt group of the latter was removed (Mtt-deprotection). The resin was divided and the following steps were performed with 25 μmol resin (125 mg). To the resulting resin bound diamine (125 mg, 25 mol) a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (52.2 mg, 55 μmol, 2.2 eq), HOAt (7.5 mg, 55 μmol, 2.2 eq.), DIPEA (17.4 μl, 100 mol, 4 eq.) and DIC (17.4 μl, 55 μmol, 2.2 eq.) in DMF/DCM (1/1, 1 ml) was added after a pre-activation time of 5 minutes. In the following DIC (8.8 μl, 23 μmol, 1.1 eq. after 24 hours), (59) (23.7 mg, 25 mol, 1.0 eq, after 48 hours) and again DIC (8.8 μl, 23 μmol, 1.1 eq. after 48 hours) were added and the resin was agitated for additional 24 hours. The resin was washed with DMF (3 ml, 5×1 min) and subjected to complete resin cleavage (Cleavage Method B) for 4 hours. The residue obtained was subjected to HPLC purification (25 to 55% B in 30 min, Phenomenex Luna RP-C18 30×150 mm) to give the title compound (19.43 mg, 4.7 μmol, 18.8%). HPLC: R$_t$=5.5 min. MS: m/z=1038.79 ([M+4H]$^{4+}$, calculated 1039.01). C$_{206}$H$_{333}$N$_{33}$O$_{55}$ (MW=4152.04).

Example 12: 1206-Glutar-Ttds-Lys(DOTA)-Ttds-GABA-Arg-Arg-Pro-Tyr-Tle-Leu-OH (16)

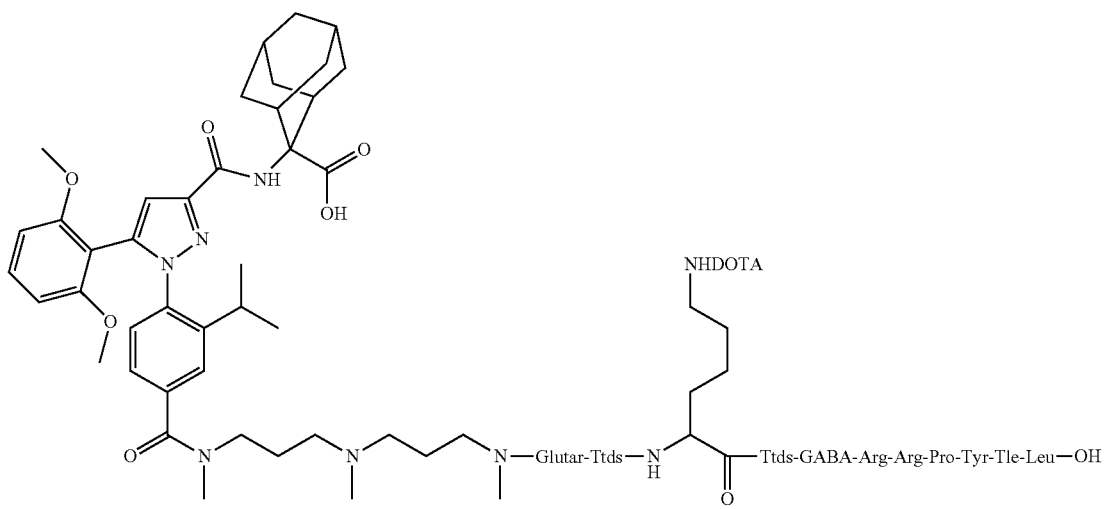

(16)

The initial steps of the synthesis of the compound were performed according to general procedures for Automated/Semi-automated Solid-Phase Synthesis. A pre-loaded Fmoc-Leu-PS resin (initial loading 0.8 mmol/g/100 µmol) was used. 8 iterative repetitions of Coupling (Coupling) and Fmoc removal (Fmoc-deprotection) (Fmoc-Tle-OH, Fmoc-Tyr(tBu)-OH, Fmoc-Pro-OH, 2× Fmoc-Arg(Pbf)-OH, Fmoc-GABA-OH, Fmoc-Ttds-OH, Dde-Lys(Fmoc)) furnished the resin bound Dde-Lys-Ttds-GABA-Arg(Pbf)-Arg(Pbf)-Pro-Tyr(tBu)-Tle-Leu peptide. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection). Fmoc-Ttds-OH was coupled to the construct and the Fmoc group of the latter removed. To the resulting resin bound peptide (50 mg, 20 µmol) a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (22.8 mg, 24.4 µmol, 1.2 eq), HOAt (3.3 mg, 24.4 µmol, 1.2 eq.), DIPEA (8.4 µl, 48.8 µmol, 2 eq.) and DIC (3.8 µl, 38 µmol, 1.2 eq.) in NMP/DCM (1/1, 0.3 ml) was added after a pre-activation time of 5 minutes. After 1 hour more DIC (10 µl, 100 µmol, 3.2 eq.) was added. After 48 hours the resin was washed with DMF (3 ml, 5×1 min) and subjected to complete resin cleavage (Cleavage Methode B) for 4 hours. The residue obtained was subjected to HPLC purification (15 to 45% B in 30 min, Agilent PLRP-S 25×150 mm) to give the title compound (1.42 mg, 0.5 µmol, 2.5%). HPLC: R$_t$=4.7 min. MS: m/z=954.44 ([M+3H]$^{3+}$, calculated 954.47). C$_{139}$H$_{223}$N$_{29}$O$_{35}$ (MW=2860.43).

Example 13: 1206-Glutar-Ttds-Lys(DOTA)-Ttds-GABA-arg-Arg-Pro-Tyr-Tle-Leu-OH (17)

The initial steps of the synthesis of the compound were performed according to general procedures for Automated/Semi-automated Solid-Phase Synthesis. A pre-loaded Fmoc-Leu-PS resin (initial loading 0.8 mmol/g/100 µmol) was used. 8 iterative repetitions of Coupling (Coupling) and Fmoc removal (Fmoc-deprotection) (Fmoc-Tle-OH, Fmoc-Tyr(tBu)-OH, Fmoc-Pro-OH, Fmoc-Arg(Pbf)-OH, Fmoc-D-Arg(Pbf)-OH, Fmoc-GABA-OH, Fmoc-Ttds-OH, Dde-Lys(Fmoc)) furnished the resin bound Dde-Lys-Ttds-GABA-Arg(Pbf)-Arg(Pbf)-Pro-Tyr(tBu)-Tle-Leu peptide. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection). Fmoc-Ttds-OH was coupled to the construct and the Fmoc group of the latter removed. The resin was divided and the following steps were performed with 25 µmol resin, which was subjected to treatment with a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (27.4 mg, 30 µmol, 1.2 eq), HOAt (4.2, 30 µmol, 1.2 eq.), DIPEA (10.3 µl, 60 µmol, 2.4 eq.) and DIC (6.2 µl, 40 µmol, 1.6 eq.) in DMF/DCM (1/1, 0.35 ml), which was added after a pre-activation time of 5 minutes. After 48 hours the resin was washed with DMF (3 ml, 5×1 min) and subjected to complete resin cleavage (Cleavage Methode B) for 3 hours. The residue obtained was subjected to HPLC purification (25 to 45% B in 30 min, Agilent PLRP-S 25×150 mm) to give the title compound (7.45 mg, 2.6 µmol, 10.4%). HPLC: R$_t$=4.6 min. MS: m/z=954.46 ([M+3H]$^{3+}$, calculated 954.47). C$_{139}$H$_{223}$N$_{29}$O$_{35}$ (MW=2860.43).

(17)

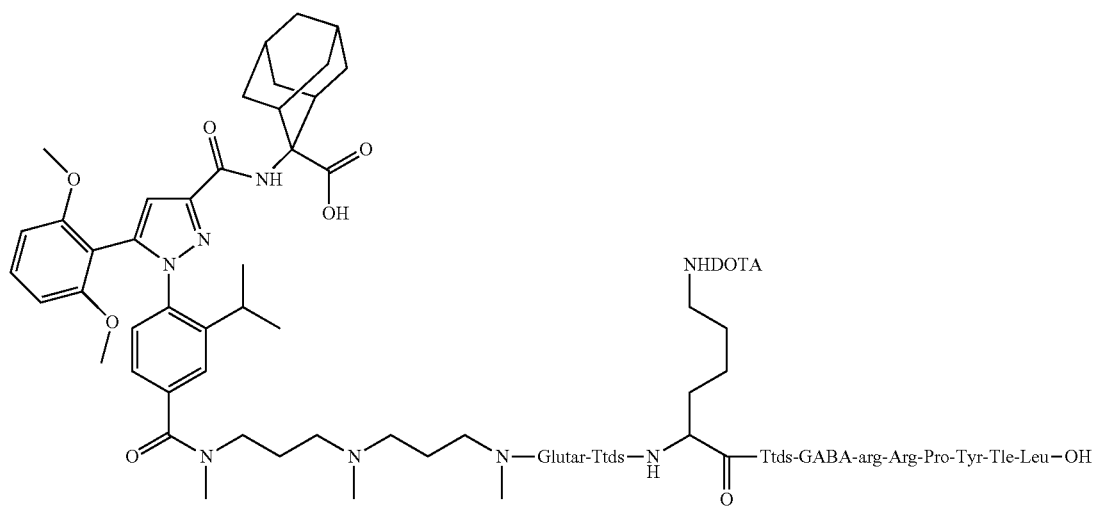

Example 14: 1206-Glutar-Ttds$_3$-Lys(DOTA)-Ttds$_3$-GABA-arg-Arg-Pro-Tyr-Tle-Leu-OH (18)

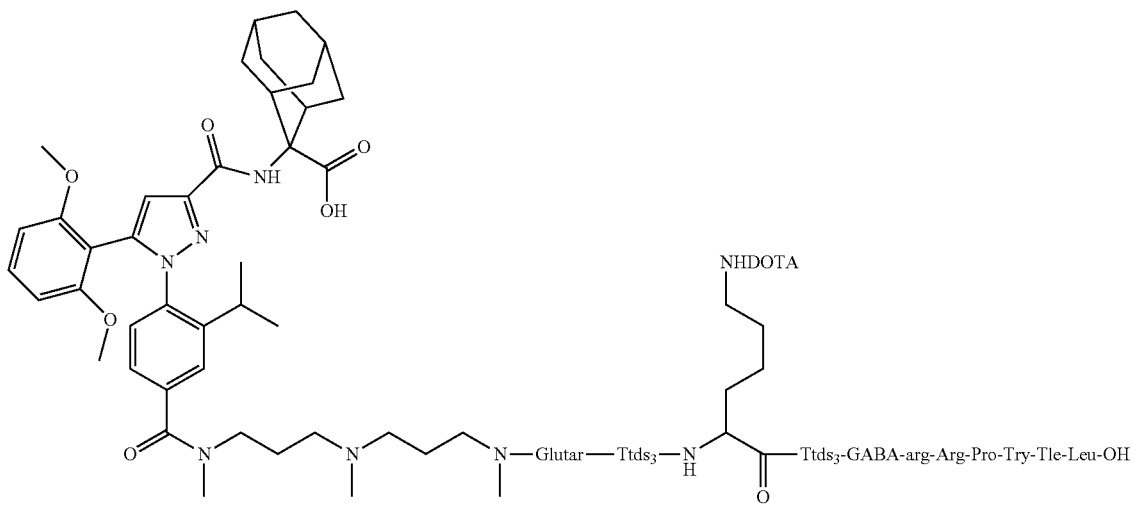

(18)

The initial steps of the synthesis of the compound were performed according to general procedures for Automated/Semi-automated Solid-Phase Synthesis. A pre-loaded Fmoc-Leu-TG resin (initial loading 0.24 mmol/g/100 µmol) was used. 10 iterative repetitions of Coupling (Coupling) and Fmoc removal (Fmoc-deprotection) (Fmoc-Tle-OH, Fmoc-Tyr(tBu)-OH, Fmoc-Pro-OH, Fmoc-Arg(Pbf)-OH, Fmoc-D-Arg(Pbf)-OH, Fmoc-GABA-OH, 3× Fmoc-Ttds-OH, Dde-Lys(Fmoc)) furnished the resin bound Dde-Lys-Ttds-Ttds-Ttds-GABA-Arg(Pbf)-Arg(Pbf)-Pro-Tyr(tBu)-Tle-Leu peptide. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection). 3 iterative repetitions of Coupling (Coupling) and Fmoc removal (Fmoc-deprotection) (3× Fmoc-Ttds-OH) furnished the resin bound H-Ttds-Ttds-Ttds-Lys(DOTA (tBu)$_3$)-Ttds-Ttds-Ttds-GABA-Arg(Pbf)-Arg(Pbf)-Pro-Tyr (tBu)-Tle-Leu peptide. The resin was divided and the following steps were performed with 25 µmol resin (517 mg), which was subjected to treatment with a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (27.4 mg, 30 µmol, 1.2 eq), HOAt (4.2, 30 µmol, 1.2 eq.), DIPEA (8.6 µl, 50 µmol, 2 eq.) and DIC (4.6 µl, 30 µmol, 1.2 eq.) in NMP/DCM (1/1, 1 ml), which was added after a pre-activation time of 5 minutes. After 24 hours additional 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (13.74 mg, 10 µmol, 0.4 eq), HOAt (2.0 mg, 10 µmol, 0.4 eq.), DIPEA (1.7 µl, 10 µmol, 0.4 eq.) and DIC (4.6 µl, 30 µmol, 1.2 eq.) were added. After 24 hours the resin was washed with DMF (3 ml, 5×1 min) and subjected to complete resin cleavage (4 hours). The residue obtained was subjected to HPLC purification (25 to 45% B in 30 min, Phenomenex Luna RP-C18 30×150 mm) to give the title compound (16.09 mg, 2.6 µmol, 10.4%). HPLC: R$_t$=4.7 min. MS: m/z=1357.78 ([M+3H]$^3$, calculated 1357.63). C$_{195}$H$_{327}$N$_{37}$O$_{55}$ (MW=4069.89).

Example 15: 1206-Glutar-Ttds-Lys(FITC)-Ttds-(ε-Lys-NH$_2$)-Glutar-1206 (19)

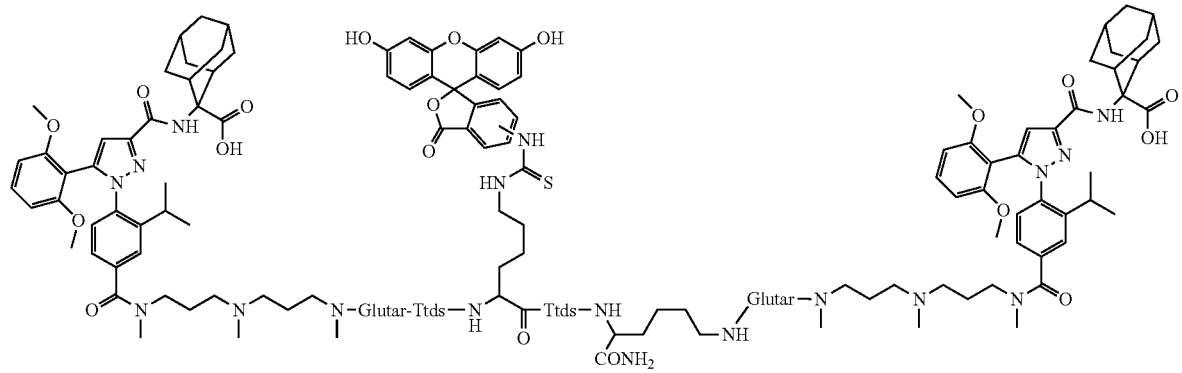

(19)

In accordance with the general procedures for Automated/Semi-automated Solid-Phase Synthesis the initial steps of the synthesis of the compound were performed. Rink amide resin (CM, initial loading 0.52 mmol/g/50 µmol) was charged with Fmoc-Lys(Mtt)-OH (Resin loading) and the Fmoc group of the latter was removed. Three iterative repetitions of Coupling (Coupling) and Fmoc removal (Fmoc-deprotection) (Fmoc-Ttds-OH, Fmoc-Lys(Boc)-OH, Fmoc-Ttds-OH) furnished the resin bound H-Ttds-Lys(Boc)-Ttds-Lys(Mtt) peptide. The Mtt group of the latter was removed (Mtt-deprotection). The resin was divided and the following steps were performed with 25 µmol resin, which was subjected to treatment with a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (54.8 mg, 60 µmol, 2.4 eq), HOAt (8.2 mg, 60 µmol, 2.4 eq.), DIPEA (17.2 µl, 100 µmol, 4 eq.) and DIC (9.2 µl, 60 µmol, 2.4 eq.) in NMP/DCM (1/1, 2 ml), which was added after a pre-activation time of 5 minutes. After 24 hours the resin was washed with DMF (3 ml, 5×1 min) and subjected to complete resin cleavage (Cleavage Methode B) for 4 hours. The obtained residue was dissolved in ACN (1 ml) and water (2 ml) and lyophilized. Of the resulting solid (38.9 mg, 15 µmol, 60%) 8 mg, (3.1 µmol) were dissolved in DMSO (0.2 ml) and combined with a solution of 5(6)-fluorescein isothiocyanate (2.43 mg, 6.2 µmol, 2 eq) in DMSO (0.1 ml). To the mixture DIPEA (10 µl, 60 µmol, 20 eq.) was added. After 48 hours again 5(6)-fluorescein isothiocyanate (2.43 mg, 6.2 µmol, 2 eq) and DIPEA (5 µl, 30 µmol, 10 eq.) was added. After 1 hour the solution was subjected to HPLC purification (25 to 45% B in 30 min, Agilent PLRP-S 25×150 mm) to give the title compound (3.32 mg, 1.1 µmol, 36.4%). HPLC: R$_t$=5.8 min. MS: m/z=983.05 ([M+3H]$^{3+}$, calculated 982.85). C$_{155}$H$_{214}$N$_{22}$O$_{33}$S (MW=2945.55).

Example 16: 1206-Glutar-Ttds-Lys(Taxol-Succinyl)-Ttds-(ε-Lys-NH$_2$)-Glutar-1206 (20)

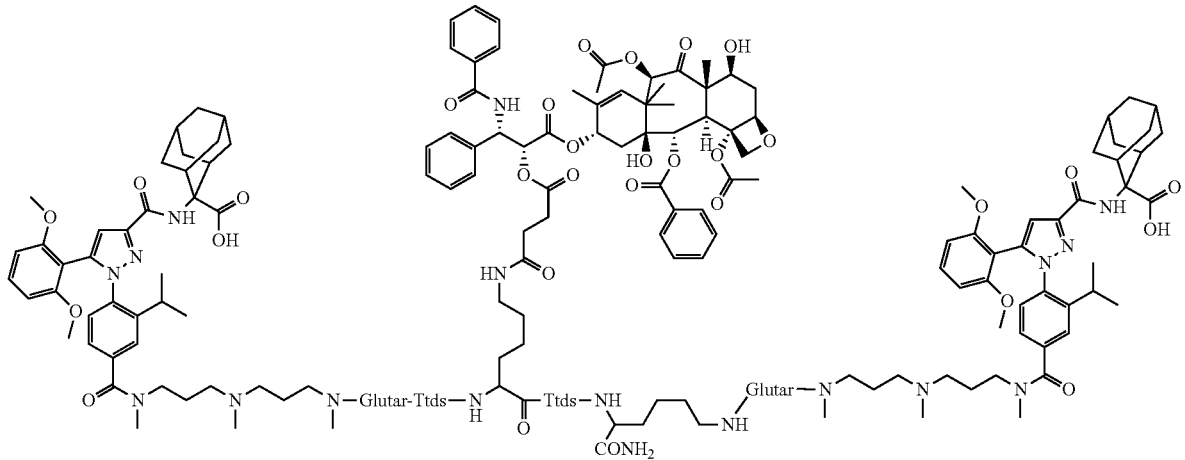

(20)

In accordance with the general procedures for Automated/Semi-automated Solid-Phase Synthesis the initial steps of the synthesis of the compound were performed. Rink amide resin (CM, initial loading 0.52 mmol/g/50 µmol) was charged with Fmoc-Lys(Mtt)-OH (Resin loading) and the Fmoc group of the latter was removed. Three iterative repetitions of Coupling (Coupling) and Fmoc removal (Fmoc-deprotection) (Fmoc-Ttds-OH, Fmoc-Lys(Boc)-OH, Fmoc-Ttds-OH) furnished the resin bound H-Ttds-Lys (Boc)-Ttds-Lys(Mtt) peptide. The Mtt group of the latter was removed (Mtt-deprotection). The resin was divided and the following steps were performed with 25 µmol resin. To the resulting resin bound diamine (25 µmol) a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (54.8 mg, 60 µmol, 2.4 eq), HOAt (8.2 mg, 60 µmol, 2.4 eq.), DIPEA (17.2 µl, 100 µmol, 4 eq.) and DIC (9.2 µl, 60 µmol, 2.4 eq.) in NMP/DCM (1/1, 2 ml) was added after a pre-activation time of 5 minutes. After 24 hours the resin was washed with DMF (3 ml, 5×1 min) and subjected to complete resin cleavage (4 hours). The obtained residue was dissolved in ACN (1 ml) and water (2 ml) and lyophilized. Of the resulting solid (38.9 mg, 15 µmol, 60%) 10.7 mg, (4.2 µmol) were dissolved in DMSO (0.2 ml) and mixed with paclitaxel-hemisuccinyl-NHS active ester (88) (prepared as described in Ryppa et al., Int J Pharm, 2009, 368, 89-97) (11.1 mg, 10.5 µmol, 2.5 eq.). To the solution DIPEA (1 µl, 5 µmol, 1.2 eq.) was added. After 24 hours the solution was subjected to HPLC purification (25 to 45% B in 30 min, Phenomenex Luna RP-C18 30×150 mm) to give the title compound (1.73 mg, 1.1 µmol, 36.4%). HPLC: $R_t$=6.1 min. MS: m/z=1165.24 ([M+3H]$^{3+}$, calculated 1165.04). $C_{185}H_{256}N_{22}O_{44}$ (MW=3492.13).

Example 17: 1206-Glutar-Ttds-Lys(DOTA)-Ttds-GABA-Asn-Ala-Val-Pro-Asn-Leu-Arg-Gly-Asp-Leu-Gln-Val-Leu-Ala-Gln-Lys-Val-Ala-Arg-Thr-NH$_2$ (21)

The initial steps of the synthesis of the compound were performed according to the general procedures for Automated/Semi-automated Solid-Phase Synthesis. Rink amide resin (CM, initial loading 0.52 mmol/g/100 µmol) was charged with Fmoc-Thr(tBu))—OH (Resin loading) and the Fmoc group of the latter removed. Through iterative repetitions of Coupling (Coupling) and Fmoc removal (Fmoc-deprotection) the resin bound Dde-Lys-Ttds-GABA-Asn(Trt)-Ala-Val-Pro-Asn(Trt)-Leu-Arg(Pbf)-Gly-Asp(tBu)-Leu-Gln(Trt)-Val-Leu-Ala-Gln(Trt)-Lys(Boc)-Val-Ala- Arg(Pbf)-Thr(tBu) (SEQ ID NO: 24) peptide was assembled. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the N-terminal deprotected lysine side chain. The coupling step was repeated once. The Dde protecting group was removed (Dde-deprotection) and a further Fmoc-Ttds-OH attached to the construct. The Fmoc group of the latter was removed. The resin was divided and the following steps were performed with 25 µmol resin, which was subjected to treatment with a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (27.4 mg, 30 µmol, 1.2 eq), HOAt (4.2, 30 µmol, 1.2 eq.), DIPEA (10.3 µl, 60 µmol, 2.4 eq.) and DIC (6.2 µl, 40 µmol, 1.6 eq.) in DMF/DCM (1/1, 0.35 ml) (after a pre-activation time of 5 minutes). After 48 hours the resin was washed with DMF (3 ml, 5×1 min) and subjected to complete resin cleavage (Cleavage Methode B) for 4 hours. The residue obtained was subjected to HPLC purification (25 to 45% B in 30 min, Phenomenex Luna RP-C18 30×150 mm) to give the title compound (11.62 mg, 2.8 µmol, 11.1%). HPLC: $R_t$=4.7 min. MS: m/z=1402.78 ([M+3H]$^{3+}$, calculated 1402.98). $C_{194}H_{323}N_{49}O_{54}$ (MW=4205.94).

(21)

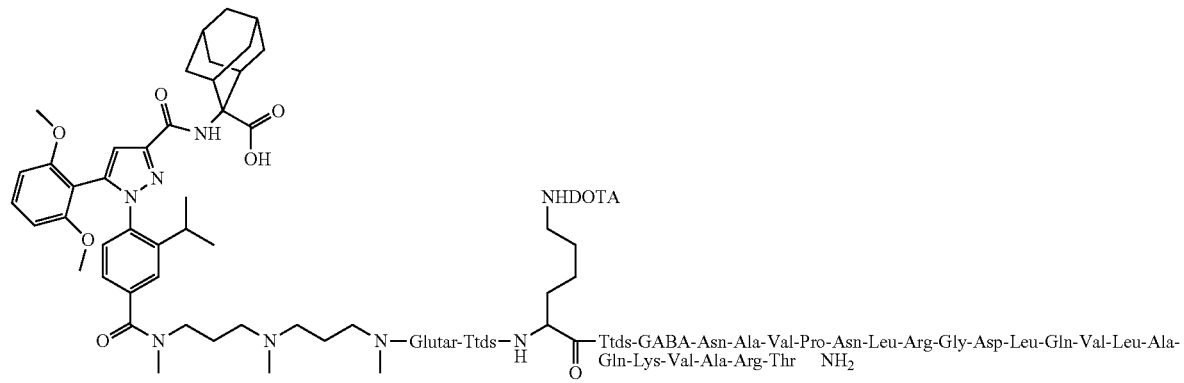

Example 18: Ac-Asn-Ala-Val-Pro-Asn-Leu-Arg-Gly-Asp-Leu-Gln-Val-Leu-Ala-Gln-Lys-Val-Ala-Arg-Thr-Ttds$_3$-Lys(DOTA)-Ttds$_3$-(ε-Lys-NH$_2$)-Glutar-1206 (22)

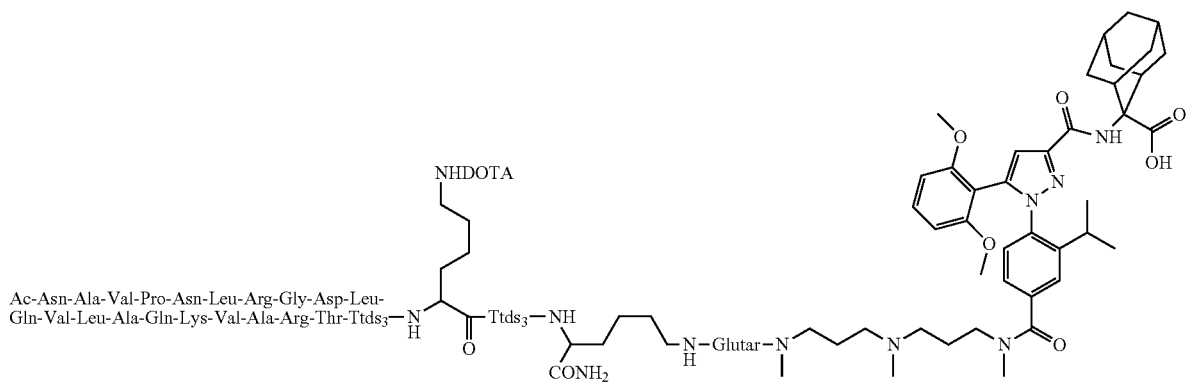

The initial steps of the synthesis of the compound were performed according to the general procedures for Automated/Semi-automated Solid-Phase Synthesis. Rink amide resin (CM, initial loading 0.52 mmol/g/50 μmol) was charged with Dde-Lys(Fmoc)-OH (Resin loading) and the Fmoc group of the latter removed. The resin was then treated with a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (58.8 mg, 60 μmol, 1.2 eq), HOAt (8.4, 60 μmol, 1.2 eq.), DIPEA (20.5 μl, 120 μmol, 2.4 eq.) and DIC (12.4 μl, 80 μmol, 1.6 eq.) in DMF/DCM (1/1, 0.7 ml) (after a pre-activation time of 5 minutes). After 48 hours the resin was washed with DMF (3 ml, 5×1 min) and the Dde group was removed (Dde-deprotection). Through iterative repetitions of Coupling (Coupling) and Fmoc removal (Fmoc-deprotection) the resin bound Dde-Lys-Ttds$_3$-(ε-Lys-NH$_2$)-Glutar-1206 construct was assembled. Then DOTA(tBu)$_3$-OH (86 mg, 0.15 mmol, 3 eq.) directly dissolved in HATU solution (0.4 ml, 3 eq.) and DIPEA solution (0.4 ml, 6 eq.) for pre-activation and improved solubility) was coupled (4 hours) to the lysine side chain. The coupling step was repeated once. The Dde protecting group was removed (Dde-deprotection). Afterwards iterative repetitions of Coupling (Coupling) and Fmoc removal (Fmoc-deprotection) were performed and a terminal acetylation step (Terminal acetylation) finalized the full sequence. The resin was subjected to complete resin cleavage (Cleavage Methode B) for 5 hours. The residue obtained was subjected to HPLC purification (25 to 45% B in 30 min, Phenomenex Luna RP-C18 30×150 mm) to give the title compound (8.77 mg, 1.6 μmol, 3.2%). HPLC: R$_t$=4.8 min. MS: m/z=798.81 ([M+7H]$^{7+}$, calculated 798.94). C$_{258}$H$_{441}$N$_{59}$O$_{76}$ (MW=5585.61).

Example 19: Ac-Asn-Ala-Val-Pro-Asn-Leu-Arg-Gly-Asp-Leu-Gln-Val-Leu-Ala-Gln-Lys-Val-Ala-Arg-Thr-Ttds$_3$-Lys(DOTA)-Ttds$_3$-(β-Cys-NH$_2$)-Mic-1206 (23)

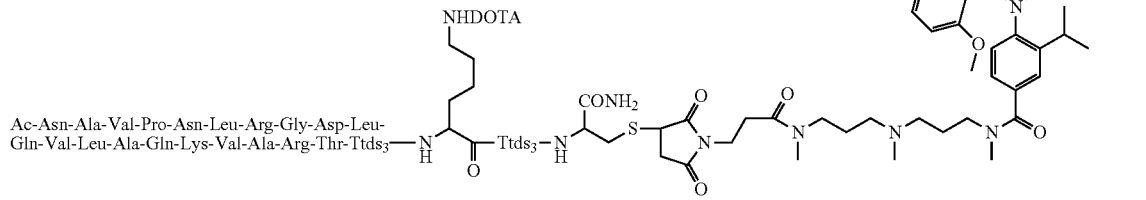

The initial steps of the synthesis of the compound were performed according to the general procedures for Automated/Semi-automated Solid-Phase Synthesis. Rink amide resin (CM, initial loading 0.52 mmol/g) (100 μmol) was charged with Fmoc-Cys(Trt))-OH (Resin loading) and the Fmoc group of the latter removed. Through iterative repetitions of Coupling (Coupling) and Fmoc removal (Fmoc-deprotection) the resin bound Dde-Lys-Ttds$_3$-Cys(Trt) construct was assembled. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the N-terminal deprotected lysine side chain. The Dde protecting group was removed (Dde-deprotection) and afterwards the assembly of the sequence was continued by iterative repetition of Coupling (Coupling) and Fmoc removal (Fmoc-deprotection). A terminal acetylation step (Terminal acetylation) finalized the full construct. The resin was subjected to complete resin cleavage (Cleavage Methode B) for 5 hours with TFA/EDT/water/TIPS (94/2.5/2.5/1, 8 ml). The residue obtained was subjected to HPLC purification (15 to 45% B in 30 min, Phenomenex Luna RP-C18 30×150 mm) to give the C-terminal cysteine peptide (43.03 mg, 9.1 µmol, 9.1%). 26.4 mg of the latter (5.6 µmol) and 2-({5-(2,6-Dimethoxy-phenyl)-1-[4-({3-[(3-{[3-(2,5-dioxo-2,5-dihydro-pyrrol-1-yl)-propionyl]-methyl-amino}-propyl)-methyl-amino]-propyl}-methyl-carbamoyl)-2-isopropyl-phenyl]-1H-pyrazole-3-carbonyl}-amino)-adamantane-2-carboxylic acid (57) (5 mg, 5.6 µmol, 1 eq.) were dissolved in DMSO (500 µl). To this mixture a trace amount of DIPEA was added to adjust the pH-value to 7.5. After 24 hours the solution was directed to HPLC purification (20 to 45% B in 30 min, Agilent PLRP-S 25×150 mm) to give the title compound (3.25 mg, 0.6 µmol, 10.7%). HPLC: R$_t$=4.9 min. MS: m/z=1404.60 ([M+3H]$^{3+}$, calculated 1404.91). C$_{257}$H$_{435}$N$_{59}$O$_{77}$S (MW=5615.62).

Example 20: 1206-Glutar-Ttds$_3$-Asn-Ala-Val-Pro-Asn-Leu-Arg-Gly-Asp-Leu-Gln-Val-Leu-Ala-Gln-Lys-Val-Ala-Arg-Thr-GABA-Ttds-(ε-Lys-NH$_2$)-DOTA (24)

The initial steps of the synthesis of the compound were performed according to the general procedures for Automated/Semi-automated Solid-Phase Synthesis. Rink amide resin (CM, initial loading 0.24 mmol/g/100 µmol) was charged with Dde-Lys(Fmoc)-OH (Resin loading) and the Fmoc group of the latter removed. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection) and afterwards the assembly of the sequence was continued by iterative repetition of Coupling (Coupling) and Fmoc removal (Fmoc-deprotection). Prior to the final coupling the resin was divided and the following step was performed with 25 µmol resin. To the resin (258 mg, 25 µmol) a mixture of 2-({5-(2,6-Dimethoxy-phenyl)-1-[2-isopropyl-4-(methyl-{3-[methyl-(3-methyl-amino-propyl)-amino]-propyl}-carbamoyl)-phenyl]-1H-pyrazole-3-carbonyl}-amino)-adamantane-2-carboxylic acid tert-butyl ester (59) (34.24 mg, 37.2 µmol, 1.5 eq), HOAt (5.1 mg, 37.2 µmol, 1.5 eq.), DIPEA (62.5 µl, 63 µmol, 2.5 eq.) and DIC (5.3 µl, 34.2 µmol, 1.5 eq.) in NMP/DCM (1/1, 3 ml) was added after a pre-activation time of 5 minutes. After 24 hours the resin was washed with DMF (3 ml, 5×1 min) and subjected to complete resin cleavage (Cleavage Methode B) for 4 hours. The residue obtained was subjected to HPLC purification (25 to 45% B in 30 min, Phenomenex Luna RP-C18 30×150 mm) to give the title compound (6.66 mg, 2.8 µmol, 11.1%). HPLC: R$_t$=4.8 min. MS: m/z=1203.59 ([M+4H]$^{4+}$, calculated 1203.67). C$_{222}$H$_{375}$N$_{53}$O$_{64}$ (MW=4810.67).

(24)

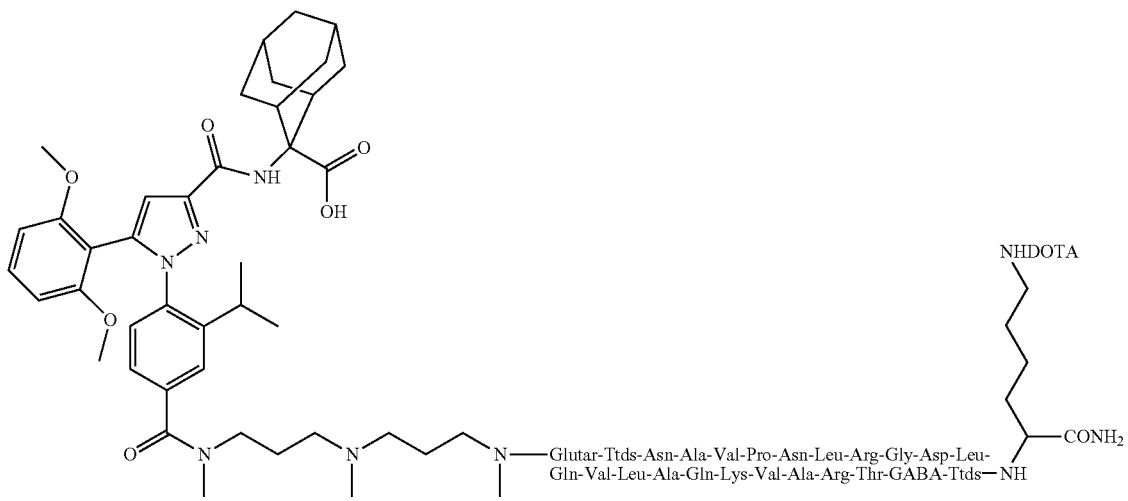

Example 21: 1206-Glutar-Ttds-Lys(1206-Glutar-Ttds)-Ttds-Asn-Ala-Val-Pro-Asn-Leu-Arg-Gly-Asp-Leu-Gln-Val-Leu-Ala-Gln-Lys-Val-Ala-Arg-Thr-GABA-Ttds-(ε-Lys-NH₂)-DOTA (25)

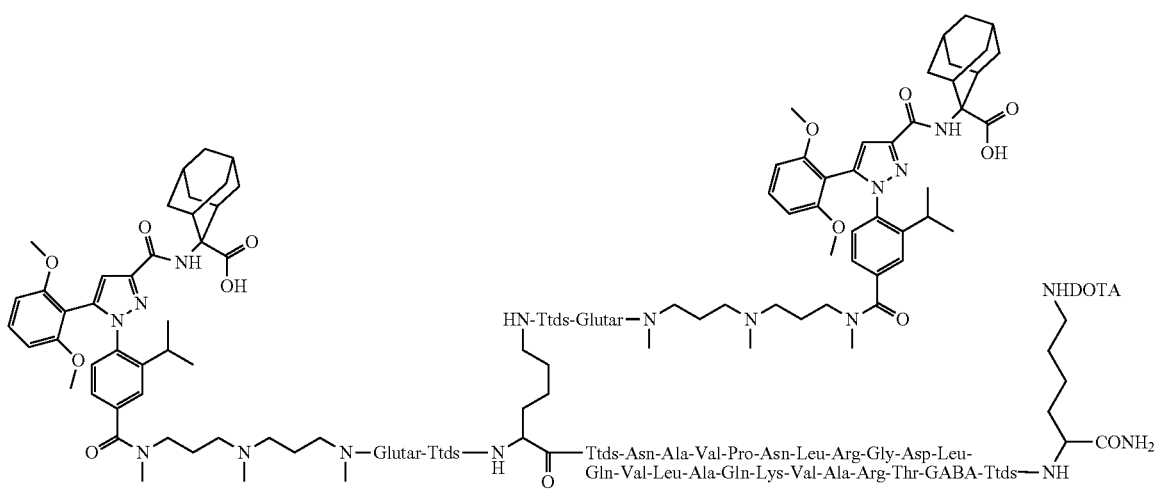

(25)

The initial steps of the synthesis of the compound were performed according to the general procedures for Automated/Semi-automated Solid-Phase Synthesis. Rink amide resin (CM, initial loading 0.24 mmol/g/100 µmol) was charged with Dde-Lys(Fmoc)-OH (Resin loading) and the Fmoc group of the latter removed. Then DOTA(tBu)₃-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection) and afterwards the assembly of the sequence was continued by iterative repetition of Coupling (Coupling) and Fmoc removal (Fmoc-deprotection) to furnish the resin bound H-Ttds-Asn(Trt)-Ala-Val-Pro-Asn(Trt)-Leu-Arg(Pbf)-Gly-Asp(tBu)-Leu-Gln(Trt)-Val-Leu-Ala-Gln(Trt)-Lys(Boc)-Val-Ala-Arg(Pbf)-Thr(tBu)-Lys(DOTA(tBu)₃) peptide. Two further iterative repetitions of Coupling (Coupling) and Fmoc removal (Fmoc-deprotection) (Fmoc-Lys(Fmoc)-OH and Fmoc-Ttds-OH (the coupling of Fmoc-Ttds-OH was repeated twice to ensure the complete acylation of both ε and s amino function of the N-terminal lysine)) were performed. The resin was divided and the following steps were performed with 25 µmol resin. To the resin (267 mg, 25 µmol) a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (68.48 mg, 75 µmol, 3 eq.), HOAt (10.2 mg, 75 mol, 3 eq.), DIPEA (21.8 µl, 125 µmol, 5 eq.) and DIC (10.6 µl, 75 µmol, 3 eq.) in NMP/DCM (1/1, 3 ml) was added after a pre-activation time of 5 minutes. After 24 hours the resin was washed with DMF (3 ml, 5×1 min) and subjected to complete resin cleavage (Cleavage Methode B) for 4 hours. The residue obtained was subjected to HPLC purification (25 to 45% B in 30 min, Phenomenex Luna RP-C18 30×150 mm) to give the title compound (8.12 mg, 1.4 µmol, 5.6%). HPLC: $R_t$=5.2 min. MS: m/z=1445.40 ([M+4H]⁴⁺, calculated 1445.47). $C_{275}H_{449}N_{61}O_{73}$ (MW=5777.87).

Example 22: 1206-Glutar-Ttds-Lys(DOTA)-Ttds-GABA-Lys-Arg-Pro-Hyp-Gly-Cha-Ser-Pro-Leu-OH (26)

(26)

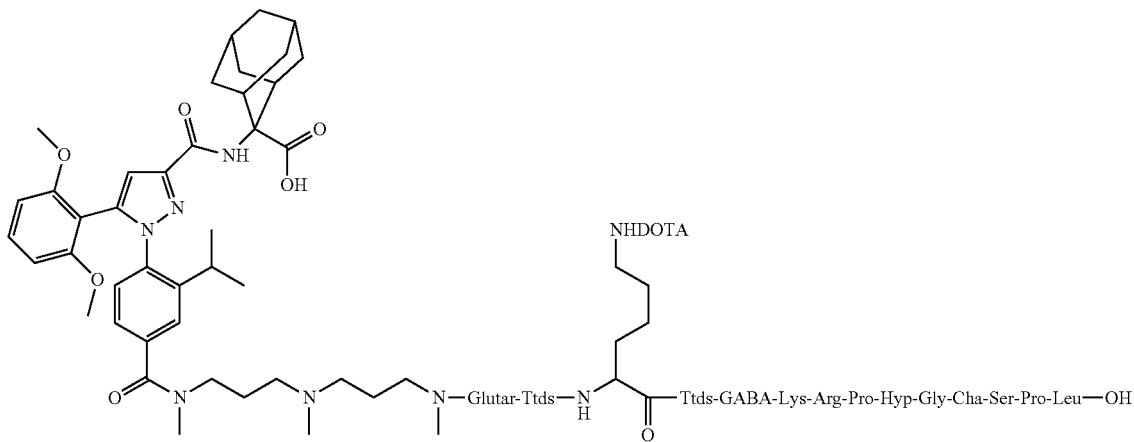

The initial steps of the synthesis of the compound were performed according to the general procedures for Automated/Semi-automated Solid-Phase Synthesis. A pre-loaded Fmoc-Leu-TG resin (initial loading 0.24 mmol/g/100 µmol) was used. 11 iterative repetitions of Coupling (Coupling) and Fmoc removal (Fmoc-deprotection) (Fmoc-Leu-OH, Fmoc-Pro-OH, Fmoc-Ser(tBu)-OH, Fmoc-Cha-OH, Fmoc-Gly-OH, Fmoc-Hyp(tBu)-OH, Fmoc-Pro-OH, Fmoc-Arg(Pbf)-OH, Fmoc-Lys(Boc)-OH, Fmoc-GABA-OH, Fmoc-Ttds-OH, Dde-Lys(Fmoc)) furnished the resin bound Dde-Lys-Ttds-GABA-Lys(Boc)-Arg(Pbf)-Pro-Hyp(tBu)-Gly-Cha-Ser(tBu)-Pro-Leu peptide. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the free N-terminal lysine side chain. The Dde protecting group was removed (Dde-deprotection). Fmoc-Ttds-OH was coupled to the construct and the Fmoc group of the latter removed. The resin was divided and the following steps were performed with 25 µmol resin. To the resin (510 mg, 25 µmol) a mixture of 2-({5-(2,6-Dimethoxy-phenyl)-1-[2-isopropyl-4-(methyl-{3-[methyl-(3-methyl-amino-propyl)-amino]-propyl}-carbamoyl)-phenyl]-1H-pyrazole-3-carbonyl}-amino)-adamantane-2-carboxylic acid tert-butyl ester (59) (27.4 mg, 30 µmol, 1.2 eq), HOAt (4.2, 30 µmol, 1.2 eq.), DIPEA (8.6 µl, 50 µmol, 2 eq.) and DIC (4.6 µl, 30 µmol, 1.2 eq.) in NMP/DCM (1/1, 1 ml) was added after a pre-activation time of 5 minutes. After 24 hours additional 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazazole-3-carbonyl}-amino)-adamantane-2-carboxylic acid tert-butyl ester (59) (13.74 mg, 10 µmol, 0.4 eq), HOAt (2.0 mg, 10 µmol, 0.4 eq.), DIPEA (1.7 L1, 10 µmol, 0.4 eq.) and DIC (4.6 µl, 30 µmol, 1.2 eq.) were added. After 24 hours the resin was washed with DMF (3 ml, 5×1 min) and subjected to complete resin cleavage (Cleavage Methode B) for 4 hours. The residue obtained was subjected to HPLC purification (25 to 40% B in 30 min, Phenomenex Luna RP-C18 30×150 mm) to give the title compound (14.59 mg, 4.9 µmol, 19.6%). HPLC: R$_f$=4.7 min. MS: m/z=994.10 ([M+3H]$^{3+}$, calculated 993.85). C$_{144}$H$_{233}$N$_{29}$O$_{38}$ (MW=2978.56).

Example 23: 1206-Glutar-Ttds-Lys(DOTA)-Ttds-GABA-Orn-Arg-Oic-Pro-Gly-Amf-Ser-nal-Ile-OH (27)

(27)

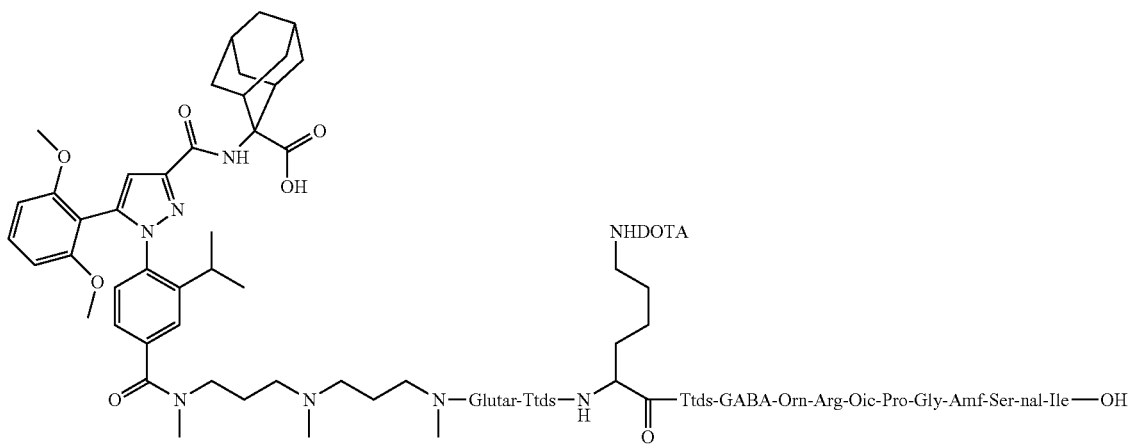

The initial steps of the synthesis of the compound were performed according to the general procedures for Automated/Semi-automated Solid-Phase Synthesis. A pre-loaded Fmoc-Ile-TG resin (initial loading 0.26 mmol/g/100 mol) was used. 11 iterative repetitions of Coupling (Coupling) and Fmoc removal (Fmoc-deprotection) (Fmoc-nal-OH, Fmoc-Ser(tBu)-OH, Fmoc-Amf-OH, Fmoc-Gly-OH, Fmoc-Pro-OH, Fmoc-Oic-OH, Fmoc-Arg(Pbf)-OH, Fmoc-Orn(Boc)-OH, Fmoc-GABA-OH, Fmoc-Ttds-OH, Dde-Lys(Fmoc)) furnished the resin bound Dde-Lys-Ttds-GABA-Orn(Boc)-Arg(Pbf)-Oic-Pro-Gly-Amf-Ser(tBu)-(D-2Ni)-Ile peptide. Then DOTA(tBu)$_3$-OH (172 mg, 0.3 mmol, 3 eq.) directly dissolved in HATU solution (0.75 ml, 3 eq.) and DIPEA solution (0.7 ml, 6 eq.) for pre-activation and improved solubility) was coupled (4 hours) to the lysine side chain. The Dde protecting group was removed (Dde-deprotection). Fmoc-Ttds-OH was coupled to the construct and the Fmoc group of the latter removed. The resin was divided and the following steps were performed with 25 µmol resin. To the resin (543 mg, 25 µmol) a mixture of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (27.4 mg, 30 µmol, 1.2 eq), HOAt (4.2 mg, 30 µmol, 1.2 eq.), DIPEA (8.6 µl, 50 µmol, 2 eq.) and DIC (4.6 µl, 30 µmol, 1.2 eq.) in NMP/DCM (1/1, 1 ml) was added after a pre-activation time of 5 minutes. After 24 additional 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (13.74 mg, 10 µmol, 0.4 eq), HOAt (2.0 mg, 10 µmol, 0.4 eq.), DIPEA (1.7 µl, 10 µmol, 0.4 eq.) and DIC (4.6 µl, 30 µmol, 1.2 eq.) were added. After 24 hours the resin was washed with DMF (3 ml, 5×1 min) and subjected to complete resin cleavage (Cleavage Methode B) for 4 hours. The residue obtained was subjected to HPLC purification (25 to 45% B in 30 min, Phenomenex Luna RP-C18 30×150 mm) to give the title compound (15.28 mg, 4.9 µmol, 19.6%). HPLC: R$_t$=5.3 min. MS: m/z=1038.1 ([M+3H]$^{3+}$, calculated 1037.91). C$_{156}$H$_{237}$N$_{29}$O$_{37}$ (MW=3110.72).

Example 24: 1206-Ttds-Biotin (28)

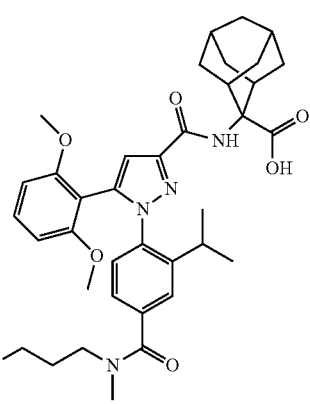

(28)

The initial steps of the synthesis of the compound were performed according to the general procedures for Automated/Semi-automated Solid-Phase Synthesis. Trityl resin (PS, 100 µmol) was charged with Fmoc-Ttds-OH (Resin loading) and the Fmoc group of the latter was removed (Fmoc-deprotection). Biotin was coupled to the resin and afterwards the resin was subjected to complete resin cleavage (Cleavage Methode B) for 10 minutes. The residue obtained was dissolved in ACN (10 ml) and water (15 ml) and lyophilized to yield 44 mg crude product. A solution of the latter (20 mg, 36.6 µmol, 1 eq.) in DMF (200 µl) and a solution of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (59) (29.3 mg, 36.6 µmol, 1.0 eq) in DMF (500 µl) were combined. After HOAt (5.5 mg, 40.3 µmol, 1.1 eq.), DIPEA (12.7 µl, 73.2 µmol, 2 eq.) and DIC (6.2 µl, 45 µmol, 1.1 eq.) were added to the mixture it was stirred for 24 hours. All volatiles were removed in the vacuum. After the residue was treated with a mixture of TIPS (50 µl) and TFA (750 µl) for 10 minutes the solution was directed to HPLC purification (25 to 45% B in 30 min, Agilent PLRP-S 25×150 mm) to give the title compound (20.45 mg, 16.1 µmol, 43.9%). HPLC: R$_t$=5.2 min. MS: m/z=1271.56 ([M+H]$^+$, calculated 1271.70). C$_{66}$H$_{98}$N$_{10}$O$_{13}$S (MW=1271.61).

Example 25: Conjugation of (60) to MAB1909 and MAB3035

NHS-ester-activated compounds are widely used to covalently conjugate such compounds to proteins (*Bioconjugate Techniques,* 2008, Academic Press). NHS-ester-activated compounds react with primary amines (N-terminus and ε-amino group of lysine) in physiologic to slightly alkaline conditions (pH 7.2 to 9) to yield stable amide bonds. The reaction releases N-hydroxysuccinimide (NHS).

The conjugation reaction was performed in a total volume of 104 µl at room temperature. Compound (60) was dissolved in DMSO to obtain a 1 mM solution. 4 µl (4 nmol) of this solution was added to 100 µl PBS containing 667 µmol antibody (MAB1909 or MAB3035). The reaction mixture was incubated 1 h with gentle agitation at room temperature. The reaction was stopped by adding 5 µl of 1 M glycine pH 7. The conjugate was purified by repeated dialysis (20 KDa MWCO membrane).

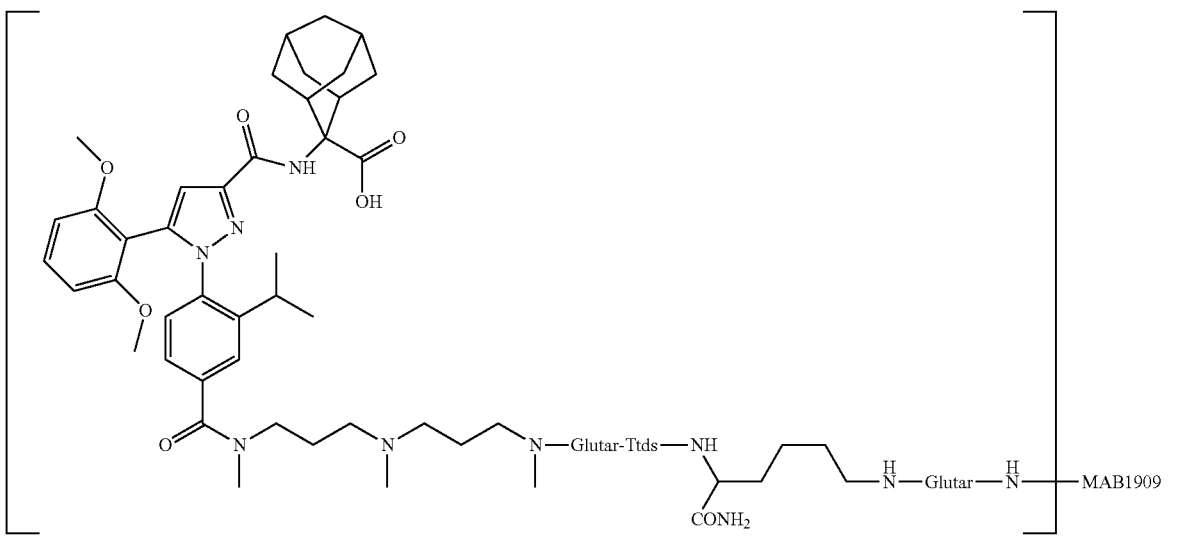

(29)

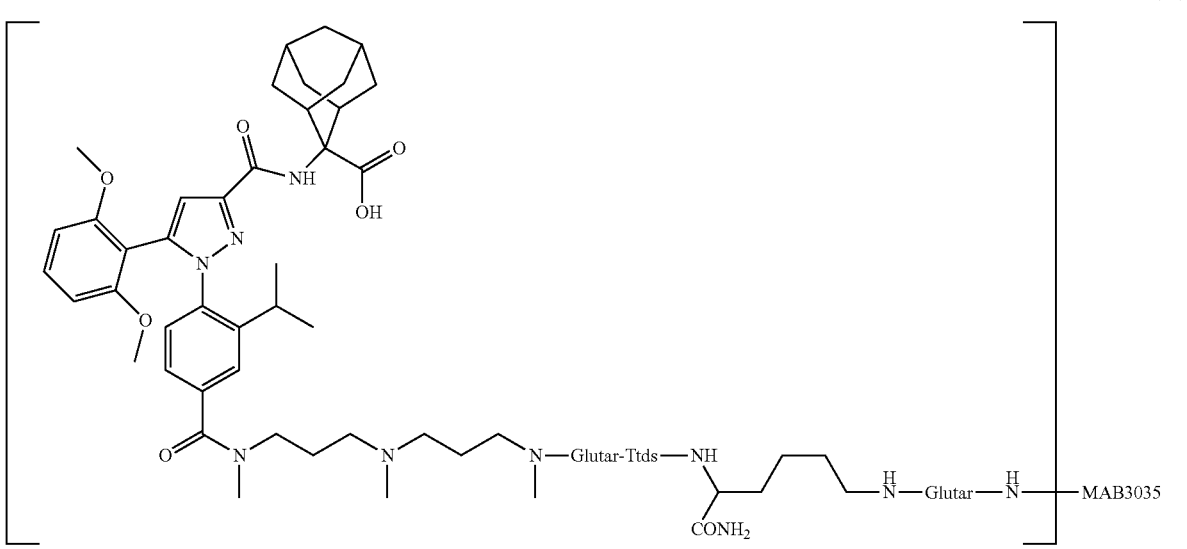

(30)

Example 25: Radioligand Binding Assay NTR1

In order to determine the binding affinity of compounds comprising a radiolabel for NTR1, a radioligand binding assay was carried out. A radioligand is a radioactive biochemical substance that is used for diagnosis or for research-oriented study of cellular receptor systems of the body. In in vivo systems it is often used to quantify the binding of a test molecule to the binding site of radioligand. The higher the affinity of the molecule, the more radioligand is displaced from the binding site. The amount of bound radioligand can be measured by scintillation counting and thereby quantified. This assay is commonly used to calculate binding constants of molecules to receptors. This example shows that conjugates of the present invention bind to NTR1 with high affinity.

The NTR1 radioligand binding assay was performed by Cerep (Celle l'Evescault, France; Catalog reference 0109) according to Vita et al., *FEBS Lett.*, 1993, 317, 139-142. NTR1 was prepared from CHO cells recombinantly expressing the human receptor and incubated with 0.05 nM $^{125}$I-(Tyr$^3$-neurotensin) and serial dilutions of the test compounds. After 60 min incubation at 4° C. and washing to remove unbound neurotensin, bound radioactivity was measured by scintillation counting. The result for each test compound is expressed as IC50 concentration and provides a measure for the affinity of the test compound for NTR1.

The results of this assay performed on some of the conjugates according to the present invention are given in the following Table 5.

TABLE 5

Results of the radioligand binding assay

| Compound | IC50 [nM] |
|---|---|
| (12) | 2.5 |
| (13) | 2.2 |
| (14) | 2.4 |
| (15) | 4.7 |

TABLE 5-continued

Results of the radioligand binding assay

| Compound | IC50 [nM] |
|---|---|
| (16) | 0.14 |
| (17) | 0.32 |
| (18) | 2.7 |
| (21) | 10 |
| (22) | 9.1 |
| (23) | 6.7 |
| (24) | 9.9 |
| (25) | 7.5 |
| (26) | 6.5 |
| (27) | 17 |
| (28) | 1.2 |

Example 26: Radioligand Binding Assay B1R

In order to determine the binding affinity of compounds comprising a radiolabel for B1R, a radioligand binding assay was carried out. A radioligand is a radioactive biochemical substance that is used for diagnosis or for research-oriented study of cellular receptor systems of the body. In in vivo systems it is often used to quantify the binding of a test molecule to the binding site of radioligand. The higher the affinity of the molecule, the more radioligand is displaced from the binding site. The amount of bound radioligand can be measured by scintillation counting and thereby quantified. This assay is commonly used to calculate binding constants of molecules to receptors. This example shows that compounds of the present invention bind to B1R with high affinity.

The B1R radioligand binding assay was performed by Cerep (Celle l'Evescault, France; Catalog reference 1189) according to (Jones et al., *Eur J Pharmacol*, 1999, 374, 423-433). B1R was prepared from CHO cells recombinantly expressing the human receptor and incubated with 0.35 nM [$^3$H]desArg$^{10}$-KD and serial dilutions of the test compounds. After 60 min incubation at 4° C. and washing to remove unbound ligand, bound radioactivity was measured by scintillation counting. The result for each test compound is expressed as percent inhibition of bound radioactivity at 100 nM compound concentration and provides a measure for the affinity of the test compound for B1R.

The results of this assay performed on some of the conjugates according to the present invention are given in the following Table 6.

TABLE 6

Results of the radioligand binding assay

| Compound | Inhibition [at 100 nM, %] |
|---|---|
| (26) | 20 |
| (27) | 17 |

Example 27: Functional Ca$^{2+}$ Mobilisation Assay

Ca$^{2+}$ ions are usually kept at nanomolar levels in the cytosol of cells, and act in a number of signal transduction pathways as second messengers. Many GPCRs including neurotensin receptor couple to induce calcium ion signaling, and many primary cellular assays employ measurement of intracellular calcium ion concentration as a functional readout of GPCR activation. Changes in calcium ion concentration in standard assay protocols can be readily detected with fluorescent dyes that emit light when changes in intracellular Ca$^{2+}$ ion concentration occur. Given the transient nature of these responses, they are often read with instrumentation that has 'inject and read' capability. This example shows that compounds of the present invention do not have any agonistic activity on NTR1-expressing cells. Furthermore, this example shows that conjugates of the present invention bind to NTR1 and inhibit the activity of an additionally present NTR1 agonist.

HT29 or NTR1-expressing HEK293 cells were trypsinized and seeded into black flat clear-bottom 96-well plates (Corning, Amsterdam, The Netherlands) at 6×10$^5$ cells per well. After 24 h incubation at 37° C. and 5% CO$_2$, cells were washed twice with wash buffer (130 mM NaCl, 5 mM KCl, 10 mM Hepes, 2 mM CaCl$_2$, 10 mM Glucose, pH 7.4) and loaded with 100 µl of Ca5 dye (Molecular Devices, Biberach, Germany) for 1 h at 37° C. and 5% CO$_2$. For agonist assays, serial dilutions of agonistic substances were added to the cells loaded with dye and the change of the fluorescent signal was recorded continually for approx. 90 s using a FlexStation II (Molecular Devices, Biberach, Germany). Addition of wash buffer served as a control. Thus, EC50 concentrations for each conjugate were computed and provided a measure for the potency of the substance. For antagonist assays, cells loaded with 100 µl of Ca5-dye were pre-incubated with serial dilutions of antagonistic substances for 30 min, before the EC80-concentration of agonist was added to the cells and the change of the fluorescent signal was recorded continually for approx. 90 s. Thus, IC50 concentrations were computed for each conjugate and provided a measure for the inhibitory activity of the conjugates at the NTR1.

The intrinsic fluorescence of fluorescein-containing conjugate (19) interfered with the Ca5-dye fluorescence. Therefore, no IC50 or EC50 values could be determined for this conjugate.

Figure 2:
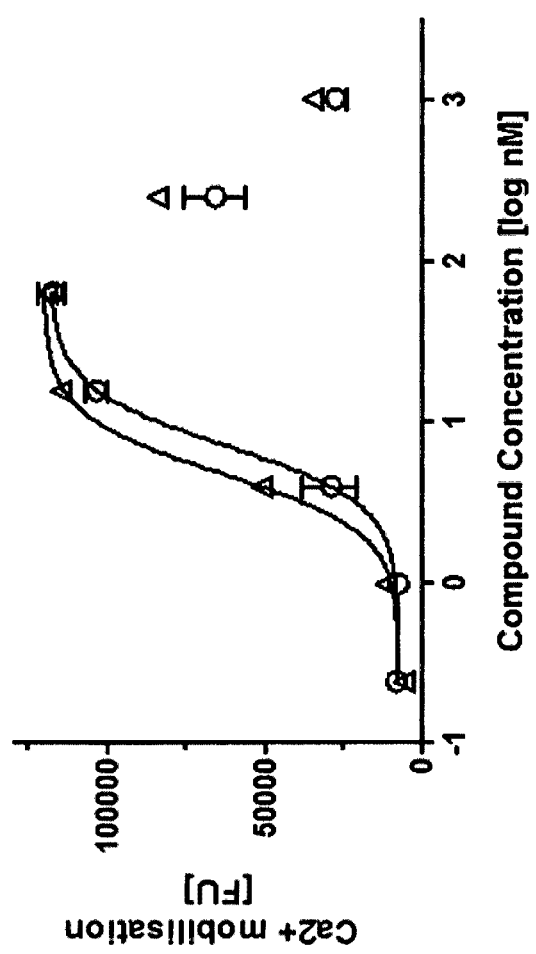
FIG. 2 shows bell-shaped EC50 curves of (16) (triangles) and (17) (circles) indicated as $Ca^{2+}$ mobilization (expressed as fluorescence units [FU]) over compound concentration (expressed as log nM of such compound concentration); fitted EC50 curves are shown as line; error bars indicate standard deviation.

Conjugates combining highly active NTR1 agonists and antagonists in a single conjugate (e.g. (16) and (17)) showed bell-shaped EC50 curves. This confirms that the agonistic as well as the antagonistic properties of the conjugate are active. The EC50 was determined using the ascending part of the curve (FIG. 2).

The results of this assay performed on some of the conjugates according to the present invention are given in the following Table 7.

TABLE 7

Results of the functional Ca2+ mobilisation assay

| Compound | Antagonistic Effect IC50 [nM] | Agonistic Effect EC50 [nM] |
|---|---|---|
| (12) | 2.5 | >50 000 |
| (13) | 6.1 | >50 000 |
| (14) | 2.3 | >50 000 |
| (15) | 2.3 | >50 000 |
| (16) | 3.8 | 4* |
| (17) | 3.4 | 7* |
| (18) | 3.8 | >50 000 |
| (19) | n.d. | n.d. |
| (20) | 32 | >50 000 |
| (21) | 18 | >50 000 |
| (22) | 21 | >50 000 |
| (23) | 15 | >50 000 |
| (24) | 38 | >50 000 |
| (25) | 12 | >50 000 |
| (30) | 1.0 | >50 000 |
| (29) | 3.3 | >50 000 |

TABLE 7-continued

Results of the functional Ca2+ mobilisation assay

| Compound | Antagonistic Effect IC50 [nM] | Agonistic Effect EC50 [nM] |
|---|---|---|
| (26) | 38 | >50 000 |
| (27) | 19 | >50 000 |
| (28) | 10 | >50 000 |

*bell-shaped curves

Example 28: Competitive αvβ6-Integrin Binding Assay

The latency-associated peptide (LAP) of transforming of TGF β1 is a natural ligand of αvβ6-Integrin. In order to determine the IC50 of conjugates that bind to αvβ6-Integrin in a competitive manner, microtiter plates were coated with LAP. Binding of αvβ6-Integrin to LAP-coated plates in the presence of competing conjugates was detected with an anti-αvβ6-Integrin antibody.

Ninety-six well MaxSorb plates (Nunc) were coated with 50 µl/well 0.3 µg/ml LAP (R&D Systems, Cat-#246-LP) in coating buffer (15 mM $Na_2CO_3$, 35 mM $NaHCO_3$, pH 9.6) over night. Plates were washed three times with wash buffer (150 mM NaCl, 1 mM $CaCl_2$, 1 mM $MgCl_2$, 0.1% BSA, 25 mM Tris pH 7.5) and blocked with 100 µl/well blocking buffer (3% BSA, 0.1% Tween20 in PBS) for at least 1 hour. Plates were then washed three times with washing buffer. A serial 1/3 dilution of the compound was prepared in washing buffer. Then 25 µl of each dilution, 25 µl washing buffer and 25 µl αvβ6-Integrin (R&D Systems, Cat-#3817-AV, 1.5 µg/ml in washing buffer) were applied to each LAP-coated and blocked microtiter plate well. The plate was incubated for 1 hours at room temperature and washed three times with washing buffer before 50 µl/well anti-αvβ6-Integrin antibody (Merck Millipore, Cat-# MAB1978, 1:1000 in washing buffer) was added. The plate was again incubated for 1 hours at room temperature and washed three times with washing buffer, before 50 µl/well secondary HRP-labeled anti-mouse-IgG antibody (Sigma, Cat-# A-5906, 1:2000 diluted in washing buffer) was added. The plate was incubated for 1 hour at room temperature and washed three times with washing buffer. Then 50 µl/well TMB solution (Seramun Diagnostica GmbH) was applied and the subsequent chromogenic conversion of TMB by HRP was detected by photometric measurement. The results of this assay performed on some of the conjugates according to the present invention are given in the following Table 8

TABLE 8

Results of the competitive αvβ6-Integrin binding assay

| Compound | IC50 [nM] |
|---|---|
| (21) | 120 |
| (22) | 130 |
| (23) | 59 |
| (24) | 130 |
| (25) | 270 |

Example 29: Cytotoxicity Assay

In order to determine the potency of the cytotoxic effector in conjugate (20), cytotoxicity of Paclitaxel was compared to the cytotoxicity of conjugate (20) using a commercial cytotoxicity assay.

The cytotoxicity assay (Roche, Cytotoxicity Detection LDH, Kit, Cat-#1 1644793001) is based on measurement of cytoplasmic enzyme activities released by damaged cells. Several enzyme-release assays have been described (e.g., for alkaline and acid phosphatase); however, many of these assays are hampered by (i) the low amount of endogenous enzyme present in many types of cells, and (ii) the elaborate kinetic assays required to quantitate the enzyme activities. In contrast, lactate dehydrogenase (LDH) is a stable cytoplasmic enzyme that is present in all cells. LDH is rapidly released into the cell-culture supernatant when the plasma membrane is damaged. Culture supernatant is collected and cells are removed from it. The cell-free supernatant is incubated with the substrate mixture from the kit. LDH activity is determined in a coupled enzymatic reaction; during this reaction, the tetrazolium salt INT is reduced to formazan. This formazan dye is easy to assay, since it is water-soluble and has a broad absorption maximum at approximately 500 nm. During the assay, LDH enzyme activity in the culture supernatant increases as the number of dead cells (or cells with damaged plasma membranes) increases. The increase in supernatant LDH activity directly correlates to the amount of formazan formed over time.

The assay was performed according to the manufactures instructions. In brief, HT29 cells were trypsinised and seeded into 96-well plates at 4000 to 10000 cells per well. After 20 h incubation at 37° C. and 5% $CO_2$, conjugates were added the cells. Final DMSO concentration was not higher than 0.7%. The cells were incubated for 48 h at 37° C. and 5% $CO_2$ before the cell culture supernatant was collected and run in the LDH assay. Supernatant from cell treated with 0.7% DMSO only served as negative control which corresponds to 0% cytotoxicity. Supernatant from cells treated with 0.7% DMSO only that were lysed using 2% Triton-X100 served as positive control which corresponds to 100% cytotoxicity. The compound concentration causing 20% cytotoxicity of some conjugates according to the invention is reported in Table 9.

TABLE 9

Results of the cytotoxicity assay

| Compound | Concentration [µM] at 20% cytotoxicity |
|---|---|
| Paclitaxel | 70 |
| (20) | 18 |

Example 30: Antibody Titration Assay

In order to determine the binding activity of MAB1909, (29), MAB3035 and (30), these antibodies and antibody conjugates were titrated on antigen-coated microtiter plates.
MAB1909 and (29):

Ninety-six well PolySorb plates (Nunc) were coated with 50 µl 10 µg/mL recombinant Tenascin comprising fibronectin domain 5, A1, A2, A3, A4, B, C and D (Trenzyme, Project #1678) in coating buffer (15 mM $Na_2CO_3$, 35 mM $NaHCO_3$, pH 9.6) for 2 h at room temperature. Plates were washed three times with wash buffer (PBS with 0.1% Tween20) and blocked with 100 µl/well blocking buffer (10% FCS, 0.1% Tween 20 in PBS) for at least 1 hour. Plates were then washed three times with washing buffer. A serial 1/2 dilution of MAB1909 or (29) was prepared in washing buffer. Then 50 µl/well of each dilution were applied to the Tenascin-coated and blocked microtiter plate. The plate was incubated for 1 hour at room temperature and washed three times with washing buffer before 50 µl/well HRP-labeled anti-mouse-IgG antibody (Sigma, Cat-# A-5906, 1:2000 diluted in washing buffer) was applied. The plate was incubated for 1 hour at room temperature and washed three times with washing buffer. Then 50 µl/well TMB solution (Seramun Diagnostica GmbH) was applied and the subsequent chromogenic conversion of TMB by HRP was detected by photometric measurement. Titration curves for selected conjugates are shown in FIG. 3.

MAB3035 and (30):

Ninety-six well PolySorb plates (Nunc) were coated with 50 µl/well 1.25 µg/mL recombinant EphA2 (Celonic, Cat-#: 13926-H20B1) in coating buffer (15 mM $Na_2CO_3$, 35 mM $NaHCO_3$, pH 9.6) for 2 h at room temperature. Plates were washed three times with washing buffer (25 mM HEPES, 175 mM NaCl, 5 mM $CaCl_2$, 0.1% Tween 80) and blocked with 100 µl/well blocking buffer (25 mM HEPES, 175 mM NaCl, 5 mM CaCl2, 0.1% Tween 80, 2% Bacto Yeast Extract, 3% BSA) for at least 1 hour. Plates were then washed three times with washing buffer. A serial 1/2 dilution of MAB3035 or (30) was prepared in washing buffer. Then 50 µl/well of each dilution were applied to the EphA2-coated and blocked microtiter plate. The plate was incubated for 1 hour at room temperature and washed three times with washing buffer before 50 µl/well HRP-labeled anti-mouse-IgG antibody (Sigma, Cat-# A-5906, 1:2000 diluted in washing buffer) was applied. The plate was incubated for 1 hour at room temperature and washed three times with washing buffer. Then 50 µl/well TMB solution (Seramun Diagnostica GmbH) was applied and the subsequent chromogenic conversion of TMB by HRP was detected by photometric measurement. Titration curves for selected conjugates are shown in FIG. 4.

Figure 3:
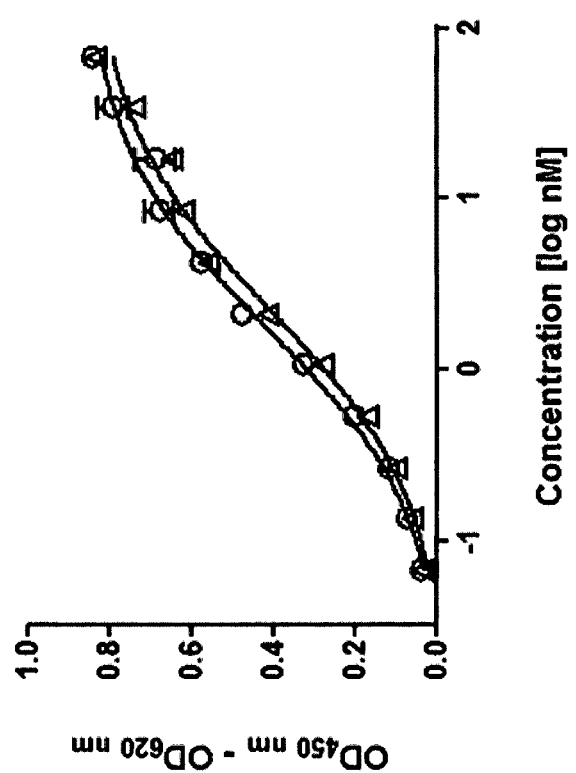
FIG. 3 shows the titration curves of MAB1909 (circles) and conjugate (29) (triangles) indicated as difference in optical density at 450 nm and 620 nm over compound concentration (expressed as log nM of such compound concentration)
Figure 4:
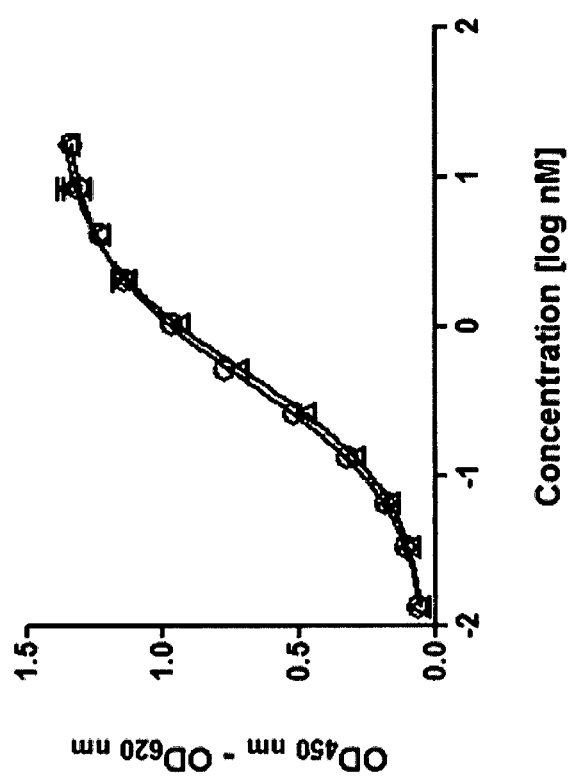
FIG. 4 shows the titration curves of MAB3035 (circles) and conjugate (30) (triangles) indicated as difference in optical density at 450 nm and 620 nm over compound concentration (expressed as log nM of such compound concentration)
Figure 5:
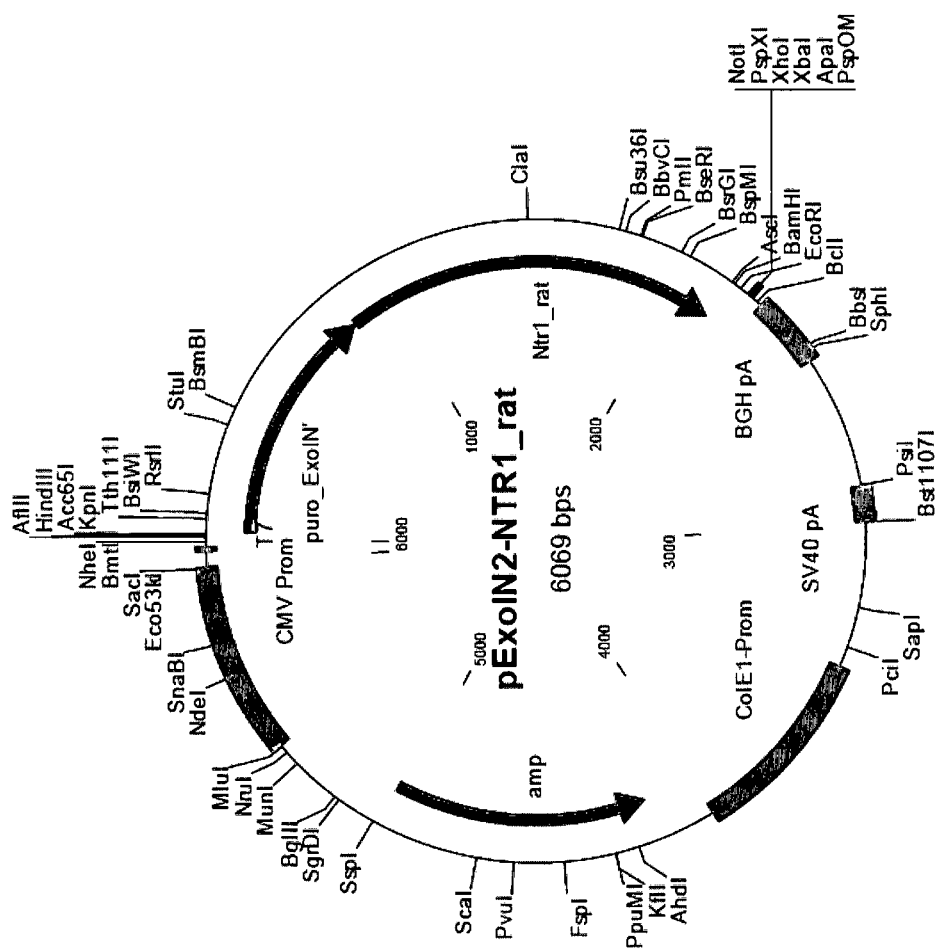
FIG. 5 shows the vector map of an exemplary pExoIN2-NTR1 plasmid used to generate the stable HEK293-NTR1 cell lines.
Figure 6:
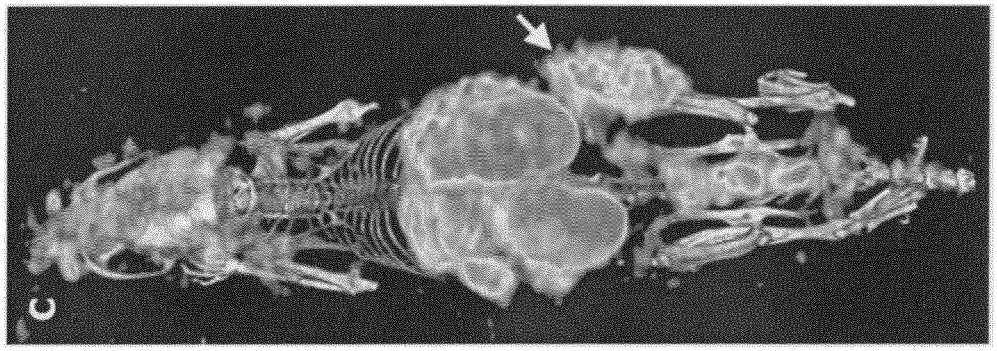
FIG. 6 shows SPECT-imaging results of 111In-(IIIa) of example part II (A), 111In-(Va) of example part II (B), and 111In-(IVa) of example part II (C) 12 hours post injection.
Figure 6:
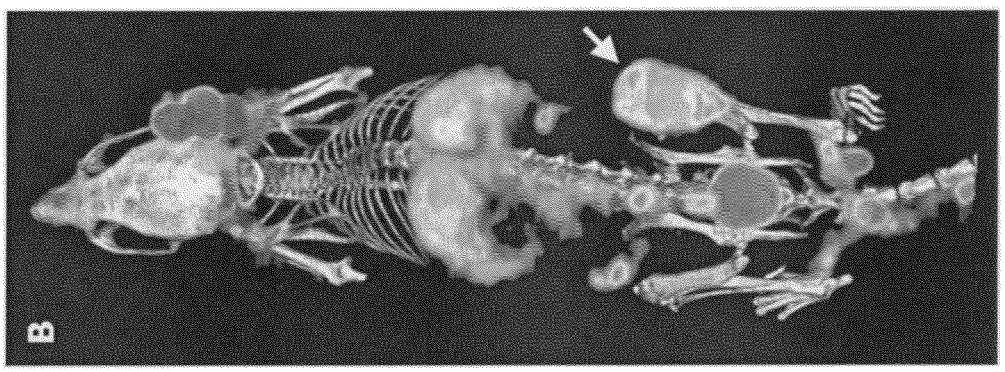
Figure 6:
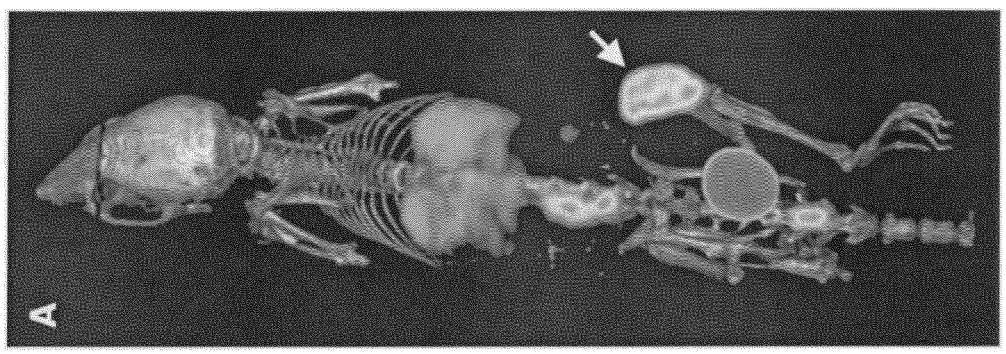
Figure 7:
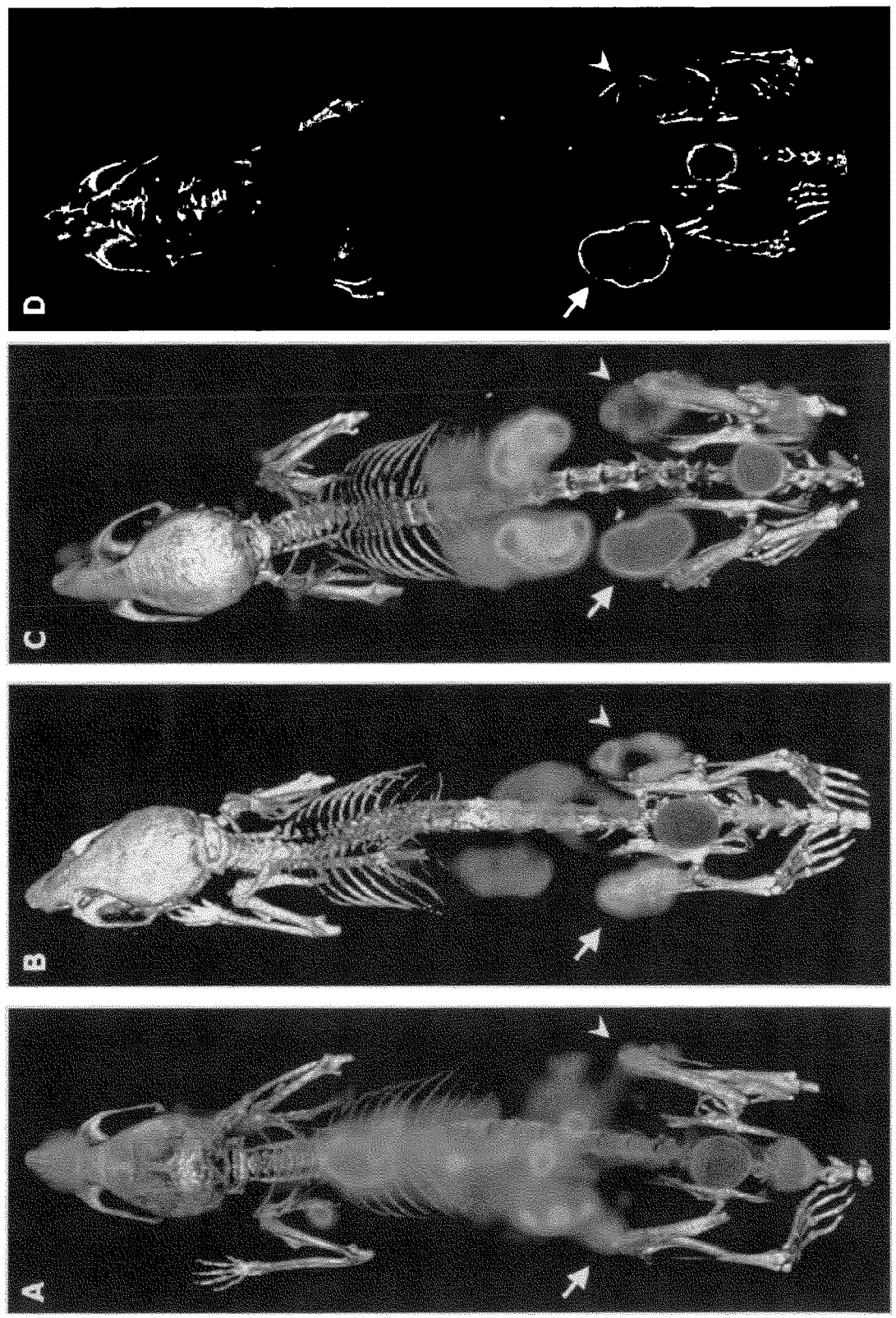
FIG. 7 shows SPECT-imaging results of 111In-(IIIa) of example part II 3 h (A), 6 h (B), 12 h (C), and 24 h (D) post injection. Arrow denotes HT29 tumor, arrowhead denotes Capan-1 tumor.
Figure 8:
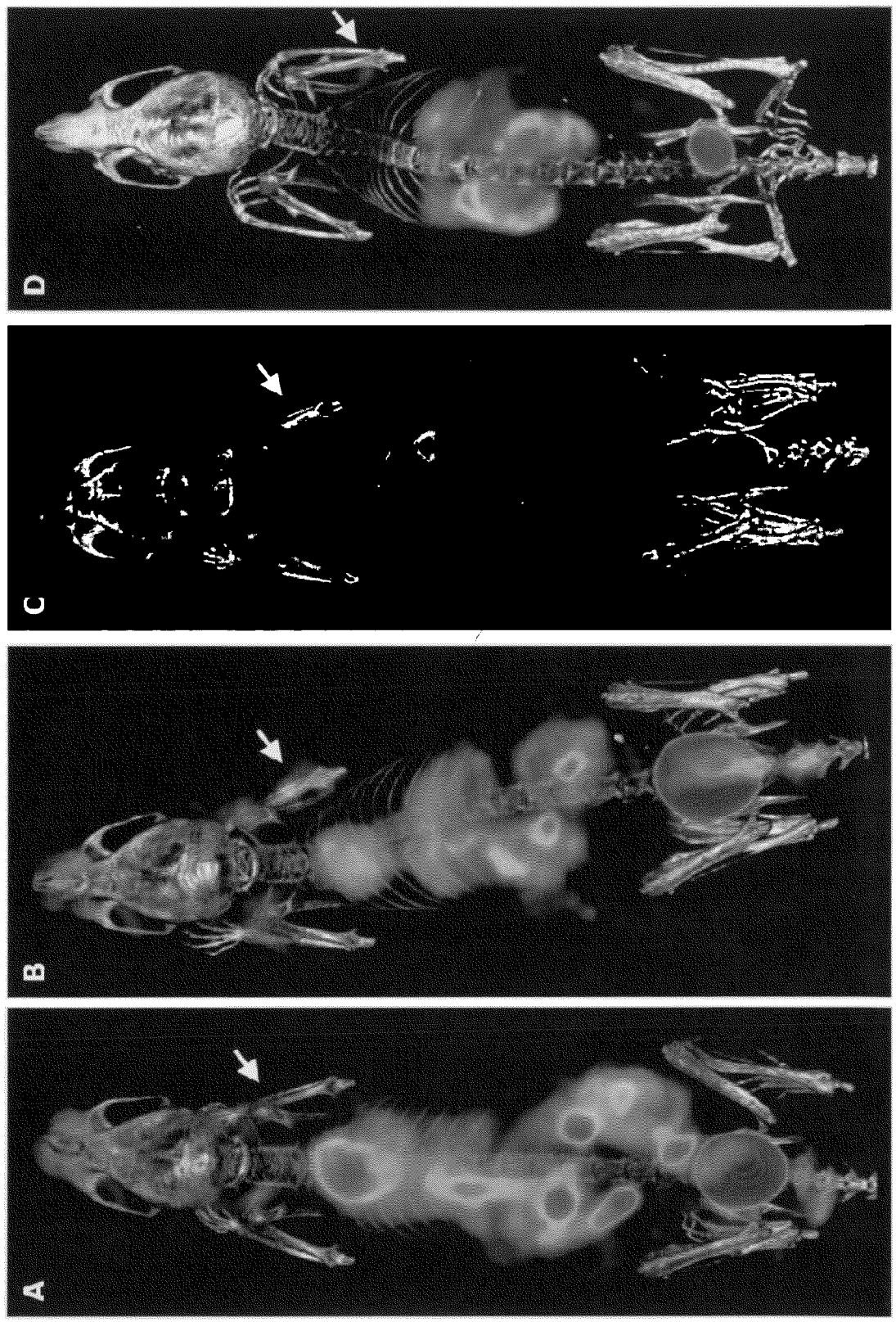
FIG. 8 shows SPECT-imaging results of 111In-(IIIa) of example part II 3 h (A), 6 h (B), 12 h (C), and 24 h (D) post injection. Arrow denotes HEK293 tumor.
Figure 9:
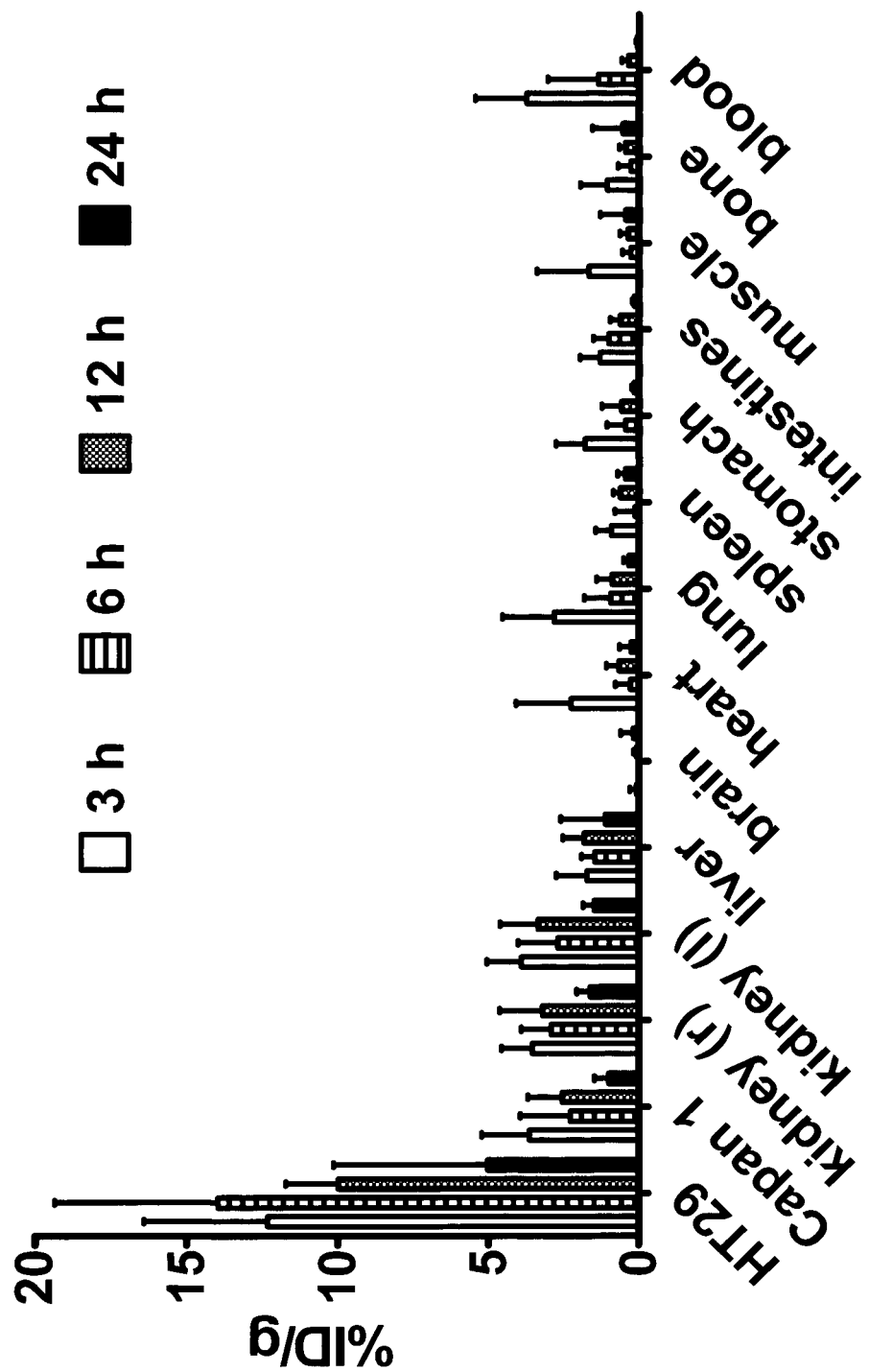
FIG. 9 shows the ex vivo biodistribution results of 111In-(IIIa) of example part II 3 h, 6 h, 12 h, and 24 h post injection in HT29 and Capan-1 tumors and various other organs.
Figure 10:
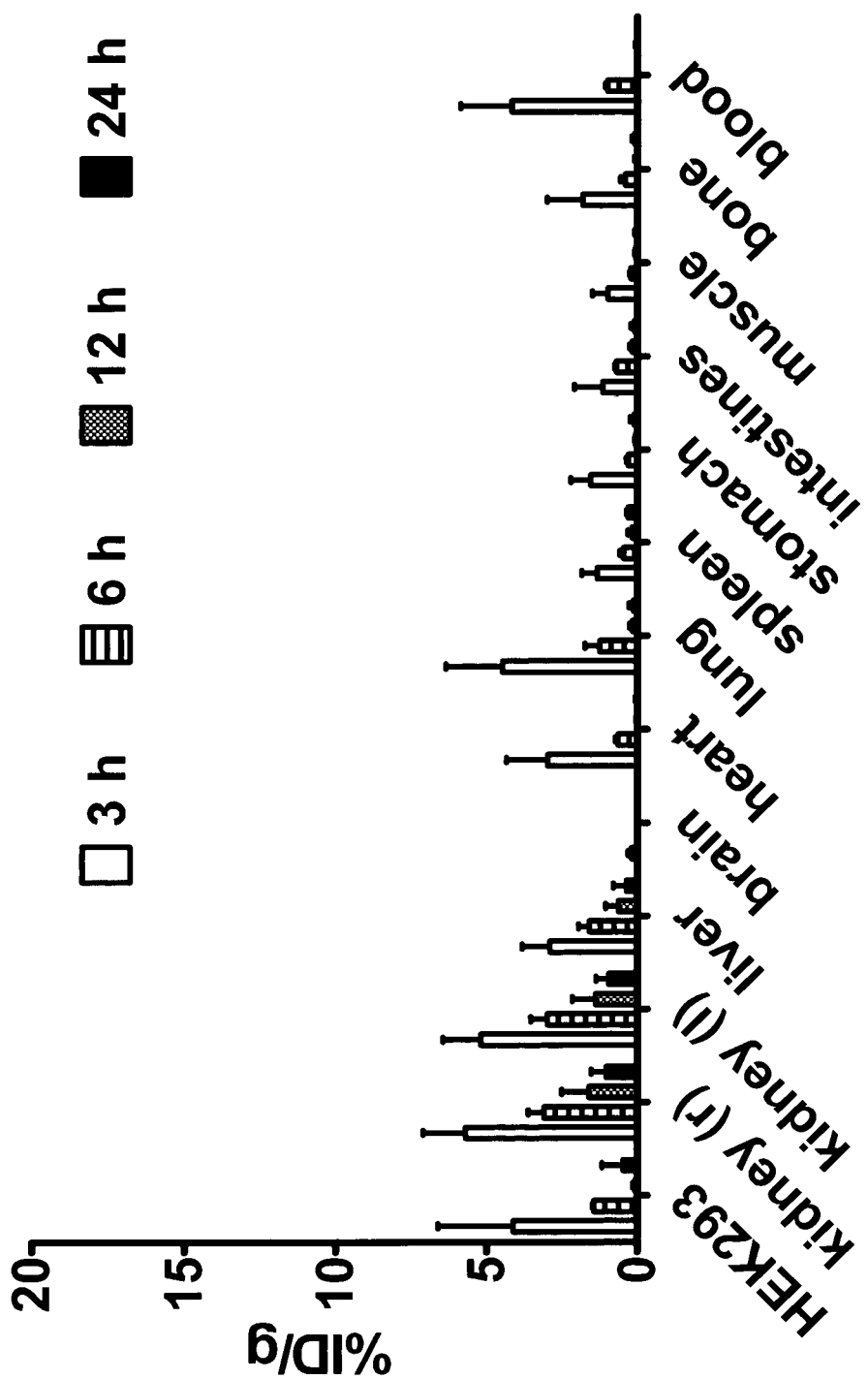
FIG. 10 shows the ex vivo biodistribution results of 111In-(IIIa) of example part II 3 h, 6 h, 12 h, and 24 h post injection in HEK293 tumors and various other organs.

As may be taken from FIGS. 3 and 4, the binding characteristics of the conjugate of the invention comprising, as the first targeting moiety, a compound of formula (1) and, as the second targeting moiety, the indicated antibody moiety, did not differ from the binding characteristics of said antibody moiety when said antibody moiety was used alone, i.e. not conjugated to the first targeting moiety.

Example 31: $^{111}$In-Labeling of Selected Compounds

In order to serve as a diagnostically or therapeutically active agent, a compound needs to be labeled with a radioactive isotope. The labeling procedure needs to be appropriate to ensure a high radiochemical yield and purity of the radiolabeled compound of the invention. This example shows that the compounds of the present invention are appropriate for radiolabeling and can be labeled in high radiochemical yield and purity.

1.6 nmol of the compounds of formula (IIIa), (13), (15), (18) and (22) were dissolved in buffer (1 M ammonium acetate, pH 5) and mixed with 50 MBq of $^{111}$In (dissolved in 0.04 M HCl). The mixture was heated to 70-95° C. for 10 to 20 min. After cooling, the labeling was analyzed by HPLC. For HPLC, the labeling solution was analysed with a Phenomenex Kinetex C18 column. Gradient A: MeCN, 0.1% TFA, Gradient B: $H_2O$, 0.1% TFA, flow rate 0.8 ml/min; detector: NaI (Raytest), DAD254 nm. Retention time of the labeled product: 9.5-9.9 min.

Radiochemical yield was ≥90%, radiochemical purity was ≥85%, specific activity: 30 MBq/nmol.

Example 32: Imaging and Biodistribution Studies

Radioactively labeled compounds can be detected by imaging methods such as SPECT and PET. Furthermore, the data acquired by such techniques can be confirmed by the direct measurement of radioactivity contained in the individual organs prepared from an animal injected with a radioactively labeled compound of the invention. Thus, the biodistribution of a radioactively labeled compound can be determined and analyzed. This example shows that the compounds of the present invention show a biodistribution appropriate for diagnostic imaging and therapeutic treatment of tumors.

All animal experiments were conducted in compliance with the German animal protection laws. Female SWISS nude mice (Crl:NU(Ico)-Foxnlnu; Charles River, Sulzfeld, Germany) were inoculated with $1\times10^7$ HT-29 cells into the right flank 24-72 hours after a whole body irradiation with a γ source (2 Gy, $^{60}$Co, BioMep, Bretenieres, France). When tumors were visible (after 14-21 days), mice received 5-10 MBq $^{111}$In-labelled (IIIa), (13), (15), (18) or (22) administered intravenously via the tail vein. Images were obtained on a NanoSPECT/CT system (BioScan Ltd., Washington, USA). Fusion of SPECT and CT data was performed with the software OsiriX Imaging Software.

The results of the imaging studies for selected compounds are shown in FIGS. 14 A and B. As may be taken from FIGS. 14 A and B, the conjugates of the invention comprising, as a first targeting moiety, a compound of formula (4) as well as a second targeting moiety (B-E) accumulate in NTR1-expressing tumors in a manner comparable to a compound comprising the first targeting moiety only (A).

EXAMPLE PART II

Abbreviations used in the instant application and the following examples in particular are as follows:
5-HT means 5-hydroxytryptamine
5-HT1A means 5-hydroxytryptamine receptor 1A
5-HT2B means 5-hydroxytryptamine receptor 1B
5-HT2A means 5-hydroxytryptamine receptor 2A
5-HT2B means 5-hydroxytryptamine receptor 2B
5-HT-3 means 5-hydroxytryptamine channel 3
5-HT5a means 5-hydroxytryptamine receptor 5a
5-HT6 means 5-hydroxytryptamine receptor 6
5-HT7 means 5-hydroxytryptamine receptor 7
% ID/g means percent injected dose per gram
A1 mean adenosine receptor 1
A2A means adenosine receptor 2A
A3 means adenosine receptor 3
alpha1 means alpha1 adrenergic receptor
alpha2 means alpha2 adrenergic receptor
ACN means acetonitrile
Ahx means 6-Aminohexanoic acid
amu means atomic mass unit
aq. means aqueous
AT 1 means angiotensin receptor 1
B2 means bradykinin receptor 2
beta1 means beta1 adrenergic receptor
beta2 means beta2 adrenergic receptor
BSA means bovine serum albumin
BZD means benzodiazepine
CB 1 means cannabinoid receptor 1
CCK1 means cholecystokinin receptor 1
CCR1 means C—C chemokine receptor type 1
CHO means Chinese hamster ovary
CT means computed tomography
CXCR2 means C—X—C chemokine receptor type 2
D1 means dopamine receptor 1
D2S means dopamine receptor 2S
DCM means dichloromethane delta2 means delta2 opioid receptor
DFO means N'-{5-[Acetyl(hydroxy)amino]pentyl}-N-[5-({4-[(5-aminopentyl) (hydroxy) amino]-4-oxobutanoyl}amino)pentyl]-N-hydroxysuccinamide
DIC means N,N'-Diisopropylcarbodiimide
DIPEA means diisopropylethylamine
DOTA means 1,4,7,10-tetraazacyclododecane-1,4,7,10-tetraacetic acid
DOTA(tBu)$_3$-OH means Tri-tert-butyl-1,4,7,10-tetraazacyclo-dodecane-1,4,7,10-tetraacetate
DMF means N,N-dimethylformamide
EC50 means half-maximal excitatory concentration
EP4 means prostaglandin e receptor type 4
ETA means endothelin receptor A
Et$_2$O means Diethylether
EtOAc means ethylacetate
Fmoc means 9-Fluorenylmethoxycarbonyl
GABA mean gamma-amino butyric acid
GAL2 means galanin receptor 2
GPCR means G-protein coupled receptor
h means hour(s)
H1 means histamine receptor 1
H2 means histamine receptor 2
HATU means O-(7-azabenzotriazol-1-yl)-N,N,N',N'-tetramethyluronium hexafluorophosphate
HOAc means acetic acid
HOAt means 1-Hydroxy-7-azabenzotriazole
HPLC means high performance liquid chromatography
IC50 means half-maximal inhibitory concentration
kappa means kappa opioid receptor
LC-MS means high performance liquid chromatography coupled with mass spectrometry
LiOH means lithium hydroxide
M1 means muscarinic receptor 1
M2 means muscarinic receptor 2
M3 means muscarinic receptor 3
max. means maximum
MC4 means melanocortin receptor 4
MeOH means Methanol
min means minute(s)
MT 1 means melatonin receptor 1
MTBE means Methyl-tert-butylether
mu means mu opioid receptor
NaHCO$_3$ means sodium hydrogencarbonate
NaCl means sodium chloride
Na$_2$SO$_4$ means sodium sulfate
n.d. means not determined
NK2 means neurokinin receptor 2
NK3 means neurokinin receptor 3
NMP means 1-methyl-2-pyrrolidone
NODAGA means 1,4,7-triazacyclononane, 1-glutaric acid-4,7-acetic acid
NOP means nociception receptor
NT means neurotensin
NTR1 means neurotensin receptor 1
PET mean positron emission tomography
prep. means preparative
PyBOP means benzotriazole-1-yl-oxy-tris-pyrrolidino-phosphonium hexafluorophosphate
RLB means radioligand binding assay
RP means reversed phase
RT means room temperature
R$_t$ means retention time
sat. means saturated
SPECT means single photon emission computed tomography
sst means somatostatin receptor
tBu means tert. butyl
TFA means trifluoroacetate or trifluoroacetic acid
TIPS means triisopropylsilane
TLC means thin layer chromatography
Ttds means N-(3-{2-[2-(3-Amino-propoxy)-ethoxy]-ethoxy}-propyl)-succinamic acid
VPAC1 means vasoactive intestinal polypeptide receptor 1
Y1 means neuropeptide Y receptor 1
Y2 means neuropeptide Y receptor 2
⇌ as used in structural formulas or figures represents a functionalized solid material (solid phase synthesis resin)

Example 1: Material and Methods

The materials and methods as well as general methods are further illustrated by the following examples.
Solvents:

Solvents were used in the specified quality without further purification. Acetonitrile (Gradient grade, Sigma-Aldrich); dichloromethane (AnalaR Normapur, VWR); ethylacetate (laboratory reagent grade, Fisher Scientific); N,N-dimethylformamide (peptide synthesis grade, Biosolve); 1-methyl-2-pyrolidone (biotech. grade, Sigma-Aldrich) 1,4-dioxane (Emplura, Merck); methanol (p. a., Merck).
Water:

Milli-Q Plus, Millipore, demineralized.
Chemicals:

Chemicals were synthesized according to or in analogy to literature procedures or purchased from Sigma-Aldrich-Fluka (Deisenhofen, Germany), Bachem (Bubendorf, Switzerland), VWR (Darmstadt, Germany), Polypeptide (Strasbourg, France), Novabiochem (Merck Group, Darmstadt, Germany), Acros Organics (distribution company Fisher Scientific GmbH, Schwerte, Germany), Iris Biotech (Marktredwitz, Germany), Amatek Chemical (Jiangsu, China), Roth (Karlsruhe, Deutschland), Molecular Devices (Chicago, USA), Biochrom (Berlin, Germany), Peptech (Cambridge, Mass., USA), Synthetech (Albany, Oreg., USA), Pharmacore (High Point, NC, USA) and Anaspec (San Jose, Calif., USA) or other companies and used in the assigned quality without further purification.

$^{177}$Lu-[NT(8-13)-Tle$^{12}$] is DOTA-D-Lys-Ttds-Arg-Arg$^9$-Pro$^{10}$-Tyr$^{11}$-Tle$^{12}$-Leu$^{13}$-OH and was synthesized according to standard Fmoc-solid-phase-peptide synthesis as described in detail in this reference ("Fmoc Solid Phase Peptide Synthesis" Editors W. Chan, P. White, Oxford University Press, USA, 2000), Fmoc-Ttds-OH is commercially available at Polypeptide (Strasbourg, France).

SR-142948 is (2-[(5-(2,6-Dimethoxy-phenyl)-1-{4-[(3-dimethylamino-propyl)-methyl-carbamoyl]-2-isopropyl-phenyl}-1H-pyrazole-3-carbonyl)-amino]-adamantane-2-carboxylic acid, >97%) and was purchased from Tocris Bioscience (Bristol, UK).

1-(4-Carboxy-2-isopropyl-phenyl)-5-(2,6-dimethoxy-phenyl)-1H-pyrazole-3-carboxylic acid methyl ester (X) was prepared according to literature procedures as disclosed in U.S. Pat. No. 5,723,483.

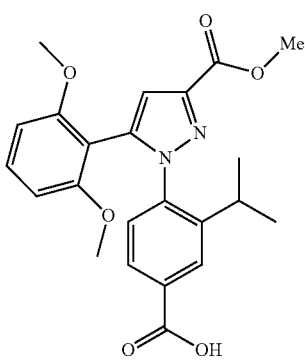 (X)

Cells:

HT29 (Cat. No. 91072201) were purchased from ECACC and Capan-1 from ATCC (Cat No. HTB-79) cells. HEK293 cells expressing human, murine, and rat NTR1 were produced by Trenzyme (Konstanz, Germany). The cells were stably transfected using an expression system encoded by the pExoIN2 plasmid vector (see FIG. 5) and consisting of hemagglutinin epitope (HA)-tagged puromycin N-acetyl-transferase fused to the N-terminus of ubiquitin, which in turn is fused to the N-terminus of NTR1. This system ensures efficient expression of the transfected protein. The generation of stable cell lines and the pExoIN vector are described in Matentzoglu et al., BioTechniques, 2009, 46, 21-28.

Plasticware for biochemical and cell-based assays was purchased from VWR (Darmstadt, Germany).

Concentrations are given as percent by volume unless otherwise stated.

HPLC/MS analyses were performed by injection of 5 µl of a solution of the sample, using a 2 step gradient for all chromatograms (5-50% B in 5 min, followed by 50-100% B in 2 min, A: 0.05% TFA in water and B: 0.05% TFA in ACN). RP columns were from Phenomenex (Type Luna C-18, 3 µm, 50×2.00 mm, flow 0.5 ml, HPLC at room temperature); Mass spectrometer: Thermo Finnigan Advantage and/or LCQ Classic (both ion trap), ESI ionization, helium served as impact gas in the ion trap. Excalibur version 1.4 was used as software. UV detection was done at λ=230 nm. Retention times ($R_t$) are indicated in the decimal system (e.g. 1.9 min=1 min 54 s) and are referring to detection in the mass spectrometer. The dead time between injection and UV detection (HPLC) was 0.45 min, and for the delay between UV detection and mass detection was corrected in the chromatogram. The accuracy of the mass spectrometer was approx. ±0.5 amu.

Preparative HPLC:

Preparative HPLC separations were done with the columns and gradients described in the individual examples. For the gradient the following solvents were used:
A: 0.05% TFA in $H_2O$
B: 0.05% TFA in ACN A linear binary gradient was used in all separations. For instance: If the gradient is described as: "20 to 60% B in 30 min", this means a linear gradient from 20% B (and 80% A) up to 60% B (and 40% A) within 30 min. The flow-rate depends on the column size: For 25 mm diameter of the column it is 30 ml/min and for 50 mm diameter of the column it is 60 ml/min, respectively.

Compounds were named using AutoNom version 2.2 (Beilstein Informationssysteme Copyright© 1988-1998, Beilstein Institut für Literatur der Organischen Chemie licensed to Beilstein Chemiedaten and Software GmbH).

Preferably, in case of chelator-containing compounds the chelator was referred to by its commonly accepted abbreviation rather than the full systematic name in order to avoid unnecessarily complex names. In case of compounds containing a protected form of the chelator the corresponding chelator abbreviation together with the name and number of the protecting group in parentheses is preferably used. For instance, if the chelator is DOTA, the abbreviation DOTA- or DOTA(tBu)$_3$- in the molecule name means that the DOTA-moiety or its three time tert. butyl protected form is covalently attached to a designated position of the molecule by one of its carboxylic acid groups. In most of the cases the carboxylic acid group of a chelator is utilized for the attachment to the molecule. But, if the chelator is DFO the abbreviation DFO- in the name means that the amino group of DFO is covalently attached to a designated position of the molecule. However, someone skilled in the art will easily understand which functional groups or atoms of a chelator are capable of forming the respective covalent attachment to the molecule. These conventions apply not only to the compounds as recited in the example part of the instant description but to each and any part thereof, including the claims.

Preparation of Compounds:

The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are incorporated herein by reference.

Specific embodiments for the preparation of compounds of the invention are provided in the following examples. Unless otherwise specified all starting materials and reagents are of standard commercial grade, and are used without further purification, or are readily prepared from such materials by routine methods. Those skilled in the art of organic synthesis will recognize in light of the instant disclosure that starting materials and reaction conditions may be varied including additional steps employed to produce compounds encompassed by the present invention.

Example 2: Synthesis of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbenyl}-amino)-adamantane-2-carboxylic acid tert-butyl ester bound to trityl resin (XVIII)

(XVIII)

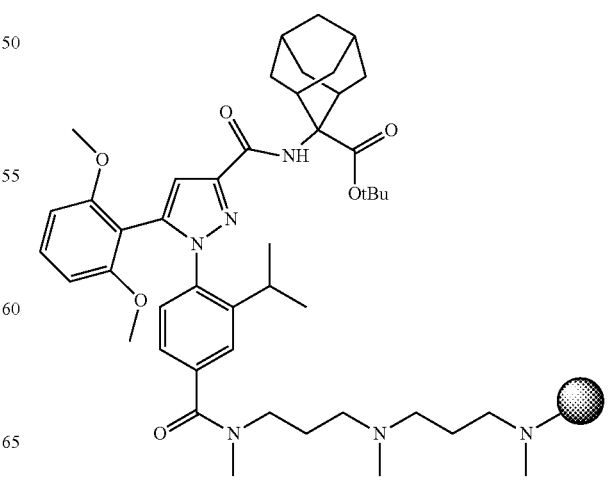

Figure 11:
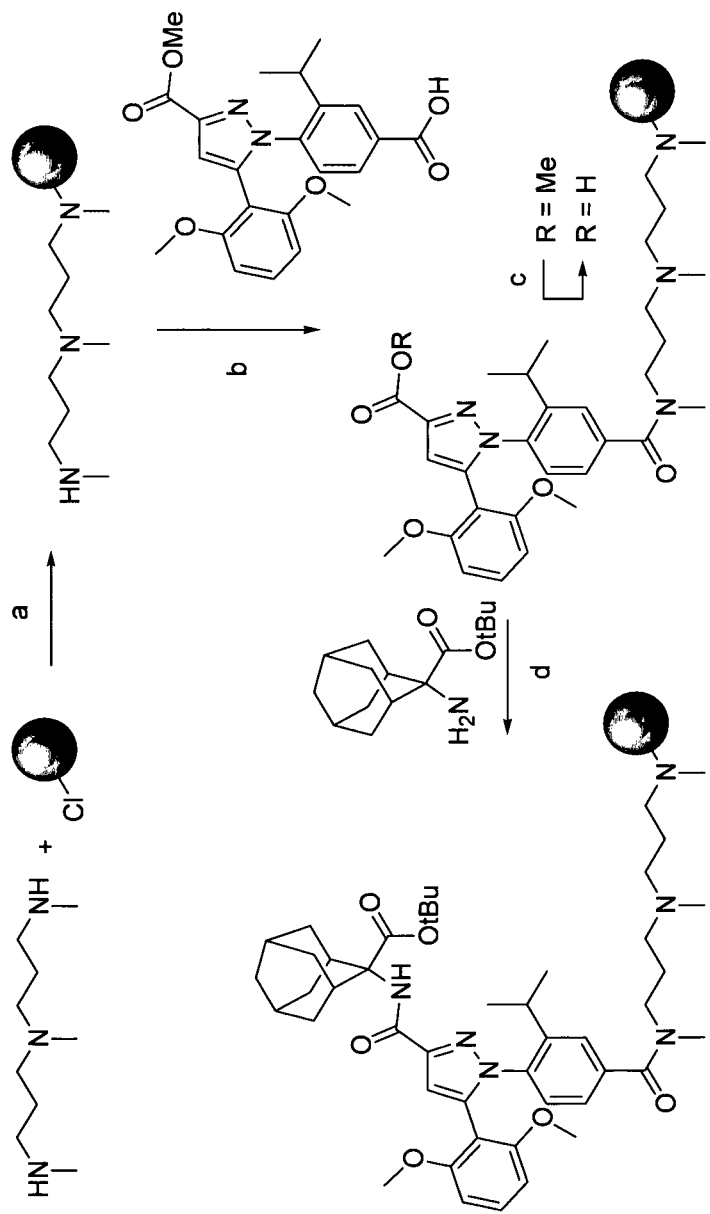
FIG. 11 shows the solid phase synthesis of derivatized resin of formula (XVIII) of example part II.

A. Loading of chlorotrityl polystyrene resin with N,N-Bis[3-(methylamino)-propyl]methylamine (FIG. 11 step a)

Tritylchloride polystyrene resin (initial loading 1.8 mmol/g, 1.11 g, 2 mmol, 1.0 eq.) was swollen in DCM for 30 min. Then N,N-Bis[3-(methylamino)-propyl]methylamine (1.6 ml, 8 mmol, 4 eq.) in DCM (6.5 ml) was added to the resin and the mixture was shaken overnight. Afterwards the resin was washed successively with DMF, DCM and diethyl ether (5/3/1) and dried in the vacuum.

B. Coupling of 1-(4-Carboxy-2-isopropyl-phenyl)-5-(2,6-dimethoxy-phenyl)-1H-pyrazole-3-carboxylic acid methyl ester (FIG. 11 step b)

N,N-Bis[3-(methylamino)-propyl]methylamine charged trityl resin (1 g, 1.8 mmol, 1.0 eq.) was swollen in DMF for 30 min. The resin was washed with DMF/DIPEA (9/1) (to remove residual N,N-Bis[3-(methylamino)-propyl]methylamine hydrochloride) and DMF (3/3). 1-(4-Carboxy-2-isopropyl-phenyl)-5-(2,6-dimethoxy-phenyl)-1H-pyrazole-3-carboxylic acid methyl ester (X) (1.15 g, 2.7 mmol, 1.5 eq.) [prepared as disclosed in U.S. Pat. No. 5,723,483], HATU (1.03 g, 2.7 mmol, 1.5 eq.) and DIPEA (937 µl, 5.4 mmol, 3 eq.) were dissolved in DMF (18 ml) and mixed thoroughly for 1 min. After addition of the activated building block the resin was shaken overnight. The resin was washed (DMF five times, DCM three times and diethyl ether) and dried in the vacuum. The completeness of the reaction was assured as follows: A resin sample was treated with a solution of benzoic acid, HATU and DIPEA (1/1/2) in DMF for 30 min. After washing with DMF and DCM, TFA was added to the resin. Absence of the benzoic acid N,N-Bis[3-(methylamino)-propyl]methyl amide in LC-MS indicated absence of free amino functions on the resin thus providing evidence of the completed coupling of 1-(4-Carboxy-2-isopropyl-phenyl)-5-(2,6-dimethoxy-phenyl)-1H-pyrazole-3-carboxylic acid methyl ester.

C. Hydrolysis of the methylester (FIG. 11 step c)

The resin (1.64 g, 1.75 mmol, 1.0 eq.) described before was treated overnight with dioxane (35 ml) and LiOH hydrate (689 mg, 16 mmol, 10 eq.) in water (12 ml). The procedure was repeated once, the resin was subsequently washed with water, DMF and DCM (3/3/3) and dried in the vacuum.

D. Coupling of 2-Amino-adamantane-2-carboxylic acid tert-butyl ester (FIG. 11 step d)

The resin (0.7 g, 0.75 mmol, 1.0 eq.) described before was swollen in DMF for 30 min. Then HOAt (153 mg, 1.13 mmol, 1.5 eq.), DIC (232 µl, 1.5 mmol, 2.0 eq.) and 2-amino-adamantane-2-carboxylic acid tert-butyl ester (942 mg, 3.75 mmol, 5.0 eq.) were dissolved in a mixture of DMF and DCM (2:1) (6 ml) and subsequently added to the resin. After 2.5 hours additional DIC (232 µl, 1.5 mmol, 2.0 eq.) was added. The resin was left to shake for 60 hours after which the reaction was complete. Afterwards the resin was washed with DMF and DCM (3/3) and dried in the vacuum.

Example 3 Synthesis of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX)

(XIX)

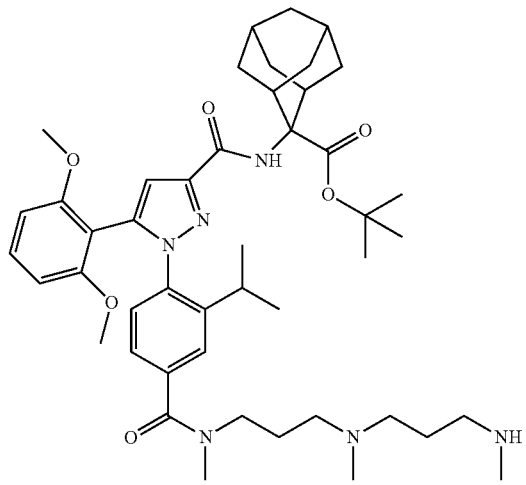

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester resin (XIX) (0.7 g, 0.75 mmol, 1.0 eq.) was treated four times with a mixture of TFA, TIPS and DCM (2/5/93). To prevent premature loss of the DOTA protecting groups the resulting solutions were immediately poured into aqueous buffer solution (10 ml, pH=8, 100 mM $NH_4(CO_3)_2$). All DCM-buffer mixtures were combined and the organic layer reduced to a minimum by evaporation. To the remaining aqueous solution ACN (5 ml) was added and the mixture was freeze-dried to yield 800 mg of crude product. The residue was subjected to HPLC purification (15 to 45% B in 30 min, Agilent PLRP-S 25×150 mm) to give the title compound (210 mg, 26.3 µmol, 35.0%). HPLC: $R_t$=5.5 min. MS: m/z=799.4 ([M+H]$^+$, calculated 799.5). $C_{46}H_{66}N_6O_6$ (MW=799.05).

Example 4: 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (III)

(III)

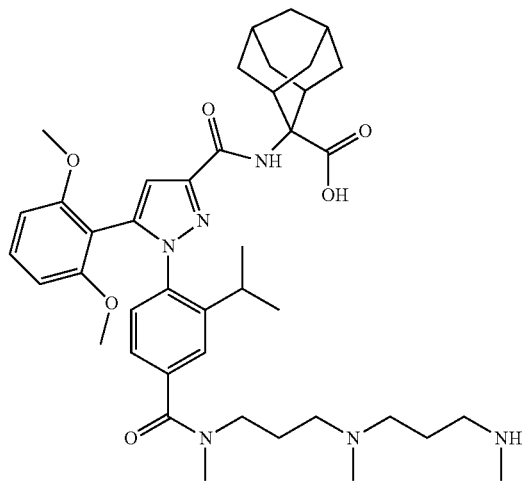

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester resin (XIX) (0.7 g, 0.75 mmol, 1.0 eq.) was treated with a mixture of TFA and DCM (1/4) for 2 h. The cleavage solution was evaporated to dryness to yield 709 mg of crude product.

The residue was purified by HPLC (20 to 50% B in 30 min, Agilent PLRP-S 25×150 mm) to give the title compound (155.5 mg, 0.21 mmol, 28%). HPLC: $R_t$=4.7 min. MS: m/z=743.4 ([M+H]$^+$, calculated 742.4). $C_{42}H_{57}N_6O_6$ (MW=741.94).

Example 5: Synthesis of 2-{[1-{4-[(3-{[3-(DOTA-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-adamantane-2-carboxylic acid (IIIa)

(IIIa)

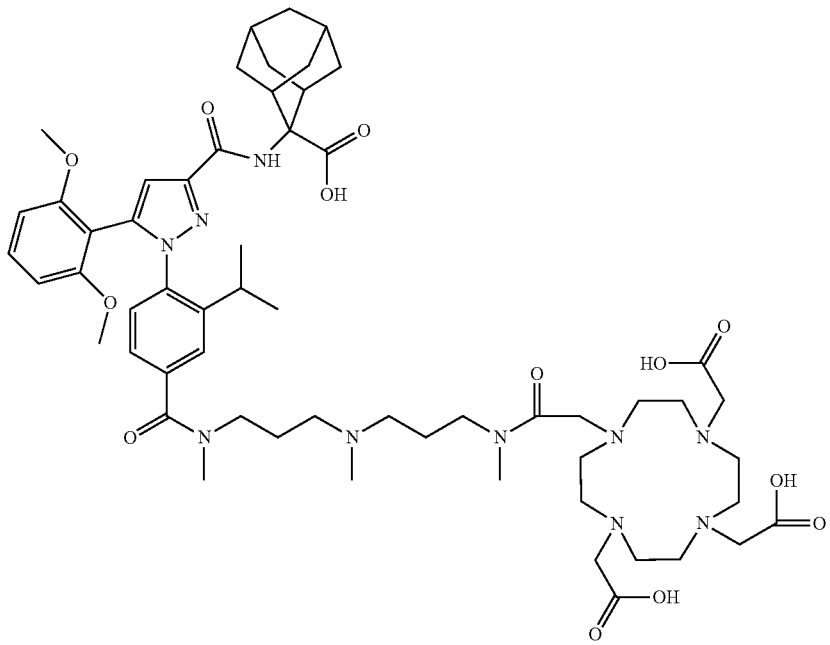

A. 1-{4-[(3-{[3-(DOTA(tBu)$_3$-methyl-amino)-propyl]-methyl-amino}-propyl)-methyl-carbamoyl]-2-isopropyl-phenyl}-5-(2,6-dimethoxy-phenyl)-1H-pyrazole-3-carboxylic acid methyl ester (XI)

DOTA(tBu)$_3$-OH (500 mg, 0.873 mmol, 1.0 eq.) was dissolved in dry DMF (5 ml). After adding N,N'-Dimethyl-N-(3-methylamino-propyl)-propane-1,3-diamine (3.5 ml, 17.5 mmol, 20 eq.) and DIPEA (0.389 ml, 2.27 mmol, 2.6 eq.) the mixture was cooled to 0° C. PyBOP (590 mg, 1.13 mmol, 1.3 eq.) was dissolved in dry DMF (5 ml). 0.5 ml of this PyBOP solution was added every 5 to 10 min to the reaction mixture until all the solution was added. After 1 h DMF was removed under vacuum. The remaining residue was dissolved in EtOAc (100 ml) and extracted with water (5×5 ml). The organic layer was dried over Na$_2$SO$_4$ and evaporated to yield 1.01 g crude material.

This crude material (1.01 g, max. 0.873 mmol) was dissolved in dry DMF (4 ml). In a separate flask 1-(4-Carboxy-2-isopropyl-phenyl)-5-(2,6-dimethoxy-phenyl)-1H-pyrazole-3-carboxylic acid methyl ester (X) (445 mg, 1.05 mmol, 1.2 eq.) [prepared as disclosed in U.S. Pat. No. 5,723,483] was dissolved in dry DMF (2.5 ml). HATU (398 mg, 1.05 mmol, 1.2 eq.) and DIPEA (0.359 ml, 2.10 mmol, 2.4 eq.) were added sequentially and the reaction was stirred for ten minutes. The dissolved crude material from the first step (DOTA modified diamine), was added dropwise to this HATU-activated carboxylic acid solution. After 1 h additional HATU-activated carboxylic acid solution was added [carboxylic acid of formula (X) (102 mg, 0.24 mmol, 0.27 eq.) in dry DMF (0.5 ml), HATU (91 mg, 0.24 mmol, 0.27 eq.) DIPEA (0.082 ml, 0.48 mmol, 0.55 eq.), 10 min preactivation]. After 15 h additional preactivated carboxylic acid of formula (X) was added [carboxylic acid of formula (X) (148 mg, 0.35 mmol, 0.40 eq.) in dry DMF (0.75 ml), HATU (133 mg, 0.35 mmol, 0.40 eq.), DIPEA (0.120 ml, 0.698 mmol, 0.80 eq.) 10 min pre-activation]. 2 h after the last addition DMF was evaporated and the residual solvents were removed under high-vacuum.

The residual oil was dissolved in ACN/water 1/1 (ca. 10 ml) and separated by prep. HPLC (20 to 60% B in 30 min, Agilent PLRP-S 50×150 mm) to give the title compound (585 mg, 0.516 mmol, 59%). HPLC: $R_t$=5.4 min. MS: m/z=1134.7 ([M+H]$^+$, calculated 1134.7). $C_{60}H_{95}N_9O_{12}$ (MW=1134.45).

B. 1-{4-[(3-{[3-(DOTA(tBu)$_3$-methyl-amino)-propyl]-methyl-amino}-propyl)-methyl-carbamoyl]-2-isopropyl-phenyl}-5-(2,6-dimethoxy-phenyl)-1H-pyrazole-3-carboxylic acid (XII)

Methylester of formula (XI) (294 mg, 0.259 mmol) was dissolved in 1,4-dioxane (1.35 ml). A 1 M aqueous solution of LiOH (1.04 ml, 1.04 mmol, 4 eq.) was added dropwise. After stirring for 5 h the pH was adjusted to 5-6 with HOAc (0.373 ml). After addition of ACN (18 ml) and water (225 ml) the cloudy solution was subjected to a solid phase extraction column (3.0 g Varian Bondesil-ENV in a 60 ml polystyrene syringe, prewashed with methanol (3×20 ml) and water (3×20 ml). The column was eluted with 60 ml of 10% ACN in water as first fraction and each of the next fractions were eluted with 60 ml of 50% ACN in water containing 0.1% TFA. After lyophylization of the fractions 3 to 8 the title compound (248 mg, 86%) was obtained. HPLC: $R_t$=4.9 min. MS: m/z=1120.7 ([M+H]$^+$, calculated 1120.7). $C_{59}H_{93}N_9O_{12}$ (MW=1120.42).

C. 2-{[1-{4-[(3-{[3-(DOTA(tBu)$_3$-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-adamantane-2-carboxylic acid (XIII)

Carboxylic acid of formula (XII) (248 mg, 0.222 mmol) was dissolved in dry NMP (3 ml). HATU (84.3 mg, 0.222 mmol, 1.0 eq.) was added as solid. To this mixture DIPEA (76 µl, 0.443 mmol, 2.0 eq.) was added. After stirring for 5 min this solution was transferred within 5 min to a suspension of 2-amino-adamantane-2-carboxylic acid (43.3 mg, 0.222 mmol, 1.0 eq.) in dry NMP (6.5 ml). After 1 h at room temperature the flask was heated with an oil bath at 65° C. bath temperature. After 6 h DIPEA (38 µl, 0.222 mol, 1.0 eq.) was added and heating was continued for additional 18 h. After cooling down ACN/water 1:1 was added and the solution was lyophilized. 100 µl DMSO/200 µl HOAc and 1 ml ACN were added to the remaining solid and the suspension was filtered. The filtrate was separated by prep. HPLC (20 to 60% B in 30 min, Agilent PLRP-S 25×150 mm) and the title compound (74 mg, 0.057 mmol, 26% yield) was obtained. HPLC: $R_t$=5.1 min. MS: m/z=1297.7 ([M+H]$^+$, calculated 1197.8). $C_{70}H_{108}N_{10}O_{13}$ (MW=1297.67).

D. 2-{[1-{4-[(3-{[3-(DOTA-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-adamantane-2-carboxylic acid (IIIa)

TFA (9 ml) was added to a solution of Tris-tBu-ester of formula (XIII) (74 mg, 0.057 mmol) and triisobutylsilane (600 µl) in dry DCM (2.4 ml). After 5 h at room temperature the mixture was evaporated under reduced pressure and purified by prep. HPLC (15 to 50% B in 30 min, Agilent PLRP-S 25×150 mm). This yielded the title compound (43 mg, 0.038 mmol, 66% yield) as TFA-salt. HPLC: $R_t$=5.3 min. MS: m/z=1129.7 ([M+H]$^+$, calculated 1129.6). $C_{58}H_{84}N_{10}O_{13}$ (MW=1129.35).

Example 6: Synthesis of DOTA-Transition Metal Complexes

A. General Procedure for the Synthesis of DOTA-Transition Metal-Complexes

A 1 mM solution of the corresponding metal salt (3.0 eq. to 5.0 eq.) was diluted with the 5-fold volume of acetate buffer (pH 5.0, 0.4 M). This solution was added to the DOTA-containing compound (3 to 10 mg, 1.0 eq.). The reaction was positioned in an oil bath (90° C. bath temperature). After 20 min the reaction mixture was cooled to RT and applied to a solid phase extraction column (250 mg Varian Bondesil-ENV in a 15 ml polystyrene syringe, pre-washed with methanol (1×5 ml) and water (2×5 ml). The column was eluted with water (2×5 ml), 5 ml of 50% ACN in water as first fraction and each of the next fractions were eluted with 5 ml of 50% ACN in water containing 0.1% TFA. The fractions containing the pure product were pooled and freeze dried.

B. Indium-Complex of a Compound of Formula (IIIa): In-(IIIa)

Complex formation was done according to the general procedure (Example 6 A) using the following reagents: Compound of formula (IIIa) (5.0 mg), InCl$_3$×4 H$_2$O (3.9 mg) yielding the title compound (4.26 mg, 3.4 µmol, 78%). HPLC: $R_t$=4.4 min. MS: m/z=1241.6 ([M+H]$^+$, calculated 1241.5). $C_{58}H_{81}InN_{10}O_{13}$ (MW=1241.14).

C. Gallium-Complex of a Compound of Formula (IIIa): Ga-(IIIa)

Complex formation was done according to the general procedure (Example 6 A) using the following reagents: Compound of formula (IIIa) (3.0 mg) and Ga(NO$_3$)$_3$ hydrate (3.9 mg), yielding the title compound (2.61 mg, 2.2 µmol, 82%). HPLC: $R_t$=4.4 min. MS: m/z=1195.6 ([M+H]$^+$, calculated 1195.5). $C_{58}H_{81}GaN_{10}O_{13}$ (MW=1196.05).

D. Yttrium-Complex of a Compound of Formula (IIIa): Y-(IIIa)

Complex formation was done according to the general procedure (Example 6 A) using the following reagents: Compound of formula (IIIa) (3.0 mg) and Y(NO$_3$)$_3$×6 H$_2$O (3.1 mg), yielding the title compound (2.54 mg, 2.1 µmol, 79%). HPLC: $R_t$=4.5 min. MS: m/z=1215.6 ([M+H]$^+$, calculated 1215.5). $C_{58}H_{81}N_{10}O_{13}Y$ (MW=1216.24).

E. Lutetium-Complex of a Compound of Formula (IIIa): Lu-(IIIa)

Complex formation was done according to the general procedure (Example 6 A) using the following reagents: Compound of formula (IIIa) (3.0 mg) and LuCl$_3$ (2.2 mg), yielding the title compound (2.88 mg, 2.2 µmol, 83%). HPLC: $R_t$=4.4 min. MS: m/z=1301.5 ([M+H]$^+$, calculated 1301.5). $C_{58}H_{81}LuN_{10}O_{13}$ (MW=1301.30).

Example 7: 2-{[1-(4-{[3-({3-[(DOTA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIb)

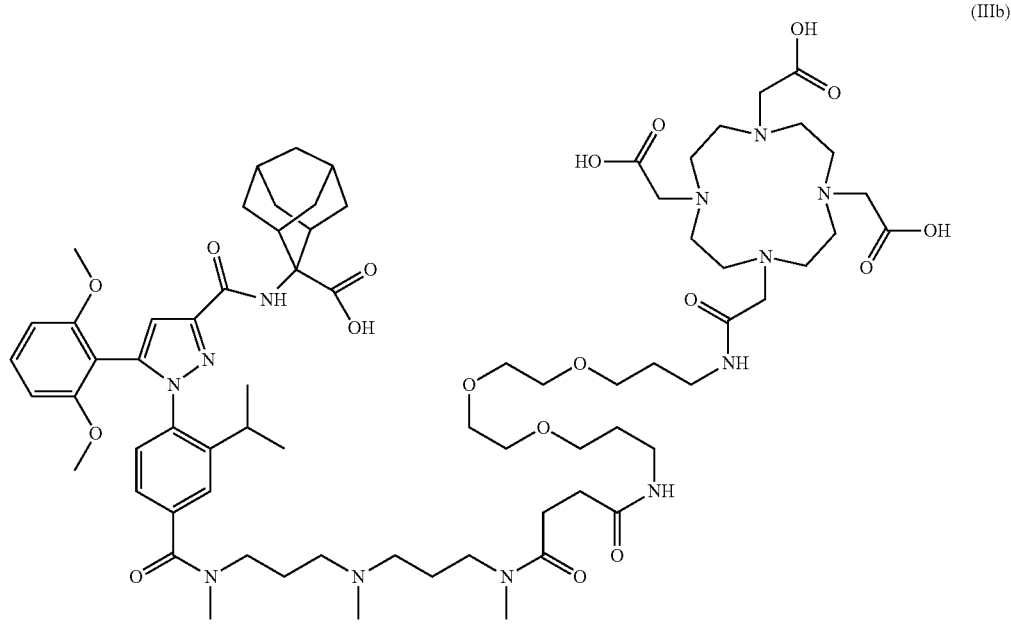 [SMILES: COc1cccc(OC)c1-c1cc(C(=O)NC2(C(=O)O)C3CC4CC(C3)CC2C4)nn1-c1ccc(C(=O)N(C)CCCN(C)CCCN(C)C(=O)CCC(=O)NCCCOCCOCCOCCCNC(=O)CN2CCN(CC(=O)O)CCN(CC(=O)O)CCN(CC(=O)O)CC2)cc1C(C)C]

(IIIb)

A. Synthesis of N-{3-[2-(2-{3-[2-(4,7,10-Tris-tert-butoxycarbonylmethyl-1,4,7,10-tetraaza-cyclododec-1-yl)-acetylamino]-propoxy}-ethoxy)-ethoxy]-propyl}-succinamic acid (DOTA(tBu)$_3$-Ttds-OH) (XX)

After chlorotrityl resin (167 mg, 0.3 mmol, 1.0 eq.) had been swollen in DCM for 1 h, a solution of Fmoc-Ttds-OH (326 mg, 0.6 mmol, 2.0 eq.) and DIPEA (155 µl, 0.9 mmol, 3.0 eq.) in DCM (4 ml) was added. After 2.5 h the solution was filtered off and the resin successively washed with DCM, MeOH, DCM and DMF (1/1/1/3). The resin was treated twice with 20% piperidine in DMF (2 min and 20 min) and washed five times with DMF afterwards. Next a mixture of Tri-tert-butyl-1,4,7,10-tetraazacyclo-dodecane-1,4,7,10-tetraacetate (DOTA(tBu)$_3$-OH) (322 mg, 0.56 mmol, 1.9 eq.), HATU (214 mg, 0.56 mmol, 1.9 eq.) and DIPEA (195 µl, 1.13 mmol, 3.8 eq.) was shaken for 5 min and subsequently added to the resin. After agitation for 2 h the resin was washed with DMF and DCM (5/2) and subsequently dried in the vacuum. The resin was treated four times with a mixture of TFA, TIPS and DCM (5/5/90) for 5 min. To prevent premature loss of the DOTA protecting groups the resulting solutions were immediately poured into aqueous buffer solution (10 ml, pH=8, 100 mM NH$_4$(CO$_3$)$_2$). The pH value of the mixture was kept above pH=7 by addition of 4N NaOH solution. DCM-buffer mixtures containing the target compound were combined, the phases were separated, the aqueous phase was extracted twice with DCM and the organic phase was evaporated to dryness. The residue was redissolved in ACN/water (1/1) and lyophilized. The residue was purified by HPLC (15 to 45% B in 30 min, Agilent PLRP-S 25×150 mm) to give the title compound (118.6 mg, 0.136 mmol, 45%). HPLC: R$_t$=4.3 min. MS: m/z=875.5 ([M+H]$^+$, calculated 875.6). C$_{42}$H$_{78}$N$_6$O$_{13}$ (MW=875.10).

B. Synthesis of 2-{[1-(4-{[3-({3-[(DOTA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIb)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX) (24.9 mg, 31.1 µmol, 1 eq.) was dissolved in DMF (0.5 ml). DIPEA (32.4 µl, 187 µmol, 6 eq.) was added to the solution to adjust the pH-value to pH=7. N-{3-[2-(2-{3-[2-(4,7,10-Tris-tert-butoxycarbonylmethyl-1,4,7,10-tetraaza-cyclododec-1-yl)-acetylamino]-propoxy}-ethoxy)-ethoxy]-propyl}-succinamic acid (DOTA(tBu)$_3$-Ttds-OH) (XX) (30.0 mg, 34.3 µmol, 1.1 q eq.) was added to the solution, followed by HOAt (16.9 mg, 124.4 µmol, 4 eq.) and DIC (14.5 µl, 93.3 µmol, 3 eq.). After stirring the mixture for 24 h the solvent was removed by evaporation. To the remaining residue water (1 ml) and EtOAc (2 ml) were added. The organic phase was separated, dried and evaporated. The remainder was treated with TFA, phenol, water and TIPS (18/1/1/2) (330 µl) for 8 h. All volatiles were removed on the vacuum. The residue was purified by HPLC (15 to 45% B in 30 min, Agilent PLRP-S 25×150 mm) to give the title compound (7.0 mg, 4.9 mol, 15.8%). HPLC: R$_t$=4.7 min. MS: m/z=1431.9 ([M+H]$^+$, calculated 1431.8). C$_{72}$H$_{110}$N$_{12}$O$_{18}$ (MW=1431.71).

Example 8: Lutetium-Complex of IIIb: Lu-(IIIb)

Complex formation was done according to the general procedure (Example 6 A) using the following reagents: Compound of formula (IIIb) (4.0 mg) and LuCl$_3$ (2.35 mg), yielding the title compound (2.61 mg, 1.6 µmol, 57%). HPLC: R$_t$=4.7 min. MS: m/z=1603.8 ([M+H]$^+$, calculated 1603.7). C$_{72}$H$_{107}$LuN$_{12}$O$_{18}$ (MW=1603.66).

Example 9: 2-{[1-(4-{[3-({3-[(DOTA-Ahx)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIc)

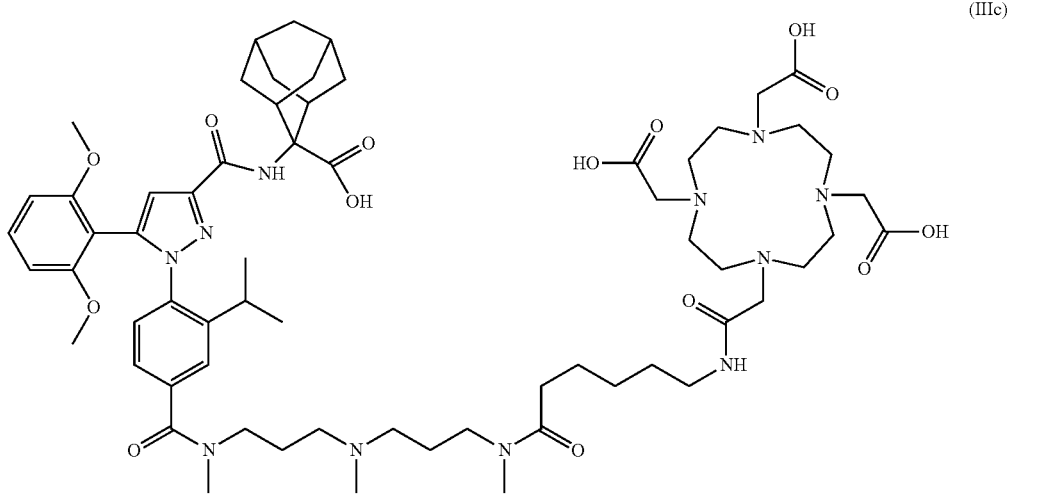 [SMILES: COc1cccc(OC)c1-c1cc(C(=O)NC2(C(=O)O)C3CC4CC(C3)CC2C4)nn1-c1ccc(C(=O)N(C)CCCN(C)CCCN(C)C(=O)CCCCCNC(=O)CN2CCN(CC(=O)O)CCN(CC(=O)O)CCN(CC(=O)O)CC2)cc1C(C)C]

(IIIc)

A. Synthesis of 6-[2-(4,7,10-Tris-tert-butoxycarbonylmethyl-1,4,7,10-tetraaza-cyclododec-1-yl)-acetylamino]-hexanoic acid (DOTA(tBu)$_3$-Ahx-OH) (XXI)

After chlorotrityl resin (167 mg, 0.3 mmol, 1.0 eq.) had been swollen in DCM for 1 h, a solution of Fmoc-Ahx-OH (212 mg, 0.6 mmol, 2.0 eq.) and DIPEA (155 µl, 0.9 mmol, 3.0 eq.) in DCM (4 ml) was added. After 1 h the solution was filtered off and the resin successively washed with DCM, MeOH, DCM and DMF (1/1/1/3). The resin was treated twice with 20% piperidine in DMF (2 min and 20 min) and washed five times with DMF afterwards. Next a mixture of Tri-tert-butyl 1,4,7,10-tetraazacyclo-dodecane-1,4,7,10-tetraacetate (DOTA(tBu)$_3$-OH, 322 mg, 0.56 mmol, 1.9 eq.), HATU (214 mg, 0.56 mmol, 1.9 eq.) and DIPEA (195 µl, 1.13 mmol, 3.8 eq.) was shaken for 5 min and subsequently added to the resin. After agitation for 4 h the resin was washed with DMF and DCM (5/2) and subsequently dried in the vacuum. The resin was treated four times with a mixture of TFA, TIPS and DCM (5/5/90) for 5 min. To prevent premature loss of the DOTA protecting groups the resulting solutions were immediately poured into aqueous buffer solution (10 ml, pH=8, 100 mM NH$_4$(CO$_3$)$_2$). The pH value of the mixture was kept above pH=7 by addition of 4N NaOH solution. All DCM-buffer mixtures were combined, the phases were separated, the aqueous phase was extracted twice with DCM and the organic phase was evaporated to dryness. The residue was re-dissolve in ACN/water (1/1) and lyophilized to yield 185 mg of crude product.

The residue was dissolved in water and a minimal amount of ACN and subjected to HPLC purification (20 to 45% B in 30 min, Agilent PLRP-S 25×150 mm) to give the title compound (86.2 mg, 0.125 mmol, 42%). HPLC: R$_t$=4.5 min. MS: m/z=686.3 ([M+H]$^+$, calculated 686.5). C$_{34}$H$_{63}$N$_5$O$_9$ (MW=685.89).

B. Synthesis of 2-{[1-(4-{[3-({3-[(DOTA-Ahx)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIc)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX) (12.7 mg, 15.9 µmol, 1 eq.) was dissolved in DMF (0.3 ml). DIPEA (16.6 µl, 95.4 µmol, 6 eq.) was added to the solution to adjust the pH-value to pH=7. 6-[2-(4,7,10-Tris-tert-butoxycarbonylmethyl-1,4,7,10-tetraaza-cyclododec-1-yl)-acetylamino]-hexanoic acid (DOTA(tBu)$_3$-Ahx-OH) (XXI) (16.4 mg, 23.85 µmol, 1.5 eq.) was added to the solution, followed by HOAt (8.7 mg, 63.6 µmol, 4 eq.) and DIC (7.4 µl, 47.7 µmol, 3 eq.). After stirring the mixture for 72 h the solvent was removed by evaporation. To the remaining residue water (1 ml) and EtOAc (2 ml) were added. The organic phase was separated, dried and evaporated. The remainder was treated with TFA, phenol, water and TIPS (18/1/1/2) (330 µl) for 8 h. All volatiles were removed in the vacuum.

The residue was purified by HPLC (20 to 50% B in 30 min, Agilent PLRP-S 25×150 mm) to give the title compound (7.78 mg, 6.3 µmol, 39.4%). HPLC: R$_t$=4.6 min. MS: m/z=1242.8 ([M+H]$^+$, calculated 1242.7). C$_{64}$H$_{95}$N$_{11}$O$_{14}$ (MW=1242.50).

Example 10: 2-{[1-(4-{[3-({3-[(NODAGA)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIId)

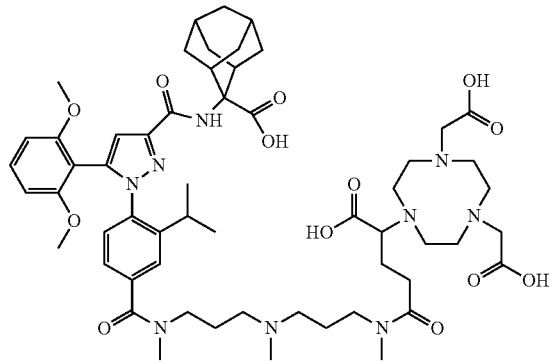

(IIId)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX) (13.4 mg, 16.7 μmol, 1 eq.) was dissolved in DMF (0.3 ml). DIPEA (17.4 μl, 100 μmol, 6 eq.) was added to the solution to adjust the pH-value to pH=7. 2-(4,7-Bis-tert-butoxycarbonylmethyl-[1,4,7]triazonan-1-yl)-pentanedioic acid 1-tert-butyl ester (NODAGA(tBu)₃-OH) (10.0 mg, 18.4 μmol, 1.1 eq.) was added to the solution, followed by HOAt (9.1 mg, 66.8 μmol, 4 eq.) and DIC (7.8 μl, 50.1 μmol, 3 eq.). After stirring the mixture for 24 h the solvent was removed by evaporation. To the remaining residue water (1 ml) and EtOAc (2 ml) were added. The organic phase was separated, dried and evaporated. The remainder was treated with TFA, phenol, water and TIPS (90/5/5/3) (1030 μl) for 5.5 h. Subsequently all volatiles were removed in the vacuum.

The residue was purified by HPLC (20 to 50% B in 30 min, Agilent PLRP-S 25×150 mm) to give the title compound (7.64 mg, 6.9 μmol, 41.6%). HPLC: $R_t$=4.9 min. MS: m/z=1100.7 ([M+H]$^+$, calculated 1100.6). $C_{57}H_{81}N_9O_{13}$ (MW=1100.31).

Example 11: Gallium-Complex of a Compound of Formula (IIId): Ga-(IIId)

Complex formation was done according to the general procedure (Example 6 A) using the following reagents: Compound of formula (IIId) (10.0 mg) and Ga(NO₃)₃ hydrate (7.47 mg), yielding the title compound (7.46 mg, 6.4 μmol, 70%). HPLC: $R_t$=4.8 min. MS: m/z=1166.6 ([M+H]$^+$, calculated 1166.5). $C_{57}H_{78}GaN_9O_{13}$ (MW=1167.0).

Example 12: 2-{[1-(4-{[3-({3-[(NODAGA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIe)

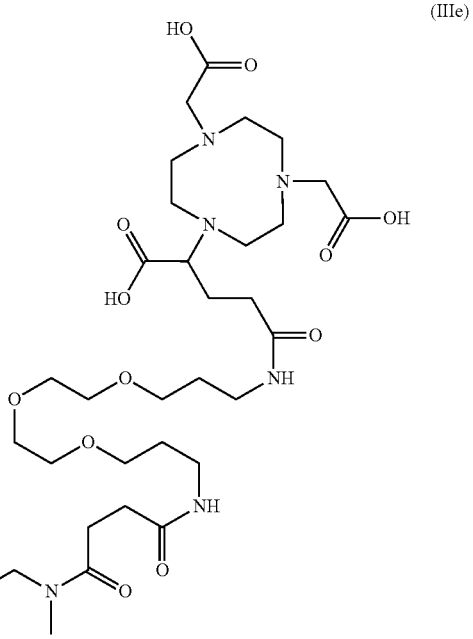

(IIIe)

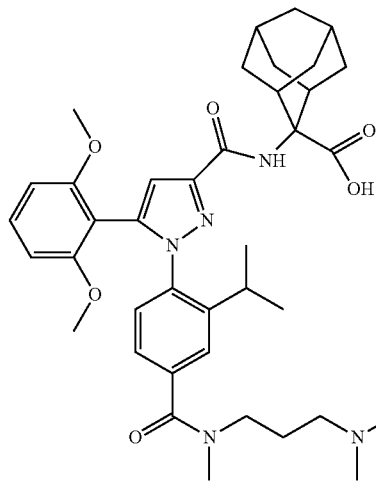

A. Synthesis of 2-(4,7-Bis-tert-butoxycarbonylmethyl-[1,4,7]triazonan-1-yl)-4-[3-(2-{2-[3-(3-carboxy-propionylamino)-propoxy]-ethoxy}-ethoxy)-propylcarbamoyl]-butyric acid tert-butyl ester (NODAGA(tBu)₃-Ttds-OH) (XXII)

After chlorotrityl resin (556 mg, 1.0 mmol, 1.0 eq.) had been swollen in DCM for 1 h, a solution of Fmoc-Ttds-OH (1085 mg, 2.0 mmol, 2.0 eq.) and DIPEA (516 μl, 3.0 mmol, 3.0 eq.) in DCM (10 ml) was added. After 2.5 h the solution was filtered off and the resin successively washed with DCM, MeOH, DCM and DMF (1/1/1/3). The resin was treated twice with 20% piperidine in DMF (2 min and 20 min), washed with DMF and DCM (5/2) and dried in the vacuum to yield 760 mg of H-Ttds-trityl resin (loading based on mass increase: approximately 0.8 mmol/g). H-Ttds-trityl-resin (375 mg, 0.3 mmol, 1.0 eq.) was swollen in DMF for 30 min. Next a mixture of 2-(4,7-Bis-tert-butoxycarbonylmethyl-[1,4,7]triazonan-1-yl)-pentanedioic acid 1-tert-butyl ester (NODAGA(tBu)$_3$-OH) (245 mg, 0.45 mmol, 1.5 eq.), HATU (171 mg, 0.45 mmol, 1.5 eq.) and DIPEA (150 µl, 0.9 mmol, 3.0 eq.) was shaken for 5 min and subsequently added to the resin. After agitation for 24 h the resin was washed with DMF and DCM (5/2) and subsequently dried in the vacuum. The resin was initially treated once with a mixture of TFA, TIPS and DCM (2/5/93) and subsequently four times with a mixture of TFA, TIPS and DCM (5/5/90) for 5 min. To prevent premature loss of the NODAGA protecting groups the resulting solutions were immediately poured into aqueous buffer solution (10 ml, pH=8, 100 mM NH$_4$(CO$_3$)$_2$). The pH value of the mixture was kept above pH=7 by addition of 4N NaOH solution. DCM-buffer mixtures containing the target compound were combined (solutions resulting from 1$^{st}$ and 2$^{nd}$ treatment), the phases were separated, the aqueous phase was extracted twice with DCM and the organic phase was evaporated to dryness. The residue was redissolved in ACN/water (1/1) and lyophilized.

The residue was purified by HPLC (25 to 50% B in 30 min, Agilent PLRP-S 25×150 mm) to give the title compound as colourless oil (105 mg, 0.120 mmol, 40%). HPLC: R$_t$=5.2 min. MS: m/z=845.5 ([M+H]$^+$, calculated 846.5). C$_{41}$H$_{75}$N$_5$O$_{13}$ (MW=846.06).

B. 2-{[1-(4-{[3-({3-[(NODAGA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIe)

2-(4,7-Bis-tert-butoxycarbonylmethyl-[1,4,7]triazonan-1-yl)-4-[3-(2-{2-[3-(3-carboxy-propionylamino)-propoxy]-ethoxy}-ethoxy)-propylcarbamoyl]-butyric acid tert-butyl ester (NODAGA(tBu)$_3$-Ttds-OH) (XXII) (65 mg, 76 µmol) was dissolved in DMF (0.5 ml). 0.3 ml of that solution (containing 39 mg NODAGA(tBu)$_3$-Ttds-OH (XXII), 46 µmol, 1.3 eq.) were used to dissolve 2-({5-(2,6-Dimethoxy-phenyl)-1-[2-isopropyl-4-(methyl-{3-[methyl-(3-methyl-amino-propyl)-amino]-propyl}-carbamoyl)-phenyl]-1H-pyrazole-3-carbonyl}-amino)-adamantane-2-carboxylic acid tert-butyl ester (XIX) (32.0 mg, 35 µmol, 1 eq.). DIPEA (42 µl, 250 µmol, 7 eq.) was added to the solution to adjust the pH-value to pH=7. Then HOAt (22 mg, 162 µmol, 4.5 eq.) and DIC (19 µl, 122 µmol, 3.5 eq.) were added to the mixture which was subsequently stirred for 6 h. Then an additional amount of the initially prepared solution (50 µl containing 6.5 mg NODAGA(tBu)$_3$-Ttds-OH (XXII), 7.7 µmol, 0.2 eq.) and DIC (10 µl, 64 µmol, 1.8 eq.) was added and the mixture stirred overnight. All volatiles were removed in the vacuum, the residue dissolved with DCM and aqueous citric acid solution (10%). The organic layer was separated, dried and evaporated to dryness. The residue was treated with TFA, TIPS and water (95/2.5/2.5).

The cleavage solution was directed to HPLC purification (20 to 45% B in 30 min, Agilent PLRP-S 25×150 mm) to give the title compound (23.96 mg, 17.1 µmol, 48.8%). HPLC: R$_t$=4.8 min. MS: m/z=1402.8 ([M+H]$^+$, calculated 1402.8). C$_{71}$H$_{107}$N$_{11}$O$_{18}$ (MW=1402.67).

Example 13: 2-({5-(2,6-Dimethoxy-phenyl)-1-[2-isopropyl-4-(methyl-{3-[methyl-(3-{1-methyl-3-[4-(3-DFO-thioureido)-phenyl]-thioureido}-propyl)-amino]-propyl}-carbamoyl)-phenyl]-1H-pyrazole-3-carbonyl}-amino)-adamantane-2-carboxylic (IIIf)

(IIIf)

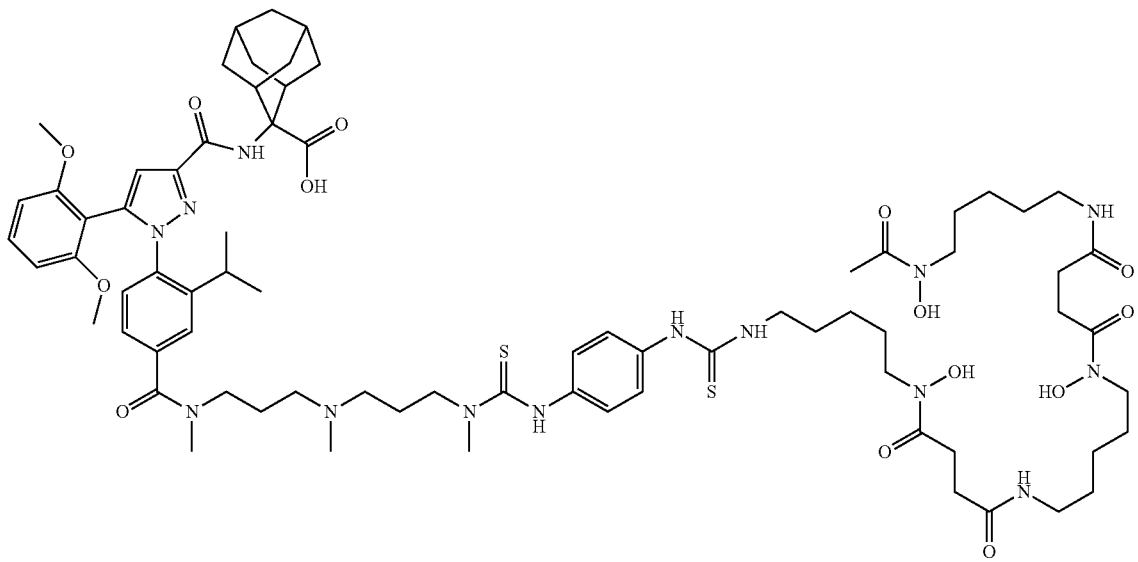

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (III) (30 mg, 40.4 µmol, 1.5 eq.) and N-[5-({3-[5-(Acetyl-hydroxy-amino)-pentylcarbamoyl]-propionyl}-hydroxy-amino)-pentyl]-N'-hydroxy-N'-{5-[3-(4-isothiocyanato-phenyl)-thioureido]-pentyl}-succinamide (20.3 mg, 26.9 µmol, 1.0 eq.) were dissolved in DMF (1.0 ml). After addition of DIPEA (9.3 µl, 53.8 µmol, 2.0 eq.) the mixture was stirred for 1 h at 50° C. Subsequently the solvent was evaporated.

The residue was purified by HPLC (15 to 45% B in 30 min, Agilent PLRP-S 25×150 mm) to give the title compound (15.6 mg, 10.4 µmol, 38.8%). HPLC: $R_t$=5.1 min. $C_{75}H_{110}N_{14}O_{14}S_2$ (MW=1495.89).

The LC-MS analytic of the compound proved to be complicated by the formation of the zirconium complex of the compound under LC-MS conditions (MS (m/z): 1581.5 $[M-3H++Zr^{4+}]^+$, $C_{75}H_{107}N_{14}O_{14}S_2Zr^+$, $R_t$=5.1 min). When the compound was treated with a 25 mM $FeCl_3$ solution directly before injection predominately the iron complex was detected. (MS (m/z): 1549.4 $[M-3H^++Fe^+H]^+$, $C_{75}H_{107}N_{14}O_{14}S_2Fe$, $R_t$=5.3 min). This finding indicated that (IIIf) formed the Zirconium complex under LC-MS measurement conditions although being actually present in the uncomplexed state.

Example 14: Zirconium-Complex of a Compound of Formula (IIIf): Zr-(IIIf)

2-({5-(2,6-Dimethoxy-phenyl)-1-[2-isopropyl-4-(methyl-{3-[methyl-(3-{1-methyl-3-[4-(3-DFO-thioureido)-phenyl]-thioureido}-propyl)-amino]-propyl}-carbamoyl)-phenyl]-1H-pyrazole-3-carbonyl}-amino)-adamantane-2-carboxylic (IIIf) (9.85 mg, 6.58 µmol, 1.0 eq.) and Zirconium(IV)acetylacetonat (12.95 mg, 26.3 µmol, 4.0 eq.) were dissolved in MeOH. After stirring for 1 h the solvent was evaporated.

The residue was directed to HPLC purification (25 to 50% B in 30 min, Agilent PLRP-S 25×150 mm) to give the title compound (2.5 mg, 1.6 mol, 24.2%). HPLC: $R_t$=5.1 min. MS: m/z=1581.6 ($[M]^+$, calculated 1581.7). $C_{75}H_{107}N_{14}O_{14}S_2Zr^+$ (MW=1584.09).

The LC-MS analytic of the compound proved to be complicated by the formation of the zirconium complex of the not complexed compound under LC-MS conditions. When the compound was treated with a 25 mM $FeCl_3$ solution directly before injection the iron complex was detected as minor component. (MS (m/z): 1549.4 $[M-3H^++Fe^+H]^+$, $C_{75}H_{107}N_{14}O_{14}S_2Fe$, $R_t$=5.3 min). In contrast when the not complexed compound (IIIf) was subjected to analytical LC-MS compound with prior $FeCl_3$ treatment the iron complex appeared to be the major compound. These findings indicate that the complexation of Zirconium by (IIIf) was successful.

Example 15: 2-{[5-(2,6-Dimethoxy-phenyl)-1-(4-{[3-({3-[(4-fluoro-benzoyl)-methyl-amino]-propyl}-methyl-amino)-propyl]-methyl-carbamoyl}-2-isopropyl-phenyl)-1H-pyrazole-3-carbonyl]-amino}-adamantane-2-carboxylic acid (IIIg)

(IIIg)

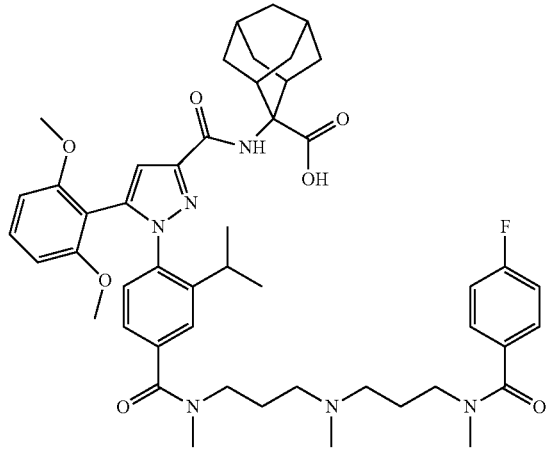

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (III) (10 mg, 13.4 µmol, 1.0 eq) were dissolved in DCM (0.4 ml). The pH-value of the solution was adjusted to pH=7 by gradual addition of DIPEA. After dropwise addition of a solution of 4-Fluorobenzoyl chloride (2.13 mg, 13.4 µmol, 1.0 eq.) in DCM (0.1 ml) the reaction mixture was stirred overnight. Then water (0.1 ml) was added, the mixture was stirred for 10 min and all volatiles were removed in the vacuum.

The oily residue was subjected to HPLC purification (25 to 55% B in 30 min, Agilent PLRP-S 25×150 mm) to give the title compound (3.24 mg, 3.75 µmol, 28.0%). HPLC: $R_t$=5.7 min. MS: m/z=865.5 ($[M+H]^+$, calculated 865.58) $C_{49}H_{61}FN_6O_7$, (MW=865.03).

Example 16: 2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester bound to trityl resin (XXIII)

(XXIII)

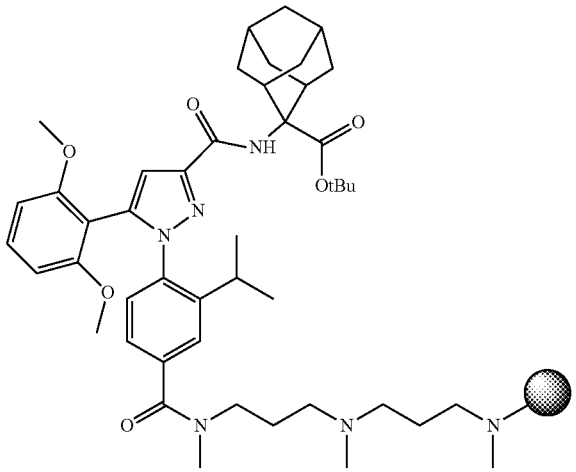

Figure 12:
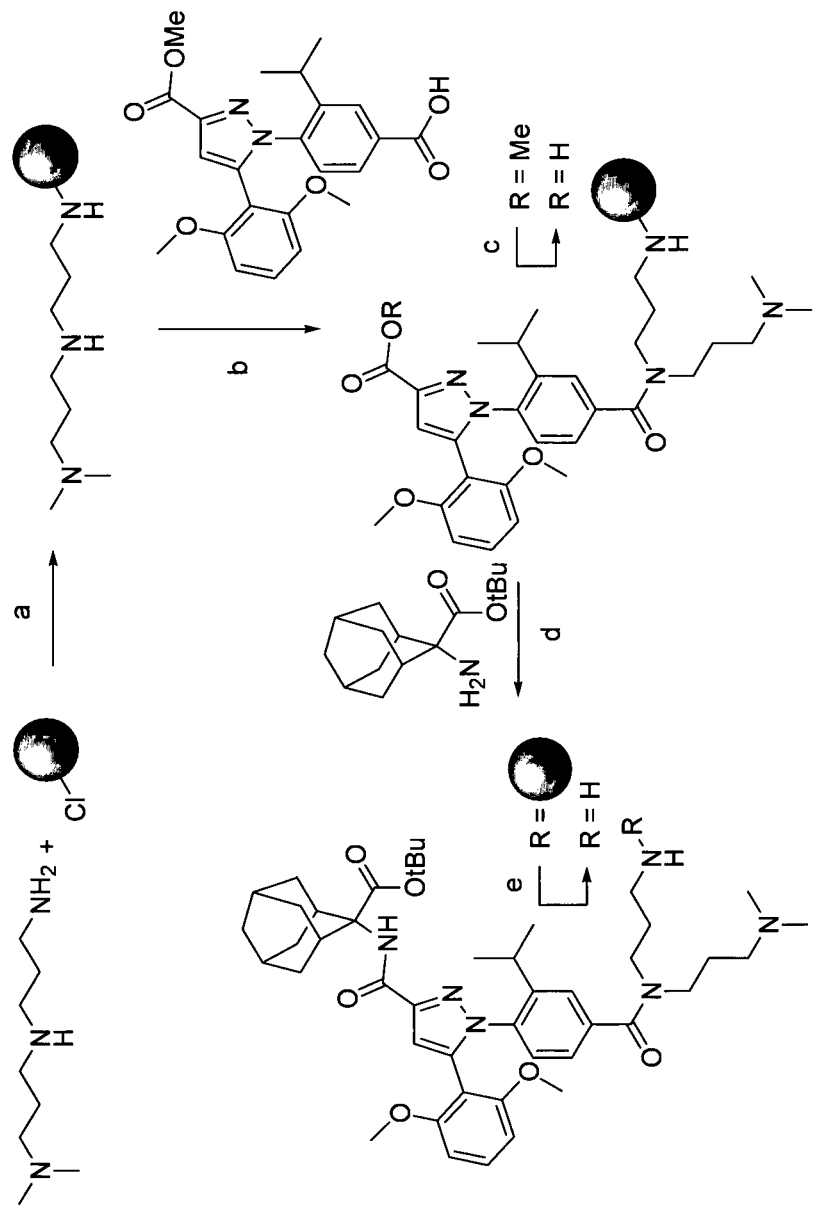
FIG. 12 shows the solid phase synthesis of derivatized resin of formula (XXIII) and tert-butyl ester of formula (XXIV) of example part II.
Figure 13:
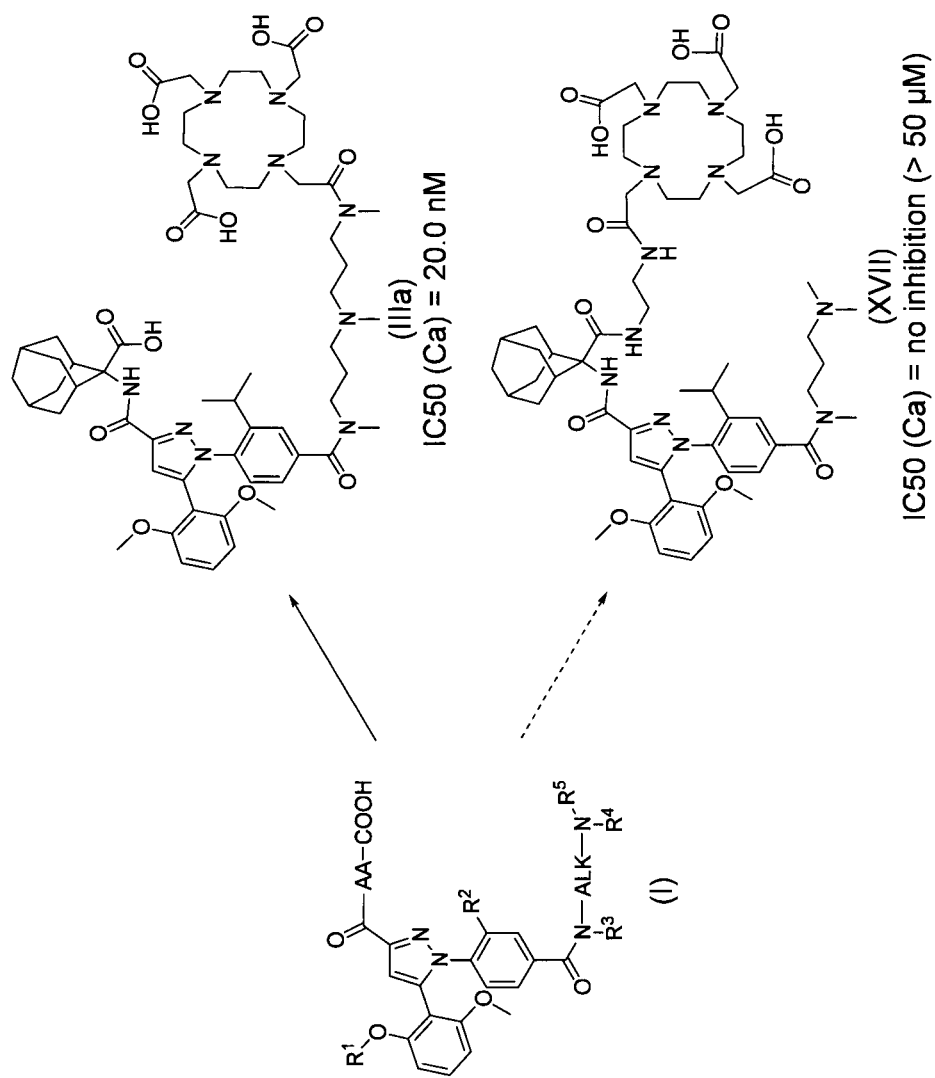
FIG. 13 is a diagram illustrating the effect of chelator positioning in a compound of formula (I) of example part II on the IC50 value in a Ca-mobilisation assay (IC50 (Ca))

A. Loading of chlorotrityl resin with N,N-Dimethyldipropylentriamine (FIG. 12 step a)

Tritylchloride resin (initial loading 1.8 mmol/g, 334 mg g, 0.6 mmol, 1.0 eq.) was swollen in DCM for 30 min. Then N,N-Dimethyldipropylentriamine (0.54 ml, 3 mmol, 5 eq.) and DIPEA (0.2 ml, 1.2 mmol, 2.0 eq.) in DCM (4 ml) were added to the resin and the mixture shaken overnight. Afterwards the resin was washed with DMF, DCM, MeOH and diethyl ether (5/3/1) and dried in the vacuum.

B. Coupling of 1-(4-Carboxy-2-isopropyl-phenyl)-5-(2,6-dimethoxy-phenyl)-1H-pyrazole-3-carboxylic acid methyl ester (FIG. 12 step b)

N,N-Dimethyldipropylentriamine charged trityl resin (0.6 mmol, 1.0 eq.) was swollen in DMF for 30 min. 1-(4-Carboxy-2-isopropyl-phenyl)-5-(2,6-dimethoxy-phenyl)-1H-pyrazole-3-carboxylic acid methyl ester (382 mg, 0.9 mmol, 1.5 eq.), HATU (342 mg, 0.9 mmol, 1.5 eq.) and DIPEA (312 µl, 2.7 mmol, 3 eq.) were dissolved in DMF (6 ml) and mixed thoroughly for 1 min. After addition of the activated building block the resin was shaken for 3 h. The resin was washed (DMF/DCM/diethyl ether 5/3/1) and dried in the vacuum.

C. Hydrolysis of the methylester (FIG. 12 step c)

The resin (0.6 mmol, 1.0 eq.) described before was swollen in dioxane for 30 min and afterwards treated with dioxane (30 ml) and LiOH hydrate (504 mg, 12 mmol, 20 eq.) in water (4 ml) at 50° C. The procedure was continued at RT overnight, the resin subsequently washed with water, DCM and Et$_2$O (3/3/3) and dried in the vacuum.

D. Coupling of 2-Amino-adamantane-2-carboxylic acid tert-butyl ester (FIG. 12 step d)

The resin (0.6 mmol, 1.0 eq.) described before was swollen in DMF for 1 h. Then HOAt (327 mg, 2.4 mmol, 4.0 eq.), DIC (279 µl, 1.8 mmol, 3.0 eq.) and 2-amino-adamantane-2-carboxylic acid tert-butyl ester (453 mg, 1.8 mmol, 3.0 eq.) were dissolved in a mixture of DMF and DCM (2:1) (6 ml) and added to the resin. The resin was left to shake for 60 hours after which the reaction was complete. The resin was washed with DMF and DCM (3/3) and dried in the vacuum.

Example 17: 2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester (XXIV), (FIG. 12 step e)

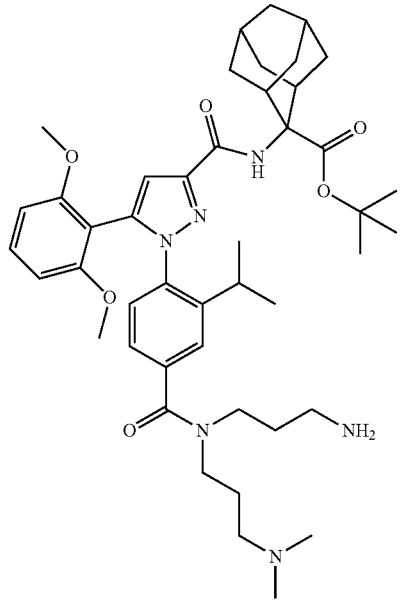

(XXIV)

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester resin (XXIII) (570 µmol, 1.0 eq.) was treated five times with a mixture of TFA, TIPS and DCM (2/5/93). To prevent premature loss of the DOTA protecting groups the resulting solutions were immediately poured into aqueous buffer solution (10 ml, pH=8, 100 mM NH$_4$(CO$_3$)$_2$). All DCM-buffer mixtures containing the target molecule were combined and the organic layer reduced to a minimum by evaporation. To the remaining aqueous solution ACN (5 ml) was added and the mixture was freeze-dried.

The residue containing the title compound (410 mg, 520 µmol, 91%) was used without further purification as crude product. HPLC: R$_t$=5.8 min. MS: m/z=785.4 ([M+H]$^+$, calculated 785.5) C$_{45}$H$_{64}$N$_6$O$_6$, (MW=785.03).

261
Example 18: 2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid (V)

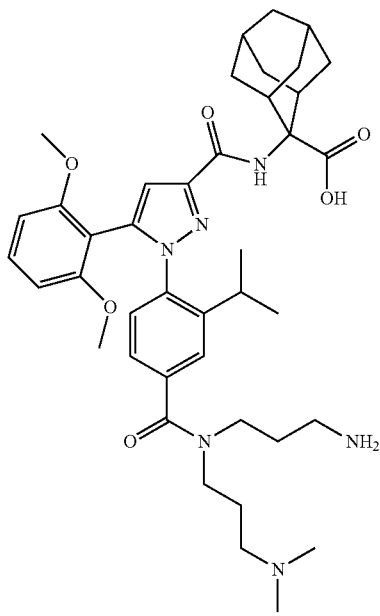

(V)

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester resin (XXIV) (41 mg, 30 μmol, 1.0 eq.) was treated with TFA, phenol, water and TIPS (36/2/2/1) (2 ml) for 2 h. The cleavage solution was poured into cyclohexan/MTBE (1/1) (20 ml).

The precipitate was subjected to HPLC purification (15 to 45% B in 30 min, Agilent PLRP-S 25×150 mm) to give the title compound (9.52 mg, 13.1 μmol, 43.5%). HPLC: $R_t$=4.8 min. MS: m/z=729.4 ([M+H]$^+$, calculated 729.4) $C_{41}H_{56}N_6O_6$, (MW=728.92).

262
Example 19: Synthesis of 2-{[1-{4-[(3-DOTA-amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid (Va)

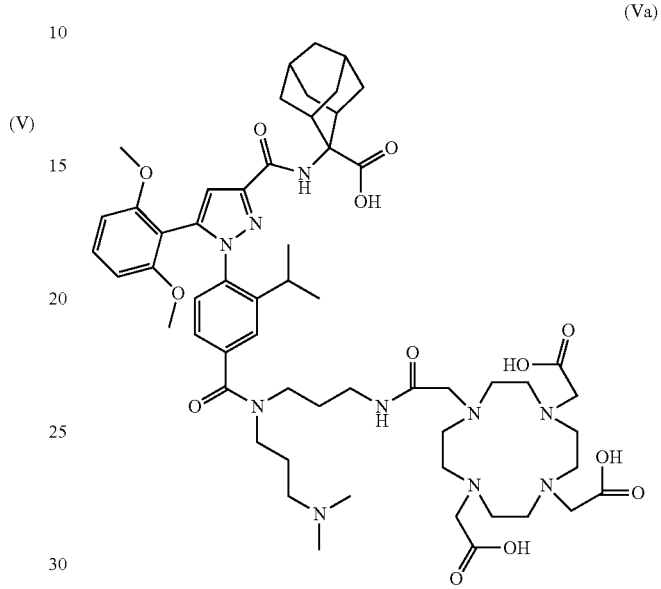

(Va)

Method A

A. 1-{4-[(3-DOTA(tBu)$_3$-amino-propyl)-(3-dimethylamino-propyl)-carbamoyl]-2-isopropyl-phenyl}-5-(2,6-dimethoxy-phenyl)-1H-pyrazole-3-carboxylic acid methyl ester (XIV)

DOTA(tBu)$_3$-OH (200 mg, 0.349 mmol, 1.0 eq.) and PyBOP (236 mg, 0.454 mmol, 1.3 eq.) were dissolved in dry DMF (5 ml). After one minute N$^1$-(3-Dimethylamino-propyl)-propane-1,3-diamine (0.315 ml, 1.75 mmol, 5 eq.) and DIPEA (0.155 ml, 0.98 mmol, 2.6 eq.) in dry DMF (2 ml) were added. After 90 min DMF was removed under vacuum. The remaining residue was dissolved in EtOAc (30 ml) and extracted with water twice. The organic layer was dried over Na$_2$SO$_4$ and evaporated to yield 0.41 g crude material.

This crude material (0.41 g, max. 0.349 mmol) was dissolved in dry DMF (25 ml). In a separate flask 1-(4-Carboxy-2-isopropyl-phenyl)-5-(2,6-dimethoxy-phenyl)-1H-pyrazole-3-carboxylic acid methyl ester (X) (178 mg, 0.419 mmol, 1.2 eq.) [prepared as disclosed in U.S. Pat. No. 5,723,483] was dissolved in dry DMF (1.0 ml), HATU (159 mg, 0.419 mmol, 1.2 eq.) and DIPEA (0.143 ml, 0.838 mmol, 2.4 eq.) were added sequentially. The dissolved crude material from the first step, the DOTA modified diamine, was added dropwise to this HATU activated solution. After stirring for 45 min DMF was evaporated and the residual solvents were removed under high-vacuum.

The residual oil was dissolved in ACN/water/AcOH (100 μl/100 μl/1 ml) and separated in 2 batches by prep. HPLC (15 to 45% B in 30 min, Agilent PLRP-S 25×150 mm) to give the title compound (229 mg, 0.205 mmol, 59%). HPLC: $R_t$=4.7 min. MS: m/z=1120.5 ([M+H]$^+$, calculated 1120.7) $C_{41}H_{56}N_6O_6$, (MW=1120.42).

B. 1-{4-[(3-DOTA(tBu)₃-amino-propyl)-(3-dimethylamino-propyl)-carbamoyl]-2-isopropyl-phenyl}-5-(2,6-dimethoxy-phenyl)-1H-pyrazole-3-carboxylic acid (XV)

Methylester of formula (XIV) (370 mg, 0.330 mmol) was dissolved in 1,4-dioxane (1.72 ml). A 1 M aqueous solution of LiOH (1.32 ml, 1.32 mmol, 4 eq.) was added dropwise. After stirring for 5 h the pH was adjusted to 4 with HOAc (0.475 ml). After addition of ACN (18 ml) and water (100 ml) the cloudy solution was freeze dried. This material was dissolved in ACN (24 ml) and water (300 ml) and applied to a solid phase extraction column (4.0 g Varian Bondesil-ENV in a 60 ml polystyrene syringe, prewashed with methanol (3×25 ml) and water (3×25 ml). The column was eluted with 80 ml of 10% ACN in water as first fraction and each of the next fractions were eluted with 80 ml of 50% ACN in water containing 0.1% TFA. After lyophylization of the fractions 4 to 6 the title compound (313 mg, 86%) was obtained. HPLC: $R_t$=4.4 min. MS: m/z=1106.5 ([M+H]⁺, calculated 1106.7) $C_{58}H_{91}N_9O_{12}$, (MW=1106.40).

C. 2-{[1-{4-[(3-(DOTA(tBu)₃-amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid (XVI)

Carboxylic acid of formula (XV) (287 mg, 0.260 mmol) was dissolved in dry NMP (3.7 ml). HATU (98.7 mg, 0.260 mmol, 1.0 eq.) was added as solid and to this mixture DIPEA (89 µl, 0.52 mmol, 2.0 eq.) was added. After stirring for 5 min this solution was transferred within 5 min to a suspension of 2-amino-adamantane-2-carboxylic acid (50.7 mg, 0.260 mmol, 1.0 eq.) and DIPEA (44 µl, 0.26 mmol, 1.0 eq.) in dry NMP (7.6 ml). After 1 h at room temperature the flask was heated with an oil bath at 65° C. bath temperature. After 6 h additional 2-amino-adamantane-2-carboxylic acid (50.7 mg, 0.260 mmol, 1.0 eq.) and DIPEA (44 µl, 0.26 mmol, 1.0 eq.) were added and heating was continued for additional 18 h. After cooling down ACN/water 1:1 was added and the solution was lyophylized. The remaining solid was separated by prep. HPLC (20 to 60% B in 30 min, Agilent PLRP-S 25×150 mm) and the title compound (40 mg, 0.031 mmol, 12% yield) was obtained. HPLC: $R_t$=5.0 min. MS: m/z=1283.7 ([M+H]⁺, calculated 1283.8) $C_{69}H_{106}N_{10}O_{13}$, (MW=1283.64).

D. 2-{[1-{4-[(3-DOTA-amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid (Va)

TFA (4.8 ml) was added to a solution of Tris-tBu-ester of formula (XVI) (40 mg, 36 µmol) and triisobutylsilane (320 µl) in dry DCM (1.3 ml). After 3.5 h at room temperature the mixture was evaporated under reduced pressure and purified by prep. HPLC (15 to 55% B in 30 min, Agilent PLRP-S 25×150 mm). This yielded the title compound (24 mg, 19 µmol, 52%) as TFA-salt. HPLC: $R_t$=4.0 min. MS: m/z=1115.6 ([M+H]⁺, calculated 1115.6) $C_{57}H_{82}N_{10}O_{13}$, (MW=1115.32).

Method B:

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester (XXIV) (24.4 mg, 31.1 µmol, 1.0 eq.) was dissolved in DMF (0.5 ml) and DIPEA (33 µl, 187 µmol, 6 eq.) was added to the solution to adjust the pH-value to pH=7. Tri-tert-butyl-1,4,7,10-tetraazacyclododecane-1,4,7,10-tetraacetate (DOTA(tBu)₃-OH, 16.9 mg, 34.3 µmol, 1.1 eq.) was added. Then HOAt (16.9 mg, 125 µmol, 4.0 eq.) and DIC (14.5 µl, 95 µmol, 3.0 eq.) were added to the mixture which was subsequently stirred for 24 h. All volatiles were removed in the vacuum and the residue dissolved in EtOAc and water. The organic layer was dried and evaporated. The residue was stirred with TFA, phenol, water and TIPS (18/1/1/2) (0.3 ml) for 12 h.

The cleavage solution was directed to HPLC purification (20 to 45% B in 30 min, Agilent PLRP-S 25×150 mm) to give the title compound (3.7 mg, 3.3 µmol, 10.6%). HPLC: $R_t$=4.4 min. MS: m/z=1115.6 ([M+H]⁺, calculated 1115.6) $C_{57}H_{82}N_{10}O_{13}$, (MW=1115.32).

Example 20: Indium-Complex of a Compound of Formula (Va): In-(Va)

Complex formation was done according to the general procedure (Example 6 A) using the following reagents: Compound of formula (Va) (3.0 mg) and InCl₃×4 H₂O (2.4 mg), yielding the title compound (2.48 mg, 2.0 µmol, 75%). HPLC: $R_t$=4.3 min. MS: m/z=1227.6 ([M+H]⁺, calculated 1227.5) $C_{57}H_{79}InN_{10}O_{13}$, (MW=1227.11).

Example 21: 2-{[5-(2,6-Dimethoxy-phenyl)-1-(4-{(3-dimethylamino-propyl)-[3-(DOTA-Ttds-amino)-propyl]-carbamoyl}-2-isopropyl-phenyl)-1H-pyrazole-3-carbonyl]-amino}-adamantane-2-carboxylic (Vb)

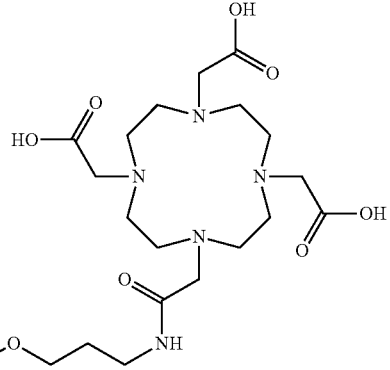
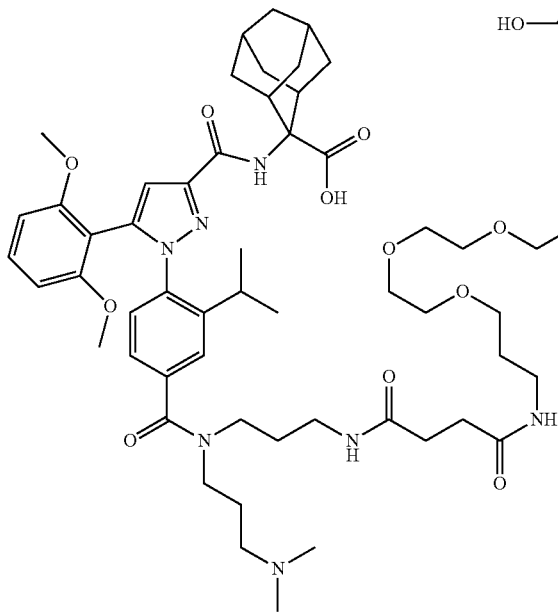

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester (XXIV) (24.4 mg, 31.1 µmol, 1.0 eq.) was dissolved in DMF (0.5 ml) and DIPEA (33 µl, 187 µmol, 6 eq.) was added to the solution to adjust the pH-value to pH=7. N-{3-[2-(2-{3-[2-(4,7,10-Tris-tert-butoxycarbonylmethyl-1,4,7,10-tetraaza-cyclododec-1-yl)-acetylamino]-propoxy}-ethoxy)-ethoxy]-propyl}-succinamic acid (DOTA(tBu)$_3$-Ttds-OH) (XX) (30 mg, 34.3 µmol, 1.1 eq.) was added. Then HOAt (16.9 mg, 125 µmol, 4.0 eq.) and DIC (14.5 µl, 95 µmol, 3.0 eq.) were added to the mixture which was subsequently stirred for 24 h. All volatiles were removed in the vacuum and the residue dissolved in EtOAc and water. The organic layer was dried and evaporated. The residue was stirred with TFA, phenol, water and TIPS (18/1/1/2) (0.3 ml) for 12 h.

The cleavage solution was directed to HPLC purification (20 to 45% B in 30 min, Agilent PLRP-S 25×150 mm) to give the title compound (4.0 mg, 2.8 µmol, 9%). HPLC: $R_t$=4.4 min. MS: m/z=1417.9 ([M+H]$^+$, calculated 1417.8) $C_{71}H_{108}N_{12}O_{18}$, (MW=1417.69).

Example 22: Synthesis of (S)-2-{[1-{4-[(3-{[3-(DOTA-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-cyclohexyl-acetic acid (IVa)

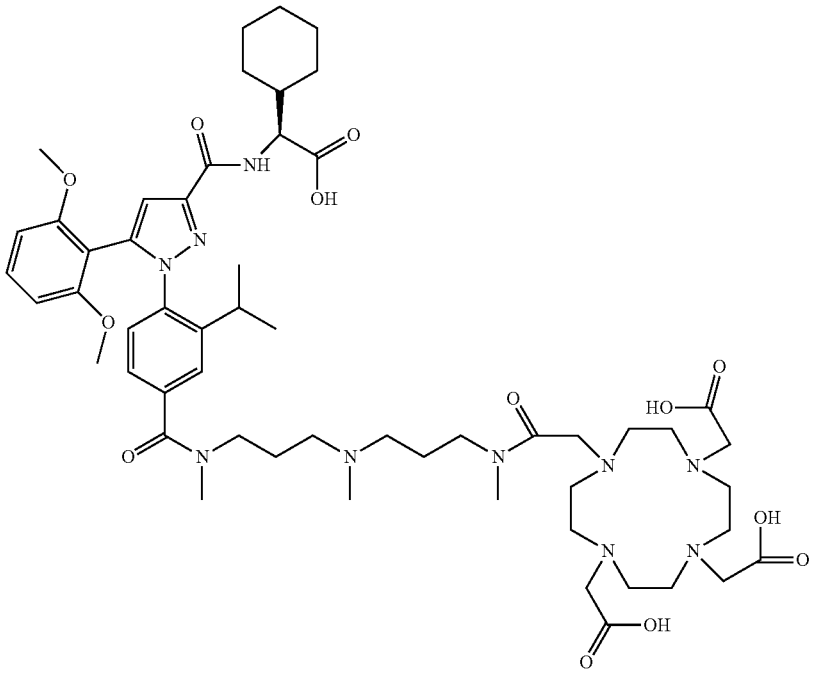

(IVa)

This solid phase synthesis was performed in a standard 2 ml plastic syringe equipped with a filter in the bottom of the syringe. In this solid phase synthesis reactor L-Cyclohexyl-glycin loaded 2-Cl-Trt-resin (75 mg resin, 50 µmol) [Prepared according to a standard procedure: "Fmoc Solid Phase Peptide Synthesis" Editors W. Chan, P. White, Oxford University Press, USA, 2000] was swollen in DMF (2 ml) for 20 min. In a flask the carboxylic acid of formula (XII) (70.0 mg, 0.0625 mmol, 1.25 eq.) was dissolved in dry NMP (0.5 ml), and HATU (18.3 mg, 0.0625 mmol, 1.25 eq.) and DIPEA (16.2 µl, 0.125 mmol, 2.5 eq.) were added. After 5 min of preactivation this solution was transferred into the syringe with the resin. The syringe was closed and shaken overnight. After 15 h the reaction mixture was removed by vacuum and the resin washed with DMF (3×1.5 ml) and DCM (2×1.5 ml). After drying of the resin under reduced pressure (1 mbar) the resin was treated with a mixture of triisobutylsilane (0.1 ml) in TFA (1.9 ml) for 2 h. The cleavage solution was evaporated under reduced pressure and purified by prep. HPLC (25 to 45% B in 30 min, Agilent PLRP-S 25×150 mm). This yielded the title compound (31 mg, 28 µmol, 57%) as TFA-salt. MS (m/z): HPLC: $R_t$=4.4 min. MS: m/z=1091.6 ([M+H]$^+$, calculated 1091.6) $C_{55}H_{82}N_{10}O_{13}$, (MW=1091.30).

This method is generally applicable. Several other compounds were prepared in an analogous manner starting from differently preloaded trityl resins (with other amino acids or small peptides). Compound of formula (IIIa) was also prepared according to this method.

Example 23: Indium-Complex of a Compound of Formula (IVa): In-(IVa)

Complex formation was done according to the general procedure (Example 6 A) using the following reagents: Compound (IVa) (3.0 mg) and $InCl_3$×4 $H_2O$ (2.42 mg), yielding the title compound (2.8 mg). HPLC: $R_t$=4.4 min. MS: m/z=1203.5 ([M+H]$^+$, calculated 1203.5) $C_{55}H_{79}InN_{10}O_{13}$, (MW=1203.09).

Example 24: Synthesis of 5-(2,6-Dimethoxy-phenyl)-1-{4-[(3-dimethylamino-propyl)-methyl-carbamoyl]-2-isopropyl-phenyl}-1H-pyrazole-3-carboxylic acid [2-(2-DOTA-amino-ethylcarbamoyl)-adamantan-2-yl]-amide (XVII)

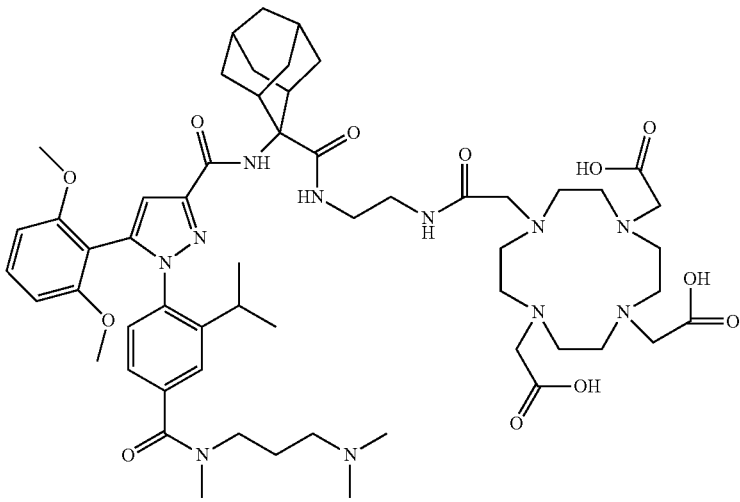

(XVII)

A. 5-(2,6-Dimethoxy-phenyl)-1-{4-[(3-dimethyl-amino-propyl)-methyl-carbamoyl]-2-isopropyl-phenyl}-1H-pyrazole-3-carboxylic acid [2-(2-DOTA(tBu$_3$)-amino-ethylcarbamoyl)-adamantan-2-yl]-amide (XVIII)

DOTA(tBu)$_3$-OH (100 mg, 0.175 mmol, 1.0 eq.) was dissolved in dry DMF (0.5 ml), HATU (66.4 mg, 0.175 mmol, 1.0 eq.) dissolved in dry DMF (0.5 ml) and Collidine (46.1 µl, 0.350 mmol, 2.0 eq.) were added. After 5 min this mixture was slowly added to a 0° C. cold solution of ethylendiamine (0.873 mmol. 5.0 eq.) in dry DMF (1.5 ml). After stirring for 19 h DMF was evaporated, the residual oil was dissolved in EtOAc (5 ml) and extracted with water (0.5 ml), sat. aq. NaHCO$_3$ (0.5 ml) and sat. aq. NaCl (0.5 ml). The organic layer was dried over Na$_2$SO$_4$, evaporated and the residue was purified by flash chromatography with DCM, DCM/methanol 20/1 and DCM/methanol 10/1 as eluents. This yielded 45 mg of monoacylated ethylendiamine. A solution of this material (18 mg, 29 µmol) in dry DMF (0.2 ml) was added to a 10 min preactivated solution of SR-142948 (20 mg, 29 µmol) [HATU (11.1 mg, 29 µmol) and DIPEA (10 µl, 58 µmol, 2 eq.) in dry DMF (0.4 ml)]. After 15 h monoacylated ethylendiamine (9 mg, 15 µmol, 0.5 eq.) in dry DMF (0.1 ml) was added. 5 h later the reaction mixture was heated to 60° C. for 30 min. Then the solvents were evaporated and the material purified by prep. HPLC (15 to 55% B in 30 min, Agilent PLRP-S 25×150 mm). This yielded the title compound of formula (XVIII) (15 mg, 12 µmol, 40%). HPLC: R$_t$=3.9 min. MS: m/z=1282.7 ([M+H]$^+$, calculated 1282.8) C$_{69}$H$_{107}$N$_{11}$O$_{12}$, (MW=1282.65).

B. 5-(2,6-Dimethoxy-phenyl)-1-{4-[(3-dimethyl-amino-propyl)-methyl-carbamoyl]-2-isopropyl-phenyl}-1H-pyrazole-3-carboxylic acid [2-(2-DOTA-amino-ethylcarbamoyl)-adamantan-2-yl]-amide (XVII)

TFA (1.5 ml) was added to a solution of Tris-tBu-ester of formula (XVIII) (15 mg, 11 µmol) and triisobutylsilane (100 µl) in dry DCM (0.4 ml). After 4 h at room temperature the mixture was evaporated under reduced pressure and purified by prep. HPLC (15 to 45% B in 30 min, Agilent PLRP-S 25×150 mm). This yielded the title compound (6.3 mg, 5.7 µmol, 48%) as TFA-salt. HPLC: R$_t$=3.4 min. MS: m/z=1114.6 ([M+H]$^+$, calculated 1114.6) C$_{57}$H$_{83}$N$_{11}$O$_{12}$, (MW=1114.33).

Example 25: Functional Ca$^{2+}$ Mobilisation Assay

Ca$^{2+}$ ions are usually kept at nanomolar levels in the cytosol of cells, and act in a number of signal transduction pathways as second messengers. Many GPCRs including neurotensin receptor couple to induce calcium ion signaling, and many primary cellular assays employ measurement of intracellular calcium ion concentration as a functional readout of GPCR activation. Changes in calcium ion concentration in standard assay protocols can be readily detected with fluorescent dyes that emit light when changes in intracellular Ca$^{2+}$ ion concentration occur. Given the transient nature of these responses, they are often read with instrumentation that has 'inject and read' capability. This example shows that compounds of the present invention do not have any agonistic activity on NTR1-expressing cells. Furthermore, this example shows that compounds of the present invention bind to NTR1 and inhibit the activity of an additionally present NTR1 agonist.

HT29 or NTR1-expressing HEK293 cells were trypsinized and seeded into black flat clear-bottom 96-well plates (Corning, Amsterdam, The Netherlands) at 6×10⁵ cells per well. After 24 h incubation at 37° C. and 5% $CO_2$, cells were washed twice with wash buffer (130 mM NaCl, 5 mM KCl, 10 mM Hepes, 2 mM $CaCl_2$, 10 mM Glucose, pH 7.4) and loaded with 100 μl of Ca5 dye (Molecular Devices, Biberach, Germany) for 1 h at 37° C. and 5% $CO_2$. For agonist assays, serial dilutions of agonistic substances were added to the cells loaded with dye and the change of the fluorescent signal was recorded continually for approx. 90 s using a FlexStation II (Molecular Devices, Biberach, Germany). Addition of wash buffer served as a control. Thus, EC50 concentrations for each compound were computed and provided a measure for the potency of the substance. For antagonist assays, cells loaded with 100 μl of Ca5-dye were pre-incubated with serial dilutions of antagonistic substances for 30 min, before the EC80-concentration of agonist was added to the cells and the change of the fluorescent signal was recorded continually for approx. 90 s. Thus, IC50 concentrations were computed for each compound and provided a measure for the inhibitory activity of the compounds at the NTR1.

affinity of the molecule, the more radioligand is displaced from the binding site. The amount of bound radioligand can be measured by scintillation counting and thereby quantified. This assay is commonly used to calculate binding constants of molecules to receptors. This example shows that compounds of the present invention bind to NTR1 with high affinity.

The NTR1 radioligand binding assay was performed by Cerep (Celle l'Evescault, France; Catalog reference 0109) according to Vita et al., *FEBS Lett.*, 1993, 317, 139-142. NTR1 was prepared from CHO cells recombinantly expressing the human receptor and incubated with 0.05 nM ¹²⁵I-(Tyr³-neurotensin) and serial dilutions of the test compounds. After 60 min incubation at 4° C. and washing to remove unbound neurotensin, bound radioactivity was measured by scintillation counting. The result for each test compound is expressed as IC50 concentration and provides a measure for the affinity of the test compound for NTR1.

The results of this assay performed on some of the compounds according to the present invention are given in the following Table 1.

TABLE 1

Results of the Ca-mobilisation assay (Ca) and the radioligand binding assay (RLB)

| Compound | Example (example part II) | Linker | Acceptor | Effector | IC50 [nM] Ca | IC50 [nM] RLB |
|---|---|---|---|---|---|---|
| (III) | 4 | R₇ = H | — | — | 7.54 | 0.87 |
| (IIIa) | 5 | — | DOTA | — | 20.0 | 2.9 |
| In-(IIIa) | 6 B | — | DOTA | In | 5.35 | 0.76 |
| Ga-(IIIa) | 6 C | — | DOTA | Ga | 7.28 | 1.0 |
| Y-(IIIa) | 6 D | — | DOTA | Y | 6.10 | 1.2 |
| Lu-(IIIa) | 6 E | — | DOTA | Lu | 5.95 | 0.59 |
| (IIIb) | 7 | Ttds | DOTA | — | 16.6 | 5.2 |
| Lu-(IIIb) | 8 | Ttds | DOTA | Lu | 10.2 | 1.6 |
| (IIIc) | 9 | Ahx | DOTA | — | 11.8 | 5.7 |
| (IIId) | 10 | — | NODAGA | — | 14.5 | 3.7 |
| Ga-(IIId) | 11 | — | NODAGA | Ga | 7.00 | 0.94 |
| (IIIe) | 12 | Ttds | NODAGA | — | 21.4 | 4.9 |
| (IIIf) | 13 | 1,4-(—CS—NH—)₂-Phenyl | DFO | — | 17.5 | 3.0 |
| Zr-(IIIf) | 14 | 1,4-(—CS—NH—)₂-Phenyl | DFO | Zr | 21.3 | 2.1 |
| (IIIg) | 15 | — | Benzoic acid | F (para) | 14.5 | 2.3 |
| (V) | 18 | R₇ = H | — | — | 8.95 | 5.3 |
| (Va) | 19 | — | DOTA | — | 12.6 | 3.4 |
| In-(Va) | 20 | — | DOTA | In | 14.4 | 1.3 |
| (Vb) | 21 | Ttds | DOTA | — | 26.0 | 2.4 |
| (IVa) | 22 | — | DOTA | — | 125 | n.d. |
| In-(IVa) | 23 | — | DOTA | In | 75 | n.d. |
| (XVII) | 24 | Not applicable | Not applicable | Not applicable | No inhibition | n.d. |

The results of this assay performed on some of the compounds according to the present invention are given in Table 1 together with the results of the radioligand binding assay (Example 26).

Example 26: Radioligand Binding Assay

In order to determine the binding affinity of compounds comprising a radiolabel for NTR1, a radioligand binding assay was carried out. A radioligand is a radioactive biochemical substance that is used for diagnosis or for research-oriented study of cellular receptor systems of the body. In in vivo systems it is often used to quantify the binding of a test molecule to the binding site of radioligand. The higher the All compounds with a reported IC50 are full antagonists and do not induce signals in the agonistic Ca-assay.

The implementation of a structural element like the group of formula (II),

(II)

which for instance could contain a chelator such as DOTA, into the structure of formula (I), is part of the present invention. A person skilled in the art would have utilized the free carboxylic acid of the structure of formula (I) in order to attach a chelator such as DOTA. A representative example of the result of such approach is the compound of formula (XVII). The inactivity of the compound of formula (XVII) in the functional Ca-assay demonstrated that modifications at this position of the structure of formula (I) destroy NTR-1 affinity. However, this compound of formula (XVII) is not within the scope of the present invention (and is not encompassed by the structure of formula (I)) since the group of formula (II) is not present at the positions defined in accordance with the present invention. On the other hand, compounds of the present invention as, for instance, the compound of formula (IIIa) where the group of formula (II) is represented by $R^4$ or $R^5$ (and also compounds as for instance the compound of formula (Va) with the group of formula (II) being represented by $R^3$) exhibit very strong NTR-1 affinities with respective Ca IC50=20 nM and RLB IC50=2.9 nM. As shown in more detail in table 1 above, also the corresponding metal complexes of, for instance, the compounds of formulae (IIIa) or (Va) exhibit similarly strong or usually even stronger NTR-1 binding affinities than their uncomplexed counterparts.

Additionally, the results shown in table 1 provide evidence that in compounds according to the present invention the NTR1-binding part thereof acts in terms of NTR1-affinity independently from the nature of the chelator as well as from the presence or absence of linkers of different structures and properties. The unmodified carboxylic acid in structures of formula (I) is an important element for high affinities toward NTR-1, but is not amenable to modifications such as the attachment of an Effector moiety as evidenced by the inactivity of the compound of formula (XVII).

Example 27: Plasma Stability Assay

The plasma stability assay was performed to measure the degradation of compounds of the present invention in plasma. This is an important characteristic of a compound as compounds, with the exception of pro-drugs, which rapidly degrade in plasma generally show poor in vivo efficacy.

In order to determine the stability of compounds of formulae (IIIa) and (Va) in human and mouse plasma, a plasma stability assay was carried out. The results show that compounds of of formulae (IIIa) and (Va) are highly stable in human and mouse plasma. The stability is sufficient for the diagnostic, therapeutic and theranostic use of these compounds according to the present invention.

The plasma was spiked with a 10 mM analyte solution in dimethyl sulfoxide to a final concentration of 10 μM, vortexed, and aliquotted to 50 μl samples. Two aliquots were stored at −20° C. until further treatment. Another two aliquots were incubated using an Eppendorf Thermomixer at 37° C. for 1, 4, and 24 hours. Sample clean-up was performed using a protein precipitation plate (Phenomenex Strata Impact, 64722-1-324-1) and using acetonitrile as precipitation agent. The filtrate was dried in a vacuum centrifuge and dissolved in 50 μl 25% aqueous acetonitrile solution. An aliquot of 10 μl was diluted with 90 μl 0.1% aqueous trifluoroacetic acid solution. The determination of the analyte in the clean sample solutions was performed on a Thermo TSQ Quantum Ultra triple quadrupole mass spectrometer equipped with a thermo Surveyor HPLC. The chromatographic separation was carried out on a Phenomenex Kinetex XB-C18 HPLC column (50×2 mm, 2.5 m particle size) with gradient elution using a mixture of 0.01% trifluoroacetic acid and 0.05% formic acid in water as eluent A and methanol as eluent B (20% B to 100% in 8 min, 400 μl/min, 40° C.). For mass spectrometric detection the selected reaction monitoring (SRM) was used.

Quantitation was performed by external matrix calibration using an internal standard.

LC-MS parameters:

Analyte compound of formula (IIIa)

retention time: 4.3 min

MS/MS transition: 1063.5→296.3 (48 V)

Analyte compound of formula (Va)

retention time: 4.5 min

MS/MS transition: 565.4→542.6 (19 V)

The results of this assay performed on some of the compounds according to the present invention are given in the following Table 2.

TABLE 2

Results of the plasma stability assay

| Compound | % remaining after 24 h incubation | |
| --- | --- | --- |
|  | Human plasma | Mouse plasma |
| (IIIa) | >90% | >80% |
| (Va) | >70% | >60% |

Example 28: Plasma Protein Binding Assay

A drug's efficiency may be affected by the degree to which it binds to the proteins within blood plasma. A drug in blood exists in two forms: bound and unbound. Depending on a specific drug's affinity for plasma protein, a proportion of the drug may become bound to plasma proteins, with the remainder being unbound. Notably, it is the unbound fraction which exhibits pharmacologic effects. It is also the fraction that may be metabolized and/or excreted. Protein binding can influence the drug's biological half-life in the body. The bound portion may act as a reservoir or depot from which the drug is slowly released as the unbound form. In order to determine the binding characteristics of the compounds of the present invention as listed in the following Table to human or mouse plasma protein, respectively, a plasma protein binding assay was carried out. All compounds have a plasma protein binding that is appropriate for diagnostic, therapeutic and theranostic use of these compounds according to the present invention.

The binding of test substances to human and murine plasma proteins was tested by Cerep (Celle l'Evescault, France; Catalog reference 2194 [human] and 2223 [mouse]) according to Banker et al., *J. Pharm. Sci.*, 2003, 92, 967-974. Test compounds were incubated with human or murine plasma proteins for 4 h at 37° C. Subsequently, the fraction of compound bound to plasma proteins was determined by equilibrium dialysis and HPLC-MS/MS detection. The result for each test compound is given as the percentage bound to plasma protein.

The results of this assay performed on some of the compounds according to the present invention are given in the following Table 3.

TABLE 3

Results of the plasma protein binding assay

| Compound | % bound [human] | % bound [mouse] |
|---|---|---|
| (IIIa) | 99 | 89 |
| In-(IIIa) | 92 | 64 |
| Ga-(IIIa) | Not determined | 74 |
| Lu-(IIIa) | 95 | 67 |
| Y-(IIIa) | 96 | 76 |
| In-(Va) | 84 | 46 |
| In-(IVa) | 84 | 41 |

Example 29: Specificity Screening

The specificity screening was carried out in order to test for unspecific binding of compounds of the present invention. The specificity for NTR1 was tested using a standard battery of assays ("ExpresSProfile") comprising 55 assays on GPCRs, ion channels, and transporter proteins. This assay was performed by Cerep (Celle l'Evescault, France; Catalog reference P1).

Unspecific binding according to this specificity screening is observed if Inhibition of Control Specific Binding is above 50%. Apart from NTR1 itself, this is only observed for NK2 (66%) at a concentration that is extremely high ($10^{-5}$ M). The results show that a compound of formula (IIIa) is highly specific and well suited for diagnostic, therapeutic and theranostic use of these compounds according to the present invention.

The results of this assays performed on a compound of the present invention are presented in the following Table 4.

TABLE 4

Results of the specificity screening (ExpresSProfile) for compound of formula (IIIa).

| Assay | Catalog Reference | Test Concentration (M) | % Inhibition of Control Specific Binding | % of Control Specific Binding 1st | 2nd | Mean | SEM % | Reference Control Compound | Ki Ref (M) | nH Ref |
|---|---|---|---|---|---|---|---|---|---|---|
| A1 (h) antagonist radioligand Townsend-Nicholson et al., *J. Biol. Chem.*, 1994, 269: 2373-2376 | 0002 | 1.0E−05 | −24 | 142.9 | 104.5 | 123.7 | 19.2 | DPCPX | 6.2E−10 | 0.8 |
| A2A (h) agonist radioligand Luthin et al., *Mol. Pharmacol.*, 1995, 47, 307-313 | 0004 | 1.0E−05 | 5 | 104.2 | 85.6 | 94.9 | 9.3 | NECA | 3.5E−08 | 1.1 |
| A3 (h) agonist radioligand Salvatore et al., *Proc. Natl. Acad. Sci. U.S.A.*, 1993, 90, 10365-10369 | 0006 | 1.0E−05 | −41 | 129.0 | 153.9 | 141.4 | 12.4 | IB-MECA | 4.8E−10 | 1.0 |
| alpha 1 (non-selective) antagonist radioligand Greengrass et al., *Eur. J. Pharmacol.*, 1979, 55, 323-326 | 0008 | 1.0E−05 | −9 | 106.2 | 111.1 | 108.7 | 2.5 | prazosin | 5.8E−11 | 1.2 |
| alpha 2 (non-selective) antagonist radioligand Uhlen et al., *Pharmacol. Toxicol.*, 1991, 69, 341-350 | 0011 | 1.0E−05 | −10 | 114.4 | 106.1 | 110.3 | 4.2 | yohimbine | 3.8E−08 | 0.7 |
| beta 1 (h) agonist radioligand Levin et al., *J. Biol. Chem.*, 2002, 277, 30429-30435 | 0018 | 1.0E−05 | 2 | 89.9 | 106.1 | 98.0 | 8.1 | atenolol | 2.7E−07 | 0.9 |
| beta 2 (h) agonist radioligand Joseph et al., *Naun.-Sch. Arch. Pharm.*, 2004, 369, 525-532 | 0020 | 1.0E−05 | −2 | 107.2 | 96.5 | 101.8 | 5.4 | ICI 118551 | 1.9E−10 | 0.9 |
| AT1 (h) antagonist radioligand Le et al., *Eur. J. Pharmacol.*, 2005, 513, 35-45 | 0024 | 1.0E−05 | −18 | 118.7 | 116.8 | 117.7 | 1.0 | saralasin | 4.4E−10 | 0.6 |
| BZD (central) agonist radioligand Speth et al., *Life Sci.*, 1979, 24, 351-358 | 0028 | 1.0E−05 | −16 | 109.4 | 122.6 | 116.0 | 6.6 | diazepam | 7.5E−09 | 1.1 |
| B2 (h) agonist radioligand Pruneau et al., *Brit. J. Pharmacol.*, 1998, 125, 365-372 | 0033 | 1.0E−05 | 11 | 98.7 | 79.9 | 89.3 | 9.4 | NPC 567 | 9.9E−09 | 0.9 |

TABLE 4-continued

Results of the specificity screening (ExpresSProfile) for compound of formula (IIIa).

| Assay | Catalog Reference | Test Concentration (M) | % Inhibition of Control Specific Binding | % of Control Specific Binding | | | SEM % Control | Reference Compound | Ki Ref (M) | nH Ref |
|---|---|---|---|---|---|---|---|---|---|---|
| | | | | 1st | 2nd | Mean | | | | |
| CB1 (h) agonist radioligand Rinaldi-Carmona et al., *J. Pharmacol. Exp. Ther.*, 1996, 278, 871-878 | 0036 | 1.0E−05 | 11 | 96.0 | 82.5 | 89.3 | 6.8 | CP 55940 | 1.6E−10 | 0.8 |
| CCK1 (CCKA) (h) agonist radioligand Bignon et al., *J. Pharmacol. Exp. Ther.*, 1999, 289, 742-751 | 0039 | 1.0E−05 | −18 | 101.6 | 135.3 | 118.5 | 16.8 | CCK-8s | 6.5E−11 | 0.6 |
| D1 (h) antagonist radioligand Zhou et al., *Nature*, 1990, 347, 76-80 | 0044 | 1.0E−05 | −5 | 114.0 | 96.3 | 105.2 | 8.8 | SCH 23390 | 9.0E−11 | 0.9 |
| D2S (h) antagonist radioligand Grandy et al., *Proc. Natl. Acad. Sci. U.S.A.*, 1989, 86, 9762-9766 | 0046 | 1.0E−05 | −9 | 112.8 | 104.7 | 108.8 | 4.1 | (+)butaclamol | 2.7E−10 | 1.0 |
| ETA (h) agonist radioligand Buchan et al., *Brit. J. Pharmacol.*, 1994, 112, 1251-1257 | 0054 | 1.0E−05 | −10 | 114.3 | 105.4 | 109.8 | 4.5 | endothelin-1 | 3.6E−11 | 1.1 |
| GABA (non-selective) agonist radioligand Tsuji et al., *Antimicrob. Agents Chemother.*, 1988, 32, 190-194 | 0057 | 1.0E−05 | −6 | 101.9 | 109.9 | 105.9 | 4.0 | GABA | 1.7E−08 | 0.8 |
| GAL2 (h) agonist radioligand Bloomquist et al., *Biochem. Biophys. Res. Commun.*, 1998, 243, 474-479 | 0410 | 1.0E−05 | 1 | 96.5 | 102.1 | 99.3 | 2.8 | galanin | 2.9E−09 | 0.9 |
| CXCR2 (IL-8B) (h) agonist radioligand White et al., *J. Biol. Chem.*, 1998, 273, 10095-10098 | 0419 | 1.0E−05 | −9 | 118.7 | 99.6 | 109.1 | 9.5 | IL-8 | 5.6E−11 | 1.4 |
| CCR1 (h) agonist radioligand Neote et al., *Cell*, 1993, 72, 415-425 | 0361 | 1.0E−05 | −6 | 103.2 | 109.1 | 106.1 | 3.0 | MIP-1alpha | 4.1E−11 | 1.1 |
| H1 (h) antagonist radioligand Smit et al., *Brit. J. Pharmacol.*, 1996, 117, 1071-1080 | 0870 | 1.0E−05 | −12 | 121.2 | 103.3 | 112.3 | 9.0 | pyrilamine | 7.6E−10 | 1.1 |
| H2 (h) antagonist radioligand Leurs et al., *Brit. J. Pharmacol.*, 1994, 112, 847-854 | 1208 | 1.0E−05 | −4 | 105.9 | 101.7 | 103.8 | 2.1 | cimetidine | 4.7E−07 | 1.2 |
| MC4 (h) agonist radioligand Schioth et al., *Neuropeptides*, 1997, 31, 565-571 | 0420 | 1.0E−05 | −8 | 113.2 | 103.7 | 108.5 | 4.7 | NDP-alpha-MSH | 2.8E−10 | 0.9 |
| MT1 (ML1A) (h) agonist radioligand Witt-Enderby et al., *Mol. Pharmacol.*, 1996, 50, 166-174 | 1538 | 1.0E−05 | 1 | 102.6 | 95.9 | 99.3 | 3.3 | melatonin | 1.3E−10 | 0.9 |
| M1 (h) antagonist radioligand Dorje et al., *J. Pharmacol. Exp. Ther.*, 1991, 256, 727-733 | 0091 | 1.0E−05 | −25 | 111.0 | 138.4 | 124.7 | 13.7 | pirenzepine | 1.4E−08 | 1.2 |

TABLE 4-continued

Results of the specificity screening (ExpresSProfile) for compound of formula (IIIa).

| Assay | Catalog Reference | Test Concentration (M) | % Inhibition of Control Specific Binding | % of Control Specific Binding | | | SEM % Control | Reference Compound | Ki Ref (M) | nH Ref |
|---|---|---|---|---|---|---|---|---|---|---|
| | | | | 1st | 2nd | Mean | | | | |
| M2 (h) antagonist radioligand Dorje et al., *J. Pharmacol. Exp. Ther.*, 1991, 256, 727-733 | 0093 | 1.0E−05 | −17 | 123.7 | 110.8 | 117.2 | 6.4 | methoctramine | 7.6E−09 | 0.9 |
| M3 (h) antagonist radioligand Peralta et al., *Embo. J.*, 1987, 6, 3923-3929 | 0095 | 1.0E−05 | −23 | 122.5 | 124.5 | 123.5 | 1.0 | 4-DAMP | 2.7E−10 | 1.1 |
| NK2 (h) agonist radioligand Aharony et al., *Mol. Pharmacol.*, 1993, 44, 356-363 | 0102 | 1.0E−05 | 66 | 34.5 | 33.7 | 34.1 | 0.4 | [Nleu10]-NKA (4-10) | 2.5E−09 | 0.8 |
| NK3 (h) antagonist radioligand Sarau et al., *J. Pharmacol. Exp. Ther.*, 1997, 281, 1303-1311 | 0104 | 1.0E−05 | −1 | 102.5 | 98.5 | 100.5 | 2.0 | SB 222200 | 4.3E−09 | 0.9 |
| Y1 (h) agonist radioligand Wieland et al., *J. Pharmacol. Exp. Ther.*, 1995, 275, 143-149 | 0106 | 1.0E−05 | −34 | 127.5 | 141.4 | 134.4 | 6.9 | NPY | 5.8E−11 | 0.7 |
| Y2 (h) agonist radioligand Fuhlendorff et al., *Proc. Natl. Acad. Sci. U.S.A.*, 1990, 87, 182-186 | 0107 | 1.0E−05 | −23 | 130.5 | 116.0 | 123.2 | 7.2 | NPY | 4.4E−11 | 0.9 |
| NTS1 (NT1) (h) agonist radioligand Vita et al., *FEBS Lett.*, 1993, 317, 139-142 | 0109 | 1.0E−05 | 99 | 2.7 | −0.1 | 1.3 | 1.4 | neurotensin | 2.4E−10 | 0.8 |
| delta 2 (DOP) (h) agonist radioligand Simonin et al., *Mol. Pharmacol.*, 1994, 46, 1015-1021 | 0114 | 1.0E−05 | −6 | 106.9 | 105.2 | 106.1 | 0.8 | DPDPE | 2.0E−09 | 0.9 |
| kappa (KOP) agonist radioligand Meng et al., *Proc. Natl. Acad. Sci. U.S.A.*, 1993, 90, 9954-9958 | 1971 | 1.0E−05 | −2 | 111.0 | 92.3 | 101.6 | 9.4 | U 50488 | 4.4E−10 | 1.2 |
| mu (MOP) (h) agonist radioligand Wang et al., *FEBS Lett.*, 1994, 338, 217-222 | 0118 | 1.0E−05 | 0 | 108.3 | 92.6 | 100.5 | 7.9 | DAMGO | 4.4E−10 | 1.0 |
| NOP (ORL1) (h) agonist radioligand Ardati et al., *Mol. Pharmacol.*, 1997, 51, 816-824 | 0358 | 1.0E−05 | −7 | 104.5 | 108.8 | 106.6 | 2.2 | nociceptin | 1.3E−10 | 1.2 |
| EP4 (h) agonist radioligand Abramovitz et al., *Biochem. Biophys. Acta.*, 2000, 1483, 285-293 | 0441 | 1.0E−05 | 8 | 89.2 | 95.5 | 92.3 | 3.2 | PGE2 | 2.4E−10 | 1.1 |
| 5-HT1A (h) agonist radioligand Mulheron et al., *J. Biol. Chem.*, 1994, 269, 12954-12962 | 0131 | 1.0E−05 | −29 | 129.9 | 128.6 | 129.2 | 0.6 | 8-OH-DPAT | 6.7E−10 | 1.1 |
| 5-HT1B antagonist radioligand Hoyer et al., *Eur. J. Pharmacol.*, 1985, 118, 1-12 | 0132 | 1.0E−05 | −7 | 107.0 | 106.3 | 106.7 | 0.3 | serotonin | 7.3E−09 | 0.9 |
| 5-HT2A (h) antagonist radioligand Bonhaus et al., *Brit. J. Pharmacol.*, 1995, 115, 622-628 | 0135 | 1.0E−05 | −2 | 100.7 | 103.0 | 101.9 | 1.2 | ketanserin | 4.4E−10 | 1.0 |

TABLE 4-continued

Results of the specificity screening (ExpresSProfile) for compound of formula (IIIa).

| Assay | Catalog Reference | Test Concentration (M) | % Inhibition of Control Specific Binding | % of Control Specific Binding | | | SEM % Control | Reference Compound | Ki Ref (M) | nH Ref |
|---|---|---|---|---|---|---|---|---|---|---|
| | | | | 1st | 2nd | Mean | | | | |
| 5-HT2B (h) agonist radioligand Choi et al., *FEBS Lett.*, 1994, 352, 393-399. | 1333 | 1.0E−05 | −22 | 118.0 | 125.1 | 121.6 | 3.5 | (±)DOI | 3.1E−09 | 1.0 |
| 5-HT3 (h) antagonist radioligand Hope et al., *Brit. J. Pharmacol.*, 1996, 118, 1237-1245 | 0411 | 1.0E−05 | −8 | 107.6 | 107.5 | 107.5 | 0.0 | MDL 72222 | 4.2E−09 | 0.8 |
| 5-HT5a (h) agonist radioligand Rees et al., *FEBS Lett.*, 1994, 355, 242-246 | 0140 | 1.0E−05 | −2 | 109.4 | 95.2 | 102.3 | 7.1 | serotonin | 1.2E−07 | 0.8 |
| 5-HT6 (h) agonist radioligand Monsma et al., *Mol. Pharmacol.*, 1993, 43, 320-327 | 0142 | 1.0E−05 | −6 | 106.5 | 105.4 | 105.9 | 0.6 | serotonin | 6.6E−08 | 0.8 |
| 5-HT7 (h) agonist radioligand Shen et al., *J. Biol. Chem.*, 1993, 268, 18200-18204 | 0144 | 1.0E−05 | 2 | 96.6 | 99.7 | 98.2 | 1.6 | serotonin | 9.4E−11 | 1.2 |
| sst (non-selective) (agonist radioligand) Brown et al., *J. Biol. Chem.*, 1990, 265, 17995-18004 | 0149 | 1.0E−05 | −11 | 111.6 | 110.0 | 110.8 | 0.8 | somatostatin-14 | 1.1E−10 | 0.8 |
| VPAC1 (VIP1) (h) agonist radioligand Couvineau et al., *Biochem. J.*, 1985, 231, 139-143 | 0157 | 1.0E−05 | −6 | 103.9 | 107.3 | 105.6 | 1.7 | VIP | 1.5E−10 | 2.0 |
| V1a (h) agonist radioligand Tahara et al., *Brit. J. Pharmacol.*, 1998, 125, 1463-1470 | 0159 | 1.0E−05 | 6 | 94.1 | 93.0 | 93.5 | 0.5 | [d(CH2)51,Tyr(Me)2]-AVP | 9.1E−10 | 1.6 |
| Ca2+ channel (L, verapamil site) (phenylalkylamine) antagonist radioligand Reynolds et al., *J. Pharmacol. Exp. Ther.*, 1986, 237, 731-738 | 0163 | 1.0E−05 | 0 | 96.1 | 103.7 | 99.9 | 3.8 | D 600 | 5.9E−09 | 0.5 |
| KV channel antagonist radioligand Sorensen et al., *Mol. Pharmacol.*, 1989, 36, 689-698 | 0166 | 1.0E−05 | −4 | 104.3 | 104.2 | 104.3 | 0.0 | alpha-dendrotoxin | 2.0E−10 | 1.7 |
| SKCa channel antagonist radioligand Hugues et al., *J. Biol. Chem.*, 1982, 257, 2762-2769 | 0167 | 1.0E−05 | 4 | 97.3 | 95.2 | 96.2 | 1.1 | apamin | 8.4E−12 | 1.3 |
| Cl-channel (GABA-gated) antagonist radioligand Lewin et al., *Mol. Pharmacol.*, 1989, 35, 189-194 | 0170 | 1.0E−05 | 2 | 106.5 | 89.1 | 97.8 | 8.7 | picrotoxinin | 9.3E−08 | 0.9 |
| norepinephrine transporter (h) antagonist radioligand Pacholczyk et al., *Nature*, 1991, 350, 350-354 | 0355 | 1.0E−05 | −12 | 118.9 | 105.0 | 111.9 | 7.0 | protriptyline | 3.8E−09 | 0.9 |
| dopamine transporter (h) antagonist radioligand Pristupa et al., *Mol. Pharmacol.*, 1994, 45, 125-135 | 0052 | 1.0E−05 | −15 | 123.5 | 106.4 | 114.9 | 8.5 | BTCP | 3.7E−09 | 1.0 |

TABLE 4-continued

Results of the specificity screening (ExpresSProfile) for compound of formula (IIIa).

| Assay | Catalog Reference | Test Concentration (M) | % Inhibition of Control Specific Binding | % of Control Specific Binding | | | SEM % Control | Reference Compound | Ki Ref (M) | nH Ref |
|---|---|---|---|---|---|---|---|---|---|---|
| | | | | 1st | 2nd | Mean | | | | |
| 5-HT transporter (h) antagonist radioligand Tatsumi et al., Eur. J. Pharmacol., 1999, 368, 277-283 | 0439 | 1.0E−05 | −13 | 102.6 | 122.8 | 112.7 | 10.1 | imipramine | 1.2E−09 | 2.1 |

Example 30: Quantitation of Receptor Binding Sites on Tissue Sections

Autoradiography allows the determination of the binding of a substance to its receptors on tissue sections. Therefore, this method was used to determine the binding of some compounds of the present invention, and the number of receptor binding sites per tissue was quantitated. Surprisingly, when comparing an agonist and antagonist of similar affinity for the receptor, the antagonist recognizes more receptor binding sites than the agonist. This underlines the particular suitability of compounds of the invention as diagnostically or therapeutically active agents.

All tissues were frozen in liquid nitrogen or dry ice immediately after surgical resection and stored at −70° C. Receptor autoradiography was performed on 20-μm-thick cryostat (HM 500, Microm) sections of the tissue samples, mounted on microscopic slides and then stored at −20° C. for at least 3 days to improve adhesion of the tissue to the slide. Sections were first incubated with 50 mM Tris-HCl buffer pH 7.4, containing 0.02% BSA for 3 times at 5 min. For autoradiography, two compounds with similar receptor affinity were chosen and labeled with $^{177}$Lu according to the method of example 31. They were then incubated with $^{177}$Lu-(IIIa) (antagonist) or $^{177}$Lu-[NT(8-13)-Tle$^{12}$] (agonist) using 8000 cpm/100 μL in 50 mM Tris-HCl buffer pH 7.4, containing 0.02% BSA, 1 mM o-Phenantrolin and 1 mM MgCl$_2$ at room temperature for 1 h. After incubation, the sections were washed 5 times in ice-cold Tris-HCl (50 mM; pH 7.4) containing 0.02% BSA and twice in ice-cold Tris-HCl without BSA. The sections were dried for 15 min under a stream of cold air and then exposed to Biomax MR (Kodak) films for 6 h-7 days (depending on the receptor density on the tumor tissue) at 4° C. For nonspecific binding, sections were incubated with $10^{-6}$ M neurotensin. The autoradiograms were quantified using a computer-assisted image processing system.

As a result, $^{177}$Lu-(IIIa) bound 1.3 (+0.5) fold more receptors per mg of tissue compared to $^{177}$Lu-[NT(8-13)-Tle$^{12}$]. Taking into account the presence of BSA in the incubation buffer and the binding of $^{177}$Lu-(IIIa) to plasma proteins, the result should be weighted according to the free fraction of substance determined in the plasma protein binding assay (example 28). When adjusting the results for BSA-binding of $^{177}$Lu-(IIIa), $^{177}$Lu-(IIIa) bound on average 4.4-fold higher numbers of receptors than the equivalent agonist $^{177}$Lu-[NT(8-13)-Tle$^{12}$].

Example 31: $^{111}$In-Labeling of Selected Compounds

In order to serve as a diagnostically or therapeutically active agent, a compound needs to be labeled with a radioactive isotope. The labeling procedure needs to be appropriate to ensure a high radiochemical yield and purity of the radiolabeled compound of the invention. This example shows that the compounds of the present invention are appropriate for radiolabeling and can be labeled in high radiochemical yield and purity.

35 nmol of compound of formula (IIIa) were dissolved in buffer (0.4 M acetate, 0.325 M gentisic acid, pH 5) and mixed with 150 MBq of $^{111}$In (dissolved in 0.04 M HCl). The mixture was heated to 95° C. for 30 min. After cooling, the labeling was analyzed by thin layer chromatography (TLC) and HPLC. For TLC analysis, 2 μl of the labeling solution was analysed using an ITLC SA system (Varian, 10×1 cm) in citrate buffer (0.1 M, pH 5) and Raytest Minigita. For HPLC, 10 μl of the labeling solution were analysed with an Aeris PEPTIDE 3.6 μm XB-C18; 100×4.6 mm (Phenomenex). Gradient A: MeCN, 0.1% TFA, Gradient B: H$_2$O, 0.1% TFA, flow rate 0.8 ml/min; detector: NaI (Raytest), DAD254 nm.

Retention time of the labeled product: 9.5-9.9 min.
Radiochemical yield was ≥95%, radiochemical purity was ≥95%, specific activity: 4 MBq/nmol.

Labeling with $^{177}$Lu was performed in analogy to this protocol with similar yields and purity.

Example 32: Imaging and Biodistribution Studies

Radioactively labeled compounds can be detected by imaging methods such as SPECT and PET. Furthermore, the data acquired by such techniques can be confirmed by the direct measurement of radioactivity contained in the individual organs prepared from an animal injected with a radioactively labeled compound of the invention. Thus, the biodistribution of a radioactively labeled compound can be determined and analyzed. This example shows that the compounds of the present invention show a biodistribution appropriate for diagnostic imaging and therapeutic treatment of tumors.

All animal experiments were conducted in compliance with the German animal protection laws. Female CD-1 Nu/Nu mice (6- to 8-week-old, Charles River, Sulzfeld, Germany) were inoculated either with 5×10$^6$ HT-29 cells in one flank and 5×10$^6$ Capan-1 cells in the other flank, or 1×10$^7$ HEK293 cells in the shoulder region. When tumors were palpable (after 14-18 days), mice received 5-50 MBq $^{111}$In-labelled (IIIa) administered intravenously via the tail vein. Images were obtained on a NanoSPECT/CT system (BioScan Ltd., Washington, USA). Fusion of SPECT and CT data was performed with the software OsiriX Imaging Software.

For biodistribution studies, animals were sacrificed by decapitation at different time points after injection (3, 6, 12, and 24 hours post injection) and then dissected. Different organs and tissues were collected and weighed, and the radioactivity was determined by γ-counting. A minimum of three animals were used per time point. Results are expressed as a percentage of injected dose per gram of tissue (% ID/g).

The results of the imaging and biodistribution studies for selected compounds are shown in FIGS. 6-10.

The features of the present invention disclosed in the specification, the claims, the sequence listing and/or the drawings may both separately and in any combination thereof be material for realizing the invention in various forms thereof.

The invention claimed is:

1. A conjugate comprising a structure of general formula (1)

[TM1]-[AD1]-[LM]-[AD2]-[TM2]   (1), wherein

TM1 is a first targeting moiety, wherein the first targeting moiety is capable of binding to a first target, AD1 is a first adapter moiety or is absent, LM is a linker moiety, wherein the linker moiety LM is of general formula:

—[X]$_a$—[Y]—[Z]$_b$—   (VIII)

wherein

[X]$_a$ is a building block moiety formed of "a" building blocks X, or is absent

[Y] is a branching moiety or is absent,

[Z]$_b$ is a building block moiety formed of "b" building blocks Z, or is absent and wherein "a" and "b" are individually and independently any integer from 0, 1, 2, 3, 4, 5, 6, 7, 8, 9, 10, 11, 12, 13, 14, 15, 16, 17, 18, 19 and 20 under the proviso that a+b is 20, 19, 18, 17, 16, 15, 14, 13, 12, 11, 10, 9, 8, 7, 6, 5, 4, 3, 2, 1 or 0, AD2 is a second adapter moiety or is absent, and TM2 is a second targeting moiety, wherein the second targeting moiety is capable of binding to a second target;

wherein the first targeting moiety and/or the second targeting moiety is a compound of formula (2):

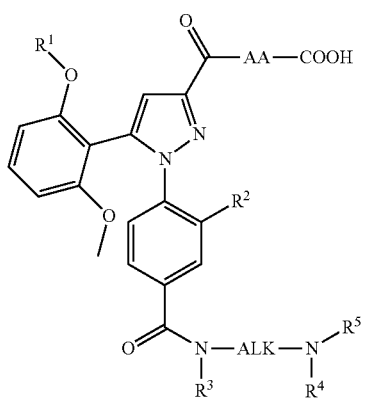

(2)

wherein $R^1$ is selected from the group consisting of hydrogen, methyl and cyclopropylmethyl;

AA-COOH is an amino acid selected from the group consisting of 2-amino-2-adamantane carboxylic acid, cyclohexylglycine and 9-amino-bicyclo[3.3.1]nonane-9-carboxylic acid;

$R^2$ is selected from the group consisting of ($C_1$-$C_6$)alkyl, ($C_3$-$C_8$)cycloalkyl, ($C_3$-$C_8$)cycloalkylmethyl, halogen, nitro and trifluoromethyl;

ALK is ($C_2$-$C_5$)alkylidene;

$R^3$, $R^4$ and $R^5$ are each and independently selected from the group consisting of hydrogen and ($C_1$-$C_4$)alkyl under the proviso that one of $R^3$, $R^4$ and $R^5$ is of the following formula (3)

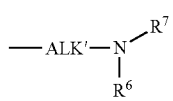

(3)

wherein

ALK' is ($C_2$-$C_5$)alkylidene;

$R^6$ is selected from the group consisting of hydrogen and ($C_1$-$C_4$)alkyl; and $R^7$ is a bond;

or a pharmacologically acceptable salt, solvate or hydrate thereof.

2. The conjugate of claim 1, wherein the conjugate comprises an Effector moiety EM, wherein the Effector moiety comprises an Effector, wherein the Effector is selected from the group consisting of a diagnostically active agent, a therapeutically active agent and a combination thereof.

3. The conjugate of claim 1, wherein the R1 is methyl.

4. The conjugate of claim 1, wherein R3, R4 and R5 are each and independently selected from the group consisting of hydrogen and methyl under the proviso that one of R3, R4 and R5 is of the following formula (3)

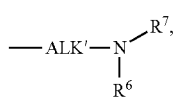

(3)

wherein

ALK' is $(C_2-C_5)$alkylidene;

$R^6$ is selected from the group consisting of hydrogen and $(C_1-C_4)$alkyl.

5. The conjugate of claim 1, wherein the first targeting moiety is selected from the group consisting of a compound of formula (4), a compound of formula (5) and a compound of formula (6), wherein the compound of formula (4) is

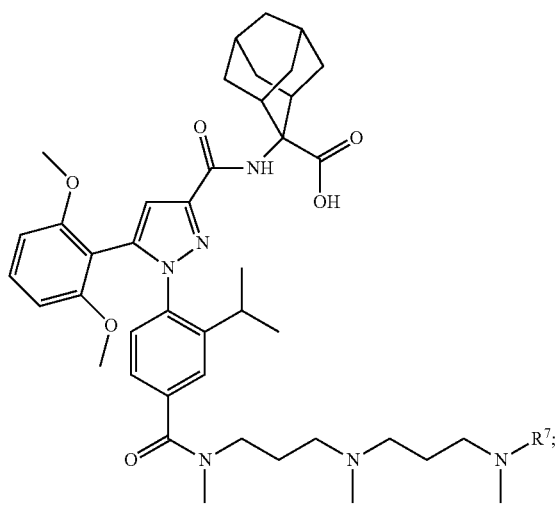

(4)

the compound of formula (5) is

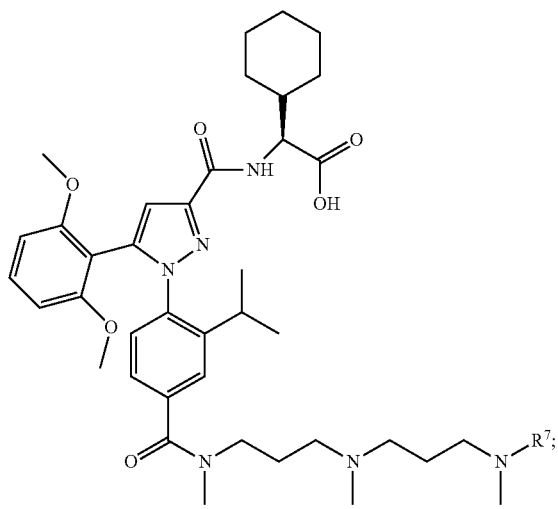

(5)

the compound of formula (6) is

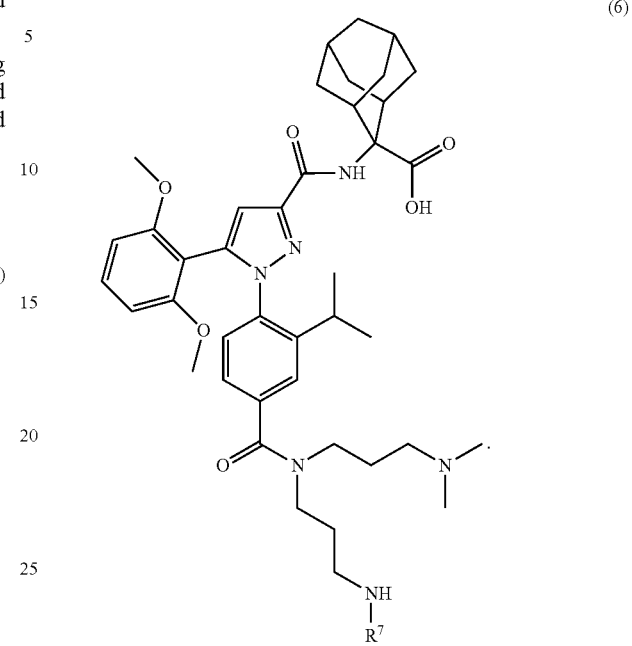

(6)

6. The conjugate of claim 1, wherein the first targeting moiety and the second targeting moiety are separated by 4 to 1000 covalent bonds.

7. The conjugate of claim 1, wherein the first adapter moiety AD1 links the first targeting moiety TM1 and an adjacent moiety, wherein the adjacent moiety is selected from the group consisting of linker moiety LM, building block moiety $[X]_a$, branching moiety Y, building block moiety $[Z]_b$, second adapter moiety AD2 and second targeting moiety TM2.

8. The conjugate of claim 1, wherein the second adapter moiety AD2 links the second targeting moiety TM2 and an adjacent moiety, wherein the adjacent moiety is selected from the group consisting of linker moiety LM, building block moiety $[Z]_b$, branching moiety Y, building block moiety $[X]_a$, first adapter moiety AD1 and first targeting moiety TM1.

9. The conjugate of claim 1, wherein the conjugate comprises a third adapter moiety AD3, wherein the adapter moiety AD3 links branching moiety [Y] and the effector moiety EM, or wherein the adapter moiety AD3 links the second targeting moiety TM2 and the effector moiety EM.

10. The conjugate of claim 2, wherein the Effector moiety EM comprises Acceptor or -[Acceptor-Effector], wherein
   Acceptor is a moiety which links the Effector to an optionally present third adapter moiety AD3, or Acceptor is a moiety which links the Effector to the branching moiety [Y], and
   Effector is selected from the group consisting of a diagnostically active agent or a therapeutically active agent.

11. The conjugate of claim 10, wherein the Acceptor is a chelator selected from the group consisting of DOTA, NOTA, DTPA, TETA, EDTA, NODAGA, NODASA, TRITA, CDTA, BAT, DFO, and HYNIC.

12. The conjugate of claim 1, wherein one of the first targeting moiety TM1 and the second targeting moiety TM2 is selected from the group consisting of an antibody, an antigen-binding antibody fragment, a camelid heavy chain IgG (hcIgG), a cartilaginous fish IgNAR antibody, a protein scaffold, a target-binding peptide, a peptide nucleic acid (PNA), a target-binding polypeptide or protein, a target binding nucleic acid molecule, a carbohydrate, a lipid and a target-binding molecule.

13. The conjugate of claim 2, wherein the Effector is a diagnostically active nuclide or a therapeutically active nuclide.

14. The conjugate of claim 2, wherein the Effector is selected from the group consisting of an antibody; an antigen-binding fragment of an antibody; an anticalin; an aptamer; a spiegelmer; an anti-proliferative agent; an anti-migration agent; an antiangiogenic agent; a cytostatic agent; a cytotoxic agent; an antithrombotic agent; an anti-inflammatory agent; an antiphlogistic agent; an anticoagulative agent; an antibacterial agent; an antiviral agent; an antimycotic agent; an endogenous fluorophore; a polycyclic aromatic, a coumarin; a quinoline; an indole; an imidazole; an UV-excited fluorophore; a fluorescein; a rhodamine; a naphthoxanthene dye; a phenanthridine; a BODIPY dye; a cyanine; a phthalocyanine; a xanthene; an acridine; an oxazine; a polyene; an oxonol; a benzimidazole; an azamethine; a styryl; a thiazole; an anthraquinone; a naphthalimide; an aza[18]annulene; a porphin; a metal-ligand-complexe; a squaraine; an 8-hydroxyquinoline-derivative; a polymethin; a nanocrystal; a fluorescent protein; a protein; a perylene; a phthalocyanine; an upconversion dye; a diketopyrrolopyrrole; a molecule of a porphyrin family selected from the group consisting of a hematoporphyrin derivative, a hematoporphyrin derivative, a benzoporphyrin derivative, a 5-aminolevulinic acid, and texaphyrin; a molecule of a chlorophyll family selected from the group consisting of a chlorin, a purpurin, and a bacteriochlorin; a dye selected from the group consisting of phtalocyanine, and naphthalocyanine, a small mononuclear or polynuclear paramagnetic chelate, a metalloporphyrin, a polymeric or macromolecular carrier, a particulate CA including a fluorinated or a nonfluorinated paramagnetic micelle or liposome and a paramagnetic or a superparamagnetic particle a Gd3+-labeled zeolite, and a diamagnetic CEST polymer; a diamagnetic hyperpolarization probe selected from the group consisting of gases and aerosols, a $^{13}$C-labeled compound or ion, an ultrasound contrast enhancing agent comprising a shell on a core, whereby the shell consists of a material selected from the group consisting of a phospholipid, a poly-[D,L-lactide-co-glycolide] acid (PLGA), serum albumin, a polymer, a perflutren, a carbon-based phase shift colloid, a perflexane, a lipid/galactose, a sulphur hexafluoride, a perfluorocyl bromide, a surfactant, anoligopeptide, and galactose and the core consists of a material selected from the group consisting of air, a perfluorocarbon, a decafluorobutane, an octafluoropropane, a dodecafluoropentane and a perfluorobutane, a carbon nanotube, a fullerene, a dendrimer, a quantum dot, a liposome, a silica nanoparticle, a magnetic nanoparticle, a lipid nanoparticle selected from the group consisting of a nanoemulsion, a polymeric nanoparticle, a albumin-based nanoparticle and a nanocrystal; a nucleic acid; an amino acid; a peptide; a protein; a carbohydrate; a lipid; glycoprotein; a glycan and lipoproteins.

15. The conjugate of claim 1, wherein the first targeting moiety TM1 is targeting NTR, and wherein the second targeting moiety TM2 is targeting a target different from neurotensin receptor 1.

16. The conjugate of claim 15, wherein the second targeting moiety TM2 is selected from the group consisting of an antibody, an antigen-binding antibody fragment, a camelid heavy chain IgG (hcIgG), a cartilaginous fish IgNAR antibody, a protein scaffold, a target-binding peptide, a peptide nucleic acid (PNA), a target-binding polypeptide or protein, a target binding nucleic acid molecule, a carbohydrate, a lipid and a target-binding molecule.

17. A method for the diagnosis of a disease in a subject, wherein the method comprises administering to the subject a diagnostically effective amount of a conjugate according to claim 1.

18. A method for the treatment of a disease in a subject, wherein the method comprises administering to the subject a therapeutically effective amount of a conjugate according to claim 1.

19. A method for identifying a subject, wherein the subject is likely to respond or likely not to respond to a treatment of a disease, wherein the method comprises carrying out a method of diagnosis comprising administering to the subject a diagnostically effective amount of a conjugate according to claim 1.

20. A method for selecting a subject from a group of subjects, wherein the subject is likely to respond or likely not to respond to a treatment of a disease, wherein the method comprises carrying out a method of diagnosis comprising administering to the subject a diagnostically effective amount of a conjugate according to claim 1.

21. A method for stratifying a group of subjects into subjects which are likely to respond to a treatment of a disease, and into subjects which are not likely to respond to a treatment of a disease, wherein the method comprises carrying out a method of diagnosis comprising administering to the subject a diagnostically effective amount of a conjugate according to claim 1.

22. The conjugate of claim 1, for use in a method for delivering an effector to neurotensin receptor, preferably neurotensin receptor 1, or for use in a method for delivering an effector to a target targeted by either the first targeting moiety TM1 or the second targeting moiety TM2, wherein the effector is selected from the group comprising a diagnostically active agent and a therapeutically active agent.

23. A pharmaceutical composition, wherein the composition comprises a compound according to claim 1 and a pharmaceutically acceptable excipient.

24. A kit comprising a compound according to claim 1, one or more optional excipient(s) and optionally one or more device(s), whereby the device(s) is/are selected from the group consisting of a labeling device, a purification device, a handling device, a radioprotection device, an analytical device or an administration device.

25. The conjugate of claim 1, wherein "a" and "b" are individually and independently any integer from 0, 1, 2, 3, 4, 5, 6, 7, 8, 9 and 10.

26. The conjugate of claim 1, wherein "a" and "b" are individually and independently any integer from 0, 1, 2, 3, 4 and 5.

27. The conjugate of claim 6, wherein the first targeting moiety and the second targeting moiety are separated by 5 to 150 covalent bonds.

28. The conjugate of claim 6, wherein the first targeting moiety and the second targeting moiety are separated by 10 to 40 covalent bonds.

29. The conjugate of claim 7, wherein the linkage is individually and independently selected from the group consisting of an amide linkage, a sulfonamide linkage, a urea linkage, a thioether linkage, an ether linkage, a carbamate linkage, an amine linkage, a triazole linkage, an oxime linkage, a hydrazone linkage, a disulfide linkage, a pyrazine linkage and a dihydropyrazine linkage.

30. The conjugate of claim 8, wherein the linkage is individually and independently selected from the group consisting of an amide linkage, a sulfonamide linkage, a urea linkage, a thioether linkage, an ether linkage, a carbamate linkage, an amine linkage, a triazole linkage, an oxime linkage, a hydrazone linkage, a disulfide linkage, a pyrazine linkage and a dihydropyrazine linkage.

31. The conjugate of claim 10, wherein the Acceptor is selected from the group consisting of DOTA, NOTA, DTPA, TETA, EDTA, NODAGA, NODASA, TRITA, CDTA, BAT, DFO, and HYNIC.

32. The conjugate of claim 10, wherein the Acceptor is DOTA.

33. The conjugate of claim 2, wherein the Effector is a diagnostically active radionuclide, or a therapeutically active radionuclide.

34. The conjugate of claim 2, wherein the Effector is a diagnostically active nuclide, or a therapeutically active nuclide.

35. The conjugate of claim 1, wherein the first targeting moiety TM1 is targeting NTR1.

36. The conjugate of claim 1, wherein the second targeting moiety TM2 is targeting a target expressed by a tumor cell.

* * * * *